(12) United States Patent
Gregor

(10) Patent No.: US 9,290,503 B2
(45) Date of Patent: *Mar. 22, 2016

(54) TRICYCLIC COMPOUND DERIVATIVES USEFUL IN THE TREATMENT OF NEOPLASTIC DISEASES, INFLAMMATORY DISORDERS AND IMMUNOMODULATORY DISORDERS

(71) Applicant: CHEMBRIDGE CORPORATION, San Diego, CA (US)

(72) Inventor: Vlad Edward Gregor, Del Mar, CA (US)

(73) Assignee: CHEMBRIDGE CORPORATION, San Diego, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/156,314

(22) Filed: Jan. 15, 2014

(65) Prior Publication Data

US 2014/0228350 A1   Aug. 14, 2014

Related U.S. Application Data

(60) Continuation-in-part of application No. 13/242,272, filed on Sep. 23, 2011, now Pat. No. 8,686,005, which is a division of application No. 11/891,604, filed on Aug. 10, 2007, now Pat. No. 8,063,225.

(60) Provisional application No. 60/837,652, filed on Aug. 14, 2006.

(51) Int. Cl.

| | |
|---|---|
| A61K 31/444 | (2006.01) |
| C07D 487/04 | (2006.01) |
| A61K 45/06 | (2006.01) |
| A61K 31/4545 | (2006.01) |
| C07D 471/04 | (2006.01) |
| A61K 31/5377 | (2006.01) |
| C07D 471/22 | (2006.01) |
| C07D 455/04 | (2006.01) |
| A61K 31/496 | (2006.01) |
| C07D 453/02 | (2006.01) |
| A61K 31/541 | (2006.01) |
| A61K 31/4439 | (2006.01) |

(52) U.S. Cl.
CPC ............ *C07D 487/04* (2013.01); *A61K 31/444* (2013.01); *A61K 31/4439* (2013.01); *A61K 31/4545* (2013.01); *A61K 31/496* (2013.01); *A61K 31/5377* (2013.01); *A61K 31/541* (2013.01); *A61K 45/06* (2013.01); *C07D 453/02* (2013.01); *C07D 455/04* (2013.01); *C07D 471/04* (2013.01); *C07D 471/22* (2013.01)

(58) Field of Classification Search
CPC .. C07D 401/00; C07D 487/04; C07D 471/04; C07D 471/22; C07D 455/04; C07D 453/02; A61K 45/06; A61K 31/4545; A61K 31/5377; A61K 31/496; A61K 31/444; A61K 31/541; A61K 31/4439
USPC ......... 514/338, 210.21, 228.5, 232.8, 253.09, 514/279, 292, 294, 305, 318; 546/272.1
See application file for complete search history.

(56) References Cited

U.S. PATENT DOCUMENTS 8,063,225 B2 * 11/2011 Gregor et al. ............... 546/273.1
8,686,005 B2 *  4/2014 Gregor ......................... 514/338

* cited by examiner

*Primary Examiner* — Celia Chang
(74) *Attorney, Agent, or Firm* — Mark S. Cohen; Pearl Cohen Zedek Latzer Baratz LLP

(57) ABSTRACT

Provided are compounds of the formula (I):

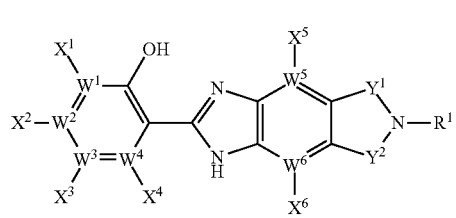

Formula (1)

or a stereoisomer, tautomer, salt, hydrate or prodrug thereof that modulate tyrosine kinase activity, compositions comprising the compounds and methods of their use.

16 Claims, 13 Drawing Sheets

TRICYCLIC COMPOUND DERIVATIVES USEFUL IN THE TREATMENT OF NEOPLASTIC DISEASES, INFLAMMATORY DISORDERS AND IMMUNOMODULATORY DISORDERS

CROSS REFERENCE TO RELATED APPLICATIONS

This application is a continuation-in-part application of U.S. patent application Ser. No. 13/242,272, filed on Sep. 21, 2011, which is a divisional application of U.S. patent application Ser. No. 11/891,604, filed on Aug. 10, 2007, which claims the benefit of U.S. Provisional Patent Application Ser. No. 60/837,652, filed on Aug. 14, 2006, all of which are incorporated herein by reference in their entirety.

FIELD OF THE INVENTION

Provided are compounds that modulate tyrosine kinase activity, compositions that comprise the compounds and methods of using the compounds for the treatment or prevention of diseases or conditions that are characterized by tyrosine kinase activity or expression.

BACKGROUND OF THE INVENTION

According to the latest American Cancer Society's annual statistical report, released in January 2005, cancer has edged out heart disease as the leading cause of death in Americans under age 85. In 2002, the most recent year for which information is available, 476,009 Americans under 85 died of cancer compared with 450,637 who died of heart disease (those under 85 comprise 98.4 percent of the US population). Protein tyrosine kinases (PTK), which historically represented the majority of first discovered oncogenes, remain today one of the most important classes of oncology drug targets.

Protein kinases are enzymes which covalently modify proteins and peptides by the attachment of a phosphate group to one or more sites on the protein or peptide (for example, PTK phosphorylate tyrosine groups). The measurement of protein kinase activity is important since studies have shown that these enzymes are key regulators of many cell functions.

Over 500 protein kinases have been identified in the human genome ("kinome") (Manning et al. (2002) Science. 298: 1912). Based on the recent advances in deciphering the human genome, the family of human PTK consists of approximately 90 members (Blume-Jensen and Hunter (2001) Nature, 411: 355-365; Robinson et al. (2000) Oncogene 19:5548-5557). This family can be divided in two major groups—receptor tyrosine kinases (RTK) and cytoplasmic (or non-receptor) tyrosine kinases (CTK)—and approximately 30 subfamilies based on structural similarity (see, e.g., Bolen et al. (1992) FASEB J. 6:3403-3409 (1992); Ullrich and Schlessinger (1990) Cell 61:203-212; Ihle (1995) Sem. Immunol. 7:247-254. PTKs are involved in regulation of many cellular processes, such as cell proliferation, survival and apoptosis. Enhanced activity of PTKs has been implicated in a variety of malignant and nonmalignant proliferative diseases. In addition, PTKs play a central role in the regulation of cells of the immune system. PTK inhibitors can thus impact a wide variety of oncologic and immunologic disorders. Such disorders may be ameliorated by selective inhibition of a certain receptor or non-receptor PTK, such as LCK, or due to the homology among PTK classes, by inhibition of more than one PTK by an inhibitor.

In some forms of cancer, a PTK mutation or structural alteration can increase the ability to proliferate, and thus, provides an advantage over surrounding cells. PTK of growth factor receptors, for instance, have been shown to be involved in the transformation of normal to cancerous cells (see, e.g., Rao (1996) Curr. Opin. Oncol. 8:516-524). PTK also play a role in the regulation of apoptosis or programmed cell death (see, e.g., Anderson (1997) Microbiol. Rev. 61:33). By activation of PTK, apoptosis mechanisms can be shut off and the elimination of cancerous cells is prevented. Thus, PTK exert their oncogenic effects via a number of mechanisms such as driving proliferation and cell motility and invasion. These PTK include HER2, BCR-ABL, SRC, and IGF1R.

There are many ways that a PTK can become oncogenic. For example, mutations (such as gain-of-function mutations) or small deletions in RTK and/or CTK are known to be associated with several malignancies (e.g., KIT/SCFR, EGFR/ERBB1, CSF-1R, FGFR1, FGFR3, HGFR, RET). Additionally, overexpression of certain types of PTK resulting, for example, from gene amplification has been shown to be associated with several common cancers in humans (e.g., EGFR/ERBB1, ERBB2/HER2/NEU, ERBB3/HER3, ERBB4/HER4, CSF-1R, PDGFR, FLK2/FLT3, FLT4/VEGFR3, FGFR1, FGFR2/K-SAM, FGFR4, HGFR, RON, EPHA2, PEHB2, EPHB4, AXL, TIE/TIE1). For a review of oncogenic kinase signaling, and mutated kinase genes that may be used in the systems and methods provided herein, see Blume-Jensen and Hunter (2001) Nature 411:355; Tibes et al (2005) Annu. Rev. Pharmacol. Toxicol. 45:357; Gschwind (2004) Nature Reviews 4:361; Paul and Mukhopadhay (2004) Int. J. Med. Sci (2004) 1:101.

The majority of PTKs are believed to be important drug targets, especially for anti-cancer therapy. Indeed, a very large proportion of known PTKs have been shown to be hyperactivated in cancer cells due to overexpression or constitutively activating mutations and to directly drive tumor growth. In addition, a subset of RTKs, such as vascular endothelial growth factor receptors (VEGFR), fibroblast growth factor receptors (FGFR) and some ephrin receptor (EPH) family members, is involved in driving angiogenesis while others (e.g., Met and discoidin domain receptor (DDR)) promote cell motility and invasion (e.g., metastasis).

The formation of new blood vessels, either from differentiating endothelial cells during embryonic development (vasculogenesis) or from pre-existing vessels during adult life (angiogenesis), is an essential feature of organ development, reproduction, and wound healing in higher organisms. Folkman and Shing, J. Biol. Chem., 267: 10931-10934 (1992); Reynolds et al., FASEB J., 6: 886-892 (1992); Risau et al., Development, 102: 471-478 (1988). Angiogenesis is implicated in the pathogenesis of a variety of disorders, including, but not limited to, solid tumors, intraocular neovascular syndromes such as proliferative retinopathies or age-related macular degeneration (AMD), rheumatoid arthritis, and psoriasis (Folkman et al., J. Biol. Chem. 267:10931-10934 (1992); Klagsbrun et al., Annu. Rev. Physiol. 53:217-239 (1991); and Garner A, "Vascular Diseases". In: Pathobiology of ocular disease. A dynamic approach. Garner A, Klintworth G K, Eds. 2nd Edition Marcel Dekker, NY, pp 1625-1710 (1994)). For example, vascularization allows tumor cells in solid tumors to acquire a growth advantage and proliferative freedom as compared to normal cells. Accordingly, a correlation has been observed between microvessel density in tumors and patient survival with various cancers and tumors (Weidner et al., N Engl J Med 324:1-6 (1991); Horak et al., Lancet 340:1120-1124 (1992); and Macchiarini et al., Lancet 340:145-146 (1992)).

A number of RTK have been identified that govern discrete stages of vascular development (Folkman et al., *Cell*, 87:1153-1155 (1996); Hanahan, D., *Science*, 277:48-50 (1997); Risau, W., *Nature*, 386:671-674 (1997); Yancopoulos et al., *Cell*, 93:661-664 (1998)). For example, VEGFR2 (FLK1), a receptor for vascular endothelial growth factor (VEGF), mediates endothelial and hematopoietic precursor cell differentiation (Shalaby et al., *Nature*, 376:62-66 (1995); Carmeliet et al., *Nature*, 380:435-439 (1996); Ferrara et al., *Nature* 380:439-442 (1996)). VEGF also governs later stages of angiogenesis through ligation of VEGFR1 (FLT1) (Fong et al., *Nature*, 376:66-70 (1995)). Mice that lack VEGFR1 have disorganized vascular endothelium with ectopic occurrence of endothelial cells from the earliest stages of vascular development, suggesting that VEGFR1 signaling is essential for the proper assembly of endothelial sheets (Fong et al., supra). Another tyrosine kinase receptor, TEK (TIE2) (Dumont et al., *Genes Dev.* 8:1897-1909 (1994); Sato et al., *Nature*, 376:70-74 (1995)) and its ligands ANG1 (Davis et al., *Cell* 87:1161-1169 (1996); Suri et al., *Cell* 87:1171-1180 (1996)) and ANG2 (Maisonpierre et al., *Science* 277:55-60 (1997)) are involved in assembly of non-endothelial vessel wall components. TIE (TIE1) is involved in maintaining endothelial integrity, and its inactivation results in perinatal lethality due to edema and hemorrhage (Sato, et al., *Nature* 376:70-74 (1995)). The TEK pathway seems to be involved in maturation steps and promotes interactions between the endothelium and surrounding vessel wall components (Suri et al., supra; and Vikkula et al., *Cell* 87:1181-1190 (1996)).

The EPH tyrosine kinase subfamily appears to be the largest subfamily of transmembrane RTK (Pasquale et al., *Curr. Opin. Cell Biol.* 9:608-615 (1997); and Orioli and Klein, *Trends in Genetics* 13:354-359 (1997)). Ephrins and their EPH receptors govern proper cell migration and positioning during neural development, presumably through modulating intercellular repulsion (Pasquale, supra; Orioli and Klein, supra). Bidirectional signaling has been observed for some Ephrin-B/EPHB ligand/receptor pairs (Holland et al., *Nature* 383:722-725 (1996); and Bruckner et al., *Science* 275:1640-1643 (1997)). For example, Ephrin-A1 and Ephrin-B1 have been-proposed to have angiogenic properties (Pandey et al., *Science* 268:567-569 (1995); and Stein et al., *Genes Dev.* 12:667-678 (1998)). Ephrin-B2, a ligand for EPHB4 receptor, was recently reported to mark the arterial compartment during early angiogenesis, and mice that lack Ephrin-B2 showed severe anomalies in capillary bed formation (Wang et al., *Cell* 93: 741-753 (1998)).

It is known that some compounds possess an ability to inhibit a tyrosine kinase activity. In particular, WO 2004/063151 discloses imidazole and pyridin derivatives as tyrosine kinase inhibitors.

Thus, modulating tyrosine kinase activity by chemical compounds represents a rational, targeted approach to cancer therapy. Additionally, because tyrosine kinases have a number of other diverse biological functions, such as regulation of metabolism, cell differentiation, inflammation, immune responses, and tissue morphogenesis, kinases are attractive for drug development outside oncology.

SUMMARY OF THE INVENTION

Provided are compounds that modulate tyrosine kinase activity, compositions that comprise the compounds and methods of using the compounds for the treatment or prevention of diseases or conditions that are characterized by tyrosine kinase activity or expression including, for example, cancer, diabetes, restenosis, arteriosclerosis, psoriasis, angiogenic diseases and immunologic disorders. (see, e.g., Powis et al., 1994, *Anti-Cancer Drugs Design* 9: 263-277; Merenmies et al., 1997, *Cell Growth Differ* 8: 3-10; Shawver et al., 1997, *Drug Discovery Today* 2:50-63; the contents of each are hereby incorporated by reference in their entireties). The compounds provided herein are described below in detail.

Provided are compounds according to formula (1), or a stereoisomer, tautomer, salt, hydrate or prodrug thereof:

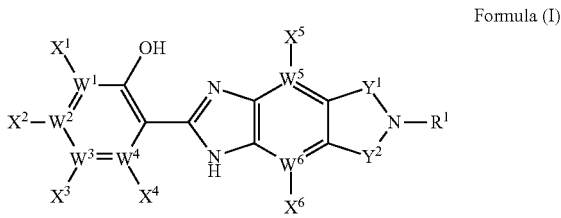

Formula (I)

wherein $X^1$, $X^2$, $X^3$, $X^4$, $X^5$, $X^6$, $W^1$, $W^2$, $W^3$, $W^4$, $W^5$, $W^6$, $Y^1$, $Y^2$ and $R^1$ are as defined below. In the description below, all combinations of the recitations for $X^1$, $X^2$, $X^3$, $X^4$, $X^5$, $X^6$, $W^1$, $W^2$, $W^3$, $W^4$, $W^5$, $W^6$, $Y^1$, $Y^2$ and $R^1$ are within the scope of this disclosure. Other embodiments are set forth below.

In one aspect, the present invention provides a method of treating multiple myeloma in a subject in need thereof comprising administering to said subject an insulin-like growth factor receptor-1 (IGF-1R) inhibitor, wherein said IGF-1R inhibitor is a compound of formula I,

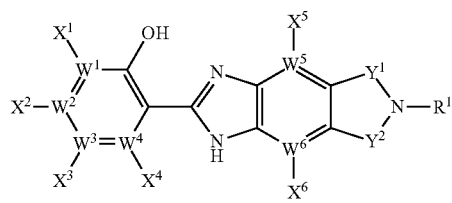

wherein:
each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

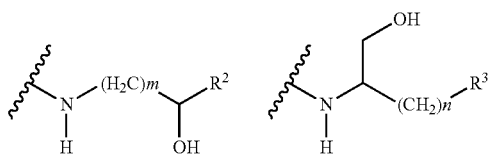

wherein:
m is an integer from 1 to 4, and n is an integer from 0 to 4;
$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —(CH$_2$)$_p$-M$^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein M$^1$ is O, S, and p is an integer between 0 and 4;

R$^3$ is selected from optionally substituted aryl, heteroaryl, wherein the heteroaryl is imidazoyl, pyridinyl, benzo-dioxanyl, benzo-imidazolyl or indolyl, —(CH$_2$)$_o$-aryl, or —(CH$_2$)$_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

Y$^1$ is

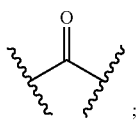 [SMILES: *C(*)=O]
;

Y$^2$ is

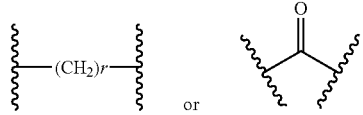

wherein: r is 1; and

R$^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, SO$_2$-alkyl, SO-alkyl, CO-alkyl, CO$_2$-alkyl, cyano, cyanoalkyl, ketoalkyl, and methanesulfonylalkyl, or a pharmaceutically acceptable salt thereof.

In another aspect, the present invention provides a method of treating multiple myeloma in a subject comprising administering to said subject a composition comprising an insulin-like growth factor receptor-1 (IGF-1R) inhibitor, wherein said IGF-1R inhibitor is a compound of formula I,

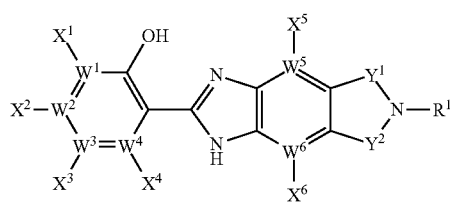

wherein:
each W$^1$ through W$^4$ is independently a carbon atom or a nitrogen atom, wherein one of W$^1$-W$^4$ is nitrogen, and W$^5$ and W$^6$ are carbon, with the proviso that when any W$^1$ through W$^4$ is N, then the corresponding substituent(s) X$^1$ through X$^4$ is (are) absent;

each X$^1$ through X$^3$ is independently selected from hydrogen, hydroxy, halogen, lower alkyl, lower alkoxy, haloalkyl, trifluoromethyl, nitro, cyano, primary, secondary or tertiary amino;

each X$^5$ and X$^6$ is independently selected from hydrogen and lower alkyl;

X$^4$ is selected from hydrogen, halogen, or is selected from the following groups:

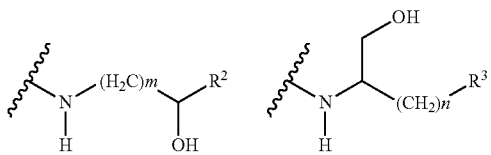

wherein:
m is an integer from 1 to 4, and n is an integer from 0 to 4;

R$^2$ is selected from optionally substituted aryl, heteroaryl wherein said heteroaryl is imidazoyl, pyridinyl, benzo-dioxanyl, benzo-dioxolyl, benzo-imidazolyl or indolyl, or —(CH$_2$)$_p$-M$^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein M$^1$ is O, S, and p is an integer between 0 and 4;

R$^3$ is selected from optionally substituted aryl, heteroaryl, wherein the heteroaryl is imidazoyl, pyridinyl, benzo-dioxanyl, benzo-imidazolyl or indolyl, —(CH$_2$)$_o$-aryl, or —(CH$_2$)$_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

Y$^1$ is

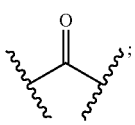
;

Y$^2$ is

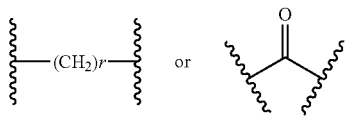

wherein: r is 1; and

R$^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, $SO_2$-alkyl, SO-alkyl, CO-alkyl, $CO_2$-alkyl, cyano, cyanoalkyl, ketoalkyl, and methanesulfonylalkyl, or a pharmaceutically acceptable salt thereof.

In another aspect, the present invention provides a method of treating a condition or disorder associated with an insulin-like growth factor receptor-1 (IGF-1R), comprising administering to a subject in need thereof an IGF-1R inhibitor, wherein said IGF-1R inhibitor is a compound of formula I,

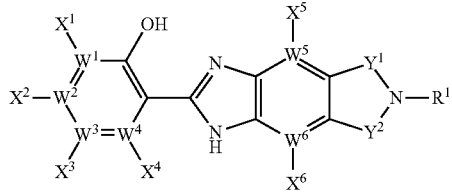

wherein:
each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, and halogen, or is selected from the following groups:

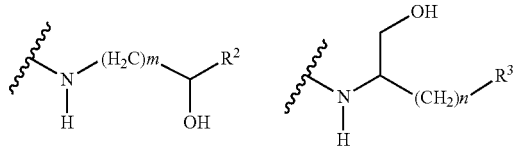

wherein:
m is an integer from 1 to 4, and n is an integer from 0 to 4;

$R^2$ is selected from optionally substituted aryl, and heteroaryl wherein said heteroaryl is imidazoyl, pyridinyl, benzo-dioxanyl, benzo-dioxolyl, benzo-imidazolyl or indolyl, or —$(CH_2)_p$-$M^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein $M^1$ is O, S, and p is an integer between 0 and 4;

$R^3$ is selected from optionally substituted aryl, heteroaryl, wherein the heteroaryl is imidazoyl, pyridinyl, benzo-dioxanyl, benzo-imidazolyl or indolyl, —$(CH_2)_o$-aryl, or —$(CH_2)_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

$Y^1$ is

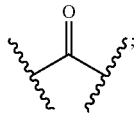

$Y^2$ is

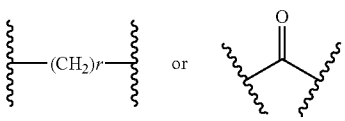

wherein: r is 1; and $R^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, $SO_2$-alkyl, SO-alkyl, CO-alkyl, $CO_2$-alkyl, cyano, cyanoalkyl, ketoalkyl, and methanesulfonylalkyl, or a pharmaceutically acceptable salt thereof.

DEFINITIONS

When describing the compounds, pharmaceutical compositions containing such compounds and methods of using such compounds and compositions, the following terms have the following meanings unless otherwise indicated. When two terms referring to chemical groups are combined, the combined term refers to the groups covalently linked in either orientation, unless specified otherwise. For instance, the term "acylamino" can refer to either "—C(O)—N(R)—" or to "—N(R)—C(O)—" unless specified otherwise and similarly sulfonamido or aminosulfonyl can refer to either —S($O_2$)—N(R)— or —N(R)—S($O_2$)—.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkenylene, alkynyl and alkynylene. Aliphatic groups typically have from 1 or 2 to about 12 carbon atoms.

"Alkyl" refers to monovalent saturated aliphatic hydrocarbyl groups, in one embodiment having up to about 11 carbon atoms, in another embodiment, as a lower alkyl, from 1 to 8 carbon atoms, and in yet another embodiment, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

"Substituted alkyl" includes those groups recited in the definition of "substituted" herein, and in one embodiment refers to an alkyl group having 1 or more substituents, in another embodiment, from 1 to 5 substituents, and yet in another embodiment, from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, alkylthio, substituted alkylthio, arylthio, thioketo, thiol, alkyl-S(O)—, aryl-S(O)—, alkyl-S(O)$_2$—, and aryl-S(O)$_2$—.

"Alkylene" refers to divalent saturated aliphatic hydrocarbyl groups in one embodiment having up to about 11 carbon atoms and in another embodiment having 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups having in one embodiment up to about 11 carbon atoms, in another embodiment from 2 to 8 carbon atoms, and in yet another embodiment from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

"Substituted alkenyl" includes those groups recited in the definition of "substituted" herein, and particularly refers to an alkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkenylene" refers to divalent olefinically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of olefinic unsaturation. This term is exemplified by groups such as ethenylene (—CH═CH—), the propylene isomers (e.g., —CH═CHCH$_2$— and —C(CH$_3$)═CH— and —CH═C(CH$_3$)—) and the like.

"Alkynyl" refers to acetylenically unsaturated hydrocarbyl groups particularly having in one embodiment up to about 11 carbon atoms and in another embodiment 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Alkanoyl" as used herein, which can include "acyl", refers to the group R—C(O)—, where R is hydrogen or alkyl as defined above.

"Alkoxy" refers to the group —OR where R is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having in one embodiment 1 or more substituents, in another embodiment from 1 to 5 substituents, and yet in another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Heteroalkyl" refers to an alkyl chain as specified above, having one or more heteroatoms selected from O, S, or N.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted in one embodiment with 1 or more substituents, in another embodiment from 1 to 5 substituents, and in yet another embodiment from 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, alkylthio, substituted alkylthio, arylthio, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring. In certain embodiments, a bicyclic compound of the invention comprises a fused aryl.

"Amino" refers to the radical —NH$_2$.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R)$_2$ is an amino group.

"Azido" refers to the radical —N$_3$.

"Carbamoyl" refers to the radical —C(O)N(R)$_2$ where each R group is independently hydrogen, alkyl, cycloalkyl or aryl, as defined herein, which may be optionally substituted as defined herein.

"Carboxy" refers to the radical —C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Cycloalkoxy" refers to the group —OR where R is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having in one embodiment 1 or more substituents, in another embodiment from 1 to 5 substituents, and in yet another embodiment from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, alkylthio, substituted alkylthio, arylthio, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C—C)—.

"Ethynyl" refers to —(C≡C)—.

"Halo" or "halogen" refers to fluoro, chloro, bromo and iodo. Particular halo groups are either fluoro or chloro.

"Hydroxy" refers to the radical —OH.

"Nitro" refers to the radical —NO$_2$.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" or "heteroaromatic" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, tetrahydroisoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, tetrahydroquinoline, quinolizine, quinoxaline, tetrazole, thiadiazole, thiazole, thiophene, triazole, xanthene, and the like. Particularly, heteroaryl can include other saturated ring systems, and can therefore be derived from indoline, indolizine, tetrahydroquinoline, and tetrahydroisoquinoline. In certain embodiments, the heteroaryl group is between 5-20 membered heteroaryl, with 5-10 membered heteroaryl being useful in certain embodiments. Particular heteroaryl groups are those derived from thiophene, pyrrole, benzothiophene, benzofuran, indole, pyridine, pyrimidine, quinoline, tetrahydroquinoline, isoquinoline, tetrahydroisoquinoline, imidazole, oxazole and pyrazine.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Sulfanyl" refers to the radical HS—. "Substituted sulfanyl" refers to a radical such as RS— wherein R is any substituent described herein. In certain embodiments, "substituted sulfanyl" refers to a radical —SR where R is an alkyl or cycloalkyl group as defined herein that may be optionally substituted as defined herein. Alkylthio or arylthio refer to the above sulfanyl group. Representative examples include, but are not limited to, methylthio, ethylthio, propylthio, butylthio, phenylthio and the like.

"Sulfinyl" refers to the radical —S(O)H. "Substituted sulfinyl" refers to a radical such as S(O)—R wherein R is any substituent described herein.

"Sulfonyl" refers to the divalent radical —S(O$_2$)—. "Substituted sulfonyl" refers to a radical such as —S(O$_2$)—R wherein R is any substituent described herein. "Aminosulfonyl" or "Sulfonamide" refers to the radical H$_2$N(O$_2$)S—, and "substituted aminosulfonyl" "substituted sulfonamide" refers to a radical such as R$_2$N(O$_2$)S— wherein each R is independently any substituent described herein. In particular embodiments, R is selected from H, lower alkyl, alkyl, aryl and heteroaryl.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms as long as the heteroaromatic ring is chemically feasible and stable.

"Pharmaceutically acceptable salt" refers to any salt of a compound of this invention which retains its biological properties and which is not toxic or otherwise undesirable for pharmaceutical use. Such salts may be derived from a variety of organic and inorganic counter-ions well known in the art and include. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Cahn et al., 1966, *Angew. Chem.* 78:413-447, *Angew. Chem., Int. Ed. Engl.* 5:385-414 (errata: *Angew. Chem., Int. Ed. Engl.* 5:511); Prelog and Helmchen, 1982, *Angew. Chem.* 94:614-631, *Angew. Chem. Internat. Ed. Eng.* 21:567-583; Mata and Lobo, 1993, *Tetrahedron: Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon use of stereoisomerically pure intermediates in their synthesis, such as pure enantiomers, or diastereomers as building blocks, prepared by chiral synthesis methodologies, or resolution by formation of diastereomeric salts with chiral acid or base and their separation, or separation by means of chromatography, including using chiral stationary phase. The racemic, or diastereomeric mixtures of embodiments (compounds) in this invention can also be separated by means of chromatography, including chiral stationary phase chromatography.

In certain embodiments, the compounds of the invention are "stereochemically pure." A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

As used herein, the terms "disorder" and "disease" are used interchangeably to refer to a condition in a subject. Certain conditions may be characterized as more than one disorder. For example, certain conditions may be characterized as both non-cancerous proliferative disorders and inflammatory disorders.

As used herein, the term "effective amount" refers to the amount of a compound of the invention which is sufficient to reduce or ameliorate the severity, duration of a disorder, cause regression of a disorder, prevent the recurrence, development, or onset of one or more symptoms associated with a disorder, or enhance or improve the prophylactic or therapeutic effect(s) of another therapy.

As used herein, the term "in combination" refers to the use of more than one therapies. The use of the term "in combination" does not restrict the order in which therapies (e.g., prophylactic and/or therapeutic agents) are administered to a subject with a disorder. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject with a disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound of the invention. In certain other embodiments, the term "prophylactic agent" does not refer a compound of the invention. In certain embodiments, a prophylactic agent is an agent which is known to be useful for, or has been or is currently being used to the prevent or impede the onset, development, progression and/or severity of a disorder. Prophylactic agents may be characterized as different agents based upon one or more effects that the agents have in vitro and/or in vivo. For example, an anti-angiogenic agent may also be characterized as an immunomodulatory agent.

As used herein, the terms "prevent," "preventing" and "prevention" refer to the prevention of the recurrence, onset, or development of one or more symptoms of a disorder in a subject resulting from the administration of a therapy, or the administration of a combination of therapies.

As used herein, the phrase "prophylactically effective amount" refers to the amount of a therapy which is sufficient to result in the prevention of the development, recurrence or onset of one or more symptoms associated with a disorder, or to enhance or improve the prophylactic effect(s) of another therapy.

As used herein, the terms "subject" and "patient" are used interchangeably herein. The terms "subject" and "subjects" refer to an animal, in certain embodiments a mammal including a non-primate (e.g., a cow, pig, horse, cat, dog, rat, and mouse) and a primate (e.g., a monkey such as a cynomolgous monkey, a chimpanzee and a human), and more particularly a human. In another embodiment, the subject is a farm animal (e.g., a horse, a cow, a pig, etc.) or a pet (e.g., a dog or a cat). In certain embodiments, the subject is a human.

As used herein, the term "synergistic" refers to a combination of a compound of the invention and another therapy which has been or is currently being used to prevent, manage or treat a disorder, which is more effective than the additive effects of the therapies. A synergistic effect of a combination of therapies permits the use of lower dosages of one or more of the therapies and/or less frequent administration of said therapies to a subject with a disorder. The ability to utilize lower dosages of a therapy and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies may avoid or reduce adverse or unwanted side effects associated with the use of either therapy alone.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound of the invention. In certain other embodiments, the term "therapeutic agent" refers does not refer to a compound of the invention. In certain embodiments, a therapeutic agent is an agent which is known to be useful for, or has been or is currently being used for the treatment, management, prevention, or amelioration a disorder or one or more symptoms thereof. Therapeutic agents may be characterized as different agents based upon one or more effects the agents have in vivo and/or in vitro, for example, an anti-inflammatory agent may also be characterized as an immunomodulatory agent.

In some embodiments, the "therapeutic agent" can be an "anti-cancer agent." An "anti-cancer agent" as used herein includes known anti-cancer treatments such as radiation therapy or cytostatic or cytotoxic agents. The anticancer agent includes, but is not limited to, tamoxifen, toremifene, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone, and the like.

As used herein, the term "therapeutically effective amount" refers to that amount of a therapy sufficient to result in the amelioration of one or more symptoms of a disorder, prevent advancement of a disorder, cause regression of a disorder, or to enhance or improve the therapeutic effect(s) of another therapy. In a specific embodiment, with respect to the treatment of cancer, an effective amount refers to the amount of a therapy that inhibits or reduces the proliferation of cancerous cells, inhibits or reduces the spread of tumor cells (metastasis), inhibits or reduces the onset, development or progression of one or more symptoms associated with cancer, or reduces the size of a tumor. In certain embodiments, a therapeutically effective of a therapy reduces the proliferation of cancerous cells or the size of a tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS").

As used herein, the terms "therapies" and "therapy" can refer to any protocol(s), method(s), and/or agent(s) that can be used in the prevention, treatment, management, or amelioration of a disorder or one or more symptoms thereof. In certain embodiments, the terms "therapy" and "therapies" refer to chemotherapy, radiation therapy, hormonal therapy, biological therapy, and/or other therapies useful in the prevention, management, treatment or amelioration of a disorder or one or more symptoms thereof known to one of skill in the art (e.g., skilled medical personnel).

As used herein, the terms "treat", "treatment" and "treating" refer to the reduction or amelioration of the progression, severity and/or duration of a disorder, or the amelioration of one or more symptoms thereof resulting from the administration of one or more therapies.

As used herein, the term "modulation" or "modulating" refers to the alteration of the catalytic activity of a tyrosine kinase. In particular, modulating can refer to the activation or to the inhibition of the tyrosine kinase. The tyrosine kinase can be any tyrosine kinase known to those of skill in the art. In certain embodiments, the tyrosine kinase is a receptor tyrosine kinase or an intracellular tyrosine kinase.

The definitions used herein are according to those generally accepted in the art and those specified herein.

Abbreviations used herein are standard abbreviations used in the art of organic chemistry:
AcOH—acetic acid
TFA—trifluoroacetic acid
DMSO—dimethyl sulfoxide
DCM—dichloromethane
BOC—tert. Butyloxycarbonyl
THF—tetrahydrofuran
p-TOS—p-Toluenesulfonyl
TEA—triethylamine
ETOH—ethanol
MeOH—methanol
DIPEA—diisopropylethylamine

DETAILED DESCRIPTION OF THE PRESENT INVENTION

Compounds

Figure 1:
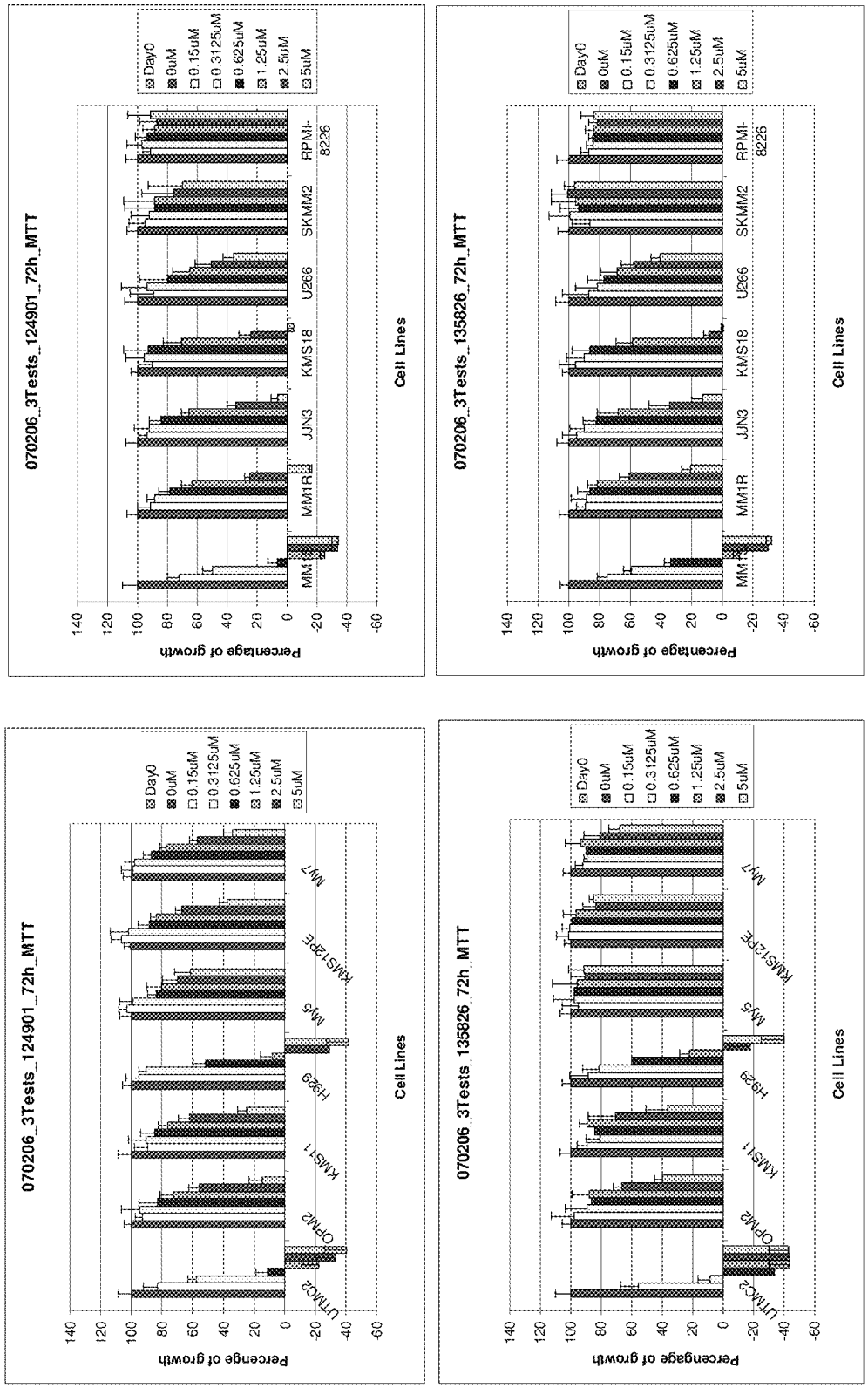
FIG. 1 depicts the effect of compound (2e) (i.e., CRL 124901) on viability of 14 human myeloma cell lines. 14 human myeloma cell lines were incubated for 72 hrs with indicated concentrations of compound (2e) and viability was determined by MTT assay. Results are reported as percent of growth (% viability $=(OD_{72h(drug)}-OD_{day0})/(OD_{72(0)}-OD_{day0})$) (Columns from left to right refer to a concentration of 0 M, 0.15 µM, 0.3125 µM, 0.625 µM, 1.25 µM, 2.5 µM, and 5 µM as indicated in FIG. 1).

In one aspect, provided are compounds according to formula (1), or a stereoisomer, tautomer, salt or hydrate thereof:

Formula (1)

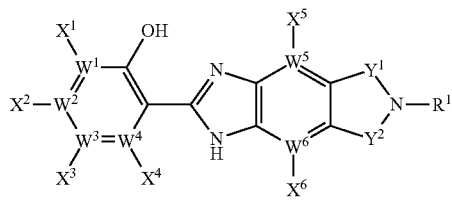

In formula (1), each $W^1$ through $W^6$ is independently a carbon atom or a nitrogen atom. When any $W^1$ through $W^6$ is N, then the corresponding substituent(s) $X^1$ through $X^6$ is (are) absent.

Compounds according to formula (1) can also be depicted in their respective "keto" form, which under certain conditions may predominate over the corresponding "enol" form. However, all possible tautomers and stereoisomers (such as for example, but not limited to: E and Z, (trans and cis) are incorporated herein. Examples of the tautomers of Formula (1) include, but are not limited to:

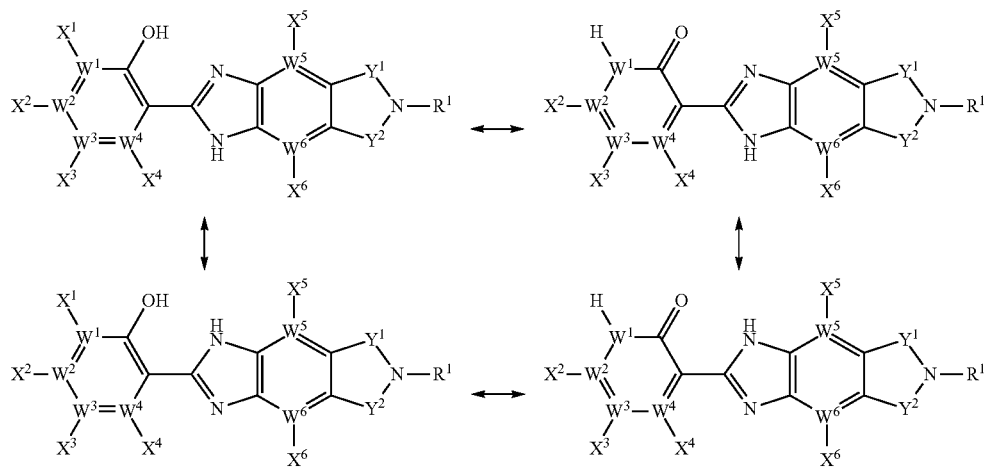

In formula (1), each $X^1$ through $X^3$, $X^5$ and $X^6$ is independently selected from hydrogen, hydroxy, halogen, optionally substituted lower alkyl, optionally substituted lower alkoxy, optionally substituted acylamino, optionally substituted sulfonamido, optionally substituted ureido, trifluoromethyl, trifluoromethoxy, nitro, cyano, optionally substituted aryl or heteroaryl, aryloxy or heteroaryloxy, arylamino or heteroarylamino (substituted by one or more groups selected from lower alkyl, lower alkoxy, lower alkylthio, lower alkylsulfinyl, lower alkylsulfonyl, carboxamide, sulfonamide, sulfamide, ureido, methylenedioxy, ethylenedioxy, primary, secondary or tertiary amino, mono or dialkyl amido, heterocyclylamido, optionally substituted heterocyclyl or cycloalkyl, optionally substituted heterocyclylalkyl, heteroalkyl), nitrogen-heterocyclyl, connected either by its nitrogen, or a carbon atom (such as piperazino, homopiperazino, morpholino, thiomorpholino, thiomorpholino-S-oxide, thiomorpholino-S,S-dioxide, pyrrolidino, piperidino, azetidino), nitrogen-heterocyclyl-alkyl, connected either by its nitrogen or a carbon atom (such as piperazinomethyl, piperazinoethyl, homopiperazinomethyl, morpholinomethyl, thiomorpholinomethyl, thiomorpholino-5-oxide-methyl, thiomorpholino-S,S-dioxide-methyl, pyrrolidinomethyl, piperidinoethyl, azetidinomethyl, all optionally substituted by groups selected from hydroxyalkyl, lower alkoxyalkyl, primary, secondary, or tertiary amino-alkyl, lower alkyl cycloalkyl or heterocycloalkyl). Such aryl and heteroaryl groups can be bicyclic in certain embodiments. In the above list, lower alkyl, lower alkoxy, acyl amino, sulfonamido and ureido can be substituted, for example, with aryl, heteroaryl, cycloalkyl or cycloheteroalkyl.

In certain embodiments, any adjacent pair of $X^1$ through $X^3$ can be joined to form a cycloalkyl, cycloheteroalkyl, aryl or heteroaryl ring fused to the ring comprising $W^1$ through $W^3$. Exemplary fused rings include naphthyl, benzodioxolyl, benzofuranyl, benzodioxinyl, dihydrobenzodioxinyl, quinolinyl, and others that will be recognized by those of skill in the art.

In formula (1), $X^4$ can be selected from hydrogen, hydroxy, halogen, trifluoromethyl, trifluoromethoxy, optionally substituted (alkyl, alkenyl, alkynyl, alkoxy, cycloalkoxy, cycloalkyl, heterocycloalkyl), optionally substituted (aryl, heteroaryl, arylalkyl, heteroarylalkyl, aryloxy, heteroaryloxy, arylalkoxy, heteroarylalkoxy, arylthio, heteroarylthio, arylsulfoxy, heteroarylsulfoxy, arylsulfonyl, heteroarylsulfonyl, arylsulfonamido, heteroarylsulfonamido, arylaminosulfonyl, heteroarylaminosulfonyl, arylamino, heteroarylamino, arylalkylamino, heteroarylalkylamino), by substituents selected from hydrogen, halogen, hydroxy, amino, cyano, nitro, carboxamido, sulfonamido, alkoxy, amino, lower-alkylamino, di-lower-alkylamino, cycloalkyl, cycloalkylalkyl, cycloalkoxy, cycloalkylalkoxy, trifluoromethyl, trifluoromethoxy, methylenedioxy, ethylenedioxy, methanesulfonyl, trifluoromethanesulfonyl, dialkylaminoalkyl, dialkylaminoalkoxy, heterocyclyl, heteroalkyl and heterocyclylalkyl.

$X^4$ is also selected from the following groups:

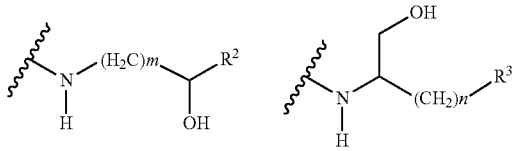

wherein:

m=1 to 4, n=0 to 4, p=1 to 5; and o=0 to 5.

$R^2$ is selected from optionally substituted aryl, or heteroaryl, —(CH$_2$)$_o$-aryl, —(CH$_2$)$_o$-heteroaryl, —(CH$_2$)$_p$-M$^1$-aryl, —(CH$_2$)$_p$-M$^1$-heteroaryl substituted by a substituent independently selected from a group consisting of hydrogen, hydroxy, halogen, trifluoromethyl, trifluoromethoxy, trifluoromethylthio, trifluoromethanesulfonyl, 2,2,2-trifluoroethoxy, lower alkyl, lower alkenyl, lower alkynyl, cycloalkyl, methylenedioxy, ethylenedioxy, trimethylene, dimethyleneoxy, cyano, nitro, primary, secondary or tertiary amino, such as dimethylamino, carboxamide, sulfonamide, lower alkylsulfonyl, lower alkylsulfinyl, lower alkylthio, lower alkylthioalkyl, lower alkylsulfonylalkyl, optionally substituted aryl or heteroaryl, wherein M$^1$ is a —(CH$_2$)— or a heteroatom O, S, or N—R*;

and R* is selected from hydrogen, hydroxy, lower alkyl, lower alkoxy, acyl, optionally substituted aryl, heteroaryl, alkylsulfonyl or arylsulfonyl;

$R^3$ is selected from optionally substituted aryl, heteroaryl, —(CH2)$_o$-aryl, —(CH2)$_o$-heteroaryl, —(CH2)$_p$-M$^2$-aryl, —(CH2)$_p$-M$^2$-heteroaryl, substituted by a substituent independently selected from a group consisting of hydrogen, hydroxy, halogen, trifluoromethyl, trifluoromethoxy, trifluoromethylthio, trifluoromethanesulfonyl, 2,2,2-trifluoroethoxy, lower alkyl, lower alkenyl, lower alkynyl, cycloalkyl, methylenedioxy, ethylenedioxy, trimethylene, dimethyleneoxy, cyano, nitro, primary, secondary or tertiary amino, such as dimethylamino, carboxamide, sulfonamide, lower alkylsulfonyl, lower alkylsulfinyl, lower alkylthio, lower alkylthioalkyl, lower alkylsulfonylalkyl, optionally substituted aryl or heteroaryl, wherein M$^2$ is a heteroatom O, S, or N—R; and R is selected from hydrogen, hydroxy, lower alkyl, lower alkoxy, acyl, optionally substituted aryl, heteroaryl, alkylsulfonyl or arylsulfonyl. In formula (1), in certain embodiments, each (CH$_2$)$_m$ or (CH$_2$)$_n$ can be optionally substituted with one or more groups selected from hydrogen, halogen, hydroxy, carboxamido, lower alkylcarbonyl, hydroxy-lower alkyl, hydroxycycloalkyl, optionally substituted (primary, secondary or tertiary amino, lower alkoxy, lower alkyl, lower heteroalkyl, cycloalkyl, heterocyclo, heterocycloalkyl, aryl, heteroaryl, aryloxy or heteroaryloxy), by groups selected from halogen, hydroxy, amino, lower alkyl, lower alkoxy, trifluoromethyl, trifluoromethoxy, trifluoromethylthio, trifluoromethanesulfonyl, cyano, nitro, carboxamido, lower alkylthio, lower alkylsulfoxy, lower alkylsulfonyl, arylthio, arylsulfoxy, arylsulfonyl, lower alkylcarbonyl, arylcarbonyl) all groups optionally substituted by groups selected from hydrogen, halogen, lower alkyl, trifluoromethyl, trifluoromethoxy, lower alkoxy, lower alkylthio, hydroxy, sulfonamido, lower acylamino. In certain embodiments the (CH$_2$)$_m$ or (CH$_2$)$_n$ can form a cyclic structure. In addition, in certain embodiments, one or more methylene of (CH$_2$)$_m$ or (CH$_2$)$_n$ can be replaced by a heteroatom selected from O, NH or N-lower alkyl and S, where appropriate according to the judgment of one of skill in the art.

In certain embodiments according to formula (1), the substituent $X^4$ is selected from the following groups:

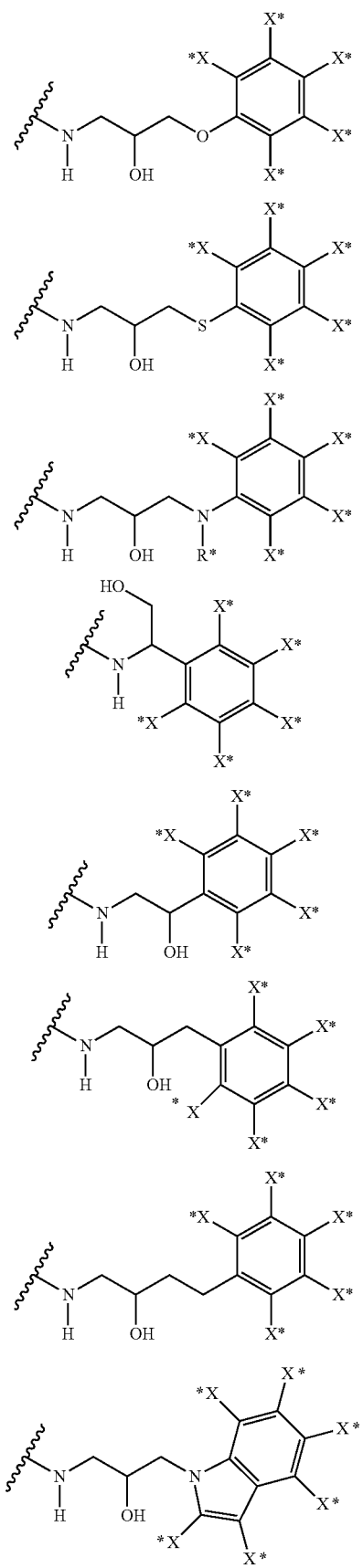

-continued

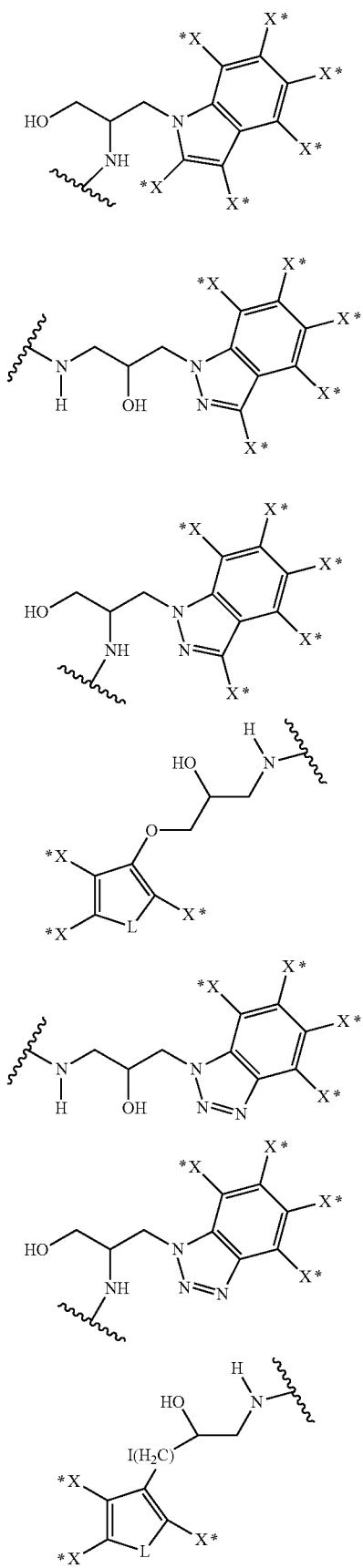

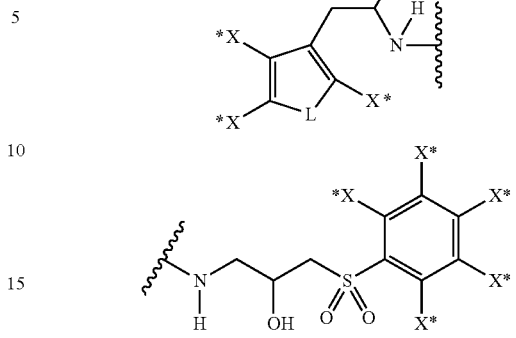

wherein:
L is selected from O, S, N—R#$_9$;
R#$_9$ is selected from hydrogen, lower alkyl, cycloalkyl, alkenyl, alkynyl, heteroalkyl, heterocyclyl, optionally substituted aryl, heteroaryl, arylalkyl, heteroarylalkyl by groups selected from hydrogen, halogen, lower alkyl, lower alkoxy, trifluoromethyl, trifluoromethoxy, lower alkylthio, nitro, azido, cyano, amido and ureido; and
each X* is independently selected from hydrogen, lower alkyl, halogen, lower alkoxy, trifluoromethyl, trifluoromethoxy, 2,2,2-trifluoroethoxy, trifluoromethylthio, azido, cyano, nitro, methylenedioxy, trimethylene and dimethyleneoxy.

In another embodiment in formula (1), $X^4$ is selected from the following:

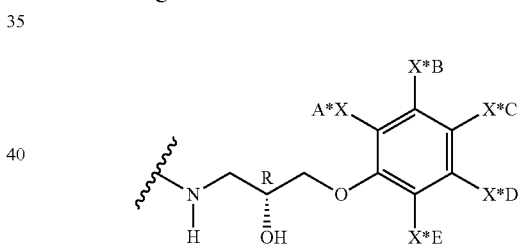

wherein:
X*A is hydrogen, halogen, optionally substituted alkyl, alkenyl, alkynyl, cycloalkyl, alkoxy, cycloalkoxy, alkylthio, cycloalkylthio, alkylsulfonyl, cycloalkylsulfonyl, aryl, heteroaryl, arylalkyl, heteroarylalkyl, arylthio, arylsulfonyl, heteroarylthio, heteroarylsulfonyl; trifluoromethyl, trifluoromethoxy, 2,2,2-trifluoroethoxy, heteroalkyl, dialkylamino, momoalkylamino, amino, nitro, cyano;
X*B is hydrogen, halogen, optionally substituted alkyl, alkenyl, alkynyl, cycloalkyl, alkoxy, cycloalkoxy, alkylthio, cycloalkylthio, alkylsulfonyl, cycloalkylsulfonyl, aryl, heteroaryl, arylalkyl, heteroarylalkyl, arylthio, arylsulfonyl, heteroarylthio, heteroarylsulfonyl; trifluoromethyl, trifluoromethoxy, 2,2,2-trifluoroethoxy, heteroalkyl, dialkylamino, momoalkylamino, amino, nitro, cyano;
X*C is hydrogen, halogen, optionally substituted alkyl, alkenyl, alkynyl, cycloalkyl, alkoxy, cycloalkoxy, alkylthio, cycloalkylthio, alkylsulfonyl, cycloalkylsulfonyl, aryl, heteroaryl, arylalkyl, heteroarylalkyl, arylthio, arylsulfonyl, heteroarylthio, heteroarylsulfonyl; trifluoromethyl, trifluoromethoxy, 2,2,2-trifluoroethoxy, heteroalkyl, dialkylamino, momoalkylamino, amino, nitro, cyano;

X*D is hydrogen, halogen, optionally substituted alkyl, alkenyl, alkynyl, cycloalkyl, alkoxy, cycloalkoxy, alkylthio, cycloalkylthio, alkylsulfonyl, cycloalkylsulfonyl, aryl, heteroaryl, arylalkyl, heteroarylalkyl, arylthio, arylsulfonyl, heteroarylthio, heteroarylsulfonyl; trifluoromethyl, trifluoromethoxy, 2,2,2-trifluoroethoxy, heteroalkyl, dialkylamino, momoalkylamino, amino, nitro, cyano;

X*E is hydrogen, halogen, optionally substituted alkyl, alkenyl, alkynyl, cycloalkyl, alkoxy, cycloalkoxy, alkylthio, cycloalkylthio, alkylsulfonyl, cycloalkylsulfonyl, aryl, heteroaryl, arylalkyl, heteroarylalkyl, arylthio, arylsulfonyl, heteroarylthio, heteroarylsulfonyl; trifluoromethyl, trifluoromethoxy, 2,2,2-trifluoroethoxy, heteroalkyl, dialkylamino, momoalkylamino, amino, nitro, cyano;

X*B and X*C or independently X*C and X*D or independently X*D and X*E can form a 5 to 7 membered ring, containing one or two heteroatoms such as oxygen, sulfur or nitrogen, (optionally substituted with a lower alkyl group), such as for example, but not limited to methylenedioxy, ethylenedioxy, propylenedioxy, dimethyleneoxy (dihydrobenzofuran ring), all optionally mono- or di-substituted and their partially, or fully fluorinated derivatives, including difluoromethylenedioxy; and X*B and X*C or independently X*C and X*D or independently X*D and X*E can form an optionally substituted condensed aromatic or heteroaromatic ring, for example, but not limited to 1- or 2-naphthyl, 4-, 5-, 6- or 7-indolyl, 4-, 5-, 6- or 7-benzofuranyl, 4-, 5-, 6- or 7-thianaphthenyl, carbazolyl by groups selected from lower alkyl, lower alkoxy, halogen, trifluoromethyl, cyano, or nitro.

In another embodiment in formula (1), $X^4$ is selected from the following:

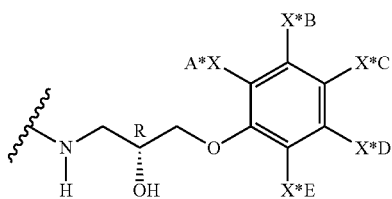

wherein:

X*A is lower alkyl, halogen, trifluoromethyl, trifluoromethoxy;

X*B is hydrogen, lower alkyl, halogen, lower alkoxy, trifluoromethyl, trifluoromethoxy, cyano, nitro, dimethylamino, diethylamino;

X*C is hydrogen, lower alkyl, halogen, lower alkoxy, trifluoromethyl, trifluoromethoxy, cyano, nitro, dimethylamino, diethylamino;

X*D is hydrogen, lower alkyl, halogen, lower alkoxy, trifluoromethyl, trifluoromethoxy, cyano, nitro, dimethylamino, diethylamino;

X*E is hydrogen, lower alkyl, halogen, lower alkoxy, trifluoromethyl, trifluoromethoxy, cyano, nitro, dimethylamino, diethylamino;

X*B and X*C or independently X*C and X*D or independently X*D and X*E can form a 5 to 7 membered ring, containing one or two heteroatoms such as oxygen, sulfur or nitrogen, (optionally substituted with a lower alkyl group), such as for example, but not limited to methylenedioxy, ethylenedioxy, propylenedioxy, dimethyleneoxy (dihydrobenzofuran ring), all optionally mono- or di-substituted and their partially, or fully fluorinated derivatives, including difluoromethylenedioxy; and X*B and X*C or independently X*C and X*D or independently X*D and X*E can form an optionally substituted condensed aromatic or heteroaromatic ring, for example, but not limited to 1- or 2-naphthyl, 4-, 5-, 6- or 7-indolyl, 4-, 5-, 6- or 7-benzofuranyl, 4-, 5-, 6- or 7-thianaphthenyl, carbazolyl by groups selected from lower alkyl, lower alkoxy, halogen, trifluoromethyl, cyano, or nitro.

In another embodiment in formula (1), each $W^1$ through $W^6$ is independently selected from carbon or nitrogen.

In another embodiment in formula (1), $Y^1$ is independently selected from:

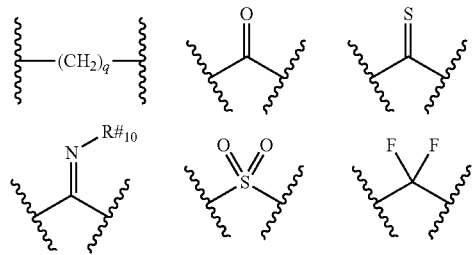

wherein:

q is an integer from 0 to 4; and $R\#_{10}$ is selected from hydrogen, lower alkyl, hydroxy and lower alkoxy.

In formula (1), in certain embodiments, each $(CH_2)_q$ can be optionally substituted with one or more groups selected from hydrogen, lower alkyl, heteroalkyl, heterocyclo, hydroxy-lower alkyl, cycloalkyl, hydroxycycloalkyl. In certain embodiments, such substituents can be joined to form a cyclic structure. In certain embodiments, one or more of the methylene groups of $(CH_2)_q$ can be replaced by a carbonyl group (C=O).

In yet another embodiment in formula (1), $Y^1$ is independently selected from:

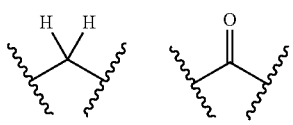

In another embodiment in formula (1), $Y^2$ is independently selected from:

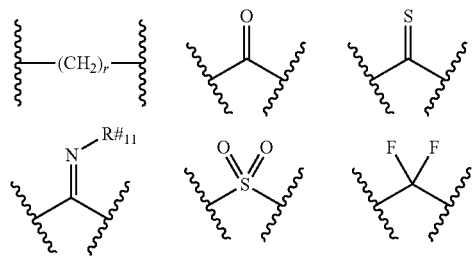

wherein:

r is an integer from 0 to 4; and $R\#_{11}$ is selected from hydrogen, lower alkyl, hydroxy and lower alkoxy.

In formula (1), in certain embodiments, each $(CH_2)_r$ can be optionally substituted with one or more groups selected from hydrogen, lower alkyl, heteroalkyl, heterocyclo, hydroxy-lower alkyl, cycloalkyl, hydroxycycloalkyl. In certain embodiments, such substituents can be joined to form a cyclic structure. In certain embodiments, one or more of the methylene groups of $(CH_2)_r$ can be replaced by a carbonyl group (C=O).

In yet another embodiment in formula (1), $Y^2$ is independently selected from:

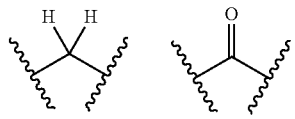

In another embodiment in formula (1), $R^1$ is independently selected from optionally substituted heterocyclyl, heterocyclylalkyl, heteroaryl, heteroarylalkyl, heterocyclyloxyalkyl, heteroalkyl, heterocyclylaminoalkyl, aminoalkyl, lower alkylaminoalkyl, di-(lower alkyl)-aminoalkyl, aminocycloalkyl, alkylaminocycloalkyl, di-(lower alkyl)-aminocycloalkyl, di-(lower alkyl)-aminocycloalkylalkyl, by groups selected from hydrogen, lower alkyl, hydroxy, lower alkoxy, amino, amidino, carboxamido, sulfonamido, hydroxy, cyano, primary, secondary or tertiary amino, halo, azido, lower alkoxyalkyl, cyanoalkyl, azidoalkyl, haloalkyl, hydroxyalkyl, methanesulfonylalkyl, primary, secondary or tertiary amino-alkyl, optionally substituted aryl, heteroaryl, heteroalkyl, heterocyclyl, cycloalkyl, alkenyl and alkynyl.

In another embodiment in formula (1), $R^1$ is independently selected from optionally substituted heterocyclyl, heterocyclylalkyl, aminoalkyl, lower alkylaminoalkyl and di-(lower alkyl)-aminoalkyl.

In another embodiment in formula (1), exemplary $R^1$ include, but are not limited to:

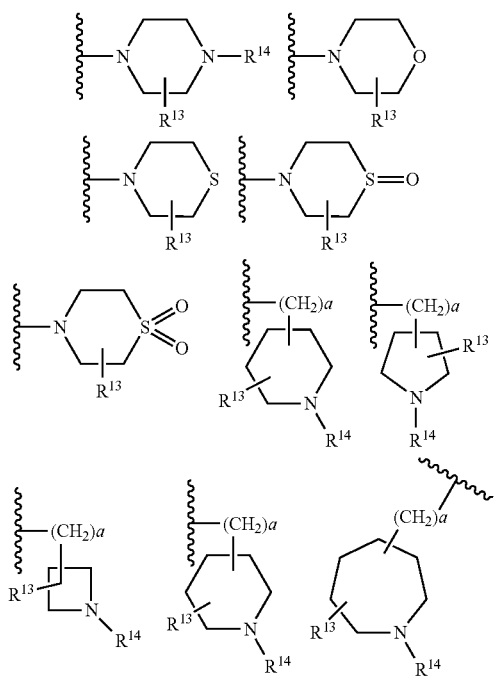

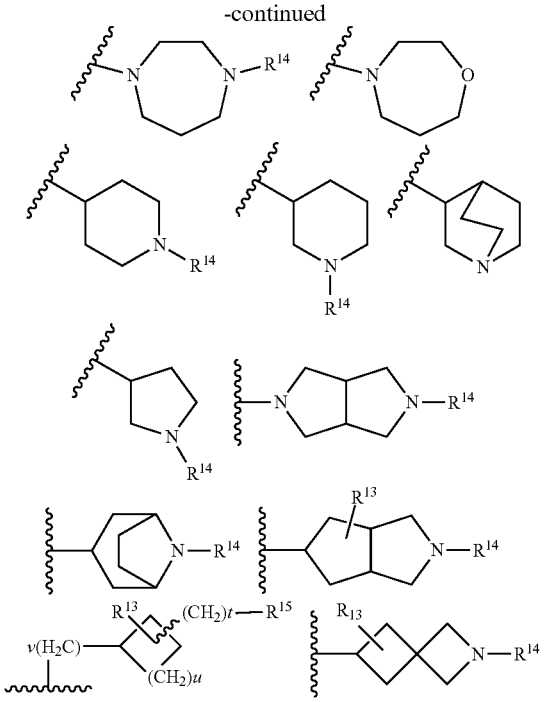

wherein:
$R^{13}$ is selected from hydrogen, lower alkyl, heteroalkyl, heterocyclyl, cycloalkyl and heterocycloalkyl;
$R^{14}$ is selected from hydrogen, hydroxy, lower alkoxy, di-(lower alkyl)amino, lower alkyl, heteroalkyl, heterocyclyl, cycloalkyl, heterocycloalkyl, lower alkoxyalkyl, cyanoalkyl, azidoalkyl, nitroalkyl, ketoalkyl, methanesulfonylalkyl, aminoalkyl, lower alkylaminoalkyl, di-(lower alkyl)aminoalkyl, optionally substituted aryl, heteroaryl, arylalkyl, heteroarylalkyl;
$R^{15}$ is selected from hydrogen, amino, lower alkylamino, di-(lower alkyl)amino, hydroxy, lower alkoxy, heteroalkyl, lower alkoxyalkyl, aminoalkyl, lower alkylaminoalkyl and di-(lower alkyl)aminoalkyl;
a is an integer from 0 to 4; and
t, u , v are independent integers from 0 to 5.
It is understood that if any of the integers is (are) 0 (zero), it means a covalent chemical bond.

In another embodiment, $R^1$ is further selected from:

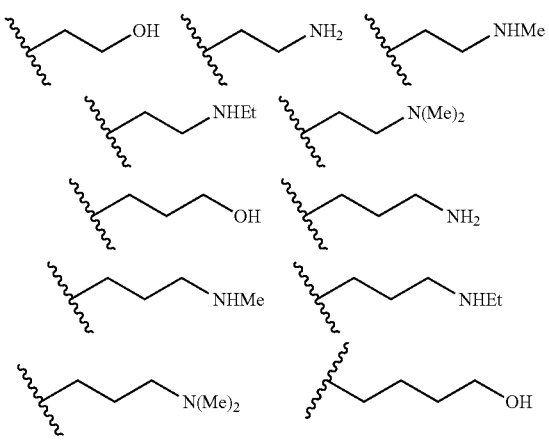

-continued

31
-continued
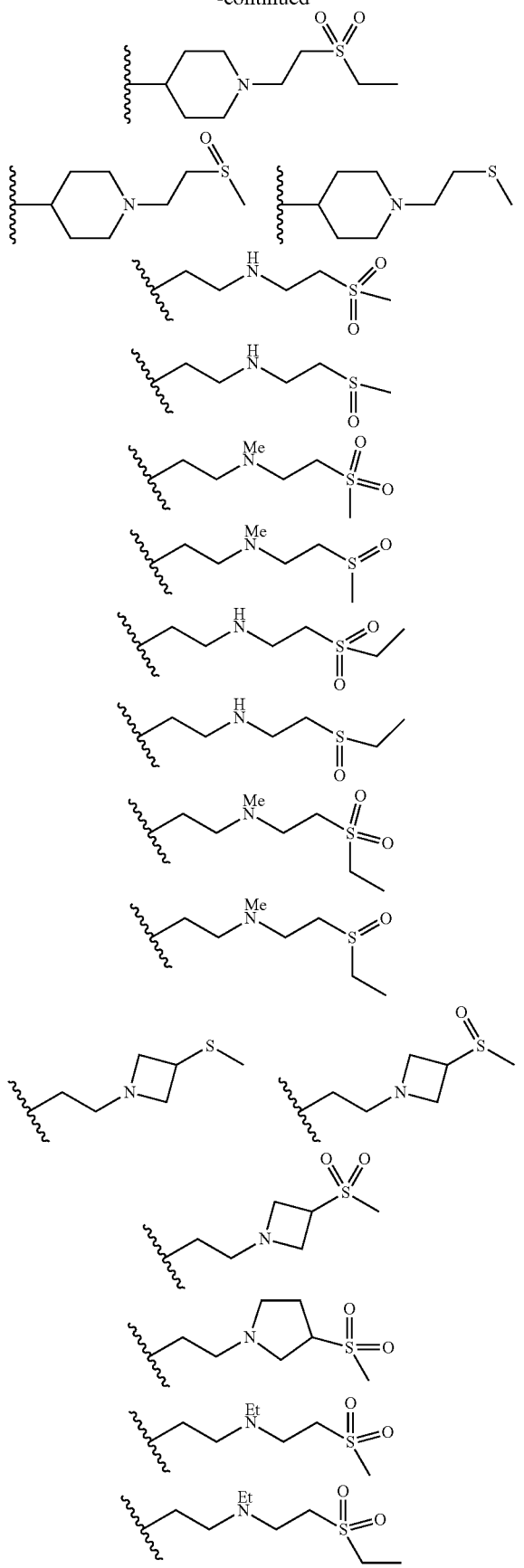
32
-continued
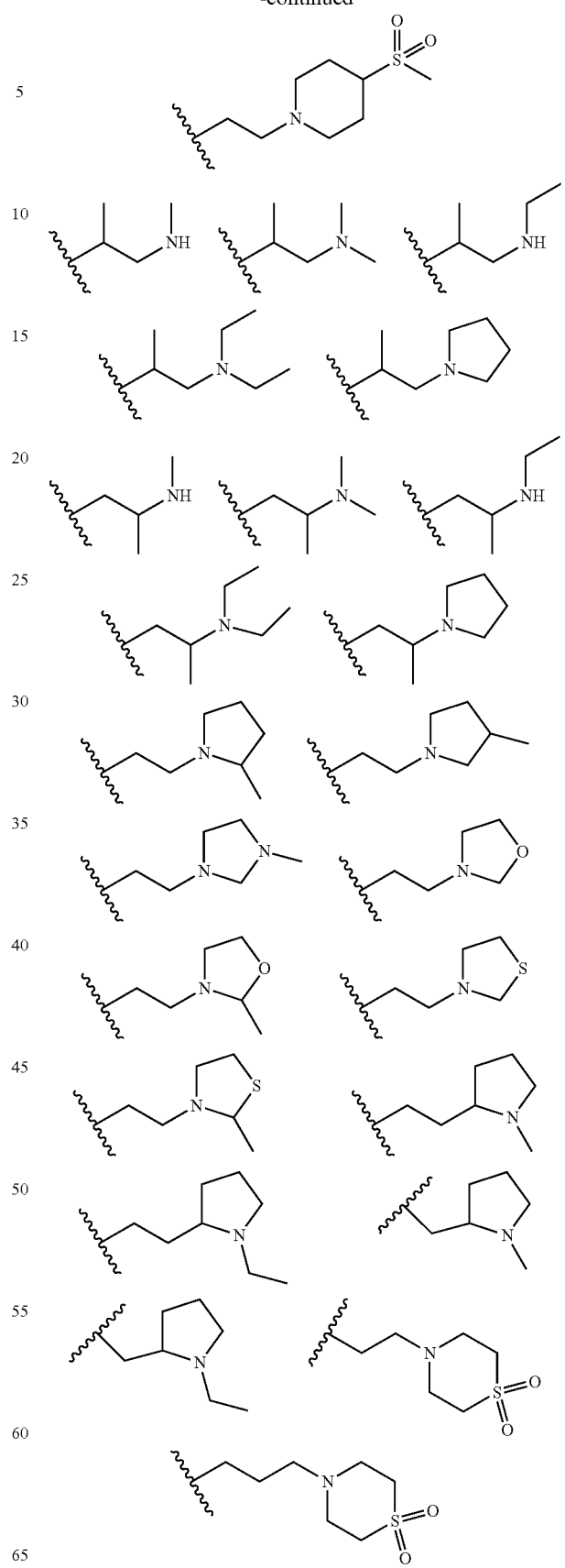

In R[1], in certain embodiments, the methylene chain between the connection and the heteroatom may be optionally substituted by one or more hydrogen, lower alkyl, hydroxy, hydroxy-lower alkyl, lower alkoxy, carboxamido or sulfonamido and one of the methylene groups can be substituted by a heteroatom, such as O, NR* or S, S=O, or S(=O)$_2$, wherein R* is selected from hydrogen, hydroxy, lower alkyl, lower alkoxy, heteroalkyl, hydroxyalkyl, aminoalkyl, lower alkylaminoalkyl and di-(lower alkyl)aminoalkyl. Any of the ring systems can also be optionally substituted by a lower alkyl or heteroalkyl group.

In another embodiment, the compounds have the following formula:

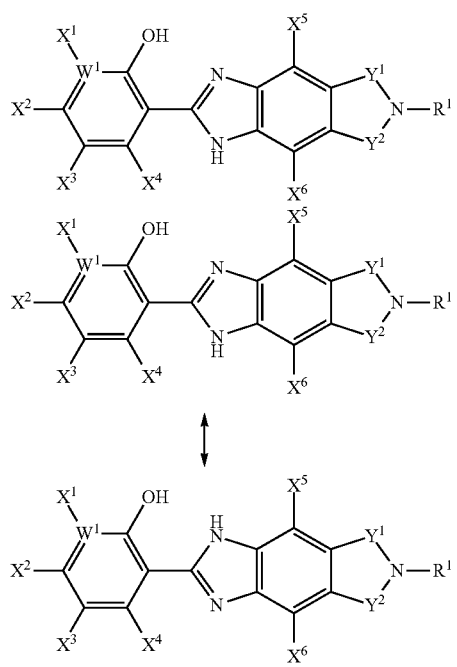

wherein W[1] is nitrogen or carbon.

The substituents are defined as described herein.

In another embodiment, the compounds have the following formulas:

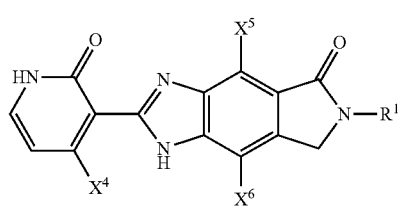

Formula 1b

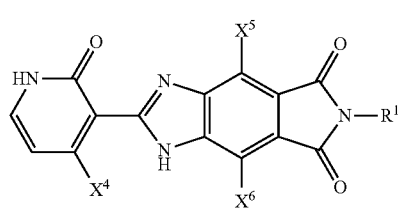

Formula 1c

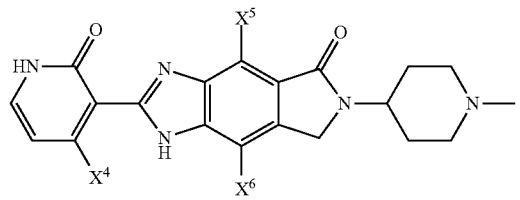

Formula 1d

-continued

Formula 1a

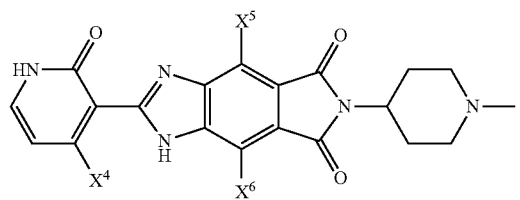

Formula 1e

-continued

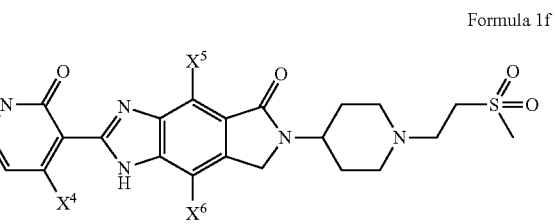

Formula 1f

Formula 1g
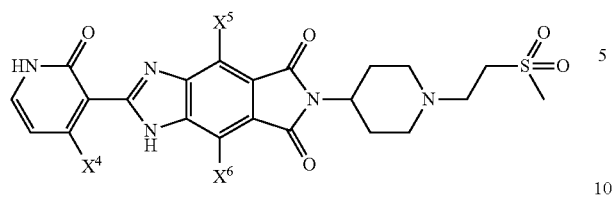
Formula 1h
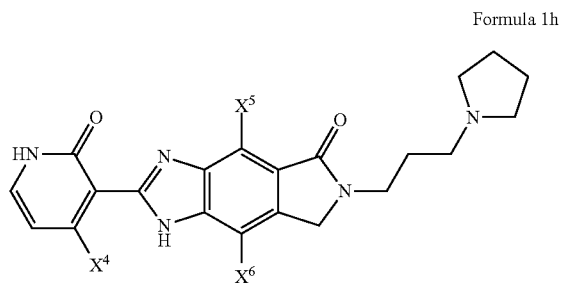
Formula 1i
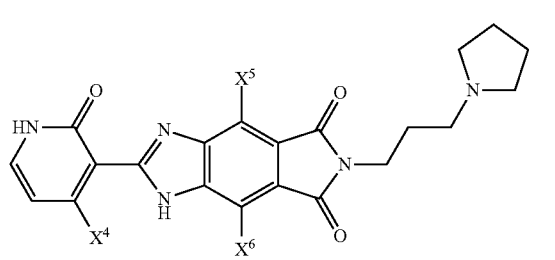
Formula 1j
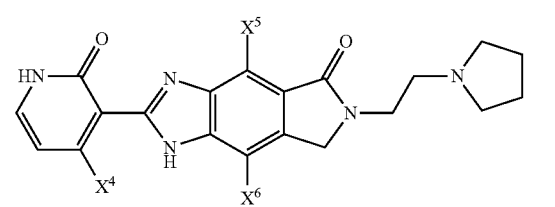
Formula 1k
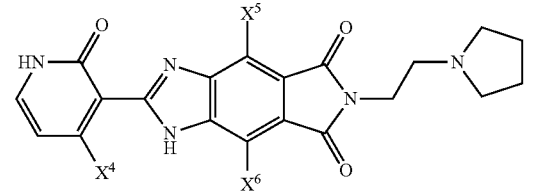
The substituents are defined as described above.
In another embodiments, compounds correspond to the following formulas:
Formula 1l
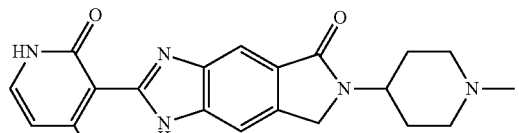
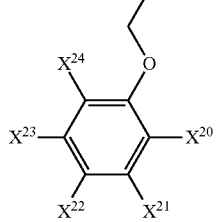
Formula 1m
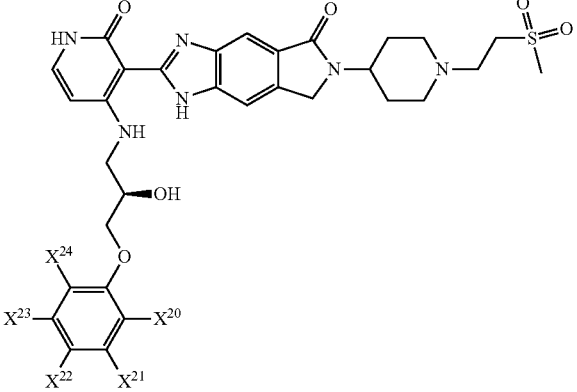
Formula 1n
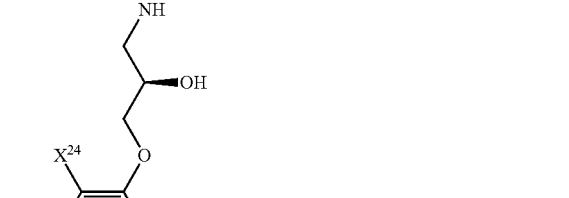

-continued

Formula 1o

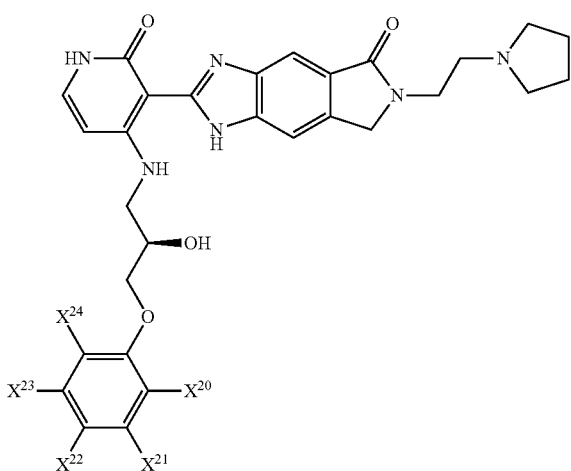

wherein
$X^{20}$ to $X^{24}$ are each independently selected from hydrogen, lower alkyl, lower alkoxy, hydroxy, halogen, trifluoromethyl, trifluoromethoxy, 2,2,2-trifluoroethoxy, heteroalkyl, cycloalkyl, heterocycloalkyl, cyano, nitro, ureido, primary, secondary or tertiary amino, methylenedioxy, ethylenedioxy and difluoromethylenedioxy.

The other compounds include those corresponding to formulas 1l-1o, wherein:
$X^{20}$=methyl; $X^{21}$=chloro; $X^{22}$=$X^{23}$=$X^{24}$=hydrogen;
$X^{20}$=methyl; $X^{21}$=methyl; $X^{22}$=$X^{23}$=$X^{24}$=hydrogen;
$X^{20}$=methyl; $X^{21}$=methoxy; $X^{22}$=$X^{23}$=$X^{24}$=hydrogen;
$X^{20}$=chloro; $X^{21}$=methyl; $X^{22}$=$X^{23}$=$X^{24}$=hydrogen;
$X^{20}$=methyl; $X^{21}$=$X^{22}$=$X^{23}$=$X^{24}$=hydrogen;
$X^{20}$=ethyl; $X^{21}$=$X^{22}$=$X^{23}$=$X^{24}$=hydrogen;
$X^{20}$=isopropyl; $X^{21}$=$X^{22}$=$X^{23}$=$X^{24}$=hydrogen;
$X^{20}$=chloro; $X^{21}$=$X^{22}$=$X^{23}$=$X^{24}$=hydrogen;
$X^{20}$=bromo; $X^{21}$=$X^{22}$=$X^{23}$=$X^{24}$=hydrogen;
$X^{20}$=iodo; $X^{21}$=$X^{22}$=$X^{23}$=$X^{24}$=hydrogen;
$X^{20}$=bromo; $X^{21}$=fluoro; $X^{22}$=$X^{23}$=$X^{24}$=hydrogen;
$X^{20}$=methyl; $X^{21}$=methoxy; $X^{22}$=methyl; $X^{23}$=$X^{24}$=hydrogen;
$X^{20}$=methyl; $X^{21}$=hydrogen; $X^{22}$=methyl; $X^{23}$=$X^{24}$=hydrogen;
$X^{20}$=methyl; $X^{21}$=fluoro; $X^{22}$=methyl; $X^{23}$=$X^{24}$=hydrogen;
$X^{20}$=bromo; $X^{21}$=hydrogen; $X^{22}$=methyl; $X^{23}$=$X^{24}$=hydrogen;
$X^{20}$=chloro; $X^{21}$-$X^{22}$=methylenedioxy; $X^{23}$=$X^{24}$=hydrogen;
$X^{20}$=methyl; $X^{21}$-$X^{22}$=methylenedioxy; $X^{23}$=$X^{24}$=hydrogen;
$X^{20}$=ethyl; $X^{21}$-$X^{22}$=methylenedioxy; $X^{23}$=$X^{24}$=hydrogen;
$X^{20}$=hydrogen; $X^{21}$-$X^{22}$=methylenedioxy; $X^{23}$=hydrogen; $X^{24}$=chloro;
$X^{20}$=hydrogen; $X^{21}$-$X^{22}$=methylenedioxy; $X^{23}$=hydrogen; $X^{24}$=methyl;
$X^{20}$=hydrogen; $X^{21}$-$X^{22}$=methylenedioxy; $X^{23}$=hydrogen; $X^{24}$=ethyl;
$X^{20}$=chloro; $X^{21}$=fluoro; $X^{22}$=$X^{23}$=hydrogen; $X^{24}$=fluoro;
$X^{20}$=bromo; $X^{21}$=fluoro; $X^{22}$=$X^{23}$=hydrogen; $X^{24}$=fluoro;
$X^{20}$=methyl; $X^{21}$=fluoro; $X^{22}$=$X^{23}$=hydrogen; $X^{24}$=fluoro;
$X^{20}$=ethyl; $X^{21}$=fluoro; $X^{22}$=$X^{23}$=hydrogen; $X^{24}$=fluoro;
$X^{20}$=methyl; $X^{21}$=fluoro; $X^{22}$=hydrogen; $X^{23}$=fluoro; $X^{24}$=hydrogen;
$X^{20}$=chloro; $X^{21}$=fluoro; $X^{22}$=hydrogen; $X^{23}$=fluoro; $X^{24}$=hydrogen;
$X^{20}$=chloro; $X^{21}$=hydrogen; $X^{22}$=methoxy; $X^{23}$=$X^{24}$=hydrogen; and
$X^{20}$=bromo; $X^{21}$=hydrogen; $X^{22}$=$X^{23}$=fluoro; $X^{24}$=hydrogen.

In another embodiment, the compounds correspond to the following formulas:

Formula 1p

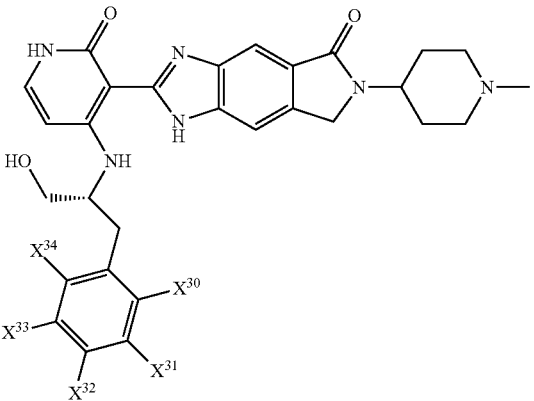

Formula 1q

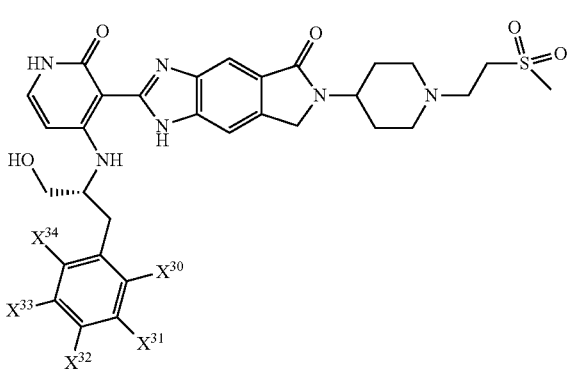

Formula 1r

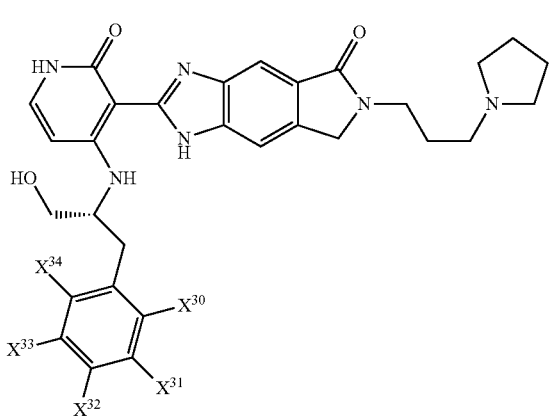

Formula 1s

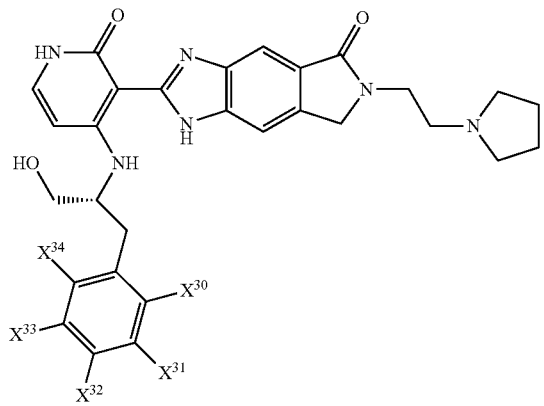

wherein $X^{30}$ to $X^{34}$ are independently selected from hydrogen, lower alkyl, lower alkoxy, hydroxy, halogen, trifluoromethyl, trifluoromethoxy, 2,2,2-trifluoroethoxy, heteroalkyl, cycloalkyl, heterocycloalkyl, cyano, nitro, ureido, primary, secondary or tertiary amino, methylenedioxy, ethylenedioxy and difluoromethylenedioxy.

Other compounds include those corresponding to formulas 1p to 1s, wherein:

$X^{30}=X^{31}=X^{32}=X^{33}=X^{34}$=hydrogen;

$X^{30}$=methyl; $X^{31}=X^{32}=X^{33}=X^{34}$=hydrogen;

$X^{30}$=chloro; $X^{31}=X^{32}=X^{33}=X^{34}$=hydrogen;

$X^{30}$=hydrogen; $X^{31}$=chloro; $X^{32}=X^{33}=X^{34}$=hydrogen;

$X^{30}=X^{31}$=hydrogen; $X^{32}$=chloro; $X^{33}=X^{34}$=hydrogen;

$X^{30}$=hydrogen; $X^{31}$=methoxy; $X^{32}=X^{33}=X^{34}$=hydrogen;

$X^{30}=X^{31}$=hydrogen; $X^{32}$=methoxy; $X^{33}=X^{34}$=hydrogen;

$X^{30}$=methyl; $X^{31}$=hydrogen; $X^{32}$=methyl; $X^{33}=X^{34}$=hydrogen; and $X^{30}$=methyl; $X^{31}=X^{32}$=hydrogen; $X^{33}$=fluoro; $X^{34}$=hydrogen.

In another embodiments, compounds correspond to the following formulas:

Formula 1t

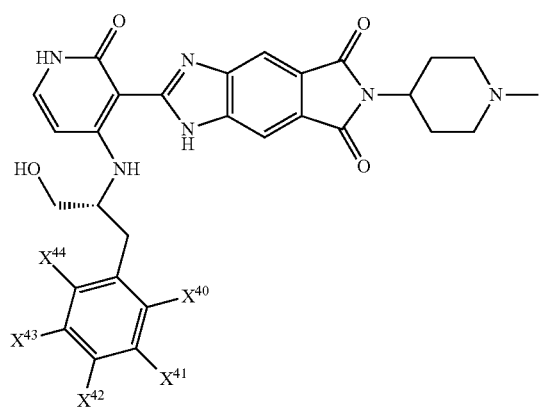

Formula 1u

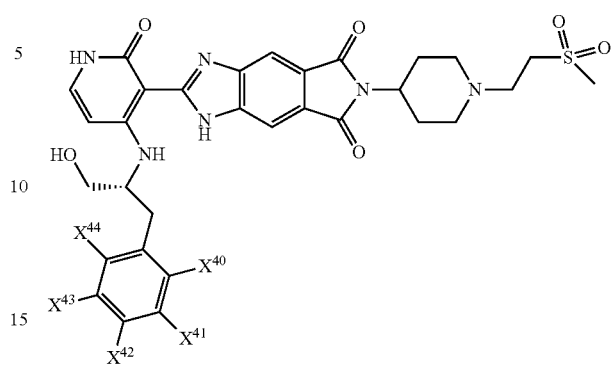

Formula 1v

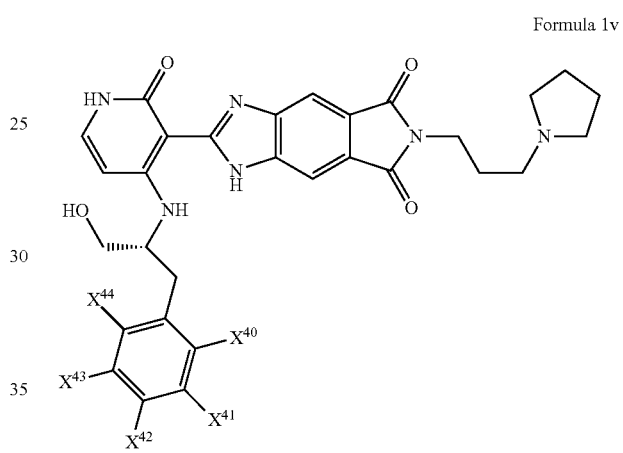

Formula 1w

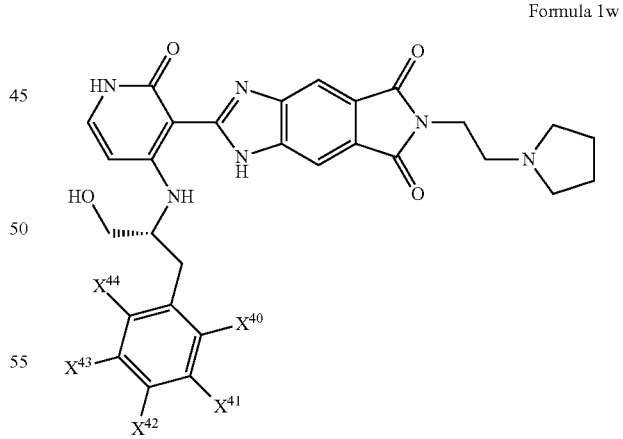

wherein $X^{40}$ to $X^{44}$ are independently selected from hydrogen, lower alkyl, lower alkoxy, hydroxy, halogen, trifluoromethyl, trifluoromethoxy, 2,2,2-trifluoromethoxy, heteroalkyl, cycloalkyl, heterocycloalkyl, cyano, nitro, ureido, primary, secondary or tertiary amino, methylenedioxy, ethylenedioxy and difluoromethylenedioxy.

Such compounds include those corresponding to formulas 1t to 1w, wherein:

$X^{40}=X^{41}=X^{42}=X^{43}=X^{44}$=hydrogen;

$X^{40}$=methyl; $X^{41}=X^{42}=X^{43}=X^{44}$=hydrogen;

$X^{40}$=chloro; $X^{41}=X^{42}=X^{43}=X^{44}$=hydrogen;

$X^{40}$=hydrogen; $X^{41}$=chloro; $X^{42}=X^{43}=X^{44}$=hydrogen;

$X^{40}=X^{41}$=hydrogen; $X^{42}$=chloro; $X^{43}=X^{44}$=hydrogen;

$X^{40}$=hydrogen; $X^{41}$=methoxy; $X^{42}=X^{43}=X^{44}$=hydrogen;

$X^{40}=X^{41}$=hydrogen; $X^{42}$=methoxy; $X^{43}=X^{44}$=hydrogen;

$X^{40}$=methyl; $X^{41}$=hydrogen; $X^{42}$=methyl; $X^{43}=X^{44}$=hydrogen; and $X^{40}$=methyl; $X^{41}=X^{42}$=hydrogen; $X^{43}$=fluoro; $X^{44}$=hydrogen.

In another embodiment, the compounds are:

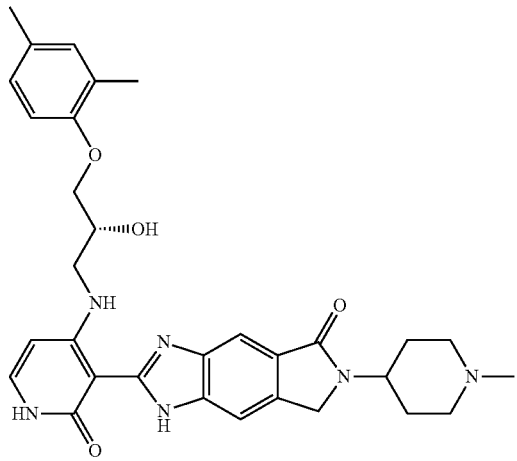

(2a)

(R)-2-(4-(3-(2,4-dimethylphenoxy)-2-hydroxypropylamino)-2-oxo-1,2-dihydropyridin-3-yl)-6-(1-methylpiperidin-4-yl)-6,7-dihydroimidazo[4,5-f]isoindol-5(1H)-one

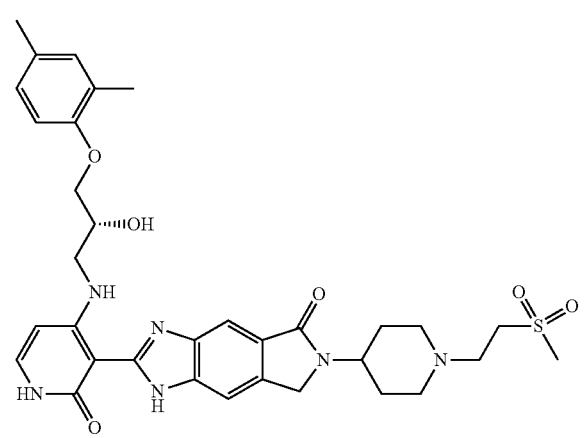

(2b)

(R)-2-(4-(3-(2,4-dimethylphenoxy)-2-hydroxypropylamino)-2-oxo-1,2-dihydropyridin-3-yl)-6-(1-(2-(methylsulfonyl)ethyl)piperidin-4-yl)-6,7-dihydroimidazo[4,5-f]isoindol-5(1H)-one

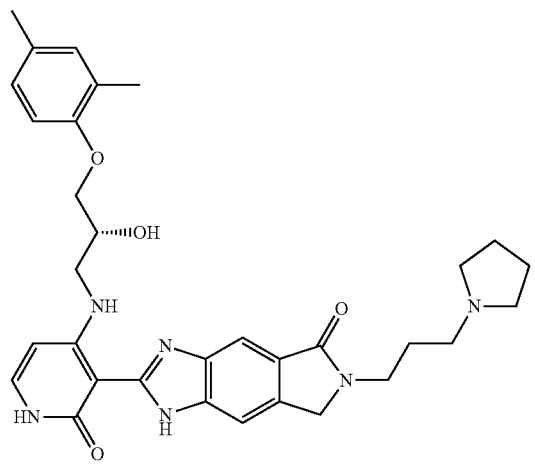

(2c)

(R)-2-(4-(3-(2,4-dimethylphenoxy)-2-hydroxypropylamino)-2-oxo-1,2-dihydropyridin-3-yl)-6-(3-(pyrrolidin-1-yl)-6,7-dihydroimidazo[4,5-f]isoindol-5(1H)-one

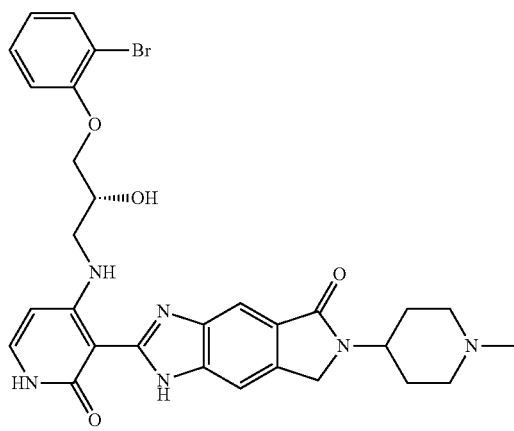

(2d)

(R)-2-(4-(3-(2-bromophenoxy)-2-hydroxypropylamino)-2-oxo-1,2-dihydropyridin-3-yl)-6-(1-methylpiperidin-4-yl)-6,7-dihydroimidazo[4,5-f]isoindol-5(1H)-one -continued (2e)

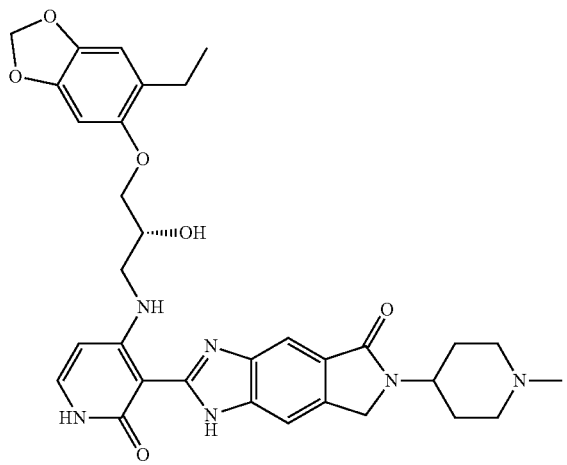

(R)-2-(4-(3-(6-ethylbenzo[d][1,3]dioxol-5-yloxy)-2-
hydroxypropylamino)-2-oxo-1,2-dihydropyridin-3-yl)-6-
(1-methylpiperidin-4-yl)-6,7-dihydroimidazo[4,5-f]isoindol-
5(1H)-one (2f)

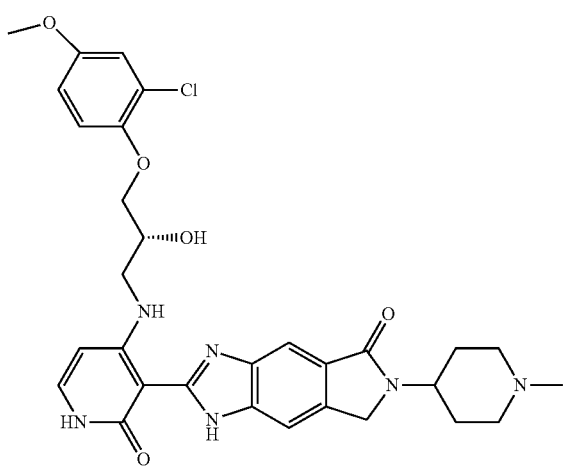

(R)-2-(4-(3-(2-chloro-4-methoxyphenoxy)-2-hydroxypropylamino)-2-
oxo-1,2-dihydropyridin-3-yl)-6-(1-methylpiperidin-4-yl)-6,7-
dihydroimidazo[4,5-f]
isoindol-5(1H)-one -continued (2g)

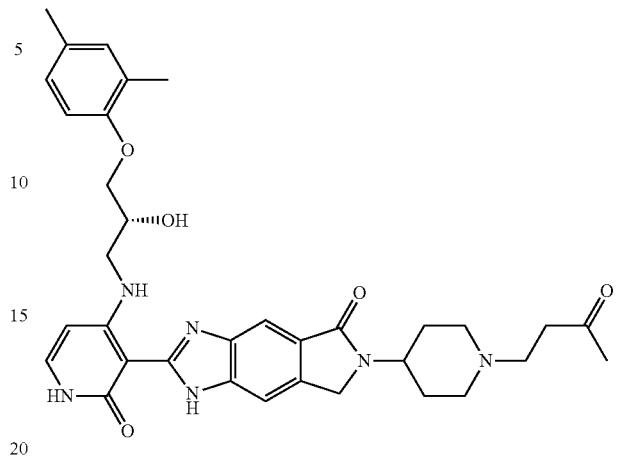

(R)-2-(4-(3-(2,4-dimethylphenoxy)-2-hydroxypropylamino)-2-
oxo-1,2-dihydropyridin-3-yl)-6-(1-(3-oxobutyl)piperidin-4-yl)-6,7-
dihydroimidazo[4,5-f]isoindol-5(1H)-one Preparation of the Compounds Compounds according to formula (1) can be prepared according to any method apparent to those of skill in the art. Provided below are exemplary methods for their preparation.

Procedure for the synthesis of substituted Imidazo[4, 5-f]isoindole-5,7(1H,6H)-diones and substituted 6,7-dihydroimidazo[4,5-f]isoindol-5(3H)-one derivatives (C,C')

In certain embodiments, compounds of formula (1) are prepared according to the following procedures, according to scheme 1.

Scheme 1 describes the preparation of the tricycles. The starting diamino phthalimides and/or diaminolactams B (and/or their derivatives) are available by the synthetic methodologies described below. The method is general and is applicable to a variety of derivatives with different groups $R^1$, $Y^1$ and $Y^2$, as well as various $X^1$ through $X^6$ and $W^1$ through $W^6$.

Scheme 1

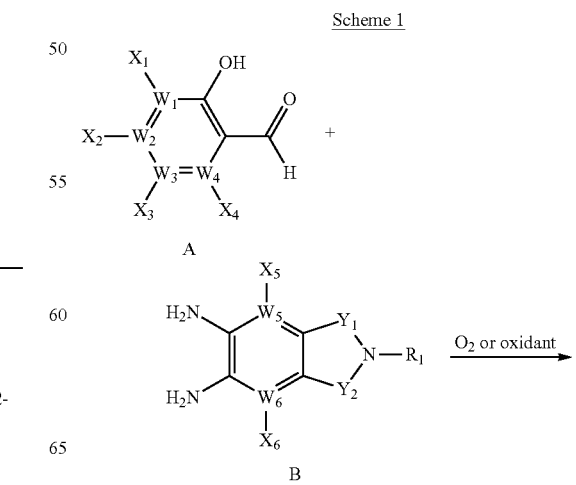

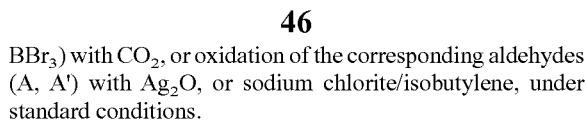

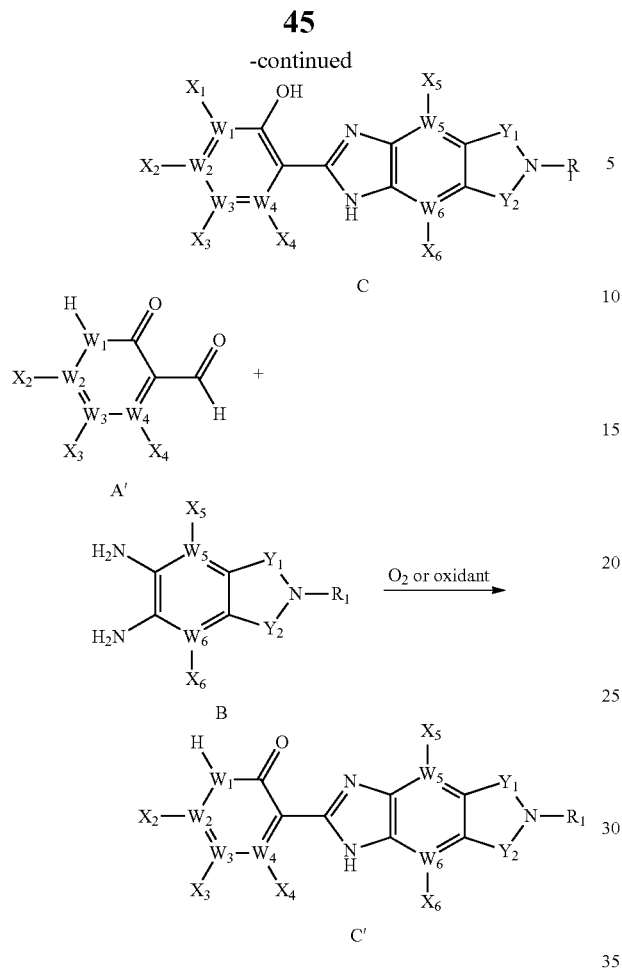

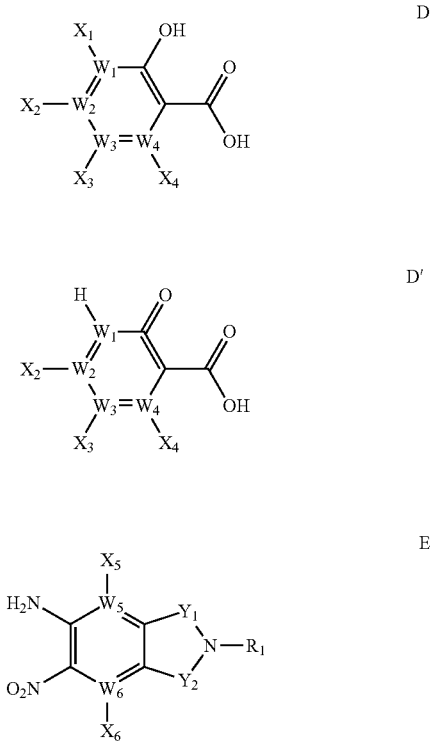

Condensations of the suitable aromatic, or heteroaromatic aldehydes (A, A') with the diamino-heterocycles (B) give in the presence of air, or a suitable oxidant the desired substituted aromatic heterotricycles (C, C'). In the addition of exposure to air, use of palladium on charcoal, Raney nickel, or dehydrogenating agents, such as sulfur, Oxone$^R$, ferric chloride, sodium bisulfite, benzoquinone, or its derivatives and the like will also accomplish dehydrogenation of the initially formed dihydroderivatives to the aromatic heterotricycles (C, C'). Other methods for cyclization of benzimidazole-type derivatives are known in the art and can be utilized in the formation of the present heterotricyclic compounds, by way of example, but not limited to: acylation of the diamines (B) with an activated form of the carboxylic acids (D, D'), such as acid chlorides, fluorides, imidazolides, DCC, or DIC and related adducts with the diamine (B), followed by formation of the imidazole ring in acidic, or basic conditions (e.g.: heating in acetic acid, or in alcoholic potassium, or sodium methoxide, or use of PPA, or POCl$_3$ in the presence of pyridine, or diisopropylethylamine, to give (C, C'). Alternatively, the 2-nitroamine (E) can be used for the acylation step, followed by reduction with titanium trichloride, or stannous chloride solution, followed by cyclization of the monoacyl diamine in acidic, or basic conditions (e.g.: heating in acetic acid, or in alcoholic potassium, or sodium methoxide, or use of PPA, or POCl3 in the presence of pyridine, or diisopropylethylamine, to give (C, C'). Carboxylic acids (D, D') are accessible by methods known in the art, including Kolbe synthesis, carboxylation of the corresponding lithium carbanions (preferably in a protected form, such as MOM ethers, or methoxy derivatives, followed by deprotection with HCl, or BBr$_3$) with CO$_2$, or oxidation of the corresponding aldehydes (A, A') with Ag$_2$O, or sodium chlorite/isobutylene, under standard conditions.

In certain embodiments, compounds of formula (1) are prepared according to the following procedures, according to schemes 2-20.

Description of a substituent as R and R' means that it may be any chemically feasible substituent, including hydrogen.

Synthesis of Tricyclic Derivatives
(Imidazo[4,5-f]isoindole-5,7(1H,6H)-diones)

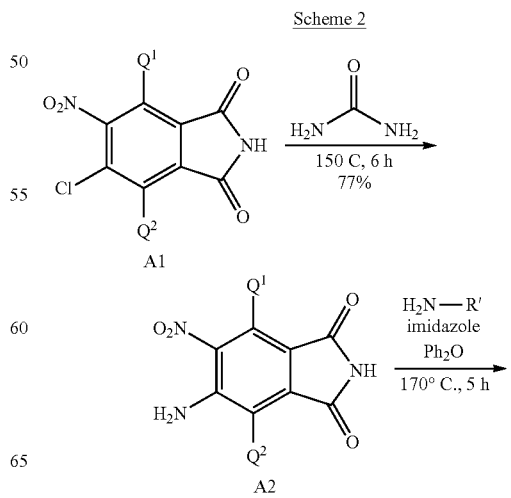

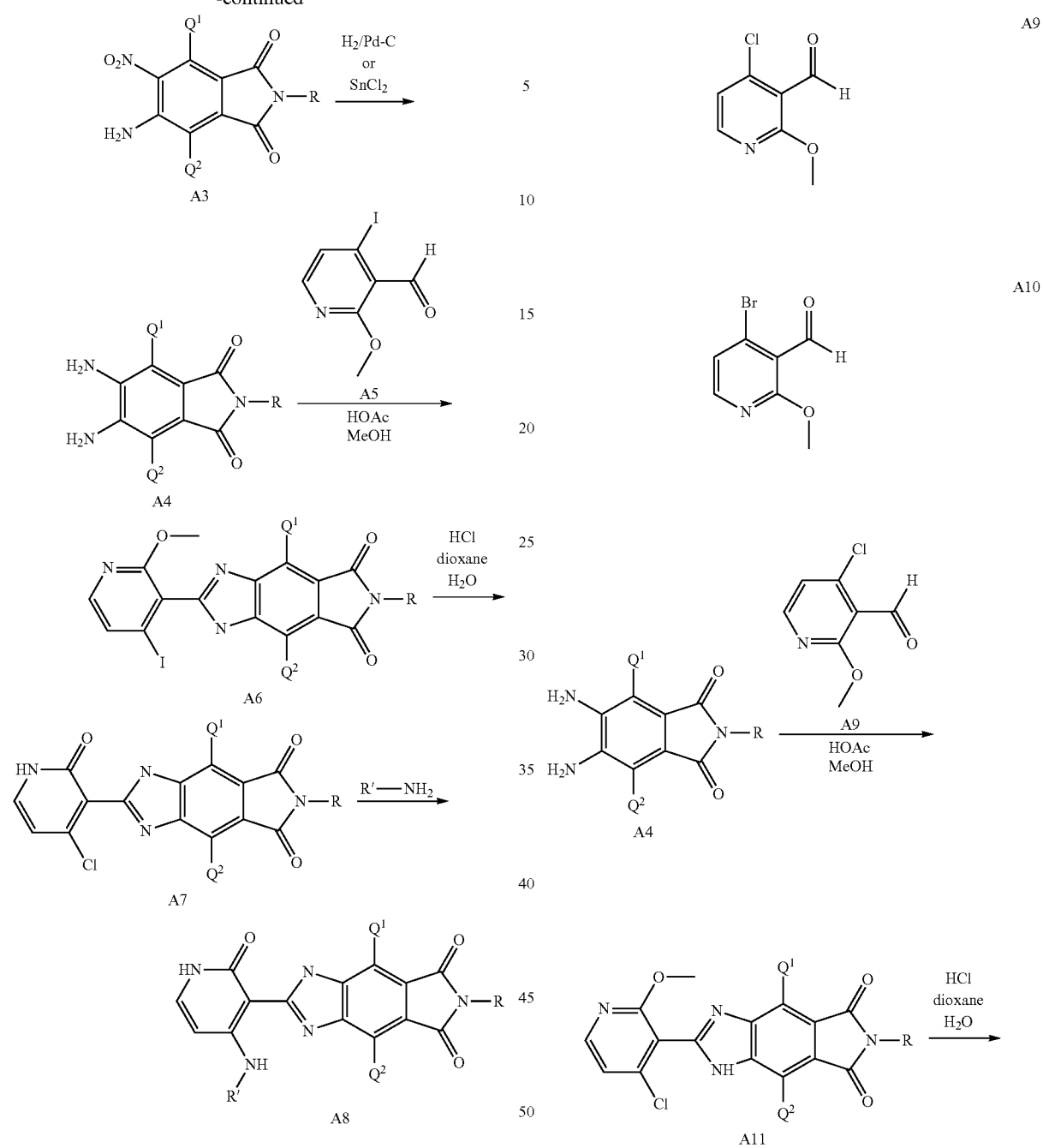
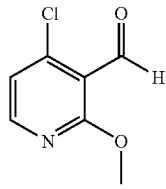
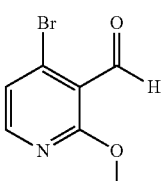
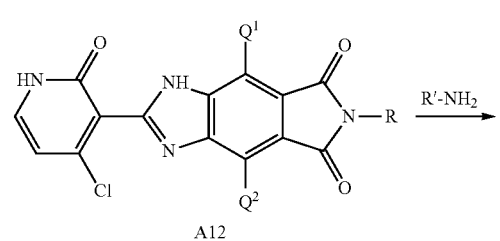

Substituent $Q^1$ in Scheme 2 corresponds to the above reaction-compatible $X^5$ of formula (1), especially hydrogen, halogen or methyl. Substituent $Q^2$ in Scheme 2 corresponds to the above reaction-compatible $X^6$ of formula (1), especially hydrogen, halogen or methyl. Synthesis of halo-, nitro- and amino-substituted phthalimides can be also found in: E. H White and K. Matsuo, JOC, 1967, 1921 and S. Cherkez, J. Herzig, and H. Yellin J. Med. Chem. 1986, 29, 947-959.

Alternatively, 4-chloro-2-methoxy-3-pyridinecarboxaldehyde (A9) or 4-bromo-2-methoxy-3-pyridinecarboxaldehyde (A10) can be used in the cyclization of the diamine derivatives (A4) and (A15) to provide the corresponding tricyclic derivatives—(6,7-dihydroimidazo[4,5-f]isoindol-5(1H)-ones and imidazo[4,5-f]isoindole-5,7(1H,6H)-diones.

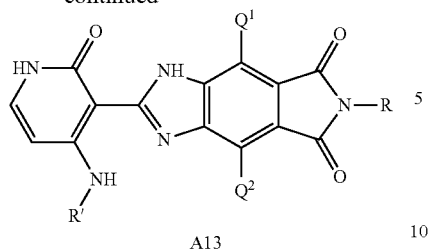

(A9) is a highly valuable precursor useful in the synthesis of biologically active compounds.

Synthesis of Lactam Derivatives (A14)
(6,7-Dihydroimidazo[4,5-f]isoindol-5(1H)-ones)

The 6,7-Dihydroimidazo[4,5-f]isoindol-5(1H)-ones (A14) were synthesized according to two basic methods.

In method A, the fully constructed substituted [4,5-f]isoindole-5,7(1H,6H)-diones (A8) were reduced by zinc in acetic acid to the lactam derivatives.

Synthesis of (6,7-Dihydroimidazo[4,5-f]isoindol-5(1H)-ones) (A14)) shown in

Scheme 3.

Method A

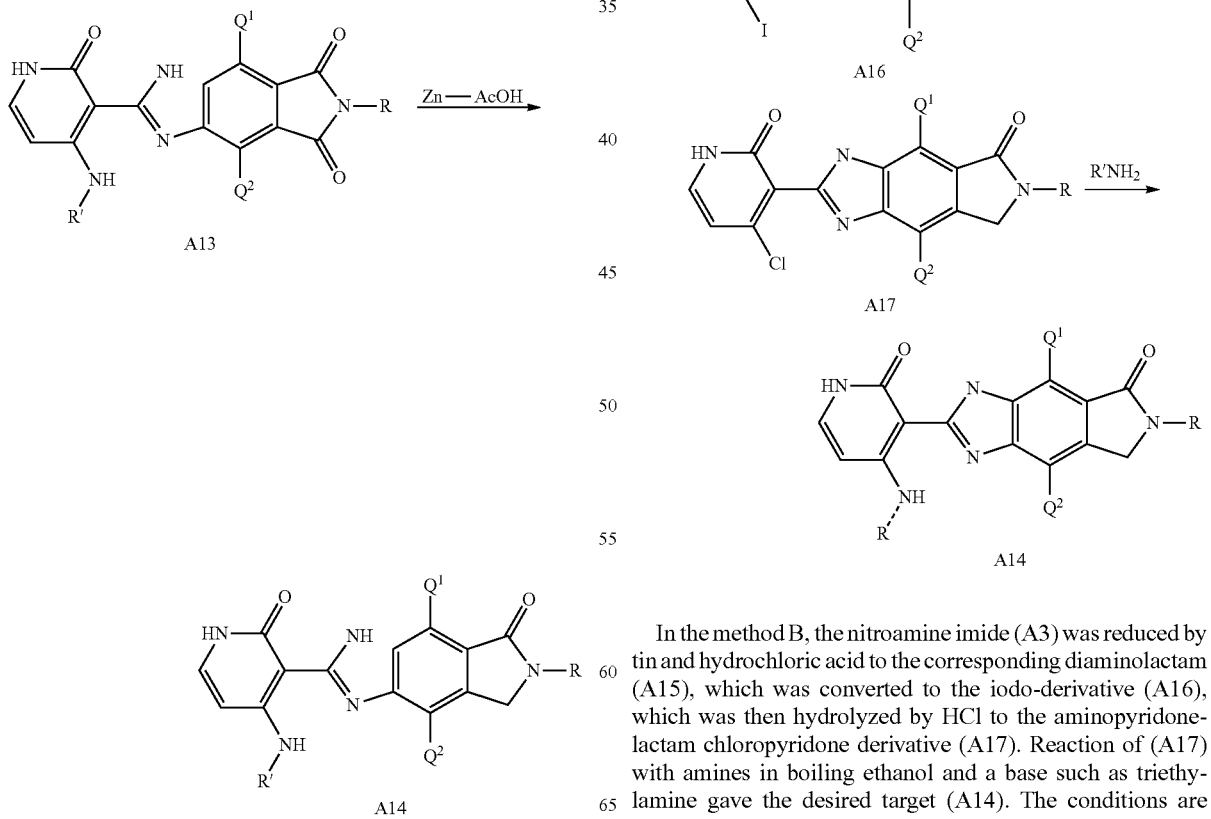

Synthesis of Lactam Derivatives (A14)
(6,7-Dihydroimidazo[4,5-f]isoindol-5(1H)-ones)

Scheme 4

Method B

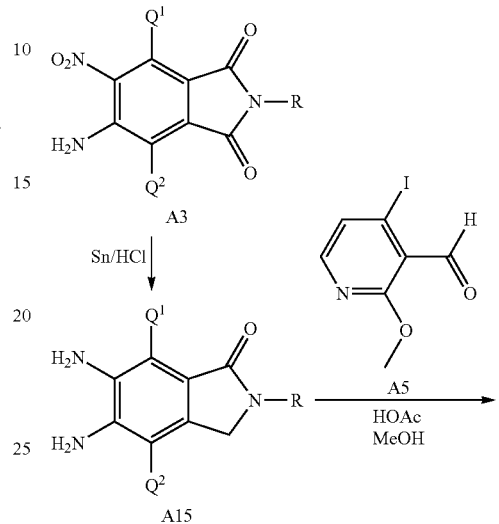

In the method B, the nitroamine imide (A3) was reduced by tin and hydrochloric acid to the corresponding diaminolactam (A15), which was converted to the iodo-derivative (A16), which was then hydrolyzed by HCl to the aminopyridone-lactam chloropyridone derivative (A17). Reaction of (A17) with amines in boiling ethanol and a base such as triethylamine gave the desired target (A14). The conditions are described below. (A17) is a highly valuable precursor useful in the production of biologically active compounds.

Synthesis of 4-chloro-2-methoxy-3-cyanopyridine (A20) and 4-chloro-2-methoxy-3-pyridinecarboxaldehyde (A9)

Scheme 5

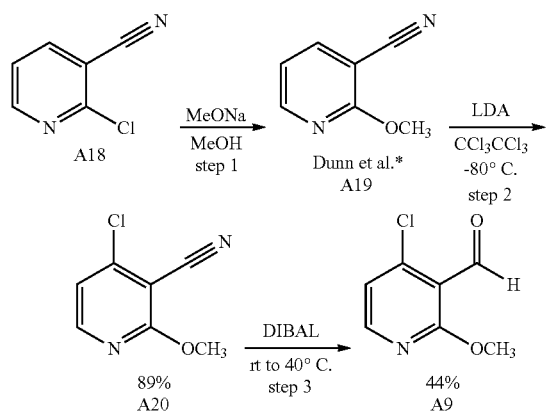

*Dunn, A. D.; Norrie, R.; Heterocycl. Chem.; 24; 1987; 85-89

Preparation of 4-bromo-3-cyano-2-methoxypyridine and 4-iodo-3-cyano-2-methoxypyridine and the corresponding aldehydes from −80° C. to about 80° C., preferably at 20° C. provides after standard workup the 4-halo-2-methoxypyridine-3-carboxaldehydes. The 4-halo-2-methoxypyridine-3-carboxaldehydes are highly valuable synthetic intermediates. 4-chloro-2-methoxy-3-pyridinecarboxaldehyde (A9) was prepared in this manner.

Preparation of the
2-Methoxy-4-iodopyridine-3-carboxaldehyde

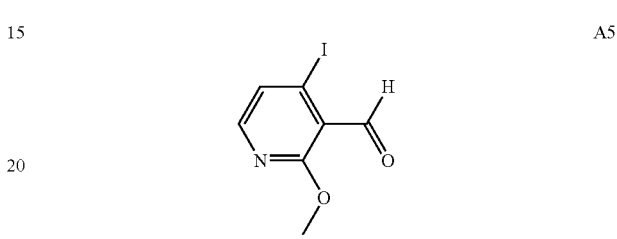

The synthetic methodology is described in the following reference: Fang F. G., Xie S., Lowery M. E., *J. Org. Chem.* 1994, 59, 6142-6143.

Scheme 6

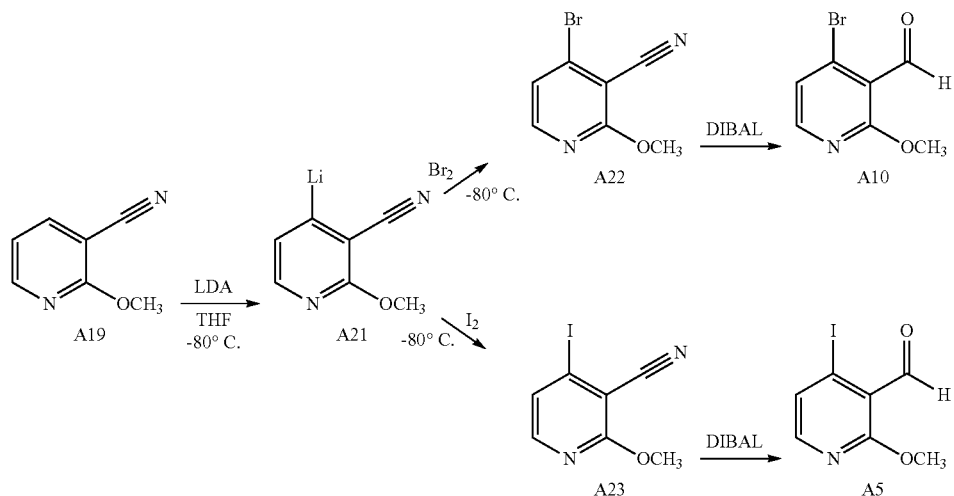

Thus, 2-chloro-3-cyanopyridine (A18) provided 2-methoxy-3-cyanopyridine (A19) upon treatment with sodium methoxide in methanol. Lithiation of the 2-methoxy-3-cyanopyridine (A19) with LDA gave the intermediate carbanion derivative 4-lithio-2-methoxy-3-cyanopyridine (A21), which upon treatment with hexachloroethane provided the 4-chloro-2-methoxy-3-cyanopyridine (A20). Analogously, reaction with bromine provides the 4-bromo-2-methoxy-3-cyanopyridine (A22) and reaction with iodine provides the 4-iodo-2-methoxy-3-cyanopyridine (A23). All 4-halo-2-methoxy-3-cyanopyridines are highly valuable intermediates, especially for the synthesis of kinase inhibitors. Reduction of the 4-halo-2-methoxy-3-cyanopyridines, for example with DIBAL (diisobutylaluminum hydride) in solvents such as toluene, dichloromethane, or tetrahydrofuran at temperatures ranging Preparation of the
4,6-dichloropyrimidine-5-carbaldehyde

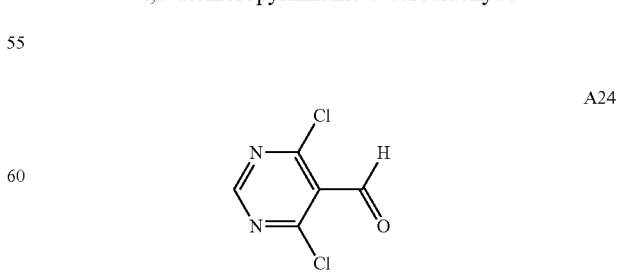

The synthesis is described in the following reference: Gomtsyan A. et al. *J. Med. Chem.,* 45 (17), 3639-3648, 2002.

Synthesis of Sultam Derivatives
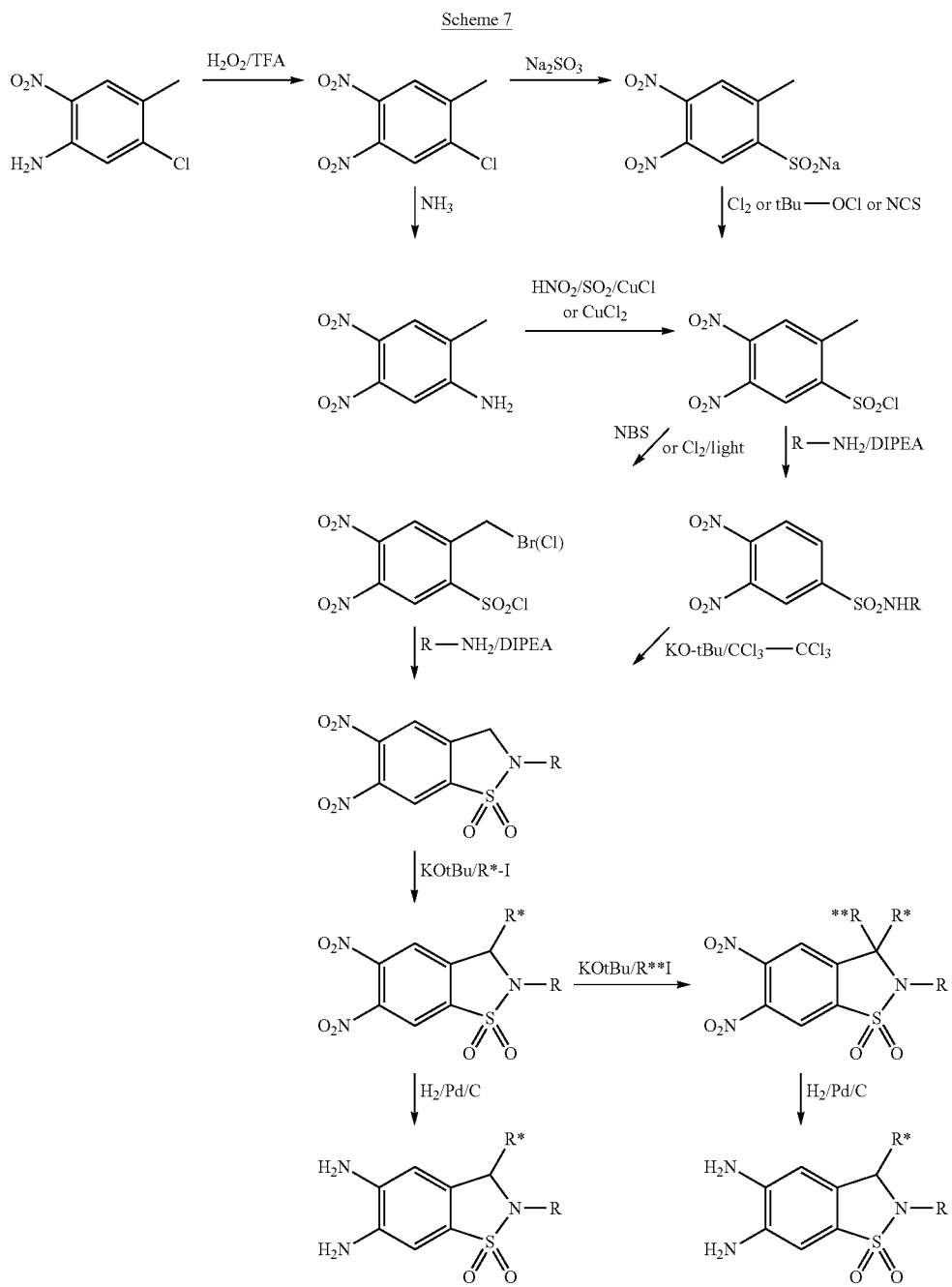
General Procedure for the Synthesis of Difluorolactam Derivatives
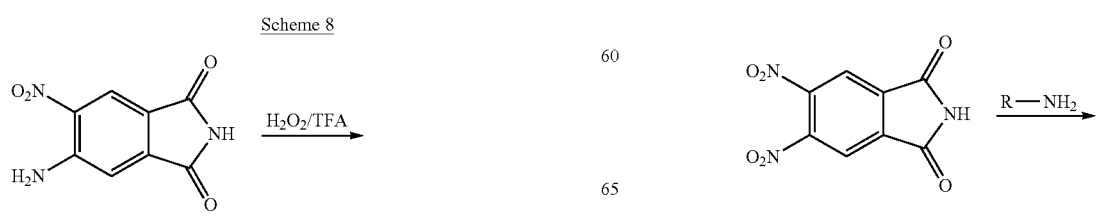

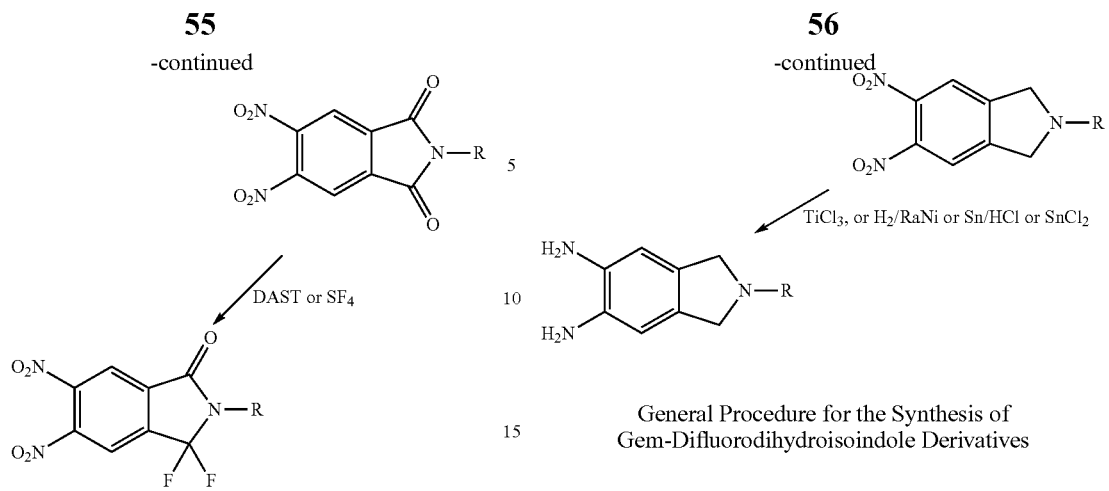
General Procedure for the Synthesis of
Dihydroisoindole Derivatives
Scheme 9
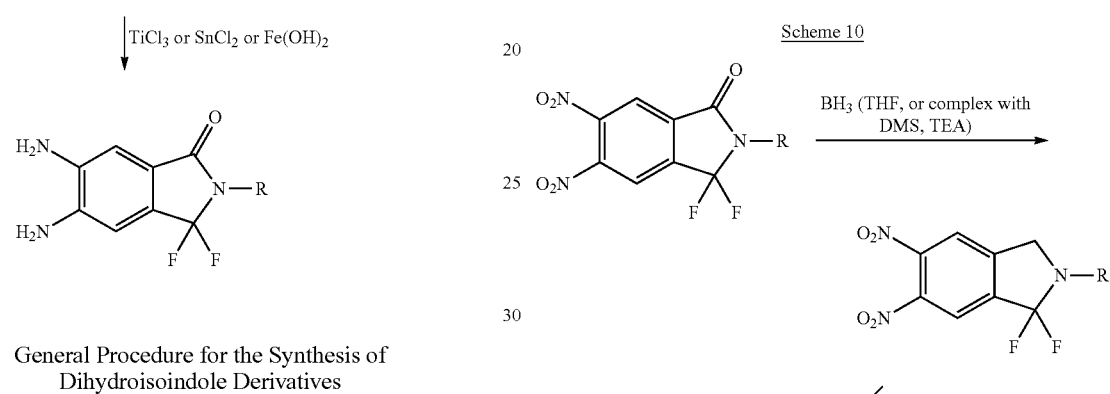
General Procedure for the Synthesis of
Gem-Difluorodihydroisoindole Derivatives
Scheme 10
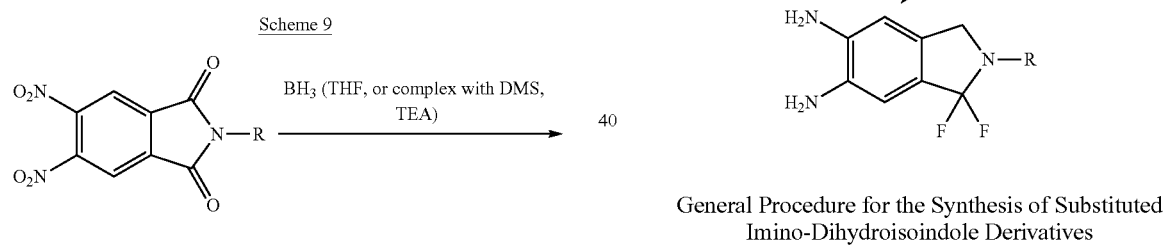
General Procedure for the Synthesis of Substituted
Imino-Dihydroisoindole Derivatives
Scheme 11
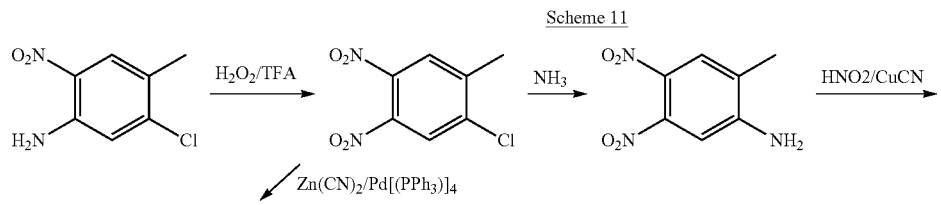
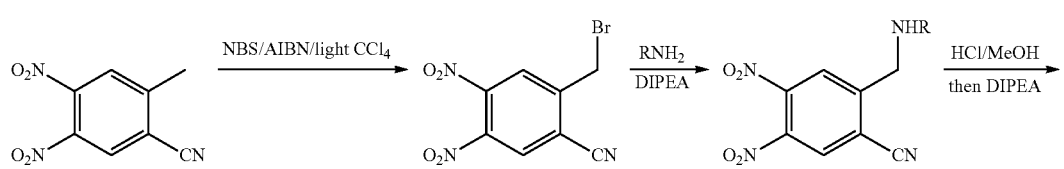

General Procedure for the Synthesis of Substituted Dihydroisoindole Derivatives
Scheme 12
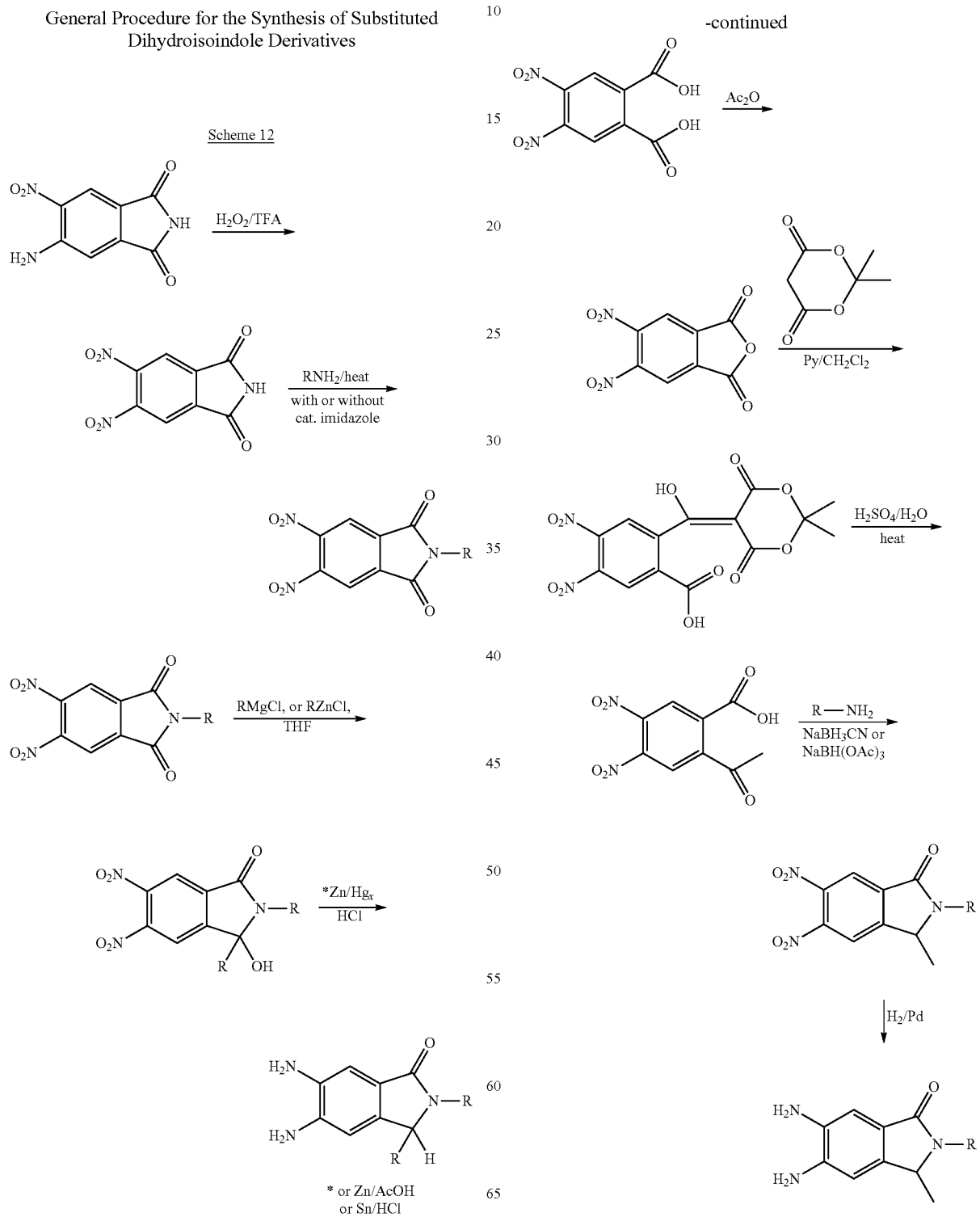
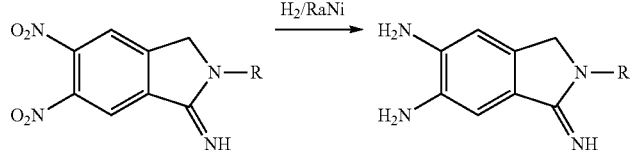

General Procedure for the Synthesis of Substituted Dihydroisoindole and Corresponding Spirocompound Derivative
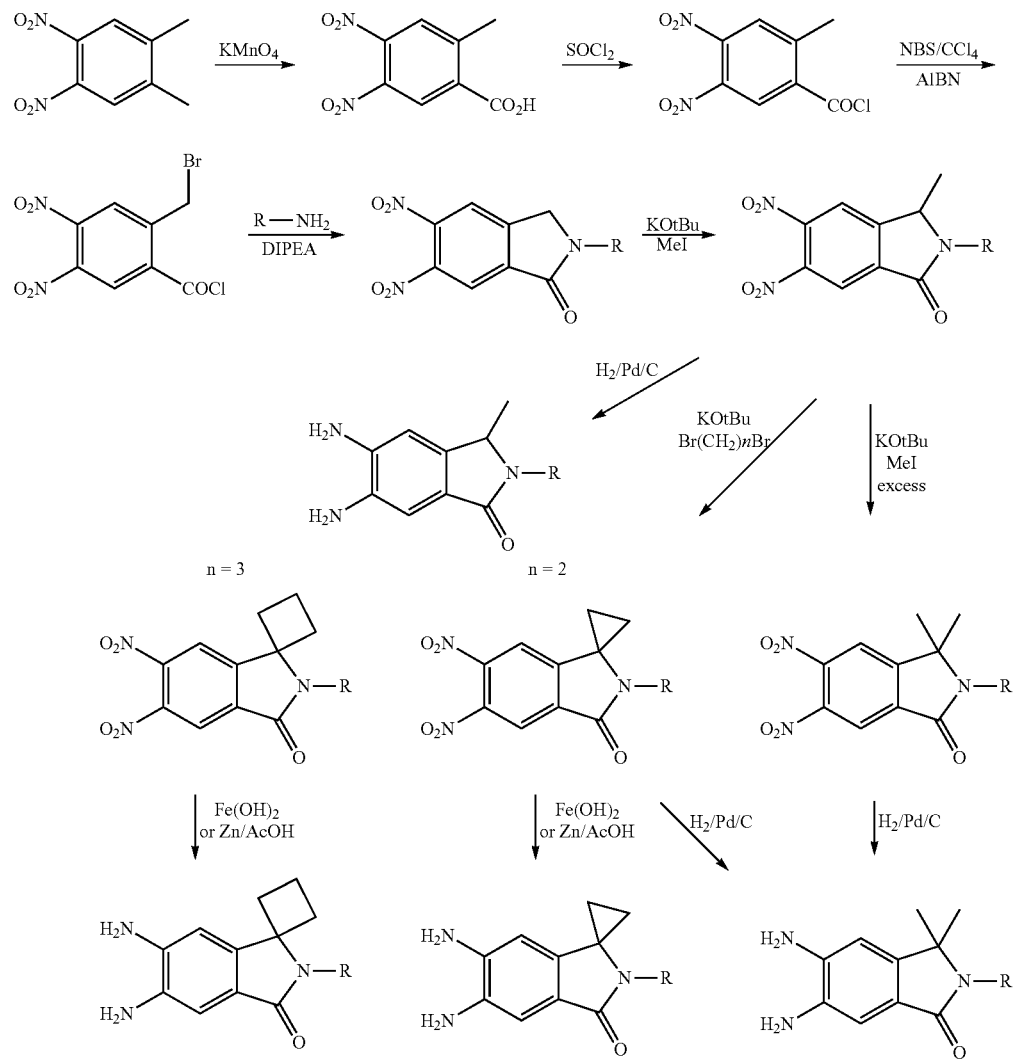
General Procedure for the Synthesis of the Intermediates for the Synthesis of the Compounds of the Invention
Scheme 14
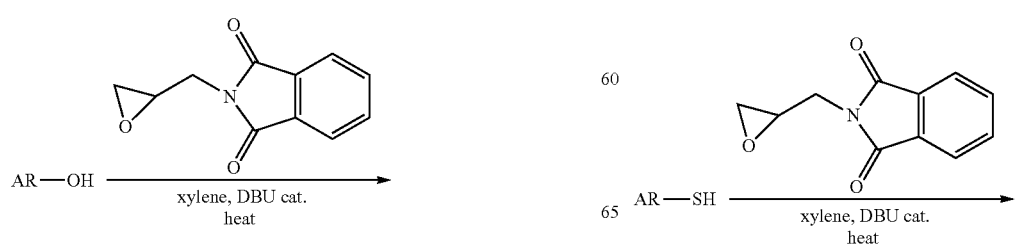
-continued
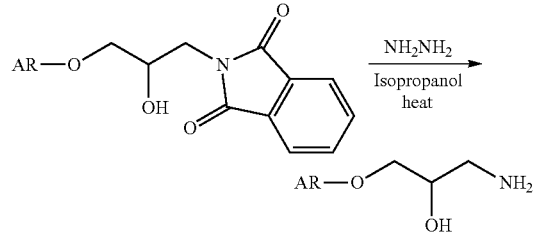

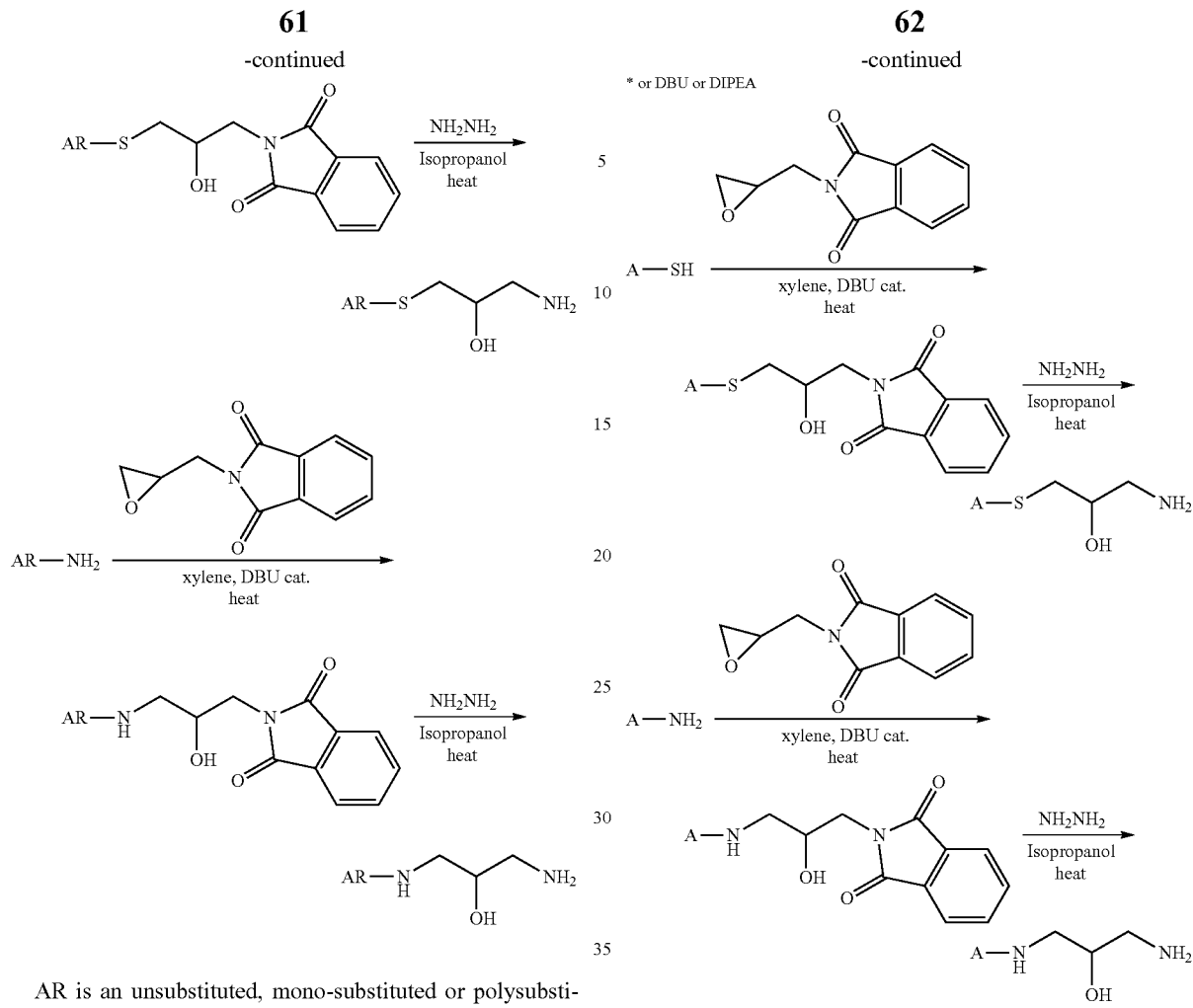

AR is an unsubstituted, mono-substituted or polysubstituted aryl or heteroaryl.

General Procedure for the Synthesis of the Intermediates for the Synthesis of the Compounds of the Invention A is an unsubstituted, mono-substituted or polysubstituted alkyl, cycloalkyl, heteroalkyl, heterocycloalkyl, aryl or heteroaryl.

General Procedure for the Synthesis of the Intermediates of the Compounds of the Invention Scheme 15

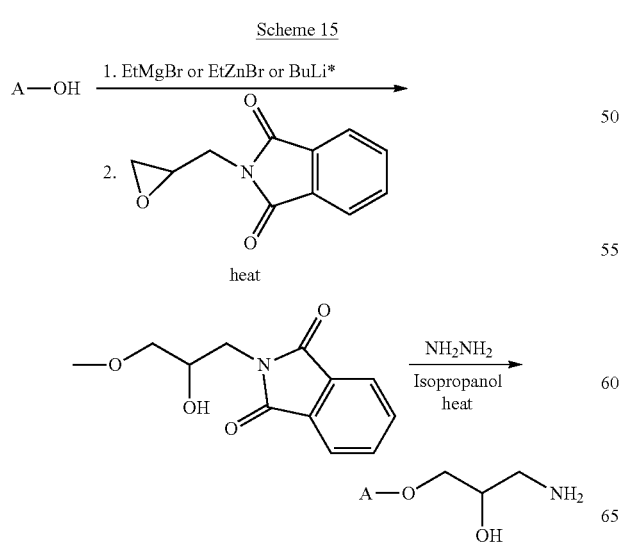

Scheme 16

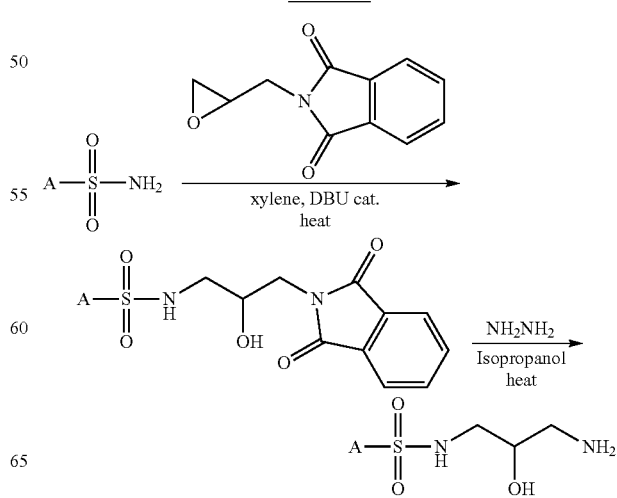

General Procedure for the Synthesis of the Intermediates of the Compounds of the Invention

Scheme 18

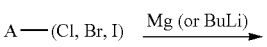
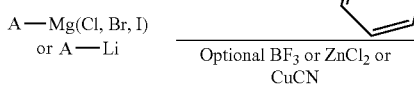
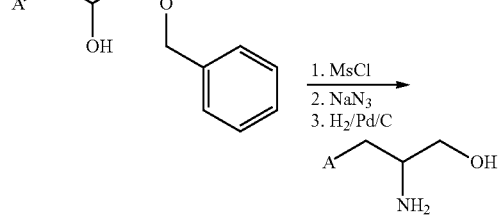
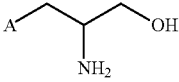

For compounds containing hydrogenolyzable groups:

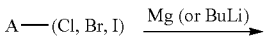
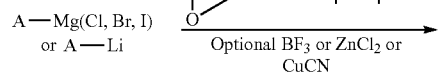
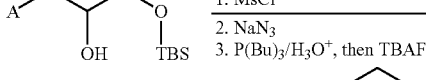
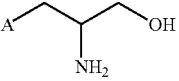

A is an unsubstituted, mono-substituted or polysubstituted alkyl, cycloalkyl, heteroalkyl, heterocycloalkyl, aryl, or heteroaryl.

Both enantiomers of the epoxide starting material are available. The reaction proceeds with inversion at the chiral center.

General Procedure for the Synthesis of the Intermediates of the Compounds of the Invention

Scheme 19

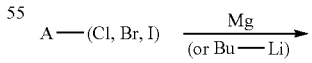
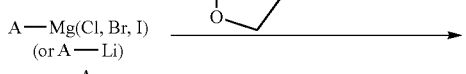
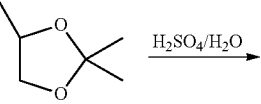

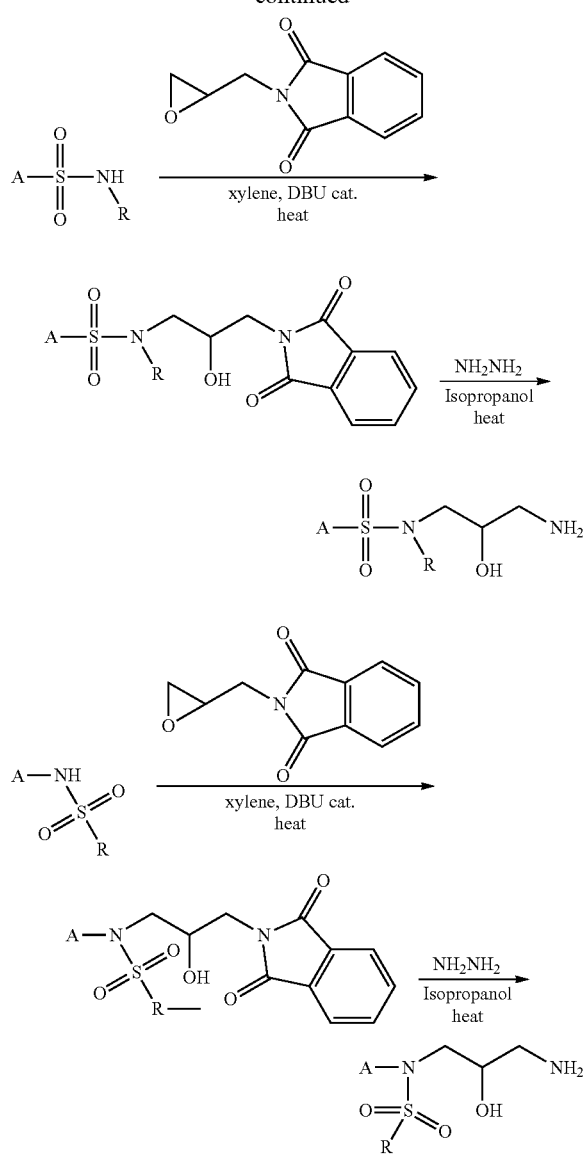

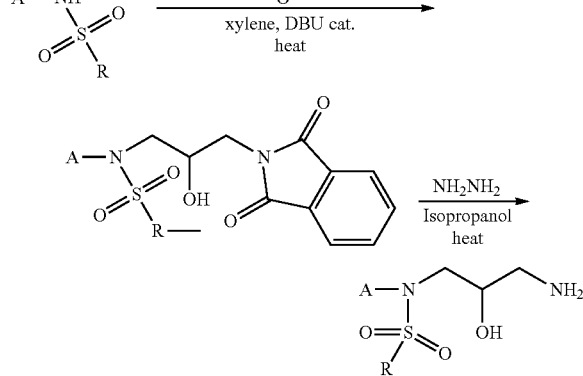

A is an unsubstituted, mono-substituted or polysubstituted alkyl, cycloalkyl, heteroalkyl, heterocycloalkyl, aryl, or heteroaryl.

General Procedure for the Synthesis of the Intermediates of the Compounds of the Invention

Scheme 17

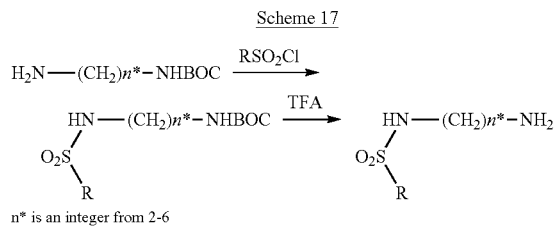

n* is an integer from 2-6

-continued

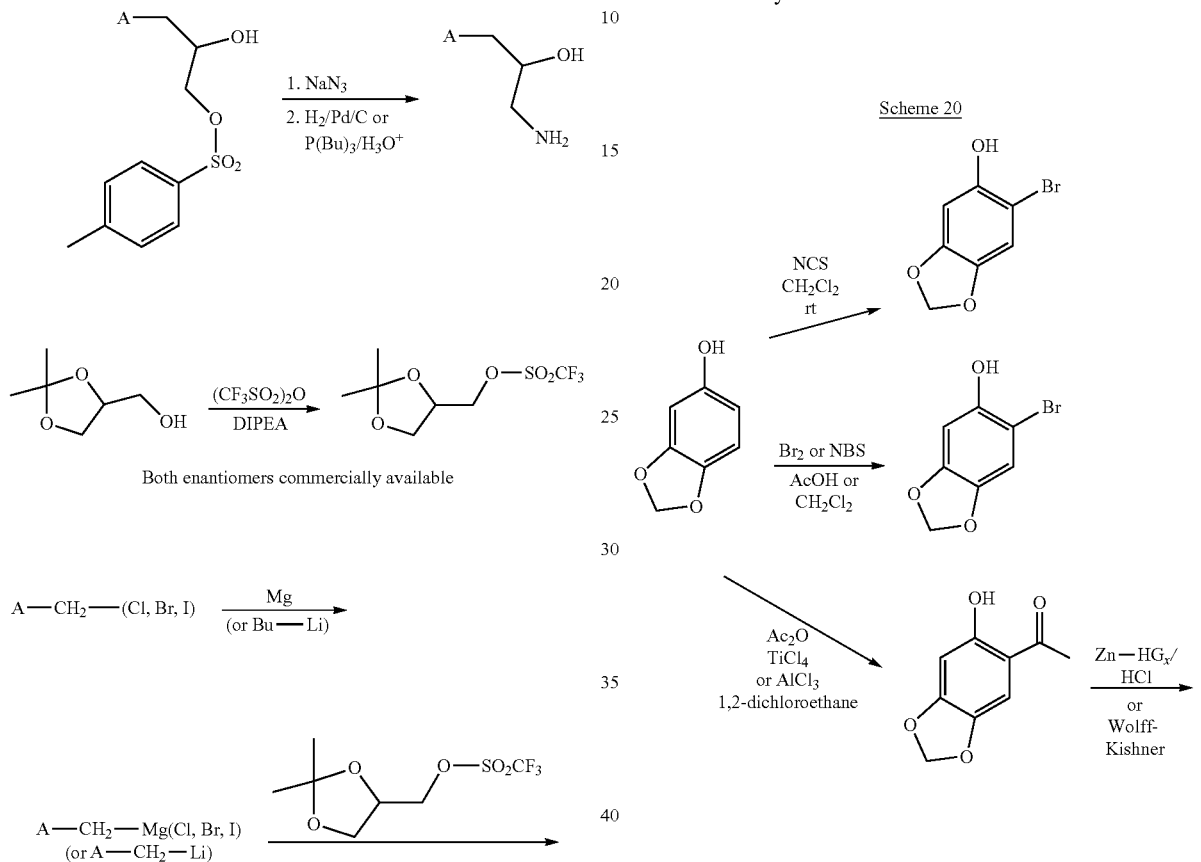

A is an unsubstituted, mono-substituted or polysubstituted alkyl, cycloalkyl, heteroalkyl, heterocycloalkyl, aryl, or heteroaryl.

General Procedure for the Synthesis of the Phenol Intermediates of the Compounds of the Invention The phenols that are not commercial products were synthesized by application methodology known in the art and routes outlined below.

Synthesis of Sesamol-Derivatives

Scheme 20

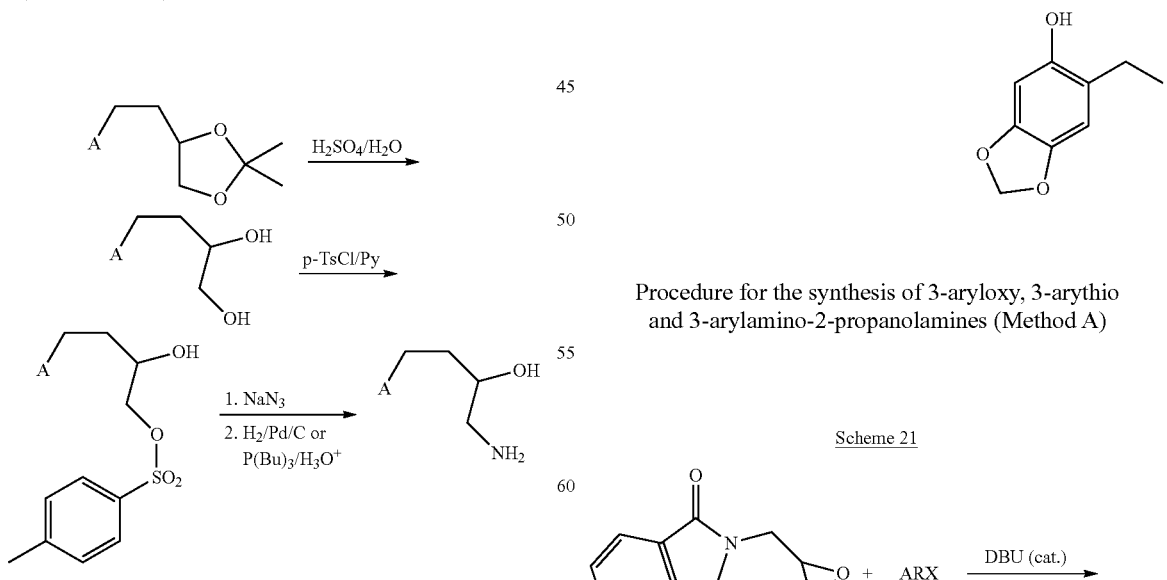

Procedure for the synthesis of 3-aryloxy, 3-arythio and 3-arylamino-2-propanolamines (Method A)

Scheme 21

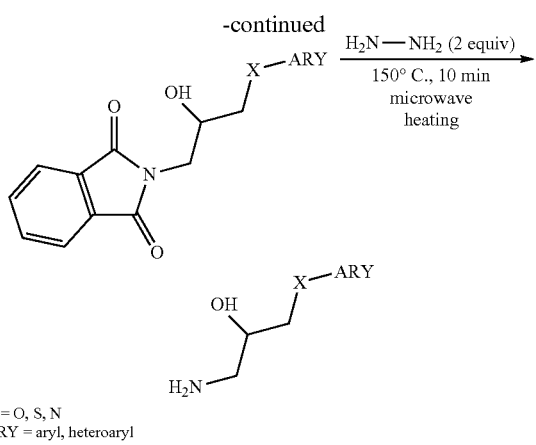

X = O, S, N
ARY = aryl, heteroaryl

A 20 mL microwaveable vial was charged with N-(2,3-epoxypropyl)-2-phthalimide (677 mg, 3.0 mmole), the appropriate phenol, thiol or aniline (1.2 equiv, 3.6 mmole), chlorobenzene (10 mL), and 1,8-diazabicyclo[5.4.0]undec-7-ene (100 uL). The vial was sealed and heated under microwaves to 220° C. for 0.5 h. Upon cooling hydrazine (0.189 mL, 6.0 mmol) was added to the reaction vessel. The vial was re-sealed and heated to 150° C. under microwaves for 12 min. Upon cooling the resulting suspension was poured onto ethyl acetate (100 mL) and extracted twice with 0.5 N NaOH (50 mL/extraction). The ethyl acetate fraction was isolated and extracted with saturated aqueous sodium chloride (25 mL). The ethyl acetate layer was isolated and dried over magnesium sulfate. The solid was removed by filtration and the volatiles were removed from the filtrate in vacuo to afford the product.

Compounds Prepared by Method A

Specific embodiments of compounds of formula (1) include, but are not limited to the following compounds that were prepared according to method A described above (Table I):

TABLE I

| Structure | Molecular Formula | $[M + H]^+$ | H NMR |
|---|---|---|---|
| (3-fluorophenoxy structure with NH2 and OH) | C9H12FNO2 | 186.2 | (CDCl$_3$): δ 7.10-7.30 (m, 1H, overlapped), 6.55-6.75 (m, 3H), 3.90-4.00 (m, 3H), 2.85-3.05 (m, 2H). |
| (3-methoxyphenylthio structure) | C10H15NO2S | 214.3 | (DMSO-d$_6$): δ 7.18-7.23 (m, 1H), 6.87-6.89 (m, 2H), 6.71-6.74 (m, 1H), 4.98 (bs, 1H), 3.80 (s, 3H), 3.48-3.52 (m, 1H), 3.05-3.11 (m, 1H), 2.87-2.94 (m, 1H), 2.50-2.70 (m, 2H, overlapped), 1.48 (brs, 2H). |
| (5-methylindoline structure) | C12H17ClN2O | 241.7 | (CD$_3$OD): δ 6.79-6.85 (m, 2H), 6.40-6.42 (m, 1H), 3.78-3.87 (m, 1H), 3.29-3.39 (m, 2H), 2.62-3.08 (m, 6H), 1.37 (s, 3H). |

TABLE I-continued

| Structure | Molecular Formula | [M + H]+ | H NMR |
|---|---|---|---|
| 3-amino-2-hydroxypropoxy-4-cyanobenzene | C10H12N2O2 | 193.2 | |
| 3-amino-2-hydroxypropoxy-3-fluorobenzene | C12H17NO2 | 208.3 | |
| 3-amino-2-hydroxypropoxy-3-nitrobenzene | C9H12N2O4 | 213.2 | |
| 3-amino-2-hydroxypropoxy-pentafluorobenzene | C9H8F5NO2 | 258.2 | |

TABLE I-continued

| Structure | Molecular Formula | [M + H]⁺ | H NMR |
|---|---|---|---|
| 3-amino-1-(2,3-dichlorophenoxy)propan-2-ol | C9H11Cl2NO2 | 237.1 | |
| 3-amino-1-(4-fluoro-2-methylphenoxy)propan-2-ol | C10H14FNO2 | 200.2 | |
| 3-amino-1-(2-bromo-4-fluorophenoxy)propan-2-ol | C9H11BrFNO2 | 265.1 | |
| 3-amino-1-(4-methyl-2-nitrophenoxy)propan-2-ol | C10H14N2O4 | 227.2 | |

TABLE I-continued

| Structure | Molecular Formula | [M + H]+ | H NMR |
|---|---|---|---|
| (1-amino-3-(3-methyl-2-nitrophenoxy)propan-2-ol) | C10H14N2O4 | 227.2 | |
| (1-amino-3-(3-chloro-2-fluoro-5-(trifluoromethyl)phenoxy)propan-2-ol) | C10H10ClF4NO2 | 288.6 | |
| (1-amino-3-(3-chloro-4-(trifluoromethoxy)phenoxy)propan-2-ol) | C10H11ClF3NO3 | 286.7 | |
| (1-amino-3-(3-(trifluoromethylthio)phenoxy)propan-2-ol) | C10H12F3NO2S | 268.3 | |

TABLE I-continued

| Structure | Molecular Formula | [M + H]+ | H NMR |
|---|---|---|---|
| 3-(2-nitro-4,6-dimethylphenoxy)-2-hydroxypropylamine | C11H16N2O4 | 241.3 | |
| 3-(2,3-dichlorophenoxy)-2-hydroxypropylamine | C9H11Cl2NO2 | 237.1 | |
| 3-[3-(1,1,2,2-tetrafluoroethoxy)phenoxy]-2-hydroxypropylamine | C11H13F4NO3 | 284.2 | |
| 3-(2-chloro-4-cyanophenoxy)-2-hydroxypropylamine | C10H11ClN2O2 | 227.7 | |

TABLE I-continued

| Structure | Molecular Formula | [M + H]+ | H NMR |
|---|---|---|---|
| 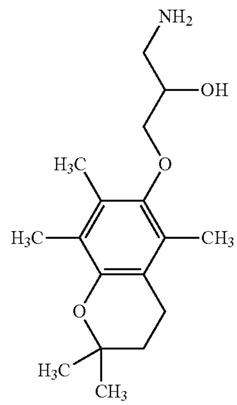 | C17H27NO3 | 294.4 | |
| 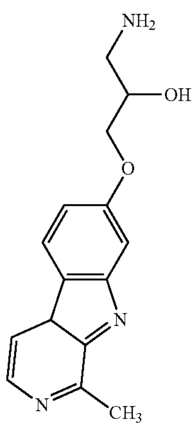 [SMILES: CC1=NC=CC2C1=Nc1cc(OCC(O)CN)ccc12] | C15H17N3O2 | 272.3 | |
| 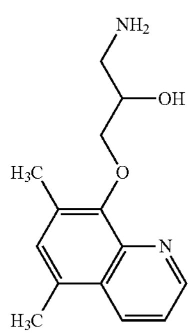 [SMILES: Cc1cc(C)c2cccnc2c1OCC(O)CN] | C14H18N2O2 | 247.3 | |
| 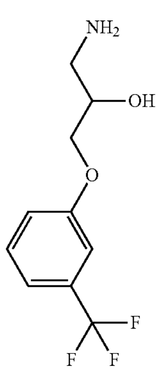 [SMILES: NCC(O)COc1cccc(C(F)(F)F)c1] | C10H12F3NO2 | 236.2 | |

TABLE I-continued

| Structure | Molecular Formula | [M + H]⁺ | H NMR |
|---|---|---|---|
| 1-amino-3-(4-(methylthio)phenoxy)propan-2-ol | C10H15NO2S | 214.3 | |
| 1-amino-3-(benzo[d][1,3]dioxol-5-yloxy)propan-2-ol | C10H13NO4 | 212.2 | |
| 1-amino-3-(4-nitrophenoxy)propan-2-ol | C9H12N2O4 | 213.2 | |
| 1-amino-3-(2-fluorophenoxy)propan-2-ol | C9H12FNO2 | 186.2 | |

TABLE I-continued

| Structure | Molecular Formula | [M + H]+ | H NMR |
|---|---|---|---|
| 1-amino-3-(4-iodo-2-methylphenoxy)propan-2-ol | C10H14INO2 | 308.1 | |
| 1-amino-3-(3,5-difluorophenoxy)propan-2-ol | C9H11F2NO2 | 204.2 | |
| 1-amino-3-(3-bromophenoxy)propan-2-ol | C9H12BrNO2 | 247.1 | |
| 1-amino-3-(3-(trifluoromethoxy)phenoxy)propan-2-ol | C10H12F3NO3 | 252.2 | |

TABLE I-continued

| Structure | Molecular Formula | [M + H]+ | H NMR |
|---|---|---|---|
| (3-tert-butylphenoxy aminopropanol) | C13H21NO2 | 224.3 | |
| (4-bromo-2-methoxyphenoxy aminopropanol) | C10H14BrNO3 | 277.1 | |
| (2,4-dichlorophenoxy aminopropanol) | C9H11Cl2NO2 | 237.1 | |
| (3-chloro-4-fluorophenoxy aminopropanol) | C9H11ClFNO2 | 220.6 | |

TABLE I-continued

| Structure | Molecular Formula | [M + H]+ | H NMR |
|---|---|---|---|
| 3,4-dichlorophenoxy-2-hydroxypropylamine | C9H11Cl2NO2 | 237.1 | |
| 3,5-dichlorophenoxy-2-hydroxypropylamine | C9H11Cl2NO2 | 237.1 | |
| 3-chloro-2-methylphenoxy-2-hydroxypropylamine | C10H14ClNO2 | 216.7 | |
| 3-chloro-2,6-difluorophenoxy-2-hydroxypropylamine | C9H10ClF2NO2 | 238.6 | |

TABLE I-continued

| Structure | Molecular Formula | [M + H]+ | H NMR |
|---|---|---|---|
| 3-amino-1-(naphthalen-2-yloxy)propan-2-ol | C13H15NO2 | 218.3 | |
| 3-amino-1-(biphenyl-2-yloxy)propan-2-ol | C15H17NO2 | 244.3 | |
| 3-amino-1-(naphthalen-1-yloxy)propan-2-ol | C13H15NO2 | 218.3 | |
| 3-amino-1-(3-chloro-4-methylphenoxy)propan-2-ol | C10H14ClNO2 | 216.7 | |

TABLE I-continued
| Structure | Molecular Formula | [M + H]+ | H NMR |
|---|---|---|---|
| 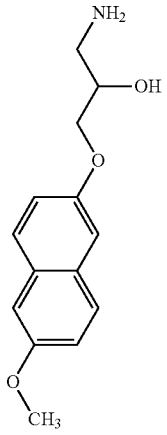 [SMILES: COc1ccc2cc(OCC(O)CN)ccc2c1] | C14H17NO3 | 248.3 | |
| 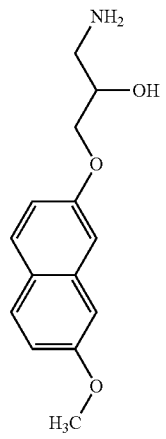 [SMILES: COc1ccc2ccc(OCC(O)CN)cc2c1] | C14H17NO3 | 248.3 | |
| 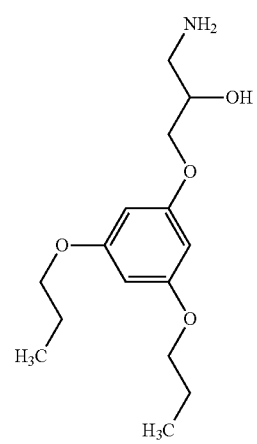 [SMILES: CCCOc1cc(OCCC)cc(OCC(O)CN)c1] | C15H25NO4 | 284.4 | |

TABLE I-continued
| Structure | Molecular Formula | [M + H]+ | H NMR |
|---|---|---|---|
| 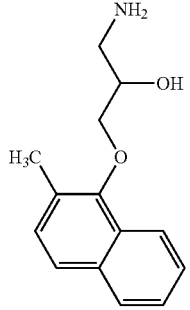 [SMILES: Cc1ccc2ccccc2c1OCC(O)CN] | C14H17NO2 | 232.3 | |
| 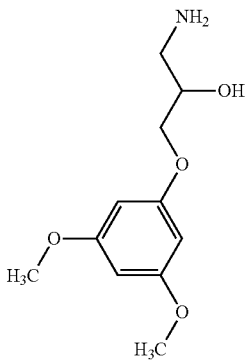 [SMILES: COc1cc(OC)cc(OCC(O)CN)c1] | C11H17NO4 | 228.3 | |
| 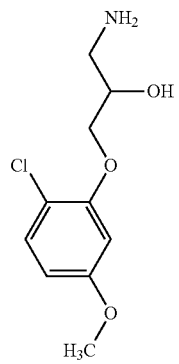 | C10H14ClNO3 | 232.7 | |
| 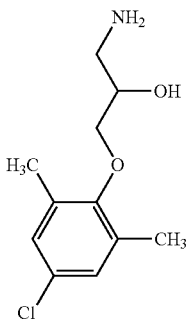 | C11H16ClNO3 | 230.7 | |

TABLE I-continued
| Structure | Molecular Formula | [M + H]+ | H NMR |
|---|---|---|---|
| 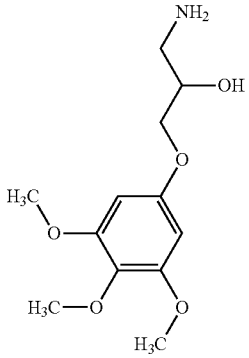 [SMILES: COc1cc(OCC(O)CN)cc(OC)c1OC] | C12H19NO5 | 258.3 | |
| 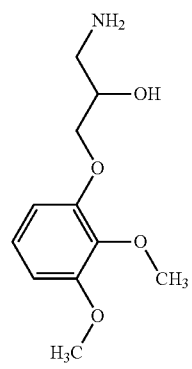 [SMILES: COc1cccc(OCC(O)CN)c1OC] | C11H17NO4 | 228.3 | |
| 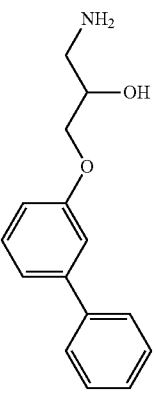 [SMILES: NCC(O)COc1cccc(-c2ccccc2)c1] | C15H17NO2 | 244.3 | |
| 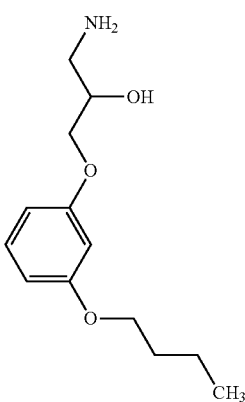 [SMILES: CCCCOc1cccc(OCC(O)CN)c1] | C13H21NO3 | 240.3 | |

TABLE I-continued

| Structure | Molecular Formula | [M + H]+ | H NMR |
|---|---|---|---|
| 3-amino-1-(4-fluoro-2-methylphenoxy)propan-2-ol | C10H14FNO2 | 200.2 | |
| 3-amino-1-([1,1'-biphenyl]-4-yloxy)propan-2-ol | C15H17NO2 | 244.3 | |
| 3-amino-1-((3-chloro-[1,1'-biphenyl]-4-yl)oxy)propan-2-ol | C15H16ClNO2 | 278.8 | |
| 3-amino-1-(3-(benzyloxy)phenoxy)propan-2-ol | C16H19NO3 | 274.3 | |

TABLE I-continued

| Structure | Molecular Formula | [M + H]+ | H NMR |
|---|---|---|---|
| 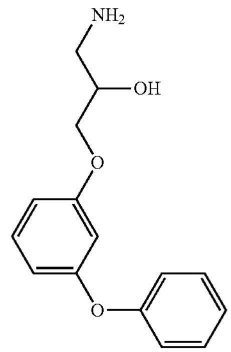 [SMILES: NCC(O)COc1cccc(Oc2ccccc2)c1] | C15H17NO3 | 260.3 | |
| 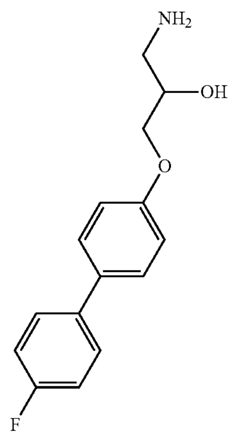 [SMILES: NCC(O)COc1ccc(-c2ccc(F)cc2)cc1] | C15H16FNO2 | 262.3 | |
| 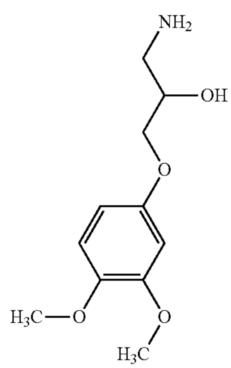 [SMILES: COc1ccc(OCC(O)CN)cc1OC] | C11H17NO4 | 228.3 | |
| 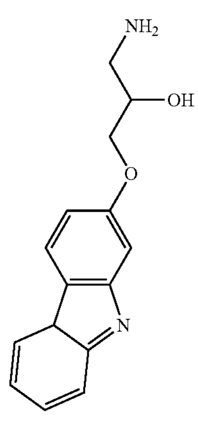 [SMILES: NCC(O)COc1ccc2c(c1)N=C1C=CC=CC12] | C15H16N2O2 | 257.3 | |

TABLE I-continued

| Structure | Molecular Formula | [M + H]+ | H NMR |
|---|---|---|---|
| (3-amino-2-hydroxypropoxy)-carbazole structure | C15H16NN2O2 | 257.3 | |
| (3-amino-2-hydroxypropoxy)-cyanobiphenyl structure | C16H16N2O2 | 269.3 | |
| (3-amino-2-hydroxypropoxy)-julolidine structure | C15H22N2O2 | 263.4 | |
| (3-amino-2-hydroxypropoxy)-chloro-cyanobenzene structure | C10H11ClN2O2 | 227.7 | |

TABLE I-continued
| Structure | Molecular Formula | [M + H]+ | H NMR |
|---|---|---|---|
| 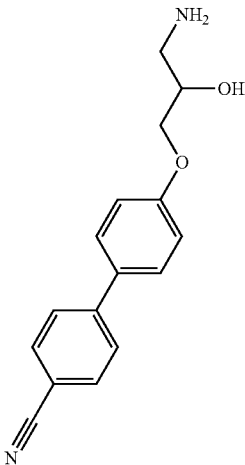 [SMILES: N#Cc1ccc(-c2ccc(OCC(O)CN)cc2)cc1] | C16H16N2O2 | 269.3 | |
| 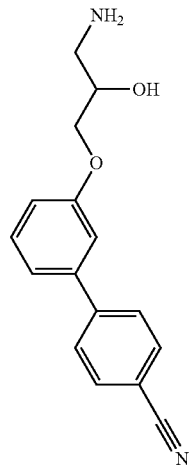 [SMILES: N#Cc1ccc(-c2cccc(OCC(O)CN)c2)cc1] | C16H16N2O2 | 269.3 | |
| 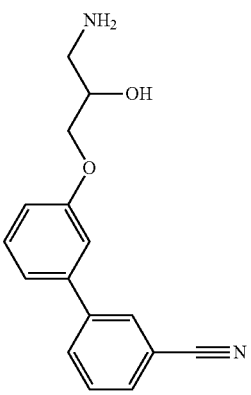 [SMILES: N#Cc1cccc(-c2cccc(OCC(O)CN)c2)c1] | C16H16N2O2 | 269.3 | |

TABLE I-continued

| Structure | Molecular Formula | [M + H]+ | H NMR |
|---|---|---|---|
| 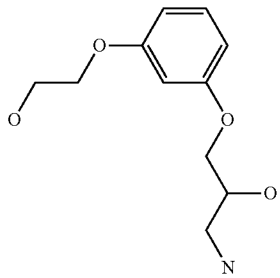 [SMILES: NCC(O)COc1cccc(OCCO)c1] | C11H17NO4 | 228.3 | |
| 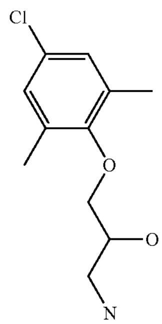 | C11H16ClNO2 | 230.7 | |
| 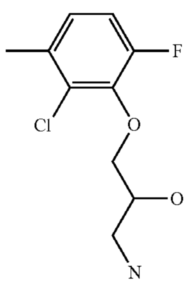 | C10H13ClFNO2 | 234.7 | |
| 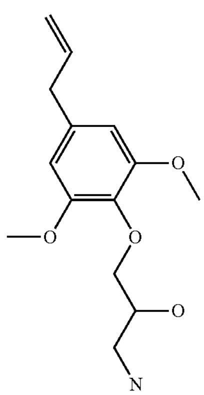 | C14H21NO4 | 268.3 | |
| 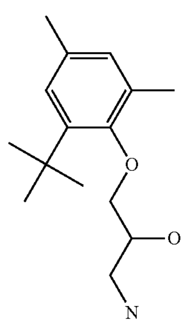 [SMILES: Cc1cc(C)c(OCC(O)CN)c(C(C)(C)C)c1] | C15H25NO2 | 252.4 | |

TABLE I-continued

| Structure | Molecular Formula | [M + H]+ | H NMR |
|---|---|---|---|
| | C11H17NO2 | 196.3 | |
| 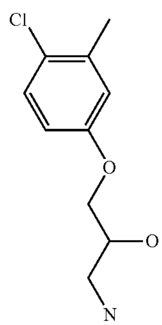 | C10H14ClNO2 | 216.7 | |
| | C11H17NO2 | 196.3 | |
| 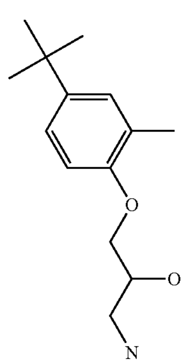 [SMILES: Cc1cc(C(C)(C)C)ccc1OCC(O)CN] | C14H23NO2 | 238.3 | |

TABLE I-continued

| Structure | Molecular Formula | [M + H]+ | H NMR |
|---|---|---|---|
| 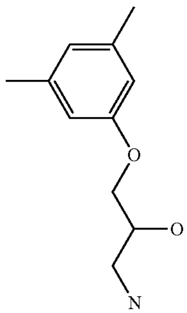 | C11H17NO2 | 196.3 | |
| | C10H15NO2 | 182.2 | |
| 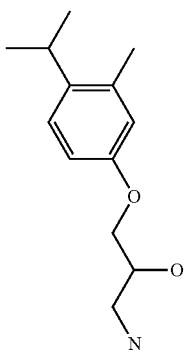 [SMILES: Cc1cc(OCC(O)CN)ccc1C(C)C] | C13H21NO2 | 224.3 | |
| | C10H15NO2 | 182.2 | |
| 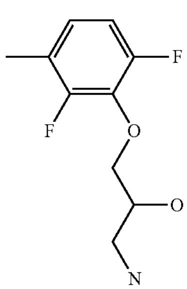 | C10H13F2NO2 | 218.2 | |

TABLE I-continued

| Structure | Molecular Formula | [M + H]⁺ | H NMR |
|---|---|---|---|
| 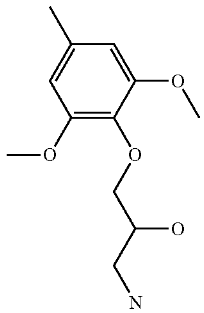 | C12H19NO4 | 242.3 | |
| | C14H23NO2 | 238.3 | |
| | C14H23NO2 | 238.3 | |
| 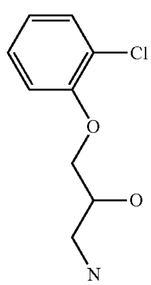 [SMILES: NCC(O)COc1ccccc1Cl] | C9H12ClNO2 | 202.7 | |
| 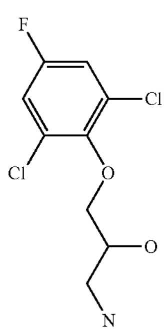 [SMILES: NCC(O)COc1c(Cl)cc(F)cc1Cl] | C9H9Cl2FNO | 236.9 | |

TABLE I-continued

| Structure | Molecular Formula | [M + H]+ | H NMR |
|---|---|---|---|
| 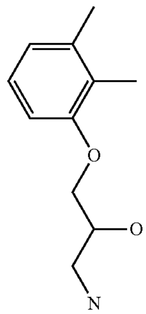 | C11H17NO2 | 196.3 | |
| 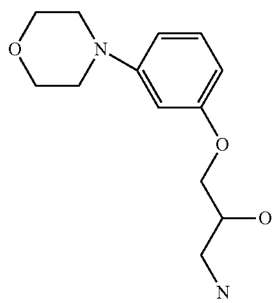 [SMILES: NCC(O)COc1cccc(N2CCOCC2)c1] | C13H20N2O3 | 253.3 | |
| 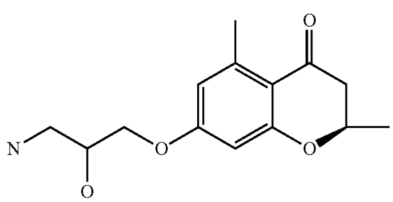 [SMILES: Cc1cc(OCC(O)CN)cc2c1C(=O)C[C@@H](C)O2] | C15H21NO4 | 280.3 | |
| 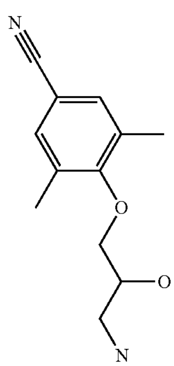 [SMILES: Cc1cc(C#N)cc(C)c1OCC(O)CN] | C12H16N2O2 | 221.3 | |
| 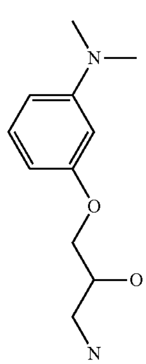 | C11H18N2O2 | 211.3 | |

TABLE I-continued

| Structure | Molecular Formula | [M + H]+ | H NMR |
|---|---|---|---|
| | C12H19NO2 | 210.3 | |
| 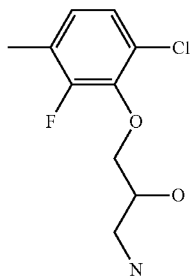 | C10H13ClFNO2 | 234.7 | |
| | C12H19NO2 | 210.3 | |
| 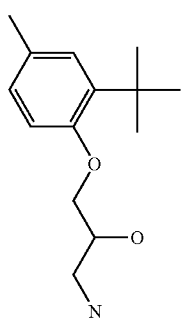 [SMILES: Cc1ccc(OCC(O)CN)c(C(C)(C)C)c1] | C14H23NO2 | 238.3 | |
| 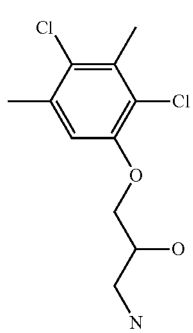 [SMILES: Cc1cc(OCC(O)CN)c(Cl)c(C)c1Cl] | C11H14Cl2NO2 | 267.9 | |

TABLE I-continued

| Structure | Molecular Formula | [M + H]⁺ | H NMR |
|---|---|---|---|
| 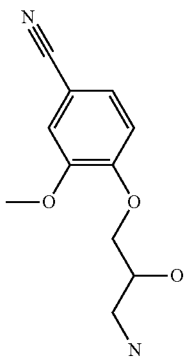 [SMILES: COc1cc(C#N)ccc1OCC(O)CN] | C11H14N2O3 | 223.2 | |
| | C11H17NO2 | 196.3 | |
| | C11H17NO2 | 196.3 | |
| 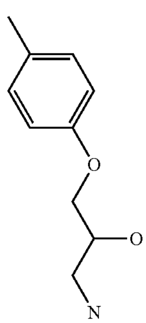 | C10H15NO2 | 182.2 | |

TABLE I-continued

| Structure | Molecular Formula | [M + H]+ | H NMR |
|---|---|---|---|
| 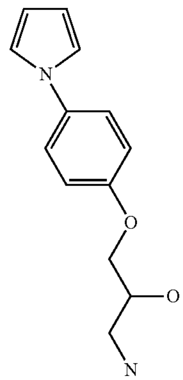 [SMILES: NCC(O)COc1ccc(-n2cccc2)cc1] | C13H16N2O2 | 233.3 | |
| 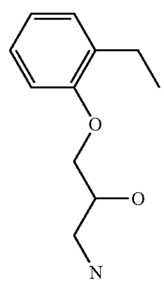 | C11H17NO2 | 196.3 | |
| 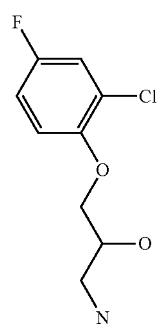 [SMILES: NCC(O)COc1ccc(F)cc1Cl] | C9H11ClFNO2 | 220.6 | |
| 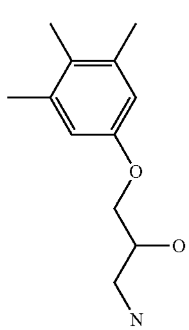 | C12H19NO2 | 210.3 | |

TABLE I-continued

| Structure | Molecular Formula | [M + H]+ | H NMR |
|---|---|---|---|
| (4-chloro-5-methyl-2-isopropylphenoxy glycidyl amine structure) | C13H20ClNO2 | 258.8 | |
| (4-cyano-3,5-dimethylphenoxy glycidyl amine structure) | C12H16N2O2 | 221.3 | |
| (2,2-dimethyl-2,3-dihydrobenzofuran-7-yloxy glycidyl amine structure) | C13H19NO3 | 238.3 | |
| (2-chloro-4-methylphenoxy glycidyl amine structure) | C10H14ClNO2 | 216.7 | |
| (2-tert-butylphenoxy glycidyl amine structure) | C13H20NO2 | 223.4 | |

TABLE I-continued

| Structure | Molecular Formula | [M + H]+ | H NMR |
|---|---|---|---|
| | C10H14FNO2 | 200.2 | |
| 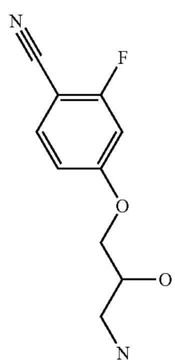 [SMILES: N#Cc1ccc(OCC(O)CN)cc1F] | C10H11FN2O2 | 211.2 | |
| | C10H14FNO2 | 200.2 | |
| 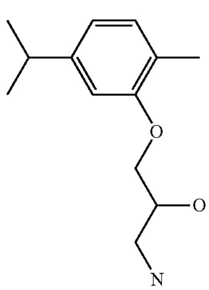 [SMILES: Cc1ccc(C(C)C)cc1OCC(O)CN] | C13H21NO2 | 224.3 | |

TABLE I-continued
| Structure | Molecular Formula | [M + H]⁺ | H NMR |
|---|---|---|---|
| 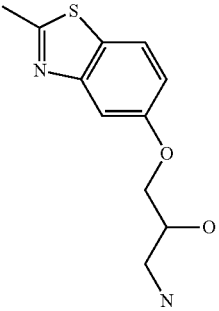 [SMILES: Cc1nc2cc(OCC(O)CN)ccc2s1] | C11H14N2O2S | 239.3 | |
| 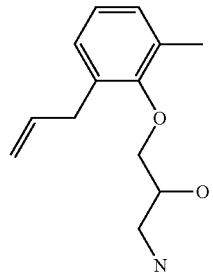 [SMILES: C=CCc1cccc(C)c1OCC(O)CN] | C13H19NO2 | 222.3 | |
| 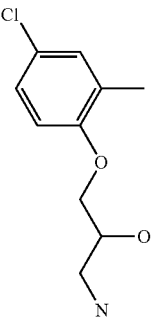 | C10H14ClNO2 | 216.7 | |
| 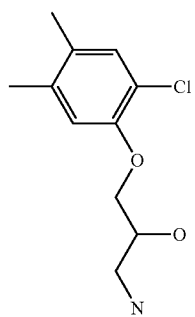 | C11H16ClNO2 | 230.7 | |

TABLE I-continued

| Structure | Molecular Formula | [M + H]+ | H NMR |
|---|---|---|---|
| 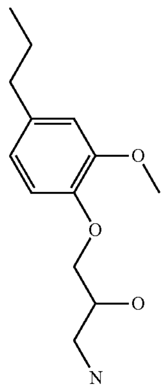 [SMILES: CCCc1ccc(OCC(O)CN)c(OC)c1] | C13H21NO3 | 240.3 | |
| 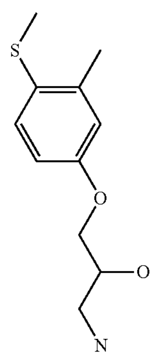 | C11H17NO2S | 228.3 | |
| 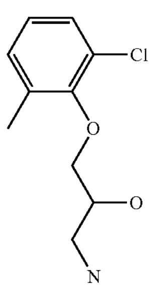 | C10H14ClNO2 | 216.7 | |
| 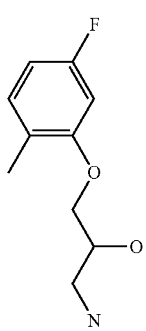 | C10H14FNO2 | 200.2 | |

TABLE I-continued

| Structure | Molecular Formula | [M + H]+ | H NMR |
|---|---|---|---|
| 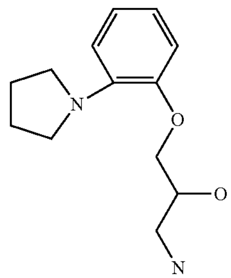 [SMILES: NCC(O)COc1ccccc1N1CCCC1] | C13H20N2O2 | 237.3 | |
| 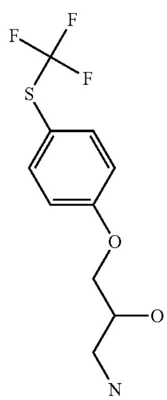 [SMILES: NCC(O)COc1ccc(SC(F)(F)F)cc1] | C10H12F3NO2S | 268.3 | |
| 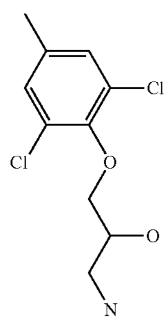 | C10H13Cl2NO2 | 251.1 | |
| | C10H14N2O4 | 227.7 | |
| | C10H14N2O4 | 227.2 | |

TABLE I-continued
| Structure | Molecular Formula | [M + H]+ | H NMR |
|---|---|---|---|
| 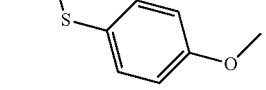 | C10H15NO2S | 214.3 | |
|  | C9H12ClNOS | 218.7 | |
| 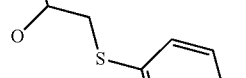 | C10H15NO2S | 214.3 | |
| 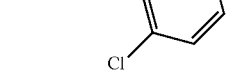 | C10H15NOS | 198.3 | |
|  | C9H12ClNOS | 218.7 | |
| 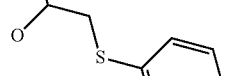 | C10H15NOS | 198.3 | |
| 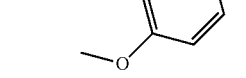 | C10H15NOS | 198.3 | |
|  | C10H15NO2S | 214.3 | |

TABLE I-continued

| Structure | Molecular Formula | [M + H]+ | H NMR |
|---|---|---|---|
| (3-chlorophenylthio-methyl aminopropanol) | C9H13ClN2O | 201.7 | |
| (6-chloro-tetrahydroquinoline N-substituted aminopropanol) | C12H17ClN2O | 241.7 | |
| (4-bromo-2,6-dimethylphenoxy aminopropanol) | C11H16BrNO2 | 275.2 | |
| (6-cyanonaphthalen-2-yloxy aminopropanol) | C14H14N2O2 | 243.3 | |
| (2,4-dimethylphenoxy aminopropanol) | C11H17NO2 | 196.3 | |
| (4-chlorophenoxy aminopropanol) | C9H12ClNO2 | 202.7 | |
| (2,4,6-trimethylphenoxy aminopropanol) | C12H19NO2 | 210.3 | |

TABLE I-continued

| Structure | Molecular Formula | [M + H]+ | H NMR |
|---|---|---|---|
| 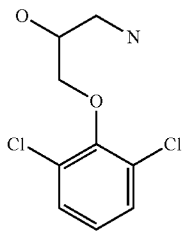 [SMILES: NCC(O)COc1c(Cl)cccc1Cl] | C9H11Cl2NO2 | 237.1 | |
| 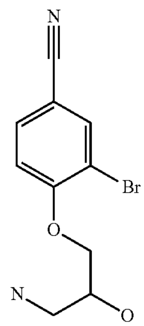 [SMILES: N#Cc1ccc(OCC(O)CN)c(Br)c1] | C10H11BrN2O2 | 272.1 | |
| 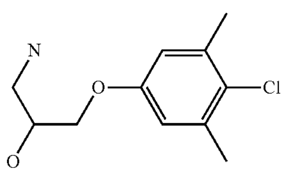 | C11H16ClNO2 | 230.7 | |
| 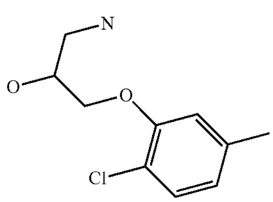 | C10H14ClNO2 | 216.7 | |
| 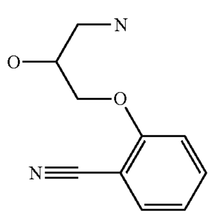 [SMILES: N#Cc1ccccc1OCC(O)CN] | C10H12N2O2 | 193.2 | |
| 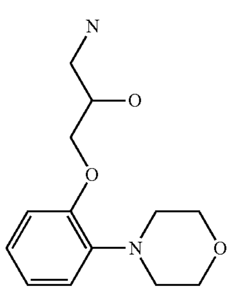 [SMILES: NCC(O)COc1ccccc1N1CCOCC1] | C13H20N2O3 | 253.3 | |

TABLE I-continued

| Structure | Molecular Formula | [M + H]+ | H NMR |
|---|---|---|---|
| (4-chloro-2-(oxiran-2-ylmethoxy)benzonitrile derivative) | C10H11ClN2O2 | 227.7 | |
| (4'-methoxybiphenyl propanolamine) | C16H19NO3 | 274.3 | |
| (2,4-dichlorophenoxy propanolamine) | C9H11Cl2NO2 | 237.1 | |
| (4-chlorophenylthio propanolamine) | C9H12ClNOS | 218.7 | |

Procedure for synthesis of 2-{4-[2-hydroxy-3-aryloxypropyl)amino]-2-oxo-1,2-dihydropyridin-3-yl]-6-(methylpiperidin-4-yl)imidazo[4,5-f]isoindole-5,7(1H,6H)-diones, 2-{4-[2-hydroxy-3-arylthiopropyl)amino]-2-oxo-1,2-dihydropyridin-3-yl}-6-(methylpiperidin-4-yl)imidazo[4,5-f]isoindole-5,7(1H,6H)-diones, and 2-{4-[2-hydroxy-3-arylaminopropyl)amino]-2-oxo-1,2-dihydropyridin-3-yl}-6-(methylpiperidin-4-yl)imidazo[4,5-f]isoindole-5,7(1H,6H)-diones (Method B)

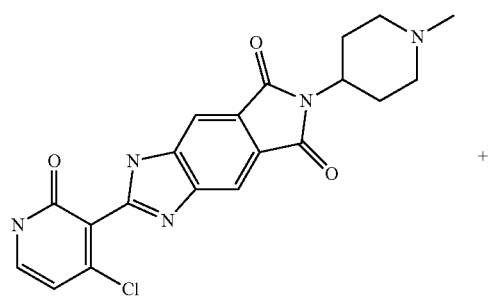

Scheme 22

An array of 8 mL vials, each containing one of the propanolamines prepared by Method A (100 umol), was prepared. A 0.1 M stock solution of 2-(4-chloro-2-oxo-1,2-dihydropyridin-3-yl)-6-(methylpiperidin-4-yl)imidazo[4,5-f]isoindole-5,7(1H,6H)-dione in 15% triethylamine in ethyl acetate (v/v) was prepared. To each of the vials was added the template stock solution (1000 uL, 1.0 equiv). The vials were capped and heated to 100° C. for 16 h. Upon cooling the volatiles were removed in vacuo and the resultant residue was purified by HPLC.

Compounds Prepared by Method B

Specific embodiments of compounds of formula (1) include, but are not limited to the following compounds that were prepared according to method B described above (Table II):

TABLE II

| Compound | Structure | Molecular Formula | [M + H]$^+$ |
|---|---|---|---|
| 1' | 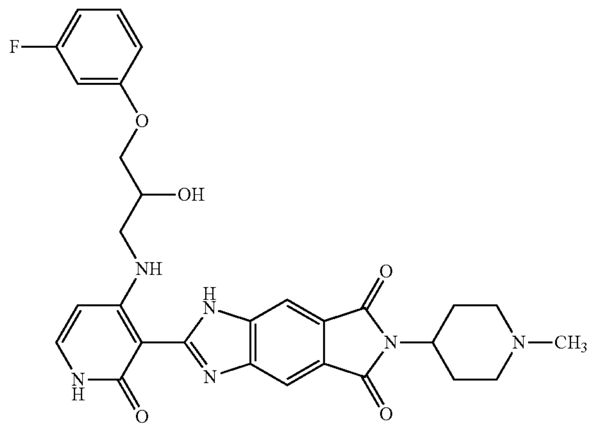 [SMILES: CN1CCC(N2C(=O)c3cc4nc(-c5c(NCC(O)COc6cccc(F)c6)cc[nH]c5=O)[nH]c4cc3C2=O)CC1] | C29H29FN6O5 | 561.6 |
| 2' | 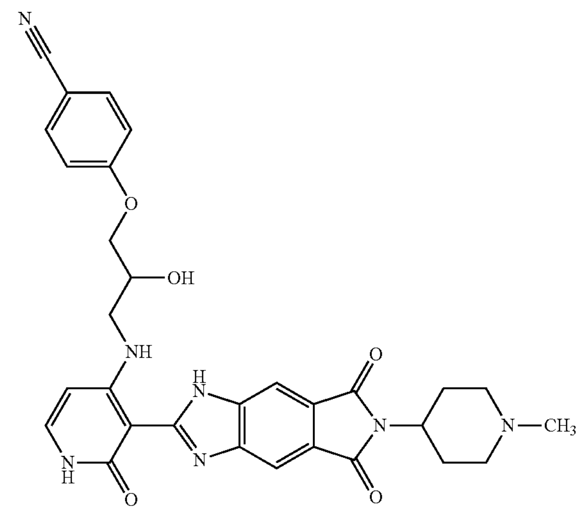 [SMILES: CN1CCC(N2C(=O)c3cc4nc(-c5c(NCC(O)COc6ccc(C#N)cc6)cc[nH]c5=O)[nH]c4cc3C2=O)CC1] | C30H29N7O5 | 568.6 |
| 3' | 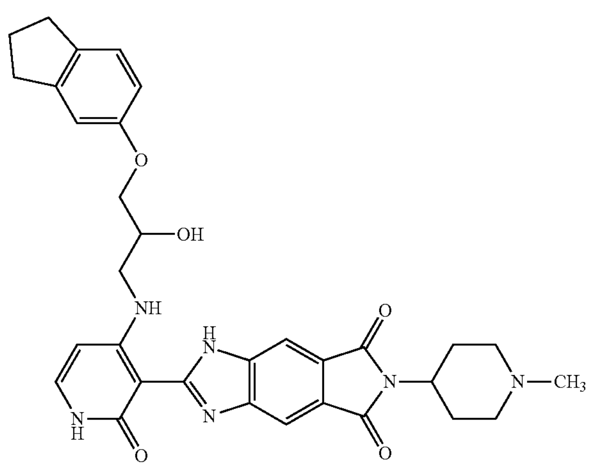 [SMILES: CN1CCC(N2C(=O)c3cc4nc(-c5c(NCC(O)COc6ccc7c(c6)CCC7)cc[nH]c5=O)[nH]c4cc3C2=O)CC1] | C32H34N6O5 | 583.7 |

TABLE II-continued

| Compound | Structure | Molecular Formula | [M + H]+ |
|---|---|---|---|
| 4' | 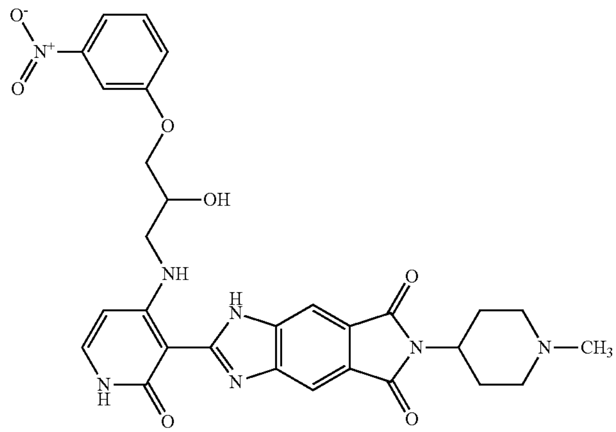 [SMILES: CN1CCC(N2C(=O)c3cc4nc(-c5c(NCC(O)COc6cccc([N+](=O)[O-])c6)cc[nH]c5=O)[nH]c4cc3C2=O)CC1] | C29H29N7O7 | 588.6 |
| 5' | 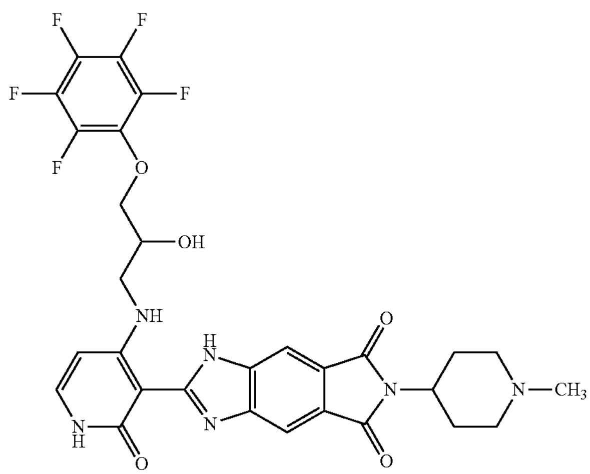 [SMILES: CN1CCC(N2C(=O)c3cc4nc(-c5c(NCC(O)COc6c(F)c(F)c(F)c(F)c6F)cc[nH]c5=O)[nH]c4cc3C2=O)CC1] | C29H25F5N6O5 | 633.5 |
| 6' | 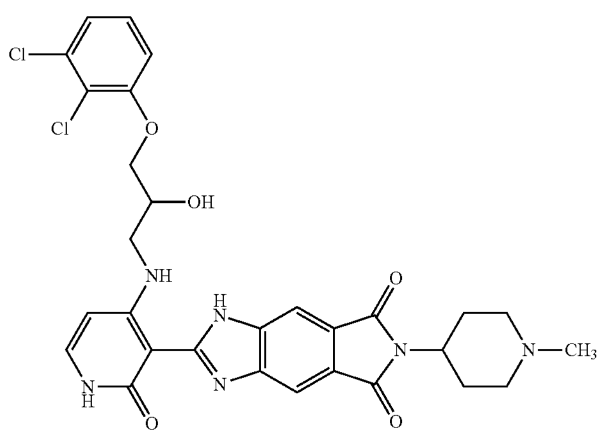 [SMILES: CN1CCC(N2C(=O)c3cc4nc(-c5c(NCC(O)COc6cccc(Cl)c6Cl)cc[nH]c5=O)[nH]c4cc3C2=O)CC1] | C29H28Cl2N6O5 | 612.5 |

TABLE II-continued

| Compound | Structure | Molecular Formula | [M + H]+ |
|---|---|---|---|
| 7' | 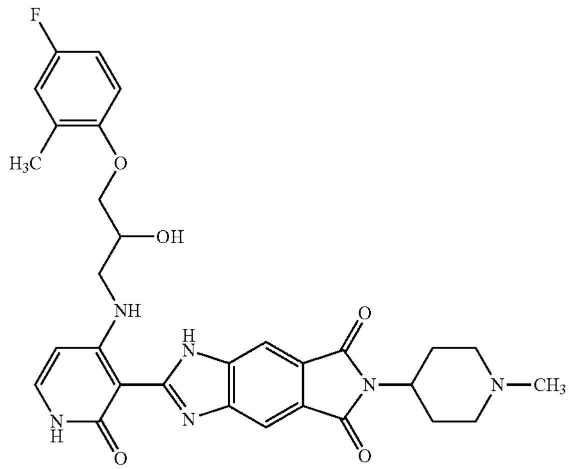 [SMILES: Cc1cc(F)ccc1OCC(O)CNc1cc[nH]c(=O)c1-c1nc2cc3c(cc2[nH]1)C(=O)N(C1CCN(C)CC1)C3=O] | C30H31FN6O5 | 575.6 |
| 8' | 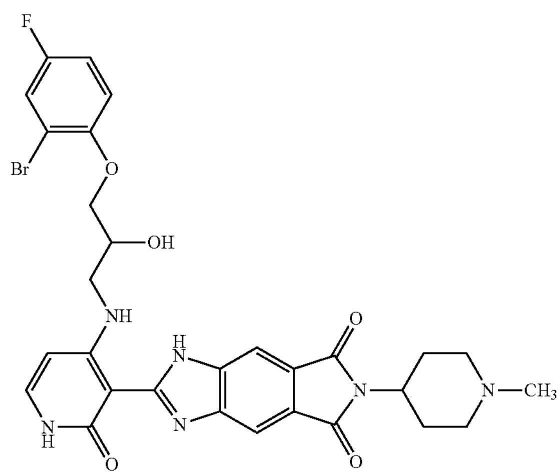 [SMILES: CN1CCC(N2C(=O)c3cc4nc(-c5c(NCC(O)COc6ccc(F)cc6Br)cc[nH]c5=O)[nH]c4cc3C2=O)CC1] | C29H28BrFN6O5 | 640.5 |
| 9' | 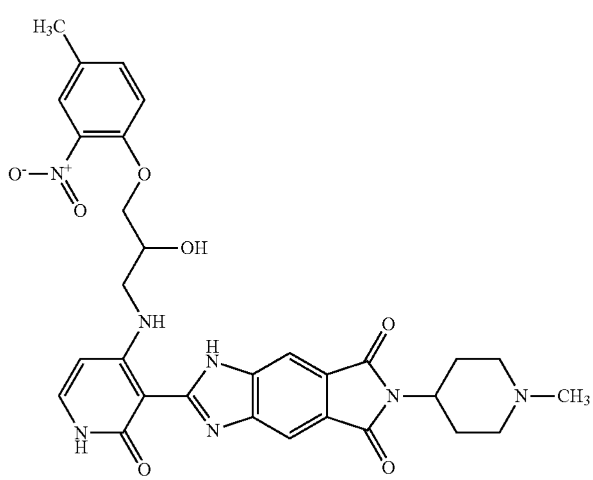 [SMILES: Cc1ccc(OCC(O)CNc2cc[nH]c(=O)c2-c2nc3cc4c(cc3[nH]2)C(=O)N(C2CCN(C)CC2)C4=O)c([N+](=O)[O-])c1] | C30H31N7O7 | 602.6 |

TABLE II-continued

| Compound | Structure | Molecular Formula | [M + H]+ |
|---|---|---|---|
| 10' | 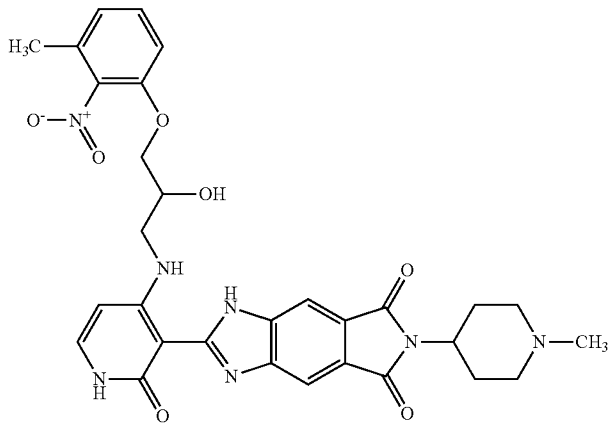 [SMILES: Cc1cccc(OCC(O)CNc2cc[nH]c(=O)c2-c2nc3cc4c(cc3[nH]2)C(=O)N(C2CCN(C)CC2)C4=O)c1[N+](=O)[O-]] | C30H31N7O7 | 602.6 |
| 11' | 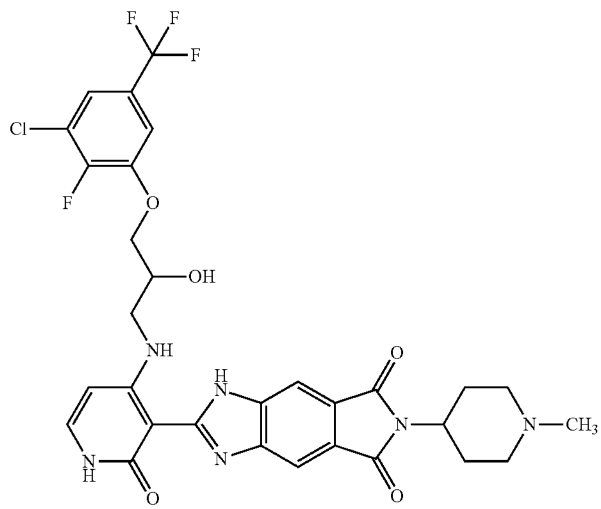 [SMILES: CN1CCC(N2C(=O)c3cc4nc(-c5c(NCC(O)COc6cc(C(F)(F)F)cc(Cl)c6F)cc[nH]c5=O)[nH]c4cc3C2=O)CC1] | C30H27ClF4N6O5 | 664.0 |
| 12' | 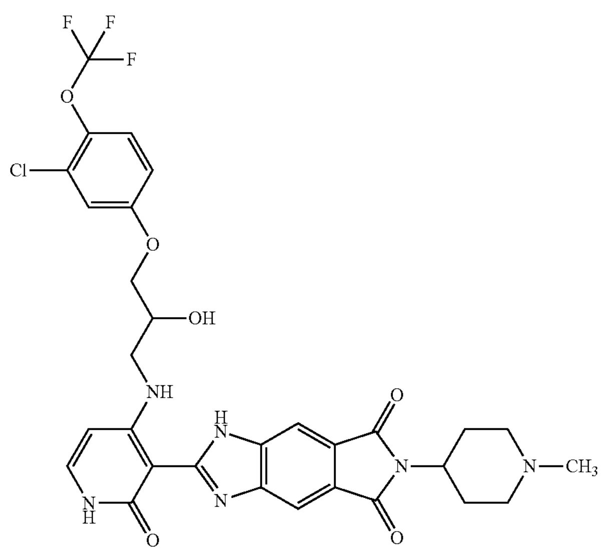 [SMILES: CN1CCC(N2C(=O)c3cc4nc(-c5c(NCC(O)COc6ccc(OC(F)(F)F)c(Cl)c6)cc[nH]c5=O)[nH]c4cc3C2=O)CC1] | C30H28ClF3N6O6 | 662.0 |

TABLE II-continued
| Compound | Structure | Molecular Formula | [M + H]+ |
|---|---|---|---|
| 13' | 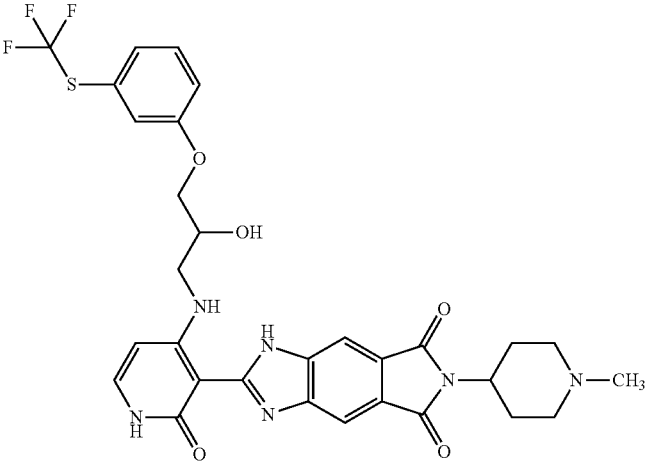 | C30H29F3N6O5S | 643.7 |
| 14' | 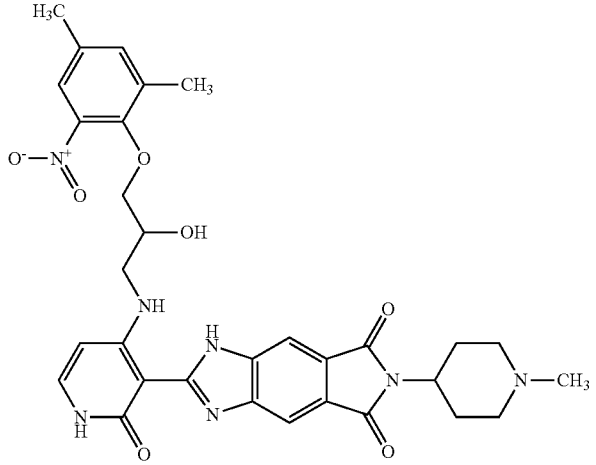 [SMILES: Cc1cc(C)c(OCC(O)CNc2cc[nH]c(=O)c2-c2nc3cc4c(cc3[nH]2)C(=O)N(C2CCN(C)CC2)C4=O)c([N+](=O)[O-])c1] | C31H33N7O7 | 616.6 |
| 15' | 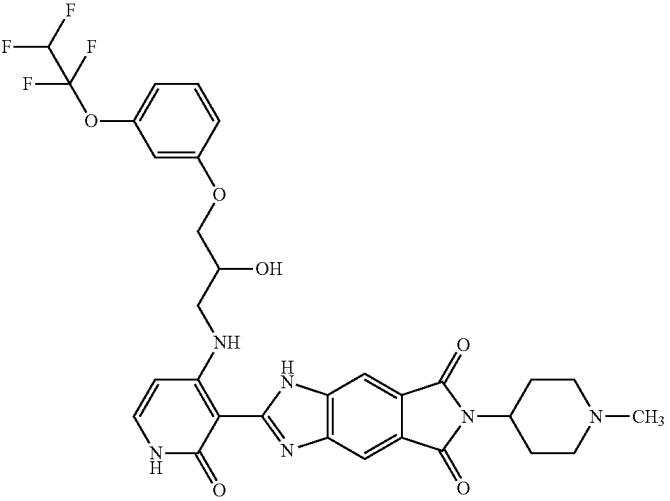 [SMILES: CN1CCC(N2C(=O)c3cc4nc(-c5c(NCC(O)COc6cccc(OC(F)(F)C(F)F)c6)cc[nH]c5=O)[nH]c4cc3C2=O)CC1] | C31H30F4N6O6 | 659.6 |

TABLE II-continued

| Compound | Structure | Molecular Formula | [M + H]+ |
|---|---|---|---|
| 16' | 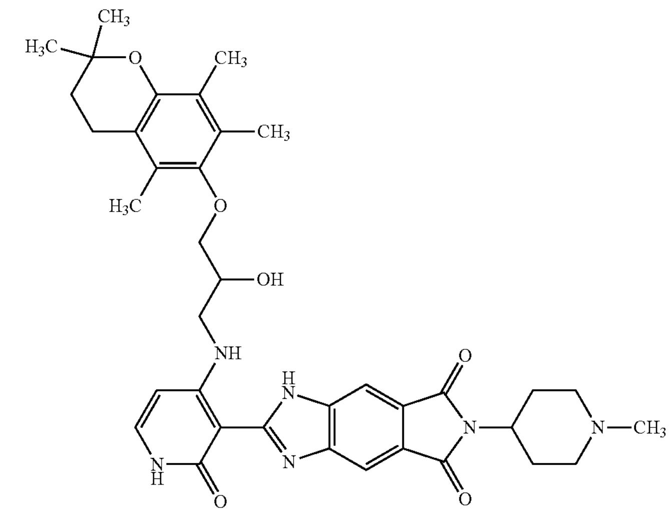 | C37H44N6O6 | 669.8 |
| 17' | 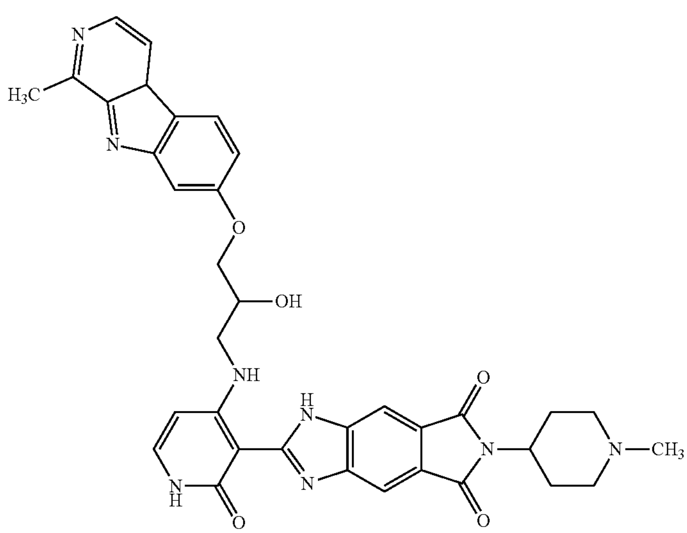 | C35H34N8O5 | 647.7 |
| 18' | 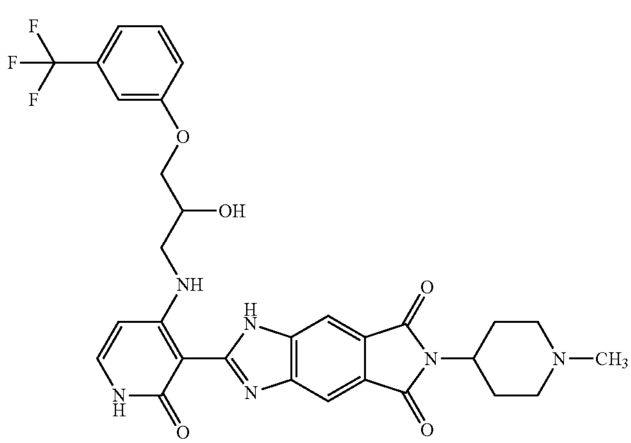 [SMILES: CN1CCC(N2C(=O)c3cc4nc(-c5c(NCC(O)COc6cccc(C(F)(F)F)c6)cc[nH]c5=O)[nH]c4cc3C2=O)CC1] | C30H29F3N6O5 | 611.6 |

TABLE II-continued
| Compound | Structure | Molecular Formula | [M + H]+ |
|---|---|---|---|
| 19' | 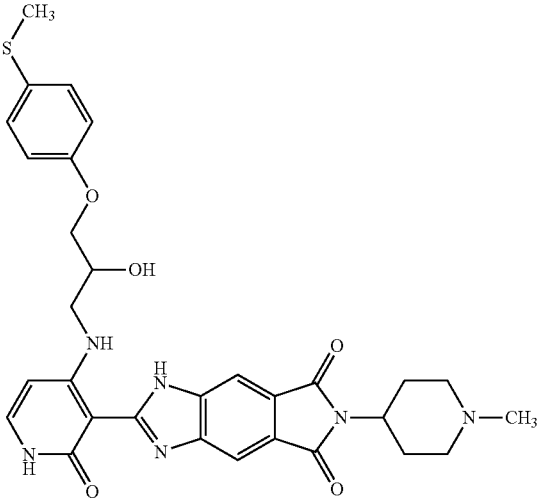 [SMILES: CSc1ccc(OCC(O)CNc2cc[nH]c(=O)c2-c2nc3cc4c(cc3[nH]2)C(=O)N(C2CCN(C)CC2)C4=O)cc1] | C30H32N6O5S | 589.7 |
| 20' | 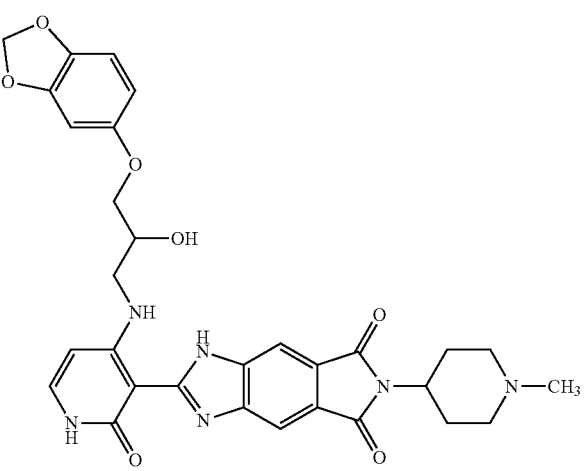 [SMILES: CN1CCC(N2C(=O)c3cc4nc(-c5c(NCC(O)COc6ccc7c(c6)OCO7)cc[nH]c5=O)[nH]c4cc3C2=O)CC1] | C30H30N6O7 | 587.6 |
| 21' | 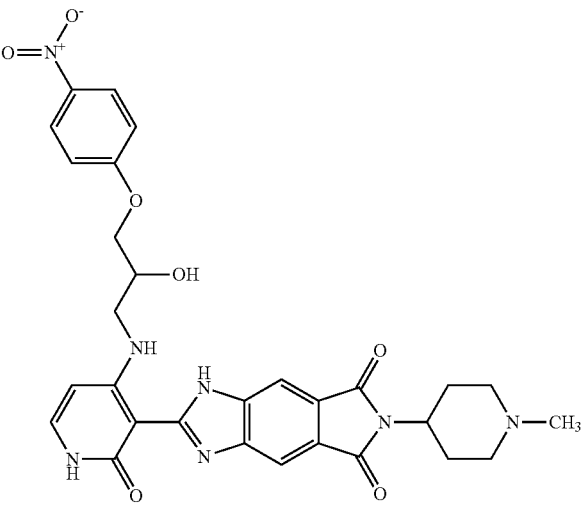 [SMILES: CN1CCC(N2C(=O)c3cc4nc(-c5c(NCC(O)COc6ccc([N+](=O)[O-])cc6)cc[nH]c5=O)[nH]c4cc3C2=O)CC1] | C29H29N7O7 | 588.6 |

TABLE II-continued

| Compound | Structure | Molecular Formula | [M + H]+ |
|---|---|---|---|
| 22' | 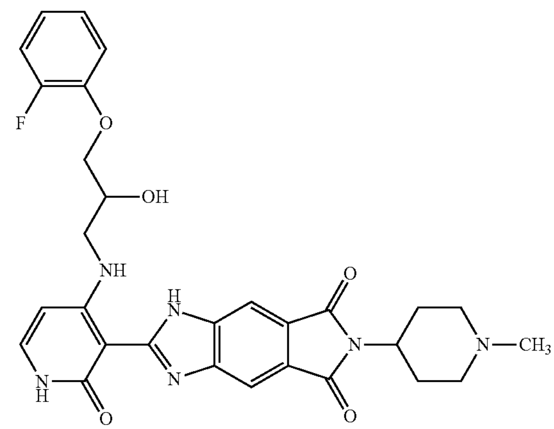 [SMILES: CN1CCC(N2C(=O)c3cc4nc(-c5c(NCC(O)COc6ccccc6F)cc[nH]c5=O)[nH]c4cc3C2=O)CC1] | C29H29FN6O5 | 561.6 |
| 23' | 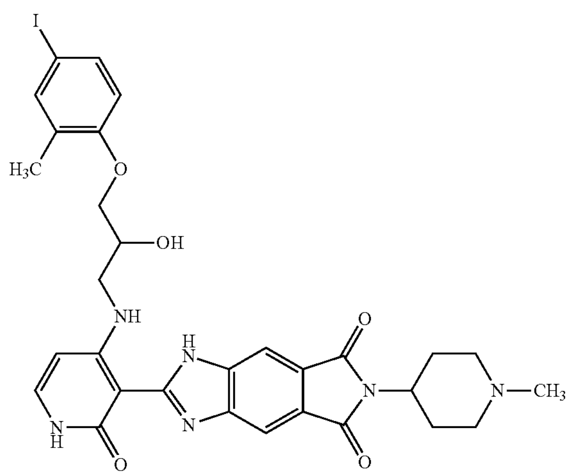 [SMILES: Cc1cc(I)ccc1OCC(O)CNc1cc[nH]c(=O)c1-c1nc2cc3c(cc2[nH]1)C(=O)N(C1CCN(C)CC1)C3=O] | C30H31IN6O5 | 683.5 |
| 24' | 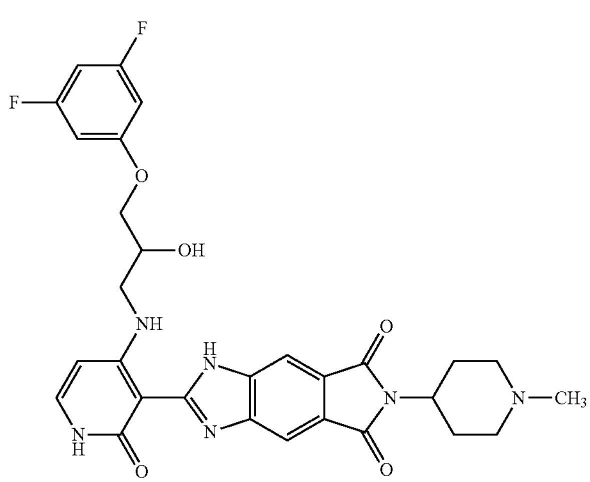 [SMILES: CN1CCC(N2C(=O)c3cc4nc(-c5c(NCC(O)COc6cc(F)cc(F)c6)cc[nH]c5=O)[nH]c4cc3C2=O)CC1] | C29H28F2N6O5 | 579.6 |

TABLE II-continued
| Compound | Structure | Molecular Formula | [M + H]+ |
|---|---|---|---|
| 25' | 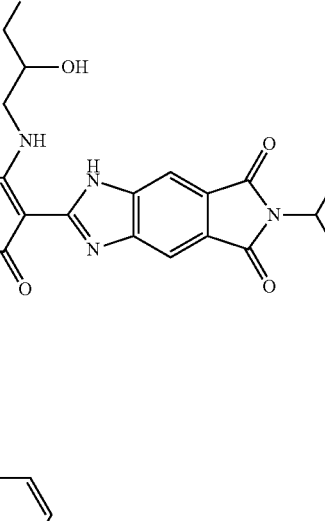 | C29H29BrN6O5 | 622.5 |
| 26' | 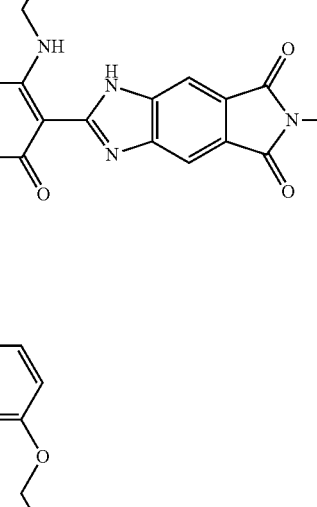 | C30H29F3N6O6 | 627.6 |
| 27' | 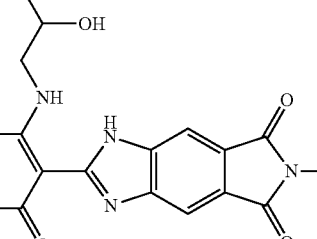 | C33H38N6O5 | 599.7 |

TABLE II-continued
| Compound | Structure | Molecular Formula | [M + H]+ |
|---|---|---|---|
| 28' | 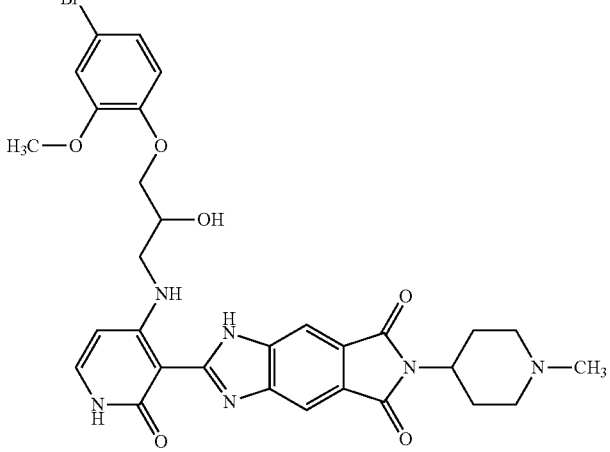 | C30H31BrN6O6 | 652.5 |
| 29' | 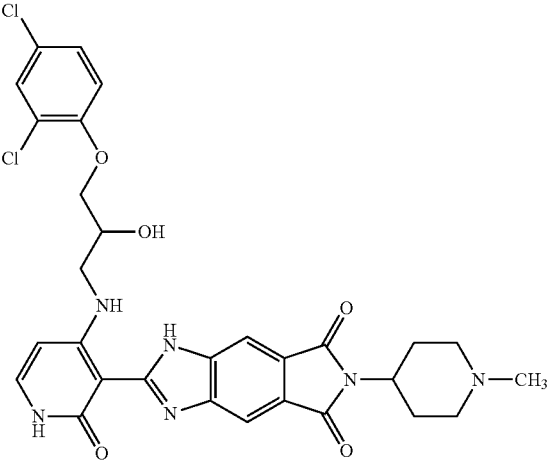 [SMILES: CN1CCC(N2C(=O)c3cc4nc(-c5c(NCC(O)COc6ccc(Cl)cc6Cl)cc[nH]c5=O)[nH]c4cc3C2=O)CC1] | C29H28Cl2N6O5 | 612.5 |
| 30' | 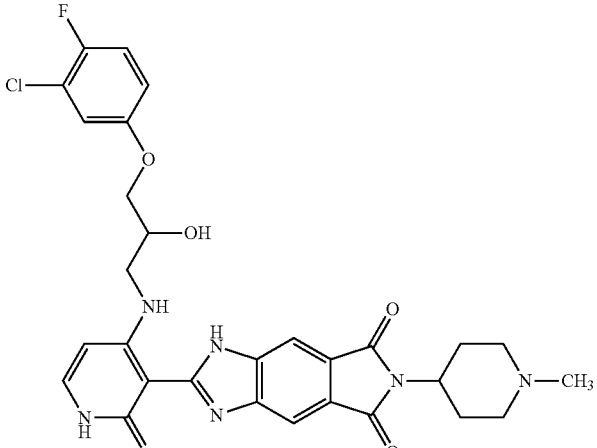 | C29H28ClFN6O5 | 596.0 |

TABLE II-continued

| Compound | Structure | Molecular Formula | [M + H]+ |
|---|---|---|---|
| 31' | (3,4-dichlorophenoxy)-CH2-CH(OH)-CH2-NH- linked to pyridin-2(1H)-one-3-yl connected to 1H-benzimidazole fused pyrrolo-dione with N-(1-methylpiperidin-4-yl) | C29H28Cl2N6O5 | 612.5 |
| 32' | (3,5-dichlorophenoxy)-CH2-CH(OH)-CH2-NH- linked to pyridin-2(1H)-one-3-yl connected to 1H-benzimidazole fused pyrrolo-dione with N-(1-methylpiperidin-4-yl) | C29H28Cl2N6O5 | 612.5 |
| 33' | (3-chloro-2-methylphenoxy)-CH2-CH(OH)-CH2-NH- linked to pyridin-2(1H)-one-3-yl connected to 1H-benzimidazole fused pyrrolo-dione with N-(1-methylpiperidin-4-yl) | C30H31ClN6O5 | 592.1 |

TABLE II-continued

| Compound | Structure | Molecular Formula | [M + H]+ |
|---|---|---|---|
| 34' | 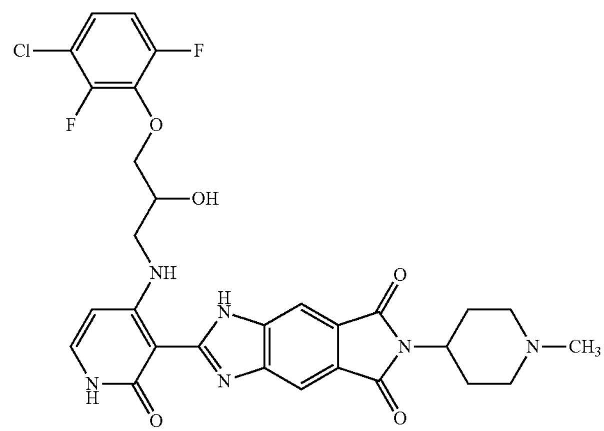 | C29H27ClF2N6O5 | 614.0 |
| 35' | 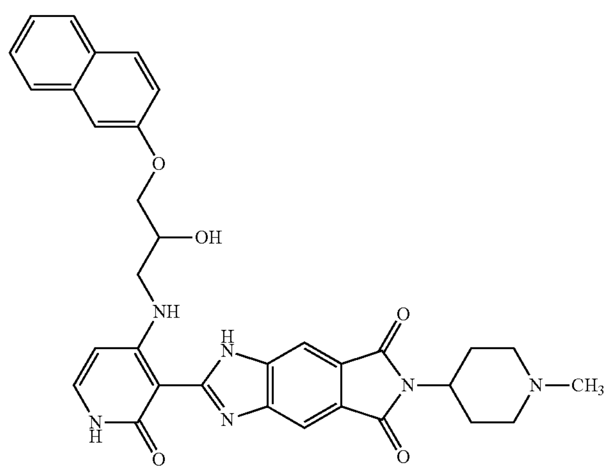 [SMILES: CN1CCC(N2C(=O)c3cc4nc(-c5c(NCC(O)COc6ccc7ccccc7c6)cc[nH]c5=O)[nH]c4cc3C2=O)CC1] | C33H32N6O5 | 593.7 |
| 36' | 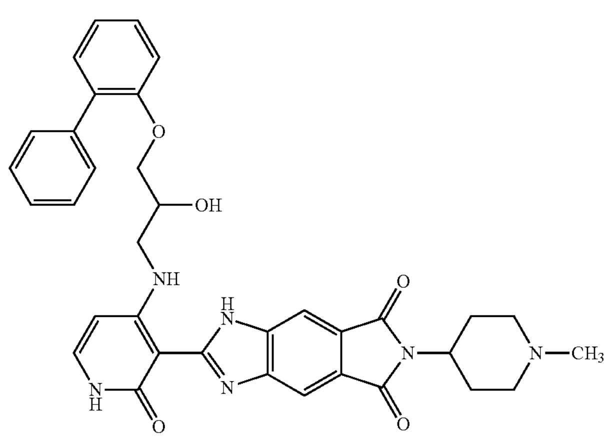 [SMILES: CN1CCC(N2C(=O)c3cc4nc(-c5c(NCC(O)COc6ccccc6-c6ccccc6)cc[nH]c5=O)[nH]c4cc3C2=O)CC1] | C35H34N6O5 | 619.7 |

TABLE II-continued
| Compound | Structure | Molecular Formula | [M + H]+ |
|---|---|---|---|
| 37' | 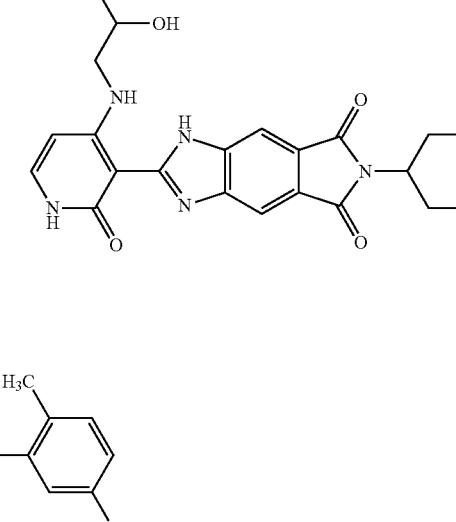 | C33H32N6O5 | 593.7 |
| 38' | 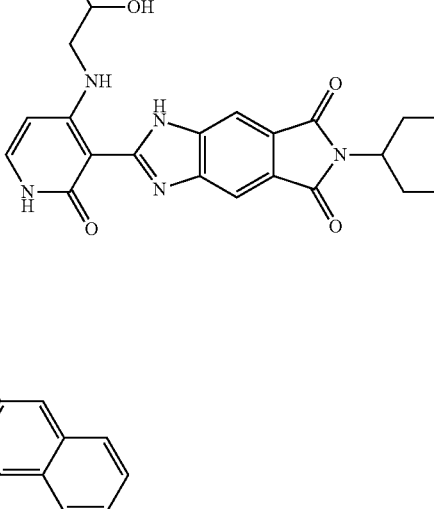 | C30H31ClN6O5 | 592.1 |
| 39' | 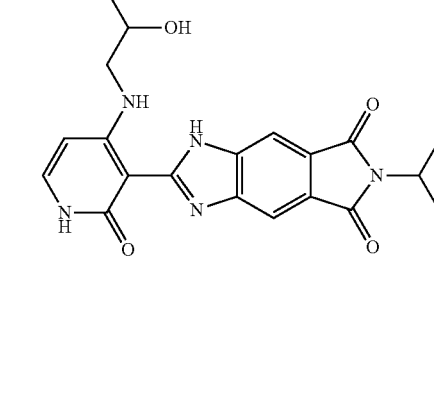 | C34H34N6O6 | 623.7 |

TABLE II-continued
| Compound | Structure | Molecular Formula | [M + H]+ |
|---|---|---|---|
| 40' | 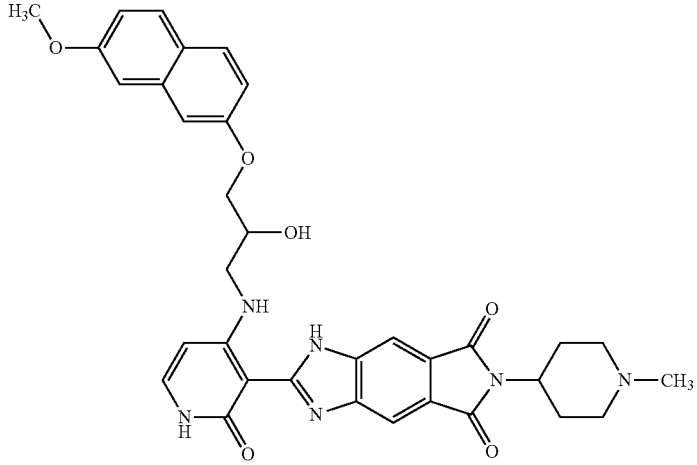 | C34H34N6O6 | 623.7 |
| 41' | 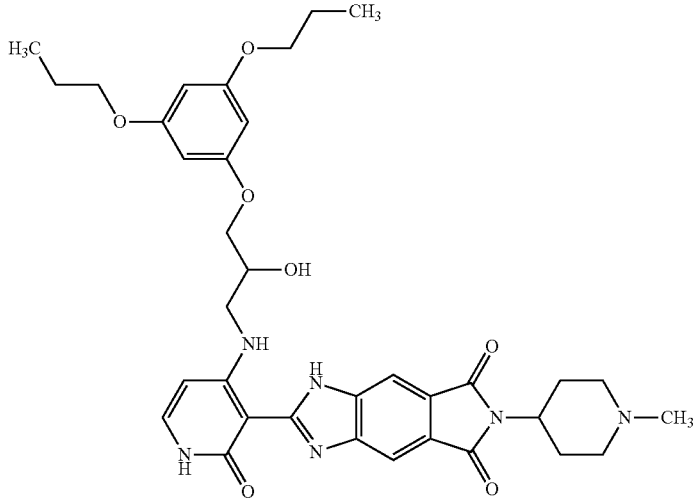 [SMILES: CCCOc1cc(OCCC)cc(OCC(O)CNc2cc[nH]c(=O)c2-c2nc3cc4c(cc3[nH]2)C(=O)N(C2CCN(C)CC2)C4=O)c1] | C35H42N6O7 | 659.8 |
| 42' | 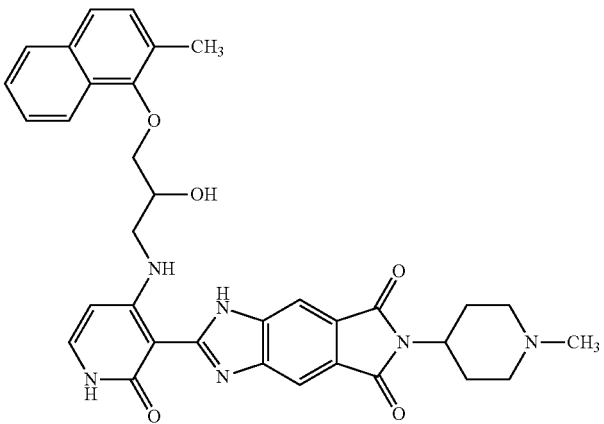 [SMILES: Cc1ccc2ccccc2c1OCC(O)CNc1cc[nH]c(=O)c1-c1nc2cc3c(cc2[nH]1)C(=O)N(C1CCN(C)CC1)C3=O] | C34H34N6O5 | 607.7 |

TABLE II-continued

| Compound | Structure | Molecular Formula | [M + H]+ |
|---|---|---|---|
| 43' | 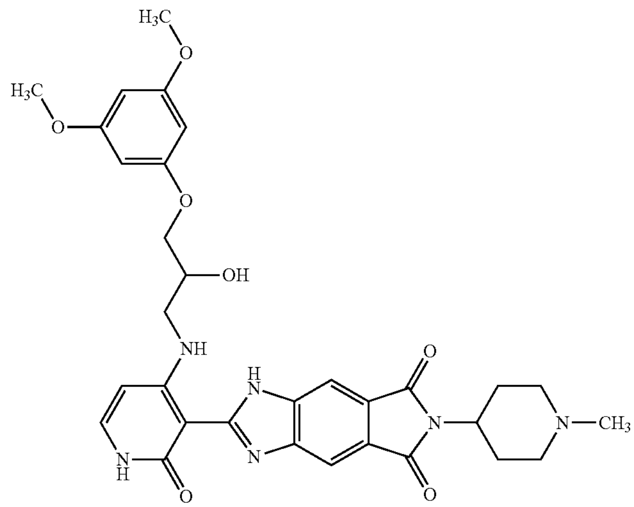 | C31H34N6O7 | 603.6 |
| 44' | 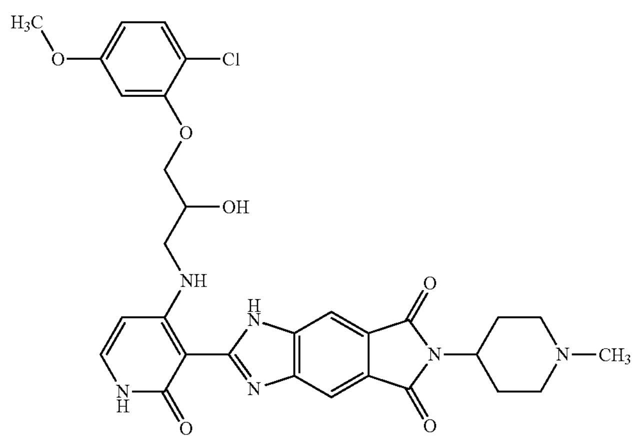 | C30H31ClN6O6 | 608.1 |
| 45' | 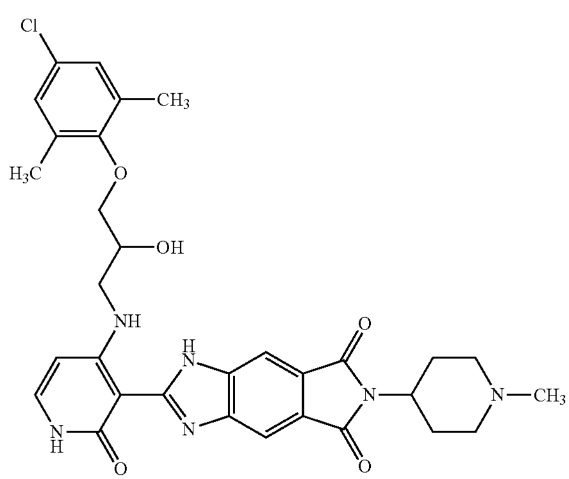 [SMILES: Cc1cc(Cl)cc(C)c1OCC(O)CNc1cc[nH]c(=O)c1-c1nc2cc3c(cc2[nH]1)C(=O)N(C1CCN(C)CC1)C3=O] | C31H33ClN6O5 | 606.1 |

TABLE II-continued

| Compound | Structure | Molecular Formula | [M + H]+ |
|---|---|---|---|
| 46' | 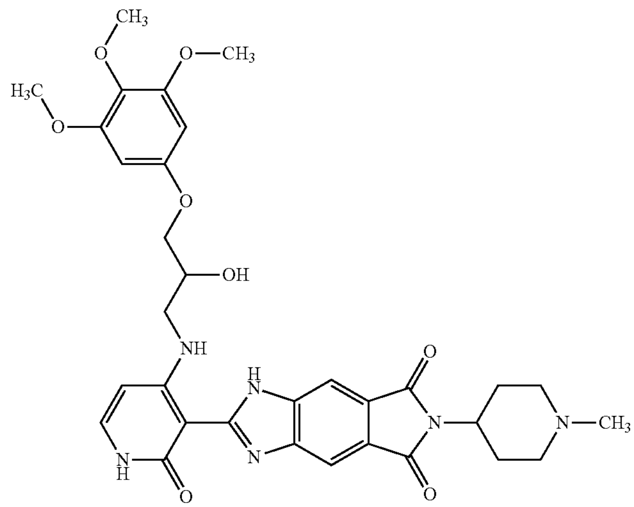 | C32H36N6O8 | 633.7 |
| 47' | 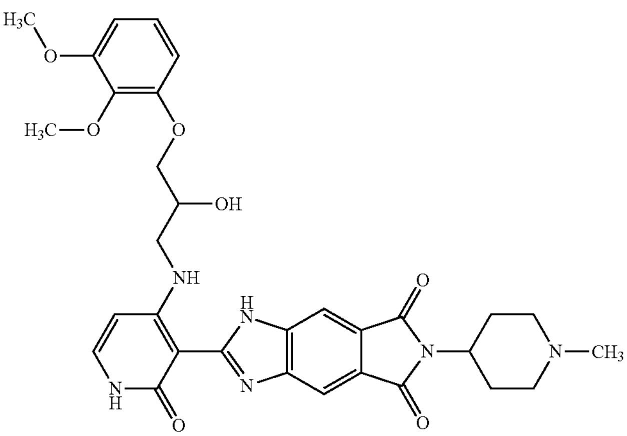 | C31H34N6O7 | 603.6 |
| 48' | 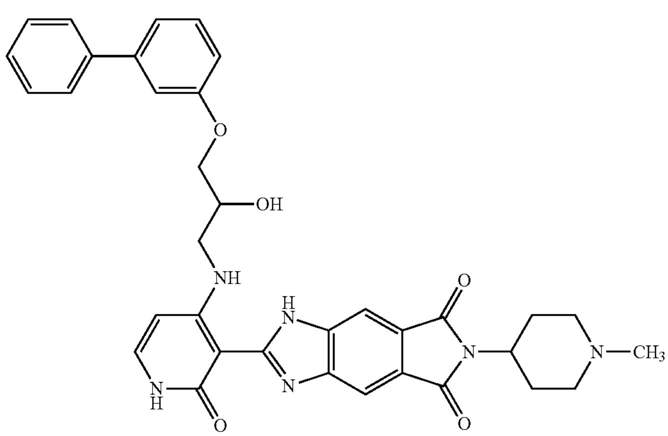 [SMILES: CN1CCC(N2C(=O)c3cc4nc(-c5c(NCC(O)COc6cccc(-c7ccccc7)c6)cc[nH]c5=O)[nH]c4cc3C2=O)CC1] | C35H34N6O5 | 619.7 |

TABLE II-continued
| Compound | Structure | Molecular Formula | [M + H]+ |
|---|---|---|---|
| 49' | 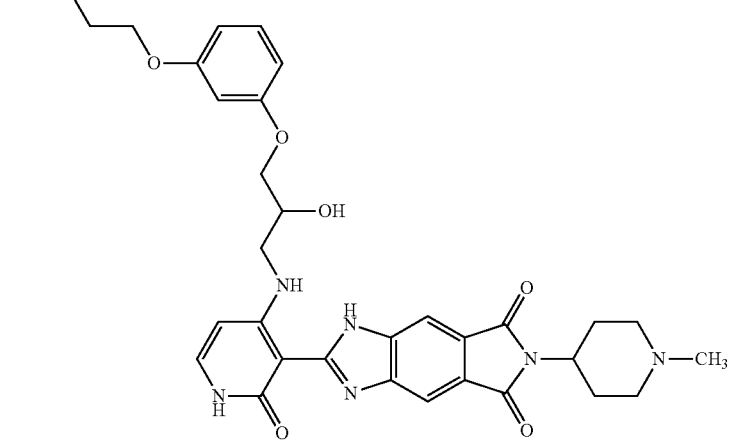 | C33H38N6O6 | 615.7 |
| 50' | 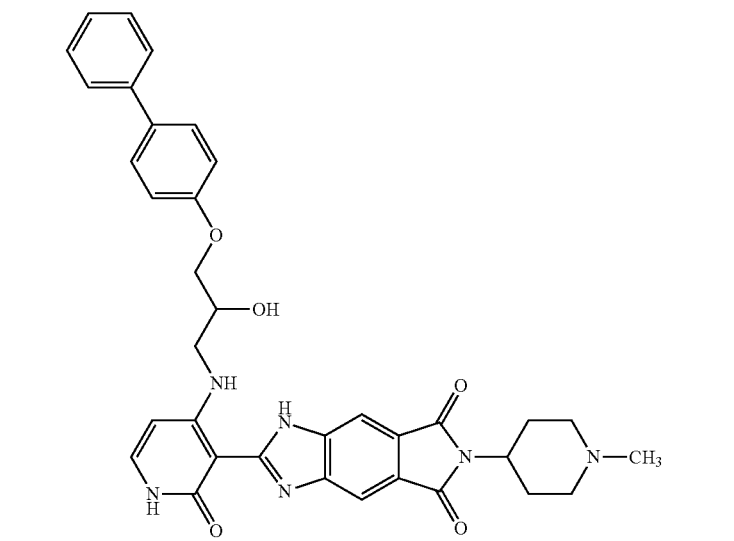 [SMILES: CN1CCC(N2C(=O)c3cc4nc(-c5c(NCC(O)COc6ccc(-c7ccccc7)cc6)cc[nH]c5=O)[nH]c4cc3C2=O)CC1] | C35H34N6O5 | 619.7 |
| 51' | 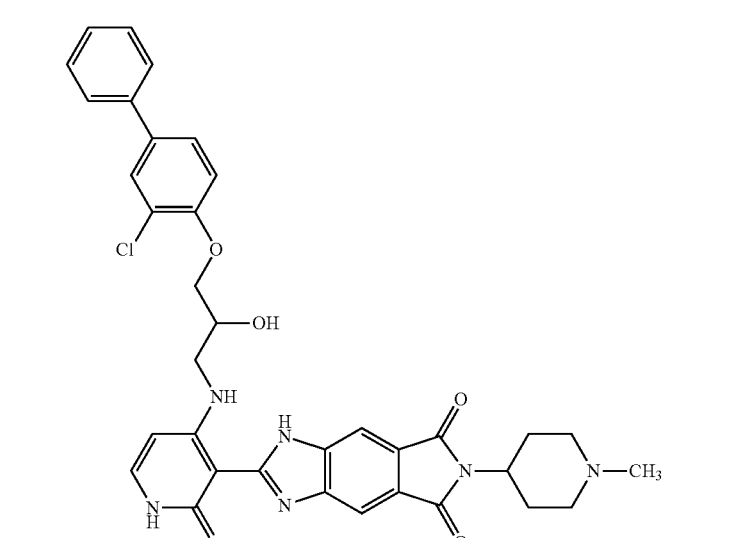 | C35H33ClN6O5 | 654.1 |

TABLE II-continued
| Compound | Structure | Molecular Formula | [M + H]+ |
|---|---|---|---|
| 52' | 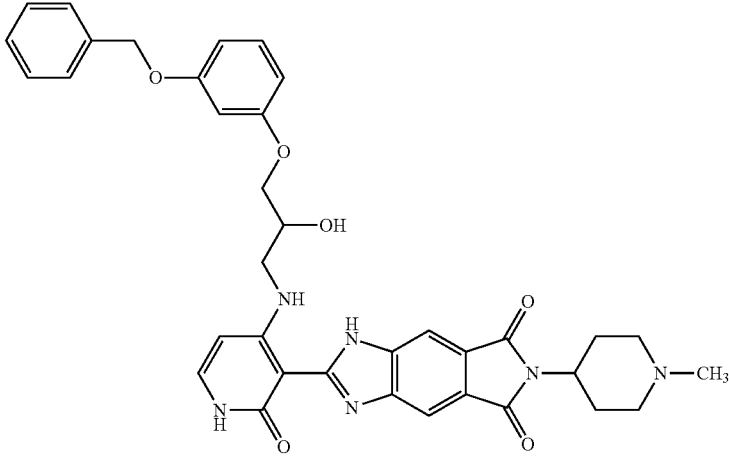 [SMILES: CN1CCC(N2C(=O)c3cc4nc(-c5c(NCC(O)COc6cccc(OCc7ccccc7)c6)cc[nH]c5=O)[nH]c4cc3C2=O)CC1] | C36H36N6O6 | 649.7 |
| 53' | 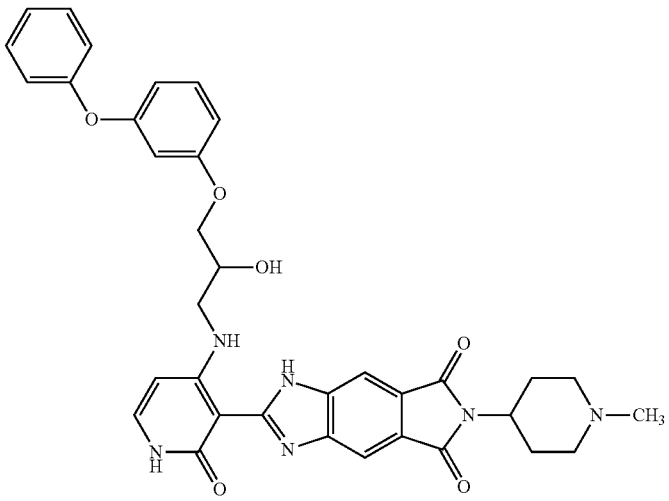 [SMILES: CN1CCC(N2C(=O)c3cc4nc(-c5c(NCC(O)COc6cccc(Oc7ccccc7)c6)cc[nH]c5=O)[nH]c4cc3C2=O)CC1] | C35H34N6O6 | 635.7 |
| 54' | 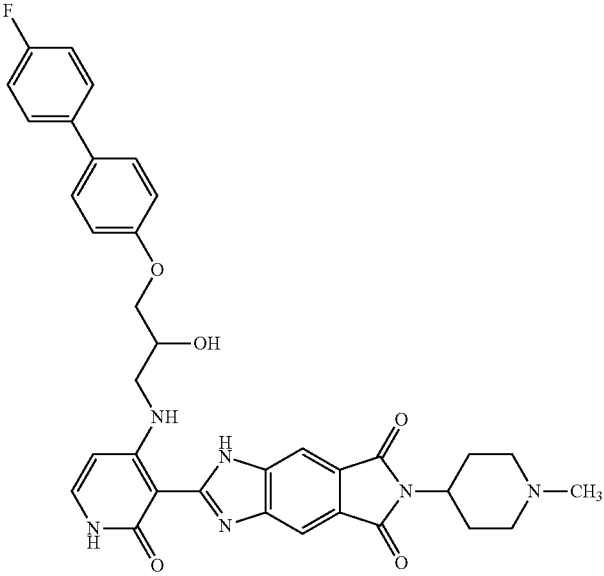 [SMILES: CN1CCC(N2C(=O)c3cc4nc(-c5c(NCC(O)COc6ccc(-c7ccc(F)cc7)cc6)cc[nH]c5=O)[nH]c4cc3C2=O)CC1] | C35H33FN6O5 | 637.7 |

TABLE II-continued
| Compound | Structure | Molecular Formula | [M + H]+ |
|---|---|---|---|
| 55' | 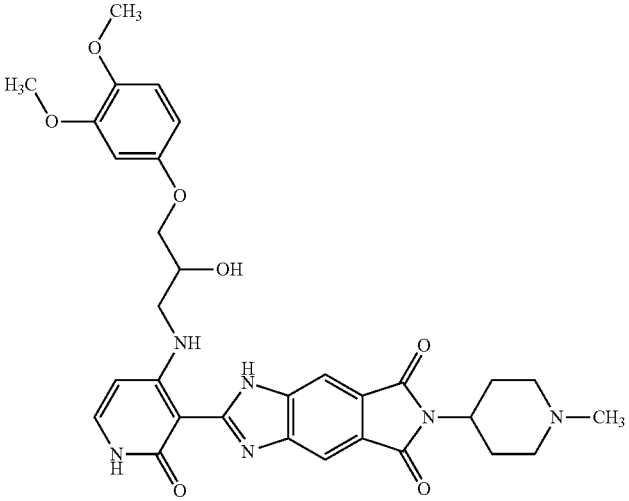 | C31H34N6O7 | 603.6 |
| 56' | 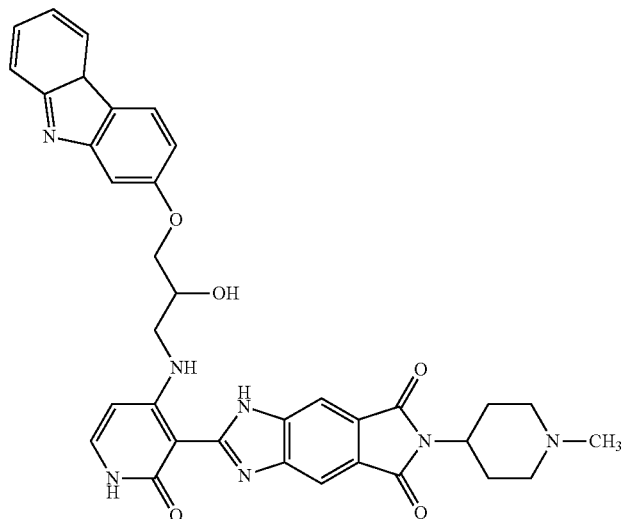 [SMILES: CN1CCC(N2C(=O)c3cc4nc(-c5c(NCC(O)COc6ccc7c(c6)N=C6C=CC=CC67)cc[nH]c5=O)[nH]c4cc3C2=O)CC1] | C35H33N7O5 | 632.7 |
| 57' | 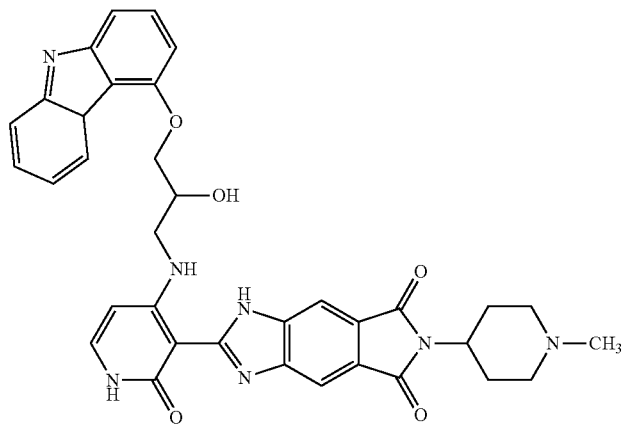 [SMILES: CN1CCC(N2C(=O)c3cc4nc(-c5c(NCC(O)COc6cccc7c6C6C=CC=CC6=N7)cc[nH]c5=O)[nH]c4cc3C2=O)CC1] | C35H33N7O5 | 632.7 |

TABLE II-continued

| Compound | Structure | Molecular Formula | [M + H]⁺ |
|---|---|---|---|
| 58' | 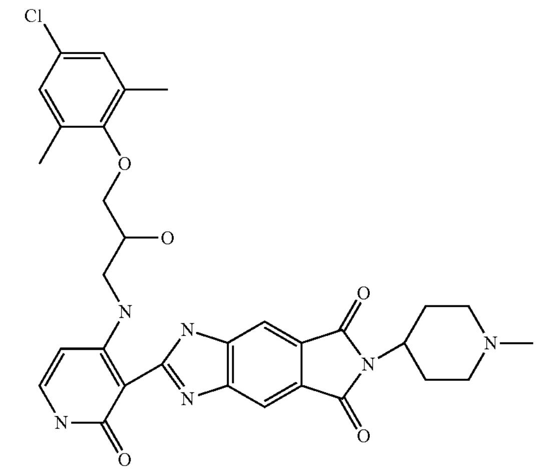 [SMILES: Cc1cc(Cl)cc(C)c1OCC(O)CNc1cc[nH]c(=O)c1-c1nc2cc3c(cc2[nH]1)C(=O)N(C1CCN(C)CC1)C3=O] | C31H33ClN6O5 | 606.1 |
| 59' | 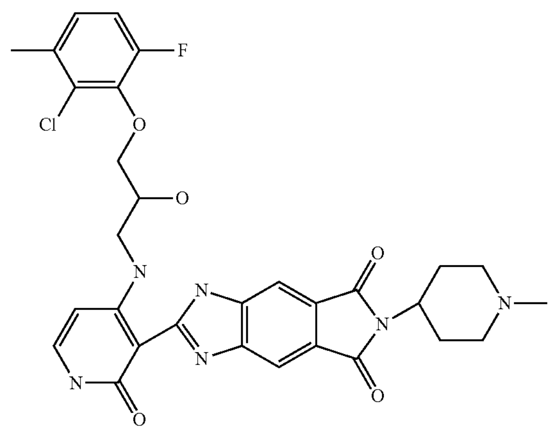 | C30H30ClFN6O5 | 610.1 |
| 60' | 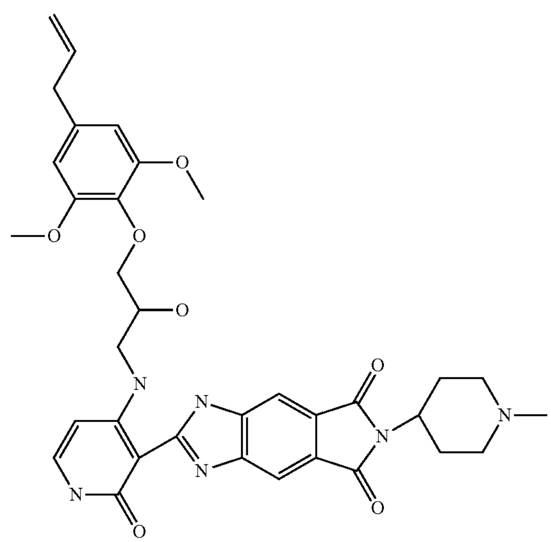 | C34H38N6O7 | 643.7 |

TABLE II-continued
| Compound | Structure | Molecular Formula | [M + H]+ |
|---|---|---|---|
| 61' | 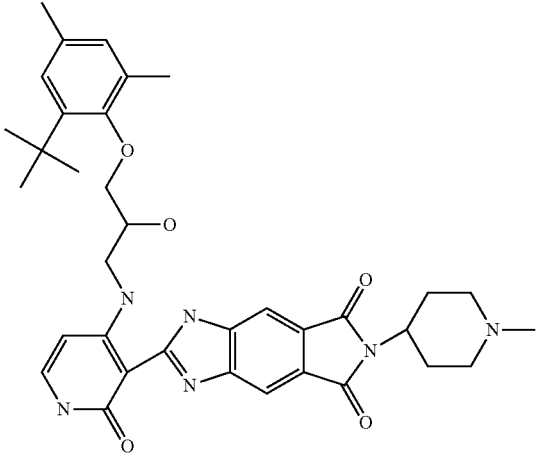 [SMILES: Cc1cc(C)c(OCC(O)CNc2cc[nH]c(=O)c2-c2nc3cc4c(cc3[nH]2)C(=O)N(C2CCN(C)CC2)C4=O)c(C(C)(C)C)c1] | C35H42N6O5 | 627.8 |
| 62' | 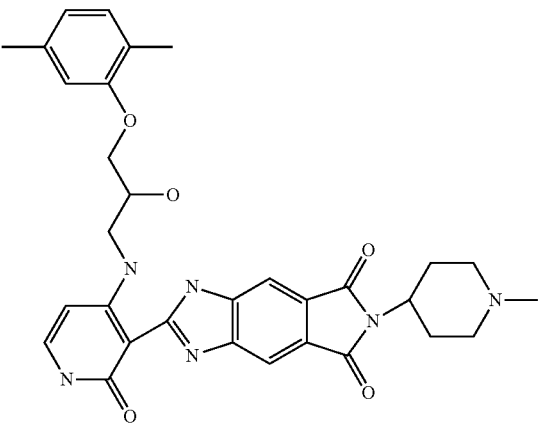 | C31H34N6O5 | 571.7 |
| 63' | 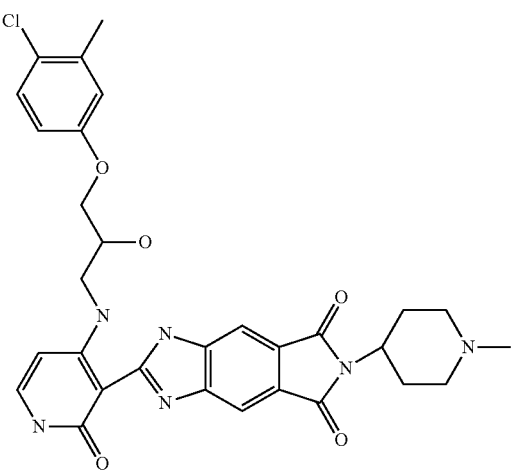 [SMILES: Cc1cc(OCC(O)CNc2cc[nH]c(=O)c2-c2nc3cc4c(cc3[nH]2)C(=O)N(C2CCN(C)CC2)C4=O)ccc1Cl] | C30H31ClN6O5 | 592.1 |

TABLE II-continued
| Compound | Structure | Molecular Formula | [M + H]+ |
|---|---|---|---|
| 64' | 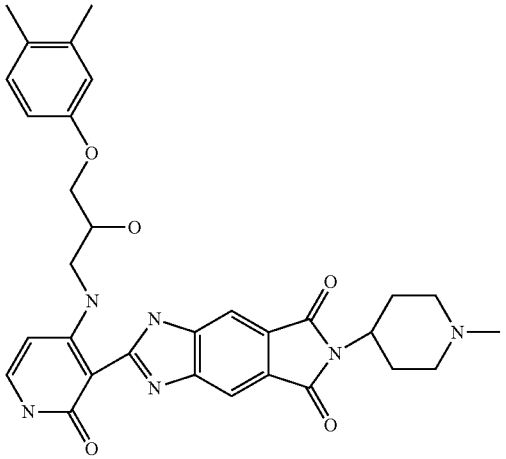 | C31H34N6O5 | 571.7 |
| 65' | 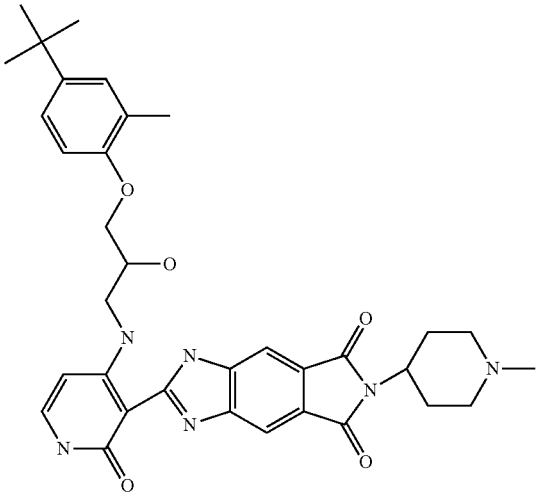 [SMILES: Cc1cc(C(C)(C)C)ccc1OCC(O)CNc1cc[nH]c(=O)c1-c1nc2cc3c(cc2[nH]1)C(=O)N(C1CCN(C)CC1)C3=O] | C34H40N6O5 | 613.7 |
| 66' | 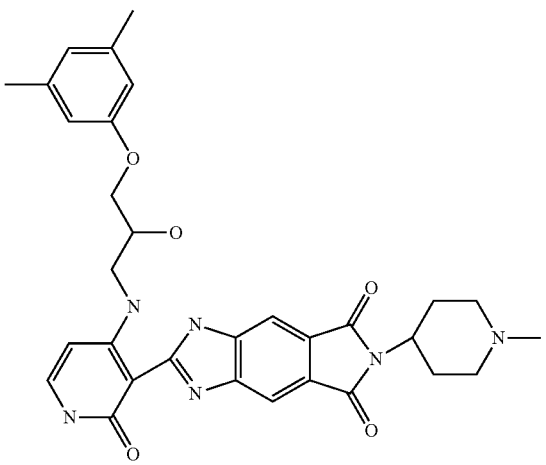 | C31H34N6O5 | 571.7 |

TABLE II-continued
| Compound | Structure | Molecular Formula | [M + H]+ |
|---|---|---|---|
| 67' | 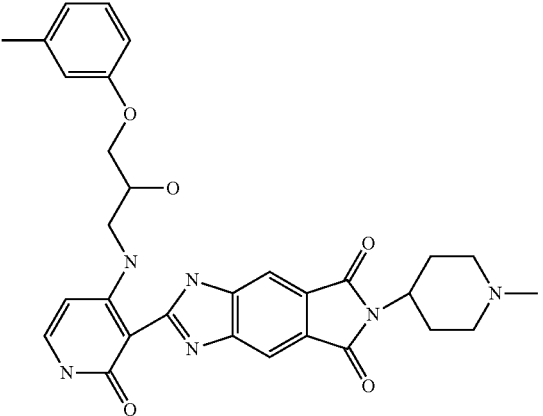 | C30H32N6O5 | 557.6 |
| 68' | 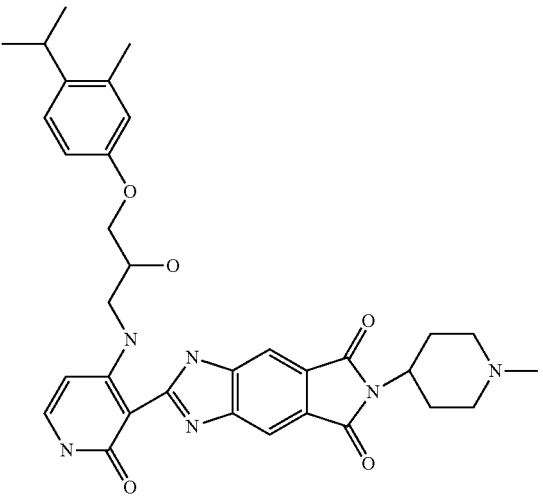 [SMILES: Cc1cc(OCC(O)CNc2cc[nH]c(=O)c2-c2nc3cc4c(cc3[nH]2)C(=O)N(C2CCN(C)CC2)C4=O)ccc1C(C)C] | C33H38N6O5 | 599.7 |
| 69' | 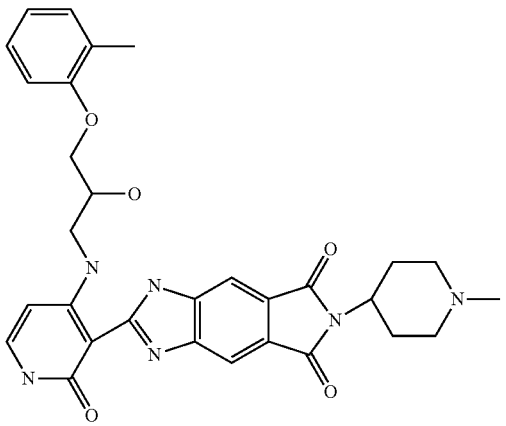 | C30H32N6O5 | 557.6 |

TABLE II-continued

| Compound | Structure | Molecular Formula | [M + H]+ |
|---|---|---|---|
| 70' | 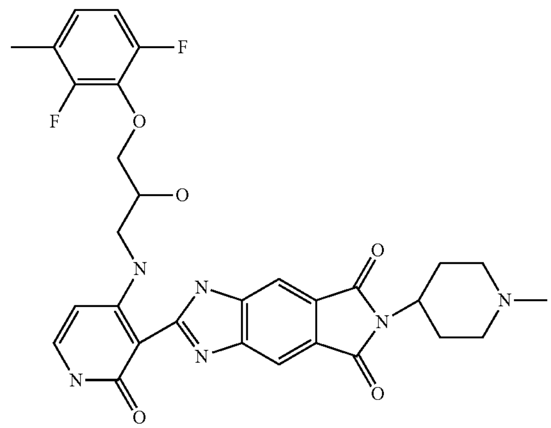 | C30H30F2N6O5 | 593.6 |
| 71' | 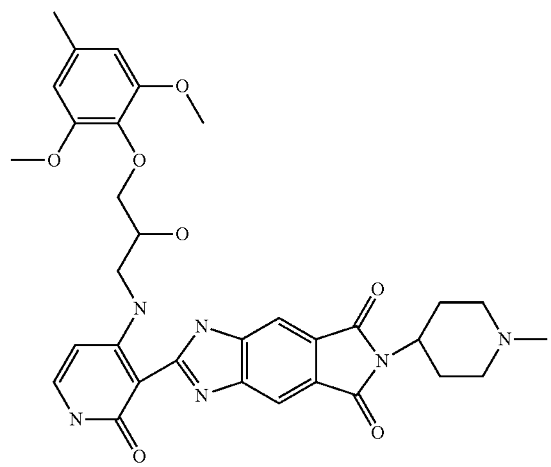 | C32H36N6O7 | 617.7 |
| 72' | 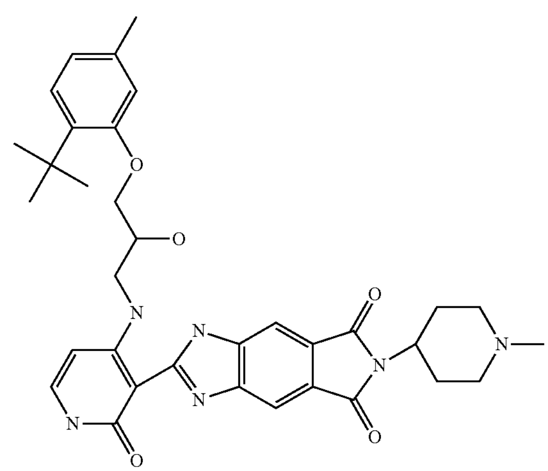 [SMILES: Cc1ccc(C(C)(C)C)c(OCC(O)CNc2cc[nH]c(=O)c2-c2nc3cc4c(cc3[nH]2)C(=O)N(C2CCN(C)CC2)C4=O)c1] | C34H40N6O5 | 613.7 |

TABLE II-continued
| Compound | Structure | Molecular Formula | [M + H]+ |
|---|---|---|---|
| 73' | 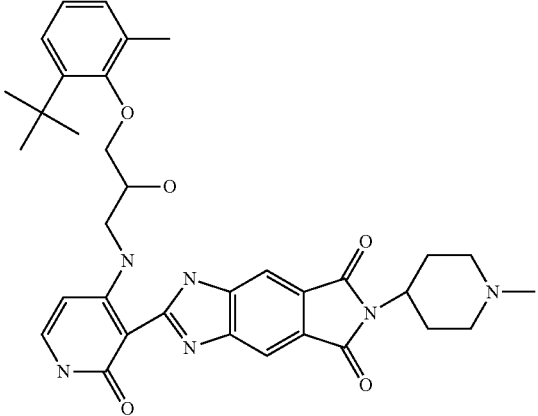 [SMILES: Cc1cccc(C(C)(C)C)c1OCC(O)CNc1cc[nH]c(=O)c1-c1nc2cc3c(cc2[nH]1)C(=O)N(C1CCN(C)CC1)C3=O] | C34H40N6O5 | 613.7 |
| 74' | 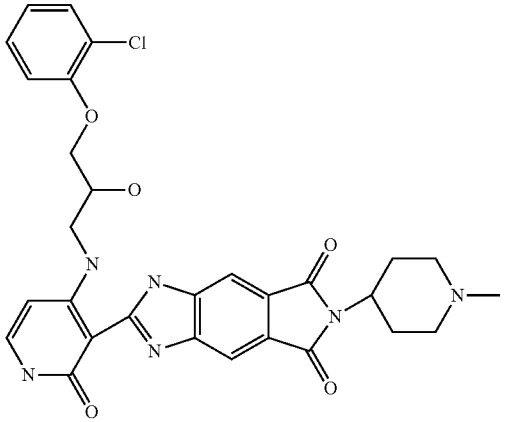 [SMILES: CN1CCC(N2C(=O)c3cc4nc(-c5c(NCC(O)COc6ccccc6Cl)cc[nH]c5=O)[nH]c4cc3C2=O)CC1] | C29H29ClN6O5 | 578.0 |
| 75' | 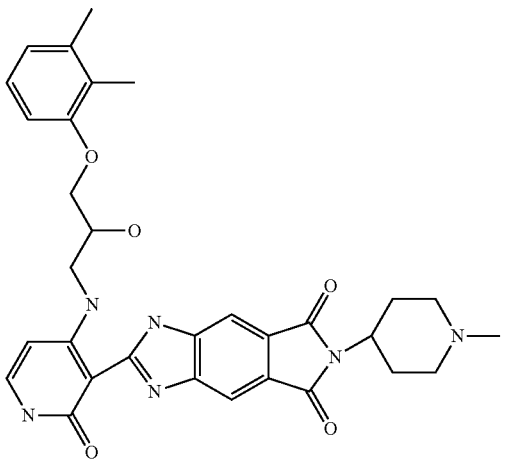 | C31H34N6O5 | 571.7 |

TABLE II-continued
| Compound | Structure | Molecular Formula | [M + H]+ |
|---|---|---|---|
| 76' | 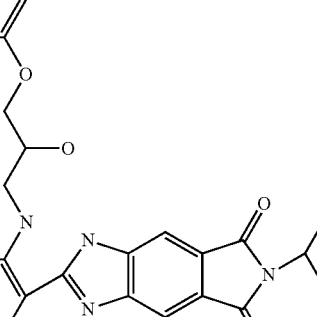 | C33H37N7O6 | 628.7 |
| 77' | 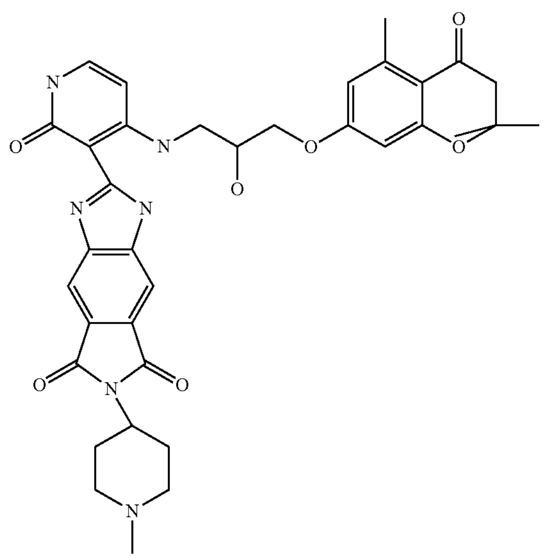 | C35H38N6O7 | 655.7 |
| 78' | 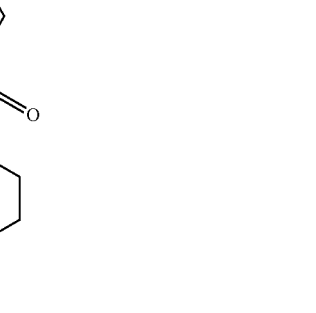 | C32H33N7O5 | 596.7 |

TABLE II-continued
| Compound | Structure | Molecular Formula | [M + H]+ |
|---|---|---|---|
| 79' | 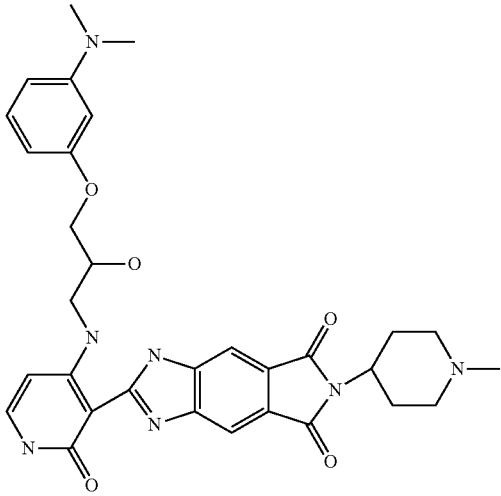 [SMILES: CN1CCC(N2C(=O)c3cc4nc(-c5c(NCC(O)COc6cccc(N(C)C)c6)cc[nH]c5=O)[nH]c4cc3C2=O)CC1] | C31H35N7O5 | 586.7 |
| 80' | 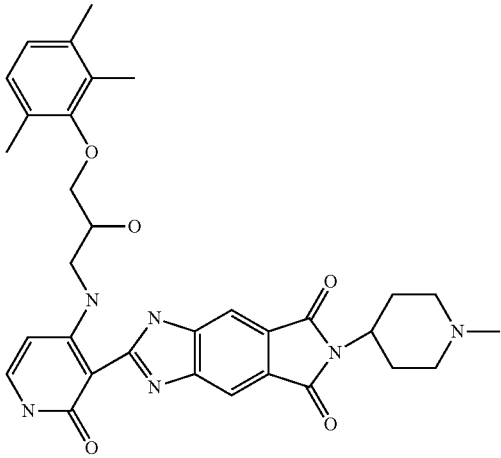 [SMILES: Cc1ccc(C)c(OCC(O)CNc2cc[nH]c(=O)c2-c2nc3cc4c(cc3[nH]2)C(=O)N(C2CCN(C)CC2)C4=O)c1C] | C32H36N6O5 | 585.7 |
| 81' | 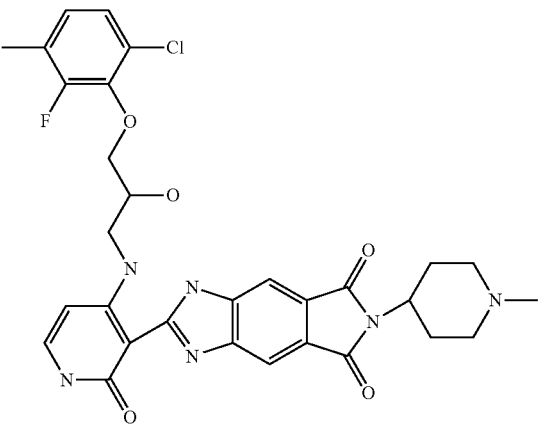 | C30H30ClFN6O5 | 610.1 |

TABLE II-continued

| Compound | Structure | Molecular Formula | [M + H]+ |
|---|---|---|---|
| 82' | 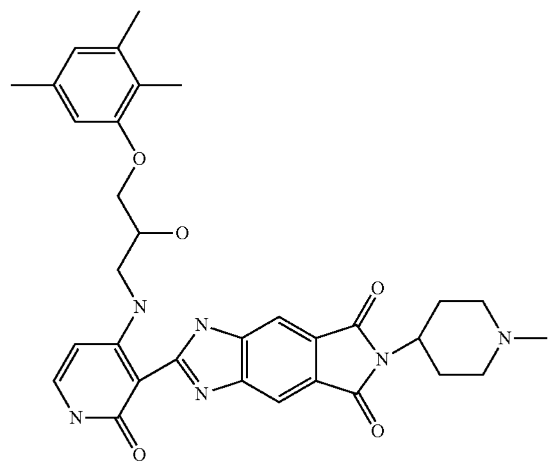 | C32H36N6O5 | 585.7 |
| 83' | 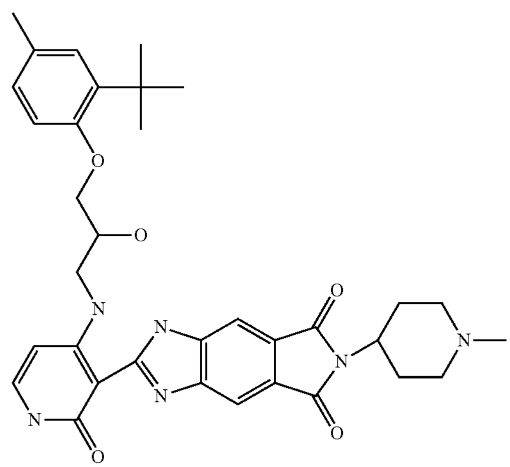 [SMILES: Cc1ccc(OCC(O)CNc2cc[nH]c(=O)c2-c2nc3cc4c(cc3[nH]2)C(=O)N(C2CCN(C)CC2)C4=O)c(C(C)(C)C)c1] | C34H40N6O5 | 613.7 |
| 84' | 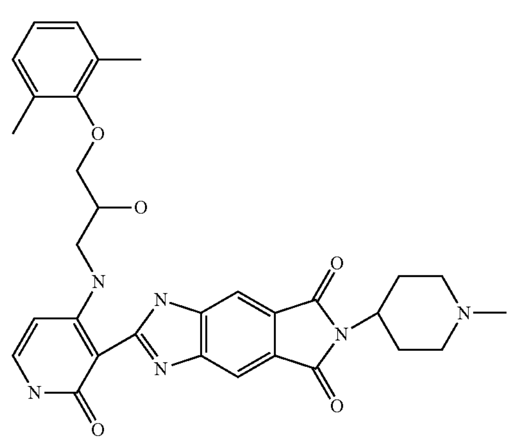 [SMILES: Cc1cccc(C)c1OCC(O)CNc1cc[nH]c(=O)c1-c1nc2cc3c(cc2[nH]1)C(=O)N(C1CCN(C)CC1)C3=O] | C31H34N6O5 | 571.7 |

TABLE II-continued
| Compound | Structure | Molecular Formula | [M + H]+ |
|---|---|---|---|
| 85' | 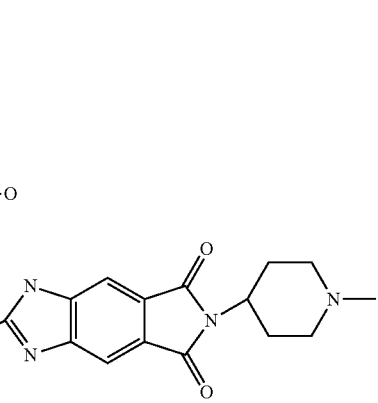 | C31H34N6O5 | 571.7 |
| 86' | 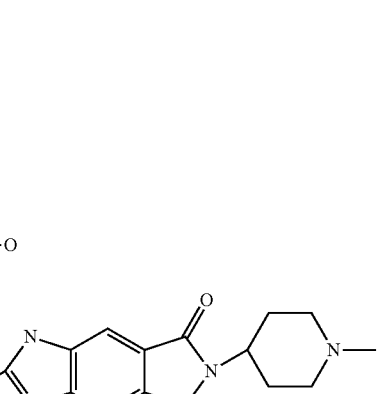 | C30H32N6O5 | 557.6 |
| 87' | 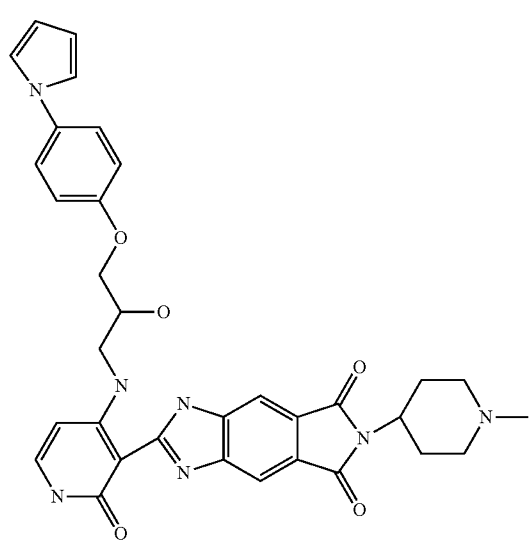 [SMILES: CN1CCC(N2C(=O)c3cc4nc(-c5c(NCC(O)COc6ccc(-n7cccc7)cc6)cc[nH]c5=O)[nH]c4cc3C2=O)CC1] | C33H33N7O5 | 608.7 |

TABLE II-continued
| Compound | Structure | Molecular Formula | [M + H]+ |
|---|---|---|---|
| 88' | 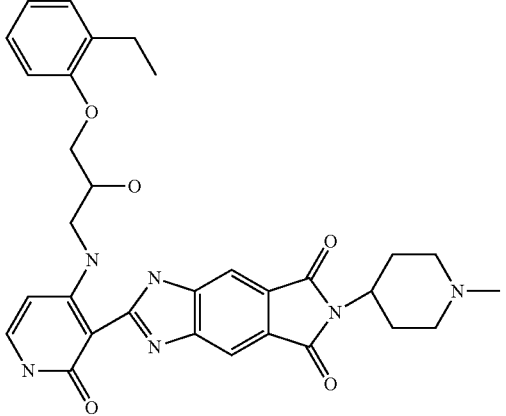 [SMILES: CCc1ccccc1OCC(O)CNc1cc[nH]c(=O)c1-c1nc2cc3c(cc2[nH]1)C(=O)N(C1CCN(C)CC1)C3=O] | C31H34N6O5 | 571.7 |
| 89' | 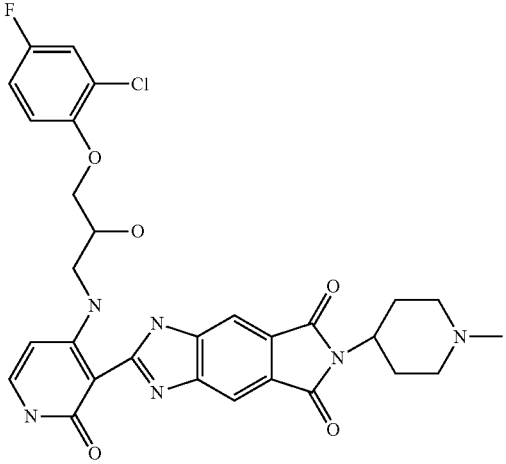 [SMILES: CN1CCC(N2C(=O)c3cc4nc(-c5c(NCC(O)COc6ccc(F)cc6Cl)cc[nH]c5=O)[nH]c4cc3C2=O)CC1] | C29H28ClFN6O5 | 596.0 |
| 90' | 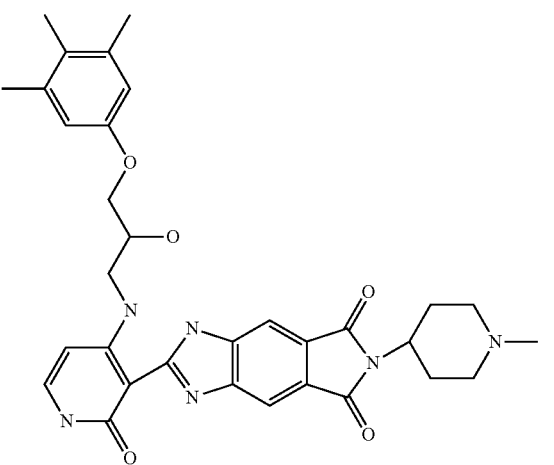 | C32H36N6O5 | 585.7 |

TABLE II-continued

| Compound | Structure | Molecular Formula | [M + H]+ |
|---|---|---|---|
| 91' | 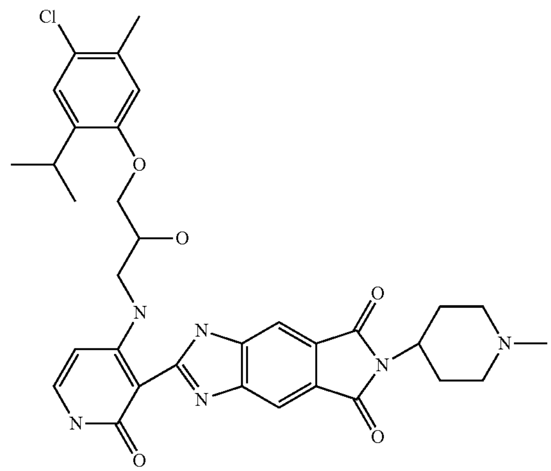 [SMILES: Cc1cc(OCC(O)CNc2cc[nH]c(=O)c2-c2nc3cc4c(cc3[nH]2)C(=O)N(C2CCN(C)CC2)C4=O)c(C(C)C)cc1Cl] | C33H37ClN6O5 | 634.2 |
| 92' | 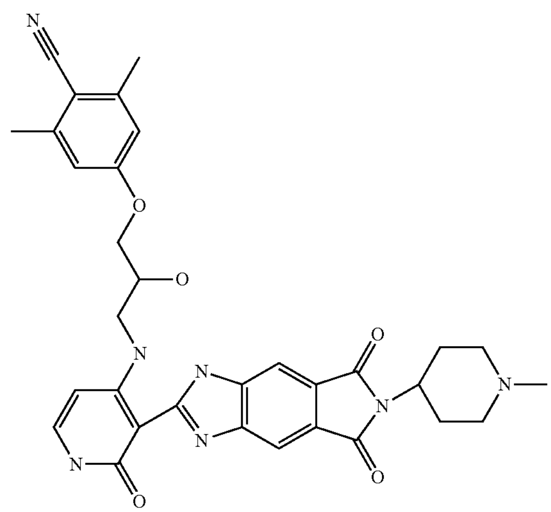 | C32H33N7O5 | 596.7 |
| 93' | 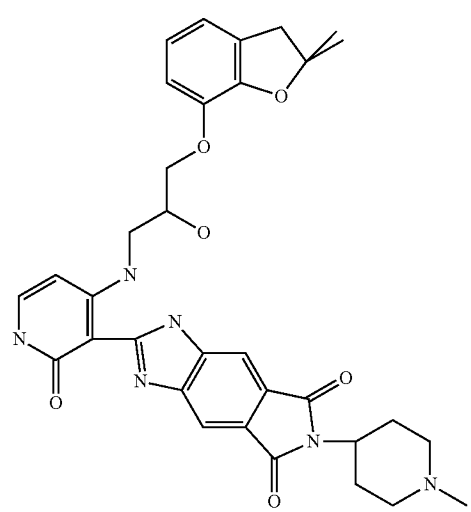 [SMILES: CN1CCC(N2C(=O)c3cc4nc(-c5c(NCC(O)COc6cccc7c6OC(C)(C)C7)cc[nH]c5=O)[nH]c4cc3C2=O)CC1] | C33H36N6O6 | 613.7 |

TABLE II-continued

| Compound | Structure | Molecular Formula | [M + H]+ |
|---|---|---|---|
| 94' | 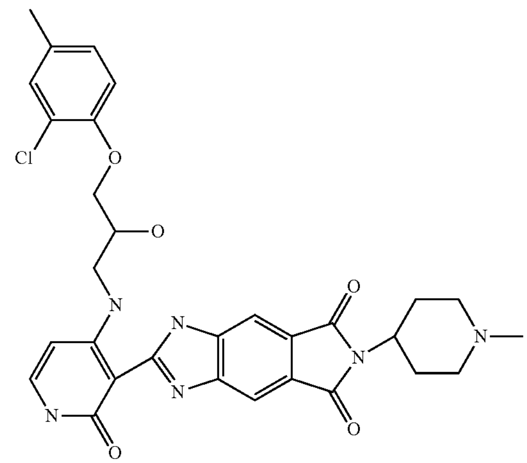 [SMILES: Cc1ccc(OCC(O)CNc2cc[nH]c(=O)c2-c2nc3cc4c(cc3[nH]2)C(=O)N(C2CCN(C)CC2)C4=O)c(Cl)c1] | C30H31ClN6O5 | 592.1 |
| 95' | 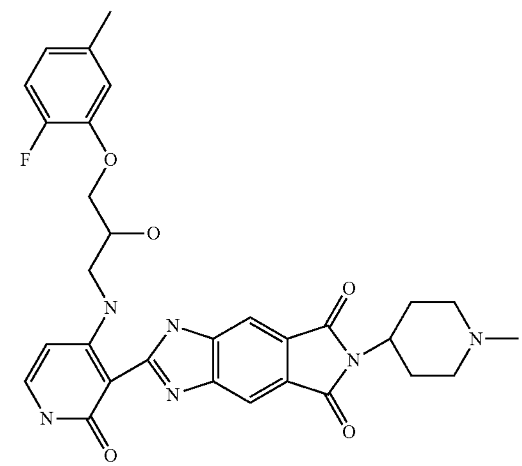 [SMILES: Cc1ccc(F)c(OCC(O)CNc2cc[nH]c(=O)c2-c2nc3cc4c(cc3[nH]2)C(=O)N(C2CCN(C)CC2)C4=O)c1] | C30H31FN6O5 | 575.6 |
| 96' | 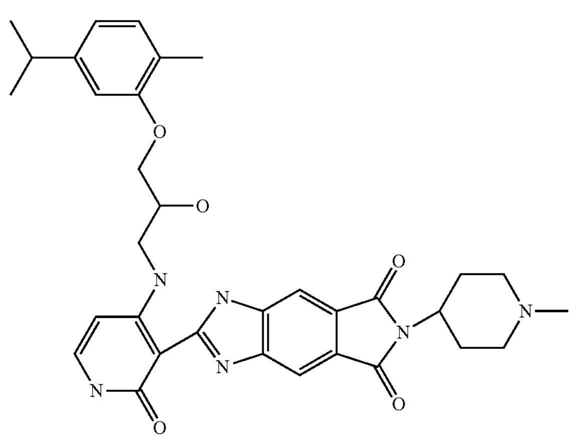 [SMILES: Cc1ccc(C(C)C)cc1OCC(O)CNc1cc[nH]c(=O)c1-c1nc2cc3c(cc2[nH]1)C(=O)N(C1CCN(C)CC1)C3=O] | C33H38N6O5 | 599.7 |

TABLE II-continued
| Compound | Structure | Molecular Formula | [M + H]+ |
|---|---|---|---|
| 97' | 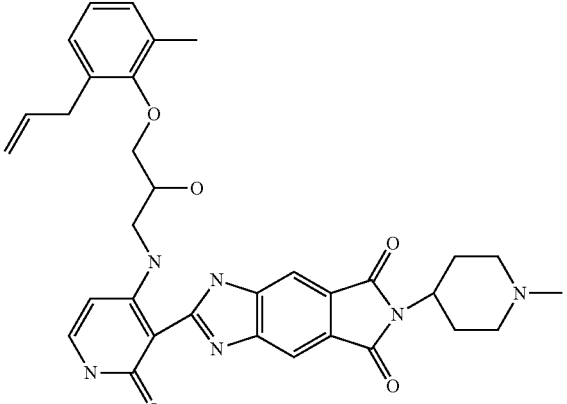 | C33H36N6O5 | 597.7 |
| 98' | 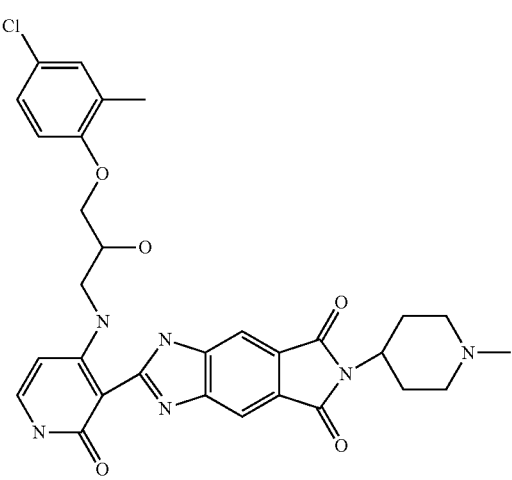 [SMILES: Cc1cc(Cl)ccc1OCC(O)CNc1cc[nH]c(=O)c1-c1nc2cc3c(cc2[nH]1)C(=O)N(C1CCN(C)CC1)C3=O] | C30H31ClN6O5 | 592.1 |
| 99' | 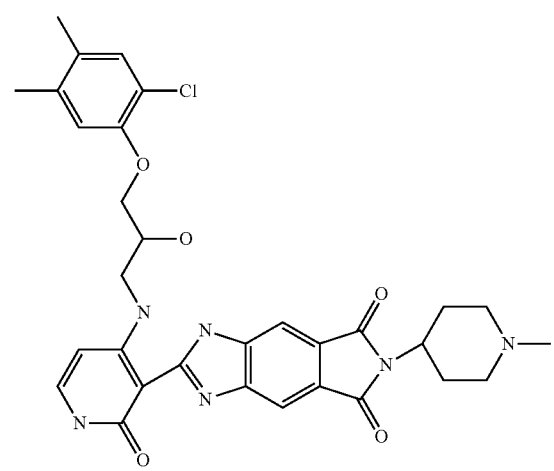 | C31H33ClN6O5 | 606.1 |

TABLE II-continued

| Compound | Structure | Molecular Formula | [M + H]+ |
|---|---|---|---|
| 100' | 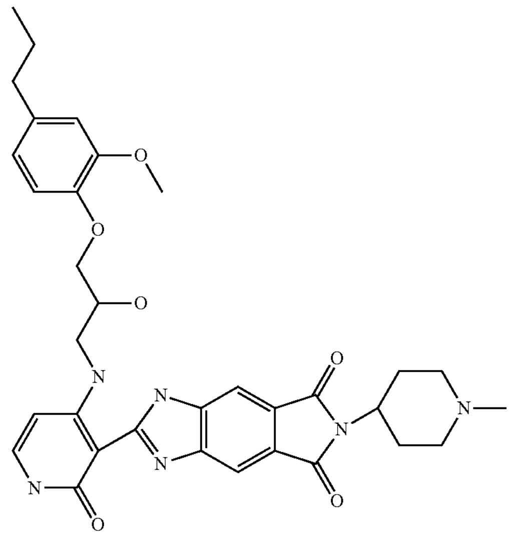 [SMILES: CCCc1ccc(OCC(O)CNc2cc[nH]c(=O)c2-c2nc3cc4c(cc3[nH]2)C(=O)N(C2CCN(C)CC2)C4=O)c(OC)c1] | C33H38N6O6 | 615.7 |
| 101' | 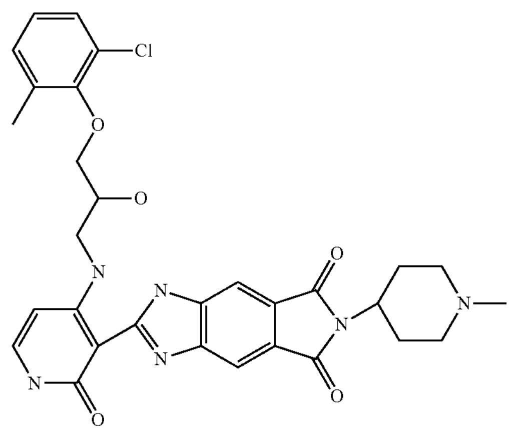 [SMILES: Cc1cccc(Cl)c1OCC(O)CNc1cc[nH]c(=O)c1-c1nc2cc3c(cc2[nH]1)C(=O)N(C1CCN(C)CC1)C3=O] | C30H31ClN6O5 | 592.1 |
| 102' | 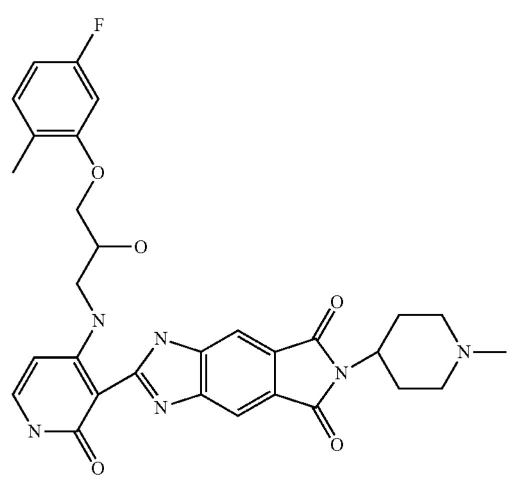 [SMILES: Cc1ccc(F)cc1OCC(O)CNc1cc[nH]c(=O)c1-c1nc2cc3c(cc2[nH]1)C(=O)N(C1CCN(C)CC1)C3=O] | C30H31FN6O5 | 575.6 |

TABLE II-continued

| Compound | Structure | Molecular Formula | [M + H]+ |
|---|---|---|---|
| 103' | 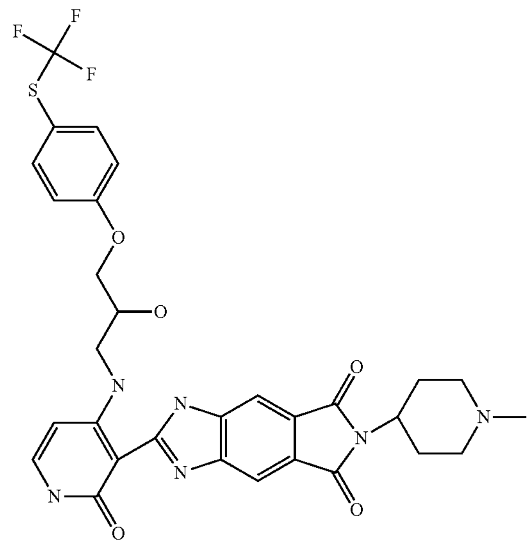 [SMILES: CN1CCC(N2C(=O)c3cc4nc(-c5c(NCC(O)COc6ccc(SC(F)(F)F)cc6)cc[nH]c5=O)[nH]c4cc3C2=O)CC1] | C30H29F3N6O5S | 643.7 |
| 104' | 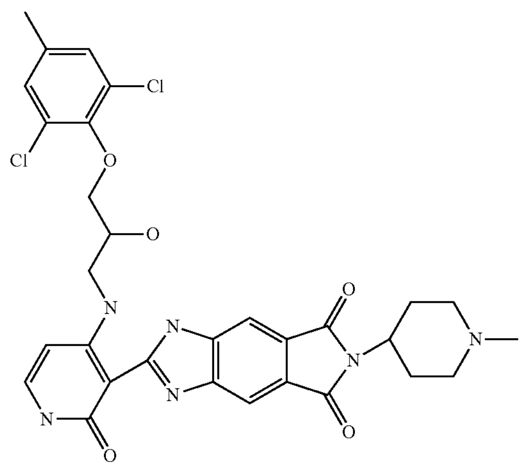 [SMILES: Cc1cc(Cl)c(OCC(O)CNc2cc[nH]c(=O)c2-c2nc3cc4c(cc3[nH]2)C(=O)N(C2CCN(C)CC2)C4=O)c(Cl)c1] | C30H30Cl2N6O5 | 626.5 |
| 105' | 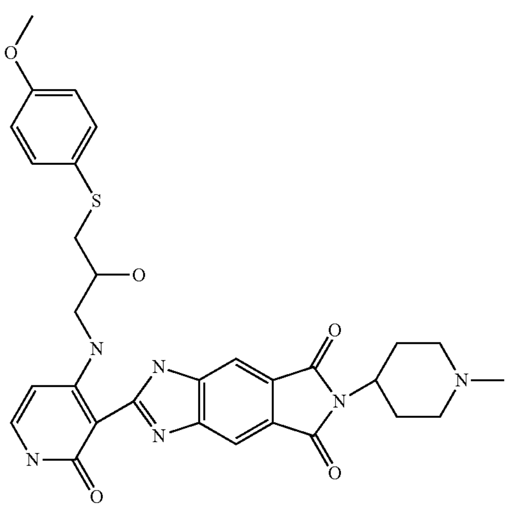 [SMILES: COc1ccc(SCC(O)CNc2cc[nH]c(=O)c2-c2nc3cc4c(cc3[nH]2)C(=O)N(C2CCN(C)CC2)C4=O)cc1] | C30H32N6O5S | 589.7 |

TABLE II-continued
| Compound | Structure | Molecular Formula | [M + H]+ |
| --- | --- | --- | --- |
| 106' | 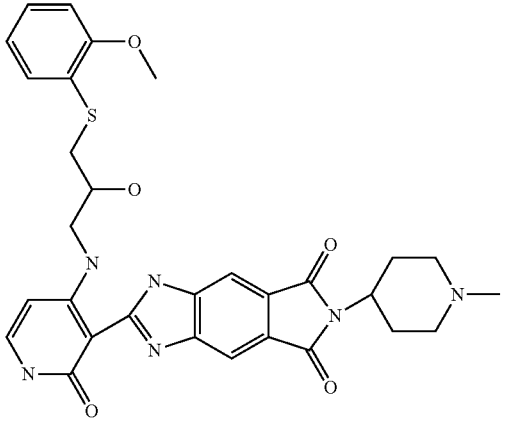 [SMILES: COc1ccccc1SCC(O)CNc1cc[nH]c(=O)c1-c1nc2cc3c(cc2[nH]1)C(=O)N(C1CCN(C)CC1)C3=O] | C30H32N6O5S | 589.7 |
| 107' | 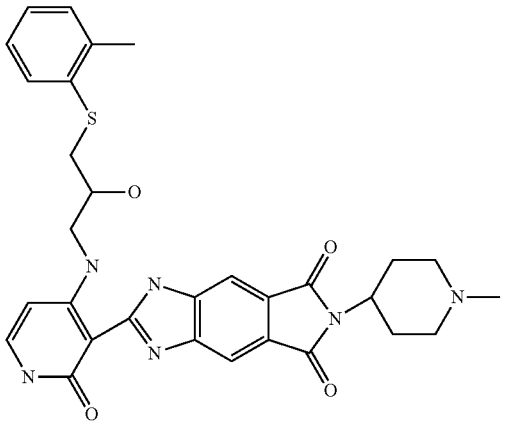 [SMILES: Cc1ccccc1SCC(O)CNc1cc[nH]c(=O)c1-c1nc2cc3c(cc2[nH]1)C(=O)N(C1CCN(C)CC1)C3=O] | C30H32N6O4S | 573.7 |
| 108' | 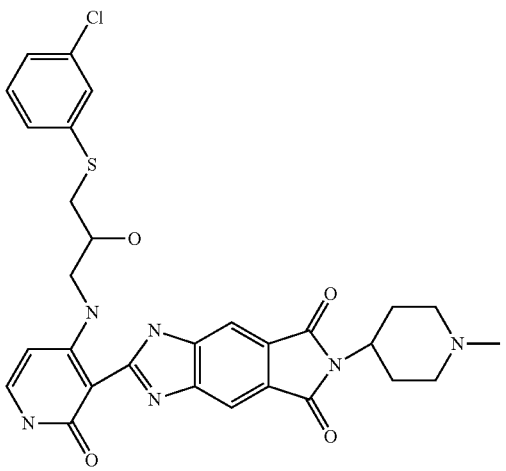 [SMILES: CN1CCC(N2C(=O)c3cc4nc(-c5c(NCC(O)CSc6cccc(Cl)c6)cc[nH]c5=O)[nH]c4cc3C2=O)CC1] | C29H29ClN6O4S | 594.1 |

TABLE II-continued
| Compound | Structure | Molecular Formula | [M + H]+ |
|---|---|---|---|
| 109' | 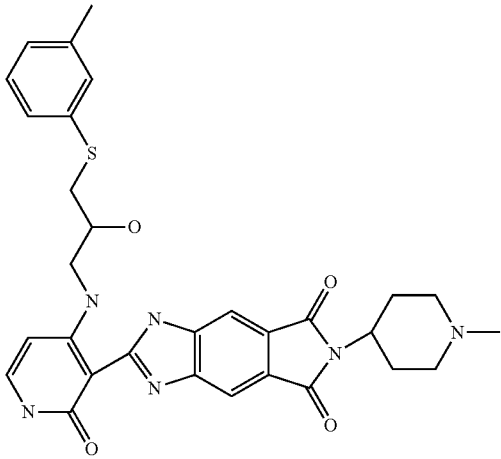 [SMILES: Cc1cccc(SCC(O)CNc2cc[nH]c(=O)c2-c2nc3cc4c(cc3[nH]2)C(=O)N(C2CCN(C)CC2)C4=O)c1] | C30H32N6O4S | 573.7 |
| 110' | 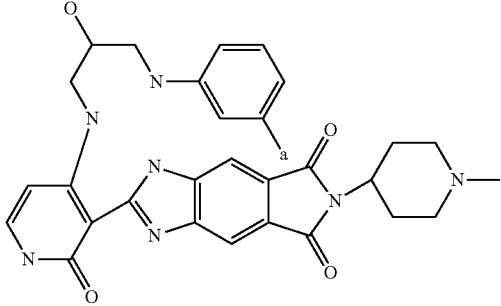 | C29H30ClN7O4 | 577.1 |
| 111' | 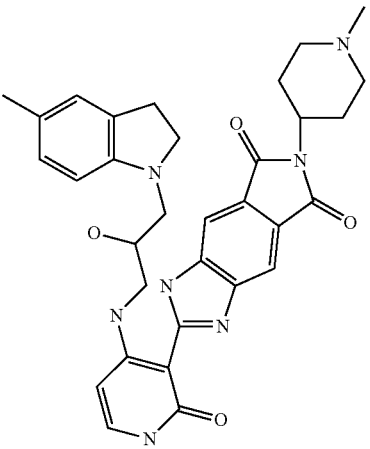 | C32H35N7O4 | 582.7 |
| 112' | 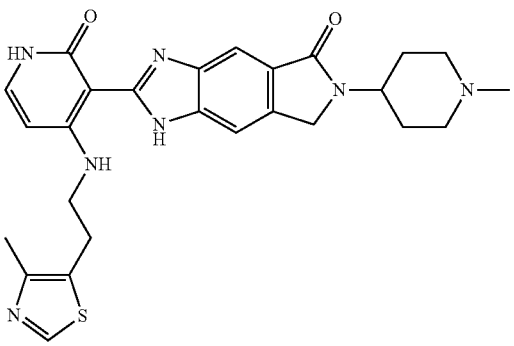 [SMILES: Cc1ncsc1CCNc1cc[nH]c(=O)c1-c1nc2cc3c(cc2[nH]1)CN(C1CCN(C)CC1)C3=O] | $C_{26}H_{29}N_7O_2S$ | 503.21 |

Methods of Use

In one aspect, provided are methods for modulating the activity of a tyrosine kinase. In general, the methods comprise the step of contacting the tyrosine kinase with a compound of the invention. The contacting can be in any environ known to those of skill in the art, for instance, in vitro, in vivo, ex vivo or otherwise. In certain embodiments, the present invention provides methods of modulating the activity of a tyrosine kinase in a mammal in need thereof comprising contacting the tyrosine kinase with a compound of the invention.

In another aspect, the protein tyrosine kinase, the catalytic activity of which is modulated by contact with a compound provided herein, or a stereoisomer, tautomer, salt, hydrate or prodrug thereof, is a receptor protein tyrosine kinase (RTK). Among the receptor protein tyrosine kinases whose catalytic activity can be modulated with a compound of this invention, are, without limitation, Alk, Axl, CSFR, DDR1, DDR2, EphB4, EphA2, EGFR, Flt-1, Flt3, Flt4, FGFR1, FGFR2, FGFR3, FGFR4, HER2, HER3, HER4, IR, IGF1R, IRR, Kit, KDR/Flk-1, Met, Mer, PDGFR.alpha., PDGFR.beta., Ret, Ros, Ron, Tie1, Tie2, TrkA, TrkB, TrkC.

In yet another aspect, the protein tyrosine kinase whose catalytic activity is modulated by contact with a compound of this invention, or a stereoisomer, tautomer, salt, hydrate or prodrug thereof, can also be a non-receptor or cellular protein tyrosine kinase (CTK). Thus, the catalytic activity of CTKs such as, without limitation, Abl, Arg, Ack, Blk, Bmx, Brk, Btk, Csk, Pyk2, Fak, Fes, Fgr, Fps, Frk, Fyn, Hck, Itk, Jak1, Jak2, Jak3, Lck, Lyn, Src, Syk, Tec, Yes, ZAP70, may be modulated by contact with a compound or a stereoisomer, tautomer, salt, hydrate or prodrug thereof provided herein.

In another aspect, provided are methods for treating or preventing a tyrosine kinase related disorder in a subject in need thereof. In general, the methods comprise administering to the subject an amount of a compound or a stereoisomer, tautomer, salt, hydrate or prodrug thereof effective to treat or prevent the disorder. The compound can be in the form of a pharmaceutical composition or a unit dose as described below.

A tyrosine kinase related disorder can be any disorder known to those of skill in the art to be related to tyrosine kinase activity. Such disorders include those related to excessive tyrosine kinase active, those related to reduced tyrosine kinase activity and to those that can be treated or prevented by modulation of tyrosine kinase activity. Excessive tyrosine kinase activity can arise as the result of, for example: (1) tyrosine kinase expression in cells which normally do not express tyrosine kinases; (2) increased tyrosine kinase expression leading to unwanted cell proliferation, differentiation and/or growth; or, (3) decreased tyrosine kinase expression leading to unwanted reductions in cell proliferation, differentiation and/or growth.

The tyrosine kinase related disorder can be a cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma in a further aspect of this invention.

Other tyrosine kinase related disorder includes an IGFR-related disorder selected from diabetes, an autoimmune disorder, Alzheimer's and other cognitive disorders, a hyperproliferation disorder, aging, cancer, acromegaly, Crohn's disease, endometriosis, diabetic retinopathy, restenosis, fibrosis, psoriasis, osteoarthritis, rheumatoid arthritis, an inflammatory disorder and angiogenesis.

Other disorders which might be treated with compounds of this invention include, without limitation, immunological and cardiovascular disorders such as atherosclerosis.

In one aspect, the present invention provides a method of treating multiple myeloma in a subject in need thereof comprising administering to said subject an insulin-like growth factor receptor-1 (IGF-1R) inhibitor, wherein said IGF-1R inhibitor is a compound of formula I,

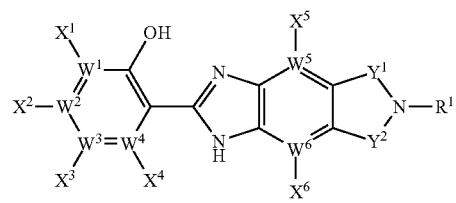

wherein:

each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

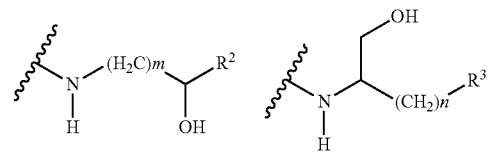

wherein:

m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —$(CH_2)_p$-$M^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein $M^1$ is O, S, and p is an integer between 0 and 4;

R³ is selected from optionally substituted aryl, heteroaryl, wherein the heteroaryl is imidazoyl, pyridinyl, benzo-dioxanyl, benzo-imidazolyl or indolyl, —(CH₂)ₒ-aryl, or —(CH₂)ₒ-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

Y¹ is

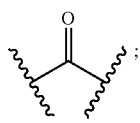

Y² is

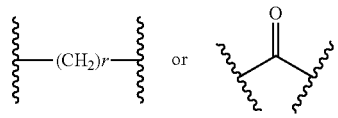

wherein: r is 1; and

R¹ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, SO₂-alkyl, SO-alkyl, CO-alkyl, CO₂-alkyl, cyano, cyanoalkyl, ketoalkyl, and methanesulfonylalkyl, or a pharmaceutically acceptable salt thereof.

In some embodiments, said compound is selected from the group consisting of (2a)

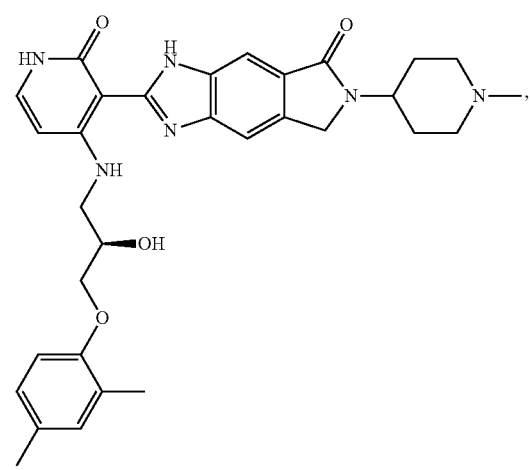

(2b)

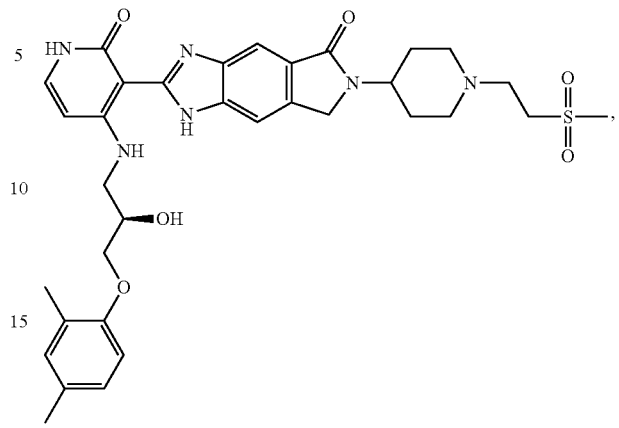

(2c)

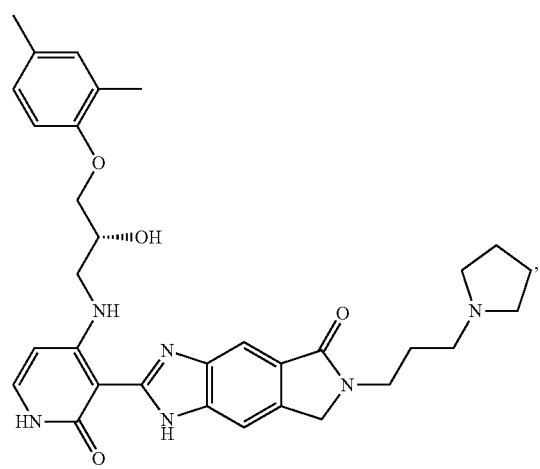

(2e)

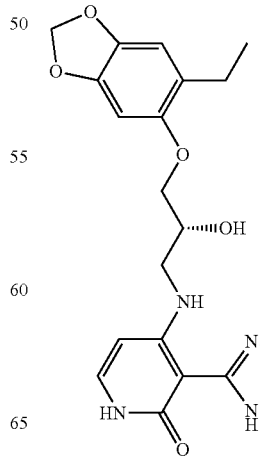

-continued (2h)
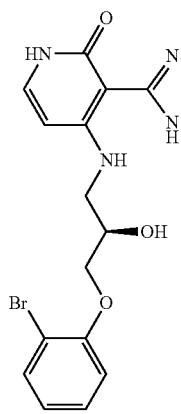

(2i)
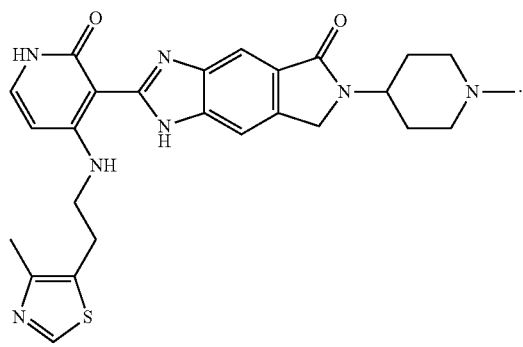

In some embodiments, said compound is (2a)
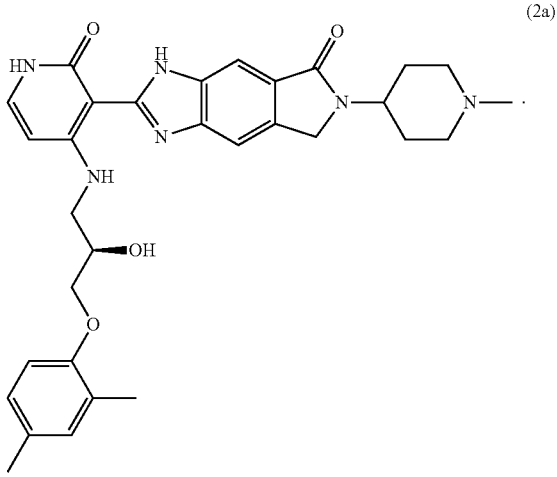

In other embodiments, said compound is (2b)
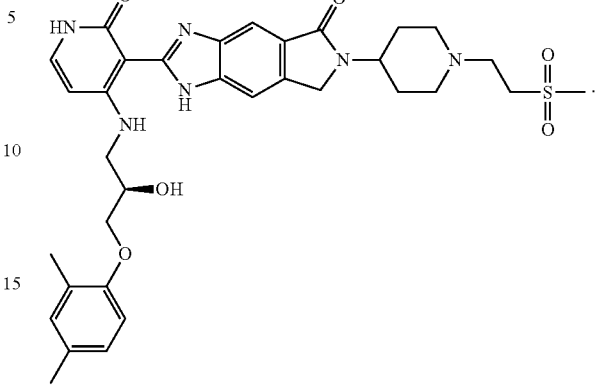

In some embodiments, said method further comprises administering at least one other anti-cancer agent.

In another aspect, the present invention provides a method of treating multiple myeloma in a subject comprising administering to said subject a composition comprising an insulin-like growth factor receptor-1 (IGF-1R) inhibitor, wherein said IGF-1R inhibitor is a compound of formula I,

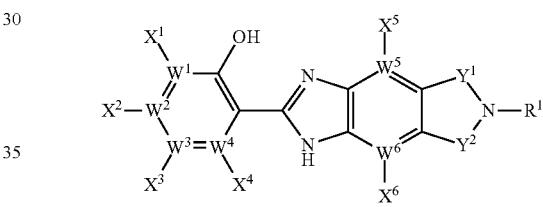

wherein:

each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

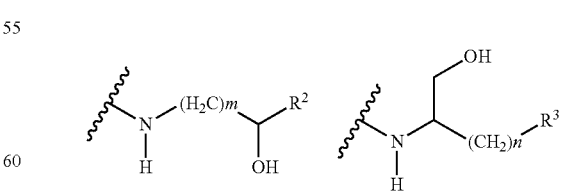

wherein:

m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —(CH$_2$)$_p$-M$^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein M$^1$ is O, S, and p is an integer between 0 and 4;

R$^3$ is selected from optionally substituted aryl, heteroaryl, wherein the heteroaryl is imidazoyl, pyridinyl, benzo-dioxanyl, benzo-imidazolyl or indolyl, —(CH$_2$)$_o$-aryl, or —(CH$_2$)$_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

Y$^1$ is

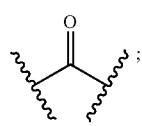 [SMILES: *C(*)=O]

Y$^2$ is

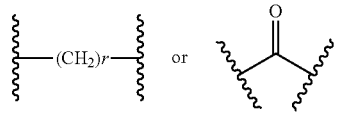

wherein: r is 1; and

R$^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, SO$_2$-alkyl, SO-alkyl, CO-alkyl, CO$_2$-alkyl, cyano, cyanoalkyl, ketoalkyl, and methanesulfonylalkyl, or a pharmaceutically acceptable salt thereof.

In some embodiments, said composition further comprises at least one other anti-cancer agent.

In some embodiments, said compound is selected from the group consisting of

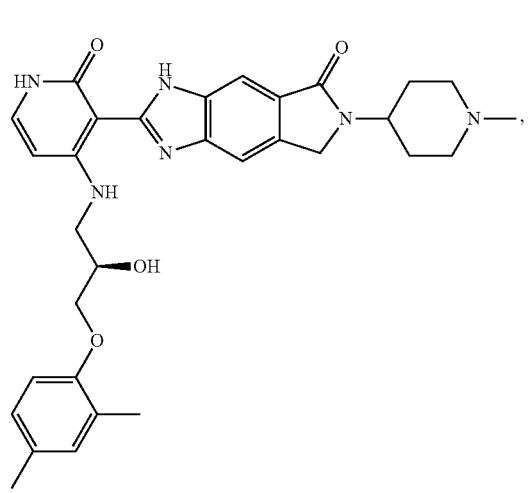

(2a)

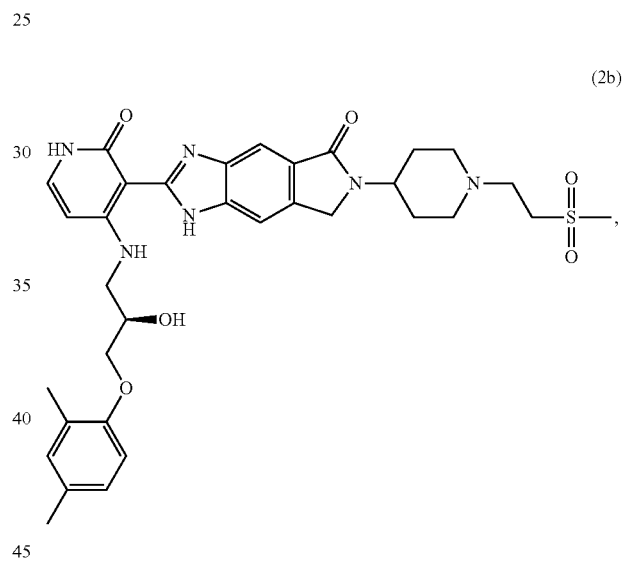

(2b)

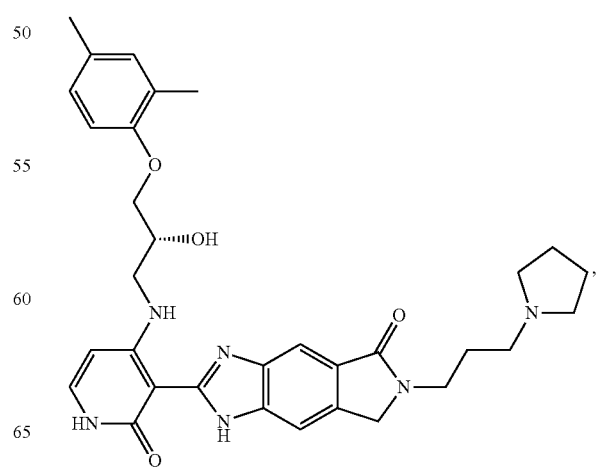

(2c)

-continued (2e)
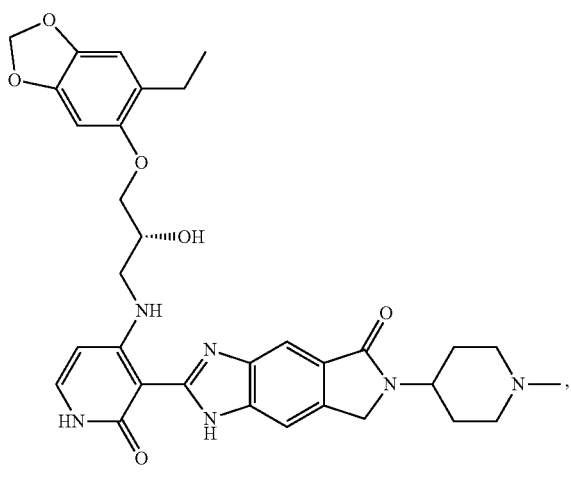

(2h)
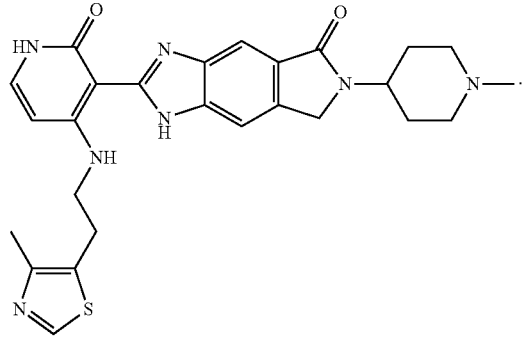, and (2i)
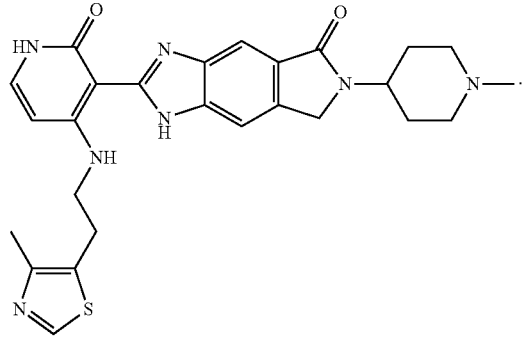

In some embodiments, said compound is (2a)
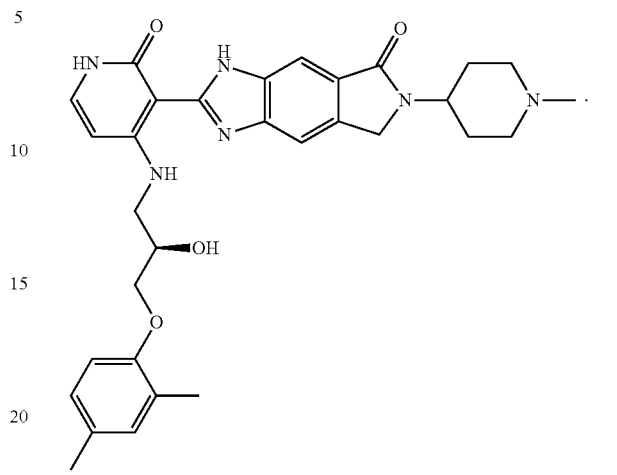

In other embodiments, said compound is (2b)
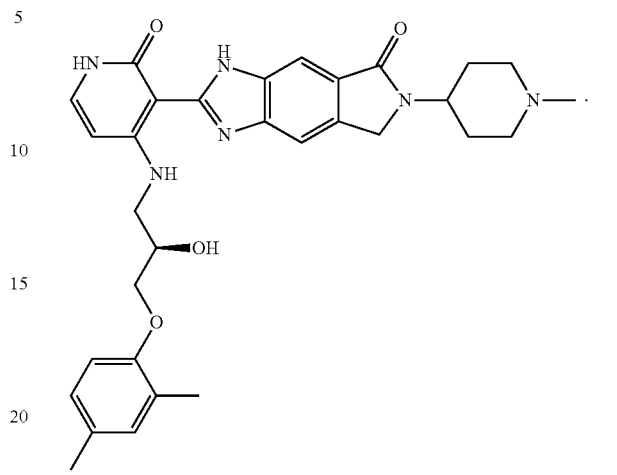

In another aspect, the present invention provides a method of treating a condition or disorder associated with an insulin-like growth factor receptor-1 (IGF-1R), comprising administering to a subject in need thereof an IGF-1R inhibitor, wherein said IGF-1R inhibitor is a compound of formula I,

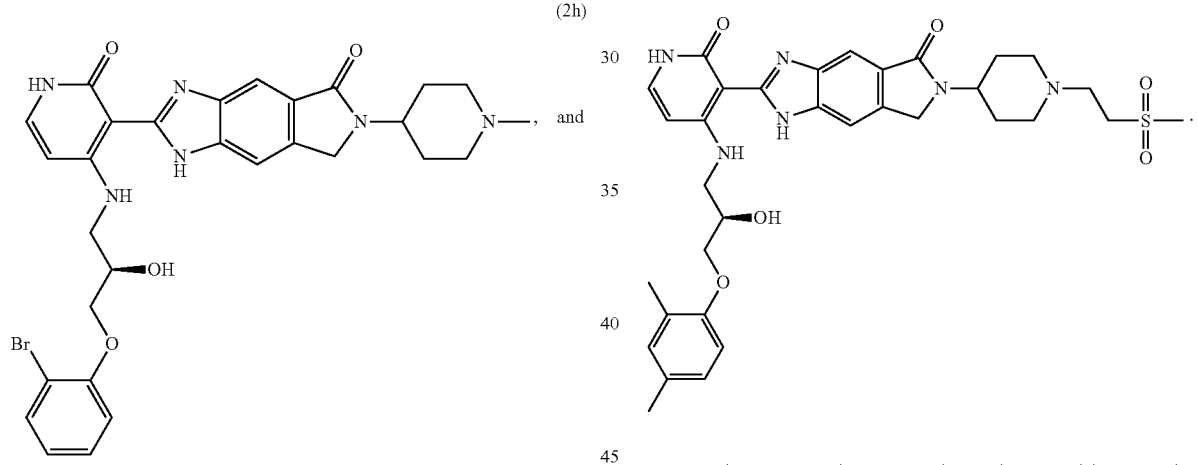

wherein:

each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

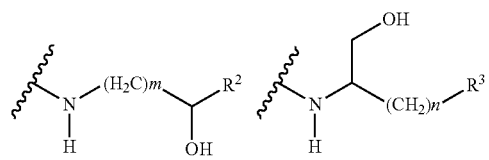

wherein:
m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —$(CH_2)_p$-$M^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein $M^1$ is O, S, and p is an integer between 0 and 4;

$R^3$ is selected from optionally substituted aryl, heteroaryl, wherein the heteroaryl is imidazoyl, pyridinyl, benzo-dioxanyl, benzo-imidazolyl or indolyl, —$(CH_2)_o$-aryl, or —$(CH_2)_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

$Y^1$ is

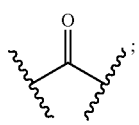

$Y^2$ is

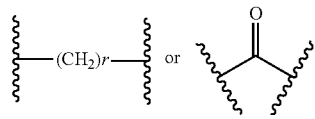

wherein: r is 1; and
$R^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl carboxamido, sulfonamido, $SO_2$-alkyl, SO-alkyl, CO-alkyl, $CO_2$-alkyl, cyano, cyanoalkyl, ketoalkyl, and methanesulfonylalkyl, or a pharmaceutically acceptable salt thereof.

In some embodiments, said condition or disorder is cancer. In some embodiments, said condition or disorder is blood cancer. In certain embodiments, said condition or disorder is multiple myeloma.

In some embodiments, said method further comprises administering at least one other anti-cancer agent.

In some embodiments, said compound is selected from the group consisting of

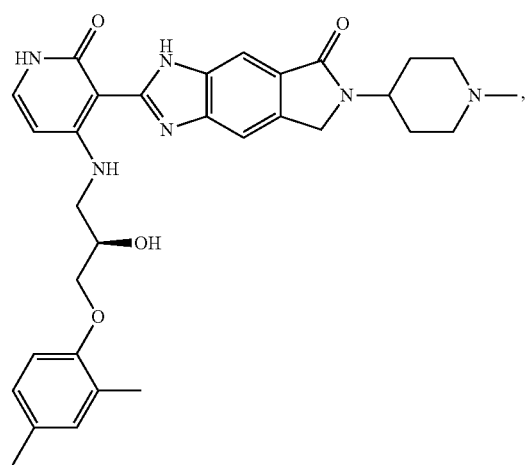

(2a)

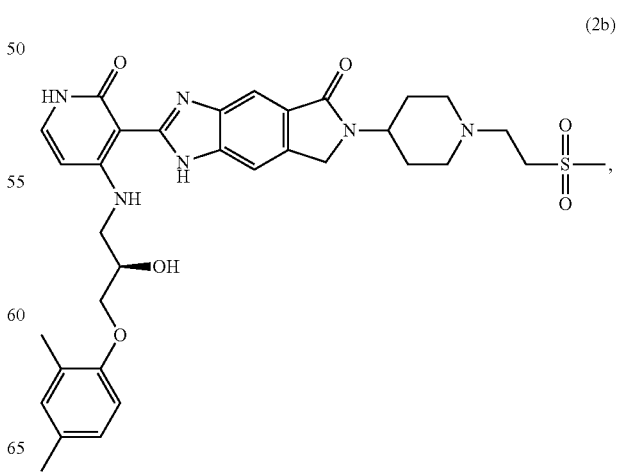

(2b)

-continued

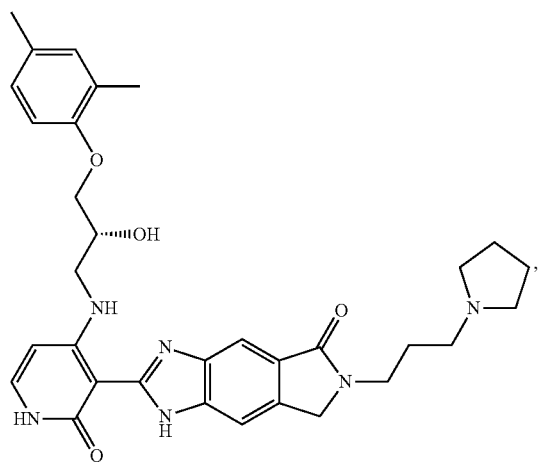

(2c)

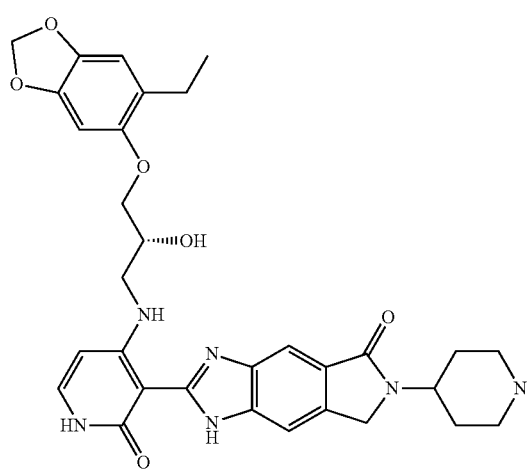

(2e)

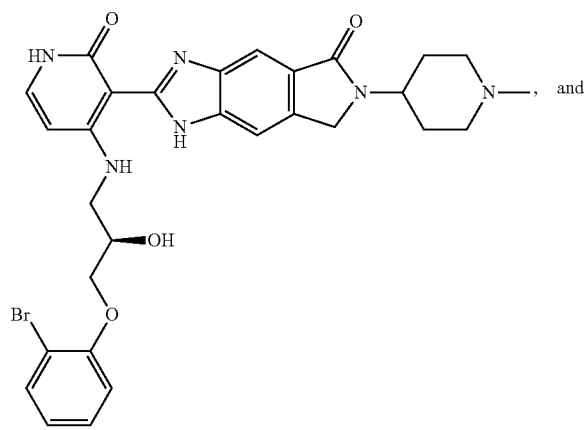

(2h)

-continued

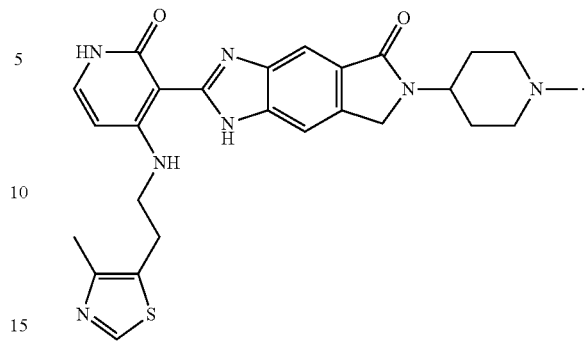

(2i)

In some embodiments, said compound is

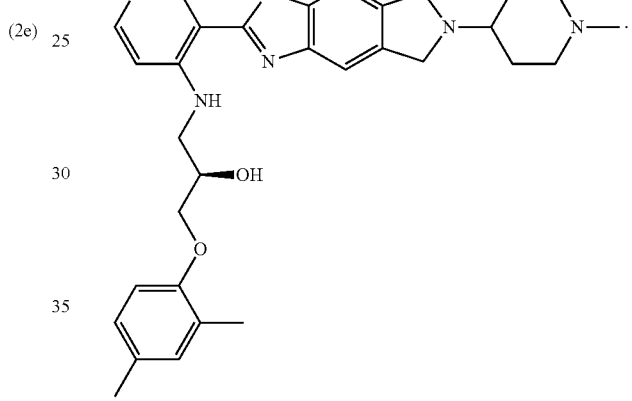

(2a)

In other embodiments, said compound is

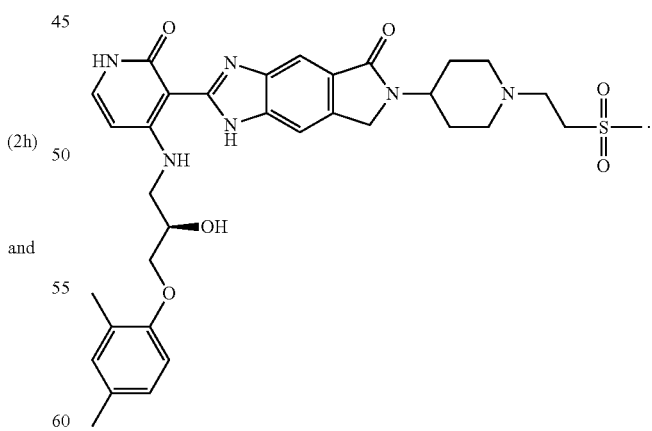

(2b)

Compositions and Method of Administration

In certain aspects, provided herein are compositions comprising a compound or a stereoisomer, tautomer, salt, hydrate or prodrug provided herein. The compositions can be used, for example, in the methods of use described herein.

In certain embodiments, a composition is a pharmaceutical composition or a single unit dosage form. Pharmaceutical compositions and single unit dosage forms comprise a prophylactically or therapeutically effective amount of one or more prophylactic or therapeutic agents (e.g., a compound of the invention, or other prophylactic or therapeutic agent), and a typically one or more pharmaceutically acceptable carriers or excipients or diluents. In one non-limiting embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

In one embodiment, pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

Lactose-free compositions of the invention can comprise excipients that are well known in the art and are listed, for example, in the U.S. Pharmocopia (USP)SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are in certain embodiments anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions are in certain embodiments packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent in certain embodiments in purified form, together with a suitable amount of carrier so as to provide the form for proper administration to the patient. The formulation should suit the mode of administration. In certain embodiments, the pharmaceutical compositions or single unit dosage forms are sterile and in suitable form for administration to a subject, in certain embodiments an animal subject, such as a mammalian subject, particularly a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of inflammation or a related disorder may contain larger amounts of one or more of the active ingredients it comprises than a dosage form used in the chronic treatment of the same disease. Also, the therapeutically effective dosage form may vary among different types of cancer. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound of the invention, or a pharmaceutically acceptable salt, solvate or hydrate thereof lie within the range of from about 0.1 mg to about 1000 mg per day. Particular dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are in certain embodiments sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Dosage & Frequency of Administration

The amount of the compound or composition provided herein which will be effective in the prevention, treatment, management, or amelioration of a disorder or one or more symptoms thereof will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems.

Exemplary doses of a compound include milligram or microgram amounts of the active peptide per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). In general, the recommended daily dose range of a compound of the invention for the conditions described herein lie within the range of from about 0.01 mg to about 1000 mg per day, given as a single once-a-day dose in certain embodiments as divided doses throughout a day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In certain embodiments, administration of the same compound may be repeated and the administrations may be separated by at least 1 day, 2 days, 3 days, 5 days, 10 days, 15 days, 30 days, 45 days, 2 months, 75 days, 3 months, or 6 months.

In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

Biological Assays

The following assays can be employed in ascertaining the activity of a small-molecule compound as an inhibitor of the catalytic kinase activity of various tyrosine kinases.

Kinase Assays

To determine inhibition of several tyrosine kinases, such as IGF1R, InsR, Alk, TrkA and Jak2, kinase assays are conducted using either Kinase-Glo (Promega) or AlphaScreen (PerkinElmer) kinase assay platforms. The Kinase-Glo Luminescent Kinase Assay is a homogeneous method for measuring kinase activity by determining the amount of ATP remaining after a kinase reaction. The luminescent signal is proportional to the amount of ATP and inversely proportional to the amount of kinase activity. Tyrosine kinase PT66 AlphaScreen Assay is a high-sensitivity homogeneous, anti-phosphotyrosine antibody-mediated luminescent proximity method measuring incorporation of phosphate in synthetic poly(Glu-Tyr) substrate. The kinase preparations used consist of purified recombinant, 6×His- or GST-tagged kinase domain fragments of the corresponding RTKs expressed in baculovirus system.

ELISA-Based Assay of IGF1 Receptor Autophosphorylation Inhibition in Cells

In another embodiment, compounds that interact with the IGF1R kinase domain are tested in a cell-based assay system. In accordance with this embodiment, cells expressing a full-length IGF1 receptor or a fragment thereof containing the IGF1R kinase domain, are contacted with a candidate or a control compound and the ability of the compound to block tyrosine kinase activity of IGF1R within a cell is determined. This assay may be used to screen a single compound or a large library of candidate compounds. Typically, the cells or cell lines are of mammalian origin and they can express the IGF1 receptor, or functional IGF1R kinase domain fragment, endogenously or be genetically engineered to express the IGF1R, or functional fragment thereof. The ability of the candidate compound to inhibit IGF1R kinase activity can be determined by methods known to those skilled in the art. For example, the inhibition can be determined by ELISA-type assay or Western blot analysis with cell lysates or immunoprecipitated IGF1R receptor using various anti-IGF1R and anti-phosphotyrosine antibodies.

In general, cells expressing IGF1R are treated with modulators (i.e., inhibitors or activators) of IGF1R kinase activity and cell lysates are produced from these treated cells. IGF1Rs are isolated from the lysate by immunoprecipitation and analyzed for phosphotyrosine content. Alternatively, or in addition, cellular protein substrates phosphorylated by IGFR may be immunoprecipitated from the lysates and their degree of tyrosine phosphorylation determined.

Cell Proliferation Inhibition Assay

IGF1R and other tyrosine kinase inhibitors can inhibit the proliferation of certain cancer cell lines indicating their possible therapeutic utility for treating the corresponding cancer types. Cancer cell lines of interest and control normal lines, including CHO, HEK293, BA/F3, MM1, H929, COLO205, PC3, DU145, MCF7, Panc1, ACHN, Hep G2, H460, K562, TT, U87-G, CAOV-3, SK-MEL5, Karpas 299, are plated in white, clear-bottomed 384-well cell culture plates at 2500-5000 cells per well and supplied with dilutions of tested compounds After a desired period of time (typically 3 days), the number of viable cells is quantitated by using Cell Titer- Glo Luminescent Cell Viability Assay (Promega), a cell proliferation assay system based on detection of total amount of ATP present as a measure of cell metabolic activity. The plated cells are mixed with the Cell Titer-Glo developing reagent and counted in a luminescence multiwell plate reader according to the standard manufacturer's protocol to generate IC50 curves for cell proliferation inhibition.

Kinase Profiling

To determine inhibitory activity of the compounds against a panel of tyrosine and serine-threonine kinases, the commercial kinase panel profiling service (Kinase Profiler, Upstate Biotechnologies) is utilized. This kinase inhibition profiling platform consists of standard radiometric kinase assays in filter binding format based on direct measurements of radioactive phosphate incorporation in specific kinase substrates by scintillation counting.

The disclosure is further described by the way of non-limiting examples.

EXAMPLES

Example 1

Synthesis of the Compounds According to Formula (1)

5-Amino-6-nitro-isoindole-1,3-dione

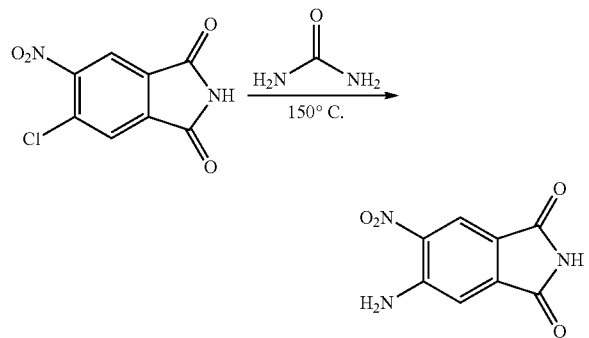

Synthesis of 5-Amino-6-nitro-isoindole-1,3-dione (4-nitro-5-aminophthalimide) from 5-chloro-6-nitroisoindoline-1,3-dione (4-chloro-5-nitrophthalimide) is described in the following: Application No. CN 1314350 A20010926 and CN 2001-111559, 20010323.

The following procedure is our modification: A mixture of 5-chloro-6-nitroisoindoline-1,3-dione (28.0 g, 0.123 mol) and urea (73.8 g, 1.23 mol) was stirred at 150° C. for 6 h. Then the temperature was reduced to 90° C., water (400 mL) was added, the mixture was stirred overnight at RT. Precipitate was collected by filtration, water (300 mL) was added and stirred for 4 h at 95° C. The solid was collected by filtration and dried under vacuum. Yellow solid, 19.6 g (94.7 mmol, 77%). LCMS [M−H]⁻ 205.9. $^1$H NMR (300 MHz, DMSO): δ 11.46 (s, 1H), 8.35 (s, 2H), 8.37 (s, 1H), 7.40 (s, 1H).

N-Substituted Phthalimides (2-substituted 5-chloro-6-nitroisoindoline-1,3-diones

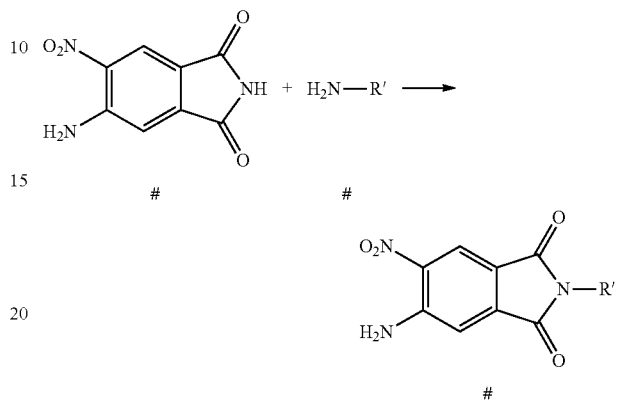

General Procedure A: A mixture of 5-amino-6-nitro-isoindole-1,3-dione 1 (207 mg, 1.0 mmol), amine 2 (1.0 mmol) and diphenyl ether (3 mL) was stirred overnight under nitrogen at 210° C., then cooled to 50° C., diluted with hexane. Precipitate was collected by filtration.

General Procedure B: A mixture of 5-amino-6-nitro-isoindole-1,3-dione 1 (12.84 g, 62.0 mmol), amine 2 (62.0 mmol), imidazole (4.22 g, 62.0 mmol) and diphenyl ether (50 mL) was stirred for 5 h under $N_2$ at 170° C. Then the reaction mixture was cooled to RT, ethanol (500 mL) was added, the mixture was refluxed for 1 h. After cooling to −20° C. yellow precipitate was collected by filtration, washed with cold ethanol and dried in vacuum at 100° C. overnight.

General Procedure C: A suspension of phthalimide 1 (292 mg, 1.41 mmol), diethylcarbonate (179 mg, 151 mmol) in 1,4-dioxane (3 mL), to which was then added DBU (0.217 ml, 1.45 mmol), was heated at 90-95° C. for 15 min. The amine 2 (1.44 mM) was then added and the reaction suspension was stirred at 100° C. for approximately 30 min at which point a dark solution had resulted. The reaction was cooled to room temperature and evaporated to reddish foam under reduced pressure. Ethanol (3 mL) was then added and a yellow suspension formed. The yellow solid was isolated via filtration and washed with ethanol, then dried in vacuum overnight to afford the product 3.

General Procedure D: To a suspension of substituted phthalimide in dioxane (1-200-fold volume [mL]/weight [g] based on the phthalimide derivative, preferably 5-20 mL of 1,4-dioxane per g of the phthalimide derivative) is added equimolar amount of the amine R'—NH₂, imidazole (between 0.01% to 100% of the molar equivalent of the phthalimide[isoindoline-1,3-dione]) and heated to between 100° C. to 200° C., preferably to between 110° C. to 150° C., when necessary in a closed pressure vessel with efficient agitation. Then the reaction mixture is cooled to RT and diluted with hexane. The product is filtered by suction and washed with a small amount of cold ether or other suitable solvent. Alternatively the mixture is concentrated in vacuo and the product may be further purified by washing with ether, hexane or ethyl acetate or their mixture. The product can also be purified by recrystallization from alcohol, or isopropanol. The product can also be purified by acid-base extraction, column chromatography, or HPLC.

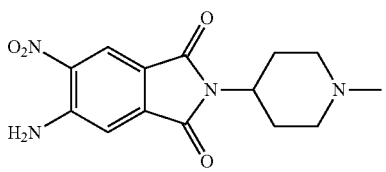 [SMILES: CN1CCC(N2C(=O)c3cc(N)c([N+](=O)[O-])cc3C2=O)CC1]

5-Amino-2-(1-methyl-piperidin-4-yl)-6-nitro-isoindole-1,3-dione was prepared by General procedure B. Yield 74%. LCMS: [M+H]+ 305.4

1H NMR: (300 MHz, DMSO) δ 8.38 (s, 2H), 8.28 (s, 1H), 7.41 (s, 1H), 3.89 (m, 1H), 2.85 (d, J 11.3 Hz, 2H), 2.30 (m, 2H), 2.18 (s, 3H), 1.92 (t, J 11.3 Hz, 2H), 1.58 (d, J 10.9 Hz, 2H).

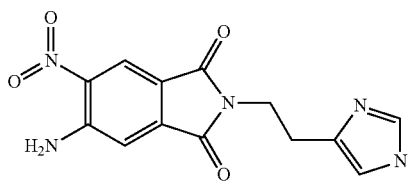 [SMILES: Nc1cc2c(cc1[N+](=O)[O-])C(=O)N(CCc1c[nH]cn1)C2=O]

5-Amino-2-[2-(1H-imidazol-4-yl)-ethyl]-6-nitro-isoindole-1,3-dione was prepared by General procedure A. The product was additionally purified by chromatography on SiO2 (CHCl3-MeOH—NH4OH 100:10:1). Yield 224 mg (0.74 mmol, 74%). LCMS [M+H]+ 302.4.

1H NMR (300 MHz, DMSO): δ 11.81 (s, 1H), 8.40 (s, 2H), 2.30 (s, 1H), 7.48 (s, 1H), 7.43 (s, 1H) 6.81 (s, 1H), 3.75 (m, 2H), 2.79 (m, 2H).

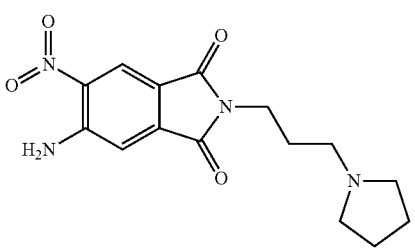 [SMILES: Nc1cc2c(cc1[N+](=O)[O-])C(=O)N(CCCN1CCCC1)C2=O]

5-Amino-6-nitro-2-(3-pyrrolidin-1-yl-propyl)-isoindole-1,3-dione was prepared by General procedure A. The product was additionally purified by reverse phase chromatography (CH3CN—H2O-TFA). Yield 60 mg (0.19 mmol, 19%). LCMS [M+H]+ 319.4.

1H NMR (300 MHz, CDCl3): δ 8.55 (s, 1H), 7.40 (s, 2H), 3.80 (m, 2H), 3.22 (m, 2H), 2.85 (m, 2H), 2.00-2.20 (6H), 1.60 (br.s., 4H).

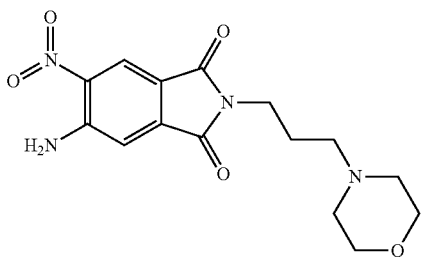 [SMILES: Nc1cc2c(cc1[N+](=O)[O-])C(=O)N(CCCN1CCOCC1)C2=O]

5-Amino-2-(3-morpholin-4-yl-propyl)-6-nitro-isoindole-1,3-dione was prepared by General procedure A. The product was additionally purified by reverse phase chromatography (CH3CN—H2O-TFA). Yield 149 mg (0.45 mmol, 45%). LCMS[M+H]+ 335.5

1H NMR (300 MHz, DMSO): δ 8.40 (s, 2H), 8.31 (s, 1H), 7.45 (s, 1H), 3.60 (m, 2H), 3.41 (m, 4H), 2.26 (m, 6H), 1.72 (m, 2H).

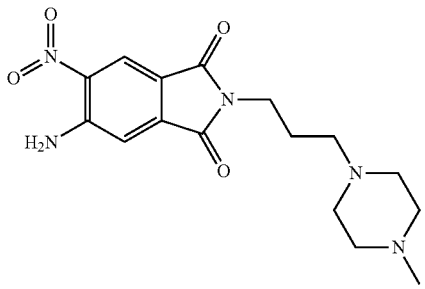 [SMILES: CN1CCN(CCCN2C(=O)c3cc(N)c([N+](=O)[O-])cc3C2=O)CC1]

5-Amino-2-[3-(4-methyl-piperazin-1-yl)-propyl]-6-nitro-isoindole-1,3-dione was prepared by General procedure A. The product was additionally purified by RP chromatography (CH3CN—H2O-TFA). Yield 110 mg (0.32 mmol, 32%). LCMS: [M+H]+ 348.3

1H NMR (300 MHz, DMSO): δ 8.44 (s, 2H), 8.32 (s, 1H), 7.47 (s, 1H), 3.60 (m, 2h), 3.50-2.70 (13H), 1.85 (m, 2H).

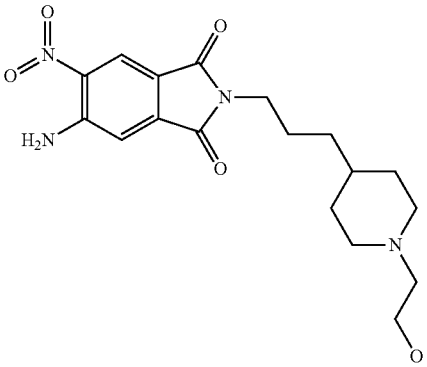 [SMILES: Nc1cc2c(cc1[N+](=O)[O-])C(=O)N(CCCC1CCN(CCO)CC1)C2=O]

5-Amino-2-[1-(2-hydroxy-ethyl)-piperidin-4-ylmethyl]-6-nitro-isoindole-1,3-dione was prepared by General procedure A. Yield 270 mg (0.77 mmol, 77%). LCMS [M+H]+ 349.3

1H NMR (300 MHz, DMSO): δ 8.39 (s, 2H), 8.30 (s, 1H), 7.45 (s, 1H), 4.33 (m, 1H), 3.43 (m, 4H), 2.81 (m, 2H), 2.35 (m, 2H), 1.87 (m, 2H), 1.55 (m, 3H), 1.15 (m, 2H).

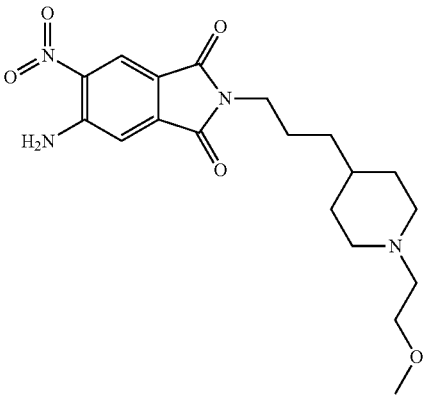 [SMILES: COCCN1CCC(CCCN2C(=O)c3cc(N)c([N+](=O)[O-])cc3C2=O)CC1]

5-Amino-2-[1-(2-methoxy-ethyl)-piperidin-4-ylmethyl]-6-nitro-isoindole-1,3-dione was prepared by General procedure B "Imidazole". Yield 267 mg (0.74 mmol, 74%).

LCMS [M+H]+ 363.5

¹H NMR (300 MHz, DMSO): δ 8.41 (s, 2H), 8.31 (s, 1H), 7.45 (s, 1H), 3.38 (m, 4H), 3.21 (s, 3H), 2.80 (m, 2H), 2.40 (m, 2H), 1.85 (m, 2H), 1.60 (m, 1H), 1.54 (m, 2H), 1.24 (m, 2H).

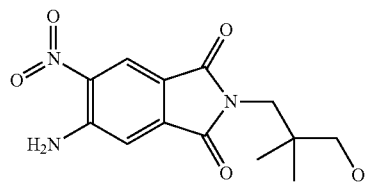 [SMILES: CC(C)(CO)CN1C(=O)c2cc(N)c([N+](=O)[O-])cc2C1=O]

5-Amino-2-(3-hydroxy-2,2-dimethyl-propyl)-6-nitro-isoindole-1,3-dione was prepared by General procedure B "Imidazole". Yield 168 mg (0.57 mmol, 57%).

LCMS [M–H]⁻ 292.3

¹H NMR (300 MHz, DMSO): δ 8.40 (s, 2H), 8.32 (s, 1H), 7.45 (s, 1H), 4.58 (t, J=5.5 Hz, 1H), 3.45 (s, 2H), 3.16 (d, J=5.5 Hz, 2H), 0.80 (s, 6H).

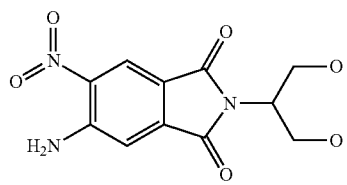 [SMILES: Nc1cc2c(cc1[N+](=O)[O-])C(=O)N(C(CO)CO)C2=O]

5-Amino-2-(2-hydroxy-1-hydroxymethyl-ethyl)-6-nitro-isoindole-1,3-dione was prepared by General procedure B "Imidazole". Yield 271 mg (0.96 mmol, 96%).

LCMS [M–H]⁻ 279.8

¹H NMR (300 MHz, DMSO): δ 8.39 (s, 2H), 8.30 (s, 1H), 7.44 (s, 1H), 4.85 (m, 2H), 4.20 (m, 1H), 3.78 (m, 2H), 3.63 (m, 2H).

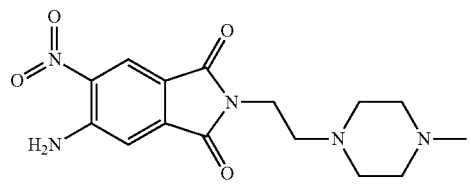 [SMILES: CN1CCN(CCN2C(=O)c3cc(N)c([N+](=O)[O-])cc3C2=O)CC1]

5-Amino-2-[2-(4-methyl-piperazin-1-yl)-ethyl]-6-nitro-isoindole-1,3-dione was prepared by General procedure C "diethylcarbonate". Yield 140 mg (0.42 mmol, 42%)

LCMS [M+H]+ 334.5

¹H NMR (300 MHz, DMSO): δ 8.59 (s, 2H), 8.40 (s, 1H), 7.45 (s, 1H), 3.65 (m, 2H), 2.20-2-10 (m, 10H), 2.10 (s, 3H).

Aminoalcohols

Scheme 23

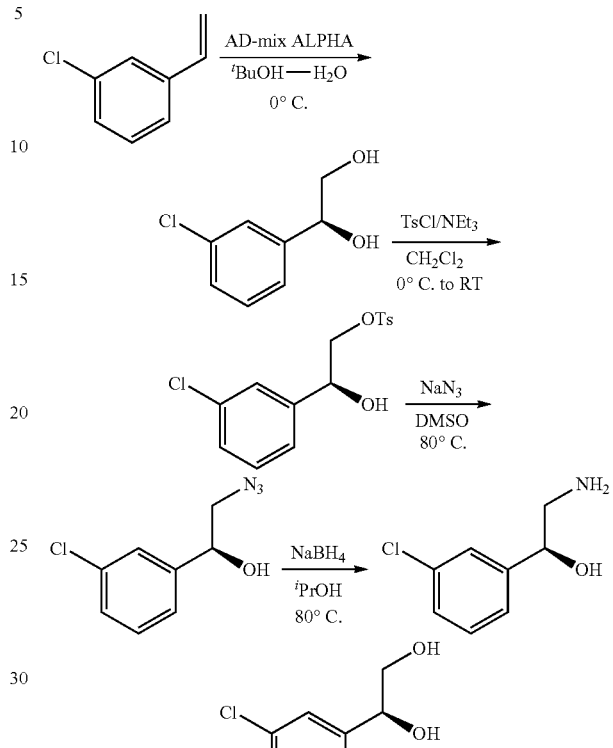

Procedure for the Synthesis of Optically Active Aminoalcohol (S)-2-(3-chlorophenyl)-2-hydroxy-ethylamine (S)-1-(3-Chlorophenyl)-ethane-1,2-diol: AD mix alpha (86.0 g) was added to a stirred mixture of tert-BuOH (300 mL) and H₂O (300 mL), mixture was stirred for 15 min at RT, than cooled to 0° C. 3-Chlorostyrene (8.51 g, 0.061 mol) was added over 15 min and the mixture was stirred at 0° C. for 48 h. The reaction mixture was quenched by adding 10% aq. sodium sulfite (120 mL) followed by addition of EtOAc (200 mL). The layers were separated and the aqueous layer was extracted with EtOAc (200 mL). The combined organic layers were washed with 0.4 M H₂SO₄ in saturated Na₂SO₄ (100 mL), followed by drying over Na₂SO₄. The solvent was evaporated and the residue was separated on SiO₂ (70 g) (CHCl₃-MeOH 0 to 10%). Colorless oil, 9.83 g (0.057 mol, 93%).

¹H NMR (300 MHz, DMSO): δ 7.20-7.40 (m, 4H), 5.39 (d, J=4.6 Hz, 1H), 4.76 (t, J=5.8 Hz, 1H), 4.54 (q, J=4.9 Hz, 1H), 3.43 (m, 2H).

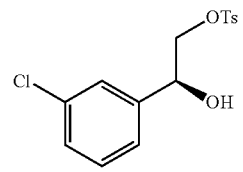 [SMILES: Cc1ccc(S(=O)(=O)OC[C@@H](O)c2cccc(Cl)c2)cc1]

Toluene-4-sulfonic acid (S)-2-(3-chlorophenyl)-2-hydroxyethyl ester: To a mixture of (S)-1-(3-Chloro-phenyl)-ethane-1,2-diol (9.83 g, 0.057 mol) and triethylamine (11.8 ml, 0.086 mol) a solution of TsCl (10.87 g, 0.057 mol) in dichloromethane (50 mL) was added at 0° C. over 30 min. The mixture was stirred at 0° C. for 4 h. Precipitate formed was removed by filtration, the filtrate was washed with water (50 mL), dried over $Na_2SO_4$ and evaporated. The residue was dissolved in $CH_2Cl_2$ (200 mL), filtered through a $SiO_2$ pad and evaporated. Colorless oil, 16.34 g (0.050 mol, 88%).

$^1$H NMR (300 MHz, DMSO): δ 7.67 (d, J=8.5 Hz, 2H), 7.42 (d, J=8.5 Hz, 2H), 7.20-7.35 (m, 4H), 5.90 (d, J=4.9 Hz, 1H), 4.79 (q, J=5.1 Hz, 1H), 4.03 (m, 2H), 2.41 (s, 3H).

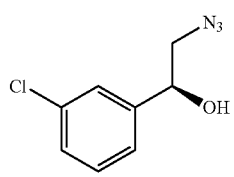

(S)-2-Azido-1-(3-chlorophenyl)-ethanol: A mixture of toluene-4-sulfonic acid (S)-2-(3-chlorophenyl)-2-hydroxyethyl ester (16.34 g, 0.050 mol), sodium azide (6.50 g, 0.10 mol) and DMSO (50 mL) was stirred for 2 h at 80° C. Water (100 mL) was added, extracted with hexane-ether (1:1) mixture (2×150 mL). Combined extract was dried over $Na_2SO_4$, evaporated. The residue was separated on $SiO_2$ (100 g), hexane-EtOAc, 0 to 20%. Colorless oil, 7.0 g, (0.035 mol, 71%).

$^1$H NMR (300 MHz, DMSO): δ 7.46 (s, 1H), 7.36 (m, 3H), 5.95 (d, J=4.5 Hz, 1H), 4.82 (q, J=5.3 Hz, 1H), 3.35 (m, 2H).

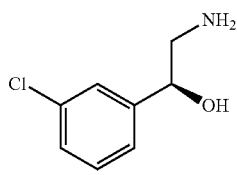 [SMILES: NC[C@@H](O)c1cccc(Cl)c1]

(S)-2-Amino-1-(3-chloro-phenyl)-ethanol: A mixture of (S)-2-Azido-1-(3-chlorophenyl)-ethanol (5.14 g, 0.026 mol), $NaBH_4$ (1.97 g, 0.052 mol) and isopropyl alcohol (100 mL) was stirred at 80° C. for 24 h. The solvent was evaporated, the residue was separated on $SiO_2$ (15 g) $CHCl_3$-MeOH (0 to 30%). Colorless oil, 3.70 g (0.021 mol, 83%). The material was reacted with $Boc_2O$ in dichloromethane and $NEt_3$ and analyzed by chiral SFC using a CHIRALPAK AD-H column, 30% MeOH and determined to be 91% ee.

LCMS [M+H]$^+$ 172.4

$^1$H NMR (300 MHz, DMSO): δ 7.24-7.39 (m, 4H), 4.46 (dd, J=4.3, 7.5 Hz, 1H), 2.68 (dd, J=4.3, 12.8 Hz, 1H), 2.57 (dd, J=7.5, 13.0 Hz, 1H).

Scheme 24

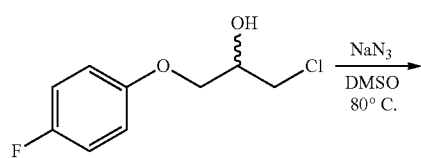

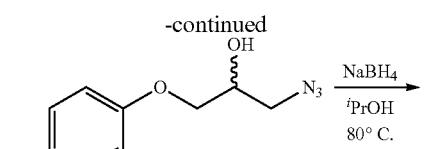

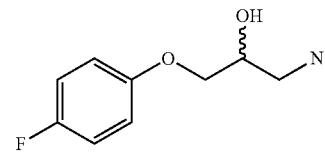

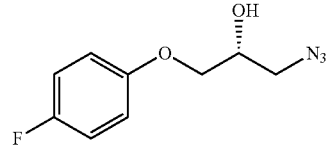

(R)-1-Azido-3-(4-fluoro-phenoxy)-propan-2-ol. A mixture of (S)-1-Chloro-3-(4-fluoro-phenoxy)-propan-2-ol (5.0 g, 24.5 mmol), sodium azide (3.19 g, 49.0 mmol) and DMSO (25 mL) was stirred at 80° C. for 6 h. Then the reaction mixture was poured into water (100 mL), extracted with hexane-$Et_2O$ (1:1) mixture (2×100 mL). Extracts were washed with brine (100 mL), dried over $Na_2SO_4$ and evaporated. The residue was dried under vacuum at RT. Colorless oil, 4.83 g (22.9 mmol, 93%).

$^1$H NMR (300 MHz, $CDCl_3$): δ 6.98 (m, 2H), 6.84 (m, 2H), 4.15 (m, 1H), 3.97 (m, 2H), 3.52 (m, 2H), 2.57 (d, J=5 Hz, 1H).

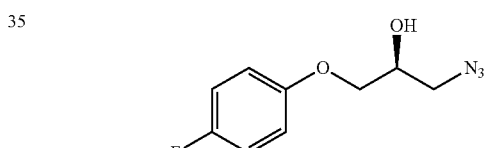

(S)-1-Azido-3-(4-fluoro-phenoxy)-propan-2-ol was prepared by the same procedure.

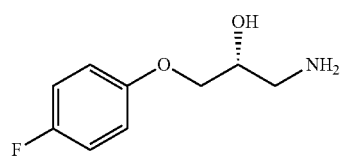 [SMILES: NC[C@@H](O)COc1ccc(F)cc1]

(R)-1-Amino-3-(4-fluoro-phenoxy)-propan-2-ol. A mixture of (R)-1-azido-3-(4-fluoro-phenoxy)-propan-2-ol (4.83 g, 22.9 mmol) $NaBH_4$ (1.73 g, 45.8 mmol) in $^i$PrOH (100 mL) was stirred at 80° C. for 24 h. After cooling to RT, aq. HCl (200 mL, 0.25 M) was added, washed with $CH_2Cl_2$ (100 mL). Saturated aq. $K_2CO_3$ (150 mL) was added to the aqueous phase. The product was extracted with $CH_2Cl_2$ (2×100 mL), extracts were dried over $Na_2SO_4$ and evaporated. The residue was dried under vacuum. White solid, 2.20 g (11.9 mmol, 52%).

LCMS [M+H]$^+$ 186.1

$^1$H NMR (300 MHz, DMSO): δ 7.00 (m, 2H), 6.86 (m, 2H), 3.93 (m, 3H), 2.96 (m, 1H), 2.86 (m, 1H), 1.71 (br. s, 3H).

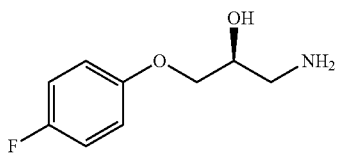 [SMILES: NC[C@H](O)COc1ccc(F)cc1]

(S)-1-Amino-3-(4-fluoro-phenoxy)-propan-2-ol was prepared by the same procedure.

Scheme 25

Procedure for the Preparation of 1-Amino-3-aryloxypropan-2-ols, 1-Amino-3-arylthiopropan-2-ols, and 1-Amino-3-arylaminopropan-2-ols and their Heteroaryl Analogs

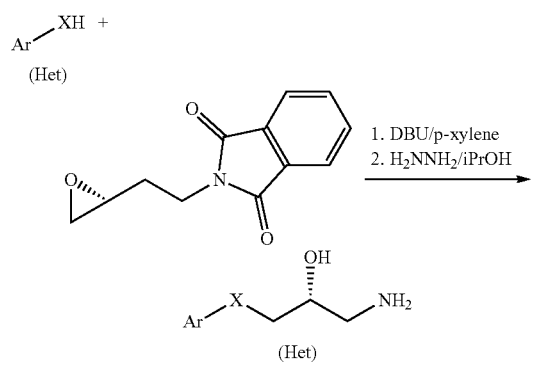

X = O, S, NH or N-lower alkyl
Ar = aryl
Het = heteroaryl

General procedure for preparation of (R)-1-amino-3-aryloxy-propan-2-ols. A mixture of (R)—N-(2,3-epoxypropyl)-phthalimide (1.02 g, 5.0 mmol), phenol (5.0 mmol), p-xylene (2 mL) and DBU (0.05 mL) was stirred under $N_2$ at 120° C. for 8 h. After cooling to 80° C. $^i$PrOH (20 mL) and anhydrous hydrazine (1 mL) were added and the mixture was heated at 80° C. for 4 h. The reaction mixture was cooled to RT, 0.5N aq. NaOH (50 mL) was added, extracted with EtOAc (100 mL). Extract was washed with 0.5N aq. NaOH (50 mL), brine (50 mL), dried over $Na_2SO_4$ and evaporated. The residue was triturated with cold $Et_2O$, the solid was collected by filtration, dried in vacuum.

The heteroaryloxy analogs and the thio and amino derivatives of are prepared analogously to the above procedure.

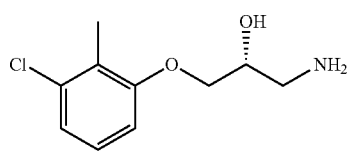

(R)-1-Amino-3-(3-chloro-2-methyl-phenoxy)-propan-2-ol
Tan solid, 0.86 g. LCMS: [M+H]$^+$ 216.1
$^1$H NMR: (300 MHz, DMSO): δ 7.16 (m, 1H), 6.97 (m, 2H), 3.93 (m, 2H), 3.73 (m, 1H), 2.66 (m, 2H).

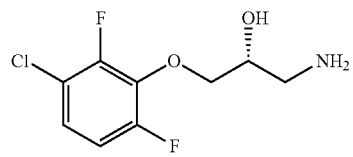 [SMILES: NC[C@@H](O)COc1c(F)ccc(Cl)c1F]

(R)-1-Amino-3-(3-chloro-2,6-difluoro-phenoxy)-propan-2-ol. Tan solid, 1.01 g. LCMS [M+H]$^+$ 239.9
$^1$H NMR (300 MHz, DMSO): δ 7.32 (m, 1H), 7.21 (m, 1H), 4.10 (m, 2H), 3.68 (m, 1H), 2.63 (m, 2H).

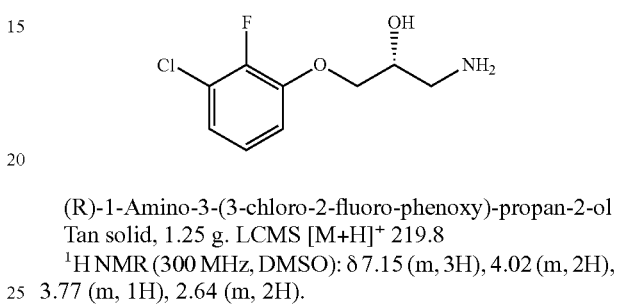

(R)-1-Amino-3-(3-chloro-2-fluoro-phenoxy)-propan-2-ol
Tan solid, 1.25 g. LCMS [M+H]$^+$ 219.8
$^1$H NMR (300 MHz, DMSO): δ 7.15 (m, 3H), 4.02 (m, 2H), 3.77 (m, 1H), 2.64 (m, 2H).

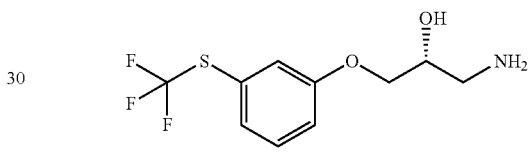

(R)-1-Amino-3-(3-trifluoromethylsulfanyl-phenoxy)-propan-2-ol
Tan solid, 1.11 g. LCMS [M+H]$^+$ 267.6
$^1$H NMR (300 MHz, DMSO): δ 7.46 (m, 1H), 7.24 (m, 3H), 4.04 (m, 1H), 3.90 (m, 1H), 3.72 (m, 1H), 2.62 (m, 2H).

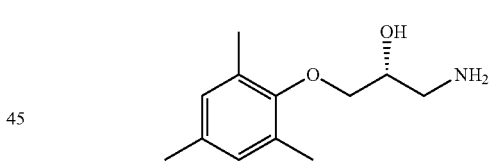

(R)-1-Amino-3-(2,4,6-trimethyl-phenoxy)-propan-2-ol
Tan solid, 0.89 g. LCMS [M+H]$^+$ 210.1
$^1$H NMR (300 MHz, DMSO): δ 6.81 (s, 2H), 3.64 (m, 3H), 2.73 (m, 1H), 2.60 (m, 1H), 2.18 (s, 9H).

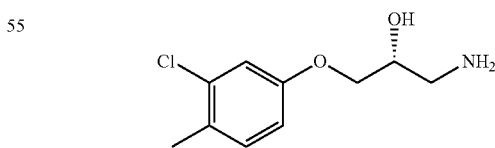

(R)-1-Amino-3-(3-chloro-4-methyl-phenoxy)-propan-2-ol
Tan solid, 0.99 g. LCMS [M+H]$^+$ 215.8
$^1$H NMR (300 MHz, DMSO): δ 7.23 (m, 1H), 7.00 (s, 1H), 6.81 (m, 1H), 3.93 (m, 1H, 3.82 (m, 1H), 3.65 (m, 1H), 2.61 (m, 2H), 2.23 (s, 3H).

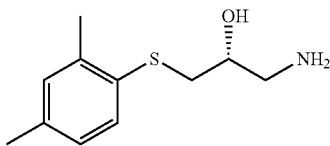

(R)-1-Amino-3-(2,4-dimethyl-phenylsulfanyl)-propan-2-ol

Off white solid, 0.88 g. LCMS [M+H]$^+$ 212.1

$^1$H NMR (300 MHz, DMSO): δ 7.22 (d, J=8.3 Hz, 1H), 7.01 (m, 2H), 4.95 (br. s., 1H), 3.48 (m, 1H), 2.97 (dd, J=5.8, 12.9 Hz, 1H), 2.83 (dd, J=6.7, 12.9 Hz, 1H), 2.58 (m, 2H), 2.25 (s, 3H), 2.22 (s, 3H).

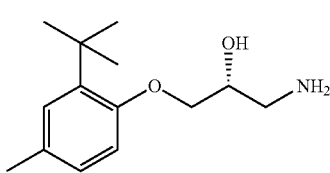 [SMILES: Cc1ccc(OC[C@H](O)CN)c(C(C)(C)C)c1]

(R)-1-Amino-3-(2-tert-butyl-4-methyl-phenoxy)-propan-2-ol

Brown solid, 0.94 g. LCMS [M+H]$^+$ 238.1

$^1$H NMR (300 MHz, DMSO): δ 6.96 (s, 1H), 6.83 (m, 2H), 3.83 (m, 3H), 2.70 (m, 2H), 2.21 (s, 3H), 1.33 (s, 9H).

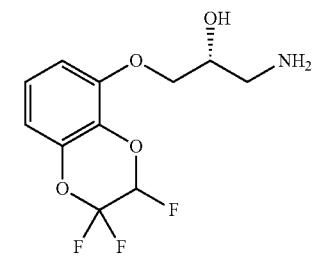 [SMILES: NC[C@@H](O)COc1cccc2c1OC(F)C(F)(F)O2]

(R)-1-Amino-3-(2,2,3-trifluoro-2,3-dihydro-benzo[1,4]dioxin-5-yloxy)-propan-2-ol White solid, 0.91 g. LCMS [M+H]$^+$ 279.9

$^1$H NMR (300 MHz, DMSO): δ 7.20-6.70 (m, 4H), 4.04 (m, 1H), 3.94 (m, 1H), 3.72 (m, 1H), 2.63 (m, 2H).

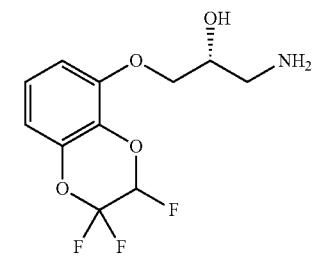 [SMILES: NC[C@@H](O)COc1cccc2c1OC(F)C(F)(F)O2]

(R)-1-Amino-3-(2,3,3-trifluoro-2,3-dihydro-benzo[1,4]dioxin-5-yloxy)-propan-2-ol Brown solid, 1.06 g. LCMS [M+H]$^+$ 279.9

$^1$H NMR (300 MHz, DMSO): δ 7.13 (m, 1H), 7.04-6.78 (m, 3H), 4.00, (m, 2H), 3.74 (m, 1H), 2.63 (m, 2H).

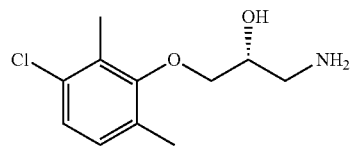

(R)-1-Amino-3-(3-chloro-2,6-dimethyl-phenoxy)-propan-2-ol

Orange solid, 0.59 g (starting from 2.9 mmol of phenol). LCMS [M+H]$^+$ 230.1

$^1$H NMR (300 MHz, DMSO): δ 7.08 (m, 2H), 3.73 (m, 2H), 3.64 (m, 1H), 2.51 (m, 2H), 2.27 (s, 3H), 2.22 (s, 2H).

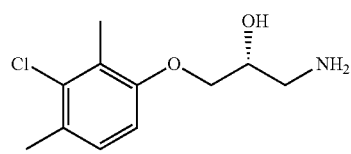

(R)-1-Amino-3-(3-chloro-2,4-dimethyl-phenoxy)-propan-2-ol

Brown solid, 0.59 g (starting from 2.9 mmol of phenol). LCMS [M+H]$^+$ 230.4

$^1$H NMR (300 MHz, CDCl$_3$): δ 7.01 (d, J=8.6 Hz, 1H), 6.68 (d, J=8.4 Hz, 1H), 3.96 (m, 3H), 2.95 (m, 2H), 2.31 and 2.29 (two overlapped singlets, 6H), 2.20 (br. s, 3H).

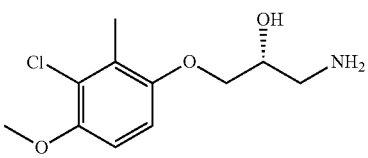 [SMILES: COc1ccc(OC[C@H](O)CN)c(C)c1Cl]

(R)-1-Amino-3-(3-chloro-4-methoxy-2-methyl-phenoxy)-propan-2-ol tan solid, 0.51 g (starting from 3.0 mmol of phenol).

LCMS [M+H]$^+$ 246.1.

$^1$H NMR (300 MHz, CDCl$_3$): δ 6.73 (s, 2H), 3.95 (m, 3H), 3.86 (s, 3H), 2.95 (m, 2H), 2.31 (s, 3H).

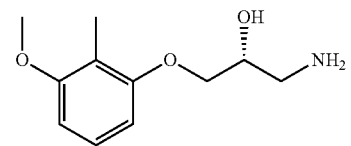

(R)-1-Amino-3-(3-methoxy-2-methyl-phenoxy)-propan-2-ol

Beige solid, 0.40 g. LCMS [M+H]$^+$ 212.3.

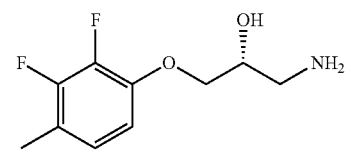

(R)-1-Amino-3-(2,3-difluoro-4-methyl-phenoxy)-propan-2-ol

White solid, 0.49 g. LCMS [M+H]+ 218.1.

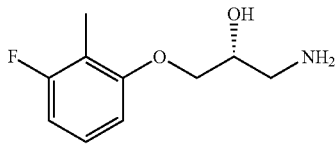

(R)-1-Amino-3-(3-fluoro-2-methyl-phenoxy)-propan-2-ol

Brown solid, 0.81 g. LCMS [M+H]+ 200.4.

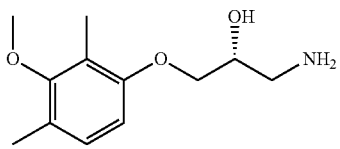 [SMILES: COc1c(C)ccc(OC[C@H](O)CN)c1C]

(R)-1-Amino-3-(3-methoxy-2,4-dimethyl-phenoxy)-propan-2-ol

Yellow solid, 0.82 g. LCMS [M+H]+ 226.4.

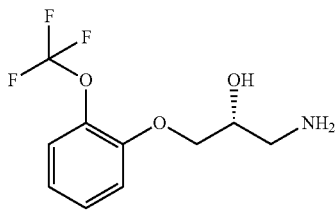 [SMILES: NC[C@@H](O)COc1ccccc1OC(F)(F)F]

(R)-1-Amino-3-(2-trifluoromethoxy-phenoxy)-propan-2-ol

LCMS [M+H]+ 251.9.

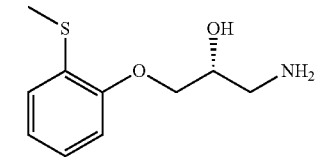

(R)-1-Amino-3-(2-methylsulfanyl-phenoxy)-propan-2-ol
LCMS [M+H]+ 213.9.

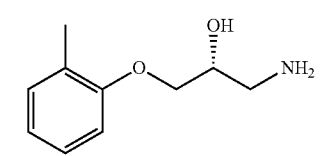

(R)-1-Amino-3-o-tolyloxy-propan-2-ol
LCMS [M+H]+ 181.9.

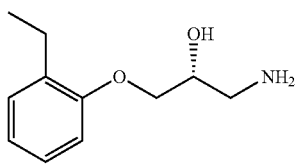

(R)-1-Amino-3-(2-ethyl-phenoxy)-propan-2-ol
LCMS [M+H]+ 196.1.

Preparation of (R)-1-Amino-3-(2,4-dimethylphenoxy)propan-2-ol

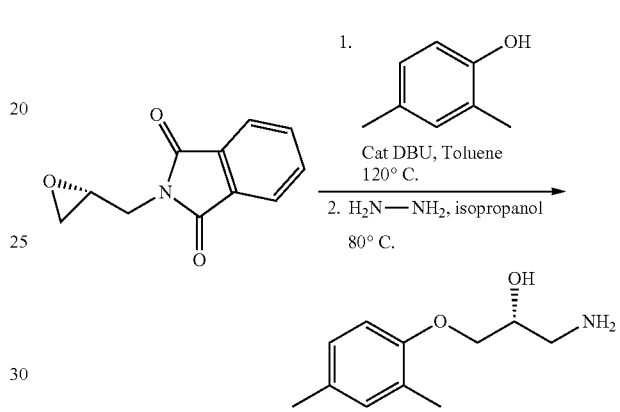

To a solution of (R)—N-(2,3-epoxypropyl)-phthalimide (3.0 g, 14.8 mmol) and 2,4-dimethylphenol (1.6 g, 13.0 mmol) in toluene (30 mL) was added DBU (1.3 mmol) and the resulting mixture was heated at 120° C. for 18 h. The reaction mixture was cooled to 75° C., diluted with isopropanol (50 mL) and treated with hydrazine (4 mL). After stirring the mixture at 80° C. for 4 h, cooled to room temperature and solvents were evaporated in vacuo. The residue was dissolved in aq. NaOH (100 mL, 5 N) and extracted with chloroform (2×100 mL). The combined organic layer was washed with brine (100 mL) and dried over Na$_2$SO$_4$. The solvent was filtered and evaporated in vacuo to afford the desired product as an off-white solid. Yield: 1.7 g, 59% LCMS [M+H]+ 196.1 The product can be recrystallized from isopropyl alcohol.

According to this methodology, many derivatives of the above can be prepared from phenols, their heteroaryl analogs, thiols, amines, alcohols and sulfonamides.

Nitration of 3-Methylphthalic Anhydride

Scheme 26

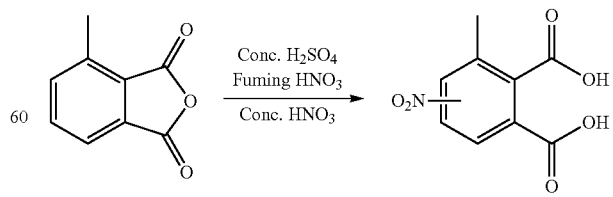

Methyl-phthalic anhydride (100.0 g) was placed in 1 L-3-neck flask equipped with thermometer, addition funnel and long reflux condenser and was added conc. H$_2$SO$_4$ (130 mL).

The suspension was heated to 70° C. using oil bath. The oil bath was removed and the fuming nitric acid (43 mL) was added dropwise while the temperature was maintained between 90-110° C. Once addition was completed, conc. HNO$_3$ (180 mL) was added at a rate the temperature of the reaction mixture don't exceed 110° C. After the addition was complete, the reaction mixture was heated at 90° C. for 2 h. The reaction mixture was cooled to room temperature and let stand overnight. The suspension was poured into ice-water (1 L) and extracted with EtOAc (2×750 mL). The combined organic layer was washed with water (1 L), dried over Na$_2$SO$_4$, filtered and concentrated in vacuo to afford light yellow solid. The obtained solid was triturated with hexanes (1 L), filtered and dried in vacuo to afford the mixture of nitro-methyl-phthalic acids as a light yellow solid. Yield: 128.0 g, 93%.

Esterification of Mixture of Nitro-3-Methylphthalic Acids

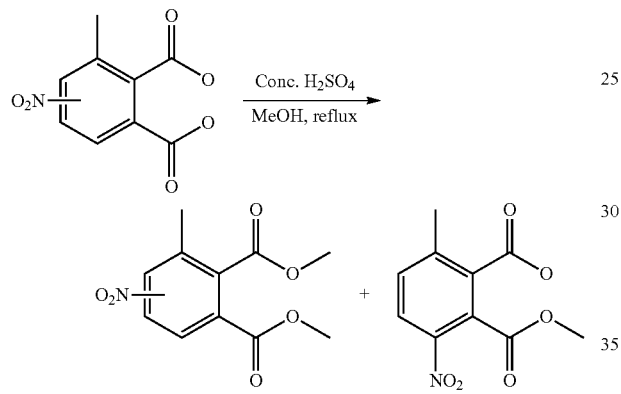

To a stirred solution of mixture of nitro-3-methylphthalic acids (124.0 g) in anhydrous MeOH (650 mL) was added conc. H$_2$SO$_4$ (40 mL) slowly and the resulting mixture was heated at reflux for 24 h. The reaction mixture was cooled to room temperature, solvent was evaporated in vacuo. The residue was dissolved in EtOAc (1.2 L), washed with water (1 L), sat. aq. NaHCO$_3$ (2×600 mL) and water (600 mL). The organic layer was dried over Na$_2$SO$_4$, filtered and evaporated in vacuo to afford the mixture of methyl-esters (3) (40.0 g, 29%) as a light yellow syrup which solidify on standing. The NaHCO$_3$ wash acidified with conc. HCl to pH=2, and extracted with EtOAc (1 L). The organic layer was dried over Na$_2$SO$_4$, filtered and concentrated in vacuo to afford the by-product mono-ester (3a) (90.0 g, 69%) as an off-white solid.

Hydrogenation of Mixture of Nitro-Esters

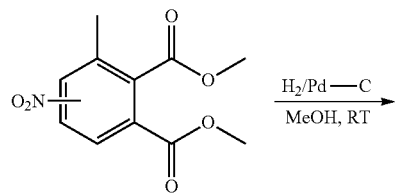

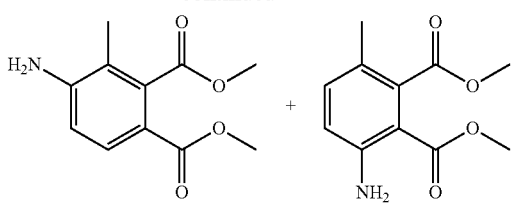

To a suspension of niro-methylphthalic esters (40.0 g) and 10% Pd/C (4.0 g) was added MeOH (400 mL) carefully and evacuated under vacuum. The flask was filled with hydrogen under balloon pressure and stirred at room temperature for overnight. If the reaction is incomplete, add HCl/ether and continue the reaction. After the reaction was completed, the mixture was filtered through Celite bed, washed with MeOH (2×200 mL). The combined filtrate was concentrated in vacuo and the residue was basified aq. NaHCO$_3$ solution. The mixture was extracted with EtOAc (2×500 mL), dried over Na$_2$SO$_4$, filtered and concentrated in vacuo to afford the mixture of aminomethylphthalic esters in quantitative yield.

Acetylation of Amino-Methylphthalic Esters

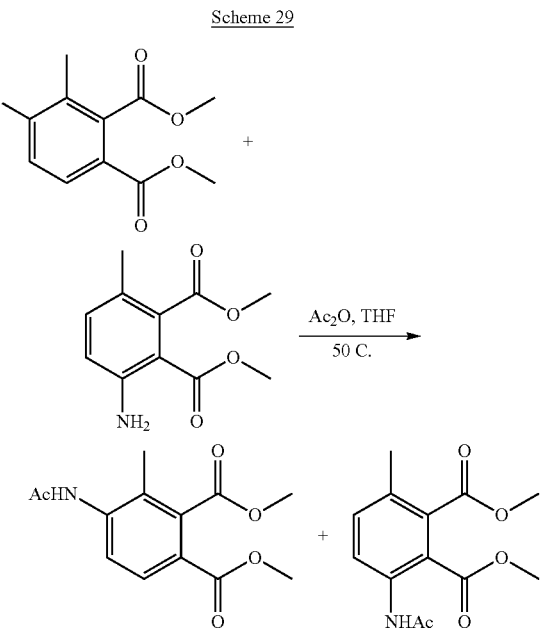

To a solution of amino-methylphthalic esters (34.3 g) in THF was added 1.2 eq of Ac$_2$O (19.0 mL) and the mixture was heated at 50° C. for 6 h. The reaction mixture was evaporated in vacuo and the residue was neutralized with aq, NaHCO$_3$ solution. The mixture was extracted with EtOAc (2×400 mL), dried over Na$_2$SO$_4$, filtered and concentrated in vacuo to afford a mixture of isomers. The mixture was triturated with ether (300 mL), filtered the precipitated solid, washed with cold ether (2×50 mL) and dried to afford 4-acetamido-3-methylphthalic acid dimethyl ester (17.1 g, 40%) as a white solid. The ether layer contains above 90% of 6-acetamido-3-methylphthalic acid dimethyl ester.

¹H NMR (CDCl₃, 300 MHz) for compound 6: δ 2.16 (s, 3H); 2.22 (s, 3H); 3.88 (s, 3H); 3.97 (s, 3H); 7.37 (br.s, 1H); 7.83 (d, J=6.0 Hz, 1H); 8.03 (d, J=6.0 Hz, 1H). ESI-MS (m/z): 266 (M+H⁺); 234 (M−32).

Synthesis of
4-Acetylamido-3-methyl-5-nitro-phthalic acid
dimethyl ester

Scheme 30

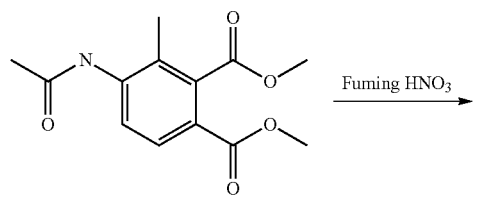

Fuming HNO₃

-continued

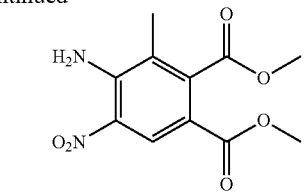

A solution of 4-acetamido-3-methyl-5-nitro-phthalic acid dimethyl ester (2.8 g, 9.03 mmol) in conc. H₂SO₄ was stirred at room temperature for 2 h. The reaction mixture was poured into ice-water (200 mL) and extracted with EtOAc (2×100 mL). The combined organic layer was washed with water (200 mL), dried over Na₂SO₄, filtered and concentrated in vacuo to afford the product 8 (1.8 g, 74%) as a yellow solid.

Synthesis of 4-Amino-3-methyl-5-nitro-phthalic acid
2-methyl ester

Scheme 32

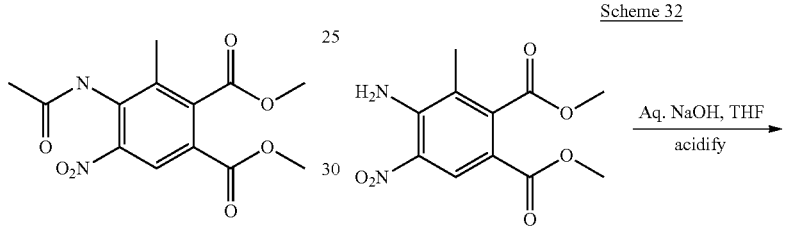

Aq. NaOH, THF
acidify

To a cold solution of fuming HNO₃ was added compound 6 (2.44 g, 9.20 mmol) in portions at 0° C. and the mixture was kept standing at 4° C. for overnight. The reaction mixture was poured into ice-water (200 mL) and extracted with EtOAc (2×200 mL). The combined organic layer was washed with aq. NaHCO₃ solution, dried over Na₂SO₄, filtered and concentrated in vacuo to afford 4-acetylamido-3-methyl-5-nitro-phthalic acid dimethyl ester (2.0 g, 71%) as a yellow solid.

Alternative work up for large scale reaction: Reaction mixture was poured into ice-water, the precipitated solid was isolated by filtration, washed with water, aq, NaHCO3 solution, water and dried in vacuo to afford the desired product as a light yellow solid.

¹H NMR (CDCl₃, 300 MHz): δ 2.12, 2.40 (2s, 6H); 3.89, 3.90 (2s, 6H); 8.25 (s, 1H); 10.27 (s, 1H). ESI-MS (m/z): 311 (M+H⁺).

Synthesis of 4-Amino-3-methyl-5-nitro-phthalic
Acid Dimethyl ester

Scheme 31

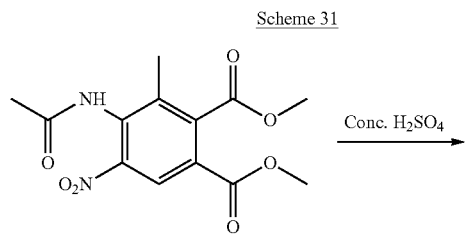

Conc. H₂SO₄

To a solution of 4-Amino-3-methyl-5-nitro-phthalic acid dimethyl ester (1.8 g, 6.72 mmol) in THF (10 mL) and water (20 mL) was added 5 N NaOH (4.0 mL) and the resulting mixture was stirred at room temperature for 24 h. The reaction mixture was acidified with conc. HCl (pH=2.0) and extracted with EtOAc (2×100 mL). The combined organic layer was dried over Na₂SO₄, filtered and concentrated in vacuo to afford the 4-Amino-3-methyl-5-nitro-phthalic acid 2-methyl ester (1.3 g, 76%) as a yellow solid.

Synthesis of 5-Amino-4-methyl-2-(1-methyl-piperi-
din-4-yl)-6-nitro-isoindole-1,3-dione Scheme 33

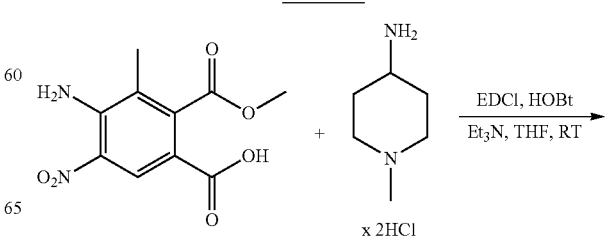

EDCl, HOBt
Et₃N, THF, RT

251

-continued

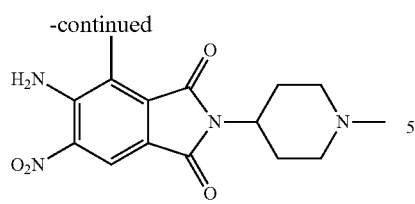

To a solution of 4-Amino-3-methyl-5-nitro-phthalic acid 2-methyl ester (1.3 g, 5.12 mmol), EDCI.HCl (1.07 g, 5.63 mmol) and HOBt (0.69 g, 5.12 mmol) was added Et₃N (3.64 mL, 25.6 mL) and stirred at room temperature for 10 min. 4-Amino-1-methylpiperidine dihydrochloride (1.04 g, 5.63 mmol) was added and the resulting mixture was stirred at room temperature for 24 h. The reaction mixture was evaporated in vacuo, the residue was dissolved in CHCl₃ (200 mL), washed with water (2×100 mL). The organic layer was filtered over Na₂SO₄ and concentrated in vacuo to afford 5-Amino-4-methyl-2-(1-methyl-piperidin-4-yl)-6-nitro-isoindole-1,3-dione (1.7 g, quant), which was used as such for further reaction.

Synthesis of 5,6-Diamino-4-methyl-2-(1-methyl-piperidin-4-yl)-isoindole-1,3-dione Scheme 34

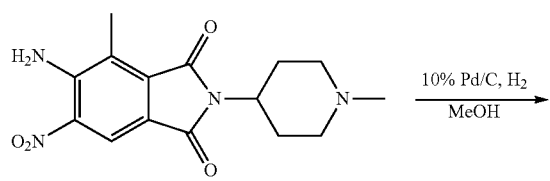

To a suspension of 5-Amino-4-methyl-2-(1-methyl-piperidin-4-yl)-6-nitro-isoindole-1,3-dione (1.7 g, 5.34 mmol) and 10% Pd/C (250 mg) was added MeOH (100 mL) carefully and evacuated in vacuo. The flask was filled with hydrogen under balloon pressure and stirred for 1 h. The reaction mixture was filtered and evaporated in vacuo to afford the crude 5,6-diamino-4-methyl-2-(1-methyl-piperidin-4-yl)-isoindole-1,3-dione (1.5 g, quant.), which was used as such for further reaction.

252

Synthesis of 2-(4-Iodo-2-methoxy-pyridin-3-yl)-4-methyl-6-(1-methyl-piperidin-4-yl)-1H-1,3,6-triaza-s-indacene-5,7-dione Scheme 35

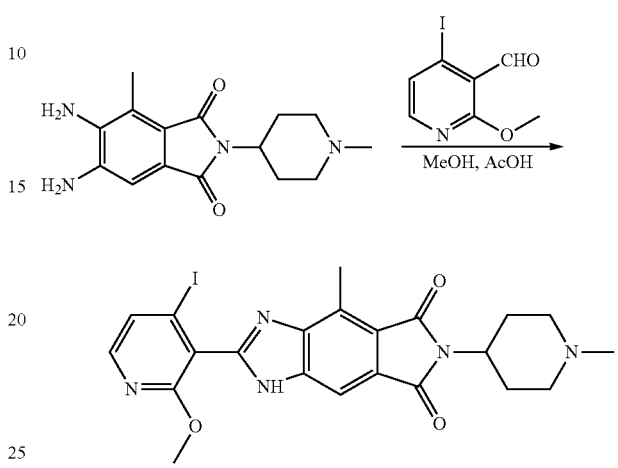

To a solution of 5,6-Diamino-4-methyl-2-(1-methyl-piperidin-4-yl)-isoindole-1,3-dione (1.7 g, 5.90 mmol) in MeOH (50 mL) were added AcOH (3 mL) and 4-iodo-2-methoxynicotinaldehyde (1.55 g, 5.90 mmol) and the resulting mixture was heated at 60° C. for overnight. The reaction mixture was evaporated in vacuo and the residue was purified by flash chromatography (5-10% (6% NH₃ in MeOH)/CHCl₃) to afford 2-(4-Iodo-2-methoxy-pyridin-3-yl)-4-methyl-6-(1-methyl-piperidin-4-yl)-1H-1,3,6-triaza-s-indacene-5,7-dione (1.48 g, 47%) as a yellow solid.

Synthesis of 2-(4-Iodo-2-oxo-1,2-dihydro-pyridin-3-yl)-4-methyl-6-(1-methyl-piperidin-4-yl)-1H-1,3,6-triaza-s-indacene-5,7-dione Hydrochloride Scheme 36

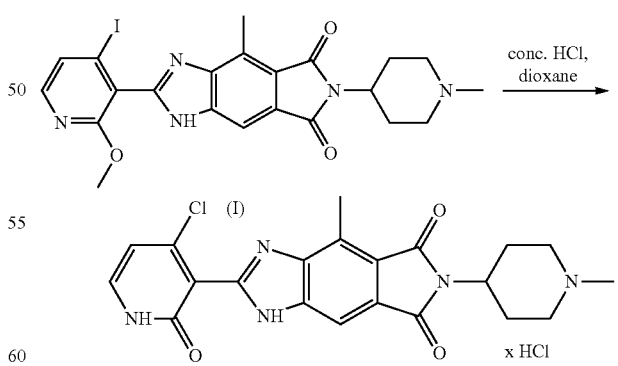

To a solution of 2-(4-Iodo-2-methoxy-pyridin-3-yl)-4-methyl-6-(1-methyl-piperidin-4-yl)-1H-1,3,6-triaza-s-indacene-5,7-dione (1.48 g, 2.78 mmol) in 1,4-dioxane (30 mL) was added conc. HCl (3 mL) and the resulting solution was stirred at room temperature for overnight. The solid precipitated was isolated by filtration, washed with THF (10 mL) and dried in vacuo to afford 2-(4-Chloro-2-oxo-1,2-dihydro-pyridin-3-yl)-4-methyl-6-(1-methyl-piperidin-4-yl)-1H-1,3,6-triaza-s-indacene-5,7-dione Hydrochloride and 2-(4-Iodo-2-oxo-1,2-dihydro-pyridin-3-yl)-4-methyl-6-(1-methyl-piperidin-4-yl)-1H-1,3,6-triaza-s-indacene-5,7-dione Hydrochloride (1.5 g, quant.) as a yellow solid.

Synthesis of 2-{[4-[(R)-3-(2,4-dimethyl-phenoxy)-2-hyrdoxy-propylamino]-2-oxo-1,2-dihydro-pyridin-3-yl}-4-methyl-6-(1-methyl-piperidin-4-yl)-1H-1,3,6-triaza-s-indacene-5,7-dione

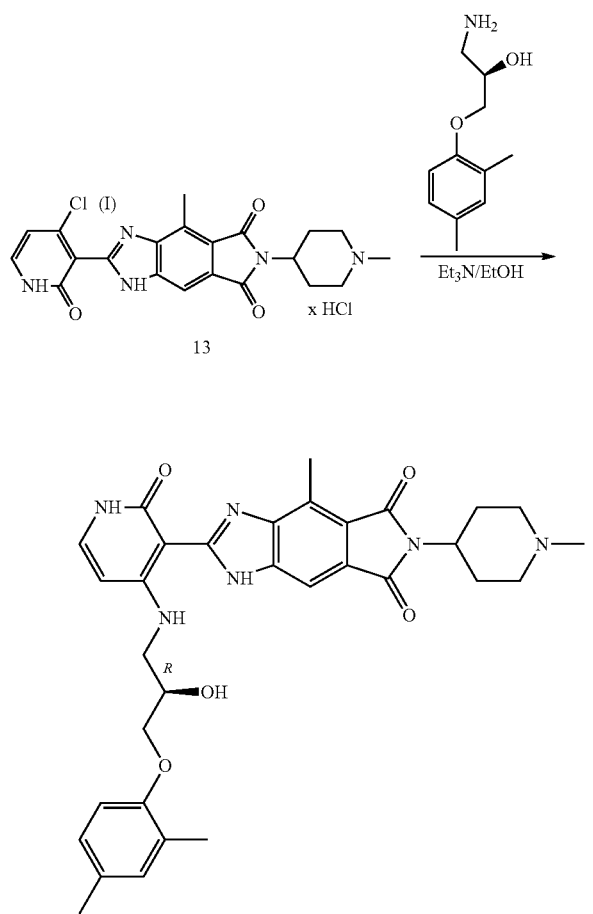

To a suspension of 2-(4-Iodo-2-oxo-1,2-dihydro-pyridin-3-yl)-4-methyl-6-(1-methyl-piperidin-4-yl)-1H-1,3,6-triaza-s-indacene-5,7-dione Hydrochloride and 2-(4-Chloro-2-oxo-1,2-dihydro-pyridin-3-yl)-4-methyl-6-(1-methyl-piperidin-4-yl)-1H-1,3,6-triaza-s-indacene-5,7-dione Hydrochloride (0.75 g, 1.45 mmol), (R)-3-amino-1-(2,4-dimethylphenoxy)-2-propanol (0.34 g, 1.73 mmol) in EtOH (20 mL) was added Et$_3$N (0.61 mL, 4.35 mmol) and the resulting mixture was heated at reflux for overnight. The reaction mixture was evaporated in vacuo and the residue was purified by flash chromatography (10% (6% NH$_3$/MeOH)/CHCl$_3$) to afford 2-{[4-[(R)-3-(2,4-dimethyl-phenoxy)-2-hydroxy-propylamino]-2-oxo-1,2-dihydro-pyridin-3-yl}-4-methyl-6-(1-methyl-piperidin-4-yl)-1H-1,3,6-triaza-s-indacene-5,7-dione (0.45 g, 57%) as a yellow solid.

$^1$H NMR (DMSO-d$_6$, 300 MHz): δ 1.58 (d, J=10.8 Hz, 2H); 1.93 (t, J=11.5 Hz, 2H); 2.15, 2.19 (2s, 9H); 2.32-2.40 (m, 2H); 2.77-2.88 (m, 6H); 3.34-3.70 (m, 2H); 3.91-4.23 (m, 5H), 5.55 (d, J=4.7 Hz, 1H), 6.20 (d, J=7.5 Hz, 1H), 6.78-6.97 (m, 3H), 7.38 (d, J=6.7 Hz, 1H); 7.94 (s, 1H), 11.13 (s, 1H), 11.29 (br.s, 1H); 13.32 (s, 1H). ESI-MS m/z 585.5 (MH$^+$). Elemental analysis calcd. for C$_{32}$H$_{36}$N$_6$O$_5$.H$_2$O: C, 63.77; H, 6.36; N, 13.94. Found: C, 63.68; H, 6.24; N, 14.07.

Synthesis of 2-{4-[(R)-3-(3-Chloro-2-methyl-phenoxy)-2-hydroxy-propylamino]-2-oxo-1,2-dihydro-pyridin-3-yl}-4-methyl-6-(1-methyl-piperidin-4-yl)-1H-1,3,6-triaza-s-indacene-5,7-dione

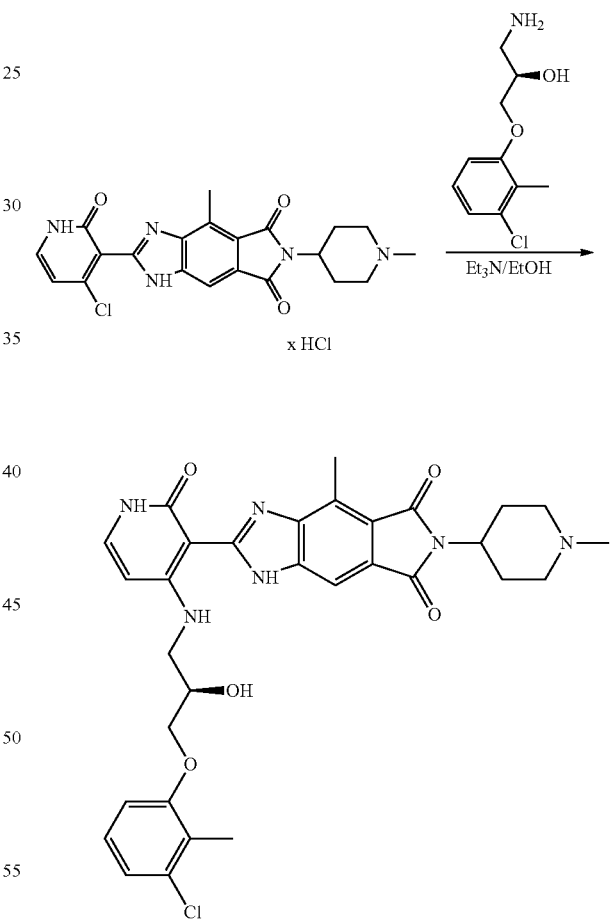

Compound was prepared following the general procedure as described above.

1H NMR (DMSO-d$_6$, 300 MHz): δ 1.59 (d, J=12.0 Hz, 2H); 1.91-1-99 (m, 3H); 2.20 (s, 3H); 2.25 (s, 3H); 2.33-2.44 (m, 2H); 2.75 (s, 3H); 2.82-2.89 (m, 3H); 3.34 (br.s, 2H); 3.55-3.74 (m, 2H); 3.90-4.20 (m, 4H); 5.62 (d, J=6.0 Hz, 1H); 6.21 (d, J=6.0 Hz, 1H); 6.94-7.17 (m, 4H); 7.40 (br.s, 1H); 7.95 (s, 1H); 11.13 (br.s, 1H); 11.29 (br.s, 1H); 13.42 (s, 1H). ESI-MS (m/z): 605.3 and 607.5.

Synthesis of 2-{4-[(R)-3-(3-Chloro-2,6-difluoro-phenoxy)-2-hydroxy-propylamino]-2-oxo-1,2-dihydro-pyridin-3-yl}-4-methyl-6-(1-methyl-piperidin-4-yl)-1H-1,3,6-triaza-s-indacene-5,7-dione Scheme 39

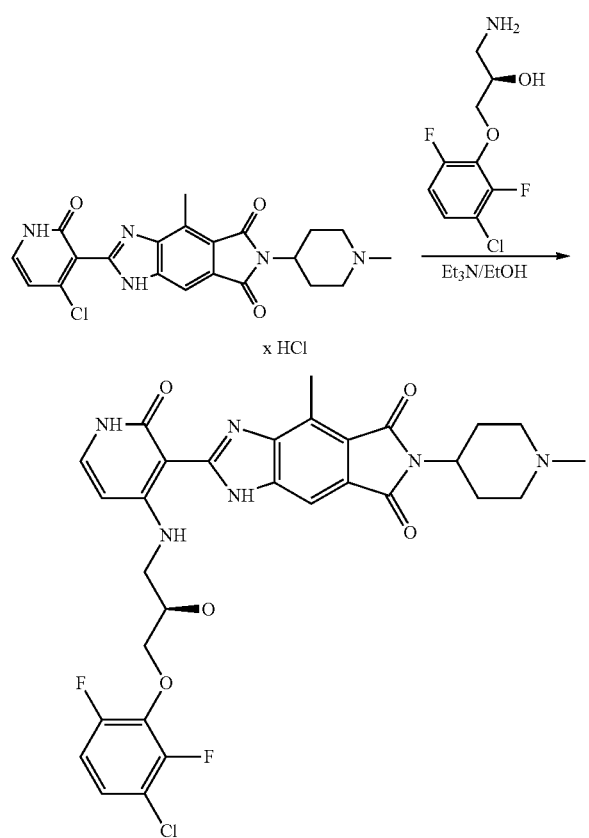

Compound was prepared following the general procedure as described above.

1H NMR (DMSO-d$_6$, 300 MHz): δ 1.59 (d, J=12.0 Hz, 2H); 1.91-1.99 (m, 3H); 2.20 (s, 3H); 2.34-2.46 (m, 2H); 2.81 (s, 3H); 2.87-2.90 (m, 3H); 3.34 (br.s, 2H); 3.55-3.72 (m, 2H); 3.91-4.10 (m, 4H); 4.28 (d, J=3.0 Hz, 2H); 5.62 (d, J=6.0 Hz, 1H); 6.21 (d, J=6.0 Hz, 1H); 7.18-7.41 (m, 4H); 7.95 (s, 1H); 11.09 (br.s, 1H); 11.31 (br.s, 1H), 13.42 (s, 1H). ESI-MS (m/z): 627.5.

Synthesis of 2-{4-[(R)-3-(2,4-Dimethyl-phenoxy)-2-hydroxy-propylamino]-2-oxo-1,2-dihydro-pyridin-3-yl}-6-((S)-1-methyl-piperidin-3-yl)-1H-1,3,6-triaza-s-indacene-5,7-dione Scheme 40

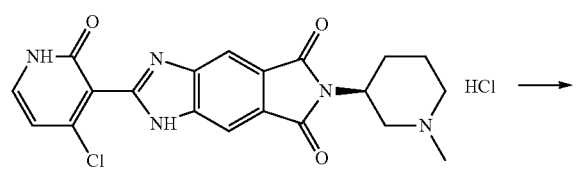

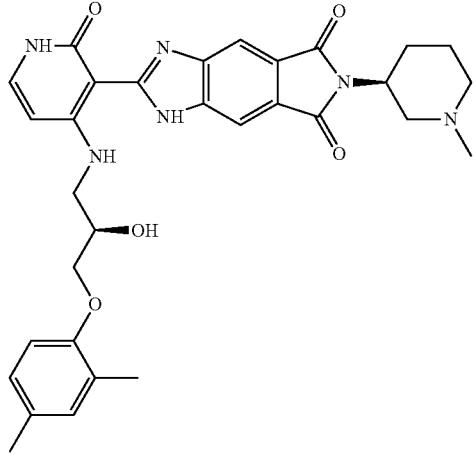

Compound was prepared following the general procedure as described above.

1H NMR (DMSO-d$_6$, 300 MHz): δ 1.53-1.61 (m, 1H); 1.72-1.90 (m, 3H); 1.99-2.21 (m, 8H); 2.74 (br.s, 2H); 3.35 (s, 3H); 3.47-3.59 (m, 2H); 3.94-4.16 (m, 4H); 5.56 (d, J=6.0 Hz, 1H); 6.23 (d, J=6.0 Hz, 1H); 6.82-6.97 (m, 3H); 7.40-7.42 (m, 1H); 7.66 (s, 1H), 8.10 (s, 1H); 10.98 (br.s, 1H); 11.32 (br.s, 1H); 13.42 (s, 1H). ESI-MS (m/z): 571.3.

Synthesis of 2-{4-[(R)-3-(2,4-Dimethyl-phenoxy)-2-hydroxy-propylamino]-2-oxo-1,2-dihydro-pyridin-3-yl}-6-((R)-1-methyl-piperidin-3-yl)-1H-1,3,6-triaza-s-indacene-5,7-dione Scheme 41

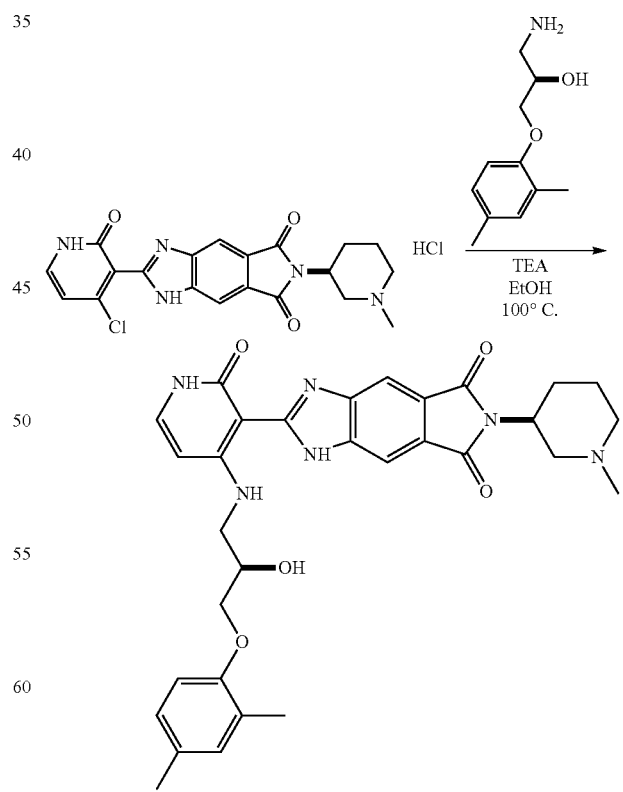

Compound was prepared following the general procedure as described above.

1H NMR (DMSO-$d_6$, 300 MHz): δ 1.53-1.61 (m, 1H); 1.72-1.90 (m, 3H); 1.99-2.21 (m, 8H); 2.74 (br.s, 2H); 3.35 (s, 3H); 3.47-3.59 (m, 2H); 3.94-4.16 (m, 4H); 5.56 (d, J=6.0 Hz, 1H); 6.23 (d, J=6.0 Hz, 1H); 6.82-6.97 (m, 3H); 7.40-7.42 (m, 1H); 7.66 (s, 1H), 8.10 (s, 1H); 10.98 (br.s, 1H), 11.32 (br.s, 1H); 13.42 (s, 1H). ESI-MS (m/z): 571.3.

Synthesis of 2-{4-[(R)-3-(5-Chloro-2,4-dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione Scheme 42

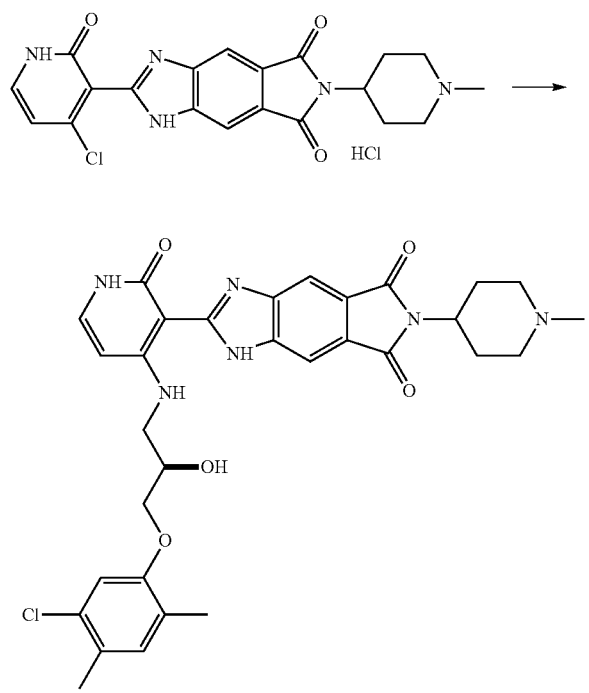

Compound was prepared following the general procedure as described above.

1H NMR (DMSO-$d_6$, 300 MHz): δ 1.62 (d, J=12.0 Hz, 2H); 1.95 (t, J=12.0 Hz, 2H); 1.21, 1.23 (2s, 6H); 2.33-2.44 (m, 2H); 2.87 (d, J=9.0 Hz, 2H); 3.56-3.74 (m, 2H); 3.88-4.17 (m, 4H); 5.62 (d, J=3.0 Hz, 1H); 6.23 (d, J=6.0 Hz, 1H); 6.84 (d, J=12.0 Hz, 2H); 7.40 (d, J=9.0 Hz, 1H); 7.69 (s, 1H); 8.08 (s, 1H); 8.33 (s, 1H); 10.96 (br.s, 1H); 11.32 (br.s, 1H); 13.40 (s, 1H). ESI-MS (m/z): 605.3.

Preparation of 1-Amino-3-heteroaryl-2-propanols

Scheme 43

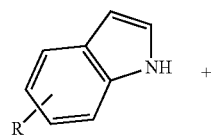 +

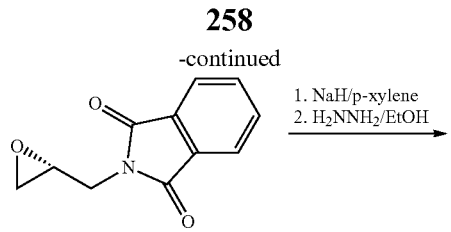

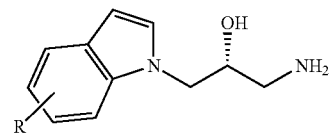

General Procedure for the Preparation of (R)-1-Amino-3-indol-1-yl-propan-2-ols: A mixture of (R)—N-(2,3-epoxypropyl)-phthalimide (1.02 g, 5.0 mmol), substituted indole (5.0 mmol), p-xylene (5 mL) and NaH (80 mg of 60% in mineral oil) was stirred under $N_2$ at 120° C. for 8 h. After cooling to 80° C. EtOH (10 mL) and anhydrous hydrazine (1 mL) were added, the mixture was heated at 80° C. for 2 h. Then the reaction mixture was cooled to RT, diluted with EtOAc (100 mL), washed with 0.5N NaOH (2×50 mL), brine (50 mL). Organic phase was dried over $Na_2SO_4$, evaporated. The residue was triturated with $Et_2O$, the precipitate was collected by filtration, dried in vacuum.

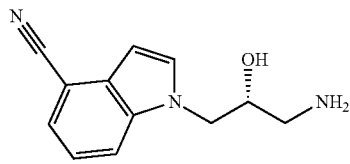 [SMILES: N#Cc1cccc2c1ccn2C[C@H](O)CN]

1-((R)-3-Amino-2-hydroxy-propyl)-1H-indole-4-carbonitrile

Tan solid, 0.56 g. LCMS [M+H]$^+$ 216.3.

$^1$H NMR (300 MHz, CDCl$_3$): δ 7.63 (d, J=8.3 Hz, 1H), 7.47 (d, J=7.5 Hz, 1H), 7.34 (d, J=3.6 Hz, 1H), 7.24 (t, J=7.9 Hz, 1H), 6.73 (d, J=3.6 Hz, 1H), 4.22 (m, 2H), 3.90 (m, 1H), 2.89 (m, 1H), 2.55 (m, 1H).

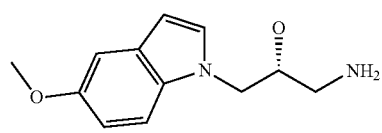 [SMILES: COc1ccc2c(ccn2C[C@H](O)CN)c1]

(R)-1-Amino-3-(5-methoxy-indol-1-yl)-propan-2-ol

Tan solid, 0.27 g. LCMS [M+H]$^+$ 221.1.

$^1$H NMR (300 MHz, CDCl$_3$): δ 7.25 (d, J=8.5 Hz, 1H), 7.12-7.08 (m, 2H), 6.85 (dd, J=2.5, 8.8 Hz, 1H), 6.43 (d, J=3.4 Hz, 1H), 4.12 (m, 2H), 3.94-3.80 (m, 4H), 2.82 (dd, J=3.9, 13.1 Hz, 1H), 2.55 (dd, J=7.7, 12.7 Hz, 1H).

259

Synthesis of (R)-2-(4-3-substituted-2-hydroxypropy-lamino)-2-oxo-1,2-dihydropyridin-3-yl)-6-(1-methylpiperidin-4-yl)imidazo[4,5-f]isoindole-5,7(1H,6H)-dione Scheme 44

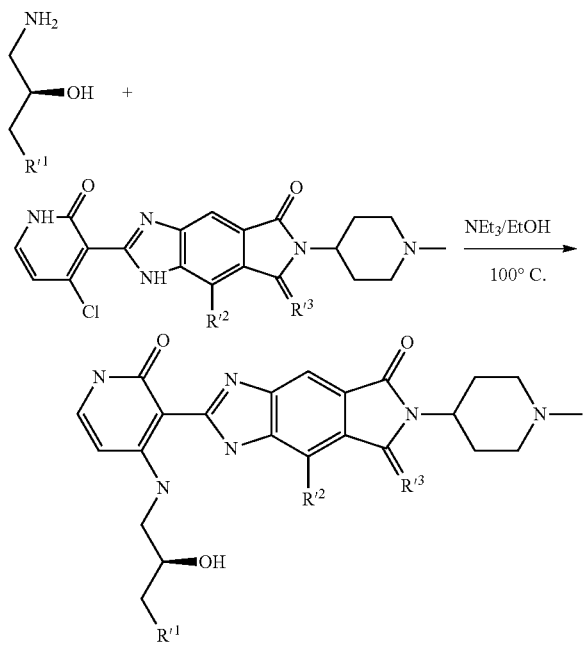

$R'^1$ = SAr', OAr', NHAr', N(lower alkyl)Ar',
$R'^2$ = H, CH$_3$
$R'^3$ = O, H$_2$
Ar = aryl or heteroaryl General Procedure A mixture of chloropyridone[2-(4-chloro-2-oxo-1,2-dihydropyridin-3-yl)-6-substituted-imidazo[4,5-f]isoindole-5,7(1H,6H)-dione] or 2-(4-chloro-2-oxo-1,2-dihydropyridin-3-yl)-6-substituted-6,7-dihydroimidazo[4,5-f]isoindol-5(1H)-one (0.25 mmol), aminoalcohol (0.35 mmol), ethanol (5 mL) and triethylamine (0.35 ml) was stirred at 100° C. overnight. Then reaction was cooled to RT, the solvent was removed in vacuum, the residue was purified by HPLC on a C18 column (acetonitrile-0.1% aq. TFA from 5:95% to 95:5%).

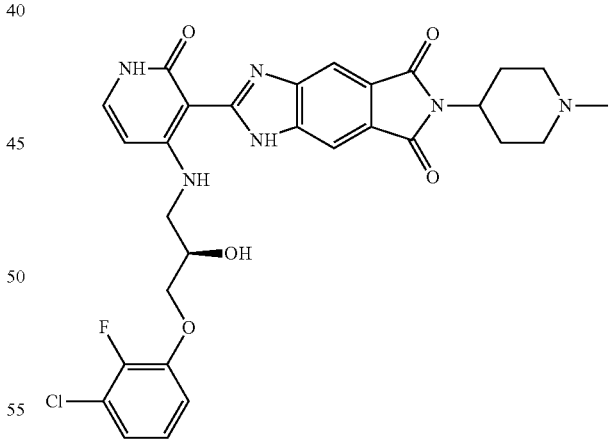

260

2-{4-[(R)-3-(3-Chloro-2-methyl-phenoxy)-2-hydroxy-propylamino]-2-oxo-2,3-dihydro-pyridin-3-yl}-6-(1-methyl-piperidin-4-yl)-1H-1,3,6-triaza-s-indacene-5,7-dione.
LCMS [M+H]$^+$ 591.3.
$^1$H NMR (300 MHz, DMSO): δ 13.45 (br.s., 1H), 11.33 (d, J=6.2 Hz, 1H), 10.96 (t, J=5.2 Hz, 1H), 9.85 (br.s., 1H), 7.60-8.20 (br.s., 2H), 7.41 (t, J=7.1 Hz, 1H), 7.17 (t, J=8.1 Hz, 1H), 7.04-6.98 (2d, 2H), 6.24 (d, J=8.1 Hz, 1H), 4.40-4.20 (m, 1H), 4.20-4.10 (m, 1H), 4.10-4.00 (m, 2H), 3.80-3.70 (m, 1H), 3.60-3.45 (m, 3H), 3.25-3.05 (m, 3H), 2.76 (d, J=4.17 Hz, 3H), 2.70-2.50 (m, 2H), 2.30-2.20 (s and m, 4H), 2.00-2.85 (m, 2H).

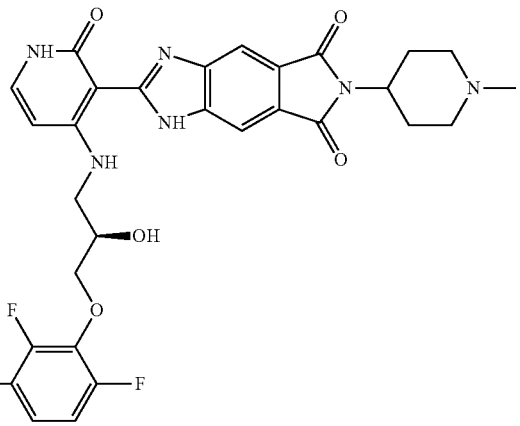

2-{4-[(R)-3-(3-Chloro-2,6-difluoro-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione.
LCMS [M+H]$^+$ 613.3.
$^1$H NMR (300 MHz, DMSO): δ 11.35 (d, J=6.2 Hz, 1H), 10.94 (t, J=4.4 Hz, 1H), 9.88 (br.s., 1H), 7.99 (br.s., 2H), 7.50-7.15 (m, 3H), 6.22 (d, J=7.1 Hz, 1H), 4.40-4.05 (m, 5H), 3.75-3.60 (m, 1H), 3.60-3.40 (m, 3H), 3.25-3.07 (m, 2H), 2.76 (d, J=4.29 Hz, 3H), 2.70-2.50 (m, 2H), 1.94 (m, 2H).

2-{4-[(R)-3-(3-Chloro-2-fluoro-phenoxy)-2-hydroxy-propylamino]-2-oxo-2,3-dihydro-pyridin-3-yl}-6-(1-methyl-piperidin-4-yl)-1H-1,3,6-triaza-s-indacene-5,7-dione.
LCMS [M+H]$^+$ 595.3.
$^1$H NMR (300 MHz, DMSO): δ 13.46 (s, 1H), 11.33 (d, J=6.0 Hz, 1H), 10.96 (m, 1H), 9.37 (br.s., 1H), 8.12 (s, 1H), 7.75 (s, 1H), 7.40 (m, 1H), 7.30-7.10 (m, 4H), 6.22 (d, J=7.0 Hz, 1H), 5.73 (br.s., 1H), 4.40-4.10 (m, 5H), 3.80-3.60 (m, 1H), 3.60-3.40 (m, 3H), 3.30-3.10 (m, 2H), 2.78 (d, J=4.20 Hz, 3H), 2.70-2.50 (m, 2H), 2.00 (m, 2H).

261

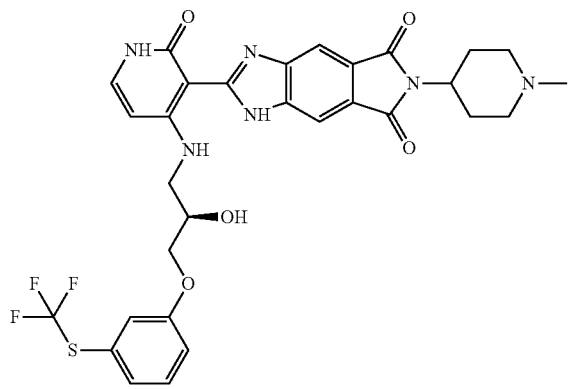 [SMILES: CN1CCC(N2C(=O)c3cc4nc(-c5c(NC[C@@H](O)COc6cccc(SC(F)(F)F)c6)cc[nH]c5=O)[nH]c4cc3C2=O)CC1]

2-{4-[(R)-2-Hydroxy-3-(3-trifluoromethylsulfanyl-phenoxy)-propylamino]-2-oxo-1,2-dihydro-pyridin-3-yl}-6-(1-methyl-piperidin-4-yl)-1H-1,3,6-triaza-s-indacene-5,7-dione. LCMS [M+H]$^+$ 643.3.

$^1$H NMR (300 MHz, DMSO): δ 13.45 (br.s. 1H), 11.33 (d, J=6.3 Hz, 1H), 10.99 (m, 1H), 9.75 (br.s., 1H), 8.20-7.60 (2H), 7.50-7.20 (m, 5H), 6.25 (d, J=7.1 Hz, 1H), 4.40-4.25 (m, 1H), 4.20-4.00 (m, 3H), 3.80-3.65 (m, 1H), 3.60-3.45 (m, 4H), 3.23-3.10 (m, 2H), 2.80-2.70 (d, J=4.2 Hz, 3H), 2.70-2.50 (m, 2H), 2.00-2.85 (m, 2H).

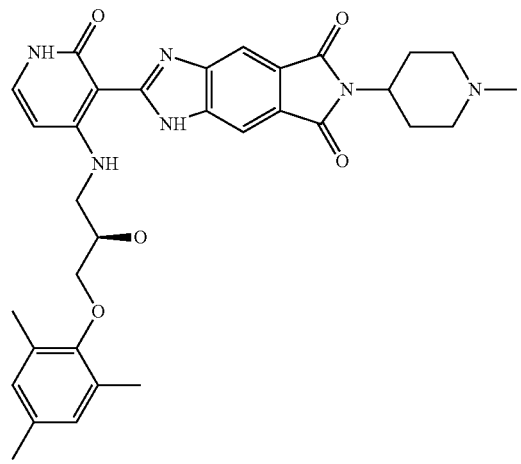 [SMILES: Cc1cc(C)c(OC[C@H](O)CNc2cc[nH]c(=O)c2-c2nc3cc4c(cc3[nH]2)C(=O)N(C2CCN(C)CC2)C4=O)c(C)c1]

2-{4-[(R)-2-Hydroxy-3-(2,4,6-trimethyl-phenoxy)-propylamino]-2-oxo-1,2-dihydro-pyridin-3-yl}-6-(1-methyl-piperidin-4-yl)-1H-1,3,6-triaza-s-indacene-5,7-dione.

LCMS [M+H]$^+$ 585.3.

$^1$H NMR (300 MHz, DMSO): δ 13.50 (br.s., 0.5H), 11.34 (d, J=6.2 Hz, 1H), 10.98 (m, 1H), 9.91 (br.s., 1H), 7.95 (br.s., 2H), 7.42 (t, J=6.9 Hz, 1H), 6.81 (s, 2H), 6.25 (d, J=7.9 Hz, 1H), 4.40-425 (m, 1H), 4.20-4.10 (m, 1H), 3.85-3.65 (m, 4H), 3.60-3.45 (m, 3H), 3.20-3.05 (m, 2H), 2.80-2.70 (m, 3H), 2.70-2.50 (m, 2H), 2.20, 2.17 (two s, 9H), 2.00-1.85 (m, 2H).

262

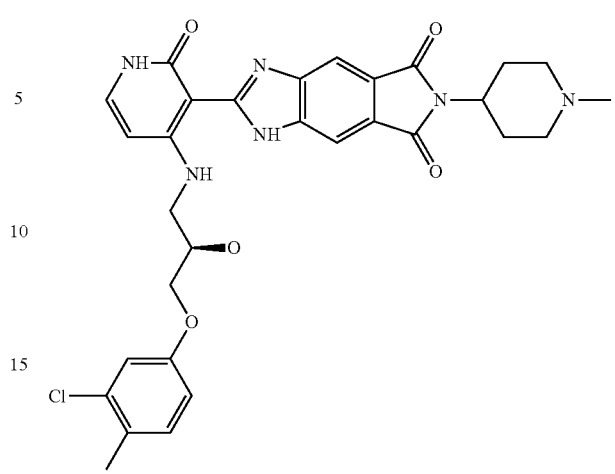

2-{4-[(R)-3-(3-Chloro-4-methyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione.

LCMS [M+H]$^+$ 591.2.

$^1$H NMR (300 MHz, DMSO): δ 13.50 (br.s., 0.5H), 11.33 (d, J=6.1 Hz, 1H), 10.94 (m, 1H), 9.90 (br.s., 1H), 8.10-7.80 (2H), 7.42 (t, J=6.9 Hz, 1H), 7.25 (d, J=8.4 Hz, 1H), 7.05 (d, J=2.4 Hz, 1H), 6.90 (dd, J=8.4, 2.4 Hz, 1H), 6.23 (d, J=7.5 Hz, 1H), 4.40-4.25 (m, 1H), 4.15-4.00 (m, 3H), 3.75-3.60 (m, 1H), 3.55-3.43 (m, 3H), 3.22-3.08 (m, 2H), 2.80-2.70 m, 3H), 2.70-2.50 (m, 2H), 2.25 (s, 3H), 2.00-1.85 (m, 2H).

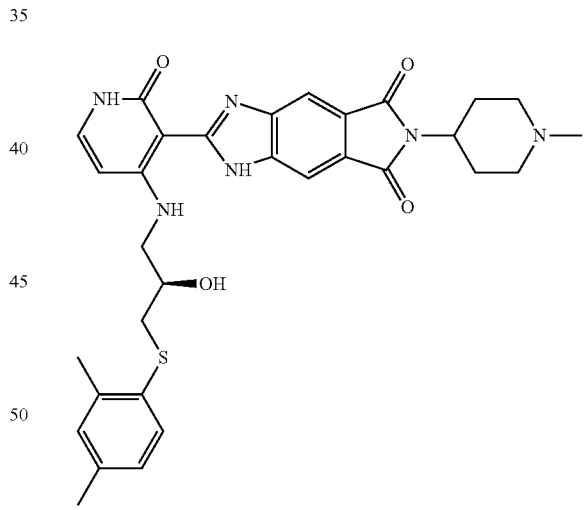

2-{4-[(R)-3-(2,4-Dimethyl-phenylsulfanyl)-2-hydroxy-propylamino]-2-oxo-1,2-dihydro-pyridin-3-yl}-6-(1-methyl-piperidin-4-yl)-1H-1,3,6-triaza-s-indacene-5,7-dione.

LCMS [M+H]$^+$ 587.2.

$^1$H NMR (300 MHz, DMSO): δ 13.43 (br.s., 1H), 11.32 (d, J=6.2 Hz, 1H), 10.92 (m, 1H), 9.43 (br.s., 1H), 8.13 (br.s., 1H), 7.87 (br.s., 1H), 7.39 (t, J=6.5 Hz, 1H), 7.26 (d, J=7.9 Hz, 1H), 7.02 (s, 1H), 6.93 (d, J=7.7 Hz, 1H), 6.14 (d, J=7.5 Hz, 1H), 5.6 (br.s., 1H), 4.32 (m, 1H), 3.90 (m, 1H), 3.30-2.90 (m, 5H), 2.80 (s, 3H), 2.70-2.50 (m, 2H), 2.30-2.20 (8H), 2.00-1.90 (m, 2H).

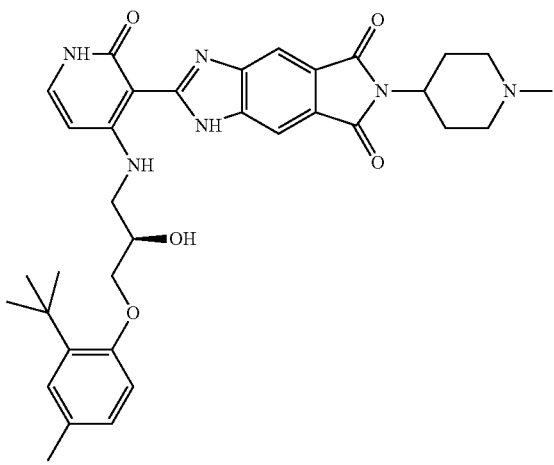 [SMILES: Cc1ccc(OC[C@H](O)CNc2cc[nH]c(=O)c2-c2nc3cc4c(cc3[nH]2)C(=O)N(C2CCN(C)CC2)C4=O)c(C(C)(C)C)c1]

2-{4-[(R)-3-(2-tert-Butyl-4-methyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione (free base). LCMS [M+H]+ 613.2.

1H NMR (300 MHz, DMSO): δ 13.41 (br.s., 1H), 11.32 (d, J=6.1 Hz, 1H), 11.01 (m, 1H), 8.09 (s, 1H), 7.59 (s., 1H), 7.41 (t, J=6.8 Hz, 1H), 7.06 (s, 1H), 6.95-6.85 (m, 2H), 6.21 (d, J=7.5 Hz, 1H), 5.56 (d, J=4.6 Hz, 1H), 4.20 (m, 1H), 4.10-3.90 (3H), 3.80-3.70 (m, 1H), 3.65-3.50 (m, 1H), 2.95-2.85 (m, 2H), 2.50-2.30 (m, 2H), 2.30-2.20 (7H), 2.10-1.90 m, 2H), 1.70-1.60 (m, 2H), 1.38 (s, 9H).

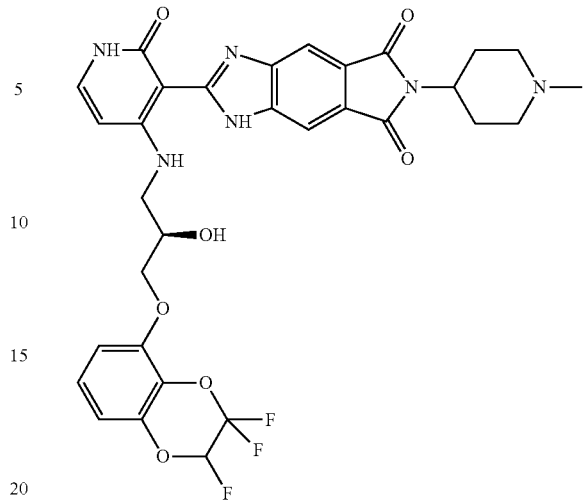

2-{4-[(R)-2-Hydroxy-3-(2,3,3-trifluoro-2,3-dihydro-benzo[1,4]dioxin-5-yloxy)-propylamino]-2-oxo-1,2-dihydro-pyridin-3-yl}-6-(1-methyl-piperidin-4-yl)-1H-1,3,6-triaza-s-indacene-5,7-dione. LCMS [M+H]+ 655.7.

1H NMR (300 MHz, DMSO): δ 13.44 (br.s., 1H), 11.33 (d, J=5.4 Hz, 1H), 10.99 (m, 1H), 9.44 (br.s, 1H), 8.13 (br.s., 1H), 7.80 (m, 1H), 7.38 (t, J=6.1 Hz, 1H), 7.20-6.95 (m, 3H), 6.95-6.80 (m, 2H), 6.23 (d, J=7.9 Hz, 1H), 5.72 (br.s., 1H), 4.32 (m, 1H), 4.25-4.15 (3H), 3.30-3.05 (m, 2H), 2.79 (m, 3H), 2.70-2.50 (m, 2H), 1.99-1.85 (m, 2H).

2-{4-[(R)-2-Hydroxy-3-(2,2,3-trifluoro-2,3-dihydro-benzo[1,4]dioxin-5-yloxy)-propylamino]-2-oxo-1,2-dihydro-pyridin-3-yl}-6-(1-methyl-piperidin-4-yl)-1H-1,3,6-triaza-s-indacene-5,7-dione. LCMS [M+H]+ 655.3.

1H NMR (300 MHz, DMSO): δ 13.44 (br.s., 1H), 11.34 (d, J=5.4 Hz, 1H), 10.99 (m, 1H), 9.49 (br.s, 1H), 8.12 (br.s., 1H), 7.84 (m, 1H), 7.40 (t, J=6.1 Hz, 1H), 7.20-7.00 n (m, 3H), 6.95-6.85 (m, 2H), 6.23 (d, J=7.9 Hz, 1H), 5.69 (br.s., 1H), 4.32 (m, 1H), 4.10-3.90 (3H), 3.60-3.40 (2H), 3.30-3.05 (m, 2H), 2.79 (s, 3H), 2.70-2.50 (m, 2H), 2.00-1.85 (m, 2H).

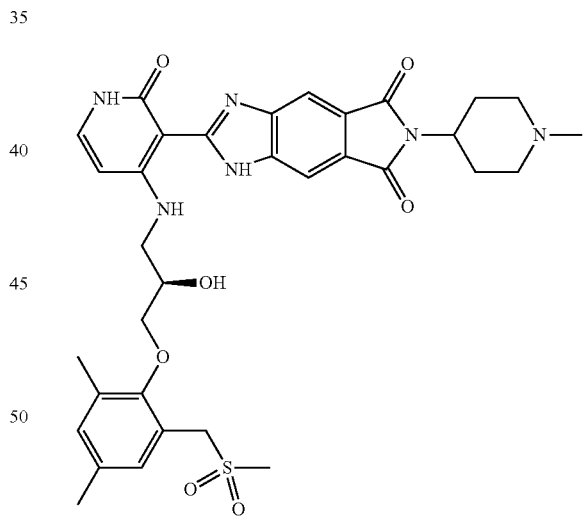

2-{4-[(R)-2-Hydroxy-3-(2-methanesulfonylmethyl-4,6-dimethyl-phenoxy)-propylamino]-2-oxo-1,2-dihydro-pyridin-3-yl}-6-(1-methyl-piperidin-4-yl)-1H-1,3,6-triaza-s-indacene-5,7-dione. LCMS [M+H]+ 663.7.

1H NMR (300 MHz, DMSO): δ 13.47 (br.s., 1H), 11.34 (d, J=5.8 Hz, 1H), 10.95 (m, 1H), 9.54 (br.s, 1H), 8.13 (br.s., 1H), 7.85 (m, 1H), 7.42 (t, J=6.8 Hz, 1H), 7.05-7.00 (m, 2H), 6.24 (d, J 8.0 Hz, 1H), 4.55-4.45 (m, 2H), 4.35-4.27 (m, 1H), 4.20-4.10 (m, 1H), 3.95-03.85 (m, 3H), 3.25-3.10 (m, 2H), 2.90 (s, 3H), 2.80-2.75 (m, 3H), 2.70-2.50 (m, 2H), 2.30-2.20 (8H), 1.99-1.85 (m, 2H).

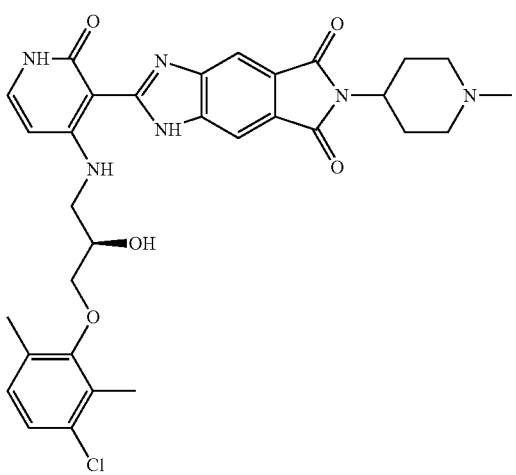 [SMILES: Cc1ccc(Cl)c(C)c1OC[C@H](O)CNc1cc[nH]c(=O)c1-c1nc2cc3c(cc2[nH]1)C(=O)N(C1CCN(C)CC1)C3=O]

2-{4-[(R)-3-(3-Chloro-2,6-dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione. LCMS [M+H]$^+$ 605.3.

$^1$H NMR (300 MHz, DMSO): δ 13.45 (br.s., 0.5H), 11.34 (d, J=5.7 Hz, 1H), 10.98 (m, 1H), 9.86 (br.s, 1H), 7.99 (br.s., 1H), 7.43 (t, J=6.7 Hz, 1H), 7.14-7.05 (m, 2H), 6.24 (d, J=7.7 Hz, 1H), 4.35-4.27 (m, 1H), 4.20-4.10 (m, 1H), 3.90-3.80 (m, 3H), 3.22-3.10 (m, 2H), 2.90 (m, 3H), 2.70-2.50 (m, 2H), 2.29 (s, 3H), 2.23 (s, 3H), 2.00-1.85 (m, 2H).

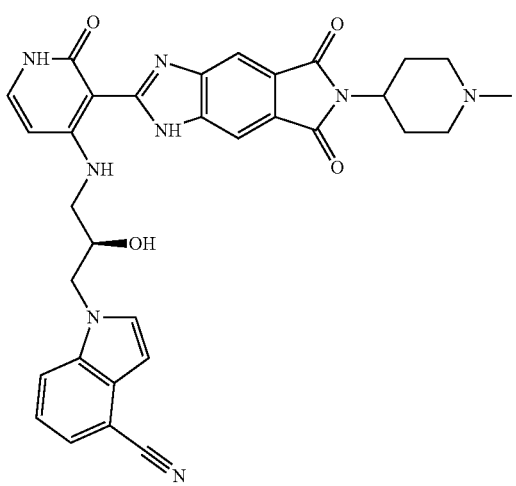 [SMILES: CN1CCC(N2C(=O)c3cc4nc(-c5c(NC[C@@H](O)Cn6ccc7c(C#N)cccc76)cc[nH]c5=O)[nH]c4cc3C2=O)CC1]

1-((R)-2-Hydroxy-3-{3-[6-(1-methyl-piperidin-4-yl)-5,7-dioxo-1,5,6,7-tetrahydro-1,3,6-triaza-s-indacen-2-yl]-2-oxo-1,2-dihydro-pyridin-4-ylamino}-propyl)-1H-indole-4-carbonitrile. LCMS [M+H]$^+$ 591.3.

$^1$H NMR (300 MHz, DMSO): δ 11.34 (d, J=6.1 Hz, 1H), 10.97 (m, 1H), 9.91 (br.s, 1H), 8.03 (br.s., 2H), 7.99 (d, J=8.3 Hz, 1H), 7.72 (d, J=3.6 Hz, 1H), 7.55 (d, J=6.7 Hz, 1H), 7.41 (t, J=7.3 Hz, 1H), 7.29-7.22 (m, 1H), 6.62 (d, J=3.1 Hz, 1H), 6.16 (d, J=7.2 Hz, 1H), 4.50 (dd, J=13.9, 4.1 Hz, 2H), 4.40-4.20 (m, 2H), 3.80-3.60 (m, 2H), 3.57 (s, 1H), 3.55-3.42 (m, 3H), 3.22-3.05 (m, 2H), 2.85 (m, 3H), 2.70-2.50 (m, 2H), 2.00-1.85 (m, 2H).

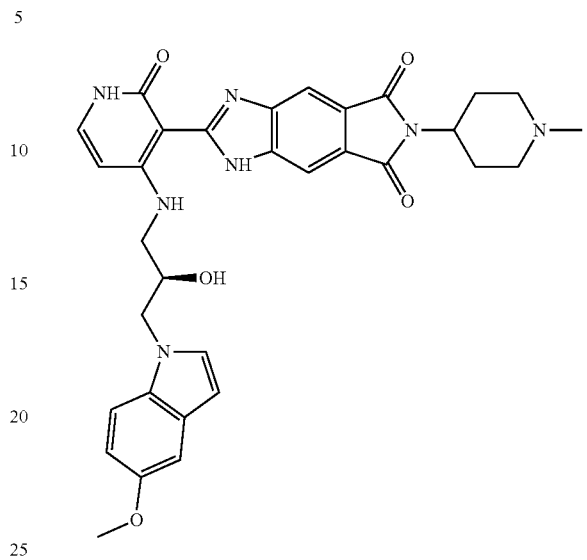

2-{4-[(R)-2-Hydroxy-3-(5-methoxy-indol-1-yl)-propylamino]-2-oxo-1,2-dihydro-pyridin-3-yl}-6-(1-methyl-piperidin-4-yl)-1H-1,3,6-triaza-s-indacene-5,7-dione.

LCMS [M+H]$^+$ 596.3.

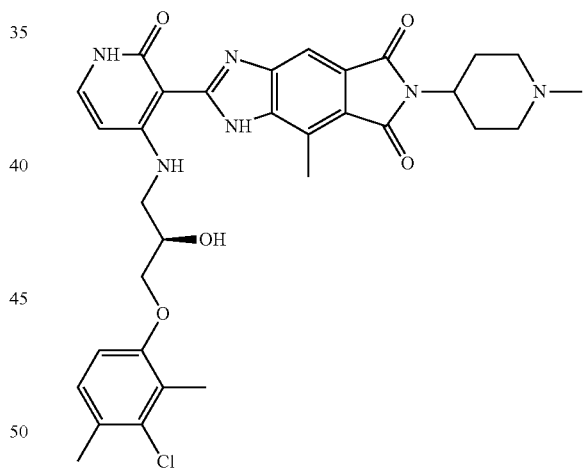

2-{4-[(R)-3-(3-Chloro-2,4-dimethyl-phenoxy)-2-hydroxy-propylamino]-2-oxo-1,2-dihydro-pyridin-3-yl}-8-methyl-6-(1-methyl-piperidin-4-yl)-1H-1,3,6-triaza-s-indacene-5,7-dione. LCMS [M+H]$^+$ 619.5.

$^1$H NMR (300 MHz, DMSO): δ 13.35 (s, 1H), 11.30 (d, J=6.6 Hz, 1H), 11.11 (m, 1H), 9.39 (br.s, 1H), 7.96 (s, 1H), 7.40 (t, J=6.6 Hz, 1H), 7.08 (d, J=8.8 Hz, 1H), 6.86 (d, J=8.8 Hz, 1H), 6.22 (d, J=8.8 Hz, 1H), 5.59 (br.s., 1H), 4.35-4.25 (m, 1H), 4.23-4.15 (m, 1H), 4.12-4.00 (m, 2H), 3.80-3.70 (m, 1H), 3.30-3.05 (m, 2H), 2.90-2.70 (7H), 2.24 (s, 7H), 2.00-1.85 (m, 2H).

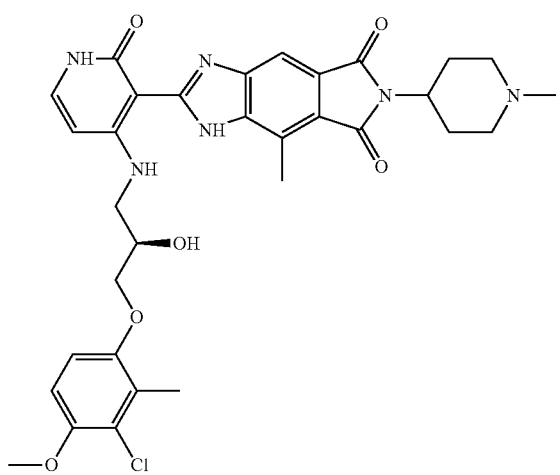

2-{4-[(R)-3-(3-Chloro-4-methoxy-2-methyl-phenoxy)-2-hydroxy-propylamino]-2-oxo-1,2-dihydro-pyridin-3-yl}-8-methyl-6-(1-methyl-piperidin-4-yl)-1H-1,3,6-triaza-s-indacene-5,7-dione. LCMS [M+H]+ 635.5.

¹H NMR (300 MHz, DMSO): δ 13.35 (s, 1H), 11.30 (d, J=5.6 Hz, 1H), 11.11 (m, 1H), 9.38 (br.s, 1H), 7.96 (s, 1H), 7.40 (t, J=6.4 Hz, 1H), 6.90 (m, 2H), 6.22 (d, J=8.2 Hz, 1H), 5.58 (br.s., 1H), 4.37-4.23 (m, 1H), 4.22-4.13 (m, 1H), 4.12-4.00 (m, 3H), 3.85-3.65 (m, 7H), 3.65-3.50 (m, 2H), 3.25-3.08 (m, 2H), 2.90-2.70 (m, 7H), 2.35-2.20 (m, 8H), 2.15-2.05 (m, 3H), 2.00-1.85 (m, 2H).

Synthesis of Lactam Derivatives

Scheme 45

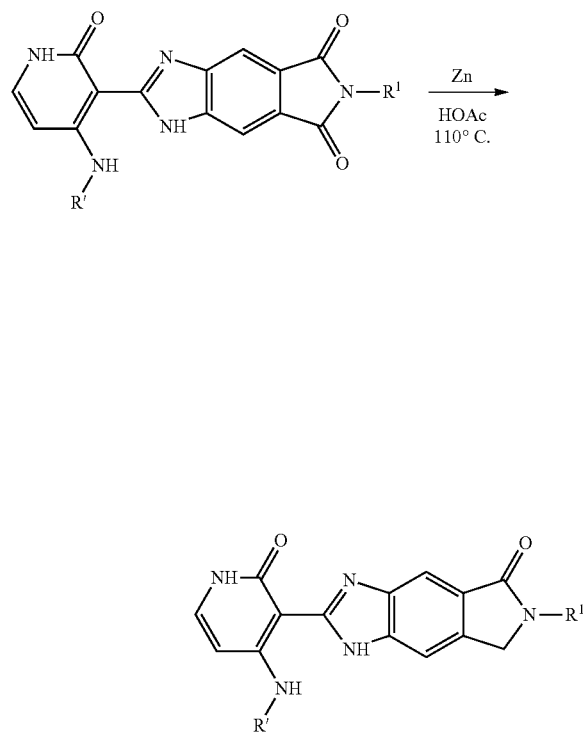

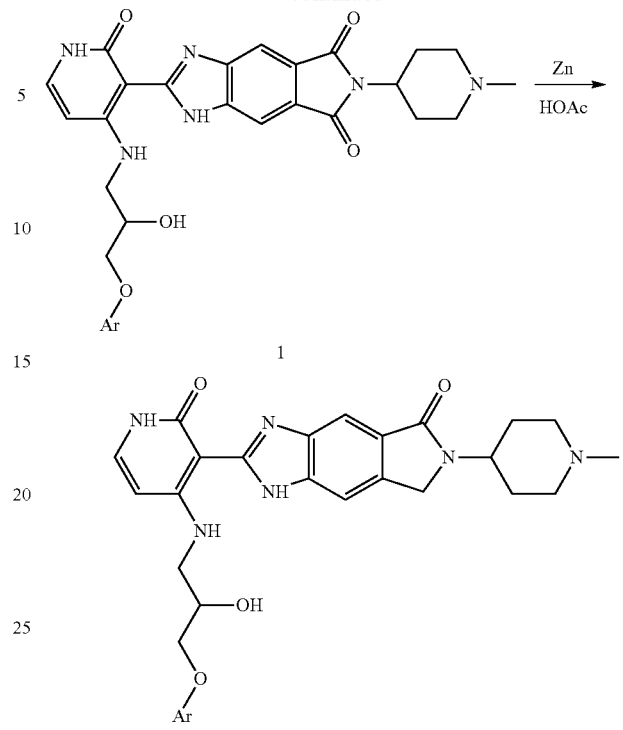

Ar = aryl or heteroaryl

General Procedure.

A mixture of phthalimide-type compound [2-(4-(substituted-amino)-2-oxo-1,2-dihydropyridin-3-yl)-6-(R1-substituted)imidazo[4,5-f]isoindole-5,7(1H,6H)-dione](20 mg), AcOH (1.0 mL), Zn (dust) (100 mg) was stirred at 70° C. for 10 h. Then the reaction mixture was cooled to RT, filtered, evaporated. The residue was purified by preparative HPLC on C18 column (acetonitrile-0.1% TFA) (5:95% to 95:5%).

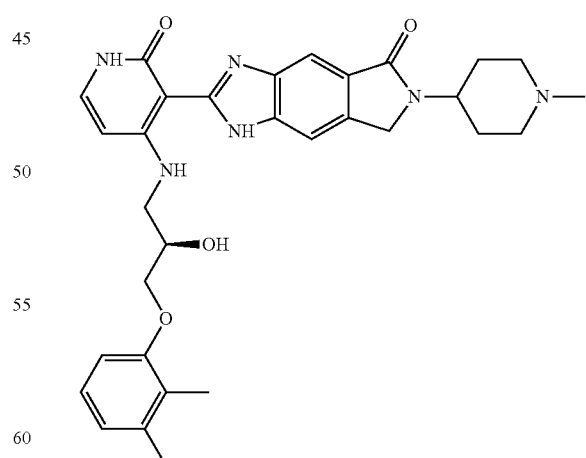

2-{4-[(R)-2-Hydroxy-3-(3-methoxy-2-methyl-phenoxy)-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]+ 573.3.

269

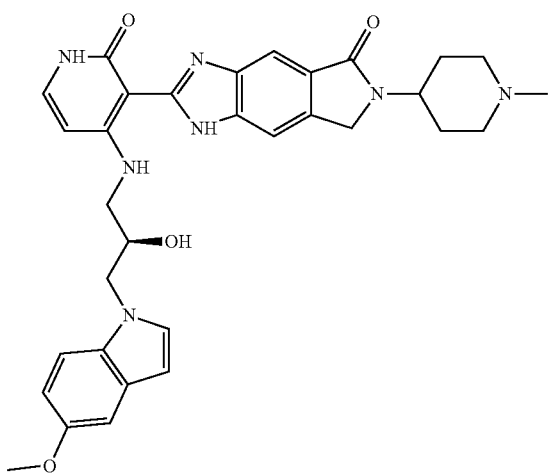

2-{4-[(R)-2-Hydroxy-3-(5-methoxy-indol-1-yl)-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]$^+$ 583.0.

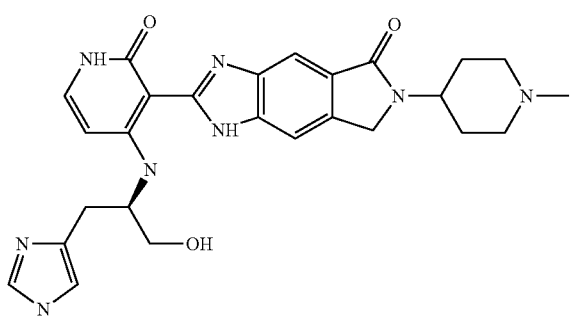 [SMILES: CN1CCC(N2Cc3cc4[nH]c(-c5c(N[C@@H](CO)Cc6c[nH]cn6)cc[nH]c5=O)nc4cc3C2=O)CC1]

2-{4-[(R)-2-Hydroxy-1-(1H-imidazol-4-ylmethyl)-ethylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]$^+$ 503.5.

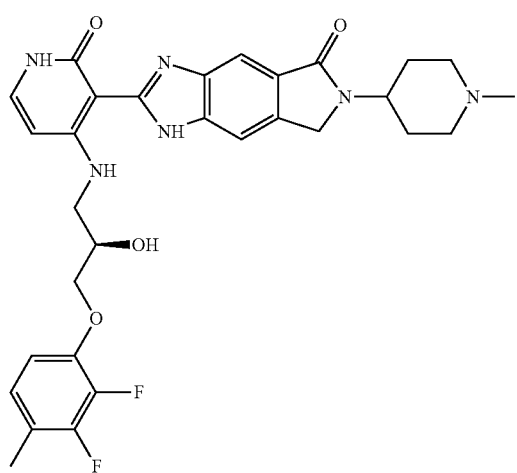 [SMILES: Cc1ccc(OC[C@H](O)CNc2cc[nH]c(=O)c2-c2nc3cc4c(cc3[nH]2)CN(C2CCN(C)CC2)C4=O)c(F)c1F]

2-{4-[(R)-3-(2,3-Difluoro-4-methyl-phenoxy)-2-hydroxy-propylamino]-2-oxo-1,2-dihydro-pyridin-3-yl}-6-(1-

270 methyl-piperidin-4-yl)-6,7-dihydro-1H-1,3,6-triaza-s-indacen-5-one. LCMS [M+H]$^+$ 579.5.

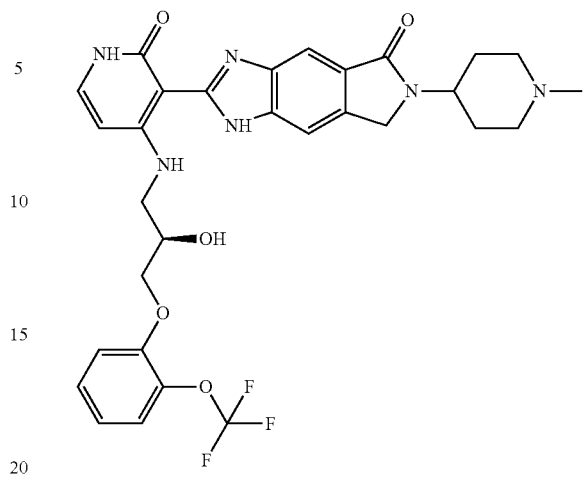

2-{4-[(R)-2-Hydroxy-3-(2-trifluoromethoxy-phenoxy)-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]$^+$ 613.3.

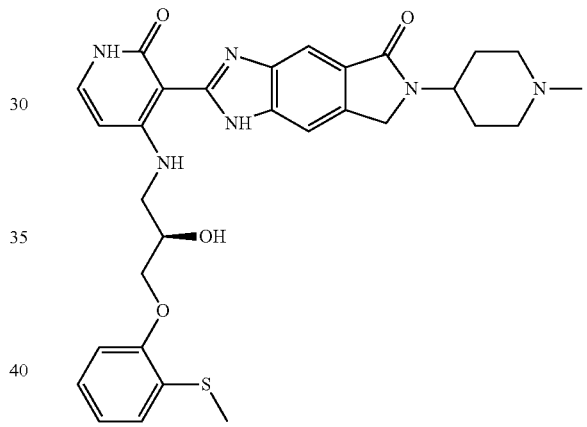

2-{4-[(R)-2-Hydroxy-3-(2-methylsulfanyl-phenoxy)-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]$^+$ 575.5.

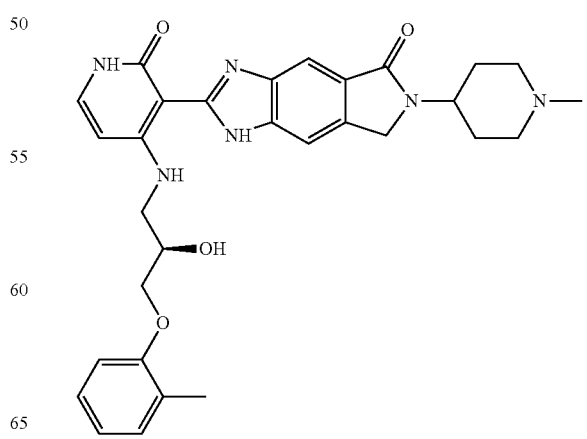

271

2-[4-((R)-2-Hydroxy-3-o-tolyloxy-propylamino)-2-oxo-1,2-dihydro-pyridin-3-yl]-6-(1-methyl-piperidin-4-yl)-6,7-dihydro-1H-1,3,6-triaza-s-indacen-5-one.

LCMS [M+H]+ 543.5.

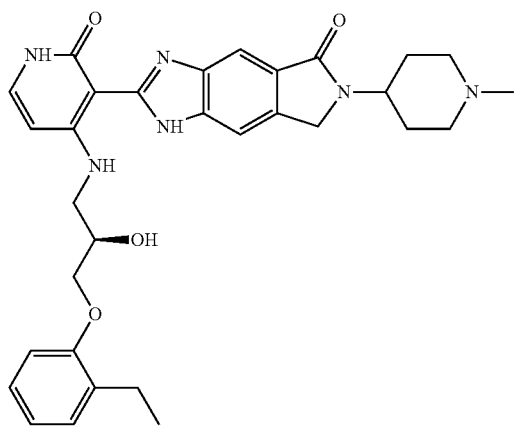 [SMILES: CCc1ccccc1OC[C@H](O)CNc1cc[nH]c(=O)c1-c1nc2cc3c(cc2[nH]1)CN(C1CCN(C)CC1)C3=O]

2-{4-[(R)-3-(2-Ethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one.

LCMS [M+H]+ 557.5

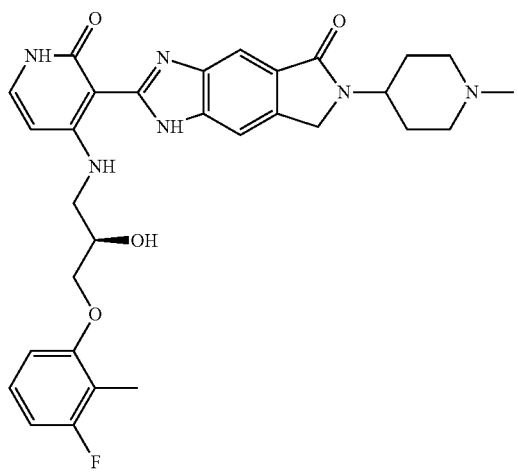 [SMILES: Cc1c(F)cccc1OC[C@H](O)CNc1cc[nH]c(=O)c1-c1nc2cc3c(cc2[nH]1)CN(C1CCN(C)CC1)C3=O]

2-{4-[(R)-3-(3-Fluoro-2-methyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]+ 561.3.

272

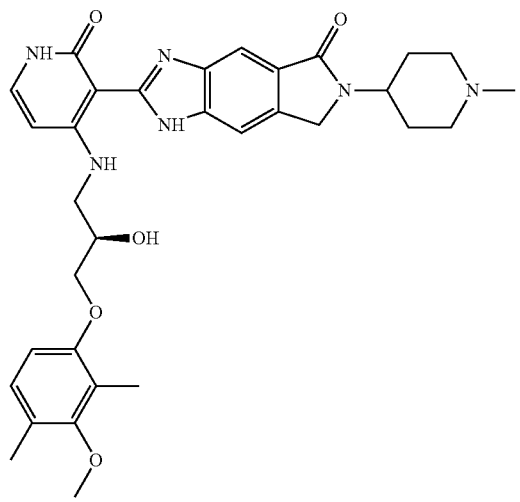 [SMILES: COc1c(C)ccc(OC[C@H](O)CNc2cc[nH]c(=O)c2-c2nc3cc4c(cc3[nH]2)CN(C2CCN(C)CC2)C4=O)c1C]

2-{4-[(R)-2-Hydroxy-3-(3-methoxy-2,4-dimethyl-phenoxy)-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]+ 587.3.

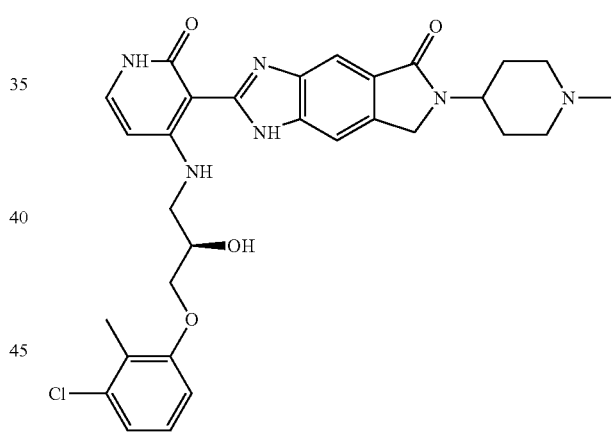

2-{4-[(R)-3-(3-Chloro-2-methyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one LCMS [M+H]+ 577.5.

$^1$H NMR (300 MHz, DMSO): δ 13.08 (br.s., 1H), 11.24 (d, J=5.9 Hz, 1H), 11.14 (m, 1H), 9.43 (br.s, 1H), 8.02-7.70 (m, 2H), 7.37 (t, J=6.4 Hz, 1H), 7.29-6.94 (m, 3H), 6.22 (d, J=7.5 Hz, 1H), 5.58 (br.s., 1H), 4.46 (s, 2H), 4.37-4.24 (m, 1H), 4.20-4.11 (m, 1H), 4.08 (s, 2H), 3.77-3.62 (m, 1H), 3.25-3.16 (m, 2H), 2.81 (d, J=4.3 Hz, 3H), 2.28 (s, 3H), 2.28-2.24 (m, 1H), 2.08 (s, 2H), 2.03-1.96 (m, 3H).

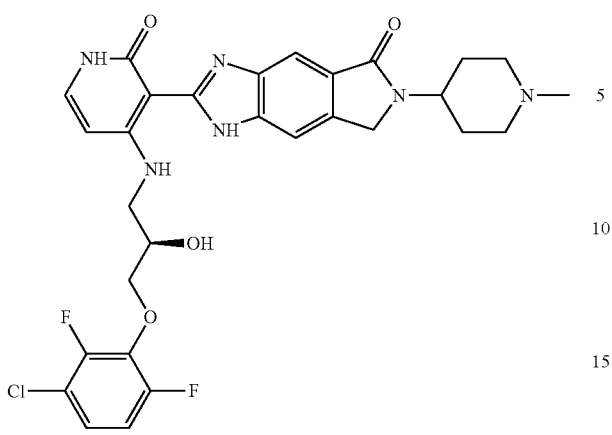

2-{4-[(R)-3-(3-Chloro-2,6-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one. LCMS [M+H]+ 599.5.

$^1$H NMR (300 MHz, DMSO): δ 13.08 (br.s., 1H), 11.26 (d, J=6.7 Hz, 1H), 11.11 (m, 1H), 9.47 (br.s, 1H), 8.05-7.60 (m, 2H), 7.40-6.95 (m, 3H), 6.20 (d, J=7.3 Hz, 1H), 5.56 (br.s., 1H), 4.48 (s, 2H), 4.42-4.28 (m, 1H), 4.18-4.05 (m, 2H), 3.77-3.62 (m, 1H), 3.60-3.35 (m, 4H), 3.30-3.10 (m, 2H), 2.81 (d, J=3.7 Hz, 3H), 2.08 (s, 1H), 2.03-1.90 (m, 3H).

Synthesis of 5,6-diamino-2-(1-methylpiperidin-4-yl)isoindolin-1-one

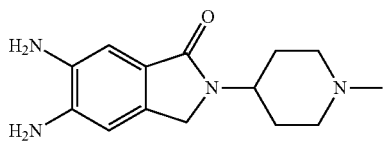 [SMILES: CN1CCC(N2Cc3cc(N)c(N)cc3C2=O)CC1]

5,6-Diamino-2-(1-methylpiperidin-4-yl)isoindoline-1-one. A mixture of 5-amino-2-(1-methyl-piperidin-4-yl)-6-nitro-isoindole-1,3-dione (10.0 g, 32.9 mmol), tin powder (39.7 g, 329 mmol), EtOH (300 mL) and conc. HCl (100 mL) was stirred at 75° C. for 4 h. After cooling to RT excess of Tin was removed by filtration, the filtrate was evaporated. The residue was dissolved in CH$_2$Cl$_2$-MeOH (1:1) mixture, basified with NH$_4$OH. Precipitate formed was removed by filtration, SiO$_2$ was added to the filtrate, stirred for 1 h, the solvent was evaporated, the residue was loaded onto SiO$_2$ (500 g) column. Eluted with CH$_2$Cl$_2$-MeOH—NH4OH (gradient from 100:0:0 to 100:10:1 v/v). Yield 7.86 g (30.2 mmol, 92%) as beige solid. LCMS [M+H]+ 261.4.

$^1$H NMR (300 MHz, DMSO): δ 6.77 (s, 1H), 6.59 (s, 1H), 5.07 (s, 2H), 4.62 (s, 2H), 3.86 (m, 1H), 3.16 (d, J=5.5 Hz, 2H), 2.82 (m, 2H), 2.17 (s, 3H), 1.94 (m, 2H), 1.73 (m, 2H), 1.55 (m, 2H).

Preparation of 3-chloro-2,4-dimethyl-phenol

Scheme 46

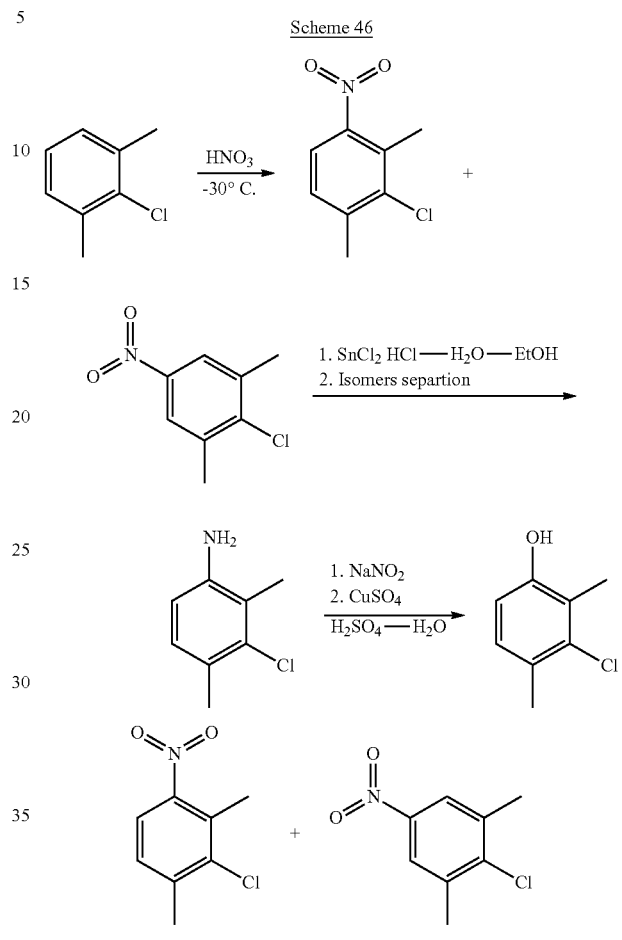

Nitration of 2-chloro-m-xylene. Nitric acid (90%, 50 mL) was cooled to −35° C. (ethanol-dry ice bath). 2-Chloro-m-xylene (10 mL) was added dropwise over 1 h keeping the temperature between −30° C. and −35° C. The reaction mixture was poured onto ice, stirred for 10 min, precipitate formed was collected by filtration, washed with water, dried. The crude product was purified on SiO$_2$ (50 g), hexane-EtOAc (0 to 2% v/v). The product—yellow solid, 12.8 g, as a mixture of 2-chloro-1,3-dimethyl-4-nitro-benzene and chloro-1,3-dimethyl-5-nitro-benzene (4:1).

$^1$H NMR (300 MHz, CDCl$_3$): δ 7.95 (s, 0.5H) (II), 7.63 (d, J=8.3 Hz, 1.0H) (I), 7.21 (d, J=8.3 Hz, 1H) (I), 2.55 (s, 3H) (I), 2.47 (s, 1.5H) (II), 2.45 (s, 3H) (I).

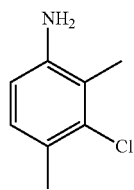

3-Chloro-2,4-dimethyl-aniline. To a solution of a mixture 2-chloro-1,3-dimethyl-4-nitro-benzene and chloro-1,3-dimethyl-5-nitro-benzene (12.8 g, 69 mmol) in EtOH (75 mL), conc. HCl (75 mL) was added. Than SnCl$_2$ (51.0 g) was added in two portions. The mixture was stirred overnight at RT, then heated at 60° C. for 30 min, cooled to 0-5° C. (ice bath). Neutralized with NaOH (70 g) in H$_2$O (500 ml). The product was extracted with Et$_2$O (500 ml). Extract was dried over Na$_2$SO$_4$, evaporated. The residue was crystallized two times from hexane providing 3.66 g 3-chloro-2,4-dimethyl-phenylamine as white crystals. The filtrates were evaporated in vacuo and the residue was separated on SiO$_2$ column (200 g), hexane-EtOAc (0 to 10% v/v). providing additionally 3.11 g of the product. Yield 6.77 g (43.5 mmol, 63%).

$^1$H NMR (300 MHz, CDCl$_3$): δ 6.89 (d, J=8.3 Hz, 1H), 6.52 (d, J=8.0 Hz, 1H), 3.57 (br.s., 2H), 2.27 (s, 3H), 2.24 (s, 3H).

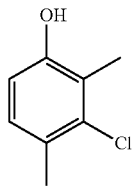

3-Chloro-2,4-dimethylphenol. To a suspension of 3-chloro-2,4-dimethyl-aniline (0.47 g, 3.0 mmol), in a mixture of water (3 mL) and conc. H$_2$SO$_4$ (2 ml), a solution of Na$_2$NO$_2$ (0.22 g) in H$_2$O (5 ml) was added dropwise at 0° C. The mixture was stirred 1 h at 0° C., than treated with urea (0.2 g), stirred for 10 min at 0° C. A solution of CuSO$_4$ (1.0 g) in water (6 mL) was added and the mixture was stirred for 60 h at RT. The reaction mixture was extracted with CH$_2$Cl$_2$ (2×20 ml), extracts were dried over Na$_2$SO$_4$ and evaporated. The residue was separated on SiO$_2$ (4.0 g) column, hexane-EtOAc (0 to 10%). Brown crystals, 45 mg (0.29 mmol, 10%).

$^1$H NMR (300 MHz, CDCl$_3$): δ 6.92 (d, J 8.3 Hz, 1H), 6.59 (d, J 8.1 Hz, 1H), 4.96 (br.s., 1H), 2.29 (s, 6H).

Preparation of 3-methoxy-2,4-dimethyl-phenol

Scheme 47

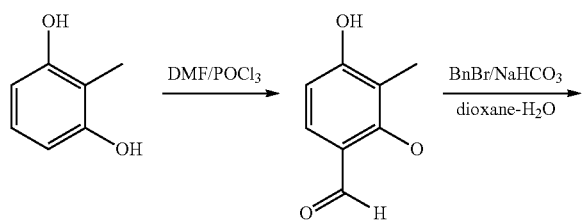

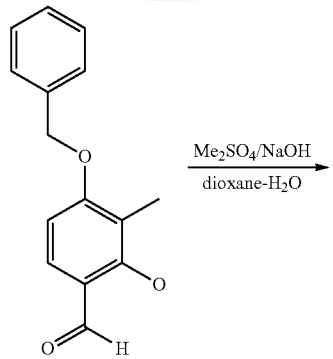

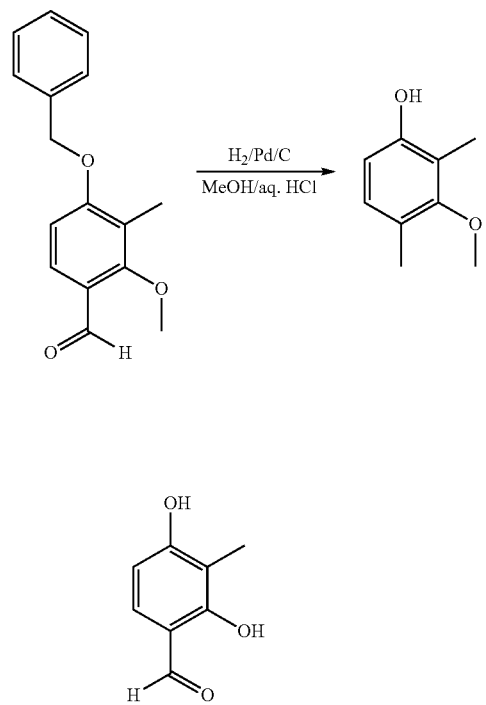

2,4-Dihydroxy-3-methyl-benzaldehyde. Phosphorus oxychloride (8.0 mL, 86 mmol) was added dropwise with stirring to DMF (26 mL, 0.336 mol) the temperature being kept at 10-20° C. This reagent was slowly added to a solution of 2-methylresorcinol (4.84 g, 39 mmol) in 26 mL DMF at 20-30° C. After 30 min the reaction mixture was poured in 2 M aq. NaOH (200 ml), extracted with Et$_2$O (2×100 mL), aqueous phase was neutralized with 5N aq. HCl, the product was extracted with Et$_2$O (2×200 mL), dried and evaporated. The residue was separated on SiO$_2$ (100 g) column, hexane-EtOAc (0 to 20% v/v). Yield 4.1 g (27 mmol, 69%) as white solid. $^1$H NMR (300 MHz, DMSO): δ 11.61 (s, 1H), 10.79 (s, 1H), 9.71 (s, 1H), 7.43 (d, J=8.4 Hz, 1H), 6.55 (d, J=8.5 Hz, 1H), 1.97 (s, 3H).

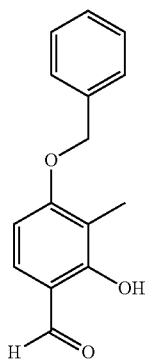 [SMILES: Cc1c(OCc2ccccc2)ccc(C=O)c1O]

4-Benzyloxy-2-hydroxy-3-methyl-benzaldehyde. A mixture of 2,4-dihydroxy-3-methyl-benzaldehyde (3.31 g, 21.8 mmol), benzylbromide (4.09 g, 23.9 mmol), NaHCO$_3$ (5.49 g, 65.4 mmol), 1,4-dioxane (30 mL) and water (12 mL) was stirred at 60° C. for overnight. Then the reaction mixture was cooled to RT, water (100 mL) was added, extracted with EtOAc (2×200 mL). The extract was dried over Na$_2$SO$_4$, evaporated. The residue was purified on SiO$_2$ (25 g) column, hexane-EtOAc (0 to 5%). Yield 1.57 g (6.48 mmol, 29%) as off-white solid.

$^1$H NMR (300 MHz, DMSO): δ 11.38 (s, 1H), 9.82 (s, 1H), 7.62 (d, J=8.7 Hz, 1H), 7-84-7.32 (m, 5H), 6.85 (d, J=8.6 Hz, 1H), 5.27 (s, 2H), 2.05 (s, 3H).

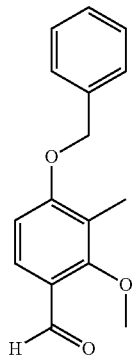

4-Benzyloxy-2-methoxy-3-methyl-benzaldehyde. A mixture of 4-benzyloxy-2-hydroxy-3-methyl-benzaldehyde (1.57 g, 6.49 mmol), dimethylsulfate (1.04 ml, 10.9 mmol), NaOH (1.02 g, 25.5 mmol), 1,4-dioxane (20 mL) and water (10 mL) was stirred at 90° C. for 6 h. The reaction mixture was cooled to RT, water (100 mL) was added, extracted with EtOAc (150 mL). The extract was washed with brine (100 mL), dried over Na$_2$SO$_4$ and evaporated. The residue was purified on SiO$_2$ (25 g) column, hexane to toluene. Yield 1.20 g (4.68 mmol, 72%), white solid. $^1$H NMR (300 MHz, DMSO): δ 10.11 (s, 1H), 7.64 (d, J=8.9 Hz, 1H), 7.49-7.32 (m, 5H), 7.05 (d, J=8.9 Hz, 1H), 5.24 (s, 2H), 3.81 (s, 3H), 2.14 (s, 3H).

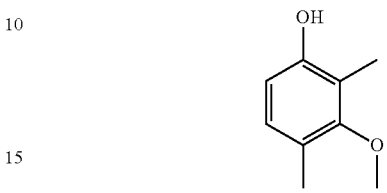

3-Methoxy-2,4-dimethyl-phenol. A mixture of 4-benzyloxy-2-methoxy-3-methyl-benzaldehyde (1.1 g, 4.68 mmol), 10% Pd/C (0.150 g), MeOH (20 mL) and conc. HCl was stirred under H$_2$ at RT for 1 h. Pd/C was removed by filtration, the filtrate was evaporated, the residue was purified on SiO$_2$ column (12 g), hexane—CH$_2$Cl$_2$ (100:0 to 50:50). Yield 0.67 g (4.40 mmol, 94%), brown oil. $^1$H NMR (300 MHz, CDCl$_3$): δ 6.88 (d, J=8.1 Hz, 1H), 6.49 (d, J=8.2 Hz, 1H), 4.73 (s, 1H), 3.70 (s, 3H), 2.21 (s, 2H), 2.18 (s, 3H).

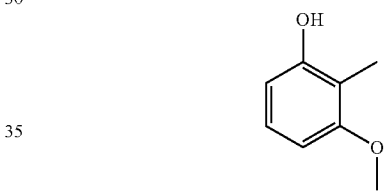

3-Methoxy-2-methyl-phenol was prepared according to published procedure: *J. Org. Chem.* 55, 5, 1990, 1469. To a solution of 2.0 g (50 mmol) NaOH and 2-methylresorcinol (6.2 g, 50 mmol) in water (50 mL), dimethylsulfate (4.8 mL, 50 mmol) was added at 95° C. over 30 min, then reaction was stirred for 2 h at 95° C. After cooling to RT, the reaction mixture was poured into aqueous NaOH (8.0 g in 200 ml H$_2$O). Extracted with Et$_2$O (2×100 mL). The aqueous phase was acidified with 5 N aq. HCl, extracted with Et$_2$O (2×100 mL), extracts were dried over Na$_2$SO$_4$ and evaporated. The residue was purified on SiO$_2$ (200 g) column, hexane-EtOAc (0 to 20%). Yield 3.37 g (24.0 mmol, 49%), colorless oil.

$^1$H NMR (300 MHz, DMSO): δ 9.21 (s, 1H), 6.93 (t, J=8.4 Hz, 1H), 6.48-6.38 (m, 2H), 3.72 (s, 3H), 1.98 (s, 3H).

Synthesis of Lactams with 2-Hydroxyamine Side Chains

Scheme 48

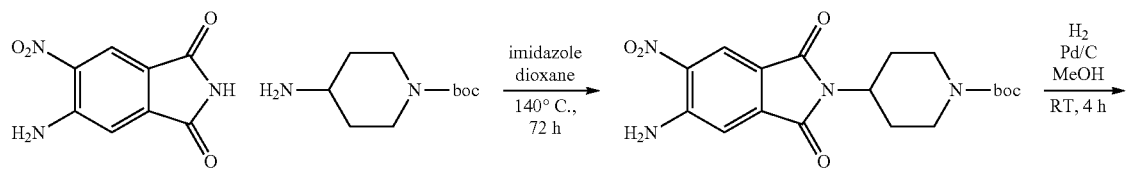

-continued
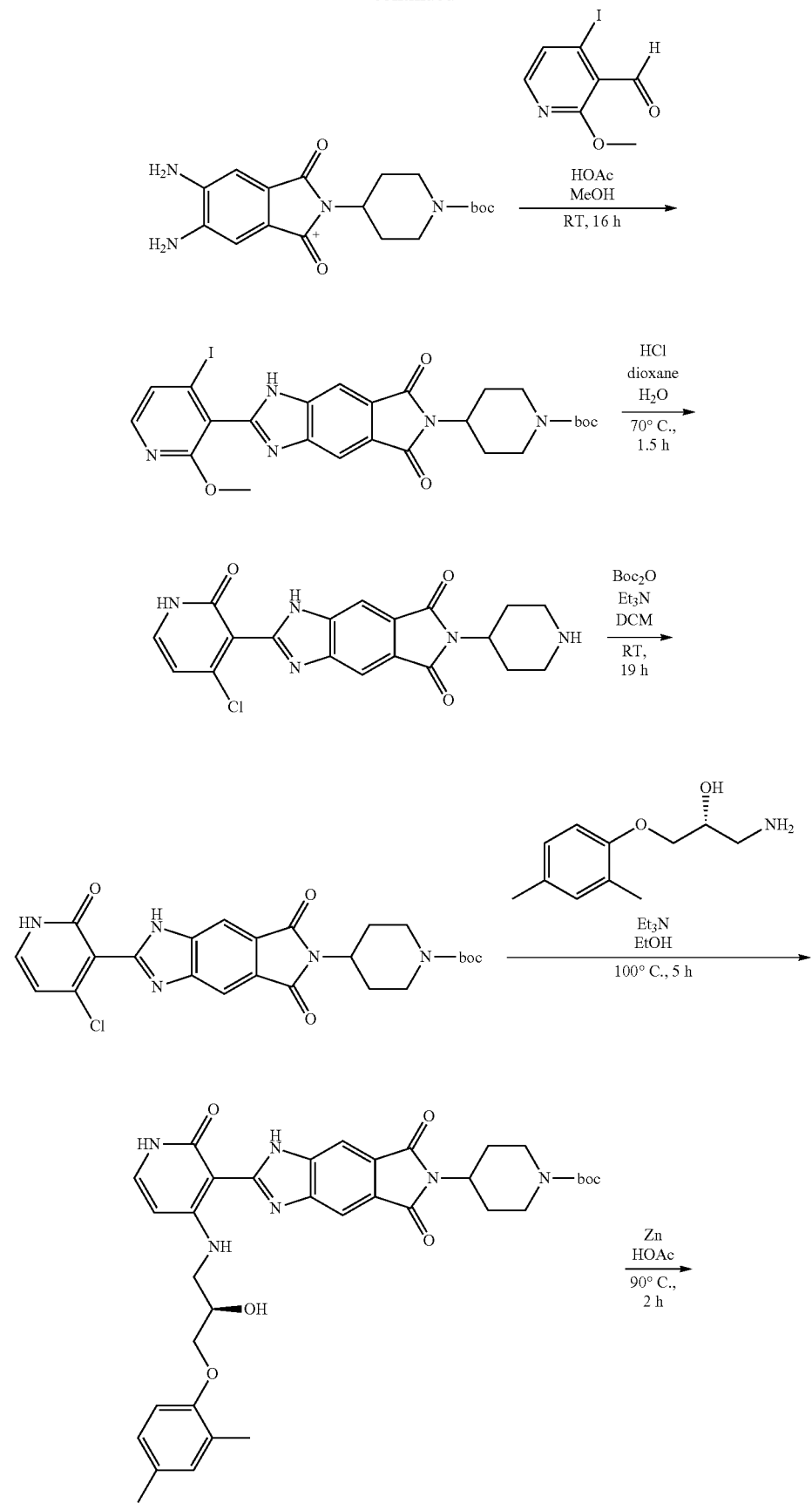

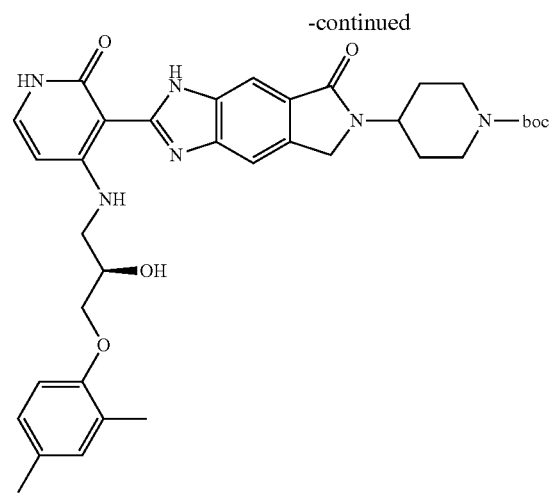

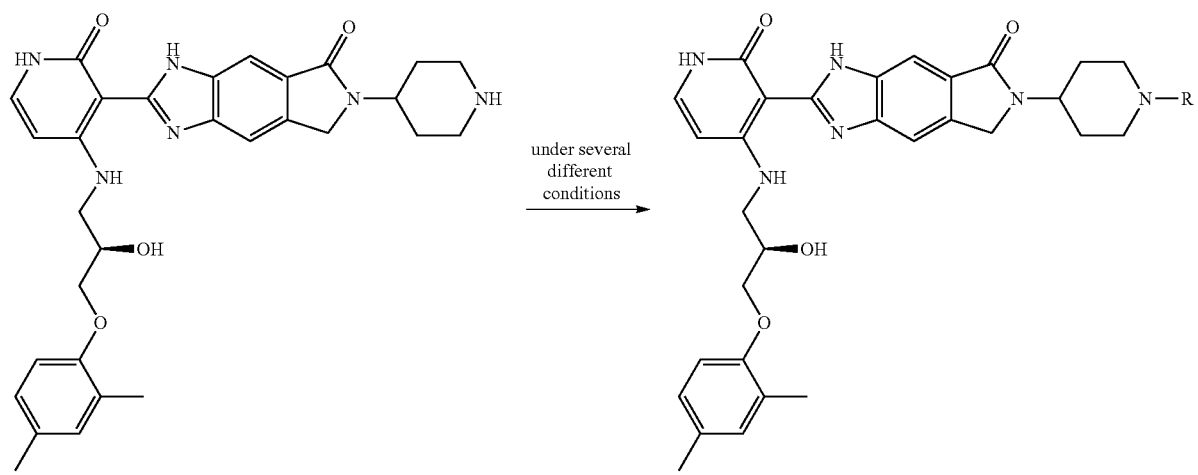

Synthesis of the Compounds Illustrated in Scheme 48

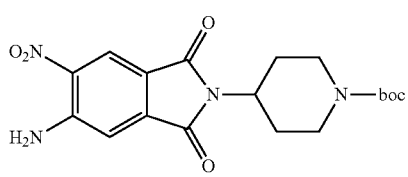

4-(5-Amino-6-nitro-1,3-dioxo-1,3-dihydro-isoindol-2-yl)-piperidine-1-carboxylic acid tert-butyl ester: A mixture of 5-amino-6-nitro-isoindole-1,3-dione (2.07 g, 10 mmol), tert-butyl 4-amino-piperidine-1-carboxylate (2.5 g, 12 mmol), imidazole (1.63 g, 24 mmol) in dioxane (100 mL) was sealed in a ChemGlass heavy wall pressure flask. After it was heated at 140° C. for 72 h, the reaction mixture was evaporated to dryness at 95° C. (the bath temperature) under reduced pressure. The chromatography of the residue with CH$_2$Cl$_2$/MeOH/28% aqueous NH$_4$OH (320:10:1) afforded the title compound (2.09 g, 54%). $^1$H NMR (CDCl$_3$) δ 1.49 (s, 9H), 1.73 (m, 2H), 2.38 (m, 2H), 2.80 (m, 2H), 4.20-4.31 (3H), 7.03 (br s, 2H, NH), 7.34 (s, 1H), 8.61 (s, 1H); ESI-MS m/z 391.5 (MH$^+$).

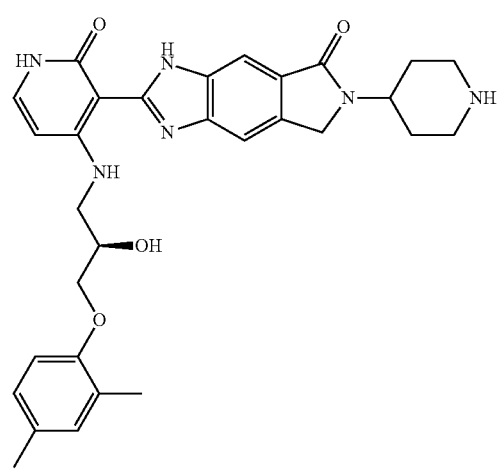 [SMILES: Cc1ccc(OC[C@H](O)CNc2cc[nH]c(=O)c2-c2nc3cc4c(cc3[nH]2)C(=O)N(C2CCNCC2)C4)c(C)c1]

2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one: To a mixture of 4-(5-amino-6-nitro-1,3-dioxo-1,3-dihydro-isoindol-2-yl)-piperidine-1-carboxylic acid tert-butyl ester (5.0 g, 12.8 mmol) and 10% Pd/C (500 mg) was added 2-propanol (20 mL), and then MeOH (230 mL). After it was stirred under atmospheric hydrogen pressure for 4 h, the reaction mixture was filtered through Celite. The filtrate was mixed with 4-iodo-2-methoxynicotinic aldehyde (3.37 g, 12.8 mmol) and AcOH (13 mL), stirred at the room temperature for 16 h, and evaporated under reduced pressure to afford a crude, which was mixed with HCl in 1,4-dioxane (4 M, 60 mL) and H$_2$O (5 mL), heated at 70° C. for 1.5 h and evaporated at 95° C. (the bath temperature) to dryness. Et$_3$N (5.35 mL, 38.4 mmol) was added to the solution of the residue in CH$_2$Cl$_2$ (250 mL) at 0° C. under N$_2$, followed by the addition of the solution of Boc$_2$O (3.35 g, 15.4 mmol). After it was stirred at 0° C. for 1 h and at the room temperature for 19 h, the reaction mixture was mixed slowly with MeOH (200 mL) at 0° C. and then evaporated at 70° C. (the bath temperature) to dryness under reduced pressure. The residue was mixed with (R)-1-amino-3-(2,4-dimethyl-phenoxy)-propan-2-ol (2.5 g, 12.8 mmol) and Et$_3$N (5.35 mL, 38.4 mmol) in EtOH (200 mL) resulting a mixture, which was heated at 100° C. for 5 h and then concentrated. Chromatography of the residual mixture with CH$_2$Cl$_2$/MeOH/28% aqueous NH$_4$OH (250:10:1) furnished a fluorescent product which was mixed with zinc dust (5.5 g, 84 mmol) and AcOH (200 mL). After it was heated at 90° C. for 2 h, the reaction mixture was filtered and the filtrate was concentrated at 70° C. (the bath temperature) under reduced pressure. The residue was mixed with HCl in dioxane (4 M, 60 mL) and H$_2$O (5 mL), heated at 70° C. for 2.5 h and evaporated at 95° C. (the bath temperature) to dryness. The residue was basified with NH$_3$ in EtOH (2 M) and concentrated. Chromatography of the crude with CH$_2$Cl$_2$/MeOH/28% aqueous NH$_4$OH (40:10:1) afforded a fluorescent product (6.5 g). 50 mg of this product was subjected to HPLC purification to furnish the title compound in TFA salt form (37 mg). $^1$H NMR (DMSO-d$_6$) δ 1.90-2.05 (4H), 2.19 (s, 3H, CH$_3$), 2.22 (s, 3H, CH$_3$), 3.13 (m, 2H), 3.42 (m, 2H), 3.55 (m, 1H), 3.69 (m, 1H), 4.03 (m, 2H), 4.13 (m, 1H), 4.39 (m, 1H), 4.46 (s, 2H), 6.22 (d, J=7 Hz, 1H), 6.84 (d, J=7 Hz, 1H), 6.94 (d, J=7 Hz, 1H), 6.98 (s, 1H), 7.39 (d, J=7 Hz, 1H), 7.55 (br s, 1H), 7.85 (br s, 1H), 11.14 (br s, 1H, NH), 11.23 (br d, J=6 Hz, 1H, NH); ESI-MS m/z 543.5 (MH$^+$).

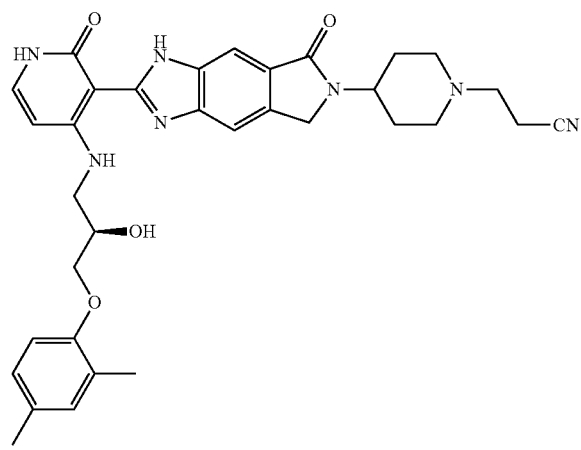 [SMILES: Cc1ccc(OC[C@H](O)CNc2cc[nH]c(=O)c2-c2nc3cc4c(cc3[nH]2)C(=O)N(C2CCN(CCC#N)CC2)C4)c(C)c1]

3-[4-(2-{4-[(R)-3-(2,4-Dimethyl-phenoxy)-2-hydroxy-propylamino]-2-oxo-1,2-dihydro-pyridin-3-yl}-7-oxo-5,7-dihydro-1H-1,3,6-triaza-s-indacen-6-yl)-piperidin-1-yl]-propionitrile: To a solution of the TFA salt of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (40 mg, 0.061 mmol) in MeOH (2.4 mL) was added DIEA (600 L, 3.4 mmol) at 0° C. under N$_2$ resulting a mixture which was stirred under N$_2$ at 0° C. for 20 min and followed by addition of acrylonitrile (197 μL, 3.0 mmol) via a syringe. The reaction mixture was stirred under N$_2$ at 0° C. for 1 h and at the room temperature for 1 h and then evaporated. The residue was subjected to HPLC purification to afford the title compound in TFA salt form. $^1$H NMR (DMSO-d$_6$) δ 1.99-2.13 (4H), 2.19 (s, 3H, CH$_3$), 2.22 (s, 3H, CH$_3$), 3.12 (m, 2H), 3.22 (m, 2H), 3.47 (m, 2H), 3.51-3.75 (4H), 4.01 (m, 2H), 4.13 (m, 1H), 4.34 (m, 1H), 4.47 (s, 2H), 6.22 (d, J=7 Hz, 1H), 6.84 (d, J=7 Hz, 1H), 6.94 (d, J=7 Hz, 1H), 6.96 (s, 1H), 7.36 (d, J=7 Hz, 1H), 7.59 (br s, 1H), 7.86 (br s, 1H), 11.13 (br s, 1H, NH), 11.23 (br d, J=6 Hz, 1H, NH); ESI-MS m/z 596.5 (MH$^+$).

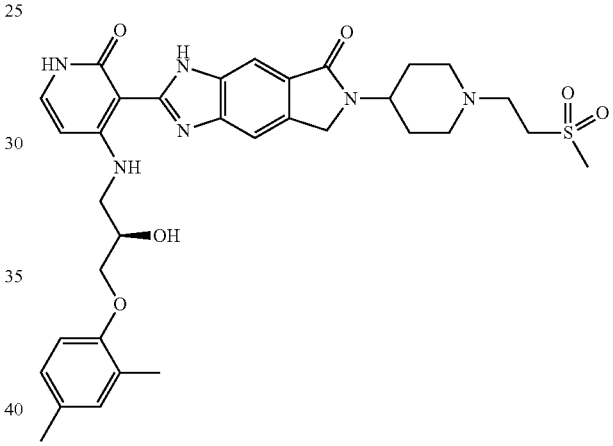

2-{4-[(R)-3-(2,4-Dimethyl-phenoxy)-2-hydroxy-propylamino]-2-oxo-1,2-dihydro-pyridin-3-yl}-6-[1-(2-methanesulfonyl-ethyl)-piperidin-4-yl]-6,7-dihydro-3H-1,3,6-triaza-s-indacen-5-one: A mixture of the TFA salt of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (40 mg, 0.061 mmol) and methyl vinyl sulfone (318.4 mg, 3.0 mmol) in EtOH (2.0 mL) was heated at 90° C. for 22 h and then evaporated. Chromatography of the residue with CH$_2$Cl$_2$/MeOH/28% aqueous NH$_4$OH (125:10:1) afforded a fluorescent product which was subjected to HPLC purification to afford the title compound in TFA salt form. $^1$H NMR (DMSO-d$_6$) δ 2.01-2.17 (4H), 2.19 (s, 3H, CH$_3$), 2.21 (s, 3H, CH$_3$), 3.15 (s, 3H, CH$_3$), 3.23 (m, 2H), 3.51-3.75 (8H), 4.01 (m, 2H), 4.15 (m, 1H), 4.34 (m, 1H), 4.47 (s, 2H), 6.22 (d, J=7 Hz, 1H), 6.84 (d, J=7 Hz, 1H), 6.94 (d, J=7 Hz, 1H), 6.98 (s, 1H), 7.36 (dd, J=7 Hz and 6 Hz, 1H), 7.59 (br s, 1H), 7.83 (br s, 1H), 11.14 (br s, 1H, NH), 11.23 (br d, J=6 Hz, 1H, NH); ESI-MS m/z 649.5 (MH$^+$).

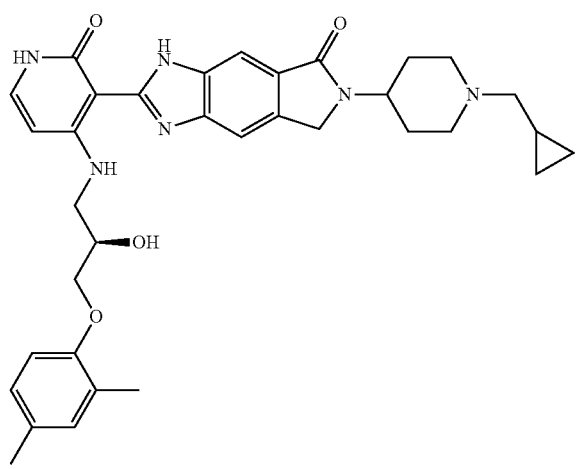 [SMILES: Cc1ccc(OC[C@H](O)CNc2cc[nH]c(=O)c2-c2nc3cc4c(cc3[nH]2)C(=O)N(C2CCN(CC3CC3)CC2)C4)c(C)c1]

6-(1-Cyclopropylmethyl-piperidin-4-yl)-2-{4-[(R)-3-(2,4-dimethyl-phenoxy)-2-hydroxy-propylamino]-2-oxo-1,2-dihydro-pyridin-3-yl}-6,7-dihydro-3H-1,3,6-triaza-s-indacen-5-one: To a solution of the TFA salt of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (40 mg, 0.061 mmol) and cyclopropanecarbaldehyde (150 μL, 2.0 mmol) in a mixed solvent of CH$_3$CN (6 mL) and H$_2$O (2 mL) was added AcOH (500 μL) at 0° C. and the resulting reaction mixture was stirred at 0° C. for 20 min and followed by addition of Na(OAc)$_3$BH (254 mg, 1.2 mmol). The reaction mixture was stirred at 0° C. for 1 h and at the room temperature for 1 h and then evaporated. The residue was subjected to HPLC purification to afford the title compound in TFA salt form. $^1$H NMR (DMSO-d$_6$) δ 0.39 (m, 2H), 0.67 (m, 2H), 1.10 (m, 1H), 2.03 (m, 2H), 2.12 (m, 2H), 2.19 (s, 3H, CH$_3$), 2.21 (s, 3H, CH$_3$), 3.01 (m, 2H), 3.18 (m, 2H), 3.50-4.15 (7H), 4.32 (m, 1H), 4.47 (s, 2H), 6.22 (d, J=7 Hz, 1H), 6.80 (d, J=7 Hz, 1H), 6.91 (d, J=7 Hz, 1H), 6.97 (s, 1H), 7.38 (d, J=7 Hz, 1H), 7.57 (br s, 1H), 7.82 (br s, 1H), 11.13 (br s, 1H, NH), 11.22 (br d, J=6 Hz, 1H, NH); ESI-MS m/z 597.3 (MH$^+$).

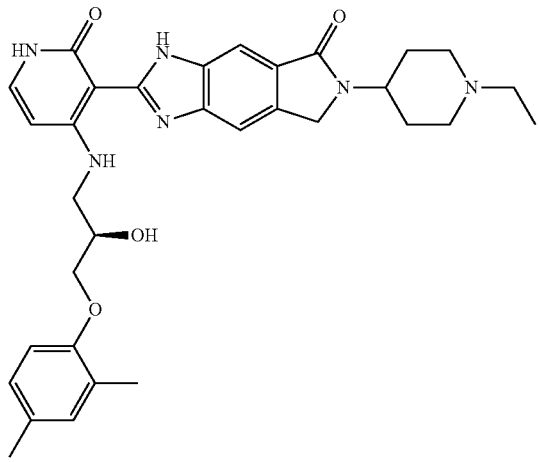 [SMILES: CCN1CCC(N2Cc3cc4nc(-c5c(NC[C@@H](O)COc6ccc(C)cc6C)cc[nH]c5=O)[nH]c4cc3C2=O)CC1]

2-{4-[(R)-3-(2,4-Dimethyl-phenoxy)-2-hydroxy-propylamino]-2-oxo-1,2-dihydro-pyridin-3-yl}-6-(1-ethyl-piperidin-4-yl)-6,7-dihydro-3H-1,3,6-triaza-s-indacen-5-one: $^1$H NMR (DMSO-d$_6$) δ 1.00 (t, J=6 Hz, 3H), 1.70 (m, 2H), 1.80 (m, 2H), 2.02 (m, 2H), 2.18 (s, 3H, CH$_3$), 2.22 (s, 3H, CH$_3$), 2.33 (m, 2H), 2.98 (m, 2H), 3.55 (m, 1H), 3.70 (m, 1H), 3.97-4.08 (3H), 4.12 (m, 1H), 4.42 (s, 1H0, 4.46 (s, 1H), 5.47 (d, J=4 Hz, 0.5H, NH), 5.53 (d, J=4 Hz, 0.5H, NH), 6.20 (d, J=7 Hz, 0.5H), 6.21 (d, J=7 Hz, 0.5H), 6.81 (d, J=7 Hz, 1H), 6.90 (s, 1H), 6.95 (d, J=7 Hz, 1H), 7.37 (s, 0.5H), 7.31 (d, J=7 Hz, 1H), 7.68 (s, 0.5H), 7.80 (s, 0.5H), 7.94 (s, 0.5H), 11.15 (br d, J=7 Hz, 1H, NH), 11.19 (br s, J=7 Hz, 1H, NH); ESI-MS m/z 571.3 (MH$^+$).

Scheme 49

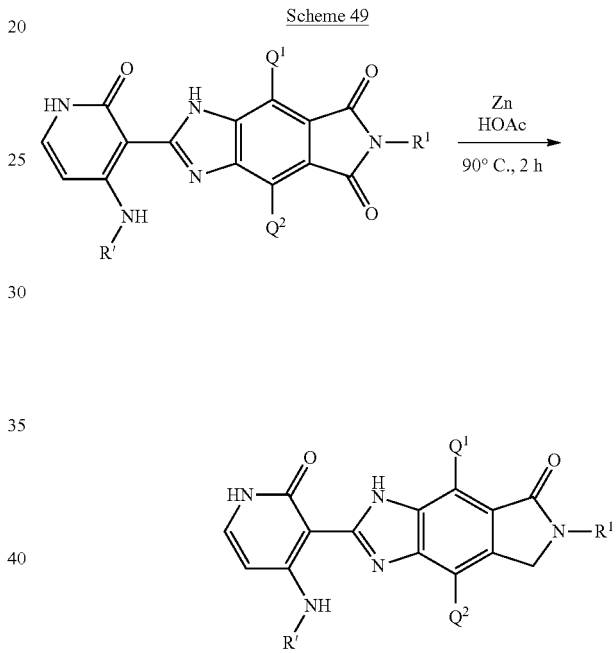

Synthesis of the Compounds Illustrated by Scheme 49

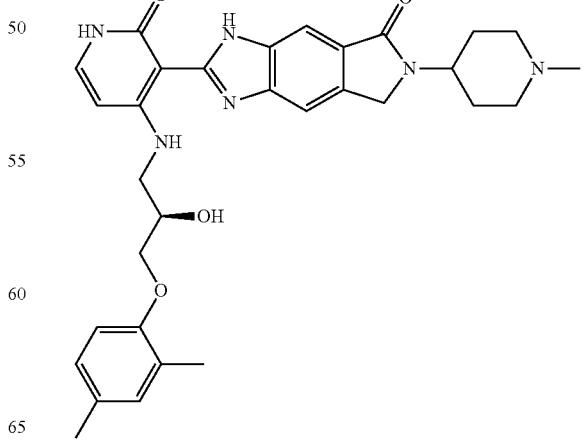

2-{4-[(R)-3-(2,4-Dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one: 2-{4-[(R)-3-(2,4-Dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione (3.0 g, 5.26 mmol) was mixed with zinc dust (6.88 g, 10.52 mmol) in AcOH (150 mL). After it was heated at 90° C. for 2 h, the reaction mixture was filtered and the filtrate was evaporated at 95° C. (the bath temperature) under reduced pressure to dryness. The residue was basified with 28% aqueous NH$_4$OH solution and concentrated. Chromatography of the residual crude with CH$_2$Cl$_2$/MeOH/28% aqueous NH$_4$OH (90:10:1) afforded the title compound (2.45 g, 84%). $^1$H NMR (DMSO-d$_6$) δ 1.70 (m, 2H), 1.80 (m, 2H), 2.05 (m, 2H), 2.20 (s, 3H, CH$_3$), 2.22 (s, 3H, CH$_3$), 2.28 (s, 3H, CH$_3$), 2.89 (m, 2H), 3.57 (m, 1H), 3.79 (m, 1H), 3.95-4.09 (3H), 4.11 (m, 1H), 4.40 (s, 1H), 4.45 (s, 1H), 5.47 (d, J=3 Hz, 0.5H, NH), 5.54 (d, J=3 Hz, 0.5H, NH), 6.21 (m, 1H), 6.80-7.00 (3H), 7.30-7.39 (1.5H), 7.69 (s, 0.5H), 7.79 (s, 0.5H), 7.93 (s, 0.5H), 11.12 (br d, J=6 Hz, 1H, NH), 11.22 (br d, J=6 Hz, 1H, NH); ESI-MS m/z 557.7 (MH$^+$).

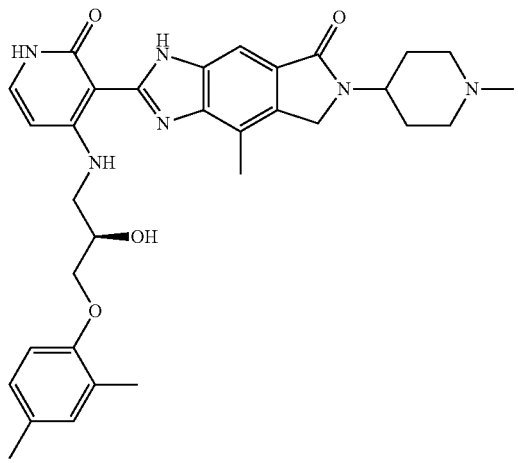

2-{4-[(R)-3-(2,4-Dimethyl-phenoxy)-2-hydroxy-propylamino]-2-oxo-1,2-dihydro-pyridin-3-yl}-8-methyl-6-(1-methyl-piperidin-4-yl)-6,7-dihydro-3H-1,3,6-triaza-s-indacen-5-one: $^1$H NMR (DMSO-d$_6$) δ 1.70 (m, 2H), 1.82 (m, 2H), 2.01 (m, 2H), 2.16 (s, 3H, CH$_3$), 2.18 (s, 3H, CH$_3$), 2.20 (s, 3H, CH$_3$), 2.50 (s, 2H, CH$_3$ on the benzoimidazole), 2.89 (m, 2H), 3.53 (m, 1H), 3.69 (m, 1H), 3.98-4.11 (3H), 4.18 (m, 1H), 4.41 (s, 2H), 5.53 (br s, 1H, NH), 6.19 (d, J=7 Hz, 1H), 6.79 (d, J=7 Hz, 1H), 6.90 (d, J=7 Hz, 1H), 6.95 (s, 1H), 7.35 (d, J=7 Hz, 1H), 7.79 (s, 1H), 11.35 (br s, 1H, NH); $^1$H NMR (MeOH-d$_4$) δ 1.78 (m, 2H), 1.87 (m, 2H), 2.12 (s, 3H, CH$_3$), 2.13 (m, 2H), 2.14 (s, 3H, CH$_3$), 2.25 (s, 3H, CH$_3$), 2.42 (s, 2H, CH$_3$ on the benzoimidazole), 2.89 (m, 2H), 3.58 (m, 1H), 3.72 (m, 1H), 4.01 (m, 2H), 4.11 (m, 1H), 4.20 (m, 2H), 4.18 (m, 1H), 4.38 (s, 2H), 6.22 (d, J=7 Hz, 1H), 6.69 (d, J=7 Hz, 1H), 6.79 (d, J=7 Hz, 1H), 6.85 (s, 1H), 7.20 (d, J=7 Hz, 1H), 7.65 (s, 1H); ESI-MS m/z 571.7 (MH$^+$).

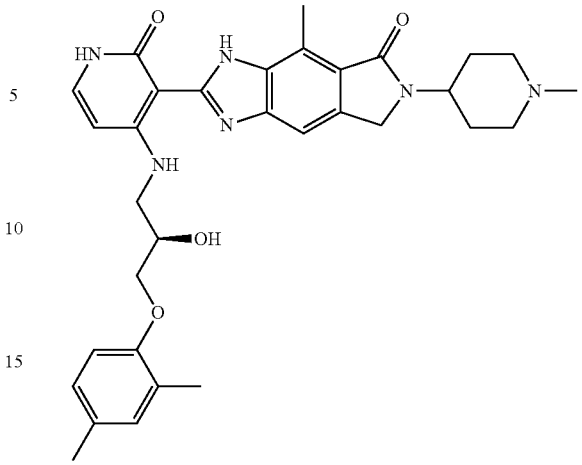

2-{4-[(R)-3-(2,4-Dimethyl-phenoxy)-2-hydroxy-propylamino]-2-oxo-1,2-dihydro-pyridin-3-yl}-4-methyl-6-(1-methyl-piperidin-4-yl)-6,7-dihydro-3H-1,3,6-triaza-s-indacen-5-one: $^1$H NMR (DMSO-d$_6$) δ 1.67 (m, 2H), 1.82 (m, 2H), 2.00 (m, 2H), 2.16 (s, 3H, CH$_3$), 2.20 (s, 3H, CH$_3$), 2.22 (s, 3H, CH$_3$), 2.80 (s, 2H, CH$_3$ on the benzoimidazole), 2.85 (m, 2H), 3.56 (m, 1H), 3.68 (m, 1H), 3.96-4.11 (3H), 4.17 (m, 1H), 4.39 (br s, 2H), 5.50 (br s, 1H, NH), 6.19 (d, J=7 Hz, 1H), 6.79 (d, J=7 Hz, 1H), 6.90 (d, J=7 Hz, 1H), 6.95 (s, 1H), 7.35 (d, J=7 Hz, 1H), 7.60 (s, 1H), 11.20 (br s, 1H, NH); 11.30 (br s, 1H, NH); ESI-MS m/z 571.7 (MH$^+$).

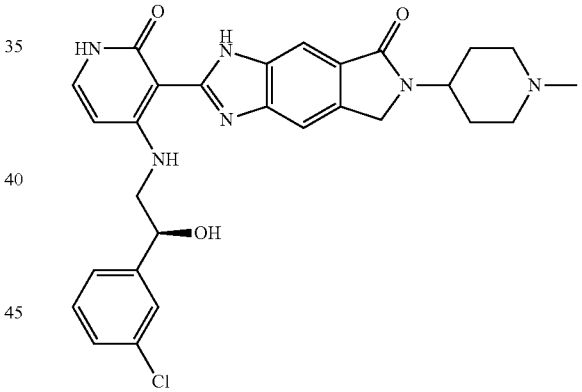

2-{4-[(S)-2-(3-Chloro-phenyl)-2-hydroxy-ethylamino]-2-oxo-1,2-dihydro-pyridin-3-yl}-6-(1-methyl-piperidin-4-yl)-6,7-dihydro-3H-1,3,6-triaza-s-indacen-5-one: 2-{4-[(S)-2-(3-Chloro-phenyl)-2-hydroxy-ethylamino]-2-oxo-1,2-dihydro-pyridin-3-yl}-6-(1-methyl-piperidin-4-yl)-1H-1,3,6-triaza-s-indacene-5,7-dione (36.1 mg, 0.066 mmol) was mixed with zinc dust (100 mg) in AcOH (4 mL) and the reaction mixture was heated at 90° C. for 2 h. After it was cooled to the room temperature, the upper clear layer of the reaction mixture was evaporated and the residue was subjected to HPLC purification to afford the title compound in TFA salt form (9.2 mg, 22%). $^1$H NMR (DMSO-d$_6$) δ 1.90-2.15 (4H), 2.75 (s, 3H, CH$_3$), 3.21 (m, 2H), 3.42-3.60 (2H), 3.65 (m, 1H), 4.31 (m, 1H), 4.50 (s, 2H), 4.98 (m, 1H), 6.19 (d, J=6 Hz, 1H), 7.31-7.41 (3H), 7.51 (d, J=6 Hz, 1H), 7.63 (s, 1H), 7.78 (s, 1H), 7.90 (s, 1H), 9.60 (br s, 1H), 11.06 (br s, 1H, NH), 11.23 (br d, J=6 Hz, 1H, NH); ESI-MS m/z 533.5 (MH$^+$).

Lactams with Sulfonamide Side Chains

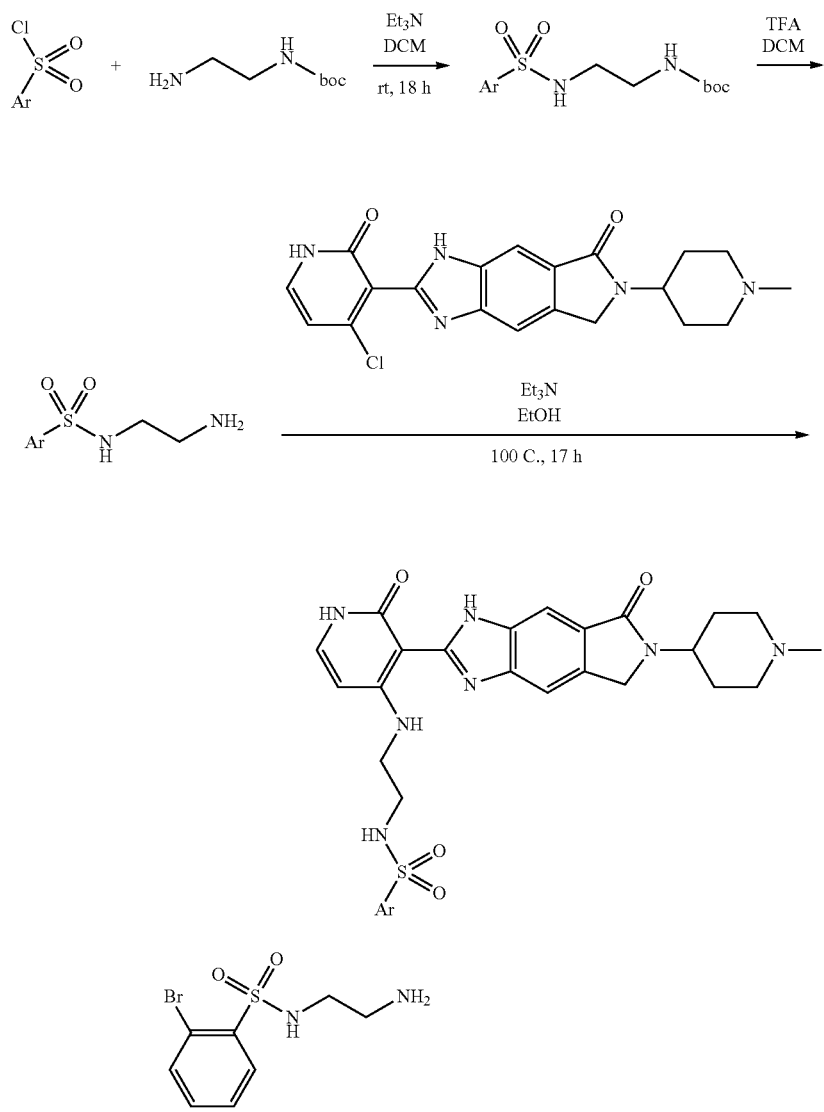

N-(2-Amino-ethyl)-2-bromo-benzenesulfonamide: To solution of (2-amino-ethyl)-carbamic acid tert-butyl ester (208 mg, 1.3 mmol) in CH$_2$Cl$_2$ (20 mL) was added DIEA (300 µL, 1.72 mmol) at 0° C., followed by the addition of 2-bromo-benzenesulfonyl chloride (383 mg, 1.5 mmol). After it was stirred at 0° C. for 1 h and at the room temperature for another 16 h, the reaction mixture was evaporated thoroughly. The residue was diluted with 20% TFA in CH$_2$Cl$_2$ (10 mL), stirred for 3 h at the room temperature, and evaporated. Chromatography of the residual crude with CH$_2$Cl$_2$/MeOH/28% aqueous NH$_4$OH (90:10:1) afforded the title compound (313 mg, 86%). $^1$H NMR (DMSO-d$_6$) δ 2.86 (t, J=8 Hz, 2H), 3.04 (t, J=8 Hz, 2H), 7.55-7.65 (2H), 7.89 (d, J=8 Hz, 1H), 8.01 (d, J=8 Hz, 1H); ESI-MS m/z 279.1 (MH$^+$).

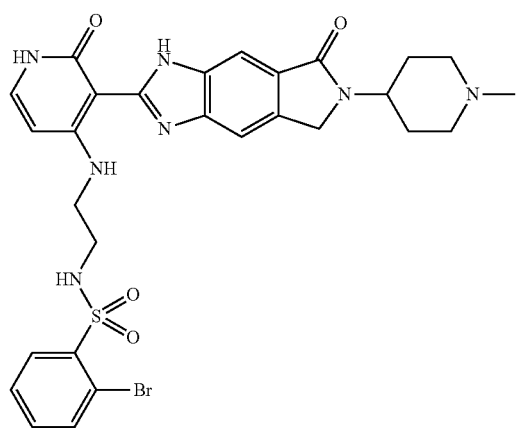 [SMILES: CN1CCC(N2Cc3cc4nc(-c5c(NCCNS(=O)(=O)c6ccccc6Br)cc[nH]c5=O)[nH]c4cc3C2=O)CC1]

2-Bromo-N-(2-{3-[6-(1-methyl-piperidin-4-yl)-7-oxo-1,5,6,7-tetrahydro-1,3,6-triaza-s-indacen-2-yl]-2-oxo-1,2-dihydro-pyridin-4-ylamino}-ethyl)-benzenesulfonamide: To a solution of 2-(4-chloro-2-oxo-1,2-dihydro-pyridin-3-yl)-6-(1-methyl-piperidin-4-yl)-6,7-dihydro-3H-1,3,6-triaza-s-indacen-5-one (40 mg, 0.1 mmol) and N-(2-amino-ethyl)-2-bromo-benzenesulfonamide (56 mg, 0.20 mmol) in EtOH (4 mL) was added Et$_3$N (500 µL, 3.6 mmol) and the reaction was heated at 95° C. for 16 h. The solvent was evaporated in vacuo and the residue was purified by flash chromatography with CH$_2$Cl$_2$/MeOH/28% aqueous NH$_4$OH (100:10:1) afforded the title compound (7.3 mg, 11%). $^1$H NMR (DMSO-d$_6$) δ 1.70 (m, 2H), 1.85 (m, 2H), 2.15 (m, 2H), 2.29 (s, 3H, CH$_3$), 2.96 (m, 2H), 3.19 (m, 1H), 3.50 (m, 2H), 4.05 (m, 1H), 4.48 (s, 1H), 6.05 (d, J=7 Hz, 1H), 7.32 (br s, 1H), 7.38-7.50 (1.5H), 7.62-7.70 (1.5H), 7.82 (s, 0.5H), 7.87 (s, 0.5H), 7.96-7.99 (2H), 8.20) br S, 1H, NH), 11.02 (br s, 1H, NH), 11.26 (br s, 1H, NH); ESI-MS m/z 640.5 (MH$^+$).

Synthesis of Phenol and Pyrimidinone Derivatives

Scheme 51

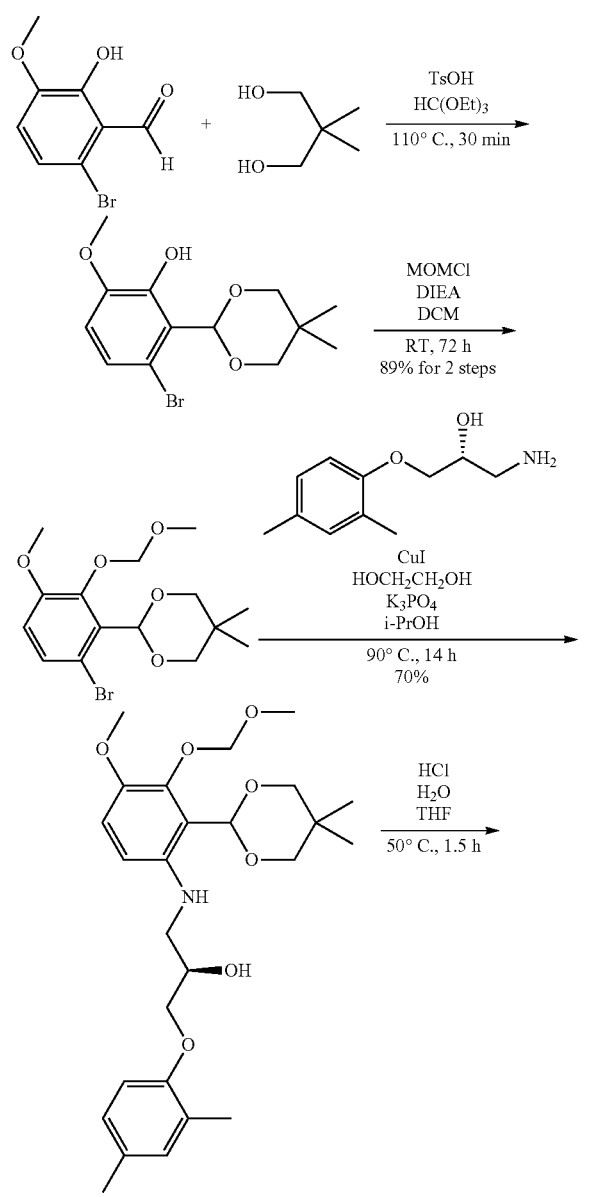

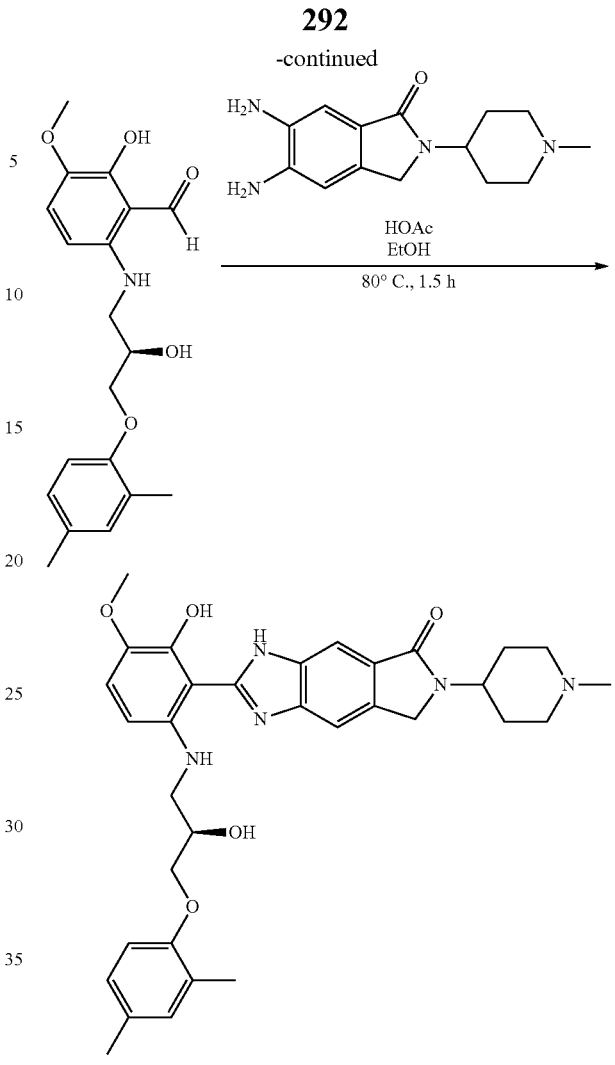

Synthesis of the Compounds Illustrated in Scheme 51:

3-Bromo-2-(5,5-dimethyl-[1,3]dioxan-2-yl)-6-methoxy-phenol: A mixture of 6-bromo-2-hydroxy-3-methoxy-benzaldehyde (2.31 g, 10.0 mmol), neopentyl glycol (1.14 g, 11.0 mmol), TsOH (9.5 mg) and triethyl orthoformate (1.93 g, 13.0 mmol) were heated at 110° C. for 30 min and then partitioned between NaHCO$_3$ (300 mL) solution and EtOAc (200 mL). The aqueous layer was extracted with EtOAc (3×30 mL) and the combined extracts were washed with brine and dried through Na$_2$SO$_4$. Evaporation of solvent afforded the title compound (3.17 g, 100%). $^1$H NMR (CDCl$_3$) δ 0.85 (s, 3H), 1.27 (s, 3H), 3.70 (s, 2H), 3.82 (s, 2H), 3.85 (s, 3H), 5.90 (s, 1H), 6.72 (d, J=8 Hz, 1H), 7.02 (d, J=8 Hz, 1H).

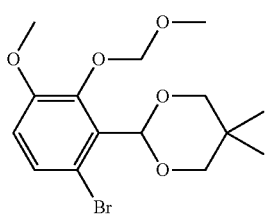 [SMILES: COCOc1c(OC)ccc(Br)c1C1OCC(C)(C)CO1]

2-(6-Bromo-3-methoxy-2-methoxymethoxy-phenyl)-5,5-dimethyl-[1,3]dioxane: To the solution of 3-bromo-2-(5,5-dimethyl-[1,3]dioxan-2-yl)-6-methoxy-phenol in DCM (20 mL) was added DIEA (697 μL, 4 mmol), followed by addition of chloromethoxymethane (228 μL, 3 mmol). After it was stirred at the room temperature for 72 h, the reaction mixture was evaporated and the residue was partitioned between NaHCO₃ (50 mL) solution and EtOAc (40 mL). The aqueous layer was extracted with EtOAc (3×10 mL) and the combined extracts were washed with brine and dried through Na₂SO₄. Evaporation of solvent afforded the title compound. ¹H NMR (CDCl₃) δ 0.80 (s, 3H), 1.45 (s, 3H), 3.57 (s, 3H), 3.65 (d, J=12 Hz, 2H), 3.79 (s, 3H), 3.80 (d, J=12 Hz, 2H), 5.11 (s, 2H), 6.00 (s, 1H), 6.76 (d, J=8 Hz, 1H), 7.32 (d, J=8 Hz, 1H).

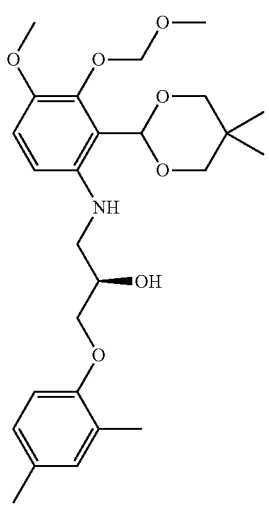 [SMILES: COCOc1c(OC)ccc(NC[C@@H](O)COc2ccc(C)cc2C)c1C1OCC(C)(C)CO1]

(R)-1-[2-(5,5-Dimethyl-[1,3]dioxan-2-yl)-4-methoxy-3-methoxymethyl-phenylamino]-3-(2,4-dimethyl-phenoxy)-propan-2-ol: A mixture of 2-(6-bromo-3-methoxy-2-methoxymethoxy-phenyl)-5,5-dimethyl-[1,3]dioxane (36 mg, 0.1 mmol), (R)-1-amino-3-(2,4-dimethyl-phenoxy)-propan-2-ol (30 mg, 0.15 mmol), CuI (51.4 mg, 0.27 mmol), ethylene glycol (168 mg, 2.7 mmol), and K₃PO₄ (573 mg, 2.7 mmol) in 2-propanol (8 mL) was heated at 90° C. in a sealed vial for 14 h and evaporated. Chromatography of the residue with hexanes and EtOAc afforded the title compound (305 mg, 71%). ¹H NMR (CDCl₃) δ 0.79 (s, 3H, CH₃), 1.29 (s, 3H, CH₃), 2.21 (s, 3H, CH₃), 2.25 (s, 3H, CH₃), 2.95 (br s, 1H, OH), 3.30 (m, 1H), 3.49 (s, 3H, OCH₃), 3.51 (m, 1H), 3.65 (m, 2H), 3.75 (s, 3H, OCH₃), 3.77 (m, 2H), 4.00 (m, 2H), 4.25 (m, 1H), 5.09 (s, 2H), 6.05 (s, 1H), 6.48 (d, J=8 Hz, 1H), 6.69 (d, J=8 Hz, H), 6.82 (d, J=8 Hz, 1H), 6.92 (d, J=8 Hz, 1H), 6.95 (s, 1H). ESI-MS m/z 476.8 (MH⁺).

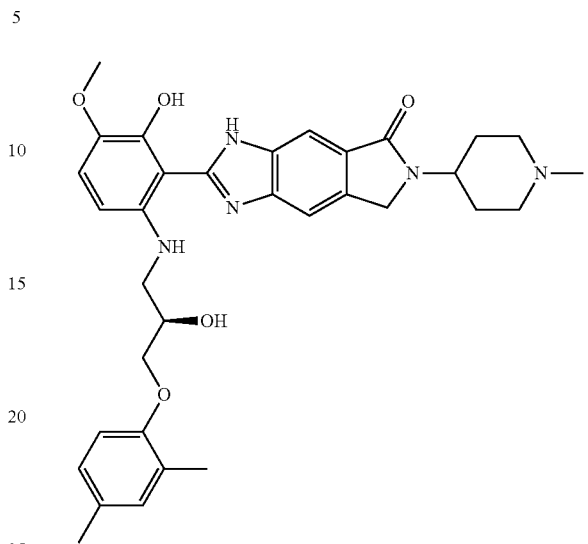

2-{6-[(R)-3-(2,4-Dimethyl-phenoxy)-2-hydroxy-propylamino]-2-hydroxy-3-methoxy-phenyl}-6-(1-methyl-piperidin-4-yl)-6,7-dihydro-3H-1,3,6-triaza-s-indacen-5-one: To a solution of (R)-1-[2-(5,5-dimethyl-[1,3]dioxan-2-yl)-4-methoxy-3-methoxymethyl-phenylamino]-3-(2,4-dimethyl-phenoxy)-propan-2-ol (102 mg, 0.21 mmol) in THF (5.0 mL) was added 36% aqueous HCl (1.0 mL). After it was heated at 50° C. for 1.5 h, the reaction mixture was evaporated and the residue was mixed with 5,6-diamino-2-(1-methyl-piperidin-4-yl)-2,3-dihydro-isoindol-1-one (76 mg, 0.21 mmol) and AcOH (0.4 mL) in EtOH (8 mL). The mixture was stirred at the room temperature for 30 min, heated at 80° C. for 1.5 h, and evaporated to dryness. Chromatography of the residual crude with CH₂Cl₂/MeOH/28% aqueous NH₄OH (40:10:1) afforded the title compound (13 mg, 10%). ESI-MS m/z 586.5 (MH⁺).

Synthesis of Pyrimidinone Derivatives

Scheme 52

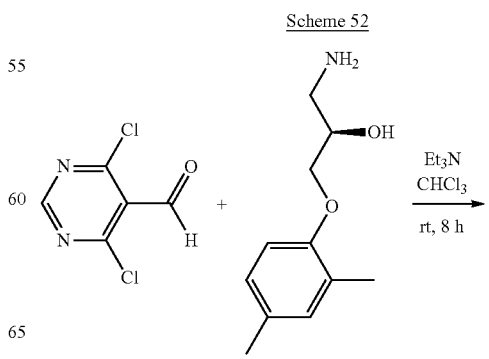

-continued

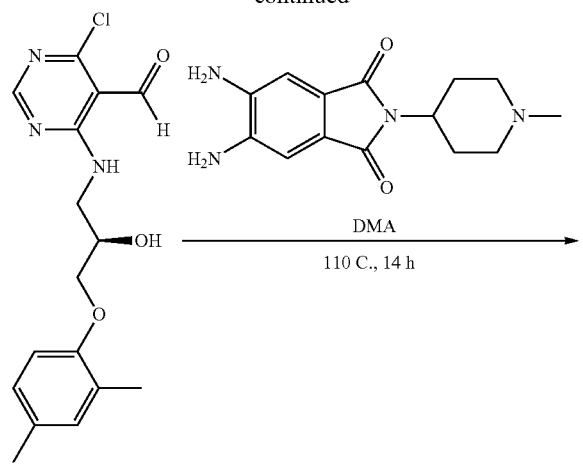

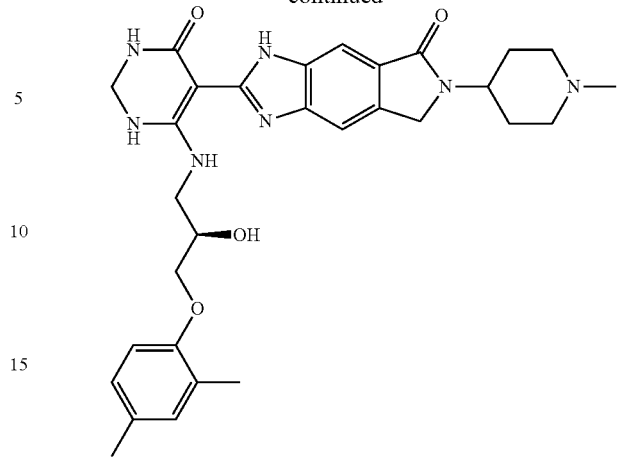

Synthesis of the Compounds Illustrated by Scheme 51

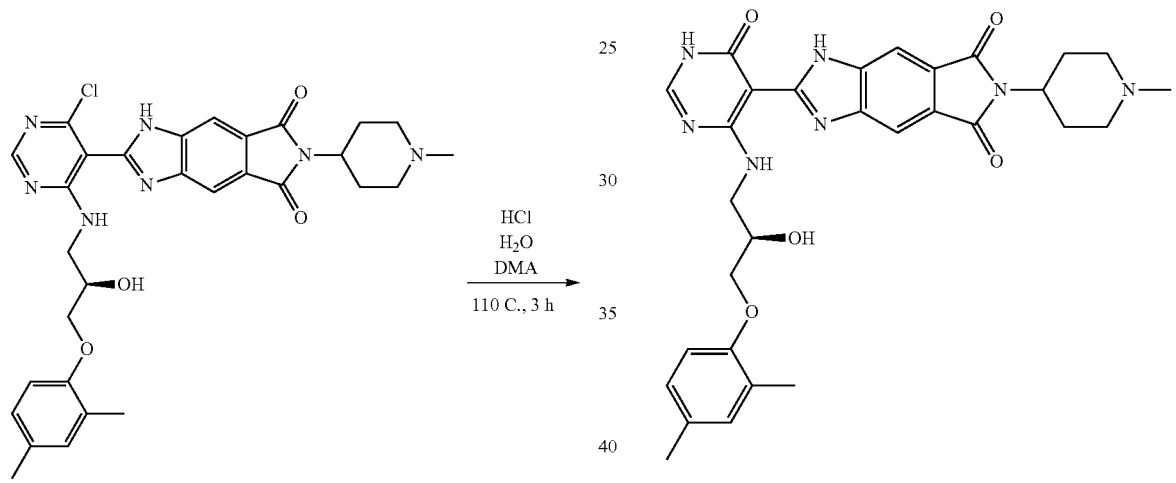

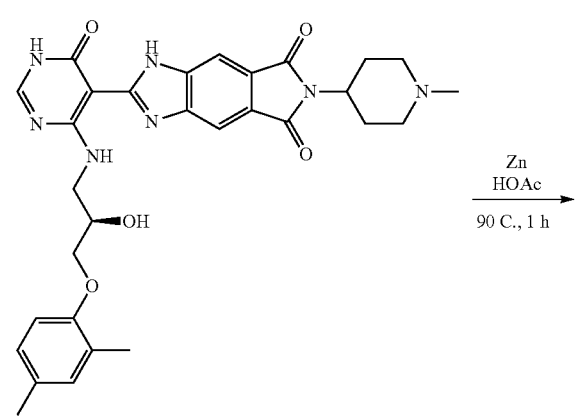

2-{4-[(R)-3-(2,4-Dimethyl-phenoxy)-2-hydroxy-propylamino]-6-oxo-1,6-dihydro-pyrimidin-5-yl}-6-(1-methyl-piperidin-4-yl)-1H-1,3,6-triaza-s-indacene-5,7-dione: To a solution of 4,6-dichloro-pyrimidine-5-carbaldehyde (177 mg, 1.0 mmol) and (R)-1-amino-3-(2,4-dimethyl-phenoxy)-propan-2-ol (195.3 mg, 1.0 mmol) in chloroform (8 mL) was added Et$_3$N (348 μL, 2.5 mmol). After it was stirred at the room temperature for 8 h, the reaction mixture was evaporated under reduced pressure thoroughly. The remaining residue was mixed with 5,6-diamino-2-(1-methyl-piperidin-4-yl)-isoindole-1,3-dione (274 mg, 1.0 mmol) in DMA (10 mL). After it was heated at 110° C. for 14 h, the reaction mixture was cooled to the room temperature and mixed with aqueous HCl solution (12 N, 1 mL). The resulting mixture was heated in a sealed vial at 110° C. for 3 h and evaporated to dryness. The residue was basified with NH$_3$ in EtOH (2 M) and concentrated. Chromatography of the crude afforded the title compound (93 mg, 17% yield for 3 steps). $^1$H NMR (DMSO-d$_6$) δ 1.62 (m, 2H), 1.97 (m, 2H), 2.14 (s, 3H, CH$_3$), 2.17 (s, 3H, CH$_3$), 2.17 (s, 3H, CH$_3$), 2.38 (m, 2H), 2.89 (m, 2H), 3.80 (m, 1H), 3.90-4.02 (4H), 4.11 (m, 1H), 5.47 (br s, 1H, NH), 6.82 (d, J=6 Hz, 1H), 6.93 (d, J=6 Hz, 1H), 6.97 (s, 1H), 8.06 (s, 1H), 8.12 (s, 1H), 10.83 (br s, 1H, NH); ESI-MS m/z 572.3 (MH$^+$).

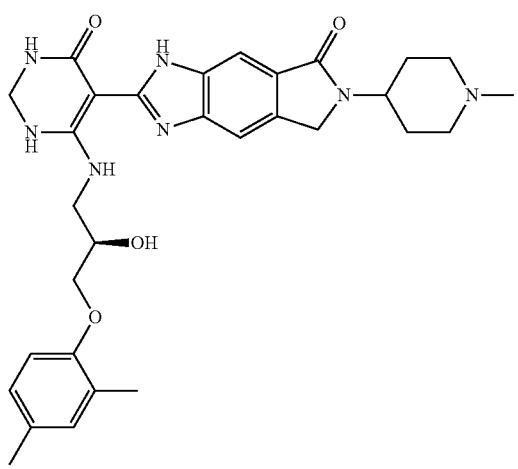 [SMILES: Cc1ccc(OC[C@H](O)CNC2=C(c3nc4cc5c(cc4[nH]3)C(=O)N(C3CCN(C)CC3)C5)C(=O)NCN2)c(C)c1]

2-{6-[(R)-3-(2,4-Dimethyl-phenoxy)-2-hydroxy-propylamino]-4-oxo-1,2,3,4-tetrahydro-pyrimidin-5-yl}-6-(1-me-thyl-piperidin-4-yl)-6,7-dihydro-3H-1,3,6-triaza-s-indacen-5-one: 2-{4-[(R)-3-(2,4-Dimethyl-phenoxy)-2-hydroxy-propylamino]-6-oxo-1,6-dihydro-pyrimidin-5-yl}-6-(1-methyl-piperidin-4-yl)-1H-1,3,6-triaza-s-indacene-5,7-dione (60.1 mg, 0.105 mmol) was mixed with zinc dust (300 mg) in AcOH (12 mL) resulting a mixture which was heated at 90° C. for 1 h, then cooled to the room temperature and filtered. The filtrate was evaporated, the residue was basified with $NH_3$ in EtOH (2 M) and purified by chromatography with $CH_2Cl_2$/MeOH/28% aqueous $NH_4OH$ (60:10:1) to furnish a fluorescent product which was subjected to HPLC purification to afford the title compound in TFA salt form (42 mg, 60%). $^1$H NMR (DMSO-$d_6$) δ 1.90-2.15 (4H), 2.13 (s, 3H, $CH_3$), 2.20 (s, 3H, $CH_3$), 2.81 (s, 3H, $CH_3$), 3.20 (m, 2H), 3.40-3.60 (4H), 3.97 (m, 2H), 4.13 (m, 1H), 4.31 (m, 1H), 4.40 (s, 2H), 4.46 (s, 2H), 6.83 (d, J=6 Hz, 1H), 6.93 (d, J=6 Hz, 1H), 6.96 (s, 1H), 7.53 (br s, 1H), 7.75 (s, 1H), 9.75 (br s, 1H); ESI-MS m/z 560.5 (MH$^+$).

Synthesis of Additional Phthalimide Derivatives

Scheme 53

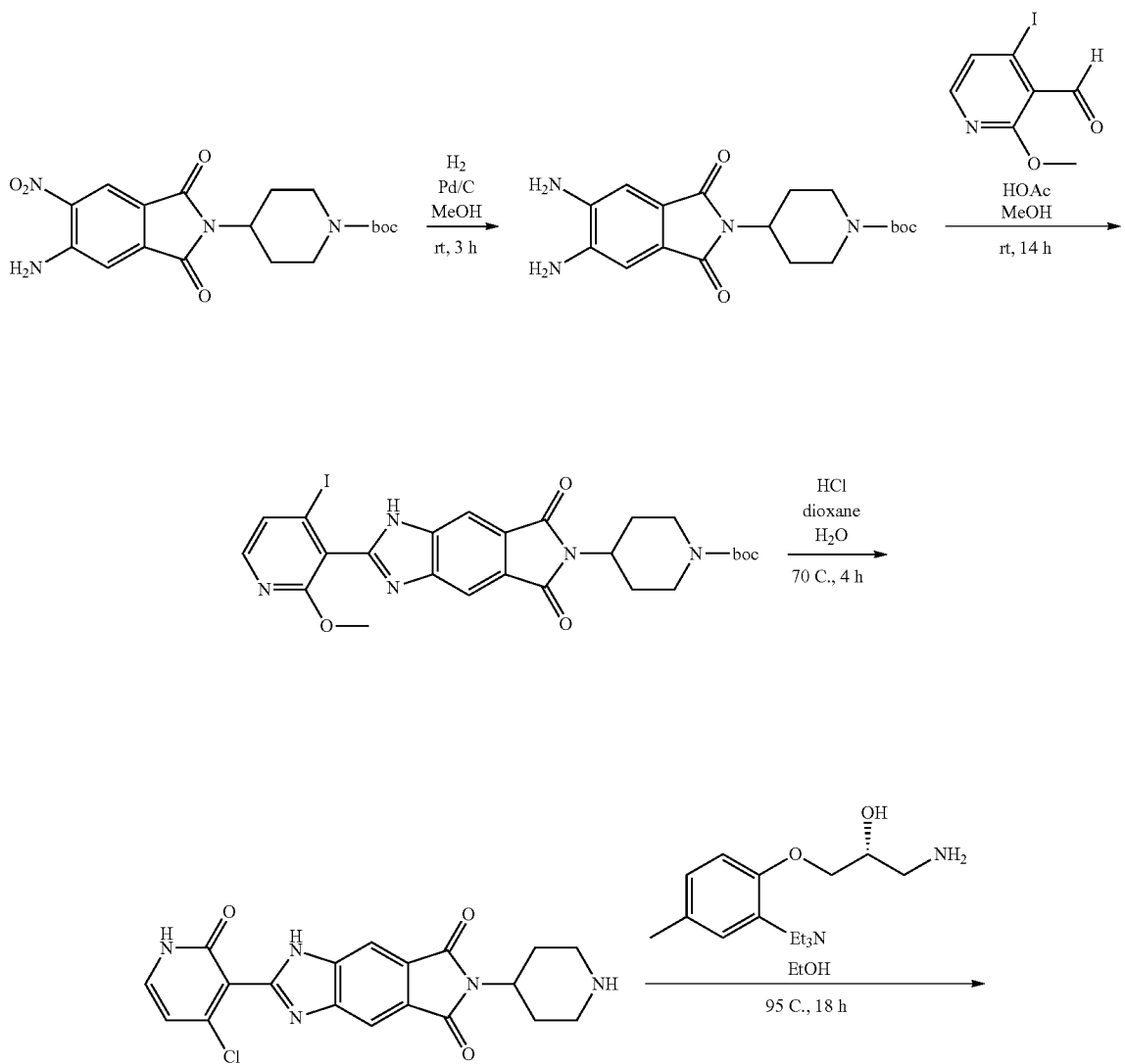

-continued

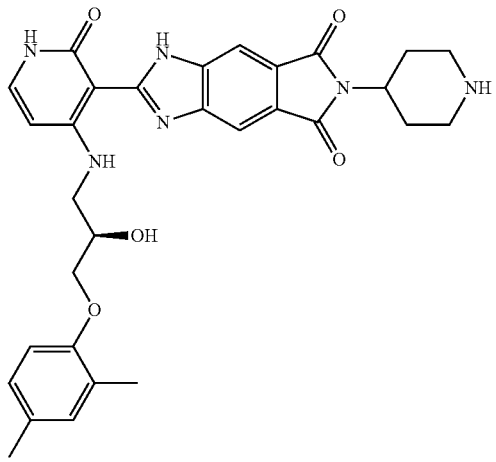

Synthesis of the Compound Illustrated by Scheme 53

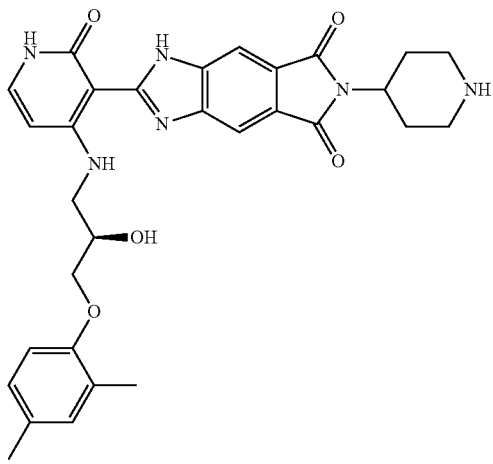 [SMILES: Cc1ccc(OC[C@H](O)CNc2cc[nH]c(=O)c2-c2nc3cc4c(cc3[nH]2)C(=O)N(C2CCNCC2)C4=O)c(C)c1]

2-{4-[(R)-3-(2,4-Dimethyl-phenoxy)-2-hydroxy-propylamino]-2-oxo-1,2-dihydro-pyridin-3-yl}-6-piperidin-4-yl-1H-1,3,6-triaza-s-indacene-5,7-dione: To a mixture of 4-(5-amino-6-nitro-1,3-dioxo-1,3-dihydro-isoindol-2-yl)-piperidine-1-carboxylic acid tert-butyl ester (203 mg, 0.52 mmol) and 10% Pd/C (20 mg) was added 2-propanol (2 mL), and then MeOH (50 mL). After it was stirred under atmospheric hydrogen pressure for 3 h, the reaction mixture was filtered through Celite. The filtrate was mixed with 4-iodo-2-methoxynicotinic aldehyde (137 mg, 0.52 mmol) and AcOH (3 mL), stirred at the room temperature for 14 h, and evaporated under reduced pressure to afford a crude, which was mixed with HCl in dioxane (4 M, 15 mL) and $H_2O$ (1 mL), heated at 70° C. for 4 h and evaporated at 95° C. (the bath temperature) to dryness. The residue was mixed with (R)-1-amino-3-(2,4-dimethyl-phenoxy)-propan-2-ol (117 mg, 0.6 mmol) and $Et_3N$ (418 µL, 3 mmol) in EtOH (8 mL) resulting a mixture, which was heated at 95° C. for 18 h and then concentrated. Chromatography of the residual mixture with $CH_2Cl_2$/MeOH/28% aqueous $NH_4OH$ (100:10:1) furnished a fluorescent product that was subjected to HPLC purification to furnish the title compound in TFA salt form (6.23 mg, 1.9%). $^1H$ NMR (DMSO-$d_6$) δ 1.90 (m, 2H), 2.19 (s, 3H, $CH_3$), 2.22 (s, 3H, $CH_3$), 3.10 (m, 2H), 3.30-3.42 (4H), 3.49 (m, 1H), 3.72 (m, 1H), 4.01 (m, 2H), 4.15 (m, 1H), 4.39 (m, 1H), 5.58 (br s, 1H, NH), 6.24 (d, J=7 Hz, 1H), 6.84 (d, J=7 Hz, 1H), 6.93 (d, J=7 Hz, 1H), 6.98 (s, 1H), 7.40 (d, J=7 Hz, 1H), 7.66 (br s, 1H), 8.11 (br s, 1H), 10.96 (br s, 1H, NH), 11.31 (br d, J=6 Hz, 1H, NH); ESI-MS m/z 557.7 (MH$^+$).

Scheme 54

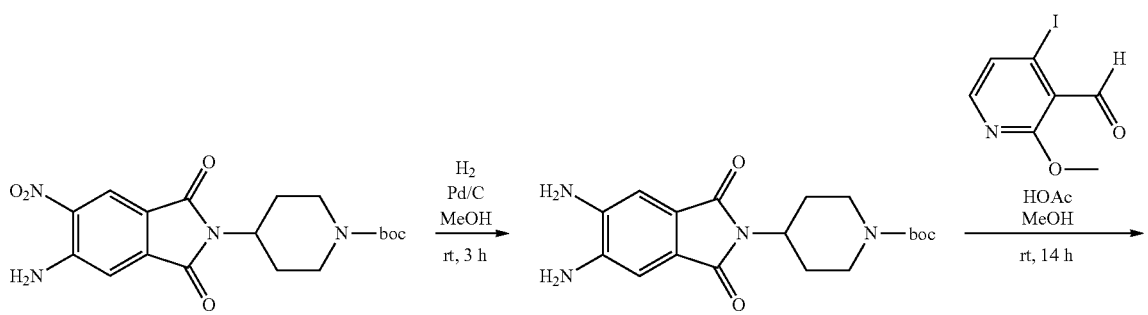

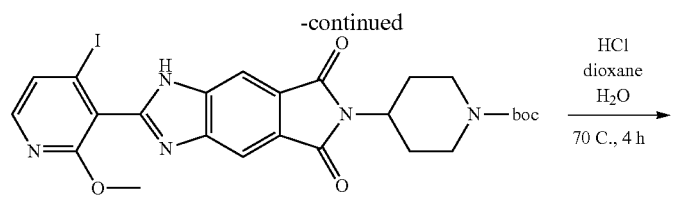

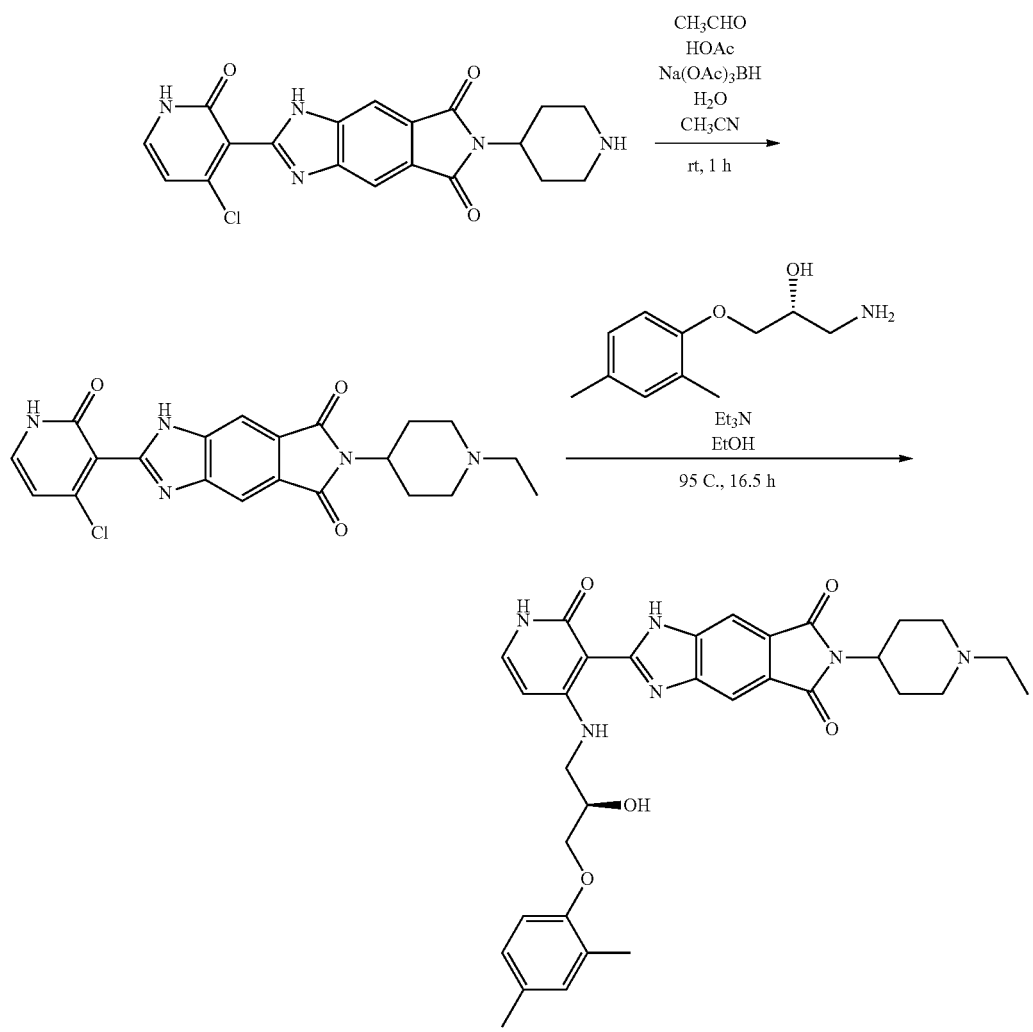

Synthesis of the Compounds Illustrated by Scheme 54:

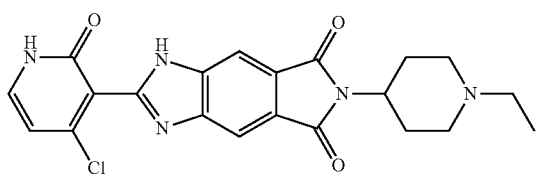 [SMILES: CCN1CCC(N2C(=O)c3cc4nc(-c5c(Cl)cc[nH]c5=O)[nH]c4cc3C2=O)CC1]

2-(4-Chloro-2-oxo-1,2-dihydro-pyridin-3-yl)-6-(1-ethyl-piperidin-4-yl)-1H-1,3,6-triaza-s-indacene-5,7-dione: To a mixture of 4-(5-amino-6-nitro-1,3-dioxo-1,3-dihydro-isoindol-2-yl)-piperidine-1-carboxylic acid tert-butyl ester (203 mg, 0.52 mmol) and 10% Pd/C (20 mg) was added 2-propanol (2 mL), and then MeOH (50 mL). After it was stirred under atmospheric hydrogen pressure for 3 h, the reaction mixture was filtered through Celite. The filtrate was mixed with 4-iodo-2-methoxynicotinic aldehyde (137 mg, 0.52 mmol) and AcOH (3 mL), stirred at the room temperature for 14 h, and evaporated under reduced pressure to afford a crude, which was mixed with HCl in dioxane (4 M, 15 mL) and H$_2$O (1 mL), heated at 70° C. for 4 h and evaporated at 95° C. (the bath temperature) to dryness. To the residue and acetaldehyde (150 μL, 2.6 mmol) in a mixture of CH$_3$CN (6 mL) and H$_2$O (2 mL) at 0° C., was added AcOH (500 μL) and the resulting mixture was stirred at 0° C. for 20 min, followed by addition of Na(OAc)$_3$BH (762 mg, 3.6 mmol). The reaction mixture was stirred at 0° C. for 1 h and at the room temperature for 1 h and then evaporated. The chromatography of the residue with CH$_2$Cl$_2$/MeOH/28% aqueous NH$_4$OH (70:10:1) afforded the title compound (143 mg, 67%). ESI-MS m/z 426.0 (MH$^+$).

303

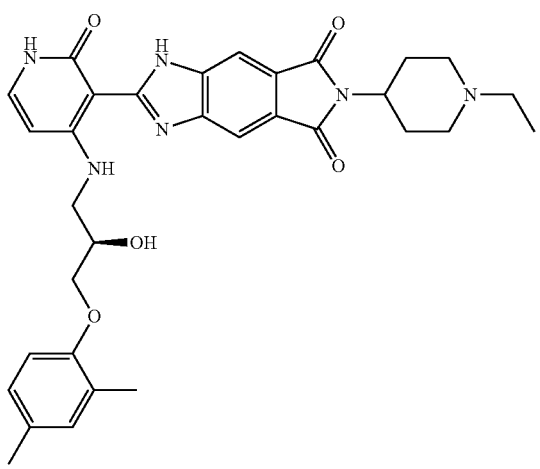 [SMILES: CCN1CCC(N2C(=O)c3cc4nc(-c5c(NC[C@@H](O)COc6ccc(C)cc6C)cc[nH]c5=O)[nH]c4cc3C2=O)CC1]

2-{4-[(R)-3-(2,4-Dimethyl-phenoxy)-2-hydroxy-propylamino]-2-oxo-1,2-dihydro-pyridin-3-yl}-6-(1-ethyl-piperidin-4-yl)-1H-1,3,6-triaza-s-indacene-5,7-dione: To a solution of 2-(4-chloro-2-oxo-1,2-dihydro-pyridin-3-yl)-6-(1-ethyl-piperidin-4-yl)-1H-1,3,6-triaza-s-indacene-5,7-dione (143 mg, 0.336 mmol) and (R)-1-amino-3-(2,4-dimethyl-phenoxy)-propan-2-ol (78 mg, 0.403 mmol) in EtOH (200 mL) was added Et$_3$N (5.35 mL, 38.4 mmol) and the mixture was heated at 95° C. for 16.5 h and then concentrated. Chromatography of the crude with CH$_2$Cl$_2$/MeOH/28% aqueous NH$_4$OH (160:10:1) (65 mg, 33%). $^1$H NMR (DMSO-d$_6$) δ 1.02 (t, J=6 Hz, 3H), 1.63 (m, 2H), 1.83 (m, 2H), 2.19 (s, 3H, CH$_3$), 2.21 (s, 3H, CH$_3$), 2.29-2.40 (4H), 2.98 (m, 2H), 3.53 (m, 1H), 3.70 (m, 1H), 3.91-4.08 (3H), 4.18 (m, 1H), 5.52 (d, J=4 Hz, 1H, NH), 6.23 (d, J=7 Hz, 1H), 6.83 (d, J=7 Hz, 1H), 6.91 (d, J=7 Hz, 1H), 6.97 (s, 1H), 7.38 (d, J=7 Hz, 1H), 7.65 (s, 1H), 8.09 (br s, 1H), 10.95 (br s, 1H, NH), 11.08 (br s, 1H, NH); ESI-MS m/z 585.5 (MH$^+$).

Scheme 55

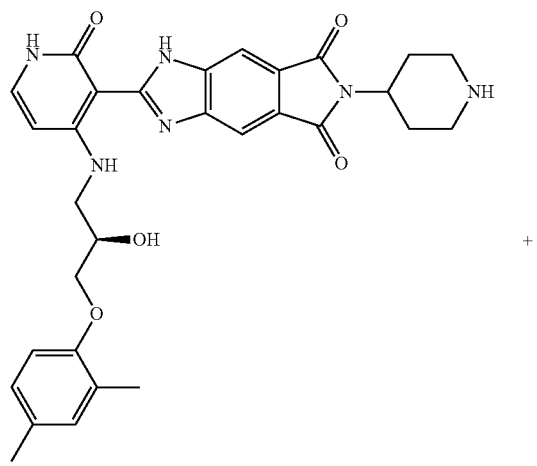

+

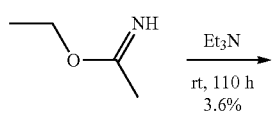

Et$_3$N
rt, 110 h
3.6%

304

-continued

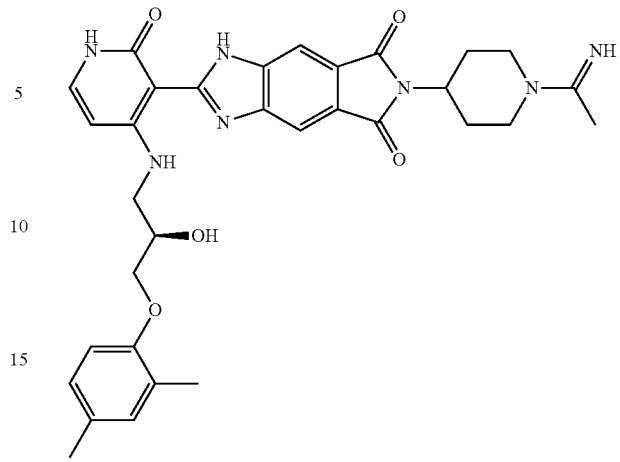

Synthesis of the Compound Illustrated by Scheme 55:

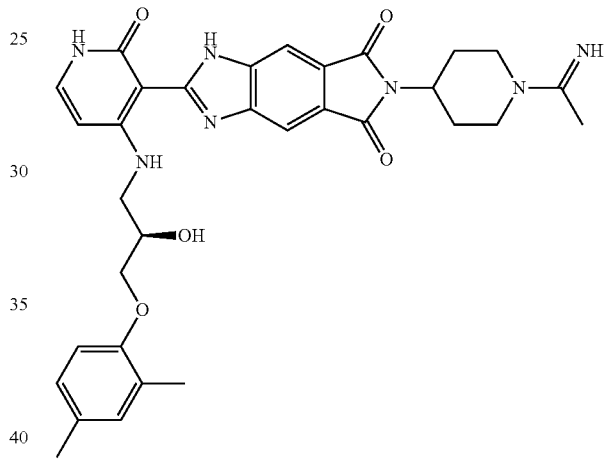

2-{4-[(R)-3-(2,4-Dimethyl-phenoxy)-2-hydroxy-propylamino]-2-oxo-1,2-dihydro-pyridin-3-yl}-6-[1-(1-iminoethyl)-piperidin-4-yl]-1H-1,3,6-triaza-s-indacene-5,7-dione: A mixture of 2-{4-[(R)-3-(2,4-dimethyl-phenoxy)-2-hydroxy-propylamino]-2-oxo-1,2-dihydro-pyridin-3-yl}-6-piperidin-4-yl-1H-1,3,6-triaza-s-indacene-5,7-dione (109 mg, 0.2 mmol) and ethyl acetimidate (3 g) in Et$_3$N (8 mL) was stirred at the room temperature for 110 h. After it was concentrated at 35° C. (the bath temperature) under reduced pressure, the mixture was subjected to chromatography [CH$_2$Cl$_2$/MeOH/28% aqueous NH$_4$OH (90:10:1)] to furnish a fluorescent product which was purified again with HPLC to afford the title compound in TFA salt form (5.06 mg, 3.6%). $^1$H NMR (DMSO-d$_6$) δ 1.93 (m, 2H), 2.19 (s, 3H, CH$_3$), 2.21 (s, 3H, CH$_3$), 2.35 (s, 3H, CH$_3$), 3.26 (m, 1H), 3.40 (m, 1H), 3.58 (m, 1H), 3.86 (m, 1H), 3.91-4.26 (7H), 4.43 (m, 1H), 6.23 (d, J=7 Hz, 1H), 6.86 (d, J=7 Hz, 1H), 6.92 (d, J=7 Hz, 1H), 7.00 (s, 1H), 7.41 (d, J=7 Hz, 1H), 7.71 (s, 1H), 8.10 (s, 1H), 8.68 (br s, 1H, NH), 9.21 (br s, 1H, NH), 10.97 (br s, 1H, NH), 11.30 (br s, 1H, NH); ESI-MS m/z 598.7 (MH$^+$).

Synthesis of Additional Phthalimide Derivatives

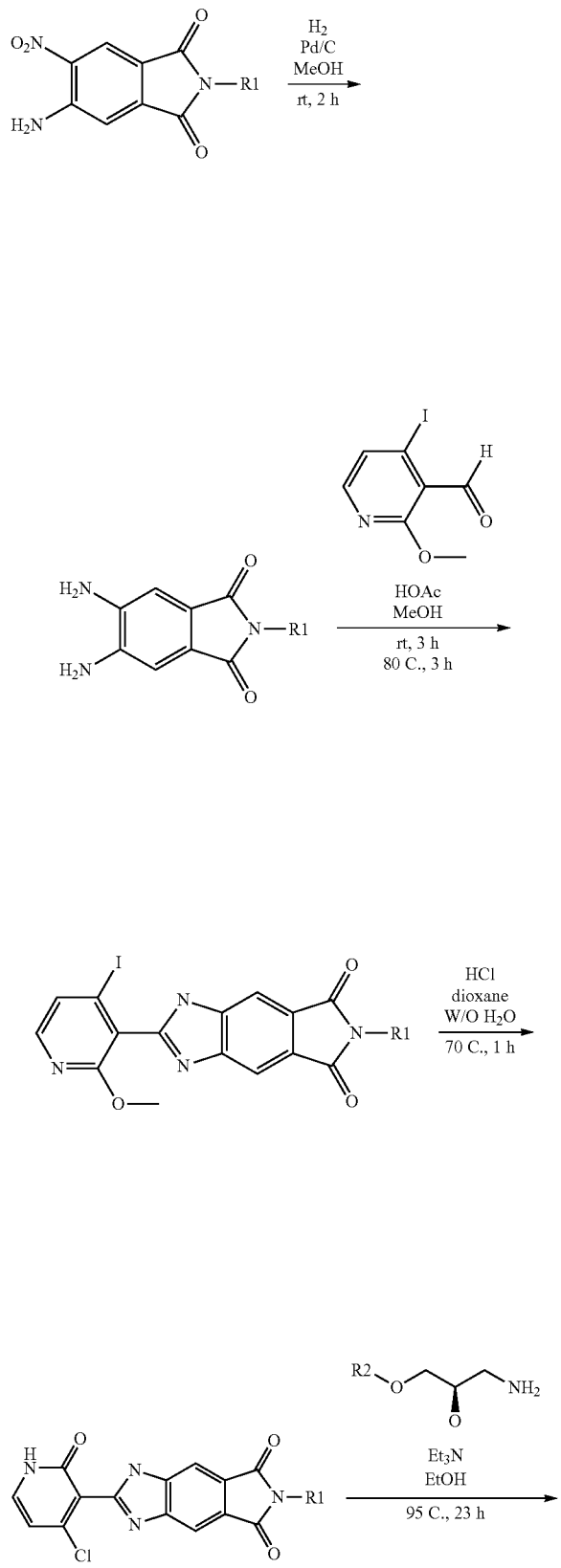

Scheme 56

2-{4-[(R)-3-(2,4-Dimethyl-phenoxy)-2-hydroxy-propylamino]-2-oxo-1,2-dihydro-pyridin-3-yl}-6-[1-(2-hydroxyethyl)-piperidin-4-ylmethyl]-1H-1,3,6-triaza-s-indacene-5,7-dione: To a solution of 5-amino-2-[1-(2-hydroxy-ethyl)-piperidin-4-ylmethyl]-6-nitro-isoindole-1,3-dione (90.0 mg, 0.258 mmol) in MeOH (30 mL) was added 10 mg of Pd/C (10%) and AcOH (1.5 mL) (the solution was purged with $N_2$ before adding Pd/C). After it was stirred under $H_2$ for 2 h, the reaction mixture was filtered through Celite. To the filtrate was added 4-iodo-2-methoxynicotinic aldehyde (100.0 mg, 0.38 mmol) and the resulting mixture was stirred at the room temperature for 1 h and heated at 80° C. for 3 h, and then evaporated to dryness under reduced pressure. The residue was mixed with 4 M HCl/dioxane (8 mL) and $H_2O$ (0.6 mL), heated at 70° C. for 1 h and evaporated to dryness under reduced pressure. The chromatography of the crude residue (50:10:1 $CH_2Cl_2$/MeOH/28% aqueous $NH_4OH$) afforded the corresponding chloropyridone intermediate (73 mg, 62% for 3 steps), which was then mixed with (S)-2-amino-1-(3-chloro-phenyl)-ethanol (12 mg, 0.06 mmol) and $Et_3N$ (18 mg, 0.18 mmol) in EtOH (1.5 mL). After it was heated at 95° C. for 23 h, the reaction mixture was concentrated and subjected to HPLC purification to furnish the title compound (40.3 mg, 34% for the last step). $^1$H NMR (DMSO-$d_6$) δ 1.50 (m, 2H), 1.83 (2H), 1.98 (m, 1H), 2.19 (s, 3H, $CH_3$), 2.21 (s, 3H, $CH_3$), 2.90 (m, 2H), 3.11 (m, 2H), 3.21-3.62 (6H), 3.70 (m, 2H), 4.00 (m, 2H), 4.15 (m, 1H), 5.32 (br s, 1H, OH), 5.55 (br s, 1H, NH), 6.24 (d, J=6 Hz, 1H), 6.80-7.00 (3H), 7.40 (m, 1H), 7.59 (s, 1H), 8.13 (s, 1H), 9.10 (br s, 1H), 10.96 (br s, 1H, NH), 11.32 (br s, 1H, NH); ESI-MS m/z 615.5 (MH$^+$).

307

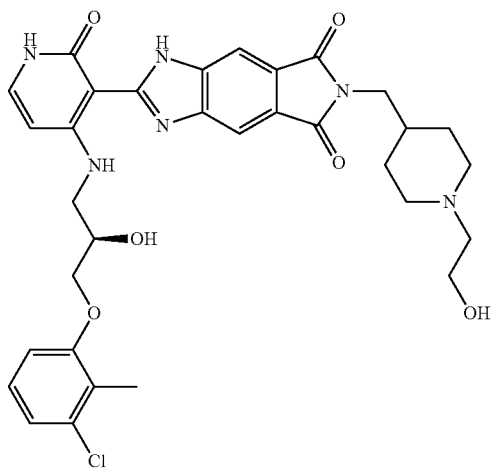 [SMILES: Cc1c(Cl)cccc1OC[C@H](O)CNc1cc[nH]c(=O)c1-c1nc2cc3c(cc2[nH]1)C(=O)N(CC1CCN(CCO)CC1)C3=O]

2-{4-[(R)-3-(3-Chloro-2-methyl-phenoxy)-2-hydroxy-propylamino]-2-oxo-1,2-dihydro-pyridin-3-yl}-6-[1-(2-hydroxy-ethyl)-piperidin-4-ylmethyl]-1H-1,3,6-triaza-s-indacene-5,7-dione: $^1$H NMR (DMSO-$d_6$) δ 1.50 (m, 2H), 1.83 (2H), 1.98 (m, 1H), 2.28 (s, 3H, CH$_3$), 2.90 (m, 2H), 3.11 (m, 2H), 3.21-3.62 (6H), 3.70 (m, 2H), 4.10 (m, 2H), 4.19 (m, 1H), 5.32 (br s, 1H, OH), 5.55 (br s, 1H, NH), 6.24 (d, J=6 Hz, 1H), 6.99-7.07 (2H), 7.15 (m, 1H), 7.40 (m, 1H), 7.71 (s, 1H), 8.14 (s, 1H), 9.12 (br s, 1H), 10.97 (br s, 1H, NH), 11.31 (br s, 1H, NH); ESI-MS m/z 635.5 (MH$^+$).

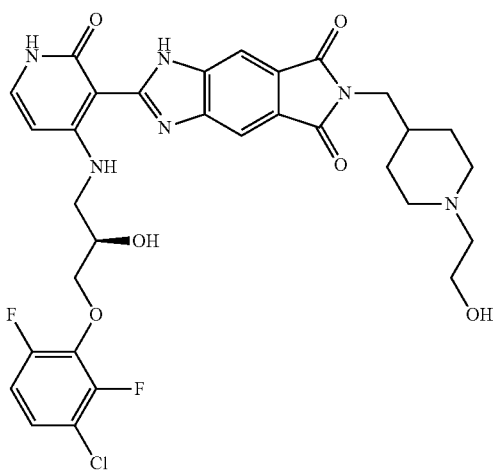 [SMILES: O=C1c2cc3nc(-c4c(NC[C@@H](O)COc5c(F)ccc(Cl)c5F)cc[nH]c4=O)[nH]c3cc2C(=O)N1CC1CCN(CCO)CC1]

2-{4-[(R)-3-(3-Chloro-2,6-difluoro-phenoxy)-2-hydroxy-propylamino]-2-oxo-1,2-dihydro-pyridin-3-yl}-6-[1-(2-hydroxy-ethyl)-piperidin-4-ylmethyl]-1H-1,3,6-triaza-s-indacene-5,7-dione: $^1$H NMR (DMSO-$d_6$) δ 1.50 (m, 2H), 1.83 (2H), 1.95 (m, 1H), 2.28 (s, 3H, CH$_3$), 2.90 (m, 2H), 3.11 (m, 2H), 3.21-3.59 (6H), 3.70 (m, 2H), 4.10 (m, 1H), 4.29 (m, 2H), 5.32 (br s, 1H, OH), 5.56 (br s, 1H, NH), 6.24 (d, J=6 Hz, 1H), 7.20 (m, 1H), 7.33 (m, 1H), 7.41 (m, 1H), 7.85 (s, 1H), 8.15 (s, 1H), 9.13 (br s, 1H), 10.94 (br s, 1H, NH), 11.35 (br s, 1H, NH); ESI-MS m/z 657.3 (MH$^+$).

308

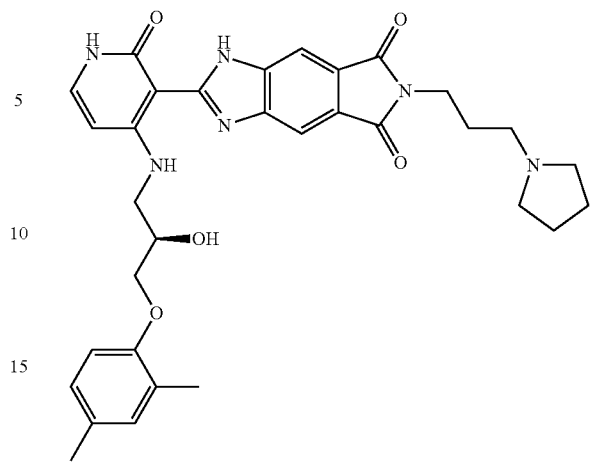

2-{4-[(R)-3-(2,4-Dimethyl-phenoxy)-2-hydroxy-propylamino]-2-oxo-1,2-dihydro-pyridin-3-yl}-6-(3-pyrrolidin-1-yl-propyl)-1H-1,3,6-triaza-s-indacene-5,7-dione: $^1$H NMR (DMSO-$d_6$) δ 1.78-2.09 (6H), 2.19 (s, 3H, CH$_3$), 2.22 (s, 3H, CH$_3$), 3.00 (m, 2H), 3.21 (m, 2H), 3.49-3.79 (6H), 4.00 (m, 2H), 4.18 (m, 1H), 5.56 (br s, 1H, NH), 6.21 (d, J=6 Hz, 1H), 6.80-6.98 (3H), 7.40 (m, 1H), 7.70 (s, 1H), 8.14 (s, 1H), 9.51 (br s, 1H), 10.95 (br s, 1H, NH), 11.33 (br s, 1H, NH); ESI-MS m/z 585.3 (MH$^+$).

Synthesis of Additional Phthalimide Derivatives

Scheme 57

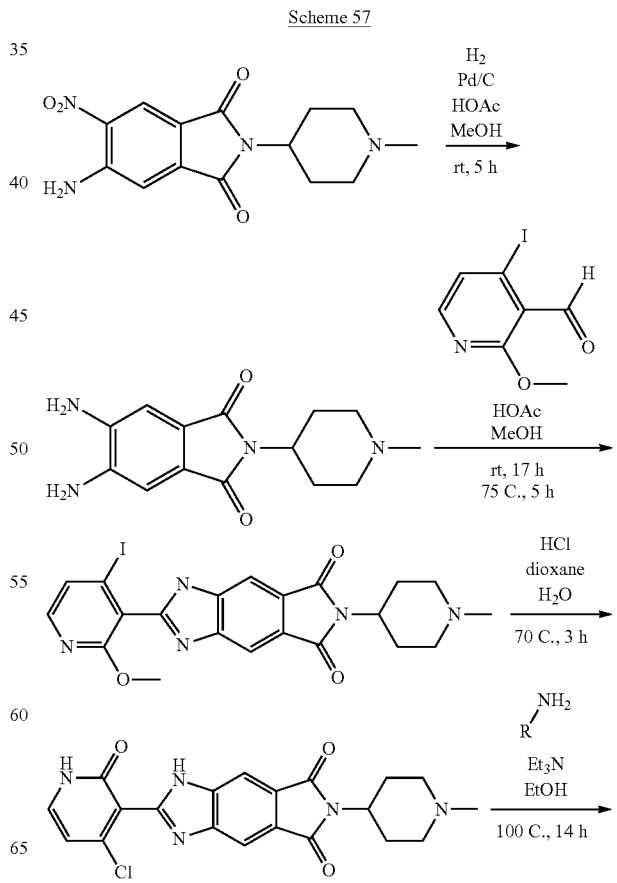

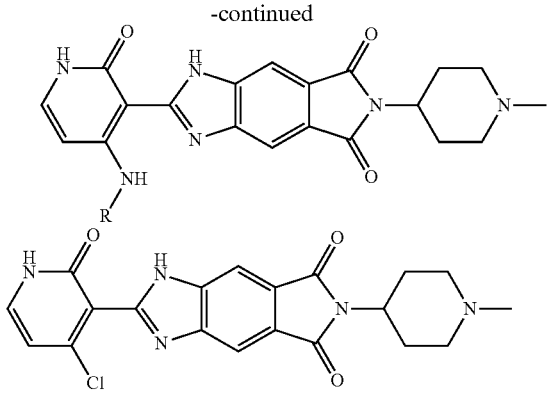

2-(4-Chloro-2-oxo-1,2-dihydro-pyridin-3-yl)-6-(1-methyl-piperidin-4-yl)-1H-1,3,6-triaza-s-indacene-5,7-dione: To a solution of 5-amino-2-(1-methyl-piperidin-4-yl)-6-nitro-isoindole-1,3-dione (1.216 g, 4.0 mmol) in MeOH (47.5 mL) was added 120 mg of Pd/C (10%) (the solution was purged with $N_2$ before adding Pd/C) and AcOH (2.5 mL). After it was stirred under atmospheric $H_2$ for 5 h, the reaction mixture was filtered through Celite. To the filtrate was added 4-iodo-2-methoxynicotinic aldehyde (1.052 g, 4.0 mmol) and the resulting mixture was stirred at the room temperature for 17 h, heated at 80° C. for 5 h, and then evaporated to dryness under reduced pressure. The residue was mixed with 4 M HCl/dioxane (40 mL) and $H_2O$ (3 mL), heated at 70° C. for 3 h and was evaporated under reduced pressure. The chromatography of the crude residue (150:10:1 $CH_2Cl_2$/MeOH/28% aqueous $NH_4OH$) afforded the title compound (688 mg, 42% for 3 steps). $^1$H NMR (DMSO-$d_6$) δ 1.65 (m, 2H), 2.05 (m, 2H), 2.24 (s, 3H), 2.40 (m, 2H), 2.92 (m, 2H), 4.01 (m, 1H), 6.60 (d, 1H, J=6.9 Hz), 7.70 (d, J=6.9 Hz, 1H), 8.03 (s, 1H), 8.05 (s, 1H); ESI-MS m/z 412.4 (MH$^+$).

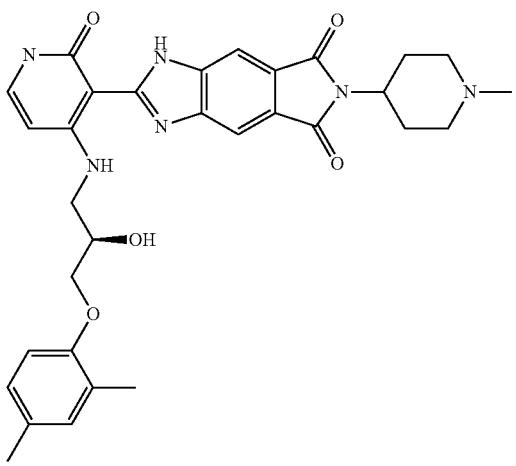 [SMILES: Cc1ccc(OC[C@H](O)CNc2cc[nH]c(=O)c2-c2nc3cc4c(cc3[nH]2)C(=O)N(C2CCN(C)CC2)C4=O)c(C)c1]

2-{4-[(R)-3-(2,4-Dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: To a solution of 2-(4-chloro-2-oxo-1,2-dihydro-pyridin-3-yl)-6-(1-methyl-piperidin-4-yl)-1H-1,3,6-triaza-s-indacene-5,7-dione (448.3 mg, 1.35 mmol) and (R)-1-amino-3-(2,4-dimethyl-phenoxy)-propan-2-ol (303.0 mg, 1.55 mmol) in EtOH (10 mL) was added $Et_3N$ (410 mg, 4.05 mmol). After it was heated at 100° C. for 14 h, the reaction mixture was concentrated under reduced pressure. The chromatography of the crude residue (150:10:1 $CH_2Cl_2$/MeOH/28% aqueous $NH_4OH$) afforded the title compound (498 mg, 45%). $^1$H NMR (DMSO-$d_6$) δ 1.60 (m, 2H), 1.95 (m, 2H), 2.18 (s, 3H, $CH_3$), 2.18 (s, 3H, $CH_3$), 2.21 (s, 3H, $CH_3$), 2.39 (m, 2H), 2.90 (m, 2H), 3.57 (m, 1H), 3.71 (m, 1H), 3.90-4.08 (3H), 4.18 (m, 1H), 5.55 (d, J=6 Hz, 1H, NH), 6.22 (d, J=6 Hz, 1H), 6.83 (d, J=6 Hz, 1H), 6.92 (d, J=6 Hz, 1H), 6.97 (s, 1H), 7.39 (d, J=6 Hz, 1H), 7.64 (s, 1H), 8.09 (s, 1H), 10.96 (br s, 1H, NH), 11.31 (br s, 1H, NH); ESI-MS m/z 571.3 (MH$^+$).

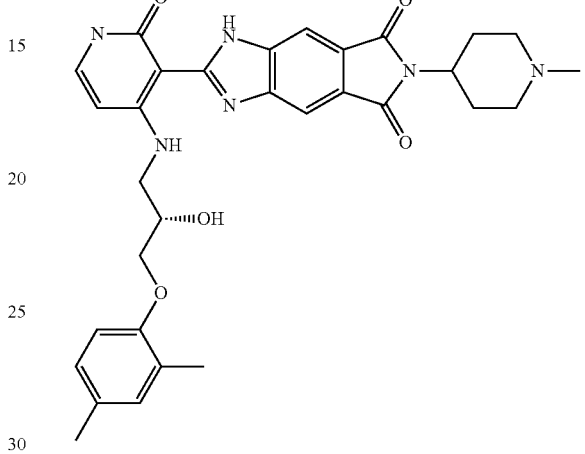

2-{4-[(S)-3-(2,4-Dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-$d_6$) δ 1.60 (m, 2H), 1.95 (m, 2H), 2.18 (s, 3H, $CH_3$), 2.18 (s, 3H, $CH_3$), 2.21 (s, 3H, $CH_3$), 2.39 (m, 2H), 2.90 (m, 2H), 3.57 (m, 1H), 3.71 (m, 1H), 3.90-4.08 (3H), 4.18 (m, 1H), 5.55 (d, J=6 Hz, 1H, NH), 6.22 (d, J=6 Hz, 1H), 6.83 (d, J=6 Hz, 1H), 6.92 (d, J=6 Hz, 1H), 6.97 (s, 1H), 7.39 (d, J=6 Hz, 1H), 7.64 (s, 1H), 8.09 (s, 1H), 10.96 (br s, 1H, NH), 11.31 (br s, 1H, NH); ESI-MS m/z 571.3 (MH$^+$).

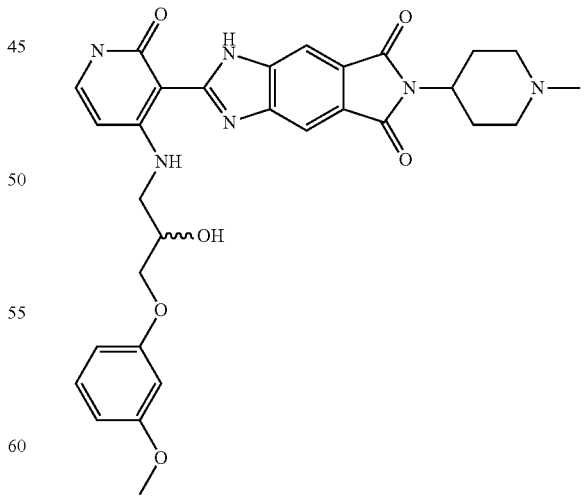

2-{4-[2-Hydroxy-3-(3-methoxy-phenoxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-$d_6$) δ 1.65 (m, 2H), 2.00 (m, 2H), 2.28 (s, 3H, $CH_3$), 2.39 (m, 2H), 2.95 (m, 2H), 3.57 (m, 1H), 3.71 (m, 1H), 3.73 (s, 3H, CH₃), 3.90-4.08 (3H), 4.15 (m, 1H), 5.59 (d, J=6 Hz, 1H, NH), 6.22 (d, J=6 Hz, 1H), 6.50-6.62 (3H), 7.18 (s, 1H), 7.39 (s, 1H), 7.73 (s, 1H), 8.11 (s, 1H), 10.97 (br s, 1H, NH), 11.30 (br d, J=6 Hz, 1H, NH); ESI-MS m/z 573.3 (MH⁺).

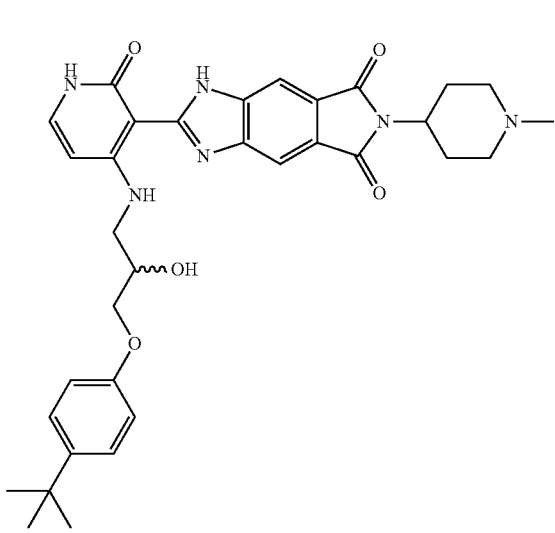 [SMILES: CN1CCC(N2C(=O)c3cc4nc(-c5c(NCC(O)COc6ccc(C(C)(C)C)cc6)cc[nH]c5=O)[nH]c4cc3C2=O)CC1]

2-{4-[3-(4-tert-Butyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d₆) δ 1.22 (s, 9H), 1.62 (m, 2H), 1.98 (m, 2H), 2.20 (s, 3H, CH₃), 2.39 (m, 2H), 2.89 (m, 2H), 3.53 (m, 1H), 3.64 (m, 1H), 3.90-4.08 (3H), 4.15 (m, 1H), 5.59 (d, J=6 Hz, 1H, NH), 6.22 (d, J=6 Hz, 1H), 6.90 (d, J=6 Hz, 2H), 7.27 (d, J=6 Hz, 2H), 7.40 (s, 1H), 7.81 (s, 1H), 8.11 (s, 1H), 10.98 (br s, 1H, NH), 11.31 (br s, 1H, NH); ESI-MS m/z 599.5 (MH⁺).

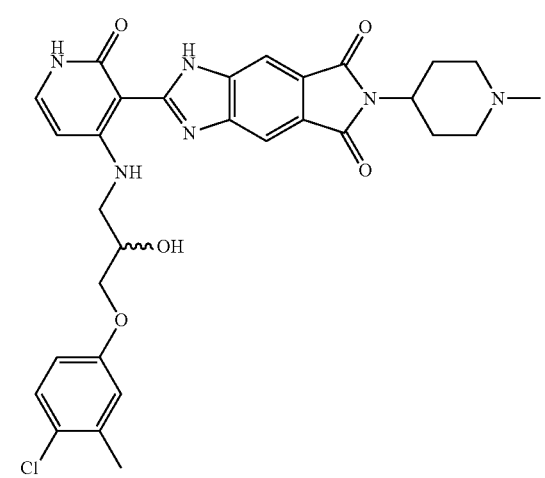 [SMILES: Cc1cc(OCC(O)CNc2cc[nH]c(=O)c2-c2nc3cc4c(cc3[nH]2)C(=O)N(C2CCN(C)CC2)C4=O)ccc1Cl]

2-{4-[3-(4-Chloro-3-methyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d₆) δ 1.62 (m, 2H), 1.95 (m, 2H), 2.20 (s, 3H, CH₃), 2.28 (s, 3H, CH₃), 2.40 (m, 2H), 2.87 (m, 2H), 3.50-4.50 (4H), 5.62 (d, J=6 Hz, 1H, NH), 6.22 (d, J=6 Hz, 1H), 6.85 (d, J=6 Hz, 1H), 7.00 (s, 1H), 7.28 (d, J=6 Hz, 1H), 7.39 (d, J=6 Hz, 1H), 7.76 (s, 1H), 8.10 (s, 1H), 10.96 (br s, 1H, NH), 11.30 (br d, J=6 Hz, 1H, NH); ESI-MS m/z 591.3 (MH⁺).

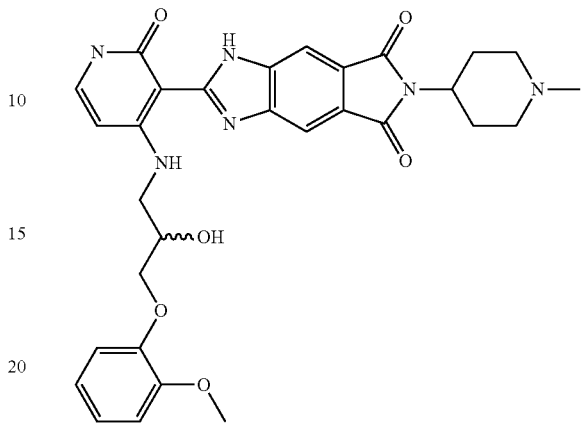

2-{4-[2-Hydroxy-3-(2-methoxy-phenoxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d₆) δ 1.95 (m, 2H), 2.53 (m, 2H), 2.69 (s, 3H, CH₃), 3.18 (m, 2H), 3.42-3.62 (3H), 3.74 (m, 1H), 3.80 (s, 3H, CH₃), 4.01 (m, 2H), 4.15 (m, 1H), 4.30 (m, 1H), 5.59 (br s, 1H, NH), 6.22 (d, J=6 Hz, 1H), 6.82-7.04 (4H), 7.39 (s, 1H), 7.80 (s, 1H), 8.13 (s, 1H), 9.60 (br s, 1H), 10.97 (br s, 1H, NH), 11.33 (br d, J=6 Hz, 1H, NH); ESI-MS m/z 573.3 (MH⁺).

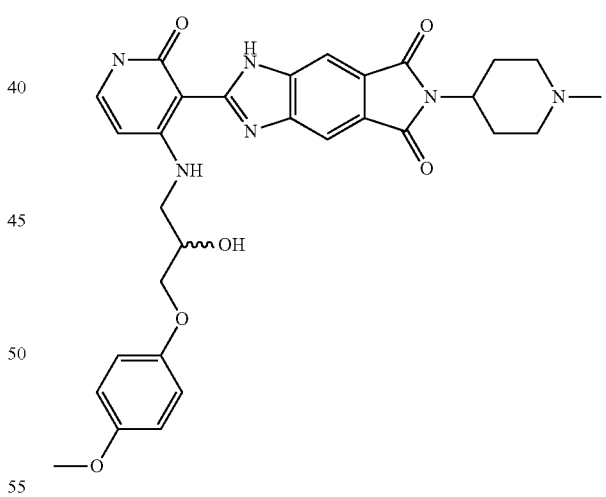

2-{4-[2-Hydroxy-3-(4-methoxy-phenoxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d₆) δ 1.95 (m, 2H), 2.53 (m, 2H), 2.80 (s, 3H, CH₃), 3.20 (m, 2H), 3.42-3.80 (4H), 3.70 (s, 3H, CH₃), 3.99 (m, 2H), 4.10 (m, 1H), 4.30 (m, 1H), 5.59 (br s, 1H, NH), 6.22 (d, J=6 Hz, 1H), 6.80-6.97 (4H), 7.40 (s, 1H), 7.79 (s, 1H), 8.13 (s, 1H), 9.60 (br s, 1H), 10.97 (br s, 1H, NH), 11.32 (br d, J=6 Hz, 1H, NH); ESI-MS m/z 573.3 (MH⁺).

313

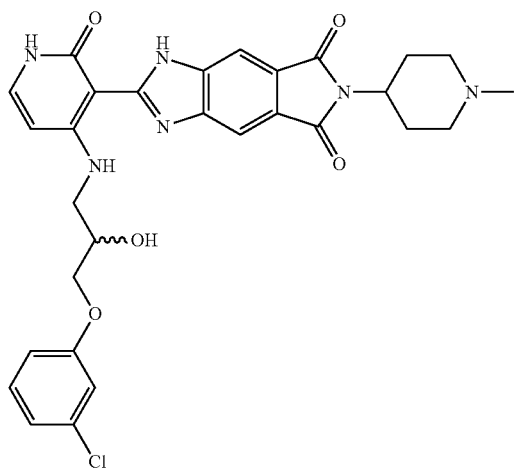 [SMILES: CN1CCC(N2C(=O)c3cc4nc(-c5c(NCC(O)COc6cccc(Cl)c6)cc[nH]c5=O)[nH]c4cc3C2=O)CC1]

2-{4-[3-(3-Chloro-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.95 (m, 2H), 2.57 (m, 2H), 2.79 (s, 3H, CH$_3$), 3.19 (m, 2H), 3.35-3.60 (3H), 3.65 (m, 1H), 4.02-4.19 (3H), 4.31 (m, 1H), 5.65 (br s, 1H, NH), 6.22 (d, J=6 Hz, 1H), 6.95-7.05 (3H), 7.30 (m, 1H), 7.39 (m, 1H), 7.79 (s, 1H), 8.10 (s, 1H), 9.62 (br s, 1H), 10.95 (br s, 1H, NH), 11.32 (br d, J=6 Hz, 1H, NH); ESI-MS m/z 577.3 (MH$^+$).

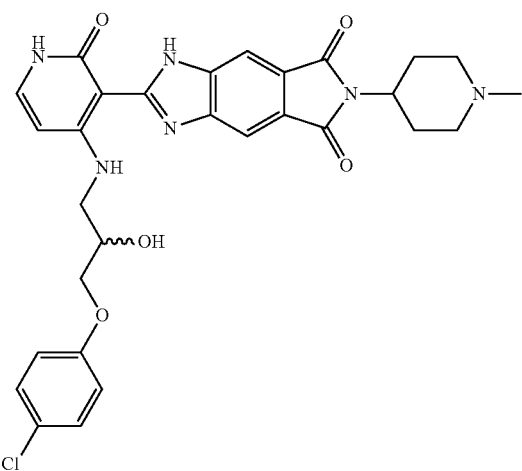 [SMILES: CN1CCC(N2C(=O)c3cc4nc(-c5c(NCC(O)COc6ccc(Cl)cc6)cc[nH]c5=O)[nH]c4cc3C2=O)CC1]

2-{4-[3-(4-Chloro-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.95 (m, 2H), 2.57 (m, 2H), 2.79 (s, 3H, CH$_3$), 3.19 (m, 2H), 3.52 (m, 2H), 3.69 (m, 1H), 4.06 (m, 2H), 4.15 (m, 1H), 4.35 (m, 1H), 5.65 (br s, 1H, NH), 6.22 (d, J=6 Hz, 1H), 7.02 (d, J=6 Hz, 2H), 7.30 (d, J=6 Hz, 2H), 7.40 (m, 1H), 7.80 (s, 1H), 8.13 (s, 1H), 9.60 (br s, 1H), 10.95 (br s, 1H, NH), 11.32 (br d, J=6 Hz, 1H, NH); ESI-MS m/z 577.3 (MH$^+$).

314

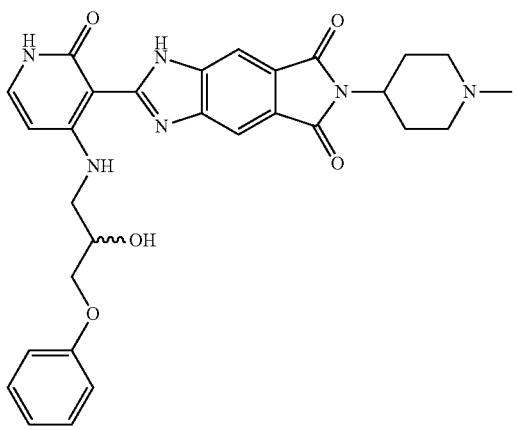 [SMILES: CN1CCC(N2C(=O)c3cc4nc(-c5c(NCC(O)COc6ccccc6)cc[nH]c5=O)[nH]c4cc3C2=O)CC1]

2-[4-(2-Hydroxy-3-phenoxy-propylamino)-2-oxo-1,2-dihydro-pyridin-3-yl]-6-(1-methyl-piperidin-4-yl)-1H-1,3,6-triaza-s-indacene-5,7-dione: $^1$H NMR (DMSO-d$_6$) δ 1.67 (m, 2H), 2.10 (m, 2H), 2.30 (s, 3H, CH$_3$), 2.42 (m, 2H), 2.95 (m, 2H), 3.51 (m, 1H), 3.68 (m, 2H), 3.95-4.06 (3H), 4.15 (m, 1H), 5.61 (d, J=6 Hz, 1H, NH), 6.22 (d, J=6 Hz, 1H), 6.95 (m, 1H), 6.99 (d, J=6 Hz, 2H), 7.30 (m, 2H), 7.39 (m, 1H), 7.74 (s, 1H), 8.11 (s, 1H), 9.60 (br s, 1H), 10.98 (br s, 1H, NH), 11.31 (br d, J=6 Hz, 1H, NH); ESI-MS m/z 543.3 (MH$^+$).

2-[4-(2-Hydroxy-2-pyridin-4-yl-ethylamino)-2-oxo-1,2-dihydro-pyridin-3-yl]-6-(1-methyl-piperidin-4-yl)-1H-1,3,6-triaza-s-indacene-5,7-dione: $^1$H NMR (DMSO-d$_6$) δ 1.68 (m, 2H), 2.19 (m, 2H), 2.28 (s, 3H, CH$_3$), 2.41 (m, 2H), 2.98 (m, 2H), 3.49 (m, 1H), 3.71 (m, 2H), 4.02 (m, 1H), 4.99 (m, 1H), 6.09 (d, J=6 Hz, 1H, NH), 6.22 (d, J=6 Hz, 1H), 7.41 (d, J=6 Hz, 1H), 7.54 (d, J=6 Hz, 2H), 7.80 (s, 1H), 8.11 (m, 1H), 8.54 (d, J=6 Hz, 2H), 10.88 (br s, 1H, NH), 11.31 (br s, 1H, NH); ESI-MS m/z 514.5 (MH$^+$).

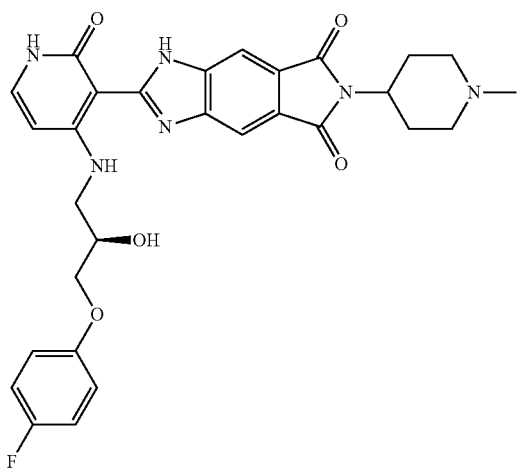 [SMILES: CN1CCC(N2C(=O)c3cc4nc(-c5c(NC[C@@H](O)COc6ccc(F)cc6)cc[nH]c5=O)[nH]c4cc3C2=O)CC1]

2-{4-[(R)-3-(4-Fluoro-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.95 (m, 2H), 2.57 (m, 2H), 2.79 (s, 3H, CH$_3$), 3.19 (m, 2H), 3.52 (m, 2H), 3.69 (m, 1H), 4.06 (m, 2H), 4.12 (m, 1H), 4.33 (m, 1H), 5.65 (br s, 1H, NH), 6.22 (d, J=6 Hz, 1H), 6.99-7.17 (4H), 7.40 (m, 1H), 7.77 (s, 1H), 8.13 (s, 1H), 9.69 (br s, 1H), 10.97 (br s, 1H, NH), 11.34 (br d, J=6 Hz, 1H, NH); ESI-MS m/z 561.3 (MH$^+$).

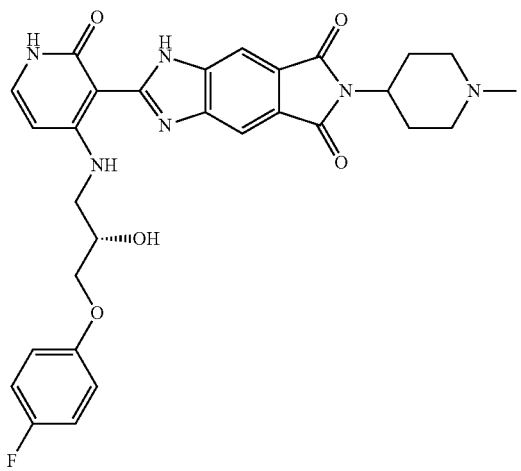 [SMILES: CN1CCC(N2C(=O)c3cc4nc(-c5c(NC[C@H](O)COc6ccc(F)cc6)cc[nH]c5=O)[nH]c4cc3C2=O)CC1]

2-{4-[(S)-3-(4-Fluoro-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.95 (m, 2H), 2.57 (m, 2H), 2.79 (s, 3H, CH$_3$), 3.19 (m, 2H), 3.52 (m, 2H), 3.69 (m, 1H), 4.06 (m, 2H), 4.12 (m, 1H), 4.33 (m, 1H), 5.65 (br s, 1H, NH), 6.22 (d, J=6 Hz, 1H), 6.99-7.17 (4H), 7.40 (m, 1H), 7.77 (s, 1H), 8.13 (s, 1H), 9.69 (br s, 1H), 10.97 (br s, 1H, NH), 11.34 (br d, J=6 Hz, 1H, NH); ESI-MS m/z 561.3 (MH$^+$).

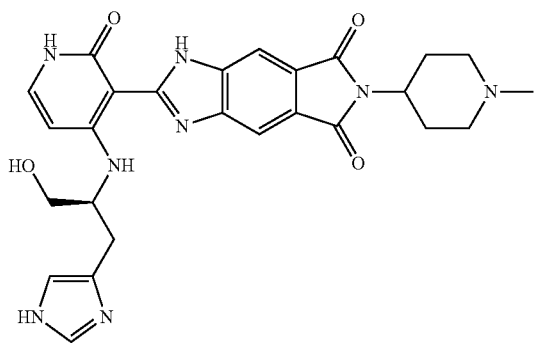 [SMILES: CN1CCC(N2C(=O)c3cc4nc(-c5c(N[C@H](CO)Cc6c[nH]cn6)cc[nH]c5=O)[nH]c4cc3C2=O)CC1]

2-{4-[(S)-1-Hydroxymethyl-2-(1H-imidazol-4-yl)-ethylamino]-2-oxo-1,2-dihydro-pyridin-3-yl}-6-(1-methyl-piperidin-4-yl)-1H-1,3,6-triaza-s-indacene-5,7-dione: $^1$H NMR (MeOH-d$_4$) δ 2.10 (m, 2H), 2.83 (m, 2H), 2.96 (s, 3H, CH$_3$), 3.16-3.36 (4H), 3.67 (m, 2H), 3.85 (m, 2H), 4.33 (m, 1H), 4.47 (m, 1H), 6.23 (d, J=7 Hz, 1H), 7.28 (d, J=7 Hz, 1H), 7.53 (s, 1H), 7.86 (s, 1H), 7.86 (s, 1H), 8.78 (s, 1H); ESI-MS m/z 517.5 (MH$^+$).

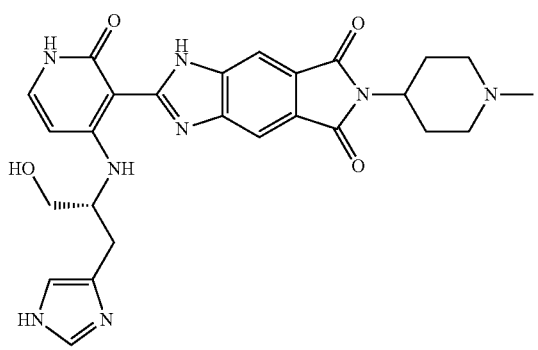 [SMILES: CN1CCC(N2C(=O)c3cc4nc(-c5c(N[C@@H](CO)Cc6c[nH]cn6)cc[nH]c5=O)[nH]c4cc3C2=O)CC1]

2-{4-[(R)-1-Hydroxymethyl-2-(1H-imidazol-4-yl)-ethylamino]-2-oxo-1,2-dihydro-pyridin-3-yl}-6-(1-methyl-piperidin-4-yl)-1H-1,3,6-triaza-s-indacene-5,7-dione: $^1$H NMR (MeOH-d$_4$) δ 2.10 (m, 2H), 2.83 (m, 2H), 2.96 (s, 3H, CH$_3$), 3.16-3.36 (4H), 3.67 (m, 2H), 3.85 (m, 2H), 4.33 (m, 1H), 4.47 (m, 1H), 6.23 (d, J=7 Hz, 1H), 7.28 (d, J=7 Hz, 1H), 7.53 (s, 1H), 7.86 (s, 1H), 7.86 (s, 1H), 8.78 (s, 1H); ESI-MS m/z 517.5 (MH$^+$).

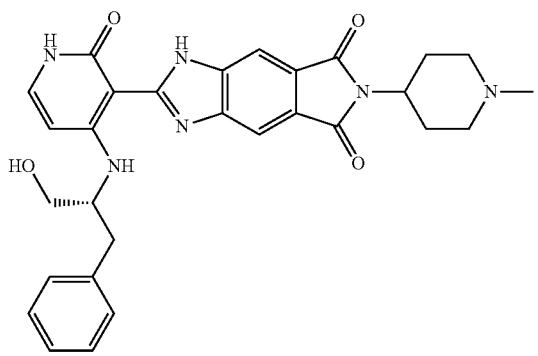 [SMILES: CN1CCC(N2C(=O)c3cc4nc(-c5c(N[C@@H](CO)Cc6ccccc6)cc[nH]c5=O)[nH]c4cc3C2=O)CC1]

2-[4-((R)-1-Hydroxymethyl-2-phenyl-ethylamino)-2-oxo-1,2-dihydro-pyridin-3-yl]-6-(1-methyl-piperidin-4-yl)-1H-1,3,6-triaza-s-indacene-5,7-dione: $^1$H NMR (MeOH-d$_4$)

δ 2.08 (m, 2H), 2.83 (m, 2H), 2.88-3.28 (4H), 2.89 (s, 3H, CH₃), 3.68 (m, 2H), 3.79 (m, 2H), 4.03 (m, 1H), 4.43 (m, 1H), 6.08 (d, J=6 Hz, 1H), 7.10-7.30 (6H), 7.78 (s, 1H), 7.78 (s, 1H); ESI-MS m/z 527.3 (MH⁺).

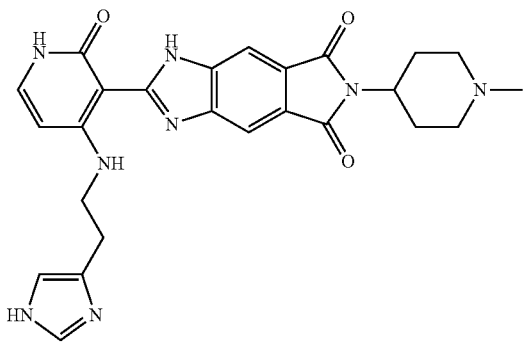 [SMILES: CN1CCC(N2C(=O)c3cc4nc(-c5c(NCCc6c[nH]cn6)cc[nH]c5=O)[nH]c4cc3C2=O)CC1]

2-{4-[2-(1H-Imidazol-4-yl)-ethylamino]-2-oxo-1,2-dihydro-pyridin-3-yl}-6-(1-methyl-piperidin-4-yl)-1H-1,3,6-triaza-s-indacene-5,7-dione: ¹H NMR (DMSO-d₆) δ 1.58 (m, 2H), 2.03 (m, 2H), 2.23 (s, 3H, CH₃), 2.40 (m, 2H), 2.87-3.95 (4H), 3.78 (m, 2H), 3.99 (m, 1H), 4.37 (t, J=6 Hz, 1H, NH), 6.19 (d, J=6 Hz, 1H), 7.04 (s, 1H), 6.99-7.17 (4H), 7.41 (m, 1H), 7.58 (s, 1H), 7.90 (s, 1H), 8.10 (s, 1H), 10.70 (br s, 1H, NH), 11.31 (br s, 1H, NH); ESI-MS m/z 487.5 (MH⁺).

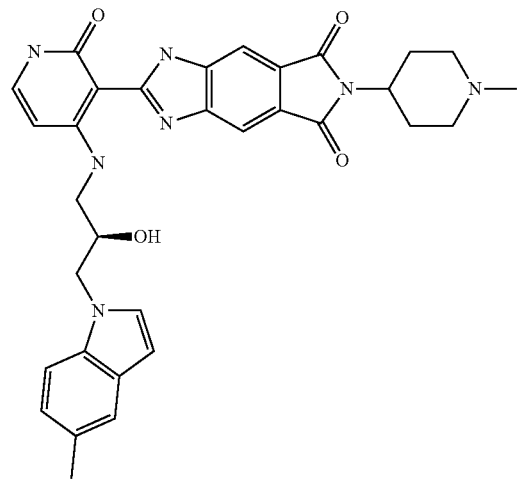 [SMILES: Cc1ccc2c(ccn2C[C@H](O)CNc2cc[nH]c(=O)c2-c2nc3cc4c(cc3[nH]2)C(=O)N(C2CCN(C)CC2)C4=O)c1]

2-{4-[(R)-2-Hydroxy-3-(5-methyl-indol-1-yl)-propylamino]-2-oxo-1,2-dihydro-pyridin-3-yl}-6-(1-methyl-piperidin-4-yl)-1H-1,3,6-triaza-s-indacene-5,7-dione: ¹H NMR (DMSO-d₆) δ 1.95 (m, 2H), 2.25-2.77 (2H), 2.37 (s, 3H, CH₃), 2.79 (m, 2H), 3.19 (s, 3H, CH₃), 3.30 (m, 1H), 3.52 (m, 2H), 4.12-4.39 (3H), 5.70 (br s, 1H, NH), 6.10 (d, J=7 Hz, 1H), 6.39 (s, 1H), 6.95 (d, J=7 Hz, 1H), 7.29-7.49 (4H), 7.99 (br s, 1H), 8.15 (br s, 1H), 9.50 (br s, 1H), 10.97 (br s, 1H, NH), 11.35 (br s, J=6 Hz, 1H, NH); ESI-MS m/z 580.8 (MH⁺).

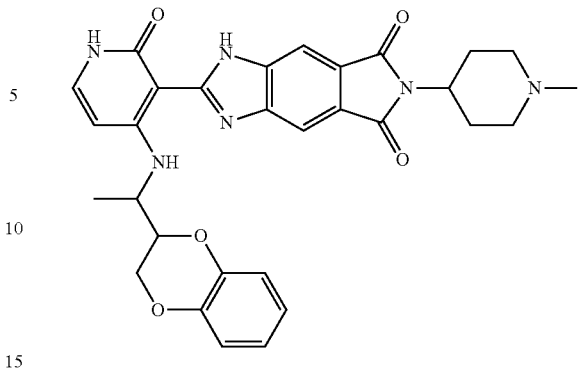

2-{4-[1-(2,3-Dihydro-benzo[1,4]dioxin-2-yl)-ethylamino]-2-oxo-1,2-dihydro-pyridin-3-yl}-6-(1-methyl-piperidin-4-yl)-1H-1,3,6-triaza-s-indacene-5,7-dione: ¹H NMR (DMSO-d₆) δ 1.40 (s, 3H, CH₃), 1.98 (m, 2H), 2.55 (m, 2H), 2.80 (s, 3H, CH₃), 3.18 (m, 2H), 3.53 (m, 2H), 4.11 (m, 1H), 4.23-4.45 (3H), 4.51 (m, 1H), 6.32 (d, J=7 Hz, 1H), 6.80-6.99 (4H), 7.45 (m, 1H), 7.94 (br s, 1H), 8.15 (br s, 1H), 9.57 (br s, 1H), 11.20 (d, J=7 Hz, 1H, NH), 11.41 (br d, J=6 Hz, 1H, NH); ESI-MS m/z 555.3 (MH⁺).

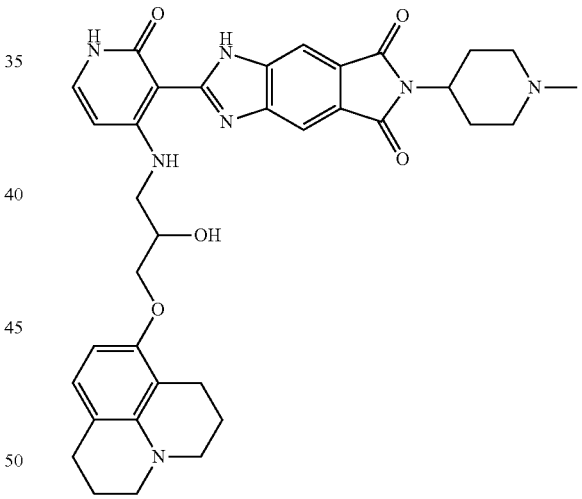

2-{4-[2-Hydroxy-3-(2,3,6,7-tetrahydro-1H,5H-pyrido[3,2,1-ij]quinolin-8-yloxy)-propylamino]-2-oxo-1,2-dihydro-pyridin-3-yl}-6-(1-methyl-piperidin-4-yl)-1H-1,3,6-triaza-s-indacene-5,7-dione: ¹H NMR (DMSO-d₆) δ 1.80-1.99 (6H), 2.50-2.65 (4H), 2.80 (s, 3H, CH₃), 2.99-3.28 (6H), 3.45-3.72 (4H), 3.97 (m, 2H), 4.11 (m, 1H), 4.31 (m, 1H), 6.17-6.29 (2H), 6.65 (d, J=7 Hz, 1H), 7.40 (m, 1H), 7.80 (br s, 1H), 8.15 (br s, 1H), 9.57 (br s, 1H), 10.95 (br s, 1H, NH), 11.33 (br d, J=6 Hz, 1H, NH); ESI-MS m/z 638.7 (MH⁺).

319

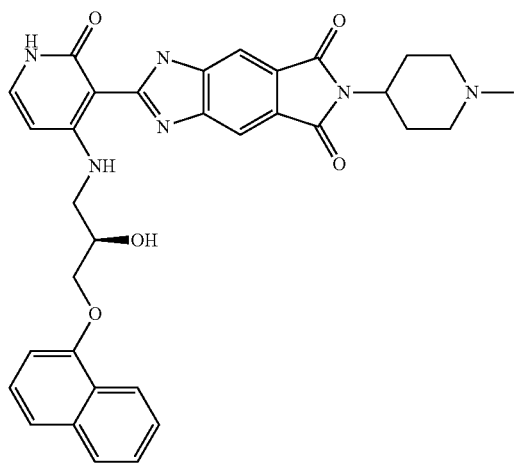 [SMILES: CN1CCC(N2C(=O)c3cc4nc(-c5c(NC[C@@H](O)COc6cccc7ccccc67)cc[nH]c5=O)[nH]c4cc3C2=O)CC1]

2-{4-[(R)-2-Hydroxy-3-(naphthalen-1-yloxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.84 (m, 2H), 2.55 (m, 2H), 2.78 (s, 3H, CH$_3$), 3.18 (m, 2H), 3.55 (m, 2H), 3.70 (m, 1H), 3.80 (m, 1H), 4.22-4.38 (4H), 5.78 (s, 1H, NH), 6.31 (d, J=7 Hz, 1H), 7.01 (d, J=7 Hz, 1H), 7.35-7.60 (6H), 7.89 (d, J=7 Hz, 1H), 8.11 (s, 1H), 8.33 (d, J=7 Hz, 1H), 11.04 (br s, 1H, NH), 11.34 (br d, J=6 Hz, 1H, NH); ESI-MS m/z 593.3 (MH$^+$).

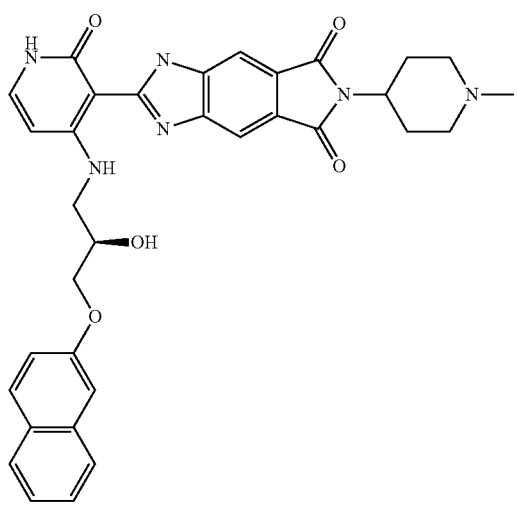 [SMILES: CN1CCC(N2C(=O)c3cc4nc(-c5c(NC[C@@H](O)COc6ccc7ccccc7c6)cc[nH]c5=O)[nH]c4cc3C2=O)CC1]

2-{4-[(R)-2-Hydroxy-3-(naphthalen-2-yloxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.99 (m, 2H), 2.55 (m, 2H), 2.78 (s, 3H, CH$_3$), 3.18 (m, 2H), 3.48-3.65 (3H), 3.75 (m, 1H), 4.18-4.38 (4H), 5.72 (s, 1H, NH), 6.29 (d, J=7 Hz, 1H), 7.21-7.48 (5H), 7.75-7.89 (4H), 8.11 (s, 1H), 9.60 (br s, 1H), 11.02 (br s, 1H, NH), 11.34 (br d, J=6 Hz, 1H, NH); ESI-MS m/z 593.3 (MH$^+$).

320

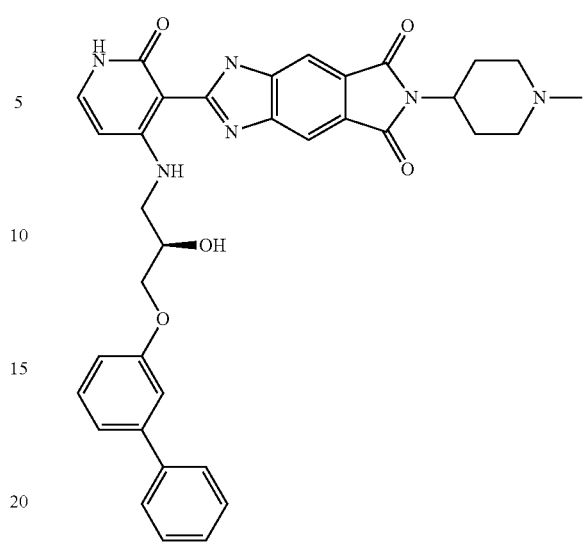

2-{4-[(R)-3-(Biphenyl-3-yloxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.99 (m, 2H), 2.55 (m, 2H), 2.78 (s, 3H, CH$_3$), 3.18 (m, 2H), 3.49-3.65 (4H), 3.71 (m, 1H), 4.19 (m, 2H), 4.31 (m, 1H), 5.68 (s, 1H, NH), 6.25 (d, J=7 Hz, 1H), 6.99 (d, J=7 Hz, 1H), 7.20-7.49 (7H), 7.59 (d, J=7 Hz, 2H), 7.70 (s, 1H), 8.12 (s, 1H), 9.60 (br s, 1H), 11.01 (br s, 1H, NH), 11.33 (br d, J=6 Hz, 1H, NH); ESI-MS m/z 619.3 (MH$^+$).

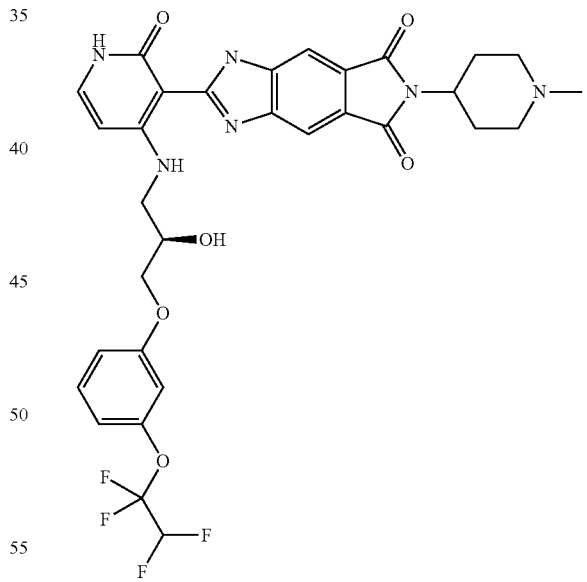

2-(4-{(R)-2-Hydroxy-3-[3-(1,1,2,2-tetrafluoro-ethoxy)-phenoxy]-propylamino}-2-oxo-1,2-dihydro-pyridin-3-yl)-6-(1-methyl-piperidin-4-yl)-1H-1,3,6-triaza-s-indacene-5,7-dione: $^1$H NMR (DMSO-d$_6$) δ 1.99 (m, 2H), 2.55 (m, 2H), 2.79 (s, 3H, CH$_3$), 3.18 (m, 2H), 3.32-3.63 (4H), 3.70 (m, 1H), 4.09-4.20 (3H), 4.32 (m, 1H), 5.68 (d, J=3 Hz, 1H, NH), 6.21 (d, J=7 Hz, 1H), 6.85-7.06 (3H), 7.35-7.48 (2H), 7.77 (s, 1H), 8.13 (s, 1H), 9.60 (br s, 1H), 10.99 (br s, 1H, NH), 11.34 (br d, J=6 Hz, 1H, NH); ESI-MS m/z 659.5 (MH$^+$).

321

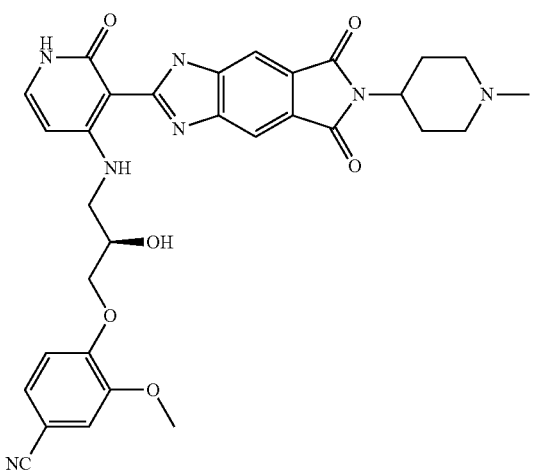 [SMILES: COc1cc(C#N)ccc1OC[C@H](O)CNc1cc[nH]c(=O)c1-c1nc2cc3c(cc2[nH]1)C(=O)N(C1CCN(C)CC1)C3=O]

4-((R)-2-Hydroxy-3-{3-[6-(1-methyl-piperidin-4-yl)-5,7-dioxo-1,5,6,7-tetrahydro-1,3,6-triaza-s-indacen-2-yl]-2-oxo-1,2-dihydro-pyridin-4-ylamino}-propoxy)-3-methoxy-benzonitrile: $^1$H NMR (DMSO-d$_6$) δ 2.00 (m, 2H), 2.55 (m, 2H), 2.81 (s, 3H, CH$_3$), 3.18 (m, 2H), 3.40-3.59 (3H), 3.69 (m, 1H), 3.93 (s, 3H, CH$_3$), 4.09-4.21 (3H), 4.32 (m, 1H), 5.70 (br s, 1H, NH), 6.21 (d, J=7 Hz, 1H), 7.19 (d, J=7 Hz, 1H), 7.37-7.47 (3H), 7.79 (s, 1H), 8.13 (s, 1H), 9.59 (br s, 1H), 10.98 (br s, 1H, NH), 11.34 (br d, J=6 Hz, 1H, NH); ESI-MS m/z 598.5 (MH$^+$).

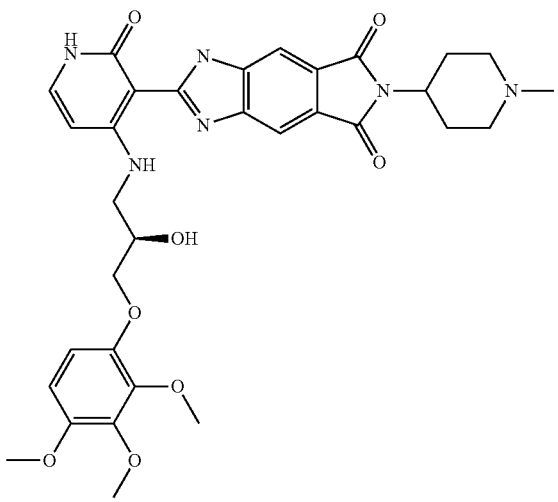

322

2-{4-[(R)-2-Hydroxy-3-(2,3,4-trimethoxy-phenoxy)-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.99 (m, 2H), 2.58 (m, 2H), 2.81 (s, 3H, CH$_3$), 3.18 (m, 2H), 3.38-3.59 (2H), 3.68-3.85 (2H), 3.75 (s, 3H, CH$_3$), 3.77 (s, 3H, CH$_3$), 3.79 (s, 3H, CH$_3$), 4.02 (m, 2H), 4.15 (m, 1H), 4.32 (m, 1H), 5.70 (br s, 1H, NH), 6.23 (d, J=7 Hz, 1H), 6.68 (d, J=7 Hz, 1H), 6.78 (d, J=7 Hz, 1H), 7.41 (m, 1H), 7.75 (s, 1H), 8.13 (s, 1H), 9.59 (br s, 1H), 10.98 (br s, 1H, NH), 11.34 (br d, J=6 Hz, 1H, NH); ESI-MS m/z 633.5 (MH$^+$).

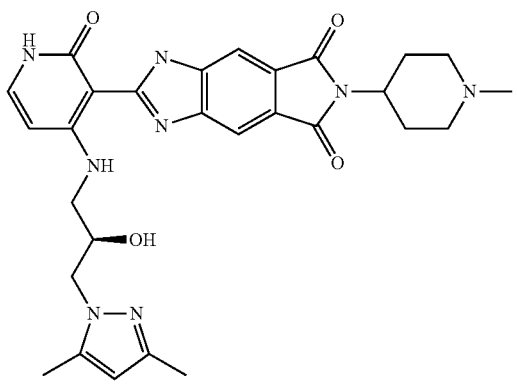 [SMILES: Cc1cc(C)n(C[C@H](O)CNc2cc[nH]c(=O)c2-c2nc3cc4c(cc3[nH]2)C(=O)N(C2CCN(C)CC2)C4=O)n1]

2-{4-[(R)-3-(3,5-Dimethyl-pyrazol-1-yl)-2-hydroxy-propylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-d$_6$) δ 1.95 (m, 2H), 2.11 (s, 3H, CH$_3$), 2.23 (s, 3H, CH$_3$), 2.56 (m, 2H), 2.78 (s, 3H, CH$_3$), 3.18 (m, 2H), 3.35 (m, 1H), 3.56 (m, 1H), 4.01-4.18 (3H), 4.32 (m, 1H), 5.80 (s, 1H), 6.12 (d, J=7 Hz, 1H), 6.68 (d, J=6 Hz, 1H), 7.40 (m, 1H), 7.99 (br s, 1H), 8.13 (br s, 1H), 9.56 (br s, 1H), 10.99 (br s, 1H, NH), 11.34 (br d, J=6 Hz, 1H, NH); ESI-MS m/z 545.3 (MH$^+$).

Synthesis of Additional Phthalimide Derivatives

<u>Scheme 58</u>

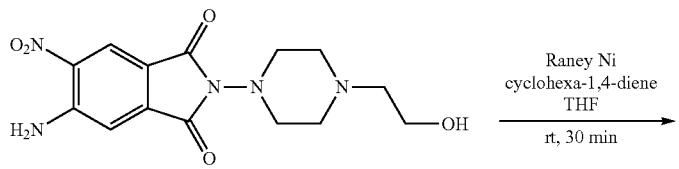

-continued
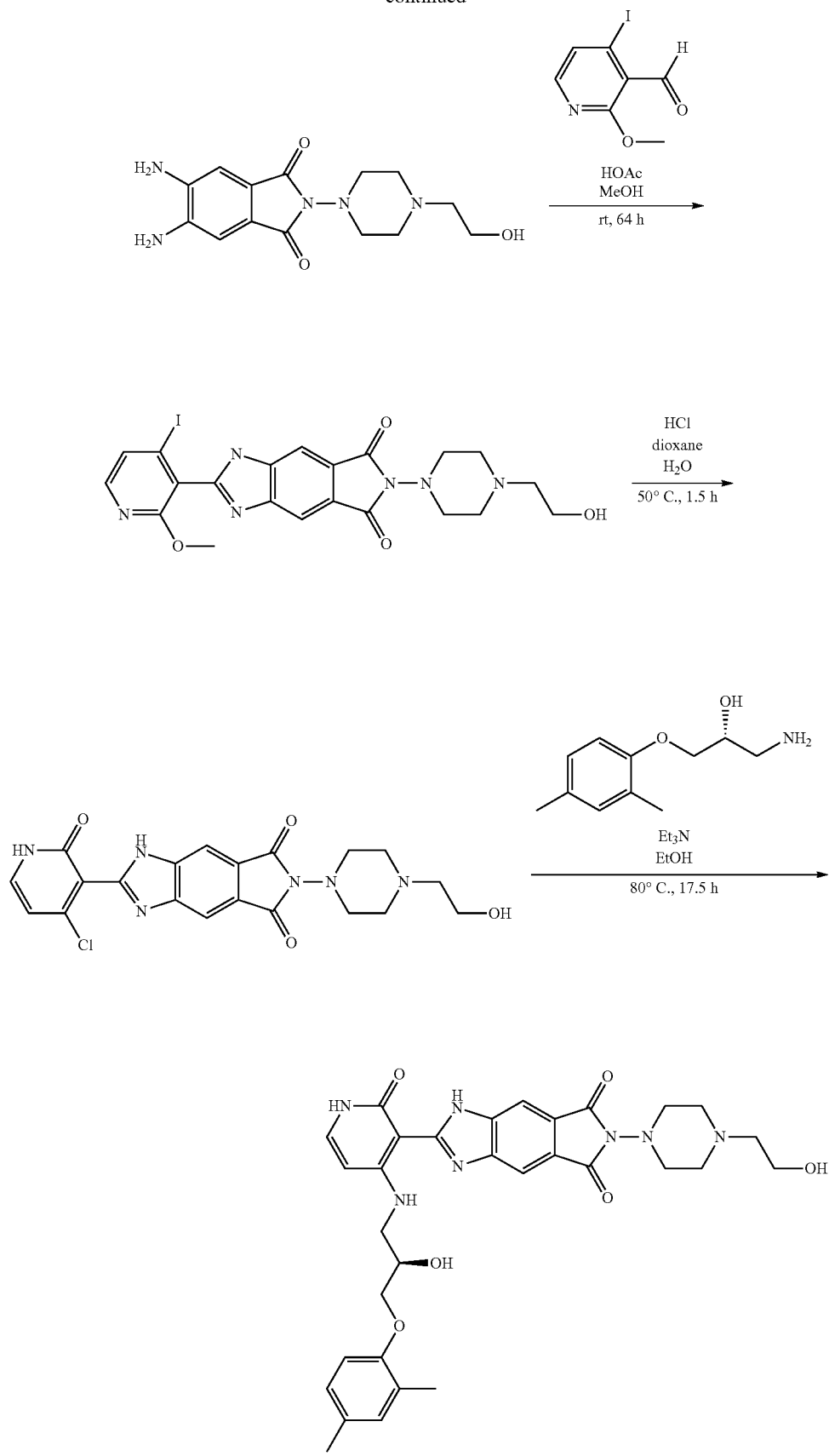

325

Synthesis of the Compound Illustrated by Scheme 58

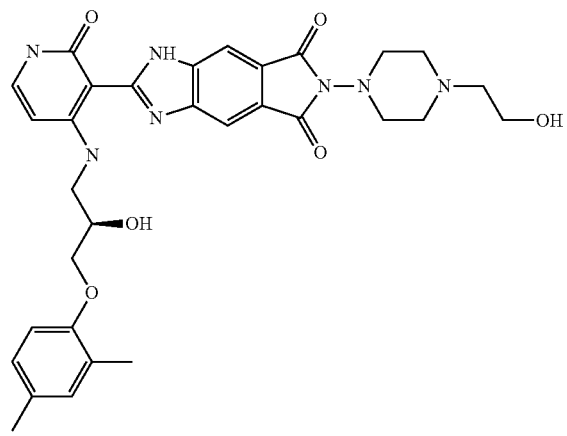 [SMILES: Cc1ccc(OC[C@H](O)CNc2cc[nH]c(=O)c2-c2nc3cc4c(cc3[nH]2)C(=O)N(N2CCN(CCO)CC2)C4=O)c(C)c1]

2-{4-[(R)-3-(2,4-Dimethyl-phenoxy)-2-hydroxy-propylamino]-2-oxo-1,2-dihydro-pyridin-3-yl}-6-[4-(2-hydroxyethyl)-piperazin-1-yl]-1H-1,3,6-triaza-s-indacene-5,7-dione: To a solution of 5-amino-2-[4-(2-hydroxy-ethyl)-piperazin-1-yl]-6-nitro-isoindole-1,3-dione (40 mg, 0.12 mmol) in THF (6 mL) was added Raney Ni in $H_2O$ (1 mL) and cyclohexa-1,4-diene (800 µL). After it was stirred at the room temperature for 30 min, the reaction mixture was loaded directly on the top of a column and washed with $CH_2Cl_2$/MeOH/28% aqueous $NH_4OH$ (90:10:1). The residue obtained from evaporation of the wash was mixed with 4-iodo-2-methoxynicotinicaldehyde (34 mg, 0.13 mmol) and AcOH (0.5 mL) in MeOH (10 mL). The mixture was stirred at the room temperature for 64 h, concentrated under reduced pressure, mixed with 4 M HCl/dioxane (8 mL) and $H_2O$ (0.6 mL), heated at 50° C. for 1.5 h, and concentrated under reduced pressure to give a crude, which was subjected to HPLC purification to furnish a fluorescent product in TFA salt form. (R)-1-Amino-3-(2,4-dimethyl-phenoxy)-propan-2-ol (45 mg, 0.24 mmol) and $Et_3N$ (70 µL, 0.5 mmol) were added into the solution of this fluorescent product and the mixture was evaporated after 17.5 h of heating at 80° C. The residual crude was subjected to HPLC to afford the title compound in TFA salt form (7.86 mg, 9.2%). $^1$H NMR (DMSO-$d_6$) δ 2.13 (s, 3H, $CH_3$), 2.19 (s, 3H, $CH_3$), 3.02-4.05 (16H), 4.15 (m, 1H), 5.35 (br s, 1H, OH), 5.53 (br s, 1H, OH), 6.23 (d, J=7 Hz, 1H), 6.84 (d, J=7 Hz, 1H), 6.92 (d, J=7 Hz, 1H), 6.98 (s, 1H), 7.39 (d, J=7 Hz, 1H), 7.65 (s, 1H), 8.11 (s, 1H), 9.78 (br s, 1H, NH), 10.94 (br s, 1H, NH), 11.30 (br s, 1H, NH); ESI-MS m/z 602.5 (MH$^+$).

Scheme 59

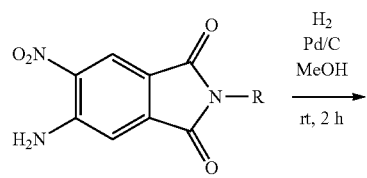

326

-continued

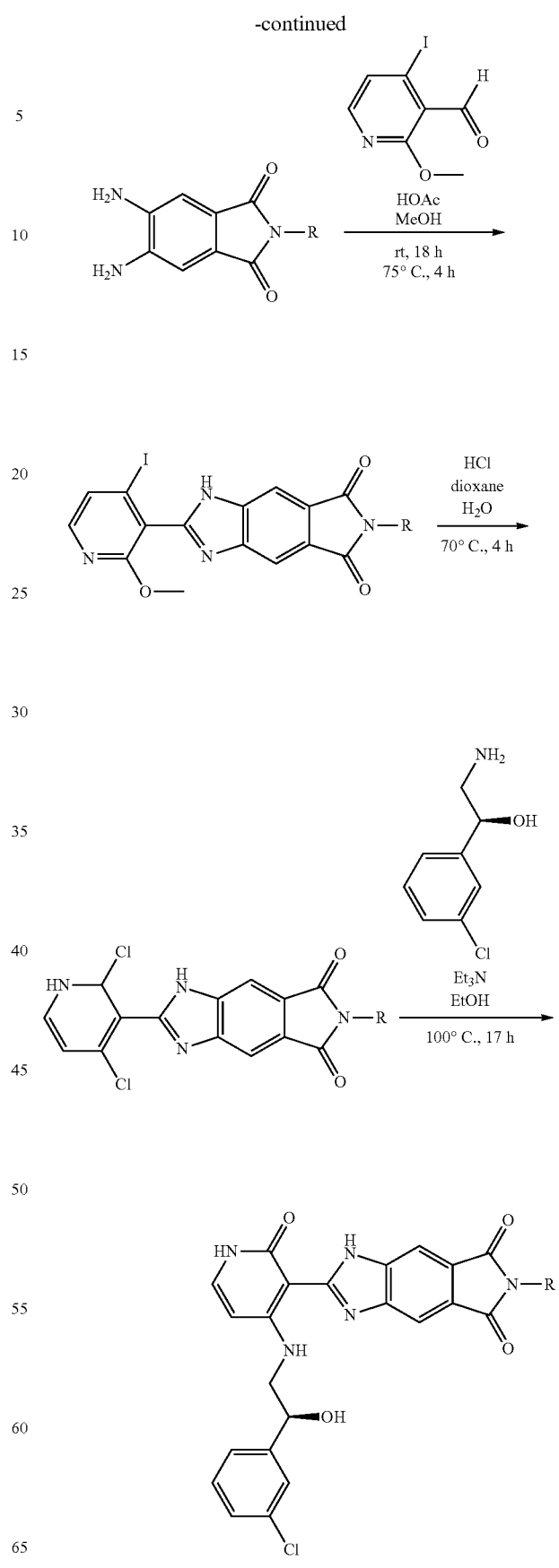

Synthesis of the Compounds Illustrated by Scheme 59:

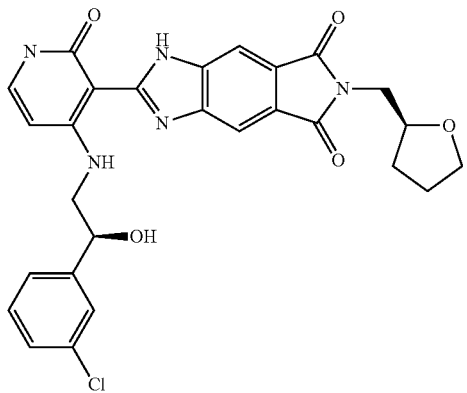 [SMILES: O=C1c2cc3nc(-c4c(NC[C@@H](O)c5cccc(Cl)c5)cc[nH]c4=O)[nH]c3cc2C(=O)N1C[C@@H]1CCCO1]

2-{4-[(S)-2-(3-Chloro-phenyl)-2-hydroxy-ethylamino]-2-oxo-1,2-dihydro-pyridin-3-yl}-6-[(S)-1-(tetrahydro-furan-2-yl)methyl]-1H-1,3,6-triaza-s-indacene-5,7-dione: To a solution of 5-amino-6-nitro-2-[(S)-1-(tetrahydro-furan-2-yl)methyl]-isoindole-1,3-dione (29.1 mg, 0.1 mmol) in MeOH (30 mL) was added 3 mg of Pd/C (10%) (the solution was purged with $N_2$ before adding Pd/C). After it was stirred under atmospheric $H_2$ for 2 h, the reaction mixture was filtered through Celite. To the filtrate was added AcOH (1.5 mL) and 4-iodo-2-methoxynicotinic aldehyde (26.3 mg, 0.1 mmol) and the resulting mixture was stirred at the room temperature for 18 h and heated at 75° C. for 4 h, and then evaporated to dryness under reduced pressure. The residue was mixed with 4 M HCl/dioxane (8 mL) and $H_2O$ (0.6 mL), heated at 70° C. for 4 h and evaporated to dryness under reduced pressure. The residue was subjected to HPLC purification to furnish the corresponding chloropyridone intermediate, which was then mixed with (S)-2-amino-1-(3-chloro-phenyl)-ethanol (7 mg, 0.02 mmol) and $Et_3N$ (10 mg, 0.1 mmol) in EtOH (1.5 mL). After it was heated at 100° C. for 17 h, the reaction mixture was concentrated and subjected to HPLC purification to furnish the title compound (15.8 mg, 30% for 4 steps). $^1$H NMR (DMSO-$d_6$) δ 1.50-1.99 (4H), 3.52-3.79 (6H), 4.13 (m, 1H), 4.99 (m, 1H), 6.00 (br s, 1H, NH), 6.20 (d, J=6 Hz, 1H), 7.30-7.39 (3H), 7.50 (d, J=6 Hz, 1H), 7.63 (s, 1H), 7.88 (s, 1H), 8.14 (s, 1H); 10.90 (br s, 1H, NH), 11.29 (br d, J=6 Hz, 1H, NH); ESI-MS m/z 534.2 (MH$^+$).

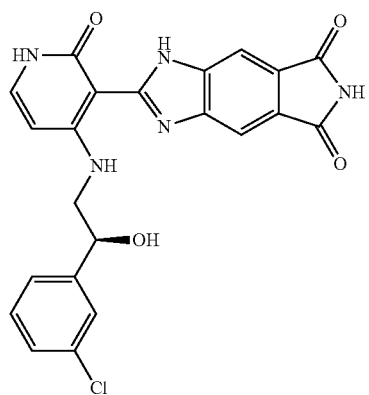 [SMILES: O=C1NC(=O)c2cc3[nH]c(-c4c(NC[C@@H](O)c5cccc(Cl)c5)cc[nH]c4=O)nc3cc21]

2-{4-[(S)-2-(3-Chloro-phenyl)-2-hydroxy-ethylamino]-2-oxo-1,2-dihydro-pyridin-3-yl}-1H-1,3,6-triaza-s-indacene-5,7-dione: $^1$H NMR (DMSO-$d_6$) δ 3.40-3.75 (2H), 4.98 (m, 1H), 6.01 (br s, 1H, NH), 6.20 (d, J=6 Hz, 1H), 7.35-7.44 (3H), 7.50 (d, J=6 Hz, 1H), 7.63 (s, 1H), 7.84 (s, 1H), 8.11 (s, 1H), 10.91 (br s, 1H, NH), 11.07 (br s, 1H, NH), 11.29 (br d, J=6 Hz, 1H, NH); ESI-MS m/z 450.4 (MH$^+$).

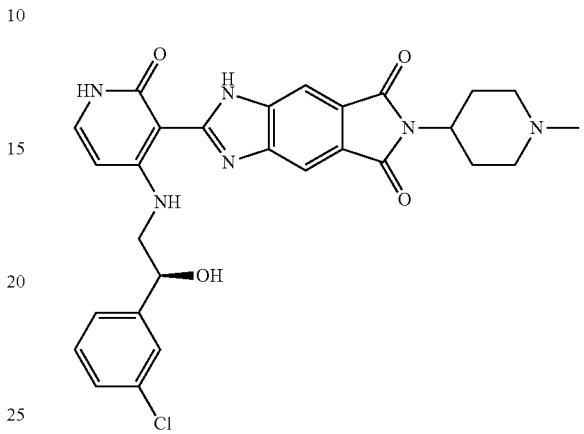

2-{4-[(S)-2-(3-Chloro-phenyl)-2-hydroxy-ethylamino]-2-oxo-1,2-dihydro-pyridin-3-yl}-6-(1-methyl-piperidin-4-yl)-1H-1,3,6-triaza-s-indacene-5,7-dione: $^1$H NMR (DMSO-$d_6$) δ 1.66 (m, 2H), 2.06 (m, 2H), 2.25 (s, 3H, CH$_3$), 2.39 (m, 2H), 2.93 (m, 2H), 3.57 (m, 1H), 3.67 (m, 1H), 3.96 (m, 1H), 4.98 (m, 1H), 6.01 (s, 1H, NH), 6.20 (d, J=6 Hz, 1H), 7.32-7.39 (3H), 7.50 (d, J=6 Hz, 1H), 7.63 (s, 1H), 7.86 (s, 1H), 8.11 (s, 1H), 10.89 (br s, 1H, NH), 11.30 (br d, J=6 Hz, 1H, NH); ESI-MS m/z 547.5 (MH$^+$).

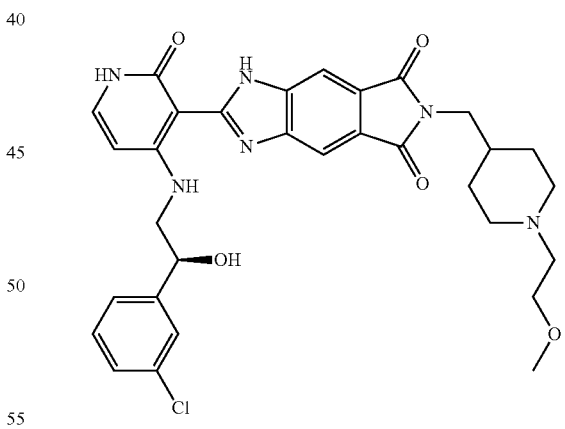

2-{4-[(S)-2-(3-Chloro-phenyl)-2-hydroxy-ethylamino]-2-oxo-1,2-dihydro-pyridin-3-yl}-6-[1-(2-methoxy-ethyl)-piperidin-4-ylmethyl]-1H-1,3,6-triaza-s-indacene-5,7-dione: $^1$H NMR (DMSO-$d_6$) δ 1.51 (m, 2H), 1.80-2.01 (3H), 2.92 (m, 2H), 3.25 (m, 2H), 3.29 (s, 3H), 3.42-3.78 (8H), 5.00 (m, 1H), 6.01 (br s, 1H, NH), 6.20 (d, J=6 Hz, 1H), 7.32-7.39 (3H), 7.50 (d, J=6 Hz, 1H), 7.64 (s, 1H), 7.89 (s, 1H), 8.15 (s, 1H), 10.87 (br s, 1H, NH), 11.30 (br d, J=6 Hz, 1H, NH); ESI-MS m/z 605.2 (MH$^+$).

329

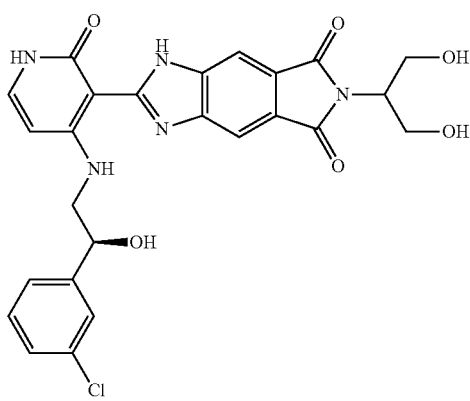 [SMILES: O=C1c2cc3nc(-c4c(NC[C@@H](O)c5cccc(Cl)c5)cc[nH]c4=O)[nH]c3cc2C(=O)N1C(CO)CO]

2-{4-[(S)-2-(3-Chloro-phenyl)-2-hydroxy-ethylamino]-2-oxo-1,2-dihydro-pyridin-3-yl}-6-(2-hydroxy-1-hydroxymethyl-ethyl)-1H-1,3,6-triaza-s-indacene-5,7-dione: $^1$H NMR (DMSO-d$_6$) δ 3.51-3.85 (6H), 4.27 (m, 1H), 4.89 (br s, 2H, OH), 4.99 (m, 1H), 6.01 (br s, 1H, NH), 6.20 (d, J=6 Hz, 1H), 7.32-7.41 (3H), 7.50 (d, J=6 Hz, 1H), 7.64 (s, 1H), 7.85 (s, 1H), 8.11 (s, 1H), 10.89 (br s, 1H, NH), 11.29 (br d, J=6 Hz, 1H, NH); ESI-MS m/z 524.5 (MH$^+$).

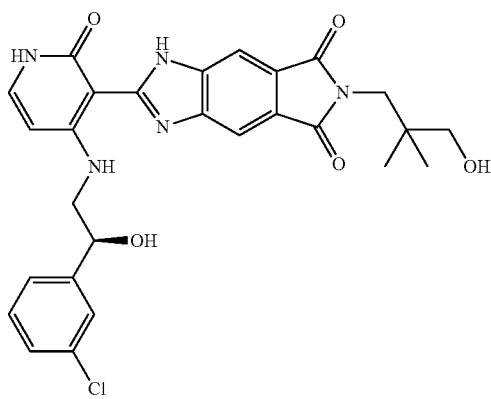 [SMILES: CC(C)(CO)CN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-(3-hydroxy-2,2-dimethyl-propyl)-1H-1,3,6-triaza-s-indacene-5,7-dione: $^1$H NMR (DMSO-d$_6$) δ 0.85 (6H), 3.01 (s, 2H), 3.47 (s, 2H), 3.61 (m, 1H), 3.69 (m, 1H), 4.57 (br s, 1H, OH), 4.99 (m, 1H), 6.01 (br s, 1H, NH), 6.20 (d, J=6 Hz, 1H), 7.32-7.41 (3H), 7.50 (d, J=6 Hz, 1H), 7.63 (s, 1H), 7.88 (s, 1H), 8.16 (s, 1H), 10.89 (br s, 1H, NH), 11.29 (br d, J=6 Hz, 1H, NH); ESI-MS m/z 536.3 (MH$^+$).

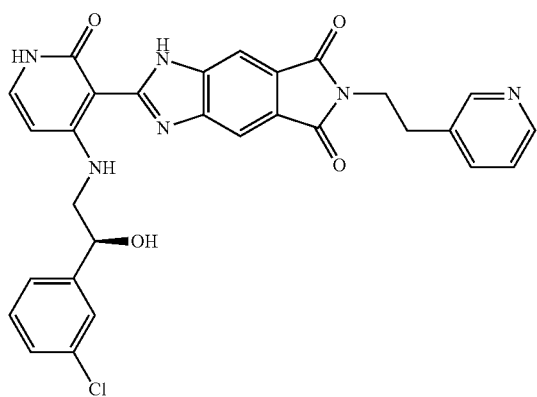 [SMILES: O=C1c2cc3nc(-c4c(NC[C@@H](O)c5cccc(Cl)c5)cc[nH]c4=O)[nH]c3cc2C(=O)N1CCc1cccnc1]

330

2-{4-[(S)-2-(3-Chloro-phenyl)-2-hydroxy-ethylamino]-2-oxo-1,2-dihydro-pyridin-3-yl}-6-(2-pyridin-3-yl-ethyl)-1H-1,3,6-triaza-s-indacene-5,7-dione: $^1$H NMR (DMSO-d$_6$) δ 3.05 (m, 2H), 3.57 (m, 1H), 3.67 (m, 1H), 3.89 (m, 2H), 4.98 (m, 1H), 5.95 (br s, 1H, NH), 6.19 (d, J=6 Hz, 1H), 7.30-7.41 (3H), 7.45-7.64 (3H), 7.80-8.13 (3H), 8.40-8.55 (2H), 10.89 (br s, 1H, NH), 11.29 (br d, J=6 Hz, 1H, NH); ESI-MS m/z 555.7 (MH$^+$).

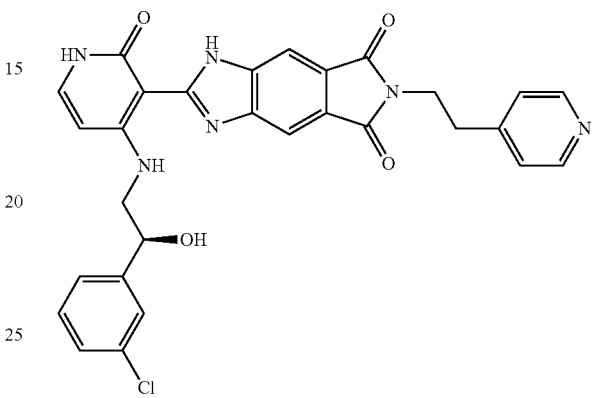

2-{4-[(S)-2-(3-Chloro-phenyl)-2-hydroxy-ethylamino]-2-oxo-1,2-dihydro-pyridin-3-yl}-6-(2-pyridin-4-yl-ethyl)-1H-1,3,6-triaza-s-indacene-5,7-dione: $^1$H NMR (DMSO-d$_6$) δ 3.16 (m, 2H), 3.60 (m, 1H), 3.70 (m, 1H), 3.97 (m, 2H), 4.98 (m, 1H), 5.99 (br s, 1H, NH), 6.19 (d, J=6 Hz, 1H), 7.19-7.79 (7H), 7.80-8.19 (2H), 8.61-8.73 (2H), 10.89 (br s, 1H, NH), 11.29 (br d, J=6 Hz, 1H, NH); ESI-MS m/z 555.7 (MH$^+$).

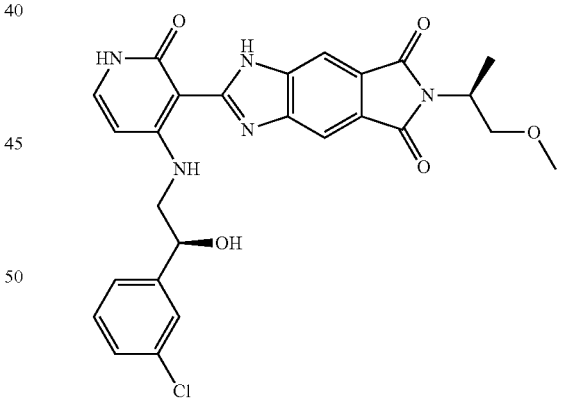

2-{4-[(S)-2-(3-Chloro-phenyl)-2-hydroxy-ethylamino]-2-oxo-1,2-dihydro-pyridin-3-yl}-6-((R)-2-methoxy-1-methyl-ethyl)-1H-1,3,6-triaza-s-indacene-5,7-dione: $^1$H NMR (DMSO-d$_6$) δ 3.23 (s, 3H), 3.50 (m, 1H), 3.60 (m, 1H), 3.69 (m, 1H), 3.87 (t, J=9 Hz, 1H), 4.48 (m, 1H), 4.99 (m, 1H), 6.00 (br s, 1H, NH), 6.20 (d, J=6 Hz, 1H), 7.32-7.42 (3H), 7.50 (d, J=6 Hz, 1H), 7.63 (s, 1H), 7.86 (s, 1H), 8.11 (s, 1H), 10.88 (br s, 1H, NH), 11.29 (br d, J=6 Hz, 1H, NH); ESI-MS m/z 522.3 (MH$^+$).

331

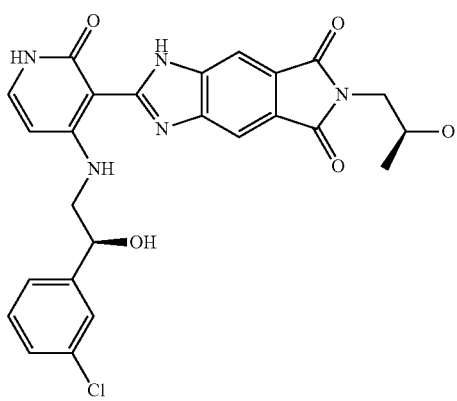 [SMILES: C[C@H](O)CN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-((S)-2-hydroxy-propyl)-1H-1,3,6-triaza-s-indacene-5,7-dione: $^1$H NMR (DMSO-d$_6$) δ 1.09 (d, J=6 Hz, 3H, CH$_3$), 3.43 (m, 1H), 3.56 (m, 2H), 3.67 (m, 1H), 3.95 (m, 1H), 4.89 (m, 1H, OH), 4.99 (m, 1H), 6.00 (br s, 1H, NH), 6.20 (d, J=6 Hz, 1H), 7.30-7.39 (3H), 7.50 (d, J=6 Hz, 1H), 7.63 (s, 1H), 7.90 (s, 1H), 8.13 (s, 1H), 10.90 (br s, 1H, NH), 11.29 (br d, J=6 Hz, 1H, NH); ESI-MS m/z 508.3 (MH$^+$).

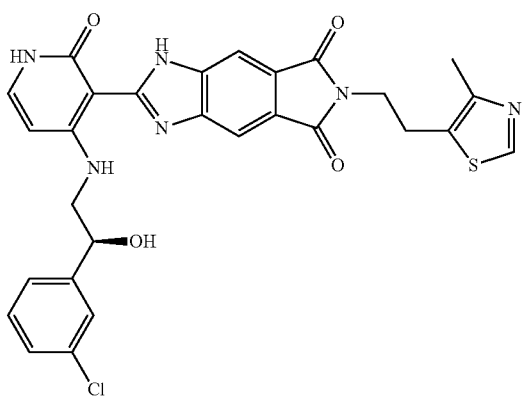 [SMILES: Cc1ncsc1CCN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-[2-(4-methyl-thiazol-5-yl)-ethyl]-1H-1,3,6-triaza-s-indacene-5,7-dione: $^1$H NMR (DMSO-d$_6$) δ 2.26 (s, 3H, CH$_3$), 3.18 (m, 2H), 3.50-3.82 (4H), 4.98 (m, 1H), 5.97 (br s, 1H, NH), 6.20 (d, J=6 Hz, 1H), 7.30-7.39 (3H), 7.50 (d, J=6 Hz, 1H), 7.63 (s, 1H), 7.87 (s, 1H), 8.11 (s, 1H), 8.80 (s, 1H), 10.88 (br s, 1H, NH), 11.28 (br d, J=6 Hz, 1H, NH); ESI-MS m/z 575.3 (MH$^+$).

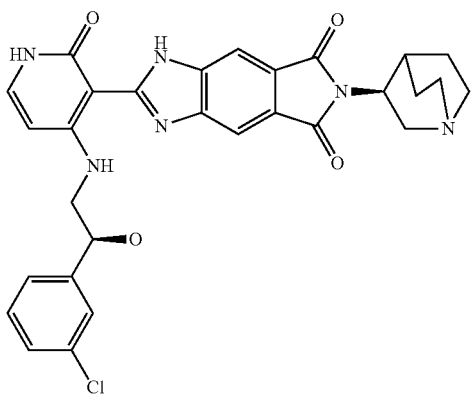 [SMILES: O=C1c2cc3nc(-c4c(NC[C@@H](O)c5cccc(Cl)c5)cc[nH]c4=O)[nH]c3cc2C(=O)N1[C@@H]1CN2CCC1CC2]

332

2-(4-((S)-2-(3-chlorophenyl)-2-hydroxyethylamino)-2-oxo-1,2-dihydropyridin-3-yl-6-((S)-quinuclidin-3-yl)imidazo[4,5-f]isoindole-5,7-(1H,6H)-dione: $^1$H NMR (DMSO-d$_6$) δ 1.72-2.18 (5H), 3.42-4.18 (8H), 4.72 (m, 1H), 4.99 (m, 1H), 6.01 (br s, 1H, NH), 6.21 (d, J=6 Hz, 1H), 7.31-7.41 (3H), 7.50 (d, J=6 Hz, 1H), 7.64 (s, 1H), 7.85 (s, 1H), 8.16 (s, 1H), 9.86 (br s, 1H), 10.87 (br s, 1H, NH), 11.31 (br d, J=6 Hz, 1H, NH); ESI-MS m/z 559.3 (MH$^+$).

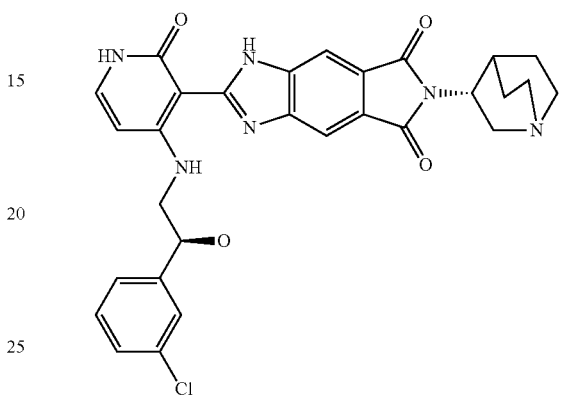

2-(4-((S)-2-(3-chlorophenyl)-2-hydroxyethylamino)-2-oxo-1,2-dihydropyridin-3-yl-6-((R)-quinuclidin-3-yl)imidazo[4,5-J]isoindole-5,7-(1H,6H)-dione: $^1$H NMR (DMSO-d$_6$) δ 1.72-2.18 (5H), 3.42-3.79 (7H), 4.13 (m, 1H), 4.72 (m, 1H), 4.99 (m, 1H), 6.01 (br s, 1H, NH), 6.21 (d, J=6 Hz, 1H), 7.31-7.41 (3H), 7.50 (d, J=6 Hz, 1H), 7.64 (s, 1H), 7.85 (s, 1H), 8.16 (s, 1H), 9.86 (br s, 1H), 10.87 (br s, 1H, NH), 11.31 (br d, J=6 Hz, 1H, NH); ESI-MS m/z 559.3 (MH$^+$).

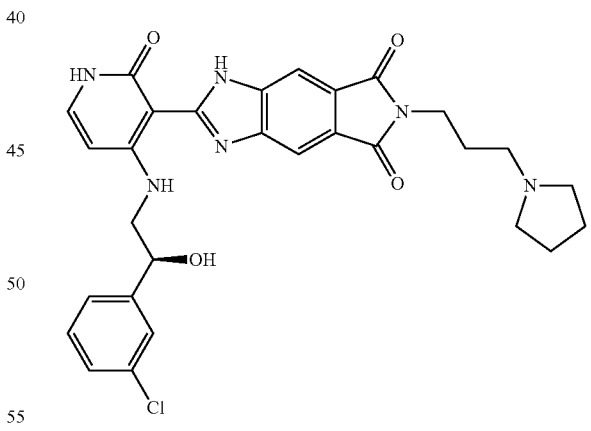

2-{4-[(S)-2-(3-Chloro-phenyl)-2-hydroxy-ethylamino]-2-oxo-1,2-dihydro-pyridin-3-yl}-6-(3-pyrrolidin-1-yl-propyl)-1H-1,3,6-triaza-s-indacene-5,7-dione: $^1$H NMR (DMSO-d$_6$) δ 1.80-2.11 (6H), 3.02 (m, 2H), 3.23 (m, 2H), 3.40-3.75 (6H), 4.99 (m, 1H), 6.00 (br s, 1H, NH), 6.21 (d, J=6 Hz, 1H), 7.31-7.41 (3H), 7.50 (d, J=6 Hz, 1H), 7.64 (s, 1H), 7.90 (s, 1H), 8.15 (s, 1H), 9.56 (br s, 1H), 10.88 (br s, 1H, NH), 11.30 (br d, J=6 Hz, 1H, NH); ESI-MS m/z 561.0 (MH$^+$).

333

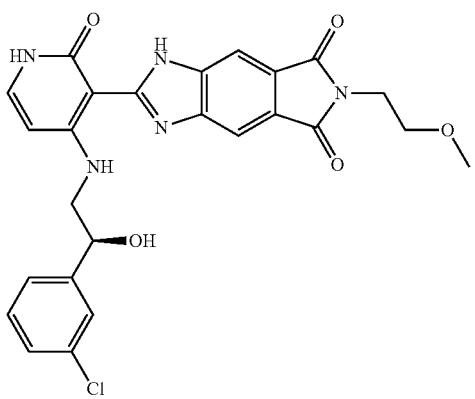 [SMILES: COCCN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-(2-methoxy-ethyl)-1H-1,3,6-triaza-s-indacene-5,7-dione: $^1$H NMR (DMSO-d$_6$) δ 3.27 (s, 3H, CH$_3$), 3.52-3.79 (6H), 4.99 (m, 1H), 6.00 (br s, 1H, NH), 6.19 (d, J=6 Hz, 1H), 7.31-7.41 (3H), 7.50 (d, J=6 Hz, 1H), 7.63 (s, 1H), 7.88 (s, 1H), 8.13 (s, 1H), 10.89 (br s, 1H, NH), 11.29 (br d, J=6 Hz, 1H, NH); ESI-MS m/z 508.4 (MH$^+$).

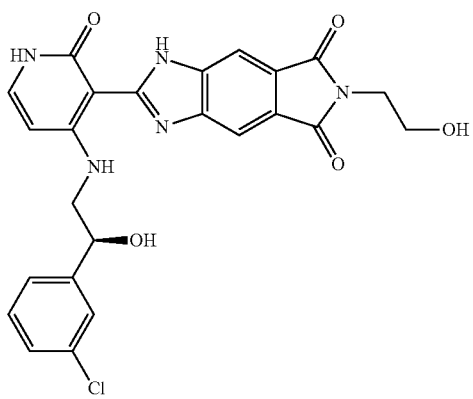 [SMILES: O=C1c2cc3nc(-c4c(NC[C@@H](O)c5cccc(Cl)c5)cc[nH]c4=O)[nH]c3cc2C(=O)N1CCO]

2-{4-[(S)-2-(3-Chloro-phenyl)-2-hydroxy-ethylamino]-2-oxo-1,2-dihydro-pyridin-3-yl}-6-(2-hydroxy-ethyl)-1H-1,3,6-triaza-s-indacene-5,7-dione: $^1$H NMR (DMSO-d$_6$) δ 3.50-3.75 (6H), 4.88 (br s, 1H, OH), 4.99 (br s, 1H), 6.00 (br s, 1H, NH), 6.20 (d, J=6 Hz, 1H), 7.32-7.42 (3H), 7.50 (d, J=6 Hz, 1H), 7.64 (s, 1H), 7.87 (s, 1H), 8.13 (s, 1H), 10.90 (br s, 1H, NH), 11.30 (br d, J=6 Hz, 1H, NH); ESI-MS m/z 494.4 (MH$^+$).

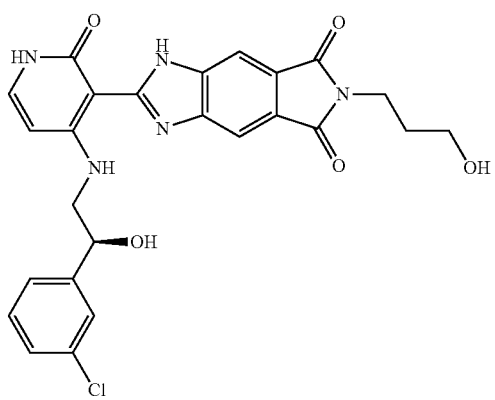 [SMILES: O=C1c2cc3nc(-c4c(NC[C@@H](O)c5cccc(Cl)c5)cc[nH]c4=O)[nH]c3cc2C(=O)N1CCCO]

334

2-{4-[(S)-2-(3-Chloro-phenyl)-2-hydroxy-ethylamino]-2-oxo-1,2-dihydro-pyridin-3-yl}-6-(3-hydroxy-propyl)-1H-1,3,6-triaza-s-indacene-5,7-dione: $^1$H NMR (DMSO-d$_6$) δ 1.76 (m, 2H), 3.45-3.72 (6H), 4.52 (br s, 1H, OH), 4.98 (br s, 1H), 6.00 (br s, 1H, NH), 6.19 (d, J=6 Hz, 1H), 7.32-7.42 (3H), 7.50 (d, J=6 Hz, 1H), 7.63 (s, 1H), 7.87 (s, 1H), 8.12 (s, 1H), 10.90 (br s, 1H, NH), 11.30 (br d, J=6 Hz, 1H, NH); ESI-MS m/z 508.5 (MH$^+$).

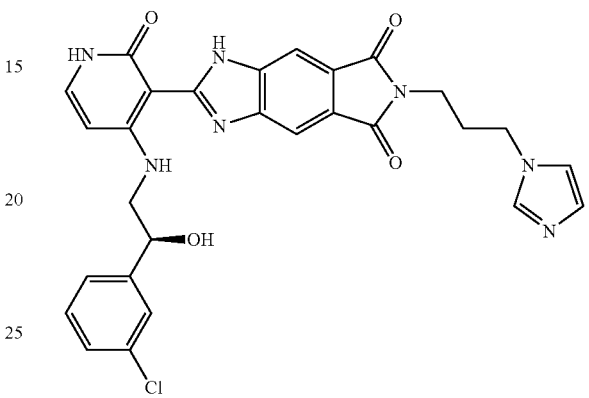

2-{4-[(S)-2-(3-Chloro-phenyl)-2-hydroxy-ethylamino]-2-oxo-1,2-dihydro-pyridin-3-yl}-6-(3-imidazol-1-yl-propyl)-1H-1,3,6-triaza-s-indacene-5,7-dione: $^1$H NMR (DMSO-d$_6$) δ 2.21 (m, 2H), 3.55-3.79 (4H), 4.28 (m, 2H), 4.99 (br s, 1H), 6.01 (br s, 1H, NH), 6.20 (d, J=6 Hz, 1H), 7.32-7.42 (3H), 7.50 (d, J=6 Hz, 1H), 7.63 (s, 1H), 7.68 (s, 1H), 7.83 (s, 1H), 7.89 (s, 1H), 8.15 (s, 1H), 9.09 (s, 1H), 10.88 (br s, 1H, NH), 11.31 (br d, J=6 Hz, 1H, NH); ESI-MS m/z 558.3 (MH$^+$).

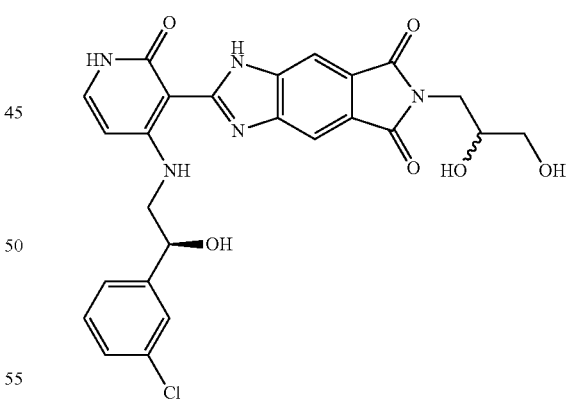

2-{4-[(S)-2-(3-Chloro-phenyl)-2-hydroxy-ethylamino]-2-oxo-1,2-dihydro-pyridin-3-yl}-6-(2,3-dihydroxy-propyl)-1H-1,3,6-triaza-s-indacene-5,7-dione: $^1$H NMR (DMSO-d$_6$) δ 3.51-3.65 (3H), 3.69 (m, 1H), 3.84 (m, 1H), 4.68 (m, 1H), 4.93 (m, 1H), 4.99 (m, 1H), 6.00 (d, J=6 Hz, NH), 6.20 (d, J=6 Hz, 1H), 7.32-7.41 (3H), 7.50 (d, J=6 Hz, 1H), 7.64 (s, 1H), 7.88 (s, 1H), 8.13 (s, 1H), 10.91 (br s, 1H, NH), 11.29 (br d, J=6 Hz, 1H, NH); ESI-MS m/z 524.5 (MH$^+$).

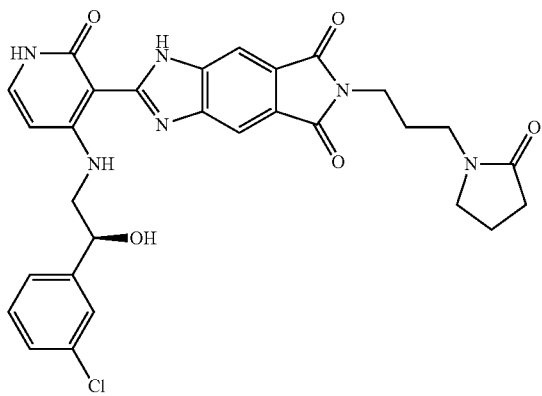 [SMILES: O=C1CCCN1CCCN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-[3-(2-oxo-pyrrolidin-1-yl)-propyl]-1H-1,3,6-triaza-s-indacene-5,7-dione: ¹H NMR (DMSO-d₆) δ 1.81 (m, 2H), 1.92 (m, 2H), 2.22 (m, 2H), 3.25 (m, 2H), 3.38 (m, 2H), 3.500-3.73 (4H), 4.98 (m, 1H), 6.00 (br s, 1H, NH), 6.19 (d, J=6 Hz, 1H), 7.31-7.41 (3H), 7.50 (d, J=6 Hz, 1H), 7.63 (s, 1H), 7.87 (s, 1H), 8.13 (s, 1H), 10.89 (br s, 1H, NH), 11.29 (br d, J=6 Hz, 1H, NH); ESI-MS m/z 575.5 (MH⁺).

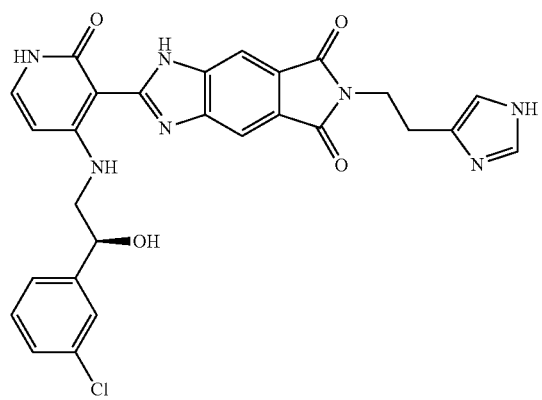 [SMILES: O=C1c2cc3nc(-c4c(NC[C@@H](O)c5cccc(Cl)c5)cc[nH]c4=O)[nH]c3cc2C(=O)N1CCc1c[nH]cn1]

2-{4-[(S)-2-(3-Chloro-phenyl)-2-hydroxy-ethylamino]-2-oxo-1,2-dihydro-pyridin-3-yl}-6-[2-(1H-imidazol-4-yl)-ethyl]-1H-1,3,6-triaza-s-indacene-5,7-dione: ¹H NMR (DMSO-d₆) δ 3.02 (m, 2H), 3.58 (m, 1H), 3.69 (m, 1H), 3.88 (m, 2H), 4.98 (br s, 1H), 5.76 (s, 1H, NH), 6.20 (d, J=6 Hz, 1H), 7.32-7.42 (3H), 7.49-7.52 (2H), 7.63 (s, 1H), 7.90 (br s, 1H), 8.05 (br s, 1H), 9.00 (s, 1H), 10.88 (br s, 1H, NH), 11.31 (br d, J=6 Hz, 1H, NH); ESI-MS m/z 544.3 (MH⁺).

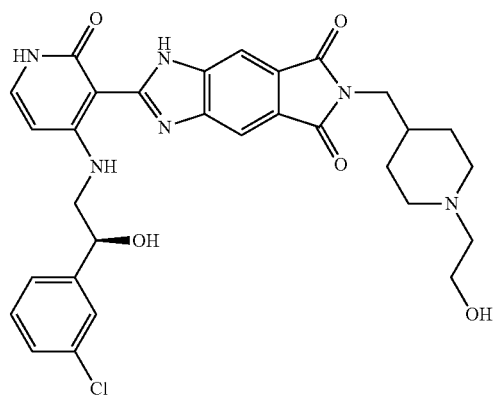 [SMILES: O=C1c2cc3nc(-c4c(NC[C@@H](O)c5cccc(Cl)c5)cc[nH]c4=O)[nH]c3cc2C(=O)N1CC1CCN(CCO)CC1]

2-{4-[(S)-2-(3-Chloro-phenyl)-2-hydroxy-ethylamino]-2-oxo-1,2-dihydro-pyridin-3-yl}-6-[1-(2-hydroxy-ethyl)-piperidin-4-ylmethyl]-1H-1,3,6-triaza-s-indacene-5,7-dione: ¹H NMR (DMSO-d₆) δ 1.23 (d, J=9 Hz, 2H), 1.58 (d, J=9 Hz, 2H), 1.70 (m, 1H), 1.95 (m, 2H), 2.39 (m, 2H), 2.87 (m, 2H), 3.35 (m, 2H), 3.42-3.52 (2H), 3.61 (m, 1H), 3.69 (1H), 4.39 (br s, 1H, OH), 4.99 (m, 1H), 6.00 (s, 1H, NH), 6.21 (d, J=6 Hz, 1H), 7.32-7.42 (3H), 7.50 (d, J=6 Hz, 1H), 7.63 (s, 1H), 7.87 (s, 1H), 8.13 (s, 1H), 10.89 (br s, 1H, NH), 11.30 (br s, 1H, NH); ESI-MS m/z 591.3 (MH⁺).

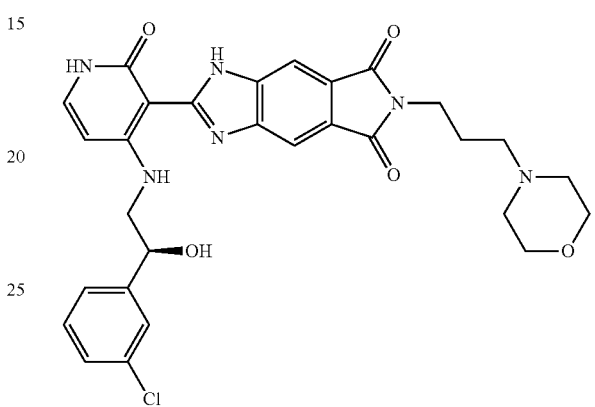

2-{4-[(S)-2-(3-Chloro-phenyl)-2-hydroxy-ethylamino]-2-oxo-1,2-dihydro-pyridin-3-yl}-6-(3-morpholin-4-yl-propyl)-1H-1,3,6-triaza-s-indacene-5,7-dione: ¹H NMR (DMSO-d₆) δ 1.76 (m, 2H), 2.20-2.38 (6H), 3.32-3.48 (4H), 3.52-3.77 (4H), 4.99 (m, 1H), 6.00 (s, 1H, NH), 6.19 (d, J=6 Hz, 1H), 7.31-7.41 (3H), 7.50 (d, J=6 Hz, 1H), 7.64 (s, 1H), 7.87 (s, 1H), 8.13 (s, 1H), 9.56 (br s, 1H), 10.89 (br s, 1H, NH), 11.29 (br d, J=6 Hz, 1H, NH); ESI-MS m/z 577.3 (MH⁺).

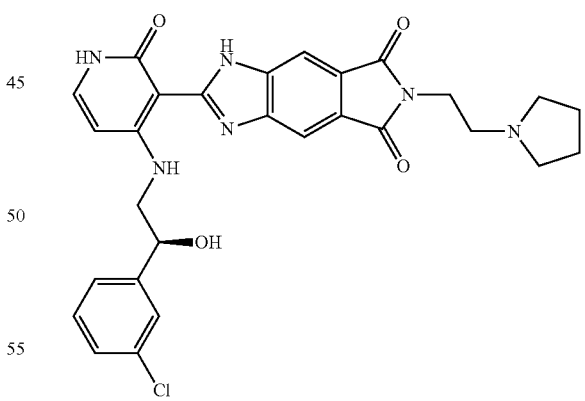

2-{4-[(S)-2-(3-Chloro-phenyl)-2-hydroxy-ethylamino]-2-oxo-1,2-dihydro-pyridin-3-yl}-6-(2-pyrrolidin-1-yl-ethyl)-1H-1,3,6-triaza-s-indacene-5,7-dione: ¹H NMR (DMSO-d₆) δ 1.81 (m, 2H), 2.03 (m, 2H), 3.15 (m, 2H), 3.50 (m, 2H), 3.53-3.74 (4H), 3.95 (m, 2H), 4.99 (m, 1H), 6.00 (s, 1H, NH), 6.21 (d, J=6 Hz, 1H), 7.29-7.41 (3H), 7.50 (d, J=6 Hz, 1H), 7.64 (s, 1H), 7.92 (s, 1H), 8.18 (s, 1H), 9.61 (br s, 1H), 10.88 (br s, 1H, NH), 11.30 (br d, J=6 Hz, 1H, NH); ESI-MS m/z 547.3 (MH⁺).

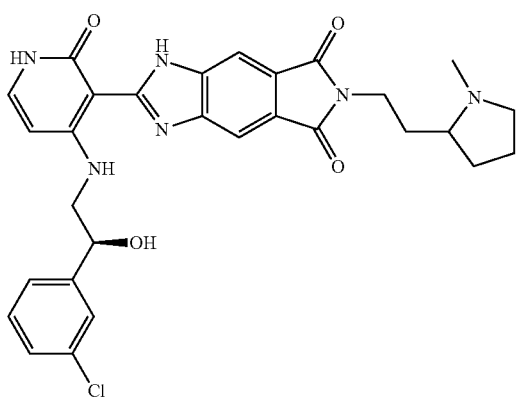 [SMILES: CN1CCCC1CCN1C(=O)c2cc3nc(-c4c(NC[C@@H](O)c5cccc(Cl)c5)cc[nH]c4=O)[nH]c3cc2C1=O]

2-{4-[(S)-2-(3-Chloro-phenyl)-2-hydroxy-ethylamino]-2-oxo-1,2-dihydro-pyridin-3-yl}-6-[2-(1-methyl-pyrrolidin-2-yl)-ethyl]-1H-1,3,6-triaza-s-indacene-5,7-dione: $^1$H NMR (DMSO-d$_6$) δ 1.43-1.68 (4H), 1.87-2.11 (4H), 2.20 (s, 3H, CH$_3$), 2.93 (m, 1H), 3.52-3.75 (4H), 4.99 (m, 1H), 6.00 (s, 1H, NH), 6.21 (d, J=6 Hz, 1H), 7.29-7.41 (3H), 7.50 (d, J=6 Hz, 1H), 7.63 (s, 1H), 7.87 (s, 1H), 8.13 (s, 1H), 10.89 (br s, 1H, NH), 11.29 (br d, J=6 Hz, 1H, NH); ESI-MS m/z 561.3 (MH$^+$).

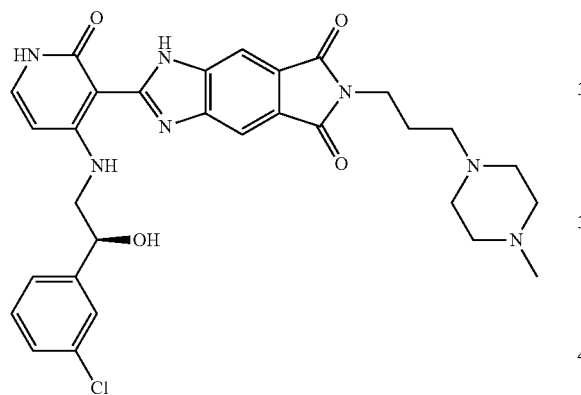

2-{4-[(S)-2-(3-Chloro-phenyl)-2-hydroxy-ethylamino]-2-oxo-1,2-dihydro-pyridin-3-yl}-6-[3-(4-methyl-piperazin-1-yl)-propyl]-1H-1,3,6-triaza-s-indacene-5,7-dione: $^1$H NMR (DMSO-d$_6$) δ 1.90 (m, 2H), 2.50-3.80 (14H), 2.70 (s, 3H, CH$_3$), 4.99 (m, 1H), 6.01 (s, 1H, NH), 6.20 (d, J=6 Hz, 1H), 7.30-7.41 (3H), 7.50 (d, J=6 Hz, 1H), 7.63 (s, 1H), 7.90 (s, 1H), 8.14 (s, 1H), 10.87 (br s, 1H, NH), 11.30 (br d, J=6 Hz, 1H, NH); ESI-MS m/z 590.5 (MH$^+$).

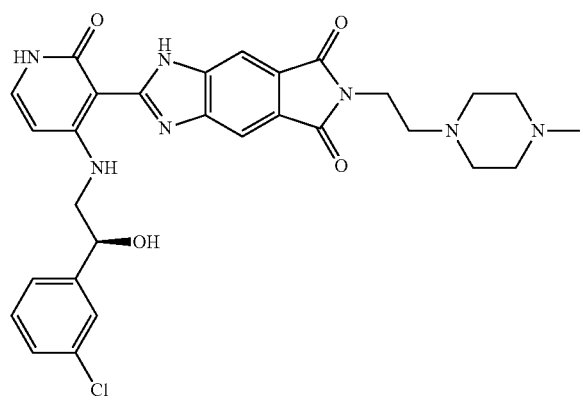 [SMILES: CN1CCN(CCN2C(=O)c3cc4nc(-c5c(NC[C@@H](O)c6cccc(Cl)c6)cc[nH]c5=O)[nH]c4cc3C2=O)CC1]

2-{4-[(S)-2-(3-Chloro-phenyl)-2-hydroxy-ethylamino]-2-oxo-1,2-dihydro-pyridin-3-yl}-6-[2-(4-methyl-piperazin-1-yl)-ethyl]-1H-1,3,6-triaza-s-indacene-5,7-dione: $^1$H NMR (DMSO-d$_6$) δ 2.35 (m, 2H), 2.68 (m, 2H), 2.75 (s, 3H, CH$_3$), 2.90 (m, 2H), 3.10 (m, 2H), 3.30-3.77 (6H), 4.99 (m, 1H), 6.01 (br s, 1H, NH), 6.20 (d, J=6 Hz, 1H), 7.30-7.41 (3H), 7.49 (d, J=6 Hz, 1H), 7.63 (s, 1H), 7.89 (s, 1H), 8.14 (s, 1H), 9.50 (br s, 1H), 10.88 (br s, 1H, NH), 11.30 (br d, J=6 Hz, 1H, NH); ESI-MS m/z 576.5 (MH$^+$).

Synthesis of (R)-1-amino-3-(2-bromo-5-fluoro-phenoxy)-propan-2-ol

Scheme 60

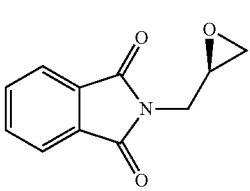

+

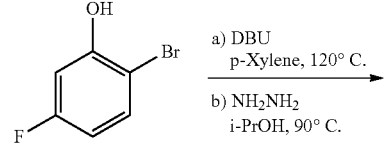

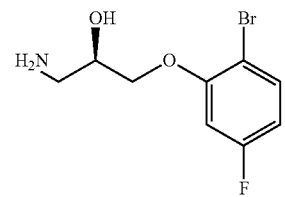

A mixture of 2-[(2R)-oxiran-2-ylmethyl]-1H-isoindole-1,3(2H)-dione (1) (0.531 g, 2.6 mmol), 2-bromo-5-fluorophenol (2) (0.500 g, 2.6 mmol), and DBU (25 μL, 0.16 mmol) in p-xylene was heated at 120° C. for throughnight. The reaction mixture was cooled and then propan-2-ol (15 mL) and hydrazine (600 μL, 18.9 mmol) were added. The resulting mixture was heated at 90° C. for 5 h and cooled to room temperature. The reaction was diluted with 1 N NaOH (30 mL) and extracted with ethyl acetate (3×20 mL). The combined extract was washed with 1 N NaOH (25 mL), dried through Na$_2$SO$_4$ and concentrated under reduced pressure to get crude (R)-1-amino-3-(2-bromo-5-fluorophenoxy)propan-2-ol (3) (0.500 g) which was used for next reaction without further purification. ESI-MS m/z 265.1 (M$^+$+1).

339

Synthesis of 2-{4-[(R)-3-(2-bromo-4-fluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

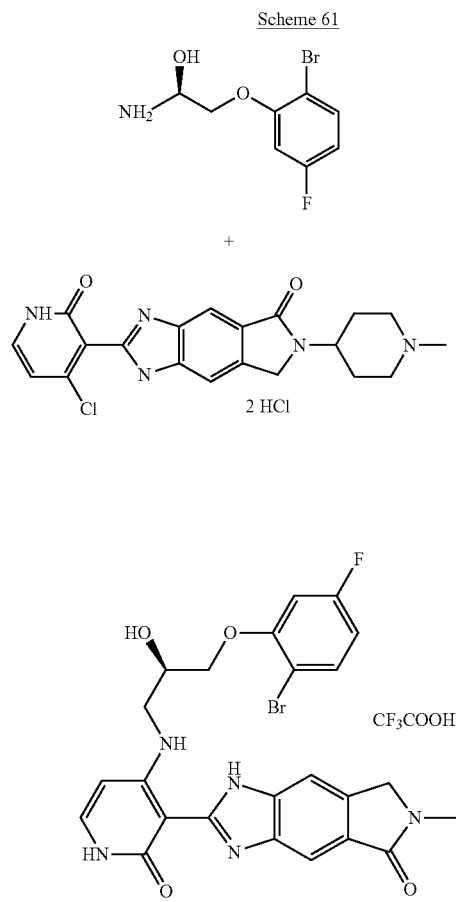

A mixture of 2-(4-chloro-2-oxo-1,2-dihydro-pyridin-3-yl)-6-(1-methyl-piperidin-4-yl)-1H-1,3,6-triaza-s-indacene-5,7-dione dihydrochloride (4) (85 mg, 18 mmol), (R)-1-amino-3-(2-bromo-5-fluorophenoxy)-propan-2-ol (50 mg, 0.18 mmol) and Et₃N (375 mg, 3.71 mmol) in EtOH (4 mL) was heated at 100° C. for 12 h. The filtrate was concentrated and the residue was passed through small silica gel column (10% NH₄OH in MeOH/CH₂Cl₂ (1:9). Column fractions were concentrated and obtained compound was subjected to HPLC purification to afford 2-{4-[(R)-3-(2-bromo-5-fluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one as TFA salt (5) (30 mg, 21%). ¹H NMR (DMSO-d₆) 1.80-2.15 (m, 4H), 2.80 (s, 3H), 3.10-3.3 (m, 2H), 3.40-4.15 (m, 7H), 4.05-4.20 (m, 2H), 4.23-4.40 (m, 1H), 4.45 (s, 2H), 5.0 (br, 1H), 6.24 (d, 1H, J=9.0 Hz), 6.76-6.83 (m, 1H), 7.12 (dd, 1H, J=3.0, 12.0 Hz) 7.36 (t, 1H, J=9.0 Hz), 7.60-7.70 (m, 1H), 9.45 (bs, 1H), 11.10 (bs, 1H), 11.24 (d, 1H, J=6.0 Hz); ESI-MS m/z 627.5 (M⁺+2).

340

The following compounds were synthesized as shown in scheme 61

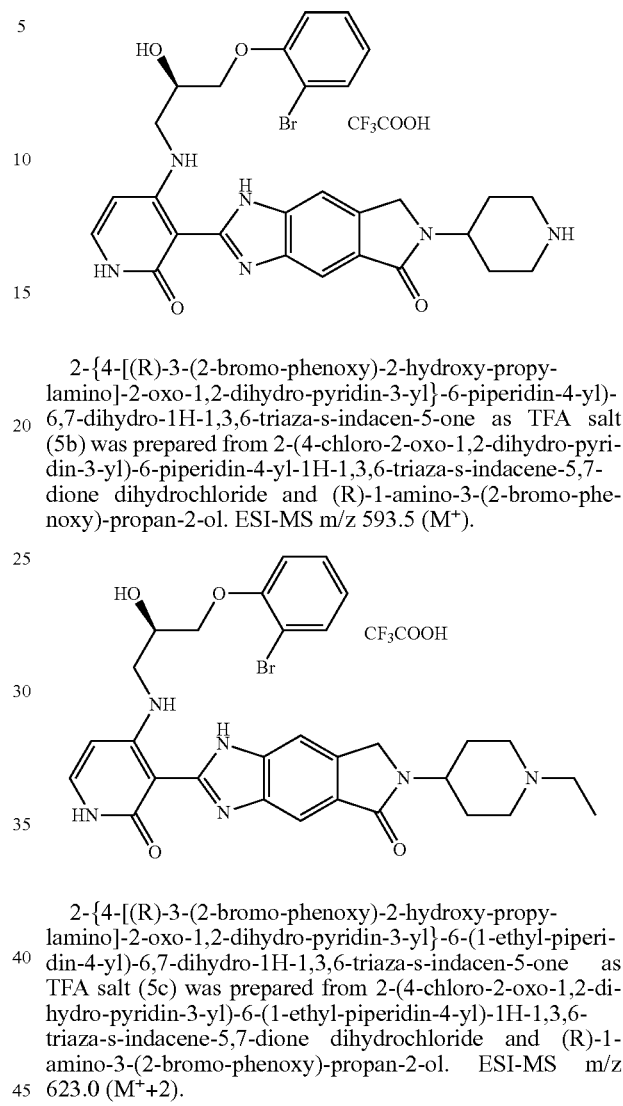

2-{4-[(R)-3-(2-bromo-phenoxy)-2-hydroxy-propylamino]-2-oxo-1,2-dihydro-pyridin-3-yl}-6-piperidin-4-yl)-6,7-dihydro-1H-1,3,6-triaza-s-indacen-5-one as TFA salt (5b) was prepared from 2-(4-chloro-2-oxo-1,2-dihydro-pyridin-3-yl)-6-piperidin-4-yl-1H-1,3,6-triaza-s-indacene-5,7-dione dihydrochloride and (R)-1-amino-3-(2-bromo-phenoxy)-propan-2-ol. ESI-MS m/z 593.5 (M⁺).

2-{4-[(R)-3-(2-bromo-phenoxy)-2-hydroxy-propylamino]-2-oxo-1,2-dihydro-pyridin-3-yl}-6-(1-ethyl-piperidin-4-yl)-6,7-dihydro-1H-1,3,6-triaza-s-indacen-5-one as TFA salt (5c) was prepared from 2-(4-chloro-2-oxo-1,2-dihydro-pyridin-3-yl)-6-(1-ethyl-piperidin-4-yl)-1H-1,3,6-triaza-s-indacene-5,7-dione dihydrochloride and (R)-1-amino-3-(2-bromo-phenoxy)-propan-2-ol. ESI-MS m/z 623.0 (M⁺+2).

Synthesis of (R)-1-amino-3-(2-chloro-4-methoxyphenoxy)-propan-2-ol

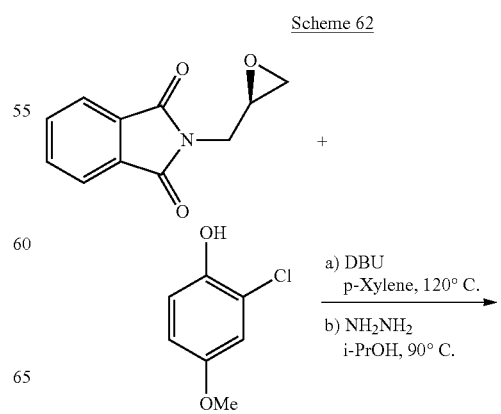

-continued

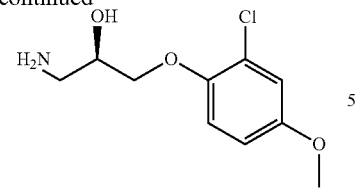

A mixture of 2-[(2R)-oxiran-2-ylmethyl]-1H-isoindole-1,3(2H)-dione (1) (0.640 g, 3.15 mmol), 2-chloro-4-methoxyphenol (2) (0.500 g, 3.15 mmol), and DBU (25 μL, 0.16 mmol) in p-xylene was heated at 120° C. for throughnight. The reaction mixture was cooled and then propan-2-ol (15 mL) and hydrazine (600 μL, 18.9 mmol) were added. The resulting mixture was heated at 90° C. for 5 h and cooled to room temperature. The reaction was diluted with 1 N NaOH (30 mL) and extracted with ethyl acetate (3×20 mL). The combined extract was washed with 1 N NaOH (25 mL), dried through $Na_2SO_4$ and concentrated under reduced pressure to get crude (R)-1-amino-3-(2-chloro-4-methoxyphenoxy)propan-2-ol (3a) (0.547 g) which was used for next reaction without further purification. ESI-MS m/z 232.4 ($M^+$+1).

The following amino alcohols were synthesized using the above procedure and designated phenol unless otherwise noted (R)-1-amino-3-(2-chloro-4-fluoro-3-methylphenoxy)propan-2-ol (3b)

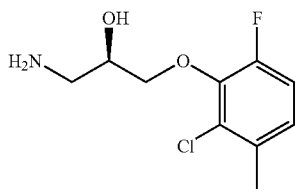

Yield: 0.567 g; ESI-MS m/z 233.9 ($M^+$+1).

(R)-1-amino-3-(2-bromo-4,6-difluorophenoxy)propan-2-ol

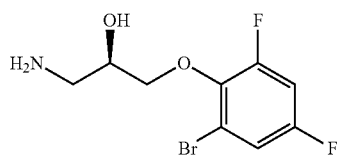 [SMILES: NC[C@@H](O)COc1c(F)cc(F)cc1Br]

Yield: 0.539 g; ESI-MS m/z 282.1 ($M^+$) and 284.1 ($M^+$+2).

(R)-1-amino-3-(2-(trifluoromethyl)phenoxy)propan-2-ol

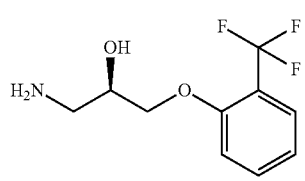 [SMILES: NC[C@@H](O)COc1ccccc1C(F)(F)F]

Yield: 0.594 g; ESI-MS m/z 236.1 ($M^+$+1).

(R)-1-amino-3-(2-chloro-5-fluorophenoxy)propan-2-ol

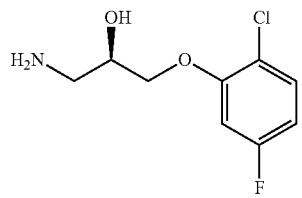 [SMILES: NC[C@@H](O)COc1cc(F)ccc1Cl]

Yield: 0.584 g; ESI-MS m/z 219.9 ($M^+$+1).

(R)-1-amino-3-(2-bromo-4-fluorophenoxy)propan-2-ol

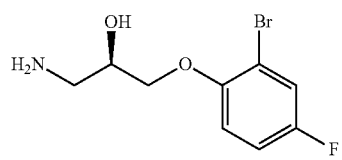 [SMILES: NC[C@@H](O)COc1ccc(F)cc1Br]

Yield: 0.497 g; ESI-MS m/z 264.3 ($M^+$) and 266.3 ($M^+$+2).

(R)-1-amino-3-(2-bromo-4-methylphenoxy)propan-2-ol (3g)

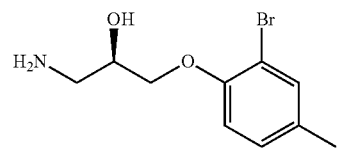

Yield: 0.485 g; ESI-MS m/z 260.4 ($M^+$) and 262.4 ($M^+$+2).

(R)-1-amino-3-(2-chloro-5-(trifluoromethyl)phenoxy)propan-2-ol (3h)

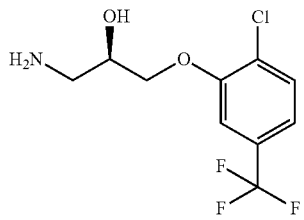 [SMILES: NC[C@@H](O)COc1cc(C(F)(F)F)ccc1Cl]

Yield: 0.500 g; ESI-MS m/z 270.0 ($M^+$+1).

343

(R)-1-amino-3-(2-bromophenoxy)propan-2-ol (3l)

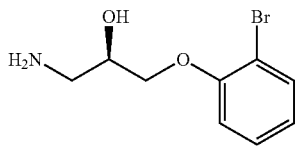 [SMILES: NC[C@@H](O)COc1ccccc1Br]

Yield: 0.533 g; ESI-MS m/z 245.8 (M$^+$) and 247.8 (M$^+$+2).

(R)-1-amino-3-(2-bromo-4,5-difluorophenoxy)propan-2-ol (3j)

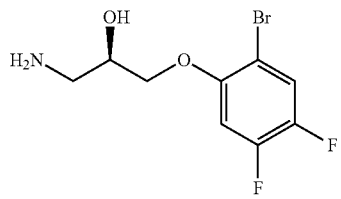 [SMILES: NC[C@@H](O)COc1cc(F)c(F)cc1Br]

Yield: 0.472 g; ESI-MS m/z 282.4 (M$^+$) and 284.4 (M$^+$+2).

(R)-1-amino-3-(2-chloro-4,5-difluorophenoxy)propan-2-ol (3k)

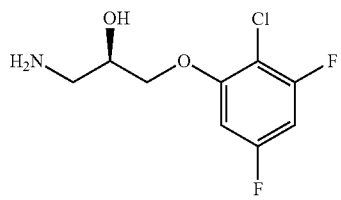 [SMILES: NC[C@@H](O)COc1cc(F)cc(F)c1Cl]

Yield: 0.527 g; ESI-MS m/z 238.1 (M$^+$+1).

(R)-1-amino-3-(2-chloro-6-fluorophenoxy)propan-2-ol (3l)

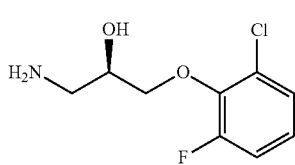 [SMILES: NC[C@@H](O)COc1c(F)cccc1Cl]

Yield: 0.532 g; ESI-MS m/z 220.1 (M$^+$).

344

(R)-1-amino-3-(2-chloro-6-fluorophenoxy)propan-2-ol (3m)

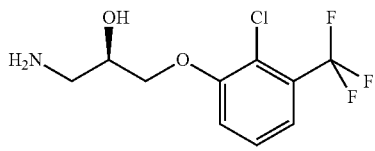 [SMILES: NC[C@@H](O)COc1cccc(C(F)(F)F)c1Cl]

Yield: 0.473 g; ESI-MS m/z 269.9 (M$^+$+1).

(R)-1-amino-3-(2-chloro-6-fluorophenoxy)propan-2-ol (3n)

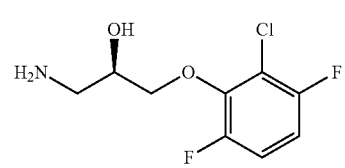 [SMILES: NC[C@@H](O)COc1c(F)ccc(F)c1Cl]

Yield: 0.519 g; ESI-MS m/z 238.4 (M$^+$+1).

(R)-1-amino-3-[(6-ethyl-1,3-benzodioxol-5-yl)oxy]propan-2-ol (3o)

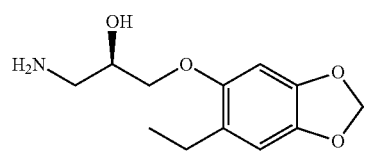 [SMILES: CCc1cc2c(cc1OC[C@H](O)CN)OCO2]

Yield: 0.503 g; ESI-MS m/z 239.9 (M$^+$+1).

(R)-1-amino-3-[(6-chloro-1,3-benzodioxol-5-yl)oxy]propan-2-ol (3p)

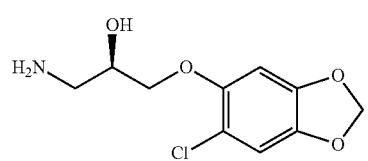 [SMILES: NC[C@@H](O)COc1cc2c(cc1Cl)OCO2]

Yield: 0.462 g; ESI-MS m/z 246.3 (M$^+$+1).

345

(R)-1-amino-3-(6-chloro-2-fluoro-3-methylphenoxy)propan-2-ol (3g)

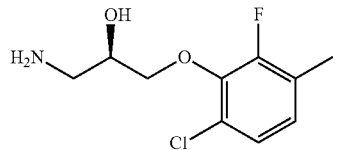

Yield: 0.516 g; ESI-MS m/z 234.3 (M⁺+1).

(R)-1-amino-3-(4-methyl-benzo[1,3]dioxol-5-yloxy)-propan-2-ol (3r)

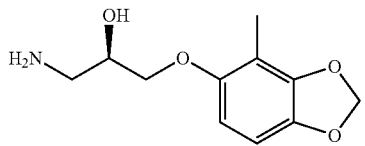 [SMILES: Cc1c(OC[C@H](O)CN)ccc2c1OCO2]

Yield: 0.550 g; ESI-MS m/z 226.3 (M⁺+1).

(R)-1-amino-3-(4-ethyl-benzo[1,3]dioxol-5-yloxy)-propan-2-ol (3s)

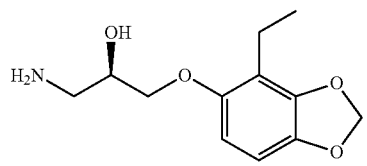 [SMILES: CCc1c(OC[C@H](O)CN)ccc2c1OCO2]

Yield: 0.400 g; ESI-MS m/z 240.2 (M⁺+1).

(R)-1-amino-3-(4-chloro-benzo[1,3]dioxol-5-yloxy)-propan-2-ol (3t)

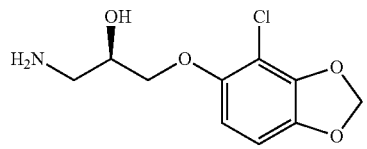 [SMILES: NC[C@@H](O)COc1ccc2c(c1Cl)OCO2]

Yield: 0.450 g; ESI-MS m/z 246.5 (M⁺+1).

346

(R)-1-amino-3-(4-fluoro-2,4-dimethyl-phenoxy)-propan-2-ol (3u)

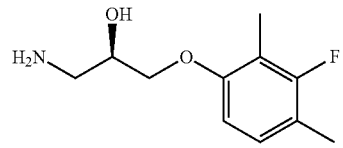

Yield: 0.300 g; ESI-MS m/z 214.1 (M⁺+1).

(R)-1-amino-3-(3-fluoro-2,4-dimethyl-phenoxy)-propan-2-ol (3u) (300 mg) was obtained from 2-[(2R)-oxiran-2-ylmethyl]-1H-isoindole-1,3(2H)-dione (1) (0.250 g, 1.78 mmol), and 3-fluoro-2,4-dimethyl-phenol (0.362 g, 1.78 mmol) by application of the above methodology.

Synthesis of 2-{4-[(R)-3-(2-chloro-4-methoxy-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

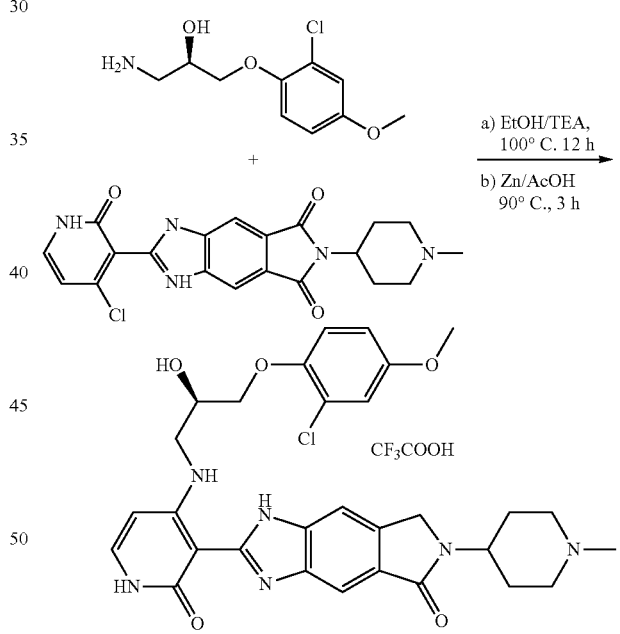

A mixture of 2-(4-chloro-2-oxo-1,2-dihydro-pyridin-3-yl)-6-(1-methyl-piperidin-4-yl)-1H-1,3,6-triaza-s-indacene-5,7-dione dihydrochloride (300 mg, 0.61 mmol), (R)-1-amino-3-(2-chloro-4-methoxyphenoxy)-propan-2-ol (175 mg, 0.80 mmol) and Et₃N (375 mg, 3.71 mmol) in EtOH (4 mL) was heated at 100° C. for 12 h. The reaction mixture was cooled and concentrated under reduced pressure to dryness (700 mg). A portion of crude mixture (100 mg) was mixed with zinc dust (250 mg) in AcOH (4 mL) and heated at 90° C. for 3 h. The mixture was cooled, filtered through celite and solid was washed with 1:1 MeOH/CH₂Cl₂ (5 mL). The filtrate was concentrated and the residue was passed through small silica gel column (10% NH4OH in MeOH/CH$_2$Cl$_2$ (1:9). Column fractions were concentrated and obtained compound was subjected to HPLC purification to afford 2-{4-[(R)-3-(2-chloro-4-methoxy-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one as TFA salt (5a) (20 mg, 31.9%, 2 steps). $^1$H NMR (DMSO-d$_6$) δ 1.80-2.15 (m, 4H), 2.80 (s, 3H), 3.10-3.3 (m, 2H), 3.40-4.15 (m, 7H), 4.20-4.38 (m, 1H), 4.45 (s, 2H), 6.22 (d, 1H, J=9.0 Hz), 6.86 (m, 1H), 7.08 (s, 1H), 7.12 (d, 1H, J=9.0 Hz) 7.36 (t, 1H, J=9.0 Hz), 7.80 (m, 2H), 9.40 (bs, 1H), 11.13 (bs, 1H), 11.24 (d, 1H, J=9.0 Hz); ESI-MS m/z 593.5 (M$^+$+1).

By application of the above methodology and using designated amino alcohol, the following compounds were synthesized.

2-{4-[(R)-3-(2-chloro-5-fluoro-3-methyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

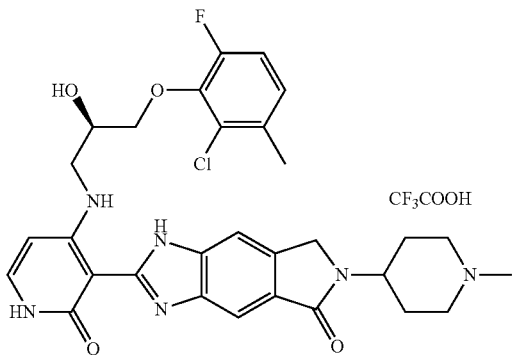 [SMILES: Cc1ccc(F)c(OC[C@H](O)CNc2cc[nH]c(=O)c2-c2nc3cc4c(cc3[nH]2)CN(C2CCN(C)CC2)C4=O)c1Cl ; "CF3COOH"]

Yield: (22 mg, 43%); $^1$H NMR (DMSO-d$_6$) δ 1.80-2.15 (m, 4H), 2.31 (s, 3H), 2.80 (s, 3H), 3.10-3.90 (m, 6H), 4.00-4.18 (m, 3H), 4.22-4.37 (m, 1H), 4.50 (s, 2H), 5.55 (bs, 1H), 6.21 (d, 1H, J=6.0 Hz), 7.05-7.25 (m, 2H), 7.40 (t, 1H, J=6.0 Hz), 7.50-8.0 (m, 2H), 9.40 (bs, 1H), 11.10 (bs, 1H), 11.23 (d, 1H, J=9.0 Hz); ESI-MS m/z 595.5 (M$^+$+1).

2-{4-[(R)-3-(2,4-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

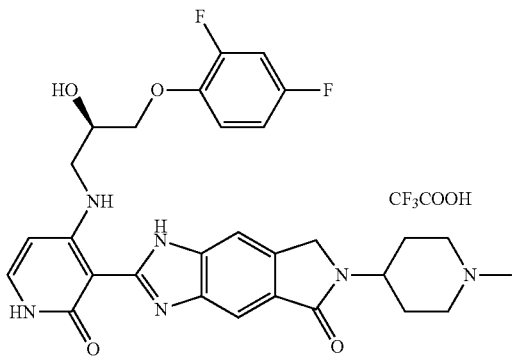 [SMILES: CN1CCC(N2Cc3cc4[nH]c(-c5c(NC[C@@H](O)COc6ccc(F)cc6F)cc[nH]c5=O)nc4cc3C2=O)CC1 ; "CF3COOH"]

Yield: (17 mg, 26%); $^1$H NMR (DMSO-d$_6$) δ 1.80-2.15 (m, 4H), 2.80 (s, 3H), 3.05-3.30 (m, 2H) 3.40-3.95 (m, 4H), 4.0-4.18 (m, 3H), 4.21-4.38 (m, 1H), 4.46 (s, 2H), 5.58 (bs, 1H), 6.21 (d, 1H, J=6.0 Hz), 6.90-7.0 (m, 1H), 7.15-7.30 (m, 3H), 7.42-8.0 (m, 2H), 9.40 (bs, 1H), 11.12 (bs, 1H), 11.23 (d, 1H, J=6.0 Hz); ESI-MS m/z 565.5 (M$^+$+1).

2-{4-[(R)-3-(2-trifluoromethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

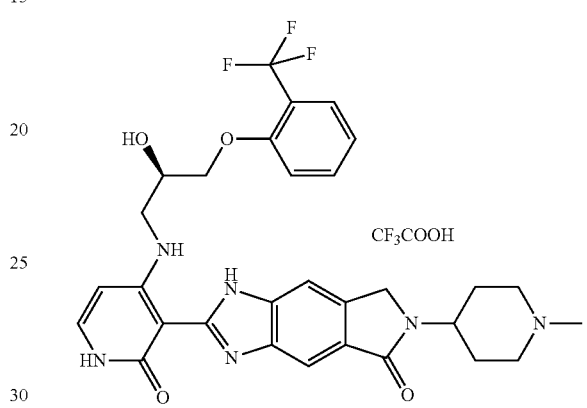

Yield: (19 mg, 31%); $^1$H NMR (DMSO-d$_6$) δ 1.80-2.15 (m, 4H), 2.82 (s, 3H), 3.1-3.35 (m, 2H) 3.40-3.95 (m, 4H), 4.0-4.40 (m, 4H), 4.46 (s, 2H), 5.57 (bs, 1H), 6.18 (d, 1H, J=6.0 Hz), 7.0-7.33 (m, 1H), 7.34-7.59 (m, 2H), 7.50-8.0 (m, 4H), 9.40 (bs, 1H), 11.14 (bs, 1H), 11.23 (d, 1H, J=3.0 Hz); ESI-MS m/z 597.2 (M$^+$+1).

2-{4-[(R)-3-(2-chloro-5-fluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

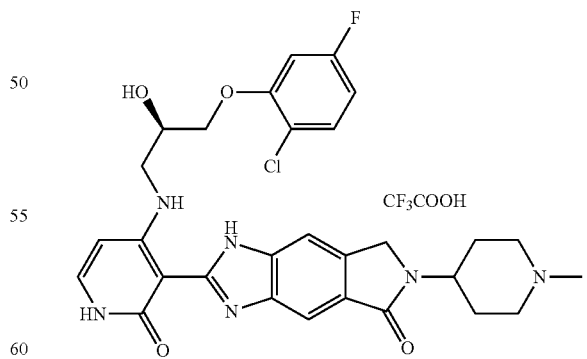

Yield: (18 mg, 27.9%); $^1$H NMR (DMSO-d$_6$) δ 1.90-2.15 (m, 4H), 2.85 (s, 3H), 3.10-3.30 (m, 2H) 3.40-3.95 (m, 4H), 4.08-4.18 (m, 3H), 4.25-4.40 (m, 1H), 4.47 (s, 2H), 5.65 (bs, 1H), 6.22 (d, 1H, J=9.0 Hz), 6.84 (t, 1H J=9.0 Hz), 7.15 (dd, 1H, J=9.0, 15.0 Hz), 7.31-7.34 (m, 1H), 7.40-7.55 (m, 1H), 7.50-8.0 (m, 2H), 9.35 (bs, 1H), 11.13 (bs, 1H), 11.24 (d, 1H, J=6.0 Hz); ESI-MS m/z 581.5 (M$^+$+1).

9.35 (bs, 1H), 11.13 (bs, 1H), 11.24 (bs, 1H); ESI-MS m/z 599.5 (M$^+$+1).

2-{4-[(R)-3-(2-chloro-5-trifluoromethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt 2-{4-[(R)-3-(2-chloro-6-fluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

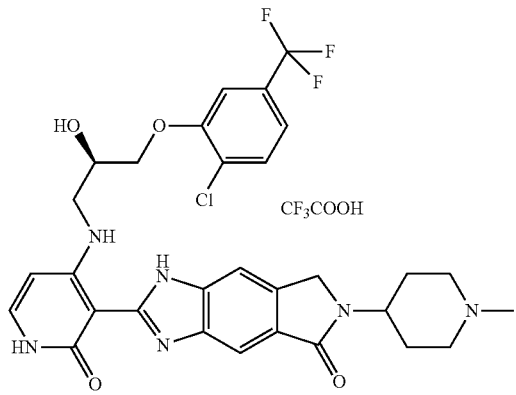

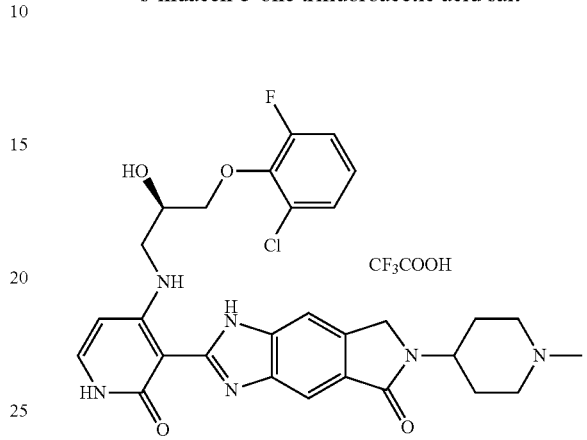

Yield: (15 mg, 23%); $^1$H NMR (DMSO-d$_6$) δ 1.80-2.10 (m, 4H), 2.80 (s, 3H), 3.10-3.28 (m, 2H) 3.40-3.95 (m, 4H), 4.08-4.35 (m, 4H), 4.47 (s, 2H), 5.62 (bs, 1H), 6.21 (d, 1H, J=6.0 Hz), 7.28-7.40 (m, 2H), 7.50 (s, 1H), 7.60-8.10 (m, 3H), 9.40 (bs, 1H), 11.13 (bs, 1H), 11.25 (bs, 1H); ESI-MS m/z 631.3 (M$^+$+1).

Yield: (20 mg, 32%); $^1$H NMR (DMSO-d$_6$) δ 1.85-2.12 (m, 4H), 2.81 (s, 3H), 3.10-3.90 (m, 4H) 4.05-4.20 (m, 3H), 4.21-4.42 (m, 1H), 4.50 (s, 2H), 5.55 (bs, 1H), 6.21 (d, 1H, J=6.0 Hz), 7.11-7.19 (m, 1H), 7.20-7.42 (m, 3H), 7.50-8.05 (m, 2H), 9.41 (bs, 1H), 11.13 (bs, 1H), 11.24 (d, 1H, J=6.0 Hz); ESI-MS m/z 581.5 (M$^+$+1)

2-{4-[(R)-3-(2-chloro-3,5-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt 2-{4-[(R)-3-(2-chloro-3-trifluoromethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

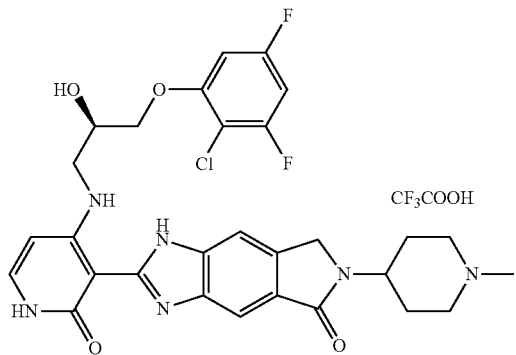 [SMILES: CN1CCC(N2Cc3cc4[nH]c(-c5c(NC[C@@H](O)COc6cc(F)cc(F)c6Cl)cc[nH]c5=O)nc4cc3C2=O)CC1 ; "CF3COOH"]

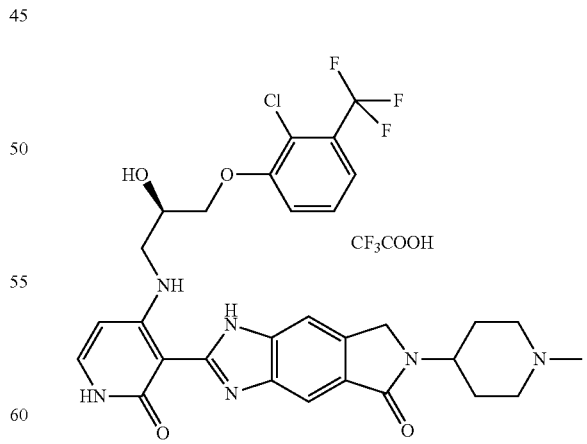

Yield: (21 mg, 28%); $^1$H NMR (DMSO-d$_6$) δ 1.80-2.10 (m, 4H), 2.80 (s, 3H), 3.10-3.80 (m, 4H), 4.08-4.20 (m, 3H), 4.21-4.40 (m, 1H), 4.49 (s, 2H), 6.22 (d, 1H, J=6.0 Hz), 7.00-7.15 (m, 2H), 7.30-7.40 (m, 1H), 7.50-8.10 (m, 2H), Yield: (17 mg, 26%); $^1$H NMR (DMSO-d$_6$) δ 1.80-2.10 (m, 4H), 2.81 (s, 3H), 3.10-3.85 (m, 4H) 4.10-4.65 (m, 6H), 5.60 (bs, 1H), 6.24 (d, 1H, J=6.0 Hz), 6.90-7.29 (m, 1H), 7.30-7.70

(m, 4H), 7.75-8.05 (m, 1H), 9.45 (bs, 1H), 11.15 (bs, 1H), 11.24 (bs, 1H,); ESI-MS m/z 631.7 (M⁺+1).

2-{4-[(R)-3-(2-chloro-3,5-difluoromethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

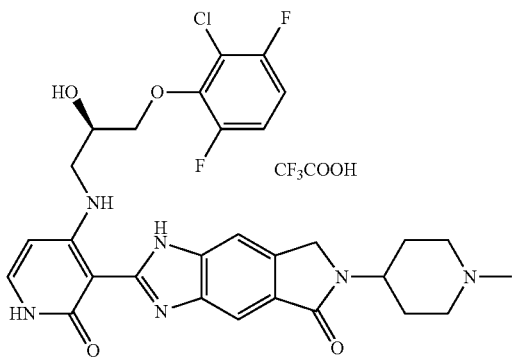

Yield: (20 mg, 30%); ¹H NMR (DMSO-d₆) δ 1.85-2.15 (m, 4H), 2.85 (s, 3H), 3.10-3.85 (m, 4H), 4.00-4.18 (m, 1H), 4.20-4.40 (m, 4H), 4.49 (s, 2H), 5.55 (bs, 1H), 6.22 (d, 1H, J=9.0 Hz), 7.10-7.29 (m, 1H), 7.30-7.45 (m, 2H), 7.50-8.0 (m, 2H), 9.38 (bs, 1H), 11.12 (bs, 1H), 11.25 (d, 1H J=6.0 Hz); ESI-MS m/z 599.7 (M⁺+1).

2-{4-[(R)-3-[(6-ethyl-1,3-benzodioxol-5-yl)oxy]-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

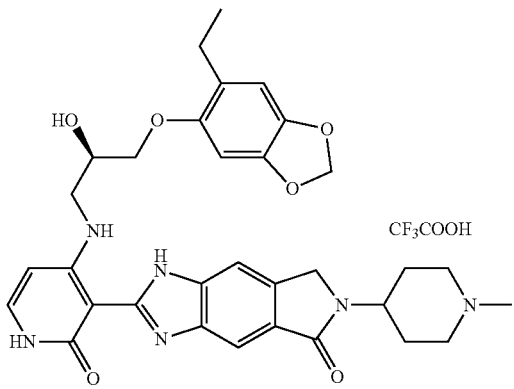 [SMILES: CCc1cc2c(cc1OC[C@H](O)CNc1cc[nH]c(=O)c1-c1nc3cc4c(cc3[nH]1)CN(C1CCN(C)CC1)C4=O)OCO2 ; "CF3COOH"]

Yield: (15 mg, 19%); ¹H NMR (DMSO-d₆) δ 1.10 (t, 3H, J=9.0 Hz), 1.90-2.15 (m, 4H), 2.50 (q, 2H, J=9.0, 15.0 Hz) 2.82 (s, 3H), 3.10-3.25 (m, 2H), 3.35-4.15 (m, 6H), 4.25-4.40 (m, 1H), 4.47 (s, 2H), 5.50 (bs, 1H), 5.91 (s, 2H), 6.20 (d, 1H, J=6.0 Hz), 6.75 (s, 1H), 6.77 (s, 1H), 7.34-7.39 (m, 1H), 7.50-8.0 (m, 2H), 9.38 (bs, 1H), 11.13 (bs, 1H), 11.23 (d, 1H, J=6.0 Hz); ESI-MS m/z 601.5 (M⁺+1).

2-{4-[(R)-3-(6-chloro-benzo[1,3]dioxol-5-yloxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

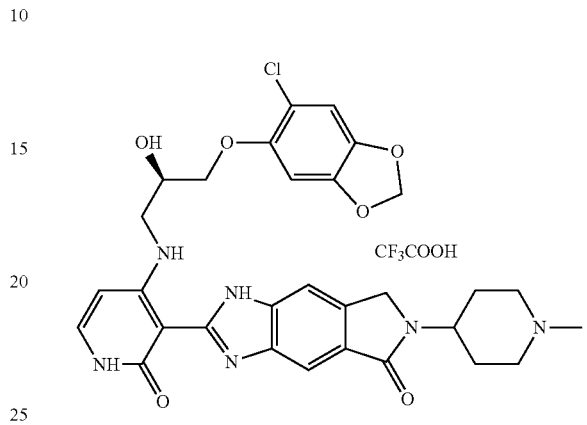

Yield: (14 mg, 22%); ¹H NMR (DMSO-d₆) δ 1.80-2.13 (m, 4H), 2.81 (s, 3H), 3.10-3.30 (m, 2H), 3.40-4.60 (m, 3H), 3.65-4.25 (m, 4H), 4.26-4.36 (m, 1H), 4.50 (s, 2H), 5.50 (bs, 1H), 6.02 (s, 2H), 6.22 (d, 1H, J=9.0 Hz), 6.98 (s, 1H), 7.10 (s, 1H), 7.36 (t, 1H, J=6.0 Hz), 7.50-7.95 (m, 2H), 9.42 (bs, 1H), 11.11 (bs, 1H), 11.23 (d, 1H, J=6.0 Hz); ESI-MS m/z 607.0 (M⁺+1).

2-{4-[(R)-3-(2-chloro-6-fluoro-5-methyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

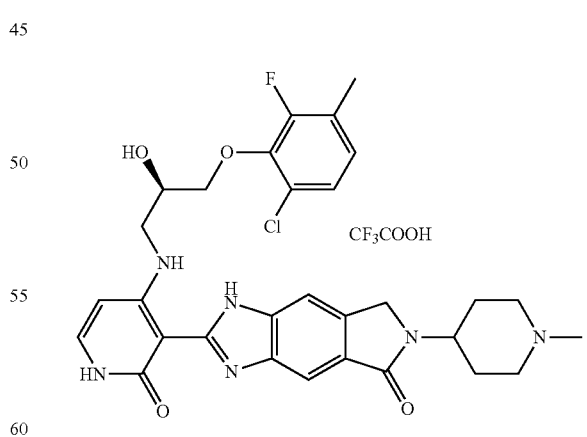

Yield: (23 mg, 37%); ¹H NMR (DMSO-d₆) δ 1.85-2.10 (m, 4H), 2.12 (s, 3H), 2.81 (s, 3H), 3.10-3.25 (m, 2H) 3.40-3.65 (m, 3H), 3.74-3.80 (m, 1H), 4.0-4.18 (m, 3H), 4.20-4.40 (m, 1H), 4.50 (s, 2H), 6.21 (d, 1H, J=6.0 Hz), 7.01-7.06 (m, 1H), 7.19-7.7.22 (m, 1H), 7.38 (m, 1H), 7.60-8.0 (m, 2H), 9.44 (bs, 1H), 11.12 (bs, 1H), 11.24 (d, 1H J=9.0 Hz); ESI-MS m/z 595.7 (M⁺+1).

2-{4-[(R)-2-hydroxy-3-(4-methyl-benzo[1,3]dioxol-5-yloxy)-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

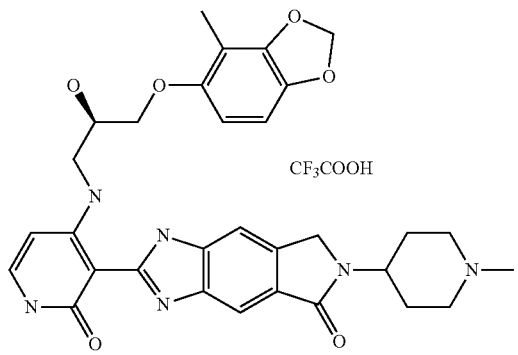

Yield: (32 mg, 41%); ¹H NMR (DMSO-d₆) δ 1.82-2.10 (m, 4H), 2.20 (s, 3H), 2.79 (s, 3H), 3.15-3.30 (m, 2H) 3.45-3.85 (m, 3H), 3.90-4.03 (m, 2H), 4.10-4.20 (m, 1H), 4.25-4.40 (m, 1H), 4.50 (s, 2H), 6.00 (s, 2H), 6.20 (d, 1H, J=9.0 Hz), 6.45 (d, 1H, J=9.0 Hz), 6.60 (d, 1H, J=9.0 Hz), 7.47 (t, 1H, J=6.0 Hz), 7.65-8.0 (m, 2H), 9.50 (bs, 1H), 11.11 (bs, 1H), 11.21 (d, 1H J=6.0 Hz); ESI-MS m/z 587.0 (M⁺+1).

2-{4-[(R)-2-hydroxy-3-(4-ethyl-benzo[1,3]dioxol-5-yloxy)-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

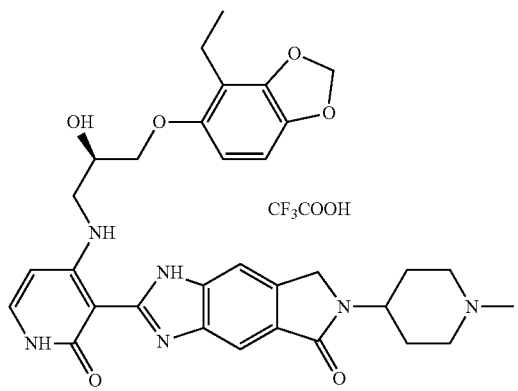 [SMILES: CCc1c(OC[C@H](O)CNc2cc[nH]c(=O)c2-c2nc3cc4c(cc3[nH]2)CN(C2CCN(C)CC2)C4=O)ccc2c1OCO2 ; "CF3COOH"]

Yield: (30 mg, 36%); ¹H NMR (DMSO-d₆) δ 1.13 (t, 3H, J=9.0 Hz), 1.87-2.18 (m, 4H), 2.58 (q, 2H, J=9.0, 15.0 Hz), 2.83 (s, 3H), 3.09-3.38 (m, 2H) 3.43-4.20 (m, 7H), 4.23-4.30 (m, 1H), 4.48 (s, 2H), 5.42 (bs, 1H), 5.98 (s, 2H), 6.21 (d, 1H, J=9.0 Hz), 6.39 (d, 1H, J=9.0 Hz), 6.58 (d, 1H, J=9.0 Hz), 7.39 (t, 1H, J=6.0 Hz), 7.63-8.0 (m, 2H), 9.44 (bs, 1H), 11.14 (bs, 1H), 11.20 (d, 1H, J=6.0 Hz); ESI-MS m/z 601.7 (M⁺+1).

Synthesis of 2-{4-[(R)-3-(2-bromo-4,6-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

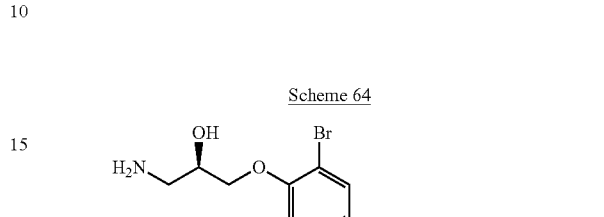

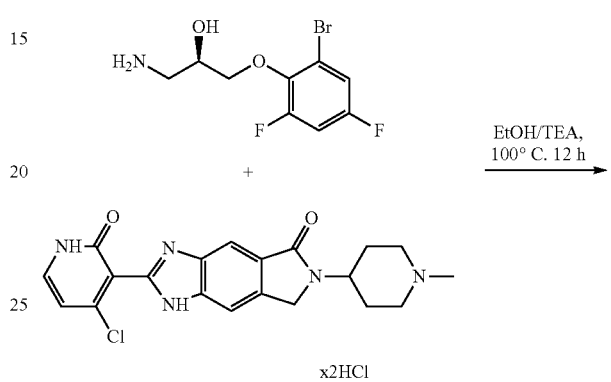

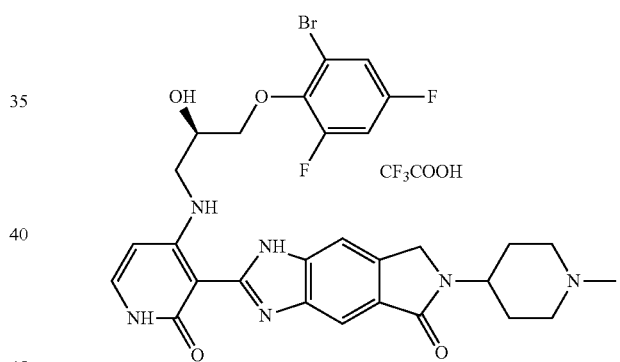

A mixture of 2-(4-chloro-2-oxo-1,2-dihydro-pyridin-3-yl)-6-(1-methyl-piperidin-4-yl)-6,7-dihydro-1H-1,3,6-triaza-s-indacene-5-one dihydrochloride (200 mg, 0.42 mmol), (R)-1-amino-3-(2-chloro-4-methoxyphenoxy)-propan-2-ol (150 mg, 0.53 mmol) and Et₃N (420 µL, 2.9 mmol) in EtOH (3 mL) was heated at 100° C. for 12 h. The reaction mixture was cooled, concentrated and the obtained residue was subjected to HPLC purification to afford the 2-{4-[(R)-3-(2-bromo-4,6-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt (5p) (35 mg, 11%). ¹H NMR (DMSO-d₆) δ 1.85-2.11 (m, 4H), 2.82 (s, 3H), 3.10-3.35 (m, 2H), 3.40-4.15 (m, 7H), 4.18-4.35 (m, 1H), 4.45 (s, 2H), 5.55 (bs, 1H), 6.22 (d, 1H, J=9.0 Hz), 7.30-7.55 (m, 3H) 7.60-8.10 (m, 2H), 9.40 (bs, 1H), 11.13 (bs, 1H), 11.24 (d, 1H, J=9.0 Hz); ESI-MS m/z 643.5 (M⁺) and 645.5 (M⁺+2).

The following compounds were synthesized using above procedure and designated amino alcohol.

2-{4-[(R)-3-(2-bromo-4-fluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

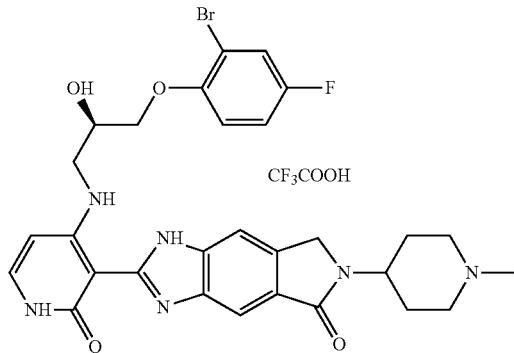 [SMILES: CN1CCC(N2Cc3cc4[nH]c(-c5c(NC[C@@H](O)COc6ccc(F)cc6Br)cc[nH]c5=O)nc4cc3C2=O)CC1 ; "CF3COOH"]

(25 mg, 8.0%). $^1$H NMR (DMSO-d$_6$) δ 1.80-2.10 (m, 4H), 2.80 (s, 3H), 3.11-3.30 (m, 2H), 3.40-4.80 (m, 4H), 4.00-4.20 (m, 3H), 4.26-4.36 (m, 1H), 4.50 (s, 2H), 5.55 (bs, 1H), 6.24 (d, 1H, J=6.0 Hz), 7.10-7.20 (m, 2H), 7.21-7.39 (m, 1H), 7.58-9.7.82 (m, 1H), 7.85-8.0 (m, 2H), 9.45 (bs, 1H), 11.10 (bs, 1H), 11.23 (d, 1H, J=6.0 Hz); ESI-MS m/z 627.3 (M$^+$+2).

2-{4-[(R)-3-(2-bromo-4-methyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

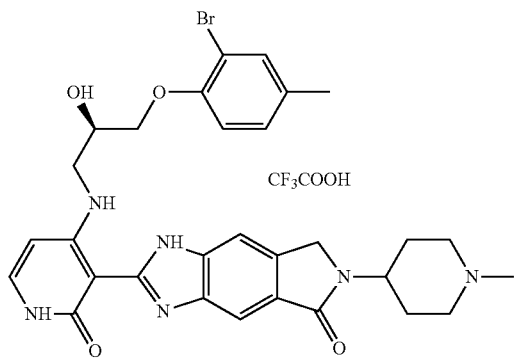 [SMILES: Cc1ccc(OC[C@H](O)CNc2cc[nH]c(=O)c2-c2nc3cc4c(cc3[nH]2)CN(C2CCN(C)CC2)C4=O)c(Br)c1 ; "CF3COOH"]

(28 mg, 9.0%). $^1$H NMR (DMSO-d$_6$) δ 1.90-2.10 (m, 4H), 2.25 (s, 3H), 2.80 (s, 3H), 3.10-3.30 (m, 2H), 3.40-3.75 (m, 4H), 4.05-4.18 (m, 3H), 4.20-4.40 (m, 1H), 4.55 (s, 2H), 5.50 (bs, 1H), 6.23 (d, 1H, J=9.0 Hz), 6.98-7.29 (m, 2H) 7.36-7.48 (m, 2H), 7.58-7.82 (m, 1H), 7.75-7.96 (m, 2H), 9.48 (bs, 1H), 11.11 (bs, 1H), 11.21 (d, 1H, J=6.0 Hz); ESI-MS m/z 621.5 (M$^+$).

2-{4-[(R)-3-(2-bromo-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

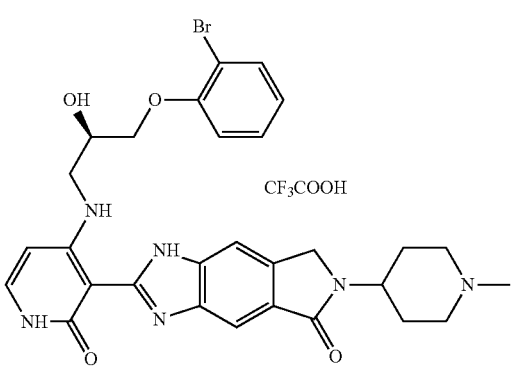 [SMILES: CN1CCC(N2Cc3cc4[nH]c(-c5c(NC[C@@H](O)COc6ccccc6Br)cc[nH]c5=O)nc4cc3C2=O)CC1 ; "CF3COOH"]

(18 mg, 6.0%). $^1$H NMR (DMSO-d$_6$) δ 1.82-2.08 (m, 4H), 2.79 (s, 3H), 3.10-3.25 (m, 2H), 3.40-3.80 (m, 4H), 4.03-4.20 (m, 3H), 4.21-4.35 (m, 1H), 4.55 (s, 2H), 5.50 (bs, 1H), 6.23 (d, 1H, J=6.0 Hz), 6.88-6.93 (m, 1H), 7.06-7.16 (m, 1H), 7.29-7.37 (m, 2H), 7.54-7.61 (m, 1H), 7.70-8.0 (m, 2H), 9.38 (bs, 1H), 11.12 (bs, 1H), 11.31 (d, 1H, J=6.0 Hz); ESI-MS m/z 607.5 (M$^+$), 609.5 (M$^+$+2).

2-{4-[(R)-3-(2-bromo-4,5-difluoro-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

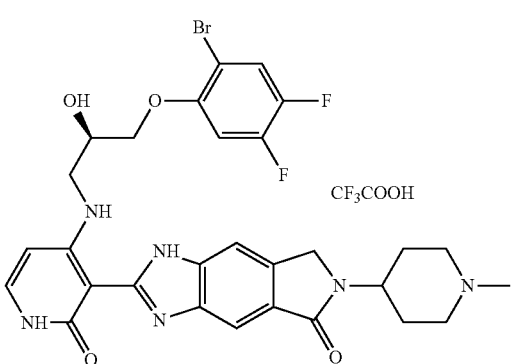 [SMILES: CN1CCC(N2Cc3cc4[nH]c(-c5c(NC[C@@H](O)COc6cc(F)c(F)cc6Br)cc[nH]c5=O)nc4cc3C2=O)CC1 ; "CF3COOH"]

(30 mg, 9.3%). $^1$H NMR (DMSO-d$_6$) δ 1.90-2.10 (m, 4H), 2.80 (s, 3H), 3.10-3.30 (m, 2H), 3.40-3.80 (m, 4H), 4.00-4.20 (m, 3H), 4.22-4.40 (m, 1H), 4.55 (s, 2H), 5.60 (bs, 1H), 6.23

(d, 1H, J=6.0 Hz), 7.25-7.50 (m, 3H), 7.60-8.0 (m, 2H), 9.39 (bs, 1H), 11.12 (bs, 1H), 11.31 (d, 1H, J=6.0 Hz); ESI-MS m/z 643.5 (M+).

2-{4-[(R)-2-hydroxy-3-(4-chloro-benzo[1,3]dioxol-5-yloxy)-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

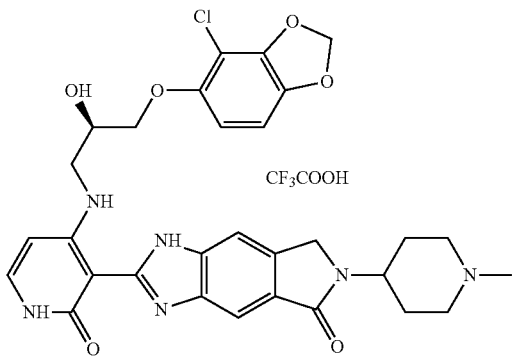 [SMILES: CN1CCC(N2Cc3cc4[nH]c(-c5c(NC[C@@H](O)COc6ccc7c(c6Cl)OCO7)cc[nH]c5=O)nc4cc3C2=O)CC1 ; "CF3COOH"]

(15 mg, 9.3%). $^1$H NMR (DMSO-d$_6$) δ 1.90-2.10 (m, 4H), 2.79 (s, 3H), 3.15-3.35 (m, 2H), 3.40-3.90 (m, 4H), 3.95-4.15 (m, 3H), 4.25-4.42 (m, 1H), 4.47 (s, 2H), 5.55 (bs, 1H), 6.08 (s, 2H), 6.21 (d, 1H, J=9.0 Hz), 6.54 (d, 1H, J=6.0 Hz), 6.79 (d, 1H, J=6.0 Hz), 7.37 (t, 1H, J=6.0 Hz), 7.60-8.0 (m, 2H), 9.45 (bs, 1H), 11.11 (bs, 1H), 11.21 (d, 1H, J=6.0 Hz); ESI-MS m/z 643.5 (M+).

2-{4-[(R)-3-(2-fluoro-2,4-dimethyl-phenoxy)-2-hydroxy-propylamino]-2-oxo-1,2-dihydro-pyridin-3-yl}-6-(1-methyl-piperidin-4-yl)-6,7-dihydro-1H-1,3,6-triaza-s-indacen-5-one trifluoroacetic acid salt

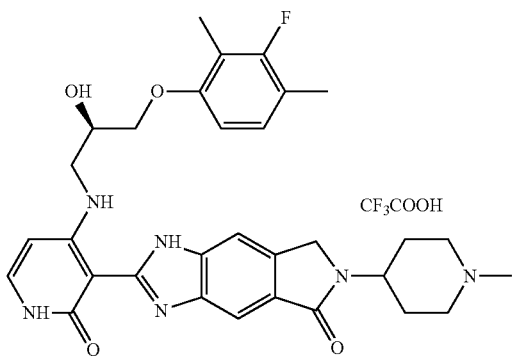 [SMILES: Cc1ccc(OC[C@H](O)CNc2cc[nH]c(=O)c2-c2nc3cc4c(cc3[nH]2)CN(C2CCN(C)CC2)C4=O)c(C)c1F ; "CF3COOH"]

(22 mg, 7.5%). $^1$H NMR (DMSO-d$_6$) δ 1.85-2.08 (m, 4H), 2.13 (s, 3H), 2.16 (s, 3H), 2.74 (s, 3H), 3.08-3.30 (m, 2H), 3.42-3.62 (m, 3H), 3.65-3.75 (m, 1H), 3.90-4.10 (m, 3H), 4.22-4.35 (m, 1H), 4.48 (s, 2H), 5.55 (bs, 1H), 6.22 (d, 1H, J=9.0 Hz), 6.73 (d, 1H, J=9.0 Hz), 7.01 (t, 1H, J=9.0 Hz), 7.37 9 (t, 1H, J=6.0 Hz), 7.60-7.95 (m, 2H), 9.48 (bs, 1H), 11.12 (bs, 1H), 11.23 (d, 1H, J=6.0 Hz); ESI-MS m/z 575.8 (M++1).

Synthesis of 4-methyl-benzo[1,3]dioxol-5-ol

Scheme 65

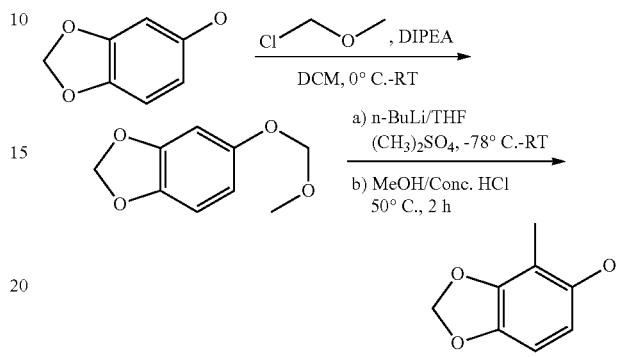

To a 0° C. cooled solution of benzo[1,3]dioxol-5-ol (1) (42.88 g, 310.52 mmol) and diisopropyl ethylamine (75.0 g g, 584.7 mmol) in dichloromethane (400 mL) was slowly added methoxymethyl chloride (50.0 g, 621.04 mmol) and stirred at room temperature for throughnight. The reaction mixture was washed with water (3×200 mL), 10% sodium hydroxide (100 mL) and then with water (100 mL). The organic layer was dried and concentrated to give 5-methoxymethoxy-benzo[1,3]dioxole. (2) (43.0 g, 74.3%) as an oil. $^1$H NMR (CDCl$_3$) δ 3.39 (s, 3H), 5.07 (s, 2H), 5.89 (s, 2H), 6.48 (dd, 1H, J=3.0 Hz, 9.0 Hz), 6.61 (d, 1H, J=3.0 Hz), 6.69 (d, 1H, J=9.0 Hz).

Synthesis of 4-methyl-benzo[1,3]dioxol-5-ol: To a cooled (−78° C.) solution of 5-methoxymethoxy-benzo[1,3]dioxole (5.0 g, 27.35 mmol) in THF (25 mL) was slowly added 2.5 M solution of n-BuLi in hexane and stirred at nitrogen atmosphere. After 30 minutes, dimethyl sulphate (6.90 g, 54.7 mmol) was added and then resulting mixture was allowed to warm to room temperature and stirred for 7 h. The reaction was diluted with water (50 mL) and extracted with ethyl acetate (2×50 mL). The organic layer was dried (Na$_2$SO$_4$) and concentrated under vacuum to get crude product. The obtained product was dissolved in methanol (50 mL) and 0.5 mL conc. HCl and then heated at 50° C. for 2 h. The reaction was concentrated, dissolved in ethyl acetate (50 mL) and washed with saturated sodium bicarbonate. The solvent was evaporated under vacuum to give crude product. Silica gel column chromatography (30% CH$_2$Cl$_2$/Hexane) gave 4-methyl-benzo[1,3]dioxol-5-ol (3a) (3.0 g, 72%). $^1$H NMR (CDCl$_3$) δ 2.13 (s, 3H), 4.60 (s, 1H), 5.95 (s, 2H), 6.25 (d, 1H, J=6.0 Hz), 6.52 (d, 1H, J=6.0 Hz).

Synthesis of 4-ethyl-benzo[1,3]dioxol-5-ol

Scheme 66

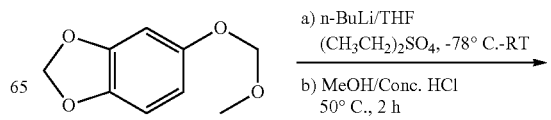

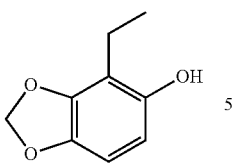

To a cooled (−78° C.) solution of 5-methoxymethoxy-benzo[1,3]dioxole (5.0 g, 27.35 mmol) in THF (25 mL) was slowly added 2.5 M solution of n-BuLi in hexane and stirred at nitrogen atmosphere. After 30 minutes, diethyl sulphate (8.43 g, 54.7 mmol) was added and then resulting mixture was allowed to warm to room temperature and stirred for 7 h. The reaction was diluted with water (50 mL) and extracted with ethyl acetate (2×50 mL). The organic layer was dried ($Na_2SO_4$) and concentrated under vacuum to get crude product. The obtained product was dissolved in methanol (50 mL) and 0.5 mL conc. HCl and then heated at 50° C. for 2 h. The reaction was concentrated, dissolved in ethyl acetate (50 mL) and washed with saturated sodium bicarbonate. The solvent was evaporated under vacuum to give crude product. Silica gel column chromatography (30% $CH_2Cl_2$/Hexane) gave 4-ethyl-benzo[1,3]dioxol-5-ol (3b) (2.8 g, 61%). $^1$H NMR ($CDCl_3$) δ 1.22 (t, 3H, J=9.0 Hz), 2.62 (q, 2H, J=9.0, 15.0 Hz) 4.45 (bs, 1H), 5.90 (s, 2H), 6.22 (d, 1H, J=6.0 Hz), 6.52 (d, 1H, J=6.0 Hz).

Synthesis of 4-chloro-benzo[1,3]dioxol-5-ol

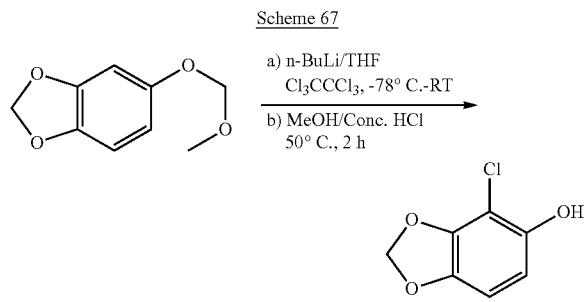

To a cooled (−78° C.) solution of 5-methoxymethoxy-benzo[1,3]dioxole (5.0 g, 27.35 mmol) in THF (25 mL) was slowly added 2.5 M solution of n-BuLi in hexane and stirred at nitrogen atmosphere. After 30 minutes, a solution of hexachloroethane (12.95 g, 54.7 mmol) in THF (25 mL) was added and then resulting mixture was allowed to warm to room temperature and stirred for 7 h. The reaction was diluted with water (50 mL) and extracted with ethyl acetate (2×50 mL). The organic layer was dried ($Na_2SO_4$) and concentrated under vacuum to get crude product. The obtained product was dissolved in methanol (50 mL) and 0.5 mL conc. HCl and then heated at 50° C. for 2 h. The reaction was concentrated, dissolved in ethyl acetate (50 mL) and washed with saturated aqueous sodium bicarbonate. The solvent was evaporated under vacuum to give crude product. Silica gel column chromatography (30% $CH_2Cl_2$/Hexane) gave 4-chloro-benzo[1,3]dioxol-5-ol (3c) (2.5 g, 53%). $^1$H NMR ($CDCl_3$) δ 5.12 (s, 1H), 6.0 (s, 2H), 6.47 (d, 1H, J=9.0 Hz), 6.62 (d, 1H, J=9.0 Hz).

Synthesis of 3-fluoro-2,4-dimethylphenol

Scheme 68

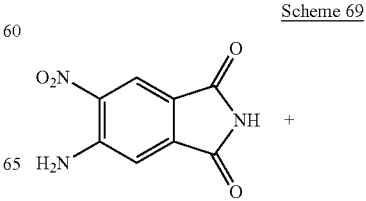

To a cooled (0° C.) solution of 2,2,6,6-tetramethylpiperidine (1.10 g, 7.84 mmol) in THF (5 mL) was slowly added 2.5 M solution of n-BuLi in hexane (3.1 mL) and stirred for 15 minutes. The reaction mixture was cooled to −78° C. and then a solution of 2-fluoro-4-methoxy-1-methyl-benzene (4) (1.0 g, 27.35 mmol) in THF (5 mL) was added. After stirring 20 minutes, methyl iodide (2.0 g 14.16 mmol) was added and the resulting mixture was allowed to warm to 0° C. through a period of 3 h. The reaction was diluted with 1 N HCl (15 mL) and extracted with ether (3×25 mL). The organic layer was dried ($Na_2SO_4$) and distilled out to get crude product. The obtained product was dissolved in dichloromethane (30 mL) and cooled to −78° C. Boron tribromide (4.0 g, 15.9 mmol) was slowly added and then mixture was allowed to warm to 0° C. After 5 h, the reaction was slowly poured in to ice water (25 mL) and extracted with dichloromethane (2×30 mL). The organic extracts were dried and solvent was evaporated at low temperature (20° C.) and vacuum to a residue. Flash column chromatography (30% $CH_2Cl_2$/Hexane) of the crude product gave 3-fluoro-2,4-dimethyl-phenol (3d) (0.65 g, 65%). $^1$H NMR ($CDCl_3$) δ 2.14 (s, 3H), 2.15 (s, 3H), 4.81 (s, 1H), 6.45 (d, 1H, J=9.0 Hz), 6.84 (t, 1H, J=9.0 Hz).

Synthesis of N-alkylated nitro-amino-phthalimide

Synthesis 5-Amino-6-nitro-2-(2-pyrrolidin-1-yl-ethyl)-1H-isoindole-1,3(2H)-dione Scheme 69

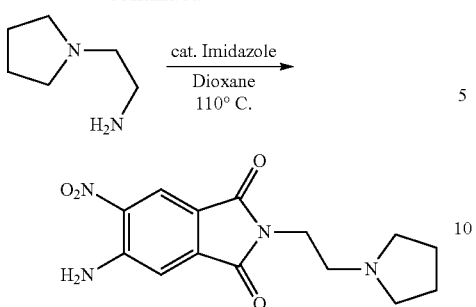

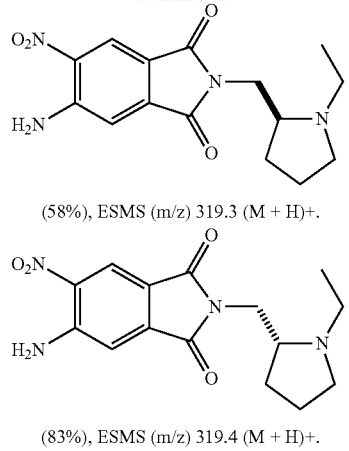

(58%), ESMS (m/z) 319.3 (M + H)+.

(83%), ESMS (m/z) 319.4 (M + H)+.

A mixture containing phthalimide (1; 2 g, 9.7 mmol, 1.0 eq.), 2-pyrrolidin-1-ylethanamine (2a, 1.1 g, 9.7 mmol, 1.0 eq.) and imidazole 0.17 g, 2.43 mmol, 0.25 eq.) in dioxane (40 mL) was heated in a capped vial at 110° C. for 14 h. Additional 0.25 eq. of imidazole was added and reaction heated for 24 h. The mixture was cooled to room temperature and concentrated in vacuo to a solid which was used as such in the next step.

The following compounds were prepared using either of the above methods.

Synthesis of Tricyclic Halopyridones 2-(4-Iodo-2-methoxypyridin-3-yl)-6-(3-pyrrolidin-1-ylpropyl)imidazo[4,5-f]isoindole-5,7(1H,6H)-dione

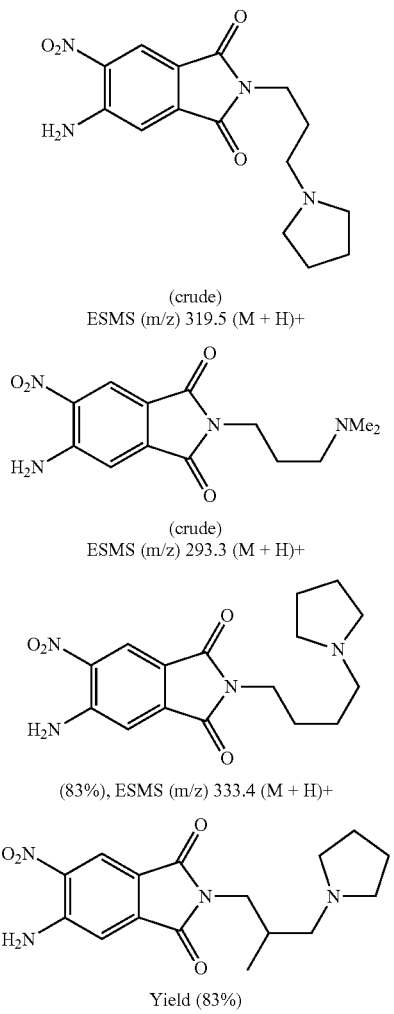

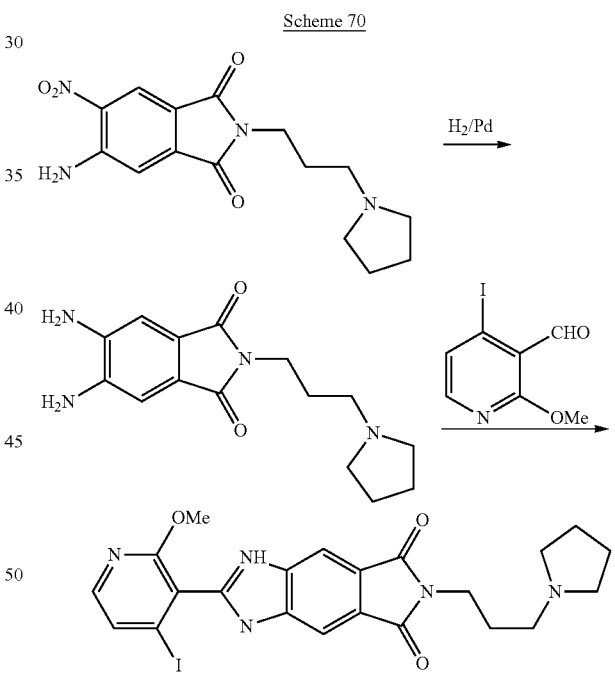

Pd/C (250 mg) was added to a solution of crude 5-amino-6-nitro-2-(3-(pyrrolidin-1-yl)propyl)isoindoline-1,3-dione in MeOH/AcOH (100 mL/5 mL) and hydrogenated for 5 h. The mixture was filtered through Celite and the filtrate was treated with 4-iodo-2-methoxynicotinaldehyde (3.2 g, 12.07 mmol) and stirred at ambient temperature open to air for 12 h and at 80° C. for 5 h. The reaction mixture was cooled to ambient temperature and concentrated in vacuo to dryness. Purification by flash chromatography gave the title 5,6-diamino-2-(3-(pyrrolidin-1-yl)propyl)isoindoline-1,3-dione as a solid (2.02 g, 32% through 4 steps). $^1$H NMR (MeOD): δ 8.15 (s, 2H), 8.01-8.08 (t, J=3 Hz 1H), 7.64 (t, J=3 Hz, 1H), 3.89-3.78 (m, 2H), 3.41-3.22 (m, 2H), 2.95-2.81 (m, 6H), 2.15-1.82 (m, 7H). ESMS (m/z) 532 (M+H)⁺.

2-(4-Halo-2-oxo-1,2-dihydropyridin-3-yl)-6-(3-pyrrolidin-1-ylpropyl)imidazo[4,5-f]isoindole-5,7(1H,6H)-dione dihydrochloride Scheme 71

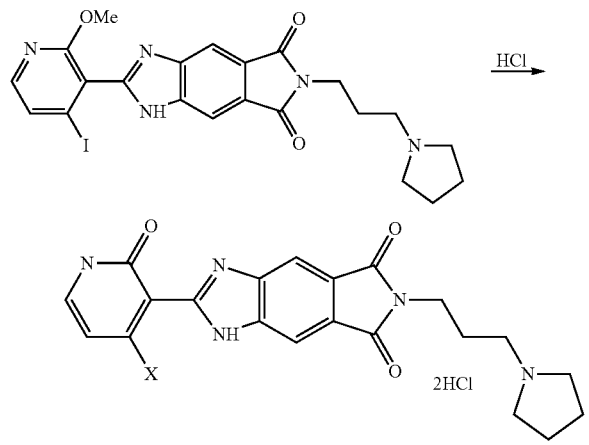

X = Cl or I

A mixture of conc. HCl (6 mL) and iodo-methoxypyridine derivative (1.97 g, 33.7 mmol) in 45 mL of dioxane was stirred at ambient temperature protected from light for 30 h. THF (25 mL) was added to the reaction mixture and the solid was isolated by filtration, washed with Et₂O (4×15 mL), dried at 45° C. in a vacuum oven to afford the title compound as a light chocolate colored solid (1.82 g). ¹H NMR (MeOH-d₄): δ 12.74 (br s, 1H), 10.60 (br s, 1H), 8.14 (s, 2H), 7.73 (d, J=9 Hz, 1H), 6.65 (d, J=9 Hz, 1H), 3.72-3.64 (m, 1H), 3.51-3.43 (m, 1H), 3.21-3.15 (m, 1H), 2.99-2.93 (m, 1H), 2.07-1.82 (m, 3H). ESMS (m/z) 426.1 (M+H)⁺ for X=Cl and 518.2 (M+H)⁺ for X=I.

Synthesis of Tricyclic Phthalimides

Scheme 72

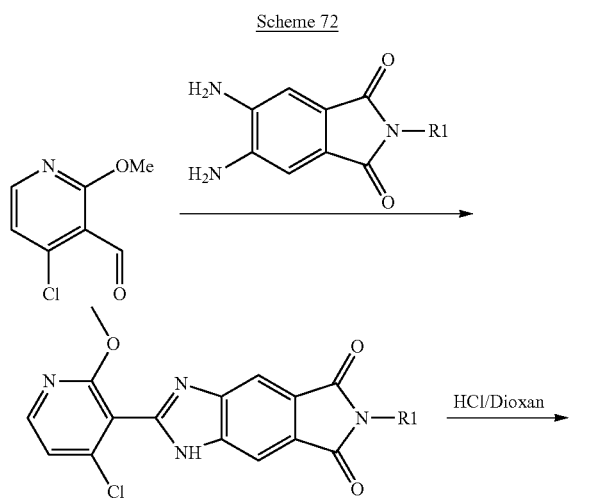

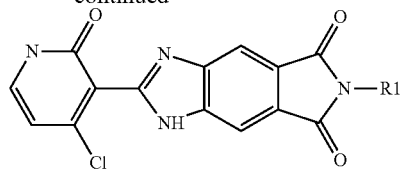

The following compounds were synthesized by this methodology:

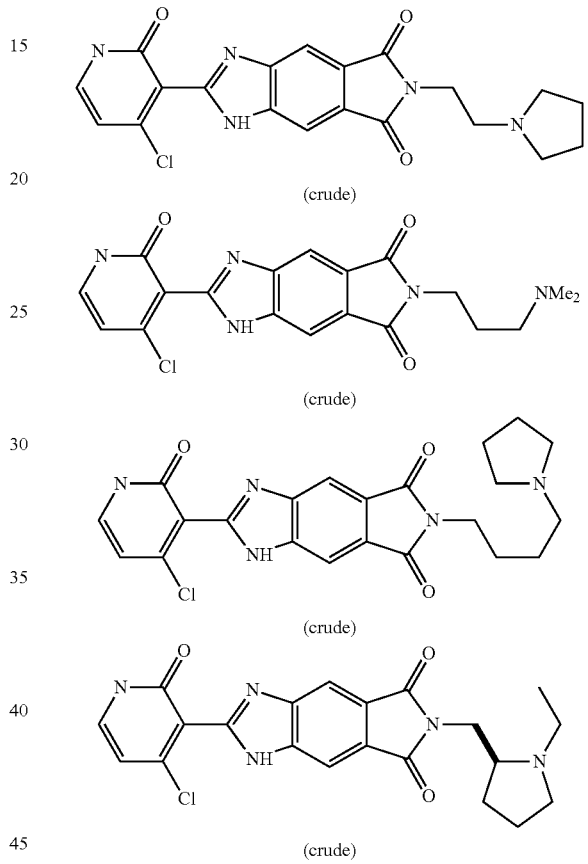

The above tricyclic phthalimides were prepared form the corresponding diamines and 4-chloro-2-methoxypyridine-3-carboxaldehyde by application of the general procedure, such as A above, or B below.

Synthesis of 4-chloro-2-methoxypyridine-3-carboxaldehyde

Scheme 73

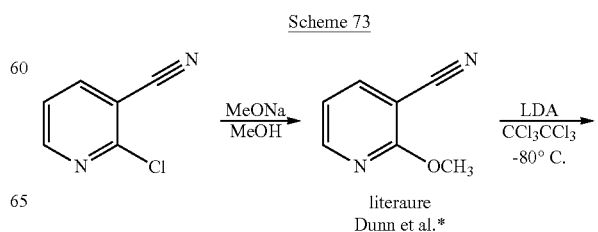

literaure
Dunn et al.*

365

-continued

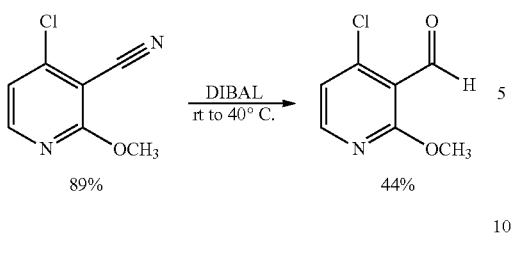

2-Methoxy-nicotinonitrile

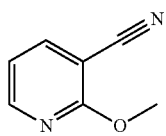

2-Methoxy-nicotinonitrile was prepared according to the literature by reaction of the 2-chloro-nicotinonitrile with MeONa in MeOH according to Dunn, A. D.; Norrie, R.; Heterocycl. Chem.; EN; 24; 1987; 85-89.

4-Chloro-2-methoxy-nicotinonitrile
(4-chloro-2-methoxy-3-cyanopyridine

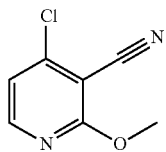

The mixture of 210 mL of THF and 18 mL of diisopropylamine (0.13 mol), degassed with nitrogen gas in an ultrasonic bath and was cooled to −78° C. Then 1.6M BuLi (81 mL, 0.13 mol) was added dropwise. The mixture was stirred at this temperature for 30 min, then cooled to −85° C. and a solution of 2-methoxy-nicotinonitrile (15.9 g, 0.119 mol) in 100 mL of degassed anhydrous THF was added dropwise. After 1 h of stirring at −80° C., a solution of hexachloroethane (56.9 g, 0.240 mol) in 200 mL of THF was added causing the temperature to rise to −40° C. The cooling bath was removed and stirred for 15 min. The reaction mixture was poured into water and extracted with ethyl acetate (2×200 mL). The extract was dried through sodium sulfate, filtered through silicagel, and evaporated under vacuum. The resulting residue was purified by column chromatography (silicagel, EtOAc/hexane, 2:1) to give 89% of product. NMR $^1$H (DMSO $d_6$, 8 ppm): 8.44 (d, 1H 6-H, J=5.5 Hz); 7.42 (d, 1H, 5-H, J=5.5 Hz); 4.02 (s, 3H, CH$_3$O).

366

4-Chloro-2-methoxy-pyridine-3-carbaldehyde
(4-Chloro-2-methoxynicotinonitrile)

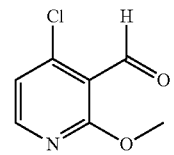

To the solution of the nitrile (2.0 g, 0.0118 mol) in 20 mL of THF was added 1.5M DIBAL in toluene (16 mL, 2.1 eq.) at room temperature. This caused the temperature to rise to 40° C. The mixture is stirred for 1.5 h and poured in portions into a solution of 3.5 mL of acetic acid in 50 mL of water. After the gas evolution ceased, the mixture was extracted first with hexane/THF (1:1), then with ethyl acetate. The combined extracts were dried through sodium sulfate, evaporated under vacuum; and the residue was purified by column (silicagel, hexane/EtOAc) to give 900 mg (44%) of the product. NMR $^1$H(CDCl$_3$, 8 ppm): 10.30 (s. 1H, CHO); 8.34 (d, 1H 6-H, J=5.6 Hz); 7.24 (d, 1H, 5-H, J=5.6 Hz); 3.99 (s, 3H, CH$_3$O).

Synthesis Of Tricyclic Halopyridones

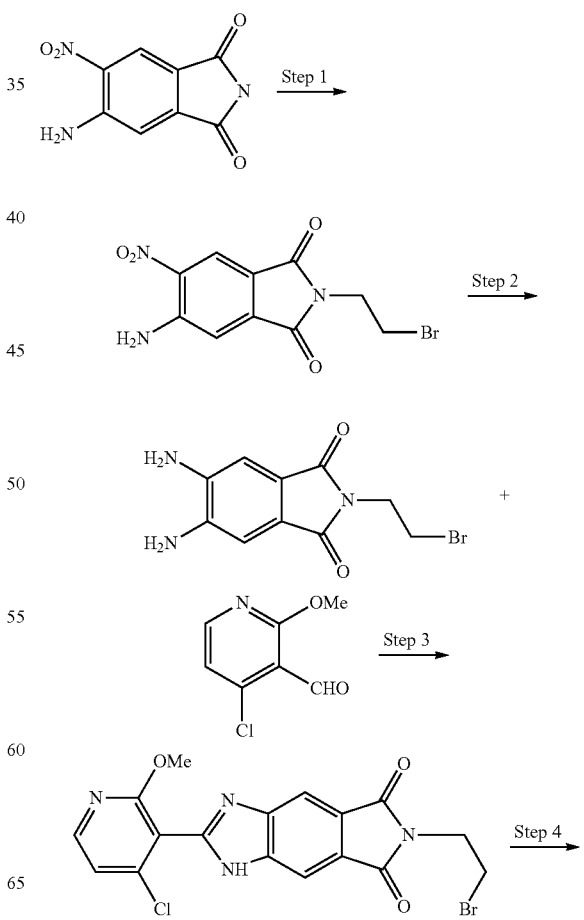

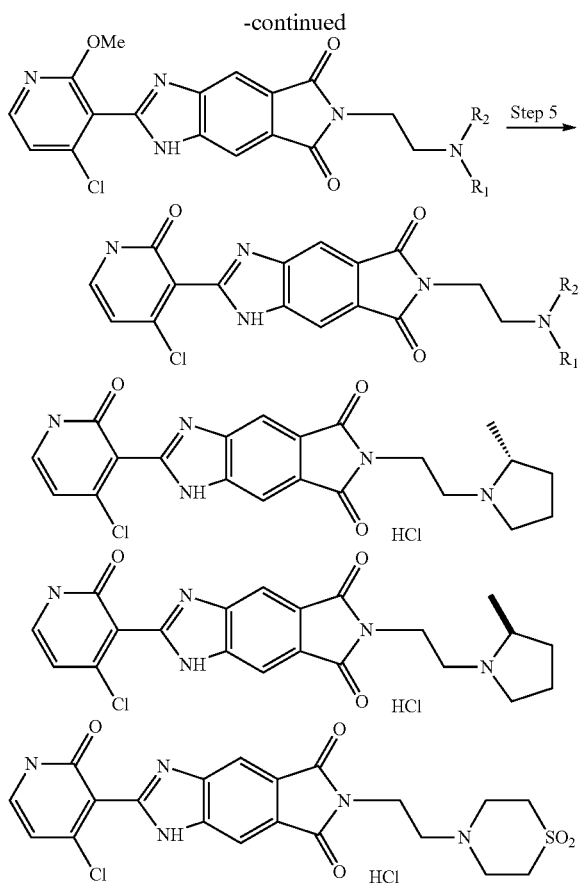

Step 1: NaH (2.05 g, 60 wt % dispersion in oil, 5.13 mmol, 1.06 eq.) was added portion wise to a solution of the phthalimide (10.0 g, 48.3 mmol, 1.0 eq.) in degassed DMF (50 mL) and heated at 60° C. for 45 min. The mixture was cooled to room temperature and stirred throughnight. Then, a solution of dibromoethane (18.1 g, 96.6 mmol) in acetone (50 mL) was added drop wise. The cake was broken up and thick slurry was refluxed throughnight. The reaction mixture was cooled to room temperature and filtered. The filtrate was concentrated in vacuo to a residual oil. The filter cake was washed with MeOH and filtered into the residual oil. Additional MeOH was added and the yellow powder obtained was isolated and washed with hexanes to afford 10.14 g (67%) of the desired product. The filtrate cake was taken up in EtOAc (100 mL) and washed with water (50 mL). The aqueous layer was back extracted with EtOAc (50 mL). The organic extracts were combined, dried (Na$_2$SO$_4$), filtered and concentrated in vacuo to afford a yellow solid (2.11 g, 14%) after drying in an oven under high vacuum. Throughall yield (12.26 g, 81%). $^1$H NMR (DMSO-d$_6$) 8.45 (br s, 2H) 8.35 (s, 1H), 7.48 (s, 1H), 3.96 (t, J=6.33 Hz, 2H), 3.70 (t, J=6.33 Hz, 2H).

Step 2: A mixture of the bromophthalimide (1.0 g, 3.2 mmol), AcOH (10 drops) in MeOH (15 mL) was hydrogenated at atmospheric pressure and ambient temperature for 3 h. The mixture was filtered through Celite, Celite was washed well with MeOH, and the filtrate was concentrated in vacuo to afford a residual solid (840 mg; 92%). $^1$H NMR (CDCl$_3$) 7.11 (s, 2H), 4.02 (t, J=6.72 Hz, 2H), 3.86 (br s, 4H), 3.57 (t, J=6.72 Hz, 2H).

Step 3: Aldehyde (508 mg, 2.96 mmol, 1.0 eq.) was added to a heterogeneous mixture of the diaminophthalimide (840 mg, 2.96 mmol, 1.0 eq.) in MeOH/AcOH (3/1; 40 mL) and stirred at ambient temperature for 48 h. The reaction mixture was concentrated in vacuo to a residual solid and purified by flash chromatography (R$_f$=0.30; 20% EtOAc/DCM) to isolate fractions corresponding to the desired product (1.25 g, 97%, 84% pure). $^1$H NMR (CDCl$_3$) 10.90 (br s, 1H), 8.18 (d, J=5.5 Hz, 1H), 7.15 (d, J=5.5 Hz, 1H), 4.15 (t, J=6.7 Hz, 2H), 3.65 (t, J=6.7 Hz, 2H). ESMS (m/z) 435.

Step 4: Bromoethylphthalimide (1 eq.) and the secondary amine (3.0 eq.) [Note: 1.2 eq. of powdered K$_2$CO$_3$ was added if secondary amine was HCl salts) in degassed, anhydrous DMF (0.13 M solution) and heated in capped vial at 75-80° C. for 6-48 h. The desired products were purified by flash chromatography to afford products as shown below.

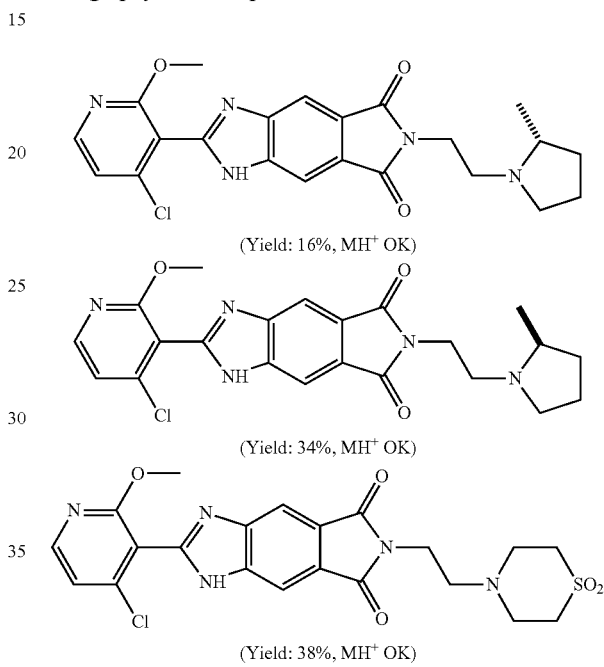

Analytical data for 2-(4-Chloro-2-methoxypyridin-3-yl)-6-{2-[(2S)-2-methylpyrrolidin-1-yl]ethyl}imidazo[4,5-f]isoindole-5,7(1H,6H)-dione.

$^1$H NMR (CDCl$_3$) 8.28 (br s, 1H), 8.17 (d, J=5.5 Hz, 1H), 8.02 (br s, 1H), 7.14 (d, J=5.5 Hz, 1H), 4.01 (s, 3H), 3.41-3.09 (m, 2H), 2.47-2.19 (m, 3H), 1.91-1.78 (m, 1H), 1.65-1.52 (m, 1H), 1.45-1.29 (m, 1H), 1.25 (br s, 1H), 1.19-1.17 (m, 1H), 1.03 (d, J=3.3 Hz, 3H) 0.91-0.72 (m, 1H). ESMS (m/z) 440.91.

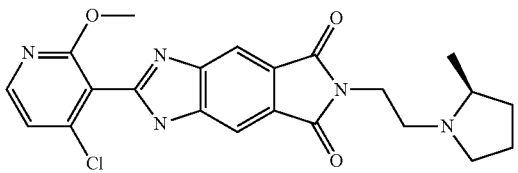 [SMILES: COc1nccc(Cl)c1-c1nc2cc3c(cc2[nH]1)C(=O)N(CCN1CCC[C@@H]1C)C3=O]

Analytical data for 2-(4-Chloro-2-methoxypyridin-3-yl)-6-[2-(1,1-dioxidothiomorpholin-4-yl)ethyl]imidazo[4,5-f]isoindole-5,7(1H,6H)-dione.

$^1$H NMR (MeOH-d$_4$) 8.32 (d, J=5.6 Hz, 1H), 8.14 (s, 2H), 7.29 (d, J=5.6 Hz, 1H), 4.05-3.94 (m, 5H), 3.53-3.37 (m, 4H), 3.29-3.10 (m, 6H). ESMS (m/z) 490.3.

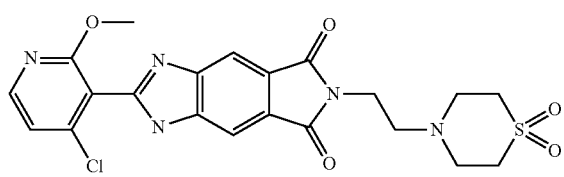 [SMILES: COc1nccc(Cl)c1-c1nc2cc3c(cc2[nH]1)C(=O)N(CCN1CCS(=O)(=O)CC1)C3=O]

Step 5: The crude product from Step 4 above was dissolved in dioxane/con HCl (5/1) and stirred at ambient temperature throughnight. The reaction mixture was concentrated in vacuo to dryness, azeotroped with EtOH (2×) to obtain the corresponding monoHCl salts as a powder. These were used in the next steps as such.

Synthesis of Lactam Containing Chloropyridones

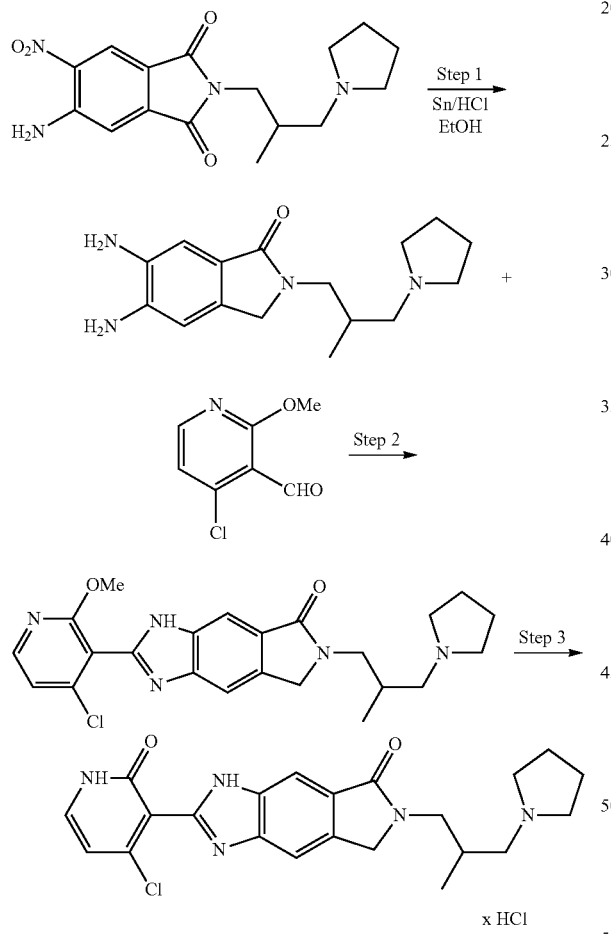

Step 1: Tin powder (1.96 g, 16.5 mmol, 10.0 eq.) was added to a solution of nitro-aminophthalimide derivative [5-amino-2-(substituted)-6-nitroisoindoline-1,3-dione](550 mg, 1.65 mmol) in EtOH (7 mL)/con HCl (1.7 mL) and refluxed for 24 h. Another batch of tin powder (1.96 g, 16.5 mmol) and con Hcl (1.7 mL) were added and reflux continued for 15 h. The reaction mixture was decanted to remove tin, and concentrated in vacuo to a residue. The residue was dissolved in MeOH and conc. aq. NH₄OH was added until no more precipitation was observed. The reaction mixture was filtered and silica gel was added to the filtrate and concentrated in vacuo. The residue was adsorbed on silica gel and purified by flash chromatography [10% (5% aq. NH₄OH/MeOH)/DCM; $R_f$=0.32] to afford the desired product as a thick yellow oil (314 mg, 66%).

Step 2: A solution of the aldehyde (189 mg, 1.1 mmol, 1.0 eq.) in MeOH (10 mL) was added drop wise to a 0-5° C. solution of the lactam (0.31 g, 1.1 mmol; from step 1) in MeOH (10 mL) and stirred at room temperature for 14 h and at 50° C. for Id. The reaction mixture was filtered through Celite, and the filtrate was concentrated in vacuo to a residue and purified by flash chromatography [10% (5% aq. NH₄OH/MeOH)/DCM; $R_f$=0.40) to isolate fractions corresponding to the desired product. The isolated product was used as such in the next step.

Step 3: Con HCl (0.8 mL) was added to a solution of the product from step 2 (225 mg, 0.51 mmol) in dioxane (3 mL) and stirred at ambient temperature throughnight and at 60° C. for 2 h. The reaction mixture was concentrated in vacuo to dryness to afford 279 mg of the desired product as a grey solid. ESMS (m/z) 426.4. This was used as such in the next steps.

In a similar fashion was synthesized 2-(4-Chloro-2-oxo-1,2-dihydropyridin-3-yl)-6-{[(2R)-1-ethylpyrrolidin-2-yl]methyl}imidazo[4,5-f]isoindole-5,7(1H,6H)-dione

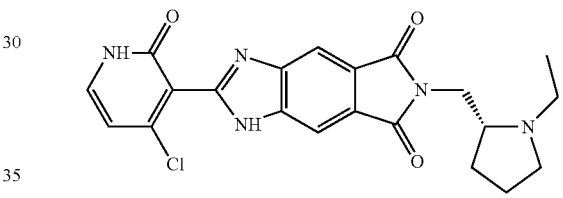

Synthesis of Aryloxypropanolamine Containing Phthalimides 2-(4-{[(2R)-3-(2,4-dimethylphenoxy)-2-hydroxypropyl]amino}-2-oxo-1,2-dihydropyridin-3-yl)-6-(3-pyrrolidin-1-ylpropyl)imidazo[4,5-f]isoindole-5,7(1H,6H)-dione Scheme 76

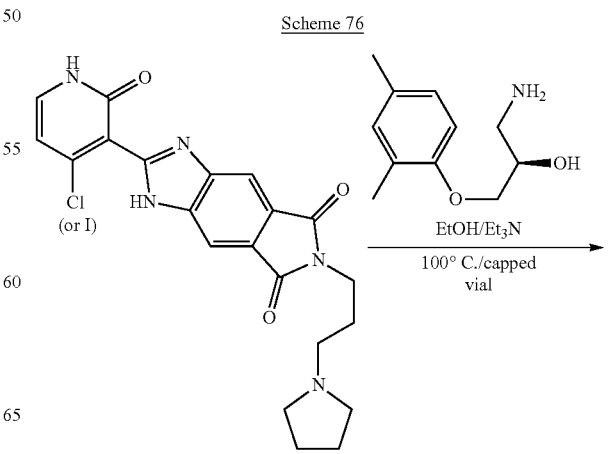

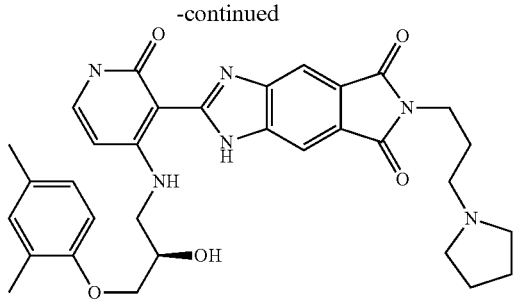

(2R)-1-amino-3-(2,4-dimethylphenoxy)propan-2-ol (75 mg, 0.38 mmol, 1.2 eq.) was added to a solution of the halo-pyridone (150 mg, 0.32 mmol, 1.0 eq.) and $Et_3N$ (150 µL, 1.05 mmol, 3.3 eq.) and heated at 100° C. for 2 h and stirred at ambient temperature throughnight. The reaction mixture was filtered and the solid was dried in a vacuum oven at 40° C. throughnight to afford the title compound as a tan colored powder (87 mg, 47%). $^1$H NMR (DMSO-$d_6$): δ 13.42 (s, 1H), 11.31 (br s, 1H), 10.97 (t, J=5.3 Hz, 1H), 8.12 (s, 1H), 7.67 (s, 1H), 7.39 (d, J=5.7 Hz, 1H), 6.97 (s, 1H), 6.92 (d, J=7.7 Hz, 1H), 6.80 (d, J=8.7 Hz, 1H), 6.22 (d, J=7.5 Hz, 1H), 5.55 (d, J=5.1 Hz, 1H), 4.11-3.85 (m, 3H), 3.80-3.51 (m, 3H), 3.16 (d, J=4.5 Hz, 2H), 3.21-2.56 (m, 4H), 2.21 (s, 3H), 2.19 (s, 3H), 1.91-1.78 (m, 2H), 1.65 (br s, 3H), 1.46-0.99 (m, 2H). ESMS (m/z) 585.5 (M+H)$^+$ 2-(4-{[(2R)-3-(2,4-dimethylphenoxy)-2-hydroxypropyl]amino}-2-oxo-1,2-dihydropyridin-3-yl)-6-(2-pyrrolidin-1-ylethyl)imidazo[4,5-f]isoindole-5,7(1H,6H)-dione Prepared by application of the above methodology.

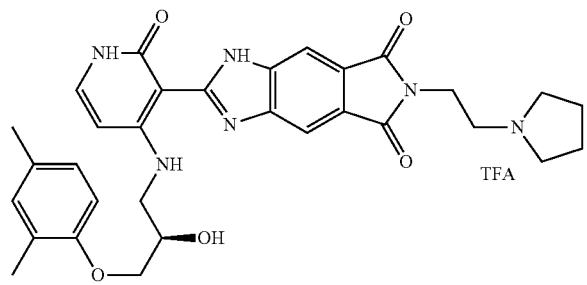 [SMILES: Cc1ccc(OC[C@H](O)CNc2cc[nH]c(=O)c2-c2nc3cc4c(cc3[nH]2)C(=O)N(CCN2CCCC2)C4=O)c(C)c1]

Purified by HPLC; Yield 26%; ESMS (m/z) 571.5

Synthesis of Aryloxypropanolamine Containing Lactams 2-(4-{[(2R)-3-(2-Ethyl-4-methylphenoxy)-2-hydroxypropyl]amino}-2-oxo-1,2-dihydropyridin-3-yl)-6-(1-methylpiperidin-4-yl)-6,7-dihydroimidazo[4,5-f]isoindol-5(3H)-one Zn (246 mg, 3.8 g atoms, 23.3 eq.) was added to a solution of the phthalimide derivative (95 mg, 0.163 mmol) in glacial acetic acid (~2 mL) and heated at 120° C. (bath) for 2 h. Reaction mixture was cooled to ambient temperature and the mixture was filtered through Celite. Celite, washed with MeOH (3×10 mL) and the filtrate was concentrated in vacuo and azeotroped with toluene (3×15 mL). Flash chromatography purification of the resultant residue [10% (5% aq. $NH_4OH$/MeOH)/DCM] afforded the desired compound as a cream solid (41 mg, 44%). $R_f$=0.40; more polar of the two UV and fluorescent spots of the crude material. $^1$H NMR (DMSO-$d_6$): δ 12.62 (s, 1H), 11.27 (br s, 1H), 11.06 and 10.75 (br singlets, 1H), 7.93 and 7.87 (s, 1H), 7.1629 (br s, 1H), 6.99-6.92 (m, 1H), 6.76 (d, J=7.1 Hz, 1H), 6.07 (br s, 1H), 4.55-4.35 (m, 2H), 4.18-4.07 (m, 2H), 3.80-3.51 (m, 2H), 3.21-3.05 (br s, 2H), 2.71-2.59 (m, 2H), 2.58-2.38 (m, 5H), 2.29-2.59 (m, 4H), 2.40-1.98 (m, 5H), 1.98-1.78 (m, 3H), 1.31-1.05 (m, 3H). ESMS (m/z) 571.5 (M+H)$^+$.

The following were prepared by application of the above methodology:

2-(4-{[(2R)-3-(2,4-Dimethylphenoxy)-2-hydroxypropyl]amino}-2-oxo-1,2-dihydropyridin-3-yl)-6-(2-pyrrolidin-1-ylethyl)-6,7-dihydroimidazo[4,5-f]isoindol-5(3H)-one (46a) ESMS (m/z) 557.5 (M+H$^+$); Yield (48%); purity 100%

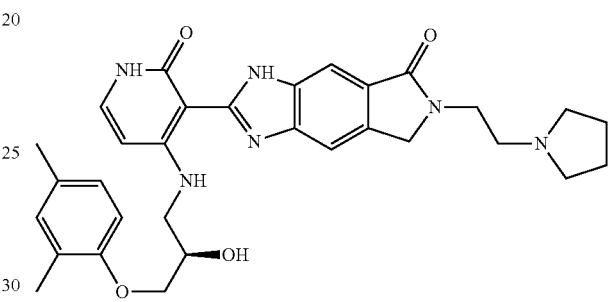

Prepared by Zn/AcOH reduction outlined above.

(R)-2-(4-(3-(2,4-dimethylphenoxy)-2-hydroxypropylamino)-2-oxo-1,2-dihydropyridin-3-yl)-6-(3-(pyrrolidin-1-yl)propyl)-6,7-dihydroimidazo[4,5-f]isoindol-5 (1H)-one Scheme 77

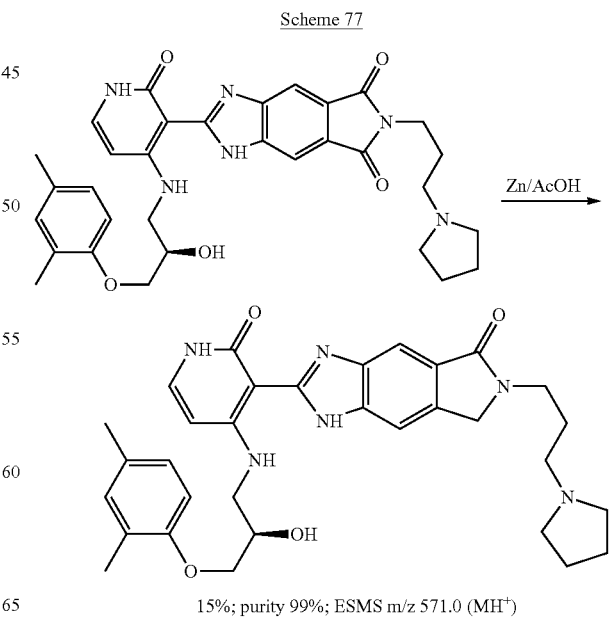

15%; purity 99%; ESMS m/z 571.0 (MH$^+$)

373

The O-acetate was also formed in the reaction:

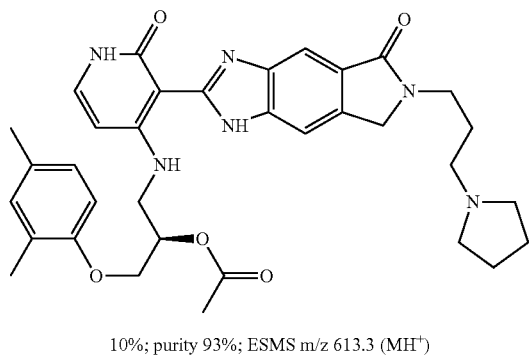 [SMILES: CC(=O)O[C@H](CNc1cc[nH]c(=O)c1-c1nc2cc3c(cc2[nH]1)CN(CCCN1CCCC1)C3=O)COc1ccc(C)cc1C]

10%; purity 93%; ESMS m/z 613.3 (MH+)

Chlorinated Compounds

Scheme 78

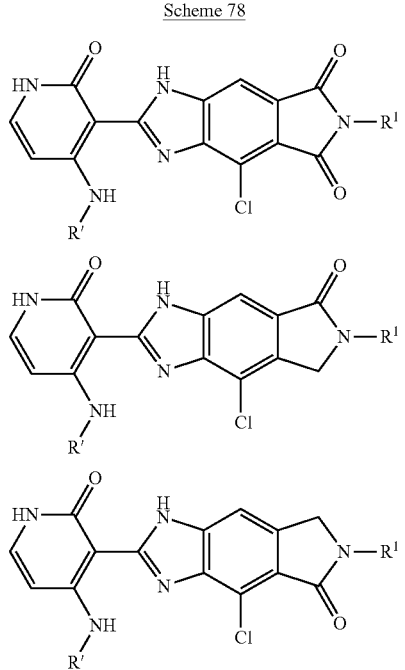

The synthesis of the above presented compounds is described in Scheme 78.

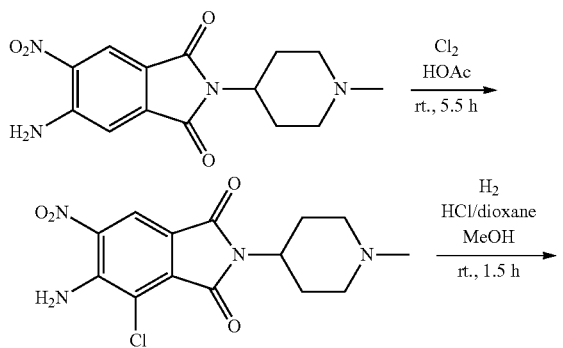

374

-continued

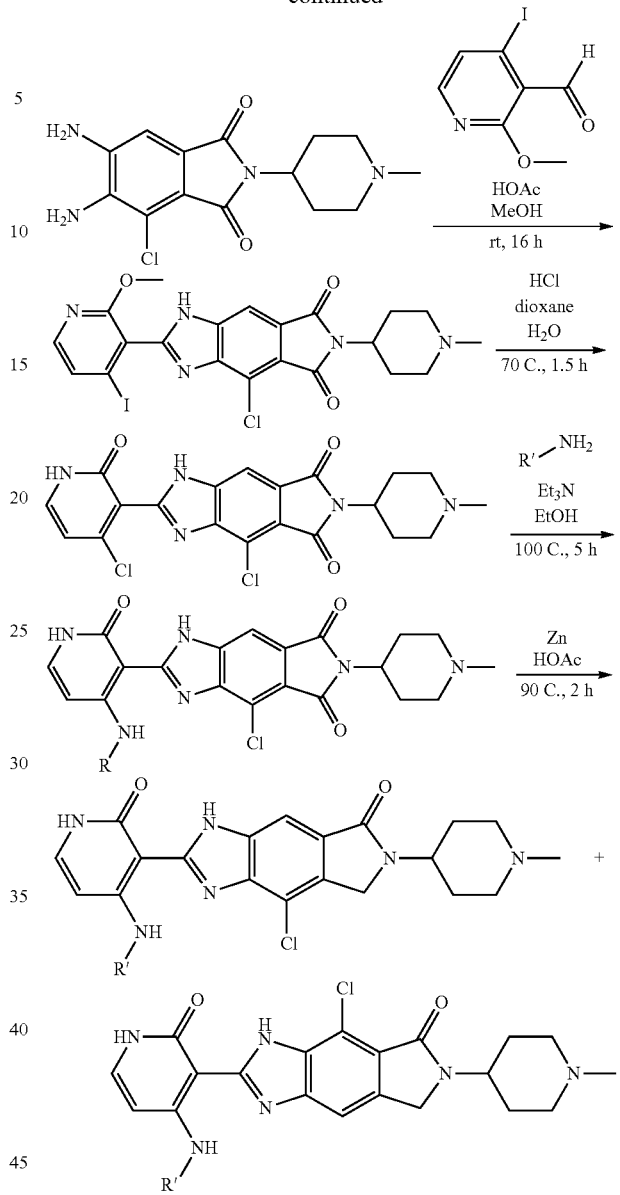

5-Amino-4-chloro-2-(1-methyl-piperidin-4-yl)-6-nitro-isoindole-1,3-dione

5-Amino-4-chloro-2-(1-methyl-piperidin-4-yl)-6-nitro-isoindole-1,3-dione: A suspension of 5-amino-2-(1-methyl-piperidin-4-yl)-6-nitro-isoindole-1,3-dione (3.04 g, 10 mmol) in HOAc (100 mL) was bubbled with $Cl_2$ gas for 5.5 h and evaporated to dryness. The residue was diluted with aqueous MeOH (25 mL, 80%) and basified with aqueous $NH_4OH$ solution (28%) resulting a solution to which NaHSO₃ (10.4 g, 100 mmol) was added. The mixture was sonicated for 30 min and loaded on silica gel. Chromatography of the mixture with mixed solvent of CH₂Cl₂/MeOH/28% aqueous NH₄OH (20:10:1) afforded the title compound which is not pure, but was used for the next step reaction directly without further purification.

5,6-Diamino-4-chloro-2-(1-methyl-piperidin-4-yl)-isoindole-1,3-dione

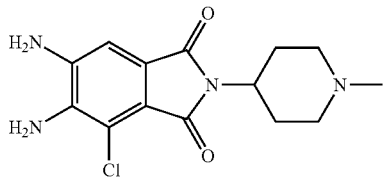 [SMILES: CN1CCC(N2C(=O)c3cc([N+](=O)[O-])c(N)c(Cl)c3C2=O)CC1]

5,6-Diamino-4-chloro-2-(1-methyl-piperidin-4-yl)-isoindole-1,3-dione: To a mixture of 5-amino-4-chloro-2-(1-methyl-piperidin-4-yl)-6-nitro-isoindole-1,3-dione (1.35 g, not pure) and 10% Pd/C (500 mg) was added 2-propanol (20 mL), HCl in dioxane (4 M, 0.1 mL) and then MeOH (230 mL). After it was stirred under atmospheric hydrogen for 1.5 h, the reaction mixture was filtered over Celite. The filtrate was concentrated, diluted with 50% DCM in MeOH, basified with aqueous NH₄OH solution (28%) and evaporated. Chromatography of the mixture with mixed solvent of CH₂Cl₂/MeOH/28% aqueous NH₄OH (50:10:1) afforded the title compound (186 mg, 6% for 2 steps). ¹H NMR (DMSO-d₆) δ 1.51 (m, 2H), 1.90 (m, 2H), 2.29 (m, 2H), 2.81 (m, 2H), 3.80 (m, 1H), 5.61 (br s, 2H, NH₂), 5.93 (br s, 2H, NH₂), 6.82 (s, 1H, ArH); ESI-MS m/z 309.4 (MH⁺).

4-Chloro-2-(4-chloro-2-oxo-1,2-dihydro-pyridin-3-yl)-6-(1-methyl-piperidin-4-yl)-1H-1,3,6-triaza-s-indacene-5,7-dione

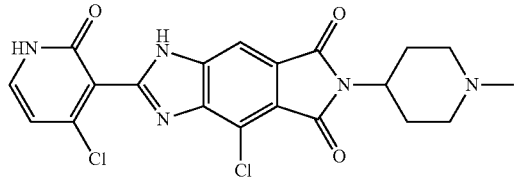 [SMILES: CN1CCC(N2C(=O)c3cc4[nH]c(-c5c(Cl)cc[nH]c5=O)nc4c(Cl)c3C2=O)CC1]

4-Chloro-2-(4-chloro-2-oxo-1,2-dihydro-pyridin-3-yl)-6-(1-methyl-piperidin-4-yl)-1H-1,3,6-triaza-s-indacene-5,7-dione: A solution of 5,6-diamino-4-chloro-2-(1-methyl-piperidin-4-yl)-isoindole-1,3-dione (62.0 mg, 0.2 mmol), 4-iodo-2-methoxynicotinic aldehyde (34.3 mg, 0.2 mmol) and HOAc (1 mL) in MeOH was stirred at the room temperature for 14 h, heated at 80° C. for 4.5 h, and concentrated to result a residue which was then mixed with HCl in dioxane (4 M, 10 mL) and H₂O (0.8 mL) and heated for 1.7 h at 70° C. for 1.5 h. The reaction mixture was evaporated, diluted with diluted with a mixed solvent of DCM/MeOH (1:5), basified with aqueous NH₄OH solution (28%) and evaporated. Chromatography of the residue with mixed solvent of CH₂Cl₂/MeOH/28% aqueous NH₄OH (40:10:1) afforded the title compound (70.2 mg, 78% for 2 steps). ESI-MS m/z 446.5 (MH⁺).

4-Chloro-2-{4-[3-(2,4-dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione

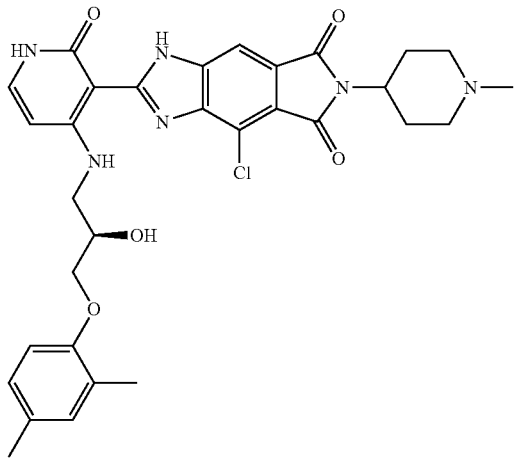 [SMILES: Cc1ccc(OC[C@H](O)CNc2cc[nH]c(=O)c2-c2nc3c(Cl)c4c(cc3[nH]2)C(=O)N(C2CCN(C)CC2)C4=O)c(C)c1]

4-Chloro-2-{4-[3-(2,4-dimethyl-phenoxy)-2-hydroxy-propylamino]-2-oxo-1,2-dihydro-pyridin-3-yl}-6-(1-methyl-piperidin-4-yl)-1H-1,3,6-triaza-s-indacene-5,7-dione: A solution of 4-chloro-2-(4-chloro-2-oxo-1,2-dihydro-pyridin-3-yl)-6-(1-methyl-piperidin-4-yl)-1H-1,3,6-triaza-s-indacene-5,7-dione (18 mg, 0.04 mmol), (R)-1-amino-3-(2,4-dimethyl-phenoxy)-propan-2-ol (12.0 mg, 0.06 mmol) and Et₃N (0.2 mL, 1.43 mmol) in EtOH (2.0 mL) was heated at 100° C. for 19 h and then concentrated to result a residue which was subjected to HPLC purification to furnish the title compound in TFA salt form (3.98 mg, 14%). ¹H NMR (DMSO-d₆) δ 1.95 (m, 2H), 2.15 (s, 3H), 2.19 (s, 3H), 2.51 (m, 2H), 2.80 (s, 3H), 3.18 (m, 2H), 3.50-3.80 (4H), 4.02 (m, 2H), 4.15 (m, 1H), 4.30 (m, 1H), 5.50 (br s, 1H, NH), 6.25 (d, J=8 Hz, 1H), 6.80-6.94 (3H), 7.40 (m, 1H), 8.08 (s, 1H), 9.49 (br s, 1H), 10.90 (br s, 1H), 11.36 (d, J=6 Hz, 1H); ESI-MS m/z 605.3 (MH⁺).

8-Chloro-2-{4-[3-(2,4-dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one

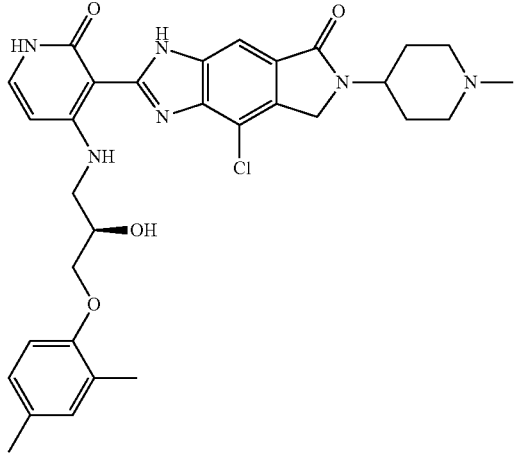 [SMILES: Cc1ccc(OC[C@H](O)CNc2cc[nH]c(=O)c2-c2nc3c(Cl)c4c(cc3[nH]2)C(=O)N(C2CCN(C)CC2)C4)c(C)c1]

8-Chloro-2-{4-[3-(2,4-dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one: 4-Chloro-2-{4-[3-(2,4-dimethyl-phenoxy)-2-hydroxy-propylamino]-2-oxo-1,2-dihydro-pyridin-3-yl}-6-

(1-methyl-piperidin-4-yl)-1H-1,3,6-triaza-s-indacene-5,7-dione (50.1 mg, 0.083 mmol) was mixed with zinc dust (196 mg, 1.0 mmol) in HOAc (15 mL). After it was heated at 90° C. for 1 h, the reaction mixture was cooled to 50° C. and diluted with a mixed solvent of MeOH:DCM (45 mL/5 mL) and filtered. The filtrate was evaporated at 95° C. (the bath temperature) under reduced pressure to dryness. The residue was diluted with a mixed solvent of DCM/MeOH (1:5) and basified with 28% aqueous NH$_4$OH solution and concentrated. Chromatography of the residual crude with CH$_2$Cl$_2$/MeOH/ 28% aqueous NH$_4$OH (16:10:1) followed by HPLC re-purification afforded the title compound in TFA salt form (9.23 mg, 19%). $^1$H NMR (DMSO-d$_6$) δ 1.95-2.12 (4H), 2.16 (s, 3H, CH$_3$), 2.19 (s, 3H, CH$_3$), 2.80 (s, 3H, CH$_3$), 3.19 (m, 2H), 3.50-3.75 (4H), 4.07 (m, 2H), 4.12 (m, 1H), 4.30 (s, 1H), 4.49 (s, 2H), 6.22 (m, 1H), 6.80-6.95 (3H), 7.40 (1H), 7.95 (s, 1H), 9.64 (br s, 1H), 11.02 (br s, H, NH), 11.29 (br s, 1H, NH); ESI-MS m/z 591.3 (MH$^+$).

Synthesis of Sulfone, Sulfoxide and Sulfide Derivatives

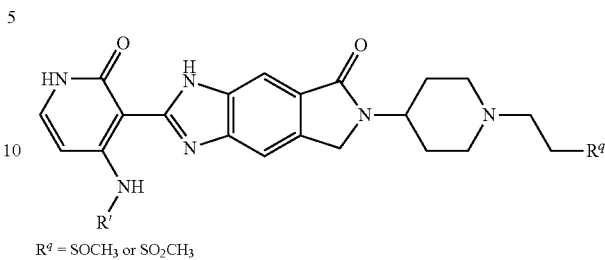

R$^q$ = SOCH$_3$ or SO$_2$CH$_3$

Scheme 79

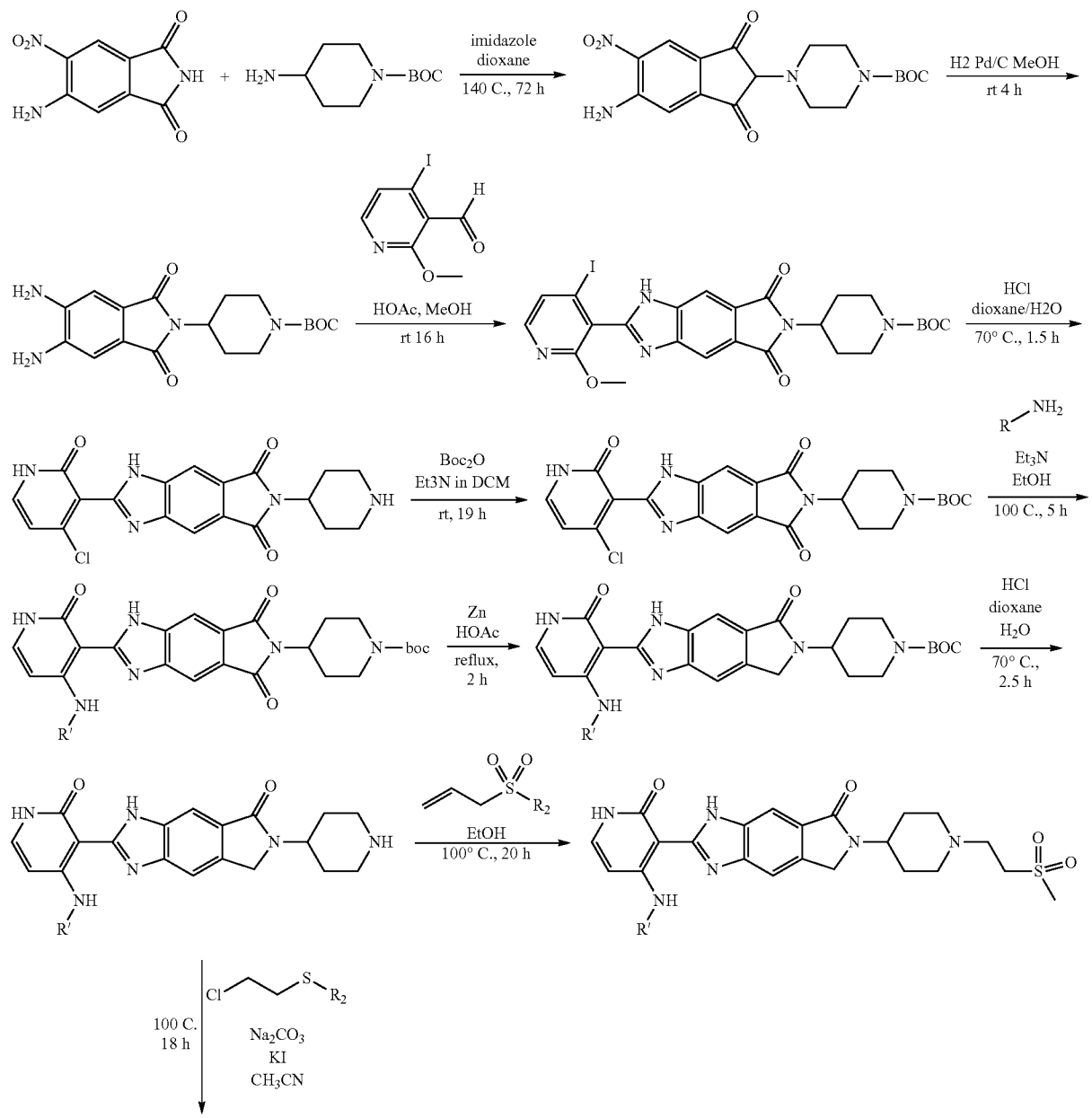

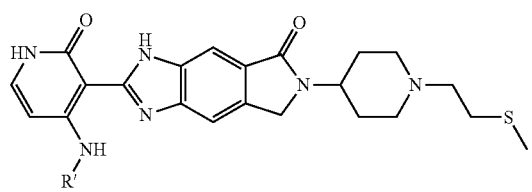

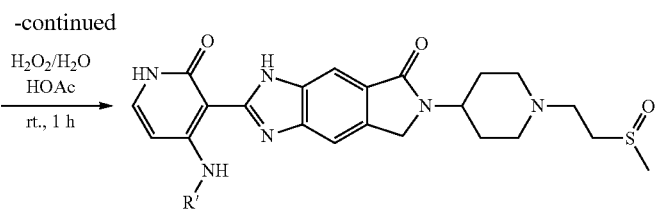

4-(5-Amino-6-nitro-1,3-dioxo-1,3-dihydro-isoindol-2-yl)-piperidine-1-carboxylic acid tert-butyl ester: A mixture of 5-amino-6-nitro-isoindole-1,3-dione

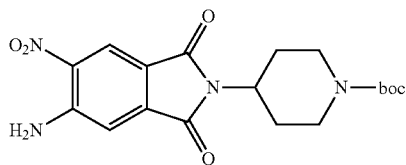

4-(5-Amino-6-nitro-1,3-dioxo-1,3-dihydro-isoindol-2-yl)-piperidine-1-carboxylic acid tert-butyl ester: A mixture of 5-amino-6-nitro-isoindole-1,3-dione (2.07 g, 10 mmol), tert-butyl 4-amino-piperidine-1-carboxylate (2.5 g, 12 mmol), imidazole (1.63 g, 24 mmol) in dioxane (100 mL) was sealed in a ChemGlass heavy wall pressure flask. After it was heated at 140° C. for 72 h, the reaction mixture was evaporated to dryness at 95° C. (the bath temperature) under reduced pressure. The chromatography of the residue with $CH_2Cl_2$/MeOH/28% aqueous $NH_4OH$ (320:10:1) afforded the title compound (2.09 g, 54%). $^1H$ NMR (CDCl$_3$) δ 1.49 (s, 9H), 1.73 (m, 2H), 2.38 (m, 2H), 2.80 (m, 2H), 4.20-4.31 (3H), 7.03 (br s, 2H, NH), 7.34 (s, 1H), 8.61 (s, 1H); ESI-MS m/z 391.5 (MH$^+$).

2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one

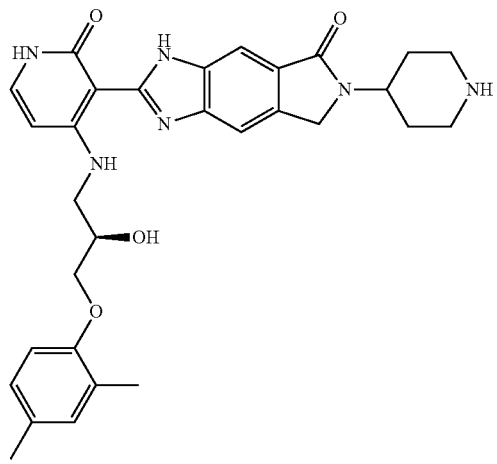 [SMILES: Cc1ccc(OC[C@H](O)CNc2cc[nH]c(=O)c2-c2nc3cc4c(cc3[nH]2)C(=O)N(C2CCNCC2)C4)c(C)c1]

2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one: To a mixture of 4-(5-amino-6-nitro-1,3-dioxo-1,3-dihydro-isoindol-2-yl)-piperidine-1-carboxylic acid tert-butyl ester (5.0 g, 12.8 mmol) and 10% Pd/C (500 mg) was added 2-propanol (20 mL), and then MeOH (230 mL). After it was stirred under atmospheric hydrogen for 4 h, the reaction mixture was filtered over Celite. The filtrate was mixed with 4-iodo-2-methoxynicotinic aldehyde (3.37 g, 12.8 mmol) and HOAc (13 mL), stirred at the room temperature for 16 h, and evaporated under reduced pressure to afford an oil crude which was mixed with HCl in dioxane (4 M, 60 mL) and $H_2O$ (5 mL), heated at 70° C. for 1.5 h and evaporated at 95° C. (the bath temperature) to dryness. Et$_3$N (5.35 mL, 38.4 mmol) was added to the solution of the residue in DCM (250 mL) at 0° C. under N$_2$ and followed by the addition of the solution of Boc$_2$O (3.35 g, 15.4 mmol). After it was stirred at 0° C. for 1 h and at the room temperature for 19 h, the reaction mixture was mixed slowly with MeOH (200 mL) at 0° C. and then evaporated at 70° C. (the both temperature) to dryness under reduced pressure. The residue was mixed with (R)-1-amino-3-(2,4-dimethyl-phenoxy)-propan-2-ol (2.5 g, 12.8 mmol) and Et$_3$N (5.35 mL, 38.4 mmol) in EtOH (200 mL) resulting a mixture which was heated at 100° C. for 5 h and then concentrated. Chromatography of the residual mixture with $CH_2Cl_2$/MeOH/28% aqueous $NH_4OH$ (250:10:1) furnished a fluorescent product which was mixed with zinc dust (5.5 g, 84 mmol) and HOAc (200 mL). After it was heated to 90° C. for 2 h, the reaction mixture was filtered and the filtrate was concentrated at 70° C. (the both temperature) under reduced pressure. The residue was mixed with HCl in dioxane (4 M, 60 mL) and $H_2O$ (5 mL), heated at 70° C. for 2.5 h and evaporated at 95° C. (the bath temperature) to dryness. The residue was basified with NH$_3$ in EtOH (2 M) and concentrated. Chromatography of the crude with $CH_2Cl_2$/MeOH/28% aqueous $NH_4OH$ (40:10:1) afforded a fluorescent product (6.5 g). 50 mg of this product was subjected to HPLC purification to furnish the title compound in TFA salt form (37 mg). $^1H$ NMR (DMSO-d$_6$) δ 1.90-2.05 (4H), 2.19 (s, 3H, CH$_3$), 2.22 (s, 3H, CH$_3$), 3.13 (m, 2H), 3.42 (m, 2H), 3.55 (m, 1H), 3.69 (m, 1H), 4.03 (m, 2H), 4.13 (m, 1H), 4.39 (m, 1H), 4.46 (s, 2H), 6.22 (d, J=7 Hz, 1H), 6.84 (d, J=7 Hz, 1H), 6.94 (d, J=7 Hz, 1H), 6.98 (s, 1H), 7.39 (d, J=7 Hz, 1H), 7.55 (br s, 1H), 7.85 (br s, 1H), 11.14 (br s, 1H, NH), 11.23 (br d, J=6 Hz, 1H, NH); ESI-MS m/z 543.5 (MH$^+$).

2-{4-[(R)-3-(2,4-Dimethyl-phenoxy)-2-hydroxy-propylamino]-2-oxo-1,2-dihydro-pyridin-3-yl}-6-[1-(2-methanesulfonyl-ethyl)-piperidin-4-yl]-6,7-dihydro-3H-1,3,6-triaza-s-indacen-5-one

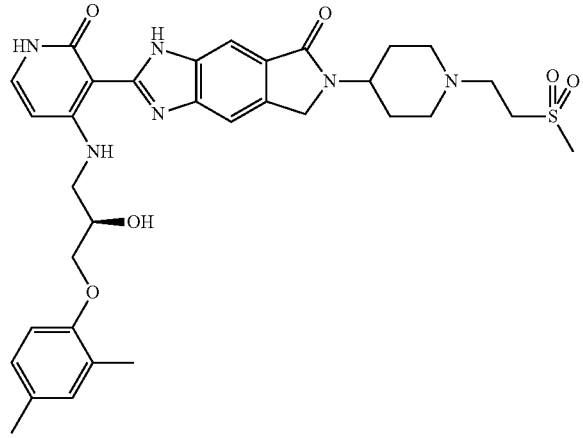 [SMILES: Cc1ccc(OC[C@H](O)CNc2cc[nH]c(=O)c2-c2nc3cc4c(cc3[nH]2)C(=O)N(C2CCN(CCS(C)(=O)=O)CC2)C4)c(C)c1]

2-{4-[(R)-3-(2,4-Dimethyl-phenoxy)-2-hydroxy-propylamino]-2-oxo-1,2-dihydro-pyridin-3-yl}-6-[1-(2-methanesulfonyl-ethyl)-piperidin-4-yl]-6,7-dihydro-3H-1,3,6-triaza-s-indacen-5-one 2-{4-[(R)-3-(2,4-Dimethyl-phenoxy)-2-hydroxy-propylamino]-2-oxo-1,2-dihydro-pyridin-3-yl}-6-[1-(2-methanesulfonyl-ethyl)-piperidin-4-yl]-6,7-dihydro-3H-1,3,6-triaza-s-indacen-5-one: A mixture of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (3.04 g, 5.6 mmol) and methyl vinyl sulfone (5.94 g, 56 mmol) in a mixed solvent of EtOH (70.0 mL) and 2-propanol (70.0 mL) was heated at 100° C. for 22 h and then evaporated. Chromatography of the residue with $CH_2Cl_2$/MeOH/28% aqueous $NH_4OH$ (190:10:1) afforded title compound (2.82 g, 78%). $^1$H NMR (DMSO-$d_6$) δ 1.68-1.85 (4H), 2.15 (m, 2H), 2.18 (s, 3H, $CH_3$), 2.21 (s, 3H, $CH_3$), 2.75 (m, 2H), 3.05 (m, 2H), 3.08 (s, 3H, $CH_3$), 3.54 (m, 1H), 3.70 (m, 1H), 3.93-4.19 (4H), 4.43 (s, 1H), 4.47 (s, 1H), 5.48 (d, J=6 Hz, 0.5H, NH), 5.53 (d, J=6 Hz, 0.5H, NH), 6.20 (m, 1H), 6.81 (m, 1H), 6.90-6.99 (2H), 7.31-7.37 (1.5H), 7.67 (s, 0.5H), 7.80 (s, 0.5H), 7.94 (s, 0.5H), 11.14 (br d, J=6 Hz, 1H, NH), 11.22 (br d, J=6 Hz, 1H, NH); ESI-MS m/z 649.5 (MH$^+$); Anal. Calcd for $C_{33}H_{40}N_6O_6S$: C, 61.09; H, 6.21; N, 12.95; S, 4.94. Found: C, 60.85; H, 6.17; N, 12.87; S, 4.85.

2-{4-[(R)-3-(2,4-Dimethyl-phenoxy)-2-hydroxy-propylamino]-2-oxo-1,2-dihydro-pyridin-3-yl}-6-[1-(2-ethanesulfonyl-ethyl)-piperidin-4-yl]-6,7-dihydro-3H-1,3,6-triaza-s-indacen-5-one

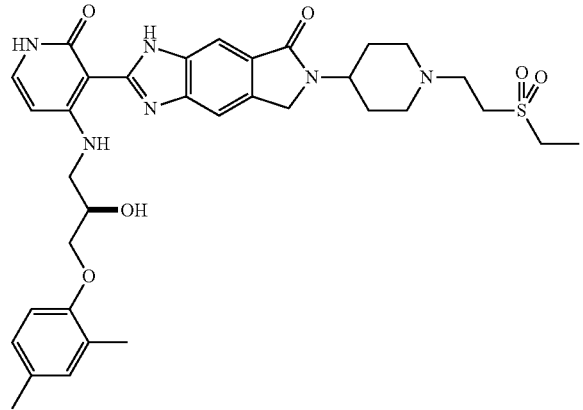 [SMILES: CCS(=O)(=O)CCN1CCC(N2Cc3cc4nc(-c5c(NC[C@@H](O)COc6ccc(C)cc6C)cc[nH]c5=O)[nH]c4cc3C2=O)CC1]

2-{4-[(R)-3-(2,4-Dimethyl-phenoxy)-2-hydroxy-propylamino]-2-oxo-1,2-dihydro-pyridin-3-yl}-6-[1-(2-ethanesulfonyl-ethyl)-piperidin-4-yl]-6,7-dihydro-3H-1,3,6-triaza-s-indacen-5-one: This compound was prepared by application of the above methodology. $^1$H NMR (DMSO-$d_6$) δ 1.23 (t, J=6 Hz, 3H, $CH_3$), 1.65-1.82 (4H), 2.15 (m, 2H), 2.19 (s, 3H, $CH_3$), 2.22 (s, 3H, $CH_3$), 2.76 (m, 2H), 3.02 (m, 2H), 3.17 (q, J=6 Hz, 2H), 3.29 (m, 2H), 3.55 (m, 1H), 3.70 (m, 1H), 3.93-4.18 (4H), 4.43 (s, 1H), 4.48 (s, 1H), 5.48 (d, J=6 Hz, 0.5H, NH), 5.54 (d, J=6 Hz, 0.5H, NH), 6.20 (m, 1H), 6.81 (m, 1H), 6.89-6.98 (2H), 7.30-7.38 (1.5H), 7.67 (s, 0.5H), 7.80 (s, 0.5H), 7.94 (s, 0.5H), 11.15 (br d, J=6 Hz, 1H, NH), 11.20 (br s, 1H, NH); ESI-MS m/z 663.7 (MH$^+$).

Acetic acid 1-(2,4-dimethyl-phenoxymethyl)-2-(3-{6-[1-(2-methanesulfonyl-ethyl)-piperidin-4-yl]-7-oxo-1,5,6,7-tetrahydro-1,3,6-triaza-s-indacen-2-yl}-2-oxo-1,2-dihydro-pyridin-4-ylamino)-ethyl ester

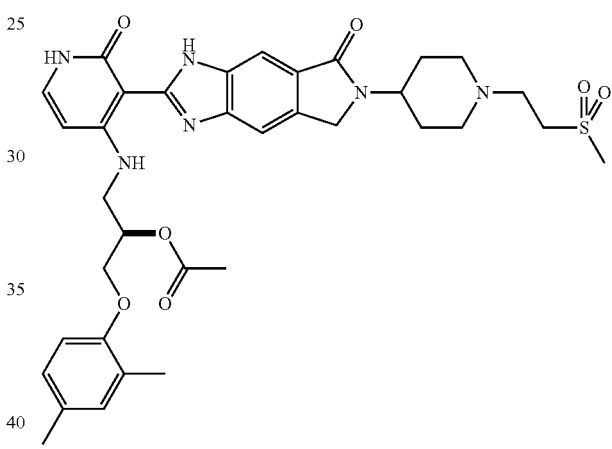

Acetic acid 1-(2,4-dimethyl-phenoxymethyl)-2-(3-{6-[1-(2-methanesulfonyl-ethyl)-piperidin-4-yl]-7-oxo-1,5,6,7-tetrahydro-1,3,6-triaza-s-indacen-2-yl}-2-oxo-1,2-dihydro-pyridin-4-ylamino)-ethyl ester: A solution of 2-{4-[(R)-3-(2,4-Dimethyl-phenoxy)-2-hydroxy-propylamino]-2-oxo-1,2-dihydro-pyridin-3-yl}-6-[1-(2-methanesulfonyl-ethyl)-piperidin-4-yl]-6,7-dihydro-3H-1,3,6-triaza-s-indacen-5-one (65 mg, 0.1 mmol) in HOAc (20 mL) was refluxed for 32 h and was evaporated. The residue was diluted with a mixed solvent of DCM/MeOH (1:5), basified with 28% aqueous $NH_4OH$ solution and concentrated. Chromatography of the residual crude with $CH_2Cl_2$/MeOH/28% aqueous $NH_4OH$ (110:10:1) followed by HPLC re-purification afforded the title compound in TFA salt form (8.69 mg, 11%). $^1$H NMR (DMSO-$d_6$) δ 1.99-2.12 (4H), 2.05 (s, 3H, $CH_3$), 2.16 (s, 3H, $CH_3$), 2.22 (s, 3H, $CH_3$), 3.15 (s, 3H, $CH_3$), 3.25 (m, 2H), 3.52 (m, 2H), 3.60-3.78 (5H), 3.90 (s, 1H), 4.10-4.38 (4H), 4.49 (br s, 2H), 5.43 (br s, 2H, NH), 6.28 (d, J=8 Hz, 1H), 6.84 (d, J=6 Hz, 1H), 6.94 (d, J=6 Hz, 1H), 6.99 (s, 1H), 7.40 (m, 1H), 7.80 (br s, 1H), 9.80 (br s, 1H), 11.14 (br s, NH), 11.33 (br d, J=6 Hz, 1H, NH); ESI-MS m/z 691.7 (MH$^+$).

2-{4-[3-(2,4-Dimethyl-phenoxy)-2-hydroxy-propylamino]-2-oxo-1,2-dihydro-pyridin-3-yl}-6-[1-(2-methylsulfanyl-ethyl)-piperidin-4-yl]-6,7-dihydro-3H-1,3,6-triaza-s-indacen-5-one

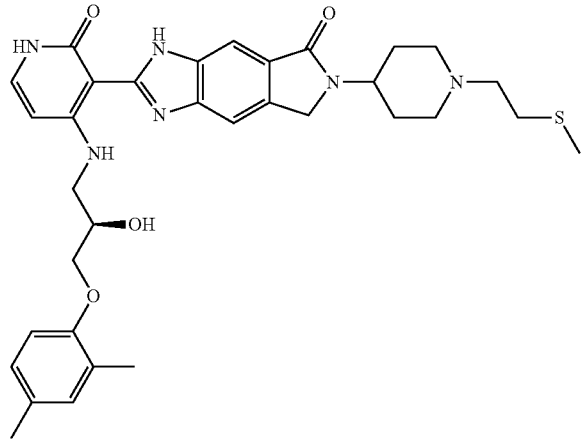 [SMILES: CSCCN1CCC(N2Cc3cc4nc(-c5c(NC[C@@H](O)COc6ccc(C)cc6C)cc[nH]c5=O)[nH]c4cc3C2=O)CC1]

2-{4-[3-(2,4-Dimethyl-phenoxy)-2-hydroxy-propylamino]-2-oxo-1,2-dihydro-pyridin-3-yl}-6-[1-(2-methylsulfanyl-ethyl)-piperidin-4-yl]-6,7-dihydro-3H-1,3,6-triaza-s-indacen-5-one: A mixture of the 2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (542 mg, 1.0 mmol), 1-chloro-2-methylsulfanyl-ethane (122 mg, 1.1 mmol), Na$_2$CO$_3$ (318 mg, 3.0 mmol) and NaI (150 mg, 1.0 mmol) in CH$_3$CN (20 mL) was heated at 100° C. for 22 h and then evaporated. Chromatography of the residue with CH$_2$Cl$_2$/MeOH/28% aqueous NH$_4$OH (200:10:1) afforded the title compound. $^1$H NMR (DMSO-d$_6$) δ 1.69-1.82 (4H), 2.09 (s, 3H, CH$_3$), 2.09 (m, 2H), 2.19 (s, 3H, CH$_3$), 2.20 (s, 3H, CH$_3$), 2.50-2.59 (4H), 3.00 (m, 2H), 3.38 (m, 2H), 3.53 (m, 1H), 3.70 (m, 1H), 3.98-4.08 (3H), 4.15 (m, 1H), 4.43 (s, 1H), 4.47 (s, 1H), 5.47 (br s, 0.5H, NH), 5.53 (br s, 0.5H, NH), 6.20 (m, 1H), 6.80-6.99 (3H), 7.30-7.36 (1.5H), 7.68 (s, 0.5H), 7.79 (s, 0.5H), 7.94 (s, 0.5H), 11.15 (br d, J=6 Hz, 1H, NH), 11.21 (br d, J=6 Hz, 1H, NH); ESI-MS m/z 617.5 (MH$^+$).

2-{4-[3-(2,4-Dimethyl-phenoxy)-2-hydroxy-propylamino]-2-oxo-1,2-dihydro-pyridin-3-yl}-6-[1-(2-methanesulfinyl-ethyl)-piperidin-4-yl]-6,7-dihydro-3H-1,3,6-triaza-s-indacen-5-one

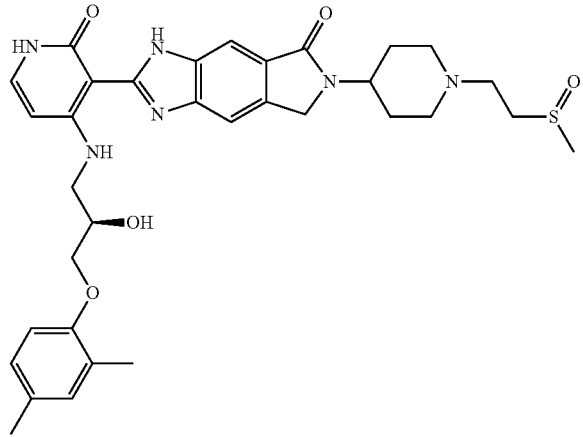 [SMILES: Cc1ccc(OC[C@H](O)CNc2cc[nH]c(=O)c2-c2nc3cc4c(cc3[nH]2)C(=O)N(C2CCN(CCS(C)=O)CC2)C4)c(C)c1]

2-{4-[3-(2,4-Dimethyl-phenoxy)-2-hydroxy-propylamino]-2-oxo-1,2-dihydro-pyridin-3-yl}-6-[1-(2-methanesulfinyl-ethyl)-piperidin-4-yl]-6,7-dihydro-3H-1,3,6-triaza-s-indacen-5-one To a solution of 2-{4-[3-(2,4-Dimethyl-phenoxy)-2-hydroxy-propylamino]-2-oxo-1,2-dihydro-pyridin-3-yl}-6-[1-(2-methylsulfanyl-ethyl)-piperidin-4-yl]-6,7-dihydro-3H-1,3,6-triaza-s-indacen-5-one (333 mg, 0.5 mmol) in HOAc (10 mL) was added H$_2$O$_2$ (30% in H$_2$O, 1 mL). After it was stirred at the room temperature for 1 h, the reaction mixture was cooled down to 0° C. and diluted with aqueous MeOH (50%, 90 mL) resulting a solution to which NaHSO$_3$ (5.2 g, 50 mmol) was added. The reaction mixture was evaporated after it was stirred at 0° C. for 1 h and the residue was diluted with a mixed solvent of DCM/MeOH (1:5), basified with 28% aqueous NH$_4$OH solution and concentrated. Chromatography of the residual crude with CH$_2$Cl$_2$/MeOH/28% aqueous NH$_4$OH (110:10:1) afforded the title compound (242 mg, 71%). $^1$H NMR (DMSO-d$_6$) 1.69-1.85 (4H), 2.10 (m, 2H), 2.19 (s, 3H, CH$_3$), 2.22 (s, 3H, CH$_3$), 2.55 (s, 3H, CH$_3$), 2.60-2.81 (2H), 3.00 (m, 2H), 3.38 (m, 2H), 3.54 (m, 1H), 3.70 (m, 1H), 3.98-4.08 (3H), 4.15 (m, 1H), 4.43 (s, 1H), 4.48 (s, 1H), 5.48 (d, J=6 Hz, 0.5H, NH), 5.53 (d, J=6 Hz, 0.5H, NH), 6.20 (m, 1H), 6.81 (m, 1H), 6.90-6.99 (2H), 7.31-7.37 (1.5H), 7.68 (s, 0.5H), 7.80 (s, 0.5H), 7.94 (s, 0.5H), 11.15 (br d, J=6 Hz, 1H, NH), 11.22 (br d, J=6 Hz, 1H, NH); ESI-MS m/z 633.5 (MH$^+$).

Synthesis of Additional Sulfones

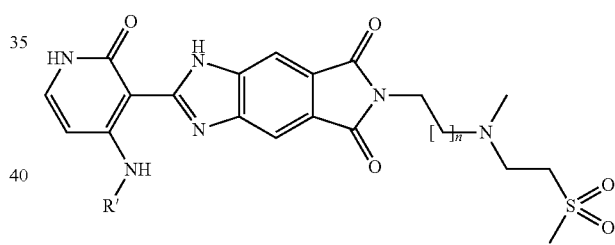

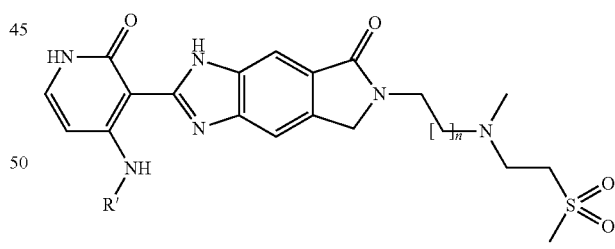

n' = 1 or 2

Scheme 80

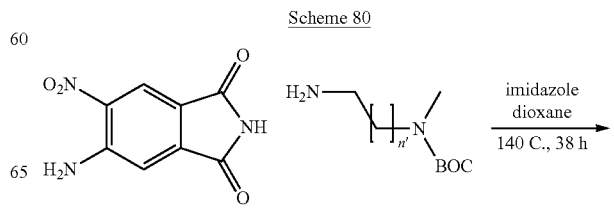

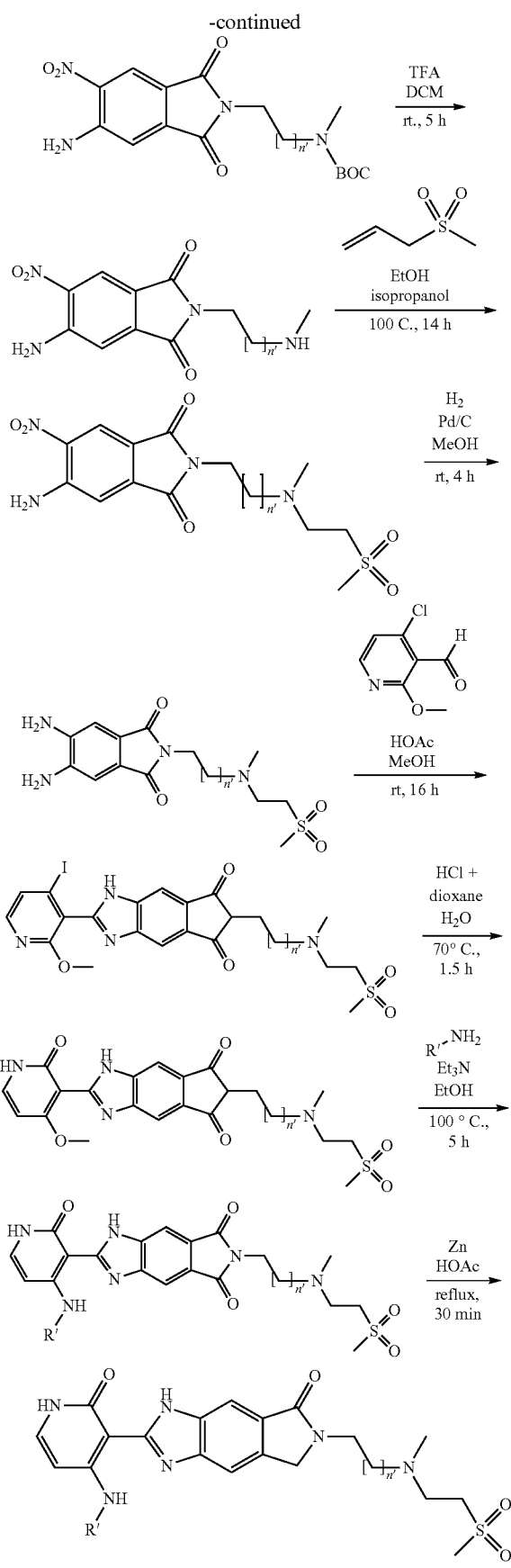

[2-(5-Amino-6-nitro-1,3-dioxo-1,3-dihydro-isoindol-2-yl)-ethyl]-methyl-carbamic acid tert-butyl ester

[2-(5-Amino-6-nitro-1,3-dioxo-1,3-dihydro-isoindol-2-yl)-ethyl]-methyl-carbamic acid tert-butyl ester: A mixture of 5-amino-6-nitro-isoindole-1,3-dione (2.07 g, 10 mmol), (2-Amino-ethyl)-methyl-carbamic acid tert-butyl ester (3.485 g, 20 mmol), imidazole (1.36 g, 20 mmol) in dioxane (30 mL) was sealed in a ChemGlass heavy wall pressure flask. After it was heated at 140° C. for 38 h, the reaction mixture was evaporated to dryness at 95° C. (the bath temperature) under reduced pressure. The chromatography of the residue with $CH_2Cl_2$/MeOH/28% aqueous $NH_4OH$ (500:10:1) afforded the title compound (3.39 g, 93%). $^1$H NMR ($CDCl_3$) δ 1.08 (s, 9H), 2.78 (s, 3H), 3.42 (m, 2H), 3.68 (m, 2H), 7.48 (s, 1H), 8.34 (s, 1H), 8.42 (br s, 2H, NH).

2-{4-[3-(2,4-Dimethyl-phenoxy)-2-hydroxy-propylamino]-2-oxo-1,2-dihydro-pyridin-3-yl}-6-{2-[(2-methanesulfonyl-ethyl)-methyl-amino]-ethyl}-1H-1,3,6-triaza-s-indacene-5,7-dione 2-{4-[3-(2,4-Dimethyl-phenoxy)-2-hydroxy-propylamino]-2-oxo-1,2-dihydro-pyridin-3-yl}-6-{2-[(2-methanesulfonyl-ethyl)-methyl-amino]-ethyl}-1H-1,3,6-triaza-s-indacene-5,7-dione: A mixture of [2-(5-amino-6-nitro-1,3-dioxo-1,3-dihydro-isoindol-2-yl)-ethyl]-methyl-carbamic acid tert-butyl ester (729 mg, 2.0 mmol) and TFA (7 mL) in DCM (28 mL) was stirred at the room temperature for 5 h and evaporated to dryness to result a residue which was diluted with a mixed solvent of DCM/MeOH (1:5), basified with 28% aqueous $NH_4OH$ solution and evaporated. The residue was mixed with methyl vinyl ketone (1.27 g, 12 mmol) in a mixed solvent of ethanol (10 mL) and isopropanol (10 mL), heated at 100° C. for 38 h, cooled to the room temperature, diluted with a solution of HOAc in MeOH (5%, 100 mL). The mixture was mixed with Pd/C (100 mg) and stirred under atmospheric $H_2$ for 2.5 h and filtered through Celite. The filtrate was mixed with 4-chloro-2-methoxynicotinic aldehyde (377.5 mg, 2.2 mmol), stirred at the room temperature for 140 h, and evaporated under reduced pressure to afford an oil crude which was mixed with HCl in dioxane (4 M, 25 mL) and $H_2O$ (2 mL), heated at 60° C. for 30 min and evaporated at 95° C. (the bath temperature) to a crude product. 1/20 of this crude product of was mixed with (R)-1-amino-3-(2,4-dimethyl-phenoxy)-propan-2-ol (29.3 mg, 0.15 mmol) and $Et_3N$ (0.3 mL, 2.1 mmol) in EtOH (2 mL) resulting a mixture which was heated at 100° C. for 5 h and then concentrated. Chromatography of the residual mixture with $CH_2Cl_2$/MeOH/ 28% aqueous $NH_4OH$ (150:10:1) furnished the title compound (42.4 mg, 27% for 6 steps). $^1$H NMR (DMSO-$d_6$) δ 2.19 (s, 3H, $CH_3$), 2.21 (s, 3H, $CH_3$), 2.64 (s, 3H, $CH_3$), 2.60 (m, 2H), 2.79 (m, 2H), 2.90 (s, 3H, $CH_3$), 3.20 (m, 2H), 3.48 (m, 1H), 3.65-3.75 (3H), 3.99 (m, 2H), 4.13 (m, 1H), 5.54 (d, J=6 Hz, 1H, NH), 6.23 (d, J=7 Hz, 1H), 6.83 (d, J=7 Hz, 1H), 6.94 (d, J=7 Hz, 1H), 6.97 (s, 1H), 7.41 (m, 1H), 7.67 (s, 1H), 8.12 (s, 1H), 10.97 (br s, 1H, NH), 11.29 (br d, J=6 Hz, 1H, NH); ESI-MS m/z 637.7 (MH$^+$).

2-{4-[3-(2,4-Dimethyl-phenoxy)-2-hydroxy-propylamino]-2-oxo-1,2-dihydro-pyridin-3-yl}-6-{2-[(2-methanesulfonyl-ethyl)-methyl-amino]-ethyl}-6,7-dihydro-3H-1,3,6-triaza-s-indacen-5-one

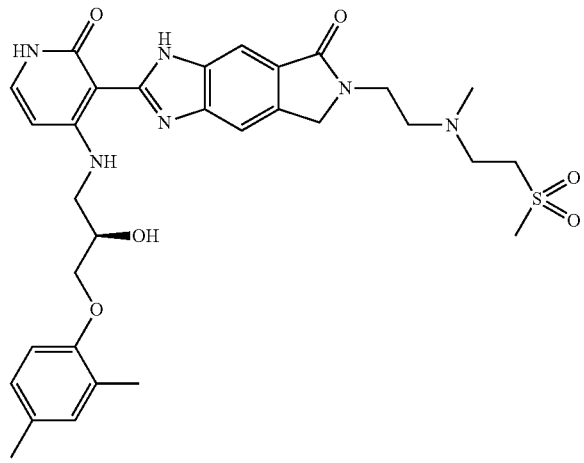 [SMILES: Cc1ccc(OC[C@H](O)CNc2cc[nH]c(=O)c2-c2nc3cc4c(cc3[nH]2)C(=O)N(CCN(C)CCS(C)(=O)=O)C4)c(C)c1]

2-{4-[3-(2,4-Dimethyl-phenoxy)-2-hydroxy-propylamino]-2-oxo-1,2-dihydro-pyridin-3-yl}-6-{2-[(2-methanesulfonyl-ethyl)-methyl-amino]-ethyl}-6,7-dihydro-3H-1,3,6-triaza-s-indacen-5-one: 2-{4-[3-(2,4-Dimethyl-phenoxy)-2-hydroxy-propylamino]-2-oxo-1,2-dihydro-pyridin-3-yl}-6-{2-[(2-methanesulfonyl-ethyl)-methyl-amino]-ethyl}-1H-1,3,6-triaza-s-indacene-5,7-dione (35 mg, 0.055 mmol) was mixed with zinc dust (196 mg, 3 mmol) and HOAc (15 mL). After it was refluxed for 30 min, the reaction mixture was filtered and the filtrate was concentrated at 70° C. (the bath temperature) under reduced pressure resulting a residue which was diluted with a mixed solvent of DCM/ MeOH (10 mL:90 mL), basified with 28% aqueous $NH_4OH$ and concentrated. Chromatography of the crude residue with $CH_2Cl_2$/MeOH/28% aqueous $NH_4OH$ (190:10:1) afforded a fluorescent product (6.98 mg, 20%). $^1$H NMR (DMSO-$d_6$) δ 2.13 (s, 3H, $CH_3$), 2.16 (s, 3H, $CH_3$), 2.22 (s, 3H, $CH_3$), 2.65 (m, 2H), 2.80 (m, 2H), 2.85 (s, 3H, $CH_3$), 3.27 (m, 2H), 3.53 (m, 1H), 3.60-3.71 (3H), 4.02 (m, 2H), 4.13 (m, 1H), 4.48 (s, 1H), 4.53 (s, 1H), 5.48 (d, J=6 Hz, 0.5H, NH), 5.53 (d, J=6 Hz, 0.5H, NH), 6.22 (d, J=7 Hz, 1H), 6.80 (d, J=7 Hz, 1H), 6.89-6.99 (2H), 7.30-7.35 (1.5H), 7.67 (s, 0.5H), 7.79 (s, 0.5H), 7.94 (s, 0.5H), 11.15 (br m, 1H, NH); ESI-MS m/z 623.5 (MH$^+$).

[2-(5-Amino-6-nitro-1,3-dioxo-1,3-dihydro-isoindol-2-yl)-propyl]-methyl-carbamic acid tert-butyl ester

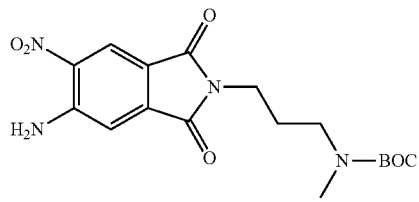 [SMILES: CN(CCCN1C(=O)c2cc(N)c([N+](=O)[O-])cc2C1=O)C(=O)OC(C)(C)C]

[2-(5-Amino-6-nitro-1,3-dioxo-1,3-dihydro-isoindol-2-yl)-propyl]-methyl-carbamic acid tert-butyl ester: $^1$H NMR (CDCl$_3$) δ 1.30 (s, 9H), 1.75 (m, 2H), 2.72 (s, 3H), 3.12 (m, 2H), 3.49 (m, 2H), 7.40 (s, 1H), 8.29 (s, 1H), 8.41 (br s, 2H, NH).

2-{4-[3-(2,4-Dimethyl-phenoxy)-2-hydroxy-propylamino]-2-oxo-1,2-dihydro-pyridin-3-yl}-6-{3-[(2-methanesulfonyl-ethyl)-methyl-amino]-propyl}-1H-1,3,6-triaza-s-indacene-5,7-dione

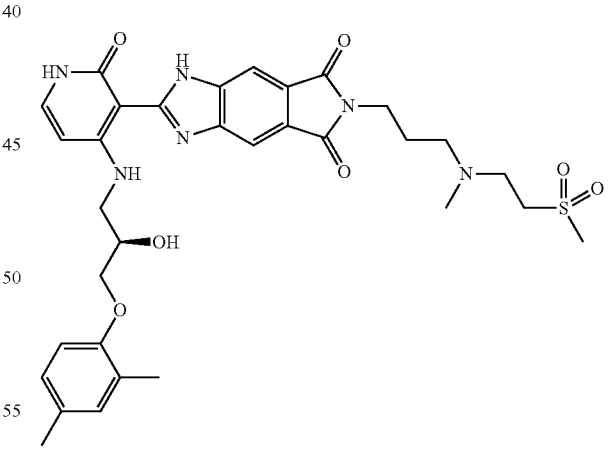

2-{4-[3-(2,4-Dimethyl-phenoxy)-2-hydroxy-propylamino]-2-oxo-1,2-dihydro-pyridin-3-yl}-6-{3-[(2-methanesulfonyl-ethyl)-methyl-amino]-propyl}-1H-1,3,6-triaza-s-indacene-5,7-dione: $^1$H NMR (DMSO-$d_6$) δ 1.75 (m, 2H), 2.19 (s, 3H, $CH_3$), 2.21 (s, 3H, $CH_3$), 2.22 (s, 3H, $CH_3$), 2.39 (m, 2H), 2.75 (m, 2H), 3.01 (s, 3H, $CH_3$), 3.23 (m, 2H), 3.60 (m, 2H), 3.75 (m, 2H), 3.99 (m, 2H), 4.13 (m, 1H), 5.54 (d, J=6 Hz, 1H, NH), 6.23 (d, J=7 Hz, 1H), 6.83 (d, J=7 Hz, 1H), 6.92 (d, J=7 Hz, 1H), 6.97 (s, 1H), 7.41 (m, 1H), 7.67 (s, 1H), 8.12 (s, 1H), 10.95 (br s, 1H, NH), 11.29 (br d, J=6 Hz, 1H, NH); ESI-MS m/z 651.5 (MH⁺).

2-{4-[3-(2,4-Dimethyl-phenoxy)-2-hydroxy-propylamino-2-oxo-1,2-dihydro-pyridin-3-yl}-6-{3-(2-methanesulfonyl-ethyl)-methyl-amino]-propyl}-6,7-dihydro-3H-1,3,6-triaza-s-indacen-5-one

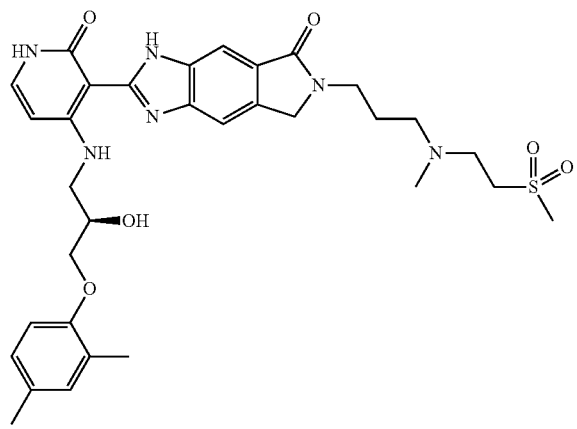 [SMILES: Cc1ccc(OC[C@H](O)CNc2cc[nH]c(=O)c2-c2nc3cc4c(cc3[nH]2)C(=O)N(CCCN(C)CCS(C)(=O)=O)C4)c(C)c1]

2-{4-[3-(2,4-Dimethyl-phenoxy)-2-hydroxy-propylamino]-2-oxo-1,2-dihydro-pyridin-3-yl}-6-{3-[(2-methanesulfonyl-ethyl)-methyl-amino]-propyl}-6,7-dihydro-3H-1,3,6-triaza-s-indacen-5-one: $^1$H NMR (DMSO-d$_6$) δ 1.76 (m, 2H), 2.19 (s, 3H, CH$_3$), 2.20 (s, 3H, CH$_3$), 2.21 (s, 3H, CH$_3$), 2.39 (m, 2H), 2.72 (m, 2H), 3.03 (s, 3H, CH$_3$), 3.29 (m, 2H), 3.55 (m, 1H), 3.67 (m, 1H), 3.82 (m, 1H), 4.00 (m, 2H), 4.12 (m, 1H), 4.46 (s, 1H), 4.50 (s, 1H), 5.48 (br s, 0.5H, NH), 5.52 (br s, 0.5H, NH), 6.22 (d, J=7 Hz, 1H), 6.80 (d, J=7 Hz, 1H), 6.89-6.99 (2H), 7.32-7.37 (1.5H), 7.67 (s, 0.5H), 7.79 (s, 0.5H), 7.94 (s, 0.5H), 11.15 (br m, 1H, NH); ESI-MS m/z 637.7 (MH⁺).

Synthesis of Lactams with Pyrrolidinylethyl or Pyrrolidinylpropyl

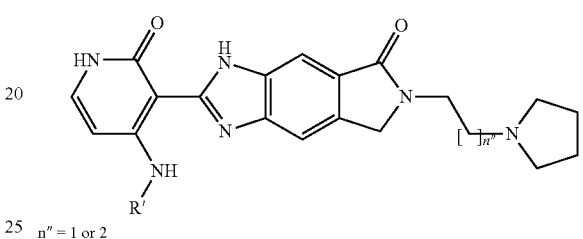

n" = 1 or 2

Scheme 81

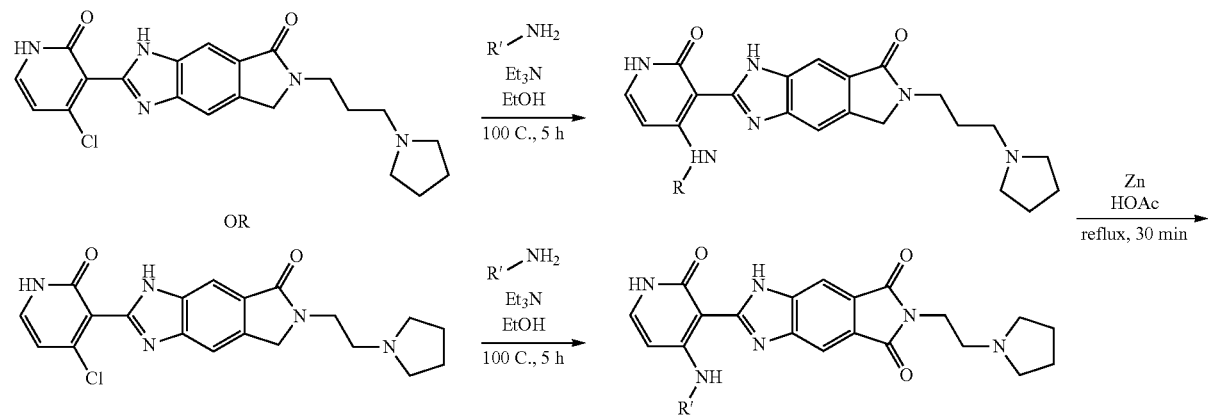

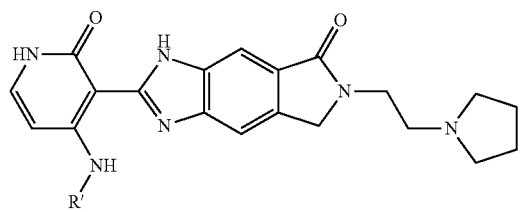

391

2-{4-[3-(2,4-Dimethyl-phenoxy)-2-hydroxy-propylamino]-2-oxo-1,2-dihydro-pyridin-3-yl}-6-{3-[(2-methanesulfonyl-ethyl)-methyl-amino]-propyl}-6,7-dihydro-3H-1,3,6-triaza-s-indacen-5-one

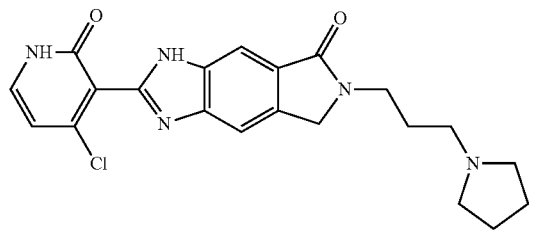 [SMILES: O=C1c2cc3[nH]c(-c4c(Cl)cc[nH]c4=O)nc3cc2CN1CCCN1CCCC1]

Synthesis of Methylated Lactams

Scheme 82

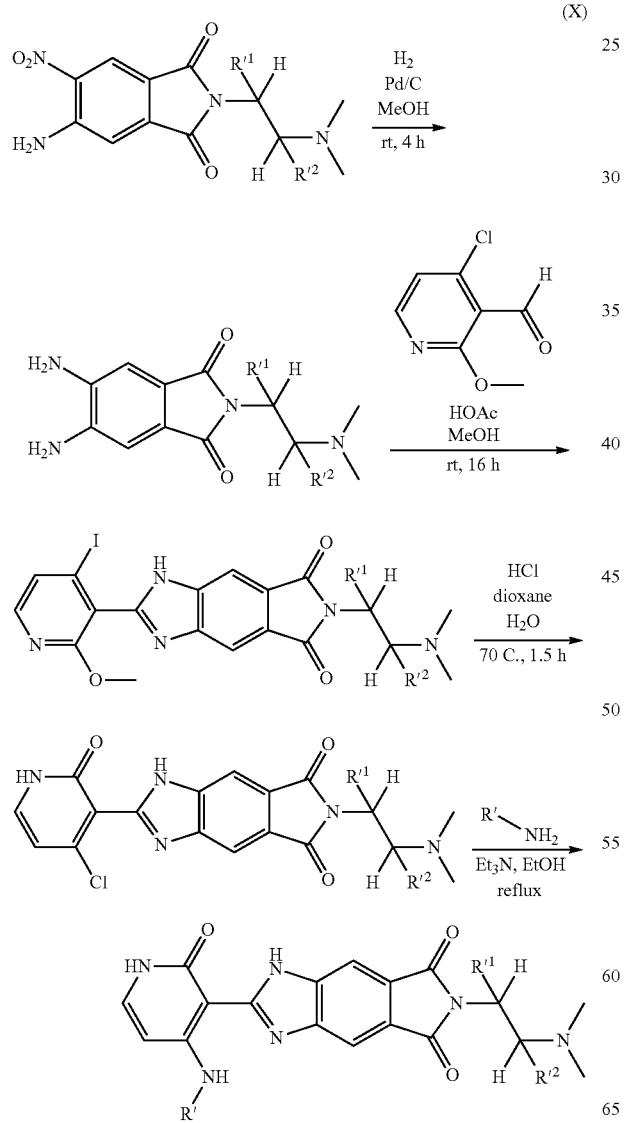

392

R'¹ and R'² are hydrogen or methyl

Scheme 83

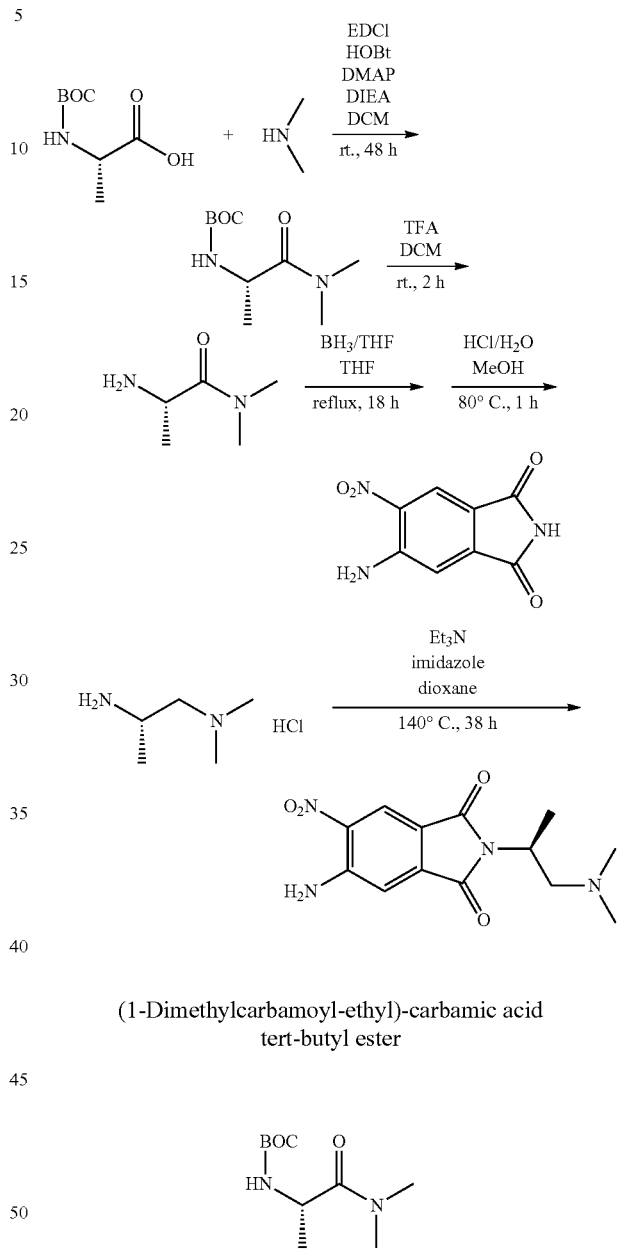

(1-Dimethylcarbamoyl-ethyl)-carbamic acid tert-butyl ester (1-Dimethylcarbamoyl-ethyl)-carbamic acid tert-butyl ester: To a solution of DMAP (10 mg, 0.08 mmol) and DIEA (6.07 g, 47 mmol) in DCM (60 mL) was added a solution of dimethylamine in THF (2.0 M, 25.7 mL, 51.3 mmol) and the mixture was stirred at 0° C. for 30 min. HOBt (6.35 g, 47 mmol) was added to a solution of N-α-tert-Boc-L-alanine (8.09 g, 42.76 mmol) in DCM (60 mL) and the mixture was stirred at 0° C. for 25 min. The two solutions were combined into one solution to which EDCI (9.03 g, 47 mmol) was added and the reaction mixture was stirred at 0° C. for 1 h, stirred at the room temperature for 48 h and concentrated. Chromatography of the residue with $CH_2Cl_2$/MeOH/28% aqueous $NH_4OH$ (240:10:1) afforded the title compound (7.95 g, 86%). $^1$H NMR ($CDCl_3$) δ 1.30 (d, J=6 Hz, 3H, $CH_3$), 1.44 (s, 9H) 2.97 (s, 3H, CH₃), 3.06 (s, 3H, CH₃), 4.62 (q, J=6 Hz, 1H), 5.51 (d, J=6 Hz, 1H, NH).

2-Amino-N,N-dimethyl-propionamide

A solution of (1-dimethylcarbamoyl-ethyl)-carbamic acid tert-butyl ester

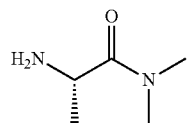

2-Amino-N,N-dimethyl-propionamide: A solution of (1-dimethylcarbamoyl-ethyl)-carbamic acid tert-butyl ester (7.95 g) in 20% TFA/DCM (200 mL) was stirred at the room temperature for 2 h and evaporated to result in a residue which was diluted with a mixed solvent of MeOH/DCM (100 mL/100 mL), basified with 28% aqueous NH₄OH, and concentrated. Chromatography of the residue with CH₂Cl₂/MeOH/28% aqueous NH₄OH (90:10:1) afforded the title compound (3.49 g, 81%). ¹H NMR (MeOH-d₄) δ 1.28 (d, J=6 Hz, 3H, CH₃), 2.95 (s, 3H, CH₃), 3.08 (s, 3H, CH₃), 4.04 (q, J=6 Hz, 1H); ESI-MS m/z 117.3 (MH⁺).

HCl Salt of 2-amino-N,N-dimethyl-propylamine

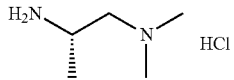

HCl salt of 2-amino-N,N-dimethyl-propylamine: To a solution of 2-amino-N,N-dimethyl-propionamide (3.49 g, 30 mmol) in THF (100 mL) was added BH₃.THF complex in THF (1.0 M, 90 mL, 90 mmol) at 0° C. resulting in a mixture which was stirred at the room temperature for 1 h and refluxed under N₂ for 18 h. After it was cooled to 0° C., the reaction mixture was quenched by adding MeOH (20 mL) slowly and dropwise at 0° C. and then stirred for 16 h. Aqueous HCl (12 N, 6 mL) was added into the reaction mixture which was then heated at 80° C. for 1 h and evaporate to afford the title compound in HCl salt form (5.3 g) which was used for the next step without purification. ¹H NMR (DMSO-d₆) δ 1.31 (d, J=6 Hz, 3H, CH₃), 2.85 (s, 6H, 2CH₃), 3.32 (m, 1H), 3.48 (m, 1H), 3.80 (m, 1H), 8.79 (br s, 2H, NH).

5-Amino-2-(2-dimethylamino-1-methyl-ethyl)-6-nitro-isoindole-1,3-dione

A mixture of 5-amino-6-nitro-isoindole-1,3-dione

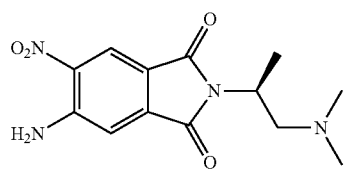 [SMILES: C[C@@H](CN(C)C)N1C(=O)c2cc(N)c([N+](=O)[O-])cc2C1=O]

5-Amino-2-(2-dimethylamino-1-methyl-ethyl)-6-nitro-isoindole-1,3-dione: A mixture of 5-amino-6-nitro-isoindole-1,3-dione (1.66 g, 8.0 mmol), HCl salt of 2-amino-N,N-dimethyl-propylamine (5.3 g, crude, <30 mmol), imidazole (1.36 g, 20 mmol) and Et₃N (8.4 mL, 6.07 g, 60 mmol) in dioxane (80 mL) was sealed in a ChemGlass heavy wall pressure flask. After it was heated at 130° C. for 72 h, the reaction mixture was evaporated to dryness at 95° C. (the bath temperature) under reduced pressure. The chromatography of the residue with CH₂Cl₂/MeOH/28% aqueous NH₄OH (240:10:1) afforded the title compound (1.49 g, 64%). ¹H NMR (DMSO-d₆) δ 1.32 (d, J=6 Hz, 3H, CH₃), 2.09 (s, 6H, 2CH₃), 2.25 (m, 1H), 2.95 (m, 1H), 4.35 (m, 1H), 7.43 (s, 1H), 8.29 (s, 1H), 8.39 (br s, 2H, NH). ESI-MS m/z 293.1 (MH⁺).

2-(4-Chloro-2-oxo-1,2-dihydro-pyridin-3-yl)-6-(2-dimethylamino-1-methyl-ethyl)-1H-1,3,6-triaza-s-indacene-5,7-dione

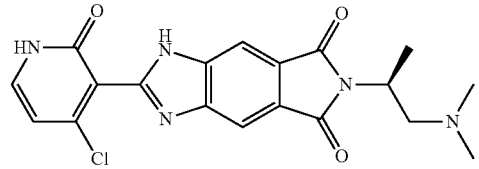 [SMILES: C[C@@H](CN(C)C)N1C(=O)c2cc3nc(-c4c(Cl)cc[nH]c4=O)[nH]c3cc2C1=O]

2-(4-Chloro-2-oxo-1,2-dihydro-pyridin-3-yl)-6-(2-dimethylamino-1-methyl-ethyl)-1H-1,3,6-triaza-s-indacene-5,7-dione: The mixture of 5-amino-2-(2-dimethylamino-1-methyl-ethyl)-6-nitro-isoindole-1,3-dione (585 mg, 2.0 mmol) and Pd/C (60 mg) in MeOH (95 mL) was stirred under atmospheric H₂ for 2.5 h and filtered through Celite. The filtrate was mixed with 4-chloro-2-methoxynicotinic aldehyde (343.2 mg, 2.0 mmol) and HOAc (5 mL), stirred at the room temperature for 62 h, and evaporated under reduced pressure to afford an oil crude which was mixed with HCl in dioxane (4 M, 25 mL) and H₂O (2 mL), heated at 70° C. for 1 h and evaporated. The residue was diluted with a mixed solvent of MeOH/DCM (50 mL/50 mL), basified with 28% aqueous NH₄OH, and concentrated. Chromatography of the residue with CH₂Cl₂/MeOH/28% aqueous NH₄OH (60:10:1) afforded the title compound (642 mg, 80%). ¹H NMR (DMSO-d₆) δ 1.39 (d, J=6 Hz, 3H, CH₃), 2.14 (s, 6H, 2CH₃), 2.29 (m, 1H), 3.04 (m, 1H), 4.40 (m, 1H), 6.59 (d, J=8 Hz, 1H), 7.69 (d, J=8 Hz, 1H), 8.04 (s, 1H), 8.05 (s, 1H); ESI-MS m/z 400.3 (MH⁺).

Synthesis of Nitroaminophthalimide

Scheme 84

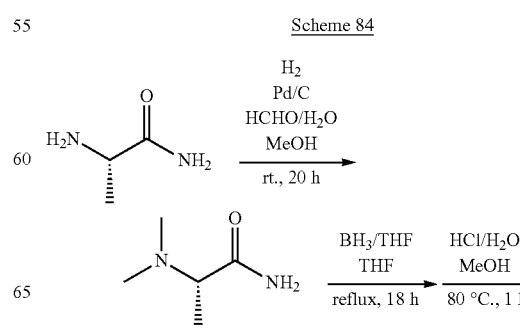

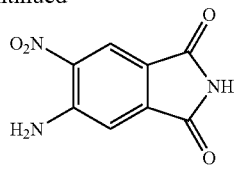

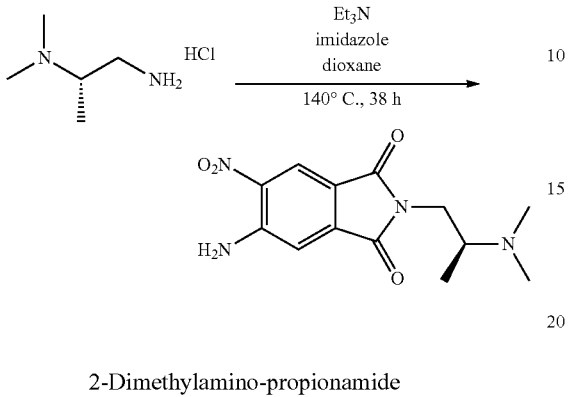

2-Dimethylamino-propionamide

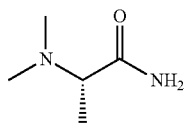

2-Dimethylamino-propionamide: A mixture of H-Ala-NH$_2$·HCl (7.47 g, 60 mmol), HCHO (37%, 14.6 mL) and Pd/C (750 mg) in MeOH (200 mL) was stirred under atmospheric H$_2$ for 16 h and filtered through Celite. The filtrate was evaporated, diluted with a mixed solvent of MeOH/DCM (150 mL/150 mL), basified with 28% aqueous NH$_4$OH, and concentrated. Chromatography of the residue with CH$_2$Cl$_2$/MeOH/28% aqueous NH$_4$OH (60:10:1) afforded the title compound (6.43 g, 92%). $^1$H NMR (DMSO-d$_6$) δ 1.06 (d, J=8 Hz, 3H, CH$_3$), 2.16 (s, 6H, 2CH$_3$), 2.83 (q, J=8 Hz, 3H, CH$_3$), 6.94 (br s, 1H, NH), 7.18 (br s, 1H, NH); ESI-MS m/z 117.3 (MH$^+$).

HCl Salt of 2-dimethylamino-propylamine

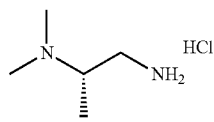

HCl salt of 2-dimethylamino-propylamine: To a solution of 2-dimethylamino-propionamide (3.49 g, 30 mmol) in THF (100 mL) was added BH$_3$·THF complex in THF (1.0 M, 90 mL, 90 mmol) at 0° C. resulting in a mixture which was stirred at the room temperature for 1 h and refluxed under N$_2$ for 22 h. After it was cooled to 0° C., the reaction mixture was quenched by adding MeOH (25 mL) slowly and dropwise at 0° C. and then stirred for 16 h. Aqueous HCl (12 N, 6 mL) was added into the reaction mixture which was then heated at 80° C. for 1 h and evaporate to afford the title compound in HCl salt form (5.5 g) which was used for the next step without purification. $^1$H NMR (DMSO-d$_6$) δ 1.06 (d, J=8 Hz, 3H, CH$_3$), 2.75 (s, 6H, 2CH$_3$), 3.40 (m, 1H), 3.60-3.76 (2H), 8.81 (br s, 2H).

5-Amino-2-(2-dimethylamino-propyl)-6-nitro-isoindole-1,3-dione

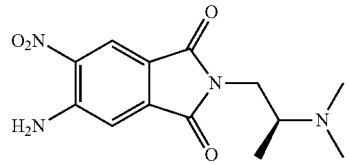 [SMILES: C[C@@H](CN1C(=O)c2cc(N)c([N+](=O)[O-])cc2C1=O)N(C)C]

5-Amino-2-(2-dimethylamino-propyl)-6-nitro-isoindole-1,3-dione: A mixture of 5-amino-6-nitro-isoindole-1,3-dione (1.66 g, 8.0 mmol), HCl salt of 2-dimethylamino-propylamine (5.5 g, crude, <30 mmol), imidazole (1.36 g, 20 mmol) and Et$_3$N (8.4 mL, 6.07 g, 60 mmol) in dioxane (80 mL) was sealed in a ChemGlass heavy wall pressure flask. After it was heated at 130° C. for 69 h, the reaction mixture was evaporated to dryness at 95° C. (the bath temperature) under reduced pressure. The chromatography of the residue with CH$_2$Cl$_2$/MeOH/28% aqueous NH$_4$OH (240:10:1) afforded the title compound (360 mg, 15%). $^1$H NMR (DMSO-d$_6$) δ 0.88 (d, J=6 Hz, 3H, CH$_3$), 2.13 (s, 6H, 2CH$_3$), 3.32 (m, 2H), 3.65 (m, 1H), 7.45 (s, 1H), 8.30 (s, 1H), 8.40 (br s, 2H, NH). ESI-MS m/z 293.3 (MH$^+$).

2-(4-Chloro-2-oxo-1,2-dihydro-pyridin-3-yl)-6-(2-dimethylamino-propyl)-1H-1,3,6-triaza-s-indacene-5,7-dione

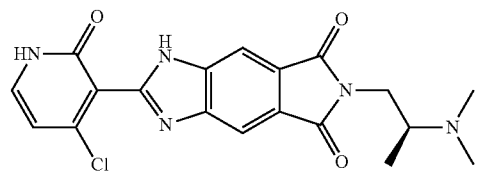 [SMILES: C[C@@H](CN1C(=O)c2cc3nc(-c4c(Cl)cc[nH]c4=O)[nH]c3cc2C1=O)N(C)C]

2-(4-Chloro-2-oxo-1,2-dihydro-pyridin-3-yl)-6-(2-dimethylamino-propyl)-1H-1,3,6-triaza-s-indacene-5,7-dione: The mixture of 5-amino-2-(2-dimethylamino-1-methyl-ethyl)-6-nitro-isoindole-1,3-dione (360 mg, 1.2 mmol) and Pd/C (40 mg) in MeOH (95 mL) was stirred under atmospheric H$_2$ for 24 h and filtered through Celite. The filtrate was mixed with 4-chloro-2-methoxynicotinic aldehyde (343.2 mg, 2.0 mmol) and HOAc (5 mL), stirred at the room temperature for 96 h, and evaporated under reduced pressure to afford an oil crude which was mixed with HCl in dioxane (4 M, 25 mL) and H$_2$O (2 mL), heated at 70° C. for 4 h and evaporated. The residue was diluted with a mixed solvent of MeOH/DCM (50 mL/50 mL), basified with 28% aqueous NH$_4$OH, and concentrated. Chromatography of the residue with CH$_2$Cl$_2$/MeOH/28% aqueous NH$_4$OH (60:10:1) afforded the title compound (281 mg, 58%). $^1$H NMR (DMSO-d$_6$) δ 0.95 (d, J=6 Hz, 3H, CH$_3$), 2.24 (s, 6H, 2CH$_3$), 3.10 (m, 1H), 3.45 (m, 1H), 3.74 (m, 1H), 6.57 (d, J=8 Hz, 1H), 7.70 (d, J=8 Hz, 1H), 8.06 (s, 1H), 8.07 (s, 1H); ESI-MS m/z 400.3 (MH$^+$).

Synthesis of Azetidine-Substituted Imidazo[4,5-f]isoindole-5,7(1H,6H)-dione Compounds
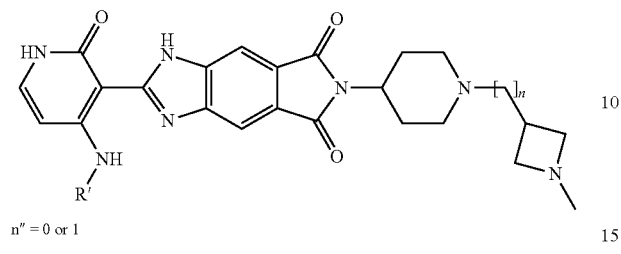
n″ = 0 or 1
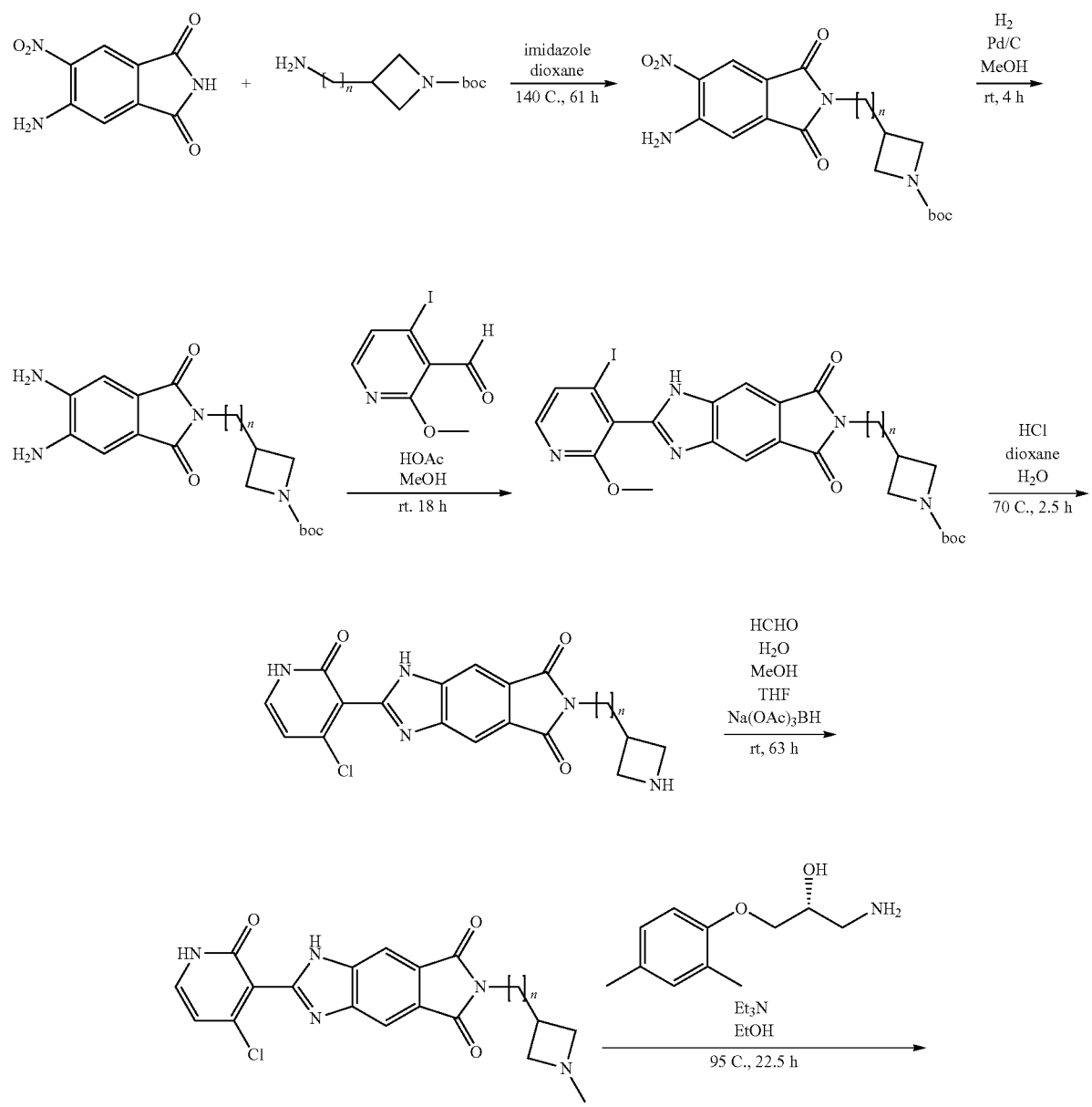
Scheme 85

-continued

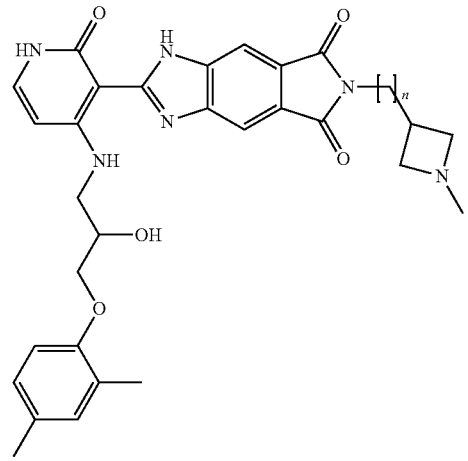

3-(5-Amino-6-nitro-1,3-dioxo-1,3-dihydro-isoindol-2-ylmethyl)-azetidine-1-carboxylic acid tert-butyl ester

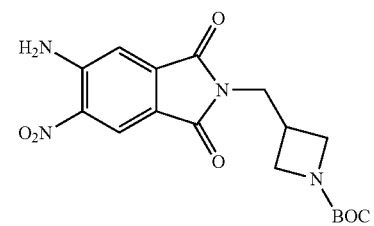 [SMILES: CC(C)(C)OC(=O)N1CC(CN2C(=O)c3cc(N)c([N+](=O)[O-])cc3C2=O)C1]

3-(5-Amino-6-nitro-1,3-dioxo-1,3-dihydro-isoindol-2-ylmethyl)-azetidine-1-carboxylic acid tert-butyl ester: A mixture of 5-amino-6-nitro-isoindole-1,3-dione (994 mg, 4.8 mmol), 3-Aminomethyl-azetidine-1-carboxylic acid tert-butyl ester (1.0 g, 5.4 mmol) and imidazole (493 mg, 7.25 mmol) in dioxane (140 mL) was sealed in a ChemGlass heavy wall pressure flask. After it was heated at 140° C. for 61 h, the reaction mixture was evaporated to dryness at 95° C. (the bath temperature) under reduced pressure. The chromatography of the residue with CH$_2$Cl$_2$/MeOH/28% aqueous NH$_4$OH (400:10:1) afforded the title compound (830 mg, 46%). $^1$H NMR (MeOH-d$_4$) δ 1.44 (s, 9H), 2.94 (m, 1H), 3.78 (m, 2H), 3.88 (d, J=6 Hz, 2H), 4.00 (m, 2H), 7.44 (s, 1H), 8.52 (s, 1H); ESI-MS m/z 377.3 (MH$^+$).

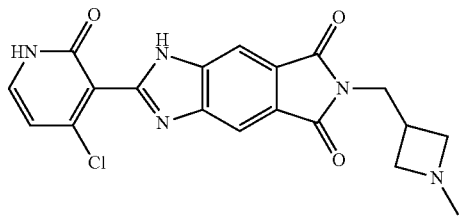 [SMILES: CN1CC(CN2C(=O)c3cc4nc(-c5c(Cl)cc[nH]c5=O)[nH]c4cc3C2=O)C1]

2-(4-Chloro-2-oxo-1,2-dihydro-pyridin-3-yl)-6-(1-methyl-azetidin-3-ylmethyl)-1H-1,3,6-triaza-s-indacene-5,7-dione: To a mixture of 3-(5-amino-6-nitro-1,3-dioxo-1,3-dihydro-isoindol-2-ylmethyl)-azetidine-1-carboxylic acid tert-butyl ester (830 mg, 2.2 mmol) and 10% Pd/C (85 mg) was added 2-propanol (10 mL), and then MeOH (90 mL). After it was stirred under atmospheric hydrogen for 4 h, the reaction mixture was filtered over Celite. The filtrate was mixed with 4-iodo-2-methoxynicotinic aldehyde (580 g, 2.2 mmol) and HOAc (5.0 mL), stirred at the room temperature for 18 h, and evaporated under reduced pressure to afford an oil crude which was mixed with HCl in dioxane (4 M, 30 mL) and H$_2$O (2.5 mL), heated at 70° C. for 2.5 h and evaporated at 95° C. (the bath temperature) to dryness. The residue was diluted with a mixed solvent of DCM/MeOH (30 mL/70 mL), basified with 28% aqueous NH$_4$OH and concentrated. Chromatography of the crude with CH$_2$Cl$_2$/MeOH/28% aqueous NH$_4$OH (25:10:1) afforded a crude product which was mixed with HOAc (2.1 mL) and HCHO (37% in H$_2$O, 2.1 mL) in a mixed solvent of MeOH/THF (24 mL/24 mL). The resulting reaction mixture was stirred at the room temperature for 10 min and followed by addition of Na(OAc)$_3$BH (2.54 g, 12.0 mmol). The reaction mixture was stirred at the room temperature for 63 h and then evaporated. Chromatography of the residue with CH$_2$Cl$_2$/MeOH/28% aqueous NH$_4$OH (90:10:1) afforded the title compound (330 mg, 38%). ESI-MS m/z 398.3 (MH$^+$).

TFA Salt of 2-{4-[3-(2,4-Dimethyl-phenoxy)-2-hydroxy-propylamino]-2-oxo-1,2-dihydro-pyridin-3-yl}-6-(1-methyl-azetidin-3-ylmethyl)-1H-1,3,6-triaza-s-indacene-5,7-dione

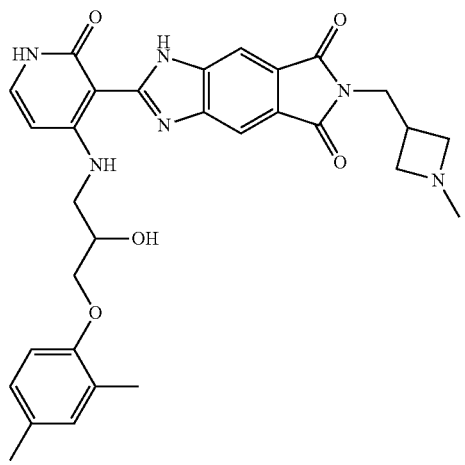 [SMILES: Cc1ccc(OCC(O)CNc2cc[nH]c(=O)c2-c2nc3cc4c(cc3[nH]2)C(=O)N(CC2CN(C)C2)C4=O)c(C)c1]

TFA salt of 2-{4-[3-(2,4-Dimethyl-phenoxy)-2-hydroxy-propylamino]-2-oxo-1,2-dihydro-pyridin-3-yl}-6-(1-methyl-azetidin-3-ylmethyl)-1H-1,3,6-triaza-s-indacene-5,7-dione: To a solution of 2-(4-chloro-2-oxo-1,2-dihydro-pyridin-3-yl)-6-(1-methyl-azetidin-3-ylmethyl)-1H-1,3,6-triaza-s-indacene-5,7-dione (40 mg, 0.1 mmol) and (R)-1-amino-3-(2,4-dimethyl-phenoxy)-propan-2-ol (20 mg, 0.1 mmol) in EtOH (2 mL) was added Et$_3$N (200 μL, 1.43 mmol). After it was heated at 95° C. for 22.5 h, the reaction mixture was concentrated under reduced pressure. HPLC purification of the residue afforded the title compound in TFA salt form (6.61 mg, 20%). $^1$H NMR (DMSO-d$_6$) δ 2.19 (s, 3H, CH$_3$), 2.21 (s, 3H, CH$_3$), 2.82 (s, 3H, CH$_3$), 3.09 (m, 1H), 3.59 (m, 1H), 3.70 (m, 1H), 3.83 (m, 2H), 3.90-4.18 (7H), 5.55 (m, 1H, NH), 6.23 (d, J=8 Hz, 1H), 6.84 (d, J=8 Hz, 1H), 6.92 (d, J=8 Hz, 1H), 6.98 (s, 1H), 7.41 (m, 1H), 7.67 (s, 1H), 8.13 (s, 1H), 9.83 (br s, 1H, NH), 10.95 (br s, 1H, NH), 11.30 (d, J=6 Hz, 1H); ESI-MS m/z 557.5 (MH$^+$).

TFA salt of 2-{4-[3-(2,4-Dimethyl-phenoxy)-2-hydroxy-propylamino]-2-oxo-1,2-dihydro-pyridin-3-yl}-6-(1-methyl-azetidin-3-yl)-1H-1,3,6-triaza-s-indacene-5,7-dione

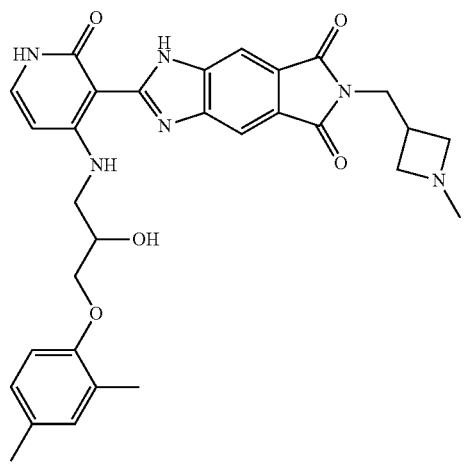 [SMILES: Cc1ccc(OCC(O)CNc2cc[nH]c(=O)c2-c2nc3cc4c(cc3[nH]2)C(=O)N(CC2CN(C)C2)C4=O)c(C)c1]

TFA salt of 2-{4-[3-(2,4-Dimethyl-phenoxy)-2-hydroxy-propylamino]-2-oxo-1,2-dihydro-pyridin-3-yl}-6-(1-methyl-azetidin-3-yl)-1H-1,3,6-triaza-s-indacene-5,7-dione:
$^1$H NMR (DMSO-d$_6$) δ 2.19 (s, 3H, CH$_3$), 2.22 (s, 3H, CH$_3$), 3.00 (s, 3H, CH$_3$), 3.50-3.69 (3H), 3.95-4.29 (4H), 4.53 (m, 2H), 6.26 (d, J=8 Hz, 1H), 6.84 (d, J=8 Hz, 1H), 6.92 (d, J=8 Hz, 1H), 6.98 (s, 1H), 7.41 (m, 1H), 7.72 (br s, 1H), 8.17 (s, 1H), 10.94 (br s, 1H, NH), 11.31 (d, J=6 Hz, 1H); ESI-MS m/z 543.2 (MH$^+$).

Synthesis of Lactams with Variety of Amine Side Chains

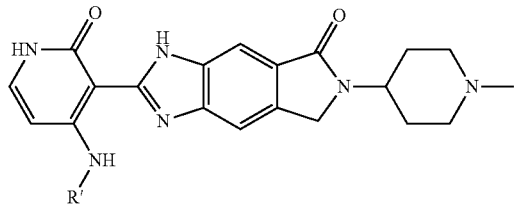

Scheme 86

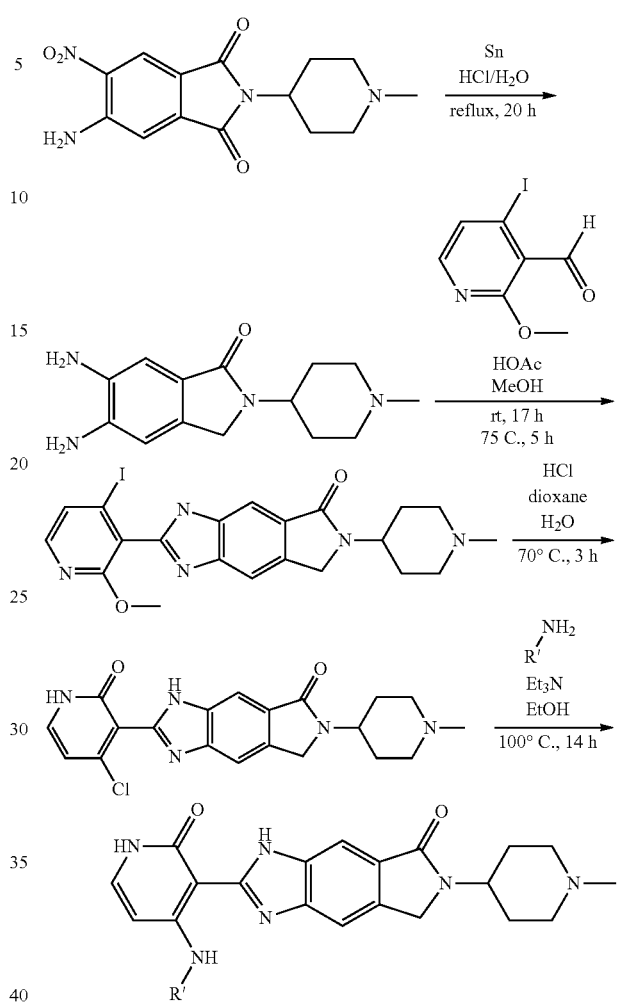

Synthesis of Lactams

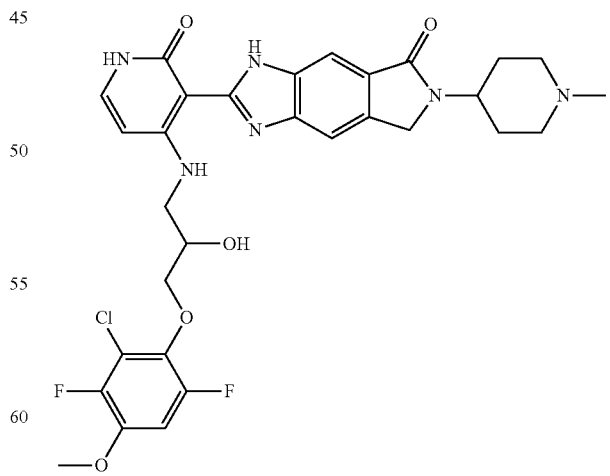

TFA salt of (R)-2-(4-(3-(2-chloro-3,6-difluoro-4-methoxyphenoxy)-2-hydroxypropylamino)-2-oxo-1,2-dihydropyridin-3-yl)-6-(1-methylpiperidin-4-yl)-6,7-dihydroimidazo[4,5-f]isoindol-5(3H)-one: $^1$H NMR (DMSO-d$_6$) δ 1.95 (m, 2H), 2.20 (m, 2H), 2.75 (s, 3H, CH$_3$), 3.20 (m, 2H), 3.50 (m, 2H), 3.75 (m, 1H), 3.85 (s, 3H, CH$_3$), 4.12 (m, 2H), 4.35 (m, 1H), 4.50 (s, 2H), 6.22 (d, J=6 Hz, 1H), 7.31 (m, 1H), 7.39 (m, 1H), 7.70 (s, 1H), 7.88 (s, 1H), 10.65 (br s, 1H), 11.04 (br s, 1H, NH), 11.27 (d, J=6 Hz, 1H); ESI-MS m/z 629.5 (MH$^+$).
Synthesis of Substituted Lactams [Substituted-2-oxo-1,2-dihydropyridin-3-yl)-6,7-dihydroimidazo[4,5-f]isoindol-5(3H)-ones]
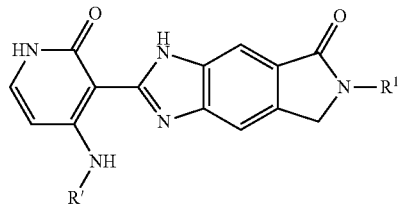
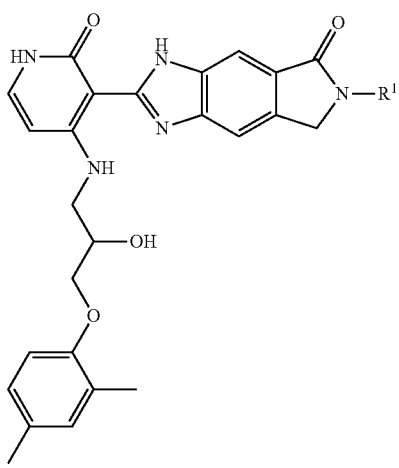
Scheme 87
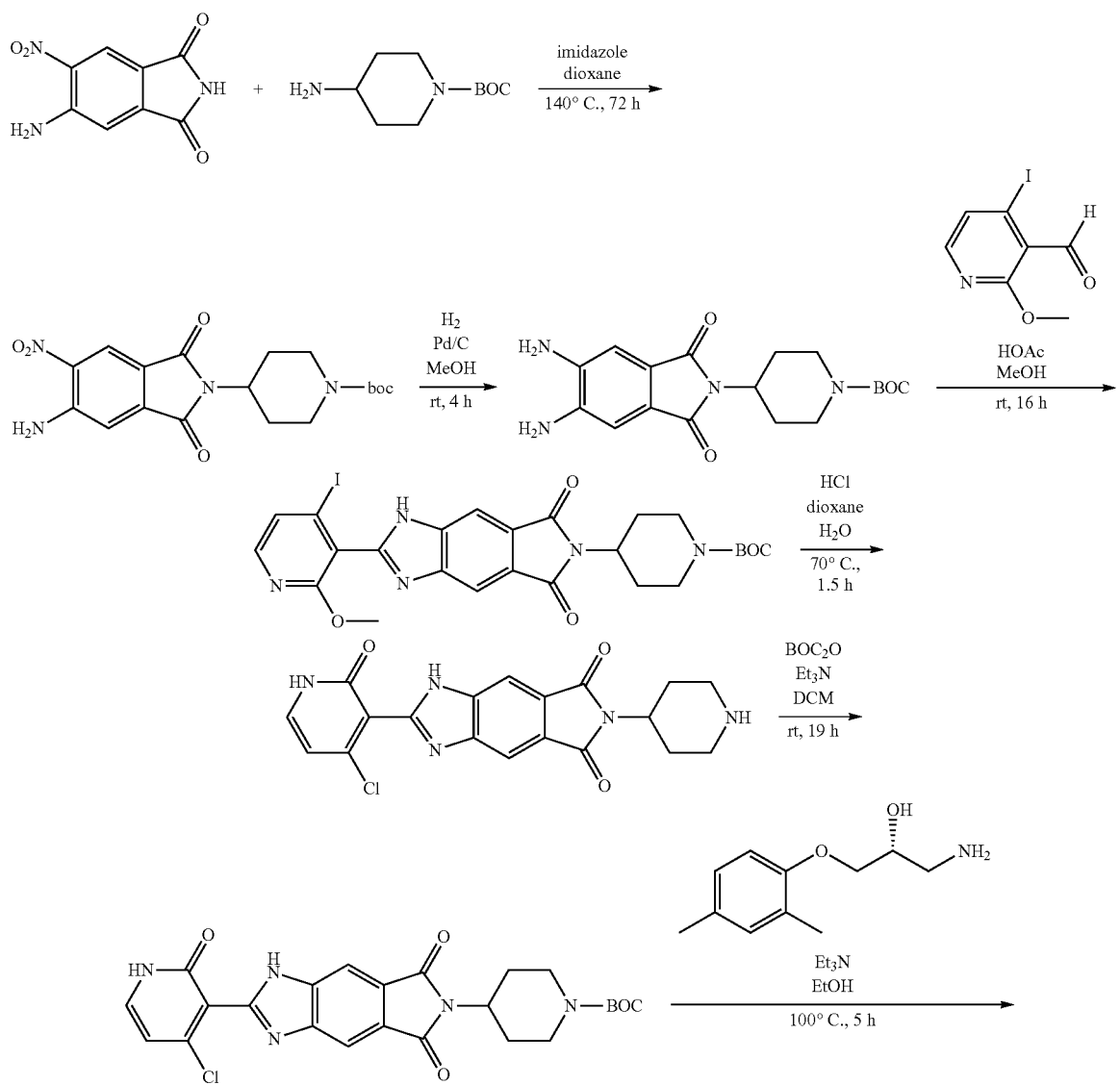

-continued
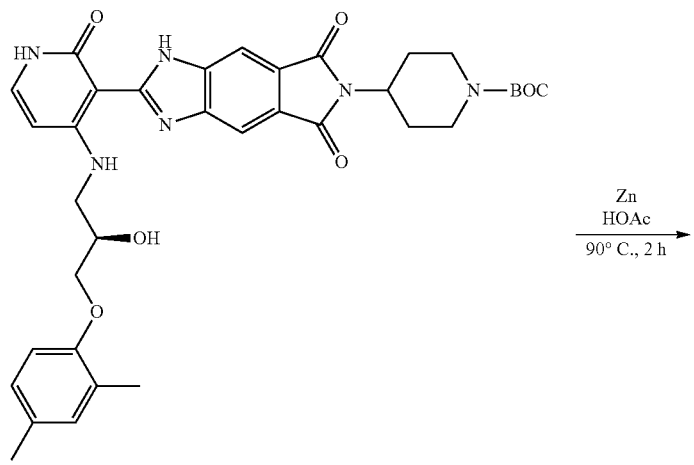
Zn
HOAc
90° C., 2 h
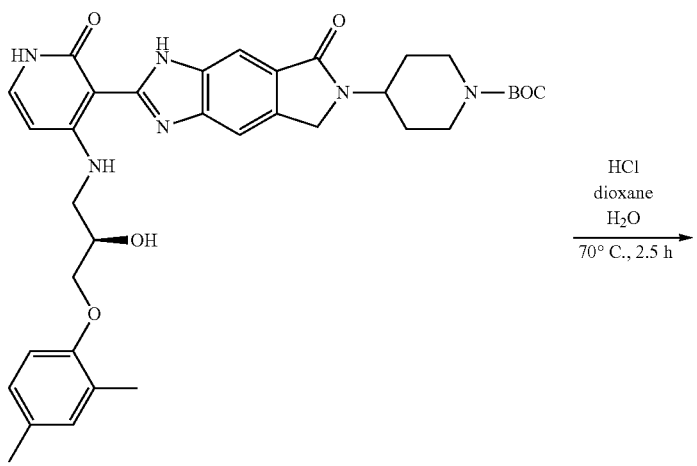
HCl
dioxane
H₂O
70° C., 2.5 h
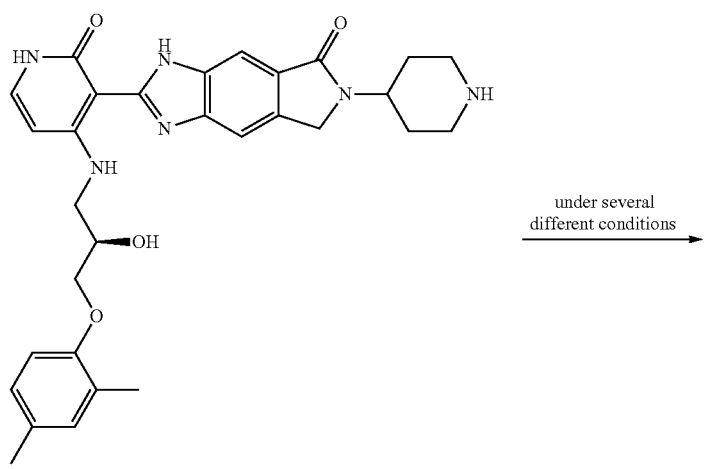
under several
different conditions

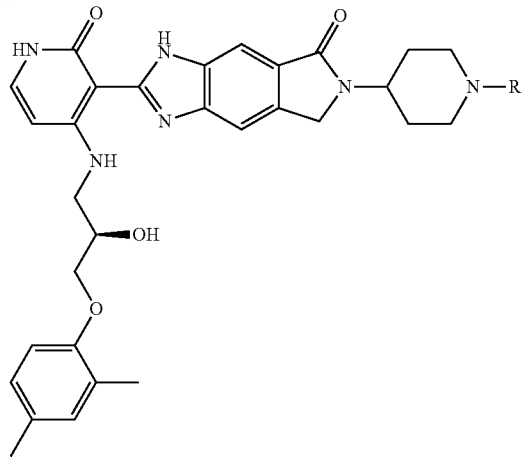

4-(5-Amino-6-nitro-1,3-dioxo-1,3-dihydro-isoindol-2-yl)-piperidine-1-carboxylic acid tert-butyl ester: A mixture of 5-amino-6-nitro-isoindole-1,3-dione

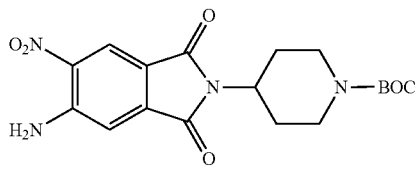 [SMILES: CC(C)(C)OC(=O)N1CCC(N2C(=O)c3cc(N)c([N+](=O)[O-])cc3C2=O)CC1]

4-(5-Amino-6-nitro-1,3-dioxo-1,3-dihydro-isoindol-2-yl)-piperidine-1-carboxylic acid tert-butyl ester: A mixture of 5-amino-6-nitro-isoindole-1,3-dione (2.07 g, 10 mmol), tert-butyl 4-amino-piperidine-1-carboxylate (2.5 g, 12 mmol), imidazole (1.63 g, 24 mmol) in dioxane (100 mL) was sealed in a ChemGlass heavy wall pressure flask. After it was heated at 140° C. for 72 h, the reaction mixture was evaporated to dryness at 95° C. (the bath temperature) under reduced pressure. The chromatography of the residue with $CH_2Cl_2$/MeOH/28% aqueous $NH_4OH$ (320:10:1) afforded the title compound (2.09 g, 54%). $^1$H NMR ($CDCl_3$) δ 1.49 (s, 9H), 1.73 (m, 2H), 2.38 (m, 2H), 2.80 (m, 2H), 4.20-4.31 (3H), 7.03 (br s, 2H, NH), 7.34 (s, 1H), 8.61 (s, 1H); ESI-MS m/z 391.5 (MH$^+$).

2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one

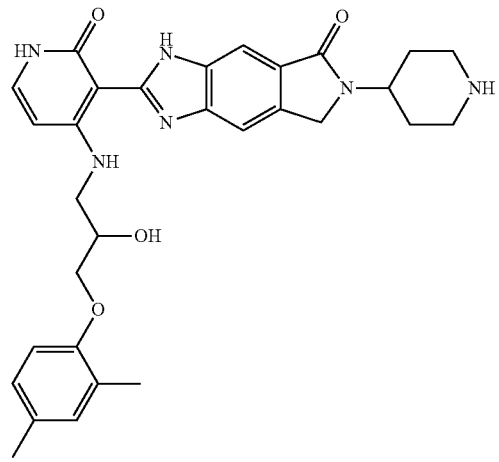 [SMILES: Cc1ccc(OCC(O)CNc2cc[nH]c(=O)c2-c2nc3cc4c(cc3[nH]2)C(=O)N(C2CCNCC2)C4)c(C)c1]

2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one: To a mixture of 4-(5-amino-6-nitro-1,3-dioxo-1,3-dihydro-isoindol-2-yl)-piperidine-1-carboxylic acid tert-butyl ester (5.0 g, 12.8 mmol) and 10% Pd/C (500 mg) was added 2-propanol (20 mL), and then MeOH (230 mL). After it was stirred under atmospheric hydrogen for 4 h, the reaction mixture was filtered over Celite. The filtrate was mixed with 4-iodo-2-methoxynicotinic aldehyde (3.37 g, 12.8 mmol) and HOAc (13 mL), stirred at the room temperature for 16 h, and evaporated under reduced pressure to afford an oil crude which was mixed with HCl in dioxane (4 M, 60 mL) and $H_2O$ (5 mL), heated at 70° C. for 1.5 h and evaporated at 95° C. (the bath temperature) to dryness. $Et_3N$ (5.35 mL, 38.4 mmol) was added to the solution of the residue in DCM (250 mL) at 0° C. under $N_2$ and followed by the addition of the solution of $Boc_2O$ (3.35 g, 15.4 mmol) in a minimum amount od DCM. After it was stirred at 0° C. for 1 h and at the room temperature for 19 h, the reaction mixture was mixed slowly with MeOH (200 mL) at 0° C. and then evaporated at 70° C. (the bath temperature) to dryness under reduced pressure. The residue was mixed with (R)-1-amino-3-(2,4-dimethyl-phenoxy)-propan-2-ol (2.5 g, 12.8 mmol) and $Et_3N$ (5.35 mL, 38.4 mmol) in EtOH (200 mL) resulting in a mixture which was heated at 100° C. for 5 h and then concentrated. Chromatography of the residual mixture with $CH_2Cl_2$/MeOH/28% aqueous $NH_4OH$ (250:10:1) furnished a fluorescent product which was mixed with zinc dust (5.5 g, 84 mmol) and HOAc (200 mL). After it was heated to 90° C. for 2 h, the reaction mixture was filtered and the filtrate was concentrated at 70° C. (the bath temperature) under reduced pressure. The residue was mixed with HCl in dioxane (4 M, 60 mL) and $H_2O$ (5 mL), heated at 70° C. for 2.5 h and evaporated at 95° C. (the bath temperature) to dryness. The residue was basified with $NH_3$ in EtOH (2 M) and concentrated. Chromatography of the crude with $CH_2Cl_2$/MeOH/28% aqueous $NH_4OH$ (40:10:1) afforded a fluorescent product (6.5 g). 50 mg of this product was subjected to HPLC purification to furnish the title compound in TFA salt form (37 mg). $^1$H NMR (DMSO-$d_6$) δ 1.90-2.05 (4H), 2.19 (s, 3H, $CH_3$), 2.22 (s, 3H, $CH_3$), 3.13 (m, 2H), 3.42 (m, 2H), 3.55 (m, 1H), 3.69 (m, 1H), 4.03 (m, 2H), 4.13 (m, 1H), 4.39 (m, 1H), 4.46 (s, 2H), 6.22 (d, J=7 Hz, 1H), 6.84 (d, J=7 Hz, 1H), 6.94 (d, J=7 Hz, 1H), 6.98 (s, 1H), 7.39 (d, J=7 Hz, 1H), 7.55 (br s, 1H), 7.85 (br s, 1H), 11.14 (br s, 1H, NH), 11.23 (br d, J=6 Hz, 1H, NH); ESI-MS m/z 543.5 (MH$^+$).

409

TFA salt of 2-{4-[3-(2,4-dimethyl-phenoxy)-2-hydroxy-propylamino]-2-oxo-1,2-dihydro-pyridin-3-yl}-6-[1-(3-oxo-butyl)-piperidin-4-yl]-6,7-dihydro-3H-1,3,6-triaza-s-indacen-5-one

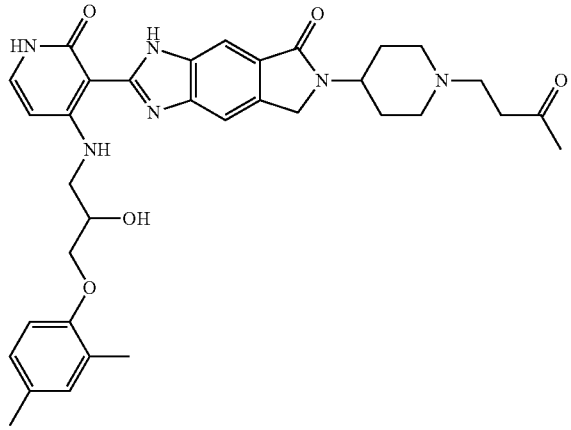 [SMILES: CC(=O)CCN1CCC(N2Cc3cc4nc(-c5c(NCC(O)COc6ccc(C)cc6C)cc[nH]c5=O)[nH]c4cc3C2=O)CC1]

TFA salt of 2-{4-[3-(2,4-dimethyl-phenoxy)-2-hydroxy-propylamino]-2-oxo-1,2-dihydro-pyridin-3-yl}-6-[1-(3-oxo-butyl)-piperidin-4-yl]-6,7-dihydro-3H-1,3,6-triaza-s-indacen-5-one: A mixture of 2-{4-[(R)-3-(2,4-Dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (54.3 mg, 1 mmol) and methyl vinyl ketone (415 µL, 5.0 mmol) in DMF (1 mL) was stirred at the room temperature for 17 h and the reaction mixture was subjected to HPLC purification to afford the title compound in TFA salt form (30.4 mg, 40%). $^1$H NMR (DMSO-d$_6$) δ 1.95 (2H), 2.10 (m, 2H), 2.18 (s, 3H, CH$_3$), 2.21 (s, 3H, CH$_3$), 3.05 (m, 2H), 3.19 (m, 2H), 3.26 (m, 2H), 3.50-3.61 (3H), 3.71 (m, 1H), 4.00 (m, 2H), 4.12 (m, 1H), 4.35 (m, 1H), 4.45 (s, 2H), 6.23 (d, J=7 Hz, 1H), 6.84 (d, J=7 Hz, 1H), 6.93 (d, J=7 Hz, 1H), 6.98 (s, 1H), 7.38 (dd, J=7 Hz and 7 Hz, 1H), 7.55 (br s, 1H), 7.85 (br s, 1H), 9.79 (br s, 1H), 11.14 (br s, 1H, NH), 11.25 (br d, J=6 Hz, 1H, NH); ESI-MS m/z 613.5 (MH$^+$).

2-{4-[3-(2,4-Dimethyl-phenoxy)-2-hydroxy-propylamino]-2-oxo-1,2-dihydro-pyridin-3-yl}-6-(1-propyl-piperidin-4-yl)-6,7-dihydro-3H-1,3,6-triaza-s-indacen-5-one

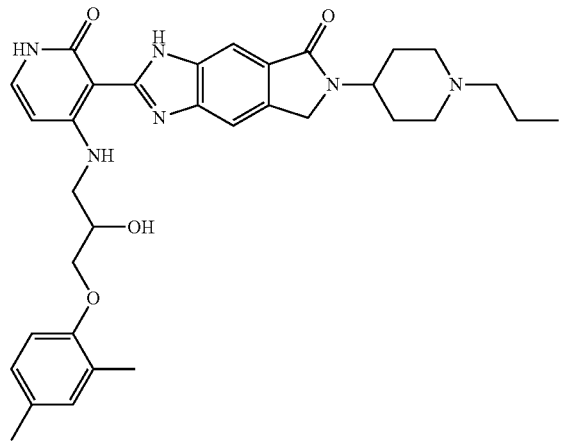 [SMILES: CCCN1CCC(N2Cc3cc4nc(-c5c(NCC(O)COc6ccc(C)cc6C)cc[nH]c5=O)[nH]c4cc3C2=O)CC1]

410

2-{4-[3-(2,4-Dimethyl-phenoxy)-2-hydroxy-propylamino]-2-oxo-1,2-dihydro-pyridin-3-yl}-6-(1-propyl-piperidin-4-yl)-6,7-dihydro-3H-1,3,6-triaza-s-indacen-5-one: To a solution of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (27.1 mg, 0.05 mmol) and propionaldehyde (150 µL) in a mixed solvent of CH$_3$CN (6 mL) and H$_2$O (2 mL) was added HOAc (500 µL) at 0° C. and the resulting reaction mixture was stirred at 0° C. for 20 min and followed by addition of Na(OAc)$_3$BH (254 mg, 1.2 mmol). The reaction mixture was stirred at 0° C. for 1 h and at the room temperature for 1 h and then evaporated. Chromatography of the residue with CH$_2$Cl$_2$/MeOH/28% aqueous NH$_4$OH (490:10:1) afforded the title compound (16.5 mg, 57%). $^1$H NMR (DMSO-d$_6$) δ 0.87 (t, J=6 Hz, 3H, CH$_3$), 1.45 (m, 2H), 1.70 (m, 2H), 1.80 (m, 2H), 2.04 (m, 2H), 2.19 (s, 3H, CH$_3$), 2.22 (s, 3H, CH$_3$), 2.97 (m, 2H), 3.55 (m, 1H), 3.70 (m, 1H), 3.95-4.06 (3H), 4.11 (m, 1H), 4.42 (s, 1H), 4.47 (s, 1H), 5.47 (d, J=3 Hz, 0.5H, NH), 5.52 (d, J=3 Hz, 0.5H, NH), 6.22 (m, 1H), 6.81 (m, 1H), 6.89-6.99 (2H), 7.32-7.38 (1.5H), 7.68 (s, 0.5H), 7.80 (s, 0.5H), 7.94 (s, 0.5H), 11.15 (d, J=6 Hz, 1H, NH), 11.21 (br d, J=6 Hz, 1H, NH); ESI-MS m/z 585.5 (MH$^+$).

2-{4-[3-(2,4-Dimethyl-phenoxy)-2-hydroxy-propylamino]-2-oxo-1,2-dihydro-pyridin-3-yl}-6-(1-isopropyl-piperidin-4-yl)-6,7-dihydro-3H-1,3,6-triaza-s-indacen-5-one

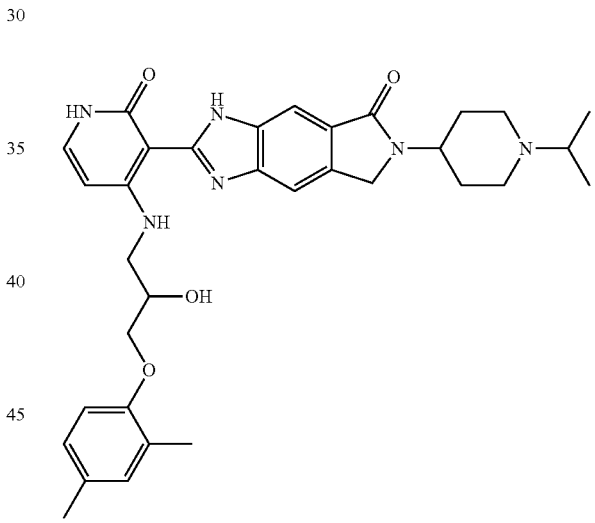

2-{4-[3-(2,4-Dimethyl-phenoxy)-2-hydroxy-propylamino]-2-oxo-1,2-dihydro-pyridin-3-yl}-6-(1-isopropyl-piperidin-4-yl)-6,7-dihydro-3H-1,3,6-triaza-s-indacen-5-one: A mixture of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (27.1 mg, 0.05 mmol), acetone (200 µL) and Ti(i-PrO)$_4$ (300 µL) was stirred at the room temperature for 2 h and diluted with MeOH (5 mL). NaBH$_4$ (190 mg, 5 mmol) was added into the reaction mixture and the mixture was stirred at the room temperature for 16 h and concentrated. Chromatography of the residue with CH$_2$Cl$_2$/MeOH/28% aqueous NH$_4$OH (490:10:1) afforded the title compound (2.06 mg, 7%). $^1$H NMR (DMSO-d$_6$) δ 1.22 (s, 3H, CH$_3$), 1.24 (s, 3H, CH$_3$), 1.25-1.45 (4H), 1.80-2.30 (6H), 3.33-3.60 (2H), 3.70 (m, 1H), 3.90-4.19 (2H), 4.35-4.50 (2H), 5.47 (m, 1H, NH), 6.22 (m, 1H), 6.81 (m, 1H), 6.89-6.99 (2H), 7.32-7.38 (1.5H), 7.68 (s, 0.5H), 7.80 (s, 0.5H), 7.94 (s, 0.5H), 11.18 (br s, 1H, NH), 11.22 (d, J=6 Hz, 1H, NH); ESI-MS m/z 585.5 (MH+).

6-(1-Cyclopropyl-piperidin-4-yl)-2-{4-[3-(2,4-dimethyl-phenoxy)-2-hydroxy-propylamino]-2-oxo-1,2-dihydro-pyridin-3-yl}-6,7-dihydro-3H-1,3,6-triaza-s-indacen-5-one

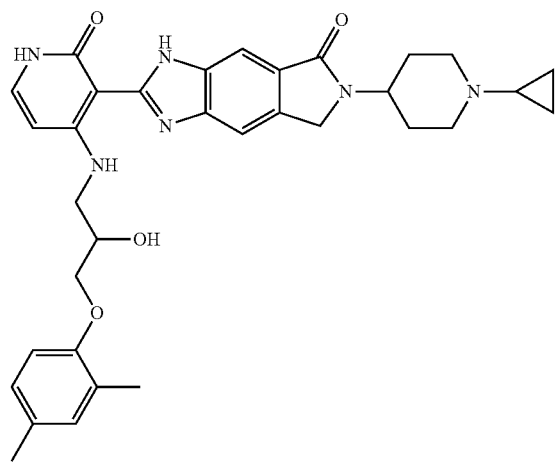 [SMILES: Cc1ccc(OCC(O)CNc2cc[nH]c(=O)c2-c2nc3cc4c(cc3[nH]2)C(=O)N(C2CCN(C3CC3)CC2)C4)c(C)c1]

6-(1-Cyclopropyl-piperidin-4-yl)-2-{4-[3-(2,4-dimethyl-phenoxy)-2-hydroxy-propylamino]-2-oxo-1,2-dihydro-pyridin-3-yl}-6,7-dihydro-3H-1,3,6-triaza-s-indacen-5-one: To a solution of 2-{4-[(R)-3-(2,4-dimethyl-phenoxy)-2-hydroxy-propylamino]-2-oxo-1,2-dihydro-pyridin-3-yl}-6-piperidin-4-yl-6,7-dihydro-3H-1,3,6-triaza-s-indacen-5-one (54.3 mg, 0.1 mmol) and bromocyclopropane (121 mg, 1.0 mmol) in $CH_3CN$ (8 mL) was added DIEA (129.3 mg, 1.0 mmol) and the resulting reaction mixture was stirred at the room temperature for 112 h and then evaporated. Chromatography of the residue with $CH_2Cl_2$/MeOH/28% aqueous $NH_4OH$ (490:10:1) afforded the title compound (3.27 mg, 5.6%). $^1$H NMR (DMSO-$d_6$) δ 1.70 (m, 2H), 1.80 (m, 2H), 2.04 (m, 2H), 2.19 (s, 3H, $CH_3$), 2.22 (s, 3H, $CH_3$), 2.90-3.00 (4H), 3.45 (m, 1H), 3.70 (m, 1H), 3.95-4.06 (3H), 4.11 (m, 1H), 4.42 (s, 1H), 4.47 (s, 1H), 5.10-5.22 (2H), 5.47 (d, J=3 Hz, 0.5H, NH), 5.52 (d, J=3 Hz, 0.5H, NH), 5.81 (m, 1H), 6.22 (m, 1H), 6.81 (m, 1H), 6.89-6.99 (2H), 7.32-7.38 (1.5H), 7.68 (s, 0.5H), 7.80 (s, 0.5H), 7.94 (s, 0.5H), 11.15 (d, J=6 Hz, 1H, NH), 11.21 (br d, J=6 Hz, 1H, NH); ESI-MS m/z 583.7 (MH+).

Synthesis of Other Tricyclic Derivatives:

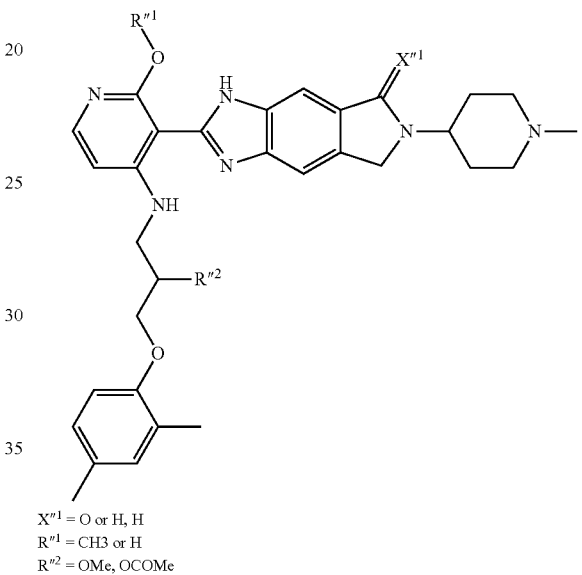

$X''^1$ = O or H, H
$R''^1$ = $CH_3$ or H
$R''^2$ = OMe, OCOMe

Scheme 88

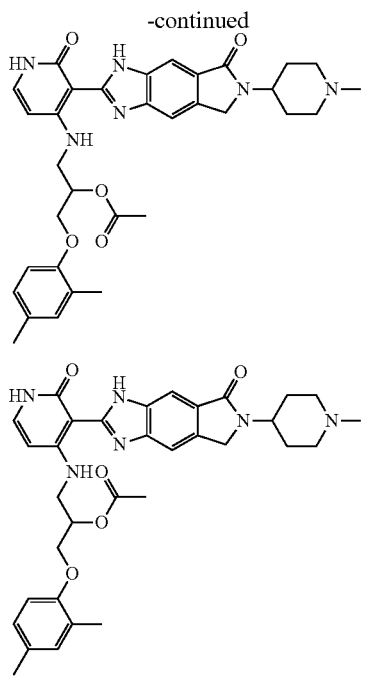

TFA salt of acetic acid 1-(2,4-dimethyl-phenoxymethyl)-2-{3-[6-(1-methyl-piperidin-4-yl)-7-oxo-1,5,6,7-tetrahydro-1,3,6-triaza-s-indacen-2-yl]-2-oxo-1,2-dihydro-pyridin-4-ylamino}-ethyl ester: A solution of 2-{4-[3-(2,4-dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one (30 mg, 0.054 mmol) in HOAc (4 mL0 was heated at 100° C. for 88 h and evaporated. The residue was subjected to HPLC purification to afford the title compound in TFA salt form (17.0 mg, 44%). $^1$H NMR (DMSO-d$_6$) δ 1.90-2.15 (4H), 2.05 (s, 3H, CH$_3$), 2.16 (s, 3H, CH$_3$), 2.22 (s, 3H, CH$_3$), 2.81 (s, 3H, CH$_3$), 3.20 (m, 2H), 3.52 (m, 2H), 3.78 (m, 1H), 3.90 (m, 1H), 4.20 (m, 2H), 4.31 (m, 1H), 4.47 (s, 2H), 5.43 (br s, 1H, NH), 6.28 (d, J=8 Hz, 1H), 6.84 (d, J=8 Hz, 1H), 6.94 (d, J=8 Hz, 1H), 6.99 (s, 1H), 7.41 (m, 1H), 7.60 (br s, 1H), 7.85 (br s, 1H), 9.60 (br s, 1H, NH), 11.13 (br s, 1H, NH), 11.33 (d, J=6 Hz, 1H); ESI-MS m/z 599.5 (MH$^+$).

Synthesis of 4-[3-(2,4-dimethyl-phenoxy)-2-hydroxy-propylamino]-3-[6-(1-methyl-piperidin-4-yl)-1,5,6,7-tetrahydro-1,3,6-triaza-s-indacen-2-yl]-1H-pyridin-2-one

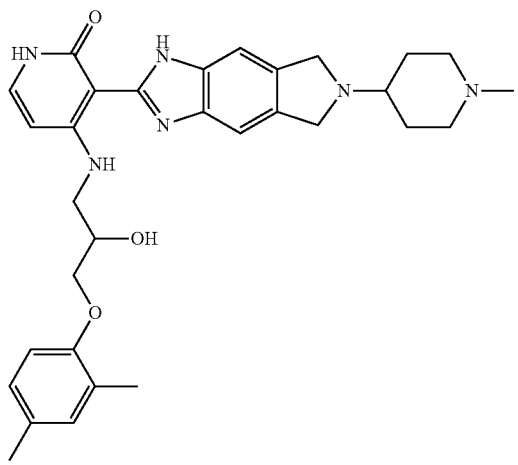 [SMILES: Cc1ccc(OCC(O)CNc2cc[nH]c(=O)c2-c2nc3cc4c(cc3[nH]2)CN(C2CCN(C)CC2)C4)c(C)c1]

TFA salt of 4-[3-(2,4-dimethyl-phenoxy)-2-hydroxy-propylamino]-3-[6-(1-methyl-piperidin-4-yl)-1,5,6,7-tetrahydro-1,3,6-triaza-s-indacen-2-yl]-1H-pyridin-2-one: To a suspension of 2-{4-[3-(2,4-dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one (20 mg, 0.036 mmol) in THF (3 mL) was added BH$_3$·S(CH$_3$)$_2$ complex in ether (2.0 M, 2 mL, 4 mmol) at 0° C. resulting in a mixture which was stirred at the room temperature for 1 h and heated at 80° C. for 2 h. After it was cooled to 0° C., the reaction mixture was quenched by adding MeOH (5 mL) slowly and dropwise at 0° C. and then stirred for 16 h. Aqueous HCl (12 N, 2 mL) was added into the reaction mixture which was then heated at 80° C. for 1 h and evaporated. The residue was diluted with a mixed solvent of DCM/MeOH (10 mL/10 mL), basified with 28% aqueous NH$_4$OH, and concentrated. Chromatography of the residue with CH$_2$Cl$_2$/MeOH/28% aqueous NH$_4$OH (110:10:1) furnished a crude product which was subjected to HPLC re-purification to afford the title compound in TFA salt form (1.67 mg, 7%). $^1$H NMR (DMSO-d$_6$) δ 1.85-2.00 (4H), 2.16 (s, 3H, CH$_3$), 2.22 (s, 3H, CH$_3$), 2.81 (s, 3H, CH$_3$), 3.10 (m, 2H), 3.52 (m, 2H), 3.78-4.11 (6H), 4.62 (s, 2H), 4.85 (s, 2H), 5.43 (br s, 1H, NH), 6.19 (d, J=8 Hz, 1H), 6.80 (d, J=8 Hz, 1H), 6.89-6.95 (2H), 7.32 (m, 1H), 7.45 (br s, 1H), 7.55 (br s, 1H), 9.95 (br s, 1H, NH), 11.00 (br s, 1H, NH), 11.20 (br s, 1H); ESI-MS m/z 543.5 (MH$^+$).

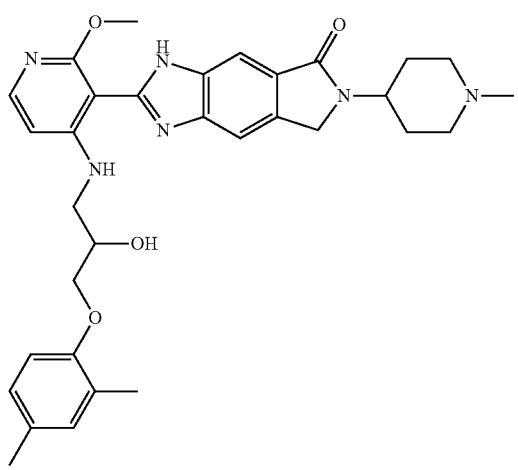 [SMILES: COc1nccc(NCC(O)COc2ccc(C)cc2C)c1-c1nc2cc3c(cc2[nH]1)C(=O)N(C1CCN(C)CC1)C3]

TFA salt of 2-{4-[3-(2,4-dimethyl-phenoxy)-2-hydroxy-propylamino]-2-methoxy-pyridin-3-yl}-6-(1-methyl-piperidin-4-yl)-6,7-dihydro-3H-1,3,6-triaza-s-indacen-5-one: To a suspension of 2-{4-[3-(2,4-dimethyl-phenoxy)-2-hydroxy-propylamino]-2-oxo-1,2-dihydro-pyridin-3-yl}-6-(1-methyl-piperidin-4-yl)-6,7-dihydro-3H-1,3,6-triaza-s-indacen-5-one (19 mg, 0.034 mmol) in a mixed solvent of THF/CH3CN (1 mL/1 mL) was added a solution of TMSCH$_2$N$_2$ (2.0 M, 2 mL, 4 mmol) at 0° C. After it was stirred at 0° C. for 2 h, the reaction mixture was mixed with MeOH (1 mL), stirred at the room temperature for 22 h, and purified with a preparative TLC plate to furnish a crude which was subjected to HPLC re-purification to afford the title compound in TFA salt form (4.98 mg, 21%). $^1$H NMR (DMSO-d$_6$) δ 1.92-2.10 (4H), 2.19 (s, 3H, CH$_3$), 2.22 (s, 3H, CH$_3$), 2.81 (s, 3H, CH$_3$), 3.20 (m, 2H), 3.40 (s, 3H, OCH$_3$), 3.45-3.55 (3H), 3.68 (m, 1H), 4.00 (s, 2H), 4.12 (m, 1H), 4.30 (m, 1H), 4.43 (s, 1H), 4.48 (s, 1H), 5.47 (br s, 1H, NH), 6.27 (d, J=6 Hz, 1H), 6.82 (d, J=8 Hz, 1H), 6.89-6.97 (2H), 6.98 (s, 1H), 7.15 (s, 0.5H), 7.30 (s, 0.5H), 7.65-7.72 (1.5H), 7.80 (s, 0.5H), 7.95 (s, 0.5H), 9.65 (br s, 1H, NH), 11.11 (br s, 1H, NH); ESI-MS m/z 571.5 (MH$^+$).

Synthesis of (S)-2-amino-1-(3-chlorophenyl)ethanol Derivatives

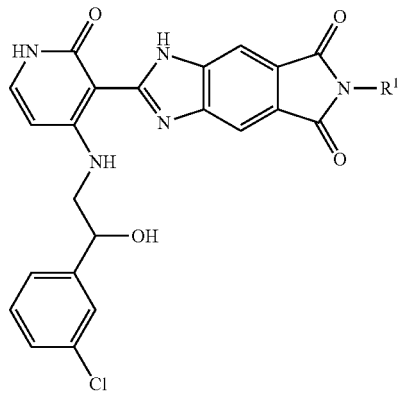

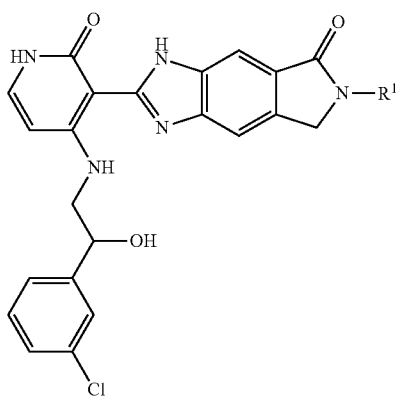

Scheme 89

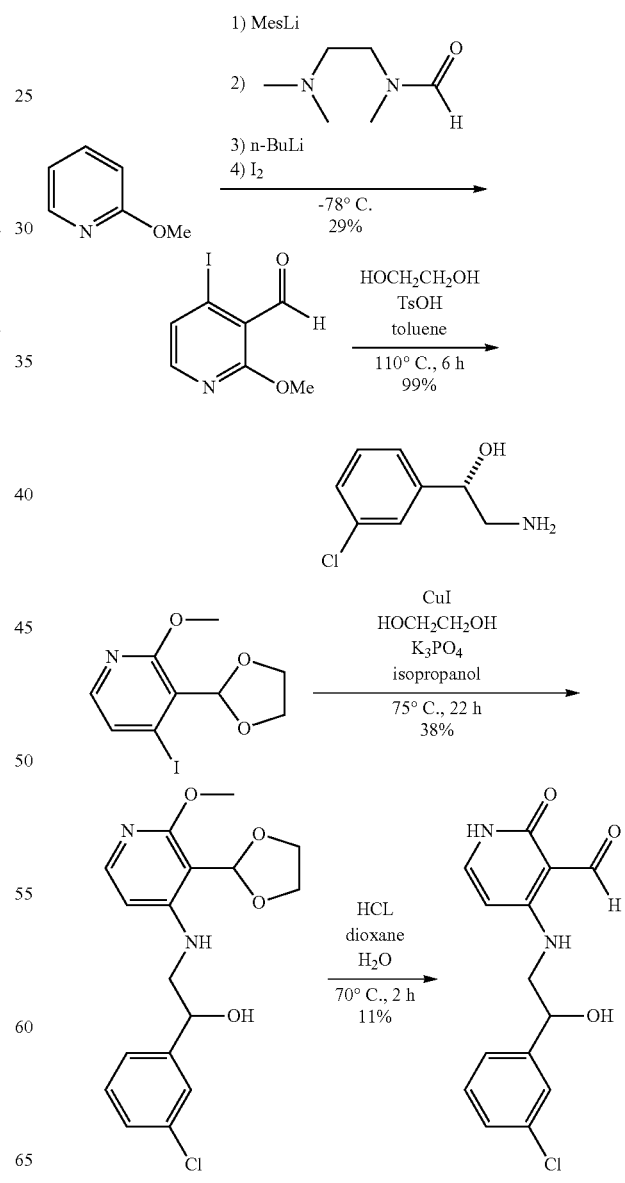

4-Iodo-2-methoxynicotinic aldehyde

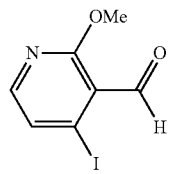 [SMILES: COc1nccc(I)c1C=O]

4-Iodo-2-methoxynicotinic aldehyde: To a solution of t-BuLi (1.7 M, 7.36 mL, 12.51 mmol) in 20 mL THF at −78° C. was added dropwise 2-bromomesitylene (0.91 mL, 5.95 mmol). After stirred for 1 h, 2-methoxypyridine (0.48 mL, 4.58 mmol) was added dropwise, and the mixture was warmed to 0° C. and stirred for 2 h. The solution was cooled to −78° C. and N-formyl-N,N',N'-trimethylethylenediamine (0.7 mL, 5.06 mmol) was added. The mixture was stirred at −78° C. for 30 min and then warmed to −23° C. A hexane solution of n-BuLi (2.5 M, 2.75 mL, 6.87 mmol) was added dropwise, and the resulting yellow mixture was stirred for 3 h. The mixture was cooled to −78° C. and transferred via a double-tipped needle to a solution of iodine (2.17 g, 8.23 mmol) in 30 mL of THF at −78° C. After stirred at −78° C. for 30 min, the cooling bath was removed and the reaction mixture was allowed to warm to the room temperature. After the reaction mixture was cooled to −5° C., aqueous solution of $NH_4Cl$ (20 mL) was added dropwise and stirred for 15 min. The reaction mixture was poured into brine (300 mL) and extracted with EtOAc (5×100 mL). The combined extracts were washed with brine (2×50 mL), dried over $Na_2SO_4$ and concentrated. The residue was purified by chromatography (25:1 hexanes/EtOAc) to afford the title compound (350 mg, 29%). $^1$H NMR ($CDCl_3$) δ 4.05 (s, 3H, $CH_3$), 7.53 (d, J=6 Hz, 1H, ArH), 7.85 (d, J=6 Hz, 1H, ArH), 10.20 (s, 1H, CHO).

3-[1,3]-Dioxolan-2-yl-4-iodo-2-methoxy-pyridine

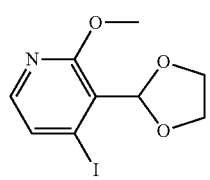

3-[1,3]Dioxolan-2-yl-4-iodo-2-methoxy-pyridine: To a solution of 4-iodo-2-methoxynicotinic aldehyde (5.26 g, 20.0 mmol) and ethylene glycol (2.48 g, 40 mmol) in toluene (400 mL) was added p-toluenesulfonic acid monohydrate (95 mg, 0.5 mmol). After it was refluxed under $N_2$ for 6 h, the reaction mixture was concentrated and the residue was diluted with 300 mL EtOAc and washed with 2×100 mL 10% $Na_2CO_3$ solution. The aqueous solution was extracted with EtOAc (3×50 mL) and the combined EtOAc extracts were washed with brine and dried over $Na_2SO_4$. Evaporation of solvent afforded the title product (6.07 g, 99%). $^1$H NMR ($CDCl_3$) δ 3.95 (s, 3H), 4.07 (m, 2H), 4.33 (m, 2H), 6.25 (s, 1H), 7.40 (d, J=6 Hz, 1H), 7.70 (d, J=6 Hz, 1H). ESI-MS m/z 308.4 ($MH^+$).

(S)-1-(3-Chloro-phenyl)-2-(3-[1,3]dioxolan-2-yl-2-methoxy-pyridin-4-ylamino)-ethanol

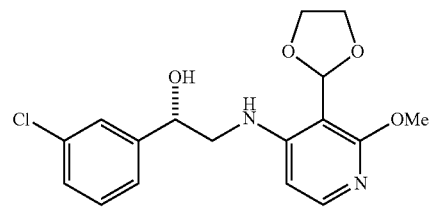 [SMILES: COc1nccc(NC[C@@H](O)c2cccc(Cl)c2)c1C1OCCO1]

(S)-1-(3-Chloro-phenyl)-2-(3-[1,3]dioxolan-2-yl-2-methoxy-pyridin-4-ylamino)-ethanol: A suspension of 3-[1,3]dioxolan-2-yl-4-iodo-2-methoxy-pyridine (3.07 g, 10.0 mmol), (S)-2-amino-1-(3-chloro-phenyl)-ethanol (1.71 g, 10 mmol), CuI (190 mg, 1.0 mmol), ethylene glycol (1.86 g, 30 mmol) and $K_3PO_4$ (6.3 g, 30 mmol) in 2-propanol (200 mL) was sealed and heated at 75° C. for 22 h (CuI and $K_3PO_4$ were crushed into powders before added). After cooled down to room temperature, the reaction mixture was loaded on silica gel. The chromatography with eluant $CH_2Cl_2$: MeOH=100:1 afforded the title product (1.27 g, 38%). $^1$H NMR ($CDCl_3$) δ 3.30 (m, 1H) 3.45 (m, 1H), 3.87 (s, 3H), 3.96-4.05 (4H), 4.85 n (m, 1H), 6.09 (s, 1H), 6.15-6.30 (2H), 7.21-7.35 (2H), 7.41 (s, 1H), 7.82 (d, J=6 Hz, 1H). ESI-MS m/z 351.4 ($MH^+$).

4-[(S)-2-(3-Chloro-phenyl)-2-hydroxy-ethylamino]-2-oxo-1,2-dihydro-pyridine-3-carbaldehyde

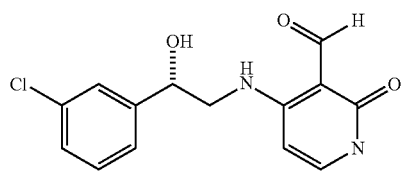 [SMILES: O=Cc1c(NC[C@@H](O)c2cccc(Cl)c2)cc[nH]c1=O]

4-[(S)-2-(3-Chloro-phenyl)-2-hydroxy-ethylamino]-2-oxo-1,2-dihydro-pyridine-3-carbaldehyde: To a mixture of (S)-1-(3-chloro-phenyl)-2-(3-[1,3]dioxolan-2-yl-2-methoxy-pyridin-4-ylamino)-ethanol (223 mg, 0.64 mmol) and $H_2O$ (0.75 mL) was added HCl solution in dioxane (4 M, 10 mL). After it was heated at 70° C. for 4 h, the reaction mixture was evaporated to dryness. HPLC purification of the residue afforded the title compound (20.1 mg, 11%). $^1$H NMR (DMSO-$d_6$) δ 3.37 (m, 1H) 3.58 (m, 1H), 4.58 (m, 1H), 5.95 (d, J=6 Hz, 1H), 7.30-7.40 (3H), 7.49 (s, 1H), 9.94 (s, 1H, CHO), 10.30 (m, 1H, NH), 10.95 (m, 1H, 1H). ESI-MS m/z 293.3 ($MH^+$).

Example 2

Kinase Assays

The IGF1R tyrosine kinase is assayed in Kinase-Glo ATP depletion assay using the synthetic polymer poly(Glu-Tyr, 4:1) (Sigma Chemicals) as a phosphoacceptor substrate. Each reaction mixture consists of a total volume of 10 µl and contains 40 ng of the enzyme, 5 µg of poly(Glu-Tyr), 10 µM of ATP and variable concentrations of test compounds. The mixtures also contain 50 mM Tris-HCl, pH 7.5; 5 mM $MgCl_2$; 5 mM $MnCl_2$; 2 mM DTT and 0.01% Tween 20. The reaction mixtures are incubated at 37° C. for 60 minutes and residual concentration of ATP in the mixture is determined by adding luciferase-containing Kinase-Glo (Promega) development reagent and counting luminescence levels using Fusion Universal Microplate Analyzer (PerkinElmer). Tested compounds are dissolved in dimethyl sulfoxide to a stock concentration of 10 mM and are typically evaluated in the assay at eight concentrations in 1 nM to 20 µM range, each in quadruplicate. The final concentration of DMSO added to the kinase assays is 0.5% or less, which has been shown to have no effect on kinase activity. IC50 values are derived by non-linear regression analysis using Prism 3.0 software (Graphpad Software). Other tyrosine kinases are assayed according to the same protocol after titrating amount of the enzyme to provide optimal signal-to-noise ratio and no more than 30% of total ATP consumption in the reaction conditions used.

The IGF1R tyrosine kinase is assayed in Phosphotyrosine (PT66 or PT100) AlphaScreen chemiluminescent assay (PerkinElmer) according to the manufacturer's recommendations. Each kinase reaction mixture consists of a total volume of 15 µl and contains 0.1-1 ng of the enzyme, 7 ng of biotinylated poly(Glu-Tyr) (Cis-Bio), 10 µM of ATP and variable concentrations of test compounds. The mixtures also contain 50 mM Tris-HCl, pH 7.5; 5 mM $MgCl_2$; 5 mM $MnCl_2$; 2 mM DTT and 0.01% Tween 20. The reaction mixtures are incubated at room temperature for 30 minutes. Ten (10) µl of the mixture of receptor and donor beads (as supplied by the manufacturer) is then added to the reaction and the incubation is continued for an additional 60 minutes. The reaction is stopped by addition of 10 µl of detection Buffer (62.5 mM HEPES, pH 7.4; 250 mM NaCl, 100 mM EDTA, 0.25% BSA. Data are collected as optical readings at 520-620 nm on an AlphaScreen Fusion microplate reader (PerkinElmer) and the IC50 values are calculated using the software Prism 3.0, a graphing program from GraphPad Software. Other tyrosine kinases are assayed according to the same protocol after titrating amount of the enzyme to provide optimal signal-to-noise ratio. Table III below shows exemplary data for biochemical inhibition (IC50).

Example 3

ELISA-Based Assay of IGF1 Receptor Autophosphorylation Inhibition in Cells

MCF7 human breast cancer cells expressing IGF1 receptor or an engineered human fibroblast cell line NIH 3T3 overexpressing full-length IGF1R are an exemplary cellular models in which to perform such assays. Such cells may be maintained in DMEM medium supplemented with 10% fetal bovine serum (FBS), 4% L-glutamine, 1% antibiotic solution (penicillin-Streptomycin) in a humidified atmosphere of 95% air and 5% $CO_2$ at 37° C. Confluent cells in T175 cell culture flasks are incubated overnight with serum-free DMEM medium. After the serum starvation step, the cells are detached and split into a standard 96-well cell culture plate (one T175 flask per plate, 30 µl of cell suspension per plate well). Tested inhibitors from their 10 mM stock solutions in DMSO are subsequently added at various concentrations in serum-free DMEM medium for 1 hour incubation at 37° C. in $CO_2$-incubator; total DMSO concentration in both treated and control wells is adjusted to 1%. Cells are then stimulated for 10 minutes with 100 nM IGF-1 added in 30 µl DMEM. After treatment, cells are lysed by addition of 30 µl of 4× lysis buffer (phosphate-buffered saline (PBS), 2% Triton-X100, 1 mM phenylmethylsulphonyl fluoride (PMSF) and 8 mM activated orthovanadate), mixing and incubation for 15 minute at room temperature.

To prepare assay plates, 96-well ELISA Plates (Pierce Chemical, Reacti-bind plates) were coated by goat-anti-rabbit Fc antiserum by adding 0.25 µg antiserum per well in 0.2M sodium bicarbonate buffer per well and incubating overnight at 4° C. After incubation, the plate is washed three times by PBS with 0.02% Tween-20, supplied with 25 ng/50 µl per well of anti-IGF1R antibody (C-20, Santa Cruz Biotechnology) and incubated for several hours to overnight. Prior to the addition of the prepared cellular lysates, the antibody solution is aspirated, wells washed with PBS and supplied with 25 µl per well of Starting Block buffer (Pierce Chemical).

To measure tyrosine phosphorylation of the beta-subunits of the IGF1R, 25-50 µl of the lysates are transferred from the stimulation plate to the wells of the prepared assay plate and incubated overnight at 4° C. The wells are washed with PBS with 0.02% Tween-20, incubated with 50 µl of 1:3000 dilution of anti-phosphotyrosine 4G10-HRP antibody conjugate (Upstate Biotechnology) for 2 hours at room temperature and washed again. The assay plate was developed with Ultra TMB ELISA HRP substrate (Pierce Chemical) and absorbance of the wells was read at 450 nm in ELISA plate reader. Alternatively, 10-50 times larger volumes of lysates prepared as described above are incubated overnight at 4° C. with 1 µg of anti-IGF1R antibody (C-20; Santa Cruz Biotechnology) and 20 µl of 50% protein-A agarose slurry. After 3 washes with lysis buffer, pellets are resuspended in SDS-PAGE sample buffer and boiled for 3 minutes. Proteins are resolved by SDS-PAGE (7.5%) and transferred by electroblotting onto nitrocellulose membranes. Tyrosine phosphorylated IGF1R is detected by immunoblotting with anti-phosphotyrosine antibody (4G10, Upstate Biotechnology) and, in a separate identical blot, with anti-IGF1R antibody. Table III below shows exemplary data for cellular receptor phosphorylation inhibition in terms of IC50 value.

Example 4

Cell Proliferation Inhibition Assay

IGF1R and other tyrosine kinase inhibitors can inhibit the proliferation of certain cancer cell lines indicating their possible therapeutic utility for treating the corresponding cancer types. Cancer cell lines of interest and control normal lines, including CHO, HEK293, BA/F3, COLO205, PC3, DU145, MCF7, Panc1, ACHN, Hep G2, H460, K562, TT, U87-MG, CAOV-3, SK-MEL5, Karpas 299 and human multiple myeloma cell lines H929, MM1s, MM1r, UTMC2, CPM2, KMS11, My5, KMS12PE, My7, JJN3, KMS18, U266, SKMM2, RPMI-8226 are plated in white, clear-bottomed 384-well cell culture plates at 2500-5000 cells per well and supplied with dilutions of tested compounds After a desired period of time (typically 3 days), the number of viable cells is quantitated by using Cell Titer-Glo Luminescent Cell Viability Assay (Promega), a cell proliferation assay system based on detection of total amount of ATP present as a measure of cell metabolic activity. The plated cells are mixed with the Cell Titer-Glo developing reagent and counted in a luminescence multiwell plate reader according to the standard manufacturer's protocol to generate IC50 curves for cell proliferation inhibition. Results are typically reported as percent of growth (% viability=$(OD_{72h(compound)}-OD_{day0}))/(OD_{72h(no\ compound)}-OD_{day0})$). Alternatively, viable cells are quantitated by using the conventional colorimetric MTT assay. The MTT assay is based on the cleavage of the yellow tetrazolium salt MTT to purple formazan crystal by metabolic active cells. The formazan is then solubilized, and the concentration determined by optical density at 570 nm. The cells plated and incubated with a compound as described above are supplemented with the solution of MTT and incubated for 2-3 hours. The growth medium is removed and dimethyl sulfoxide is added into each well to dissolve the formazan. The absorbance is measured on an ELISA plate reader with a test wavelength of 570 nm and a background subtraction wavelength of 630 nm to obtain sample signal (OD570-OD630).

Table III below shows the results of cell proliferation inhibition assay for some exemplary compounds of this invention for the following cell lines—MM1s (multiple myeloma), H929 (multiple myeloma), COL0205 (colon carcinoma), HEK293 (human normal embryonic kidney), CHO (chinese hamster ovary). The results are reported in terms of IC50 value for a particular compound and a cell line in the standard 3-day proliferation assay using Cell Titer-Glo. Table IV below shows the results of cell proliferation assay for some exemplary compounds of this invention for the following human multiple myeloma cell lines —H929, MM1s, MM1r, UTMC2, CPM2, KMS11, My5, KMS12PE, My7, JJN3, KMS18, U266, SKMM2, RPMI-8226 as well as HEK293 (human normal embryonic kidney), CHO (chinese hamster ovary). The results are reported in terms of IC50 value for a particular compound and a cell line in the standard 3-day proliferation assay using MTT assay.

TABLE III

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 1 | (structure) | ++ | +++ | +++ | ++ | | | | + | + | | ++ | +++ |
| 2 | (structure) | − | − | − | − | | − | + | + | | | | − |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 3 | 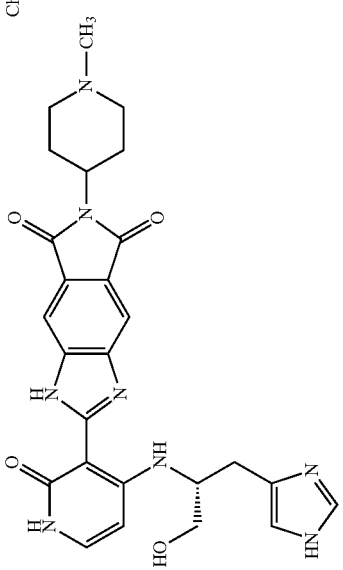 Chiral | + | ++ | ++ | − | | − | + | + | | | + | |
| 4 | 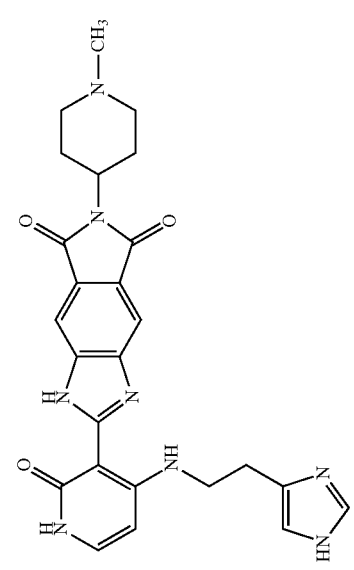 | ++ | ++ | ++ | ++ | | + | ++ | + | | | + | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 5 | 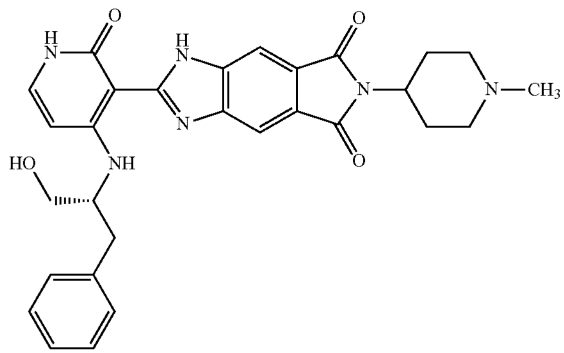 [SMILES: CN1CCC(N2C(=O)c3cc4nc(-c5c(N[C@@H](CO)Cc6ccccc6)cc[nH]c5=O)[nH]c4cc3C2=O)CC1] | +++ | ‡ | ‡ | ‡ | | ‡ | ‡ | ‡ | | | | |
| 6 | 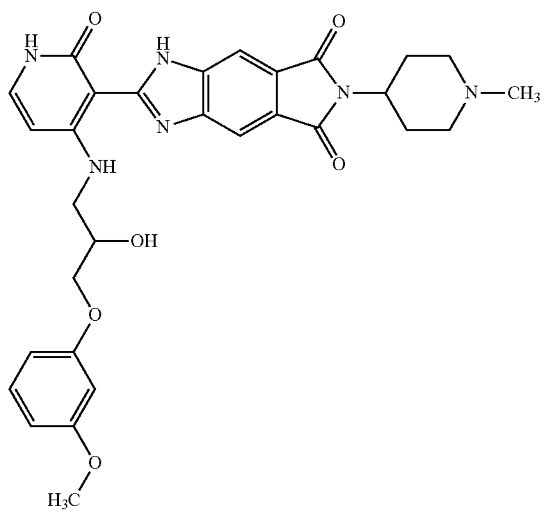 [SMILES: COc1cccc(OCC(O)CNc2cc[nH]c(=O)c2-c2nc3cc4c(cc3[nH]2)C(=O)N(C2CCN(C)CC2)C4=O)c1] | ‡ | ‡ | ‡‡‡ | ‡ | | | | | | | + | ‡ |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphor-ylation IC50 |
|---|---|---|---|---|---|---|---|---|---|---|---|---|---|
| 7 | 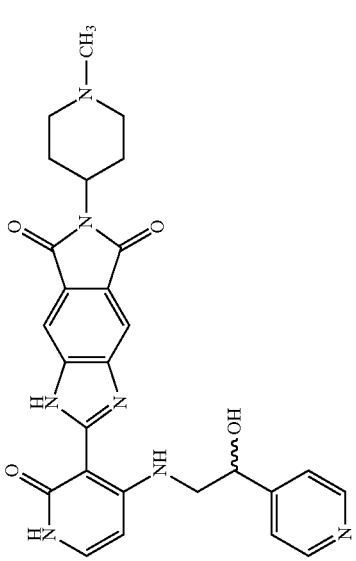 | - | + | ‡ | ‡ | | | | | | | | - |
| 8 | 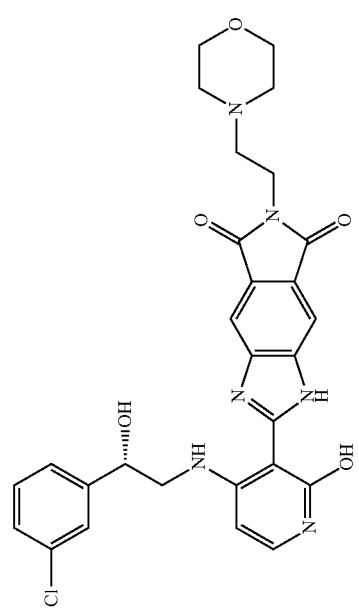 | ‡ | ‡ | ‡ | ‡ | | - | - | - | | | | |

TABLE III-continued

| # | Structure (Chiral) | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 9 | | ++ | ++ | ++ | ++ | | | | | | | | |
| 10 | | - | ++ | + | + | | | | | | | | - |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 11 | Chiral structure | + | + | - | + | | | | | | | | ++ |
| 12 | Chiral structure | - | - | - | - | | | | | | | | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 13 | Chiral | ++ | +++ | +++ | ++ | | | | | | | | ++ |
| 14 | 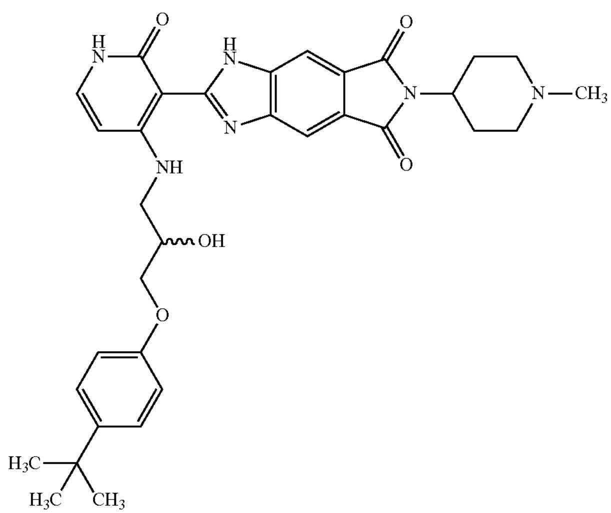 [SMILES: CN1CCC(N2C(=O)c3cc4nc(-c5c(NCC(O)COc6ccc(C(C)(C)C)cc6)cc[nH]c5=O)[nH]c4cc3C2=O)CC1] | − | ++ | ++ | ++ | | | | | | | | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 15 | 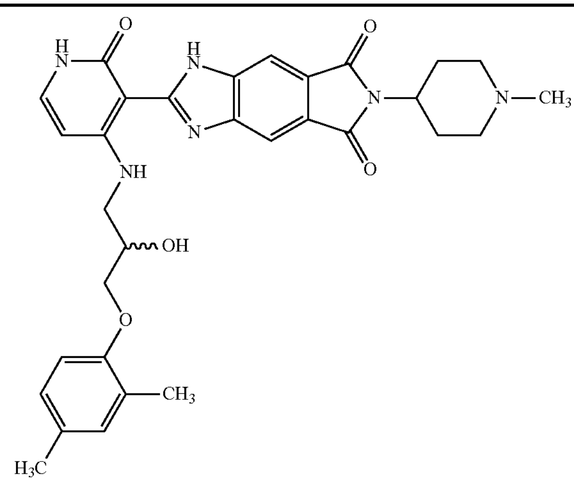 | + | +++ | +++ | ++ | +++ | | | ++ | + | | ++ | ++ |
| 16 | 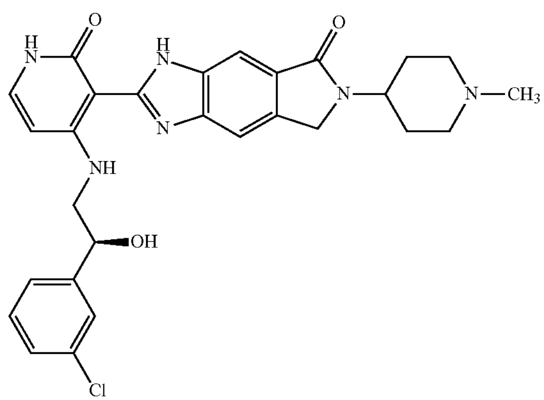 [SMILES: CN1CCC(N2Cc3cc4nc(-c5c(NC[C@@H](O)c6cccc(Cl)c6)cc[nH]c5=O)[nH]c4cc3C2=O)CC1] | +++ | +++ | +++ | ++ | +++ | | | − | + | | + | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 17 | 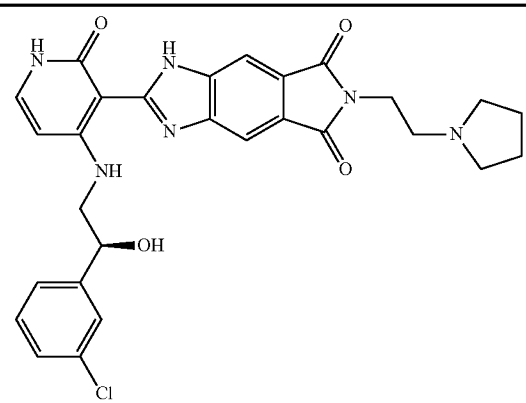 | | | | | | | | | | | | - |
| 18 | 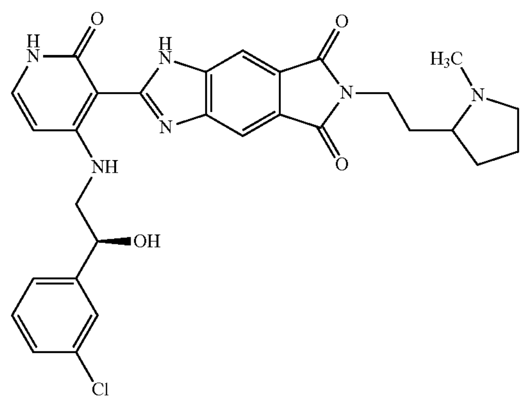 [SMILES: CN1CCCC1CCN1C(=O)c2cc3nc(-c4c(NC[C@@H](O)c5cccc(Cl)c5)cc[nH]c4=O)[nH]c3cc2C1=O] | ++ | ++ | +++ | ++ | | | | | | | | - |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 19 | 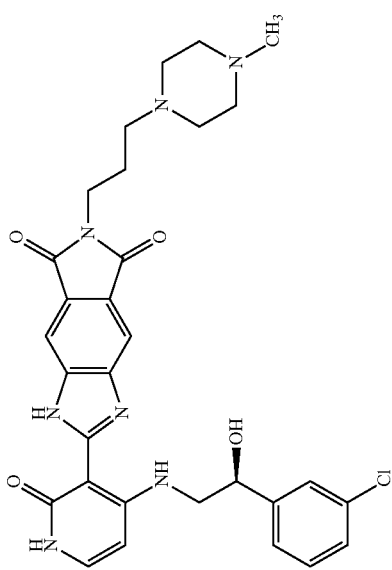 | ++ | ++ | +++ | ++ | | | | | | | | - |
| 20 | 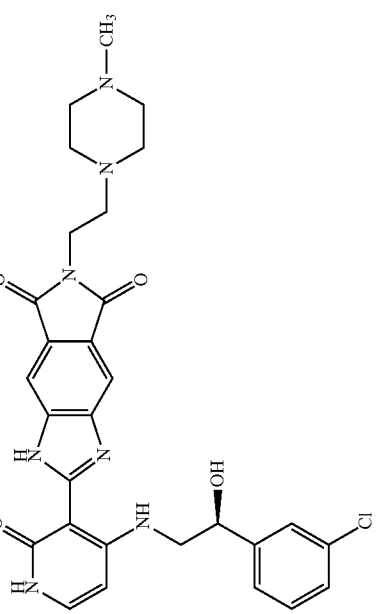 | ++ | ++ | ++ | ++ | | | | | | | | - |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 21 | Chiral structure | ++ | ++ | ++ | ++ | | | | | | | | + |
| 22 | Chiral structure | ++ | ++ | ++ | ++ | | | | | | | | − |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 23 | 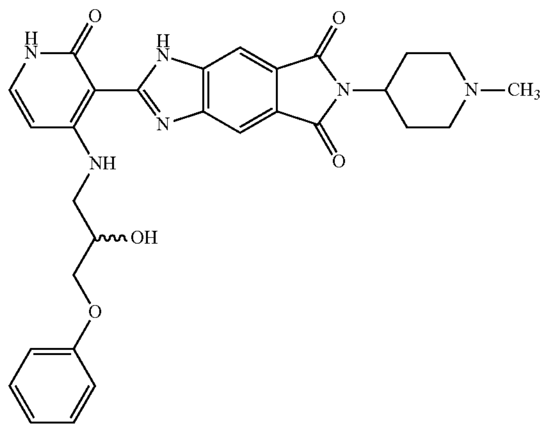 [SMILES: CN1CCC(N2C(=O)c3cc4nc(-c5c(NCC(O)COc6ccccc6)cc[nH]c5=O)[nH]c4cc3C2=O)CC1] | + | ‡ | ‡ | ‡ | | | | | | | | + |
| 24 | 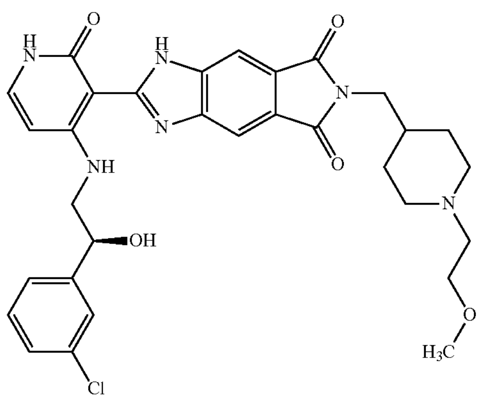 [SMILES: COCCN1CCC(CN2C(=O)c3cc4nc(-c5c(NC[C@@H](O)c6cccc(Cl)c6)cc[nH]c5=O)[nH]c4cc3C2=O)CC1] | ‡ | ‡‡ | ‡‡‡ | ‡ | | | | | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 25 | 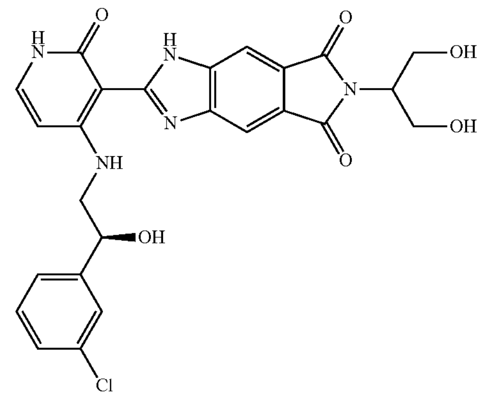 [SMILES: O=C1c2cc3nc(-c4c(NC[C@@H](O)c5cccc(Cl)c5)cc[nH]c4=O)[nH]c3cc2C(=O)N1C(CO)CO] | + | +++ | +++ | +++ | | | | | | | | |
| 26 | 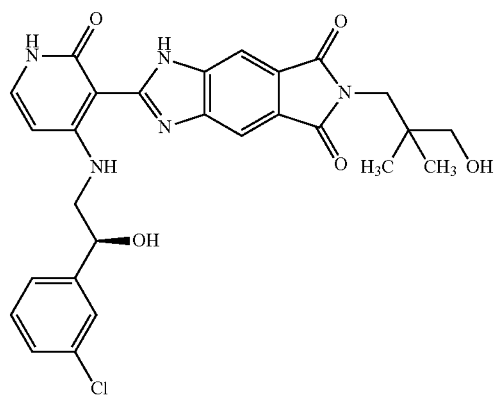 [SMILES: CC(C)(CO)CN1C(=O)c2cc3nc(-c4c(NC[C@@H](O)c5cccc(Cl)c5)cc[nH]c4=O)[nH]c3cc2C1=O] | − | + | ‡ | ‡ | | | | + | | | | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 27 | 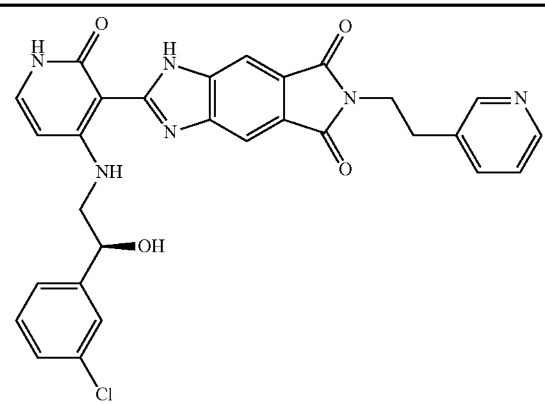 | – | – | – | – | | | | | | | | |
| 28 | 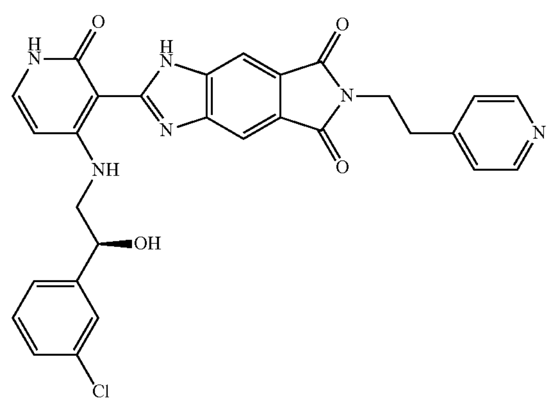 [SMILES: O=C1c2cc3nc(-c4c(NC[C@@H](O)c5cccc(Cl)c5)cc[nH]c4=O)[nH]c3cc2C(=O)N1CCc1ccncc1] | + | + | – | + | | | | | | | | – |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 29 | Chiral | - | - | - | - | | + | + | ++ | | | | - |
| 30 | Chiral | | - | - | - | | - | - | - | | | - | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 31 | Chiral | - | ++ | + | + | | - | - | + | + | | ++ | + |
| 32 | 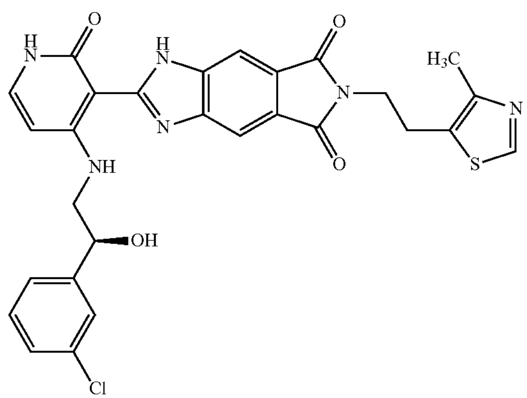 [SMILES: Cc1ncsc1CCN1C(=O)c2cc3nc(-c4c(NC[C@@H](O)c5cccc(Cl)c5)cc[nH]c4=O)[nH]c3cc2C1=O] | - | - | + | - | | ++ | - | - | | | + | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 33 | 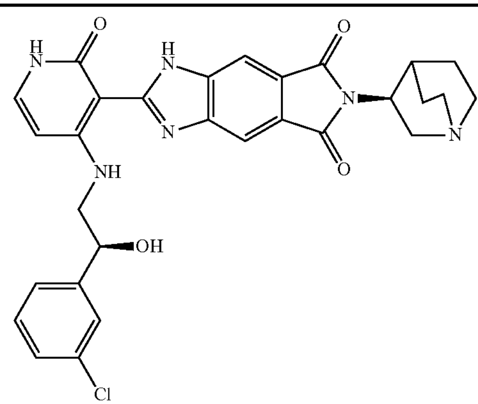 | ++ | +++ | +++ | ++ | | − | − | ++ | | | | − |
| 34 | 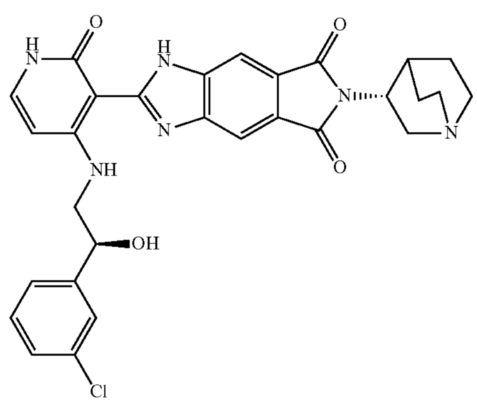 [SMILES: O=C1c2cc3nc(-c4c(NC[C@@H](O)c5cccc(Cl)c5)cc[nH]c4=O)[nH]c3cc2C(=O)N1[C@H]1CN2CCC1CC2] | ++ | ++ | +++ | ++ | | − | − | − | | | + | − |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 35 | 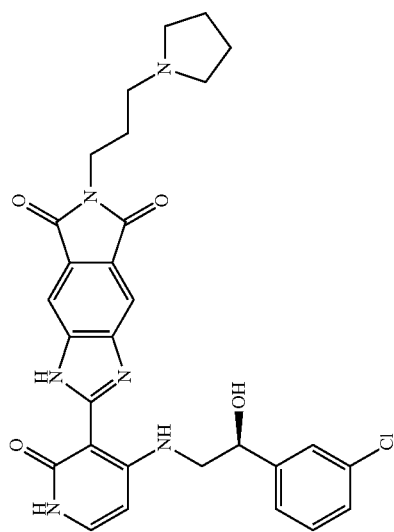 | ++ | +++ | +++ | ++ | | - | - | - | | | + | |
| 36 | 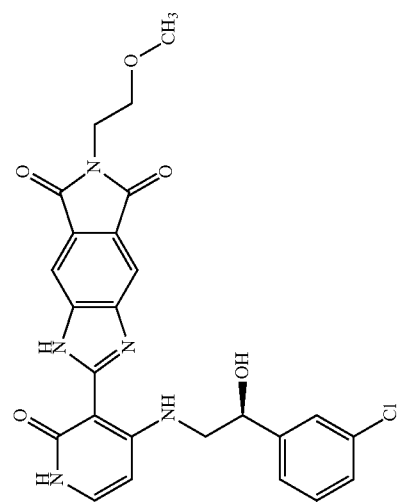 | - | - | - | - | | - | - | - | | | ++ | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 37 | 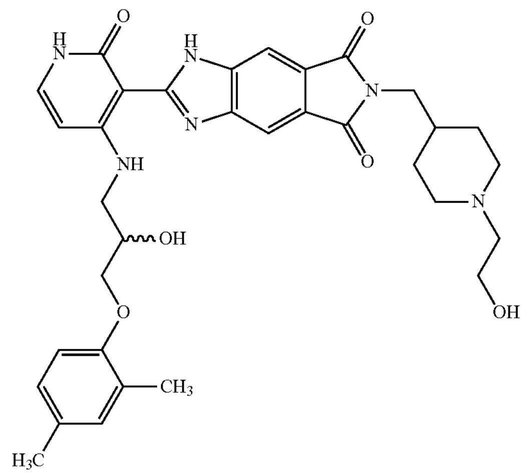 [SMILES: Cc1ccc(OCC(O)CNc2cc[nH]c(=O)c2-c2nc3cc4c(cc3[nH]2)C(=O)N(CC2CCN(CCO)CC2)C4=O)c(C)c1] | + | +++ | - | ++ | | - | - | - | | | ++ | + |
| 38 | 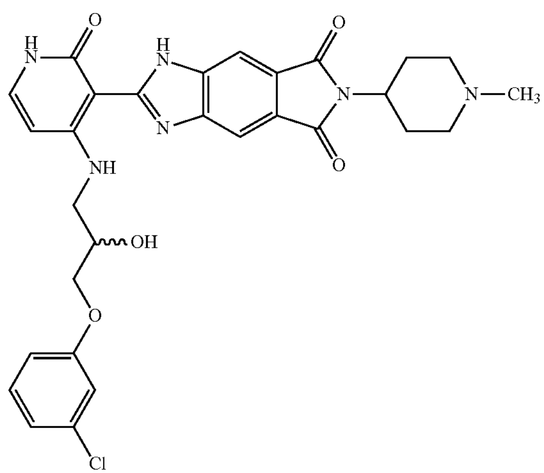 [SMILES: CN1CCC(N2C(=O)c3cc4nc(-c5c(NCC(O)COc6cccc(Cl)c6)cc[nH]c5=O)[nH]c4cc3C2=O)CC1] | ++ | ++ | ± | ± | | - | - | + | | | ± | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 39 | 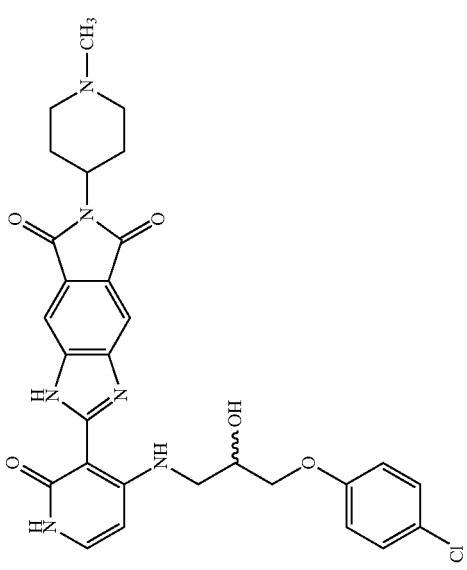 | ++ | ++ | ++ | ++ | | ++ | ++ | ++ | | | | |
| 40 | 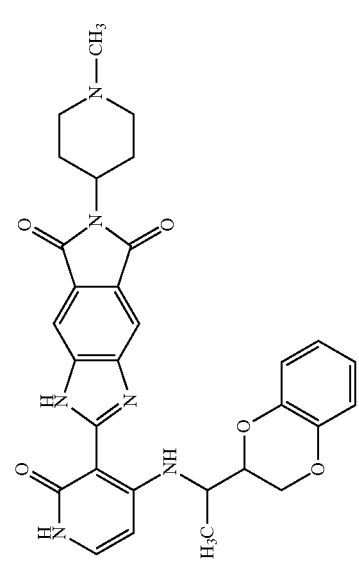 | + | + | + | ++ | | ++ | + | + | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 41 | 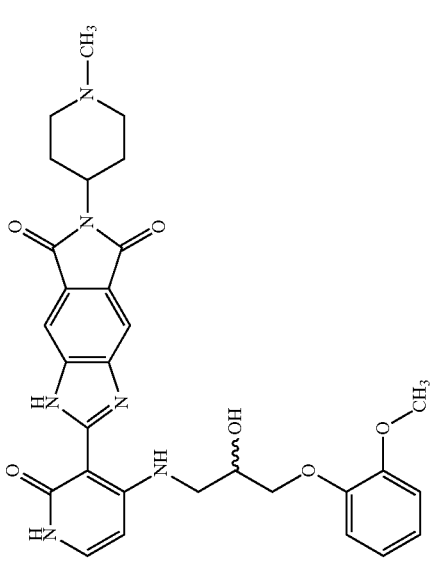 | + | ++ | ++ | + | | ++ | ++ | + | | | + | |
| 42 | 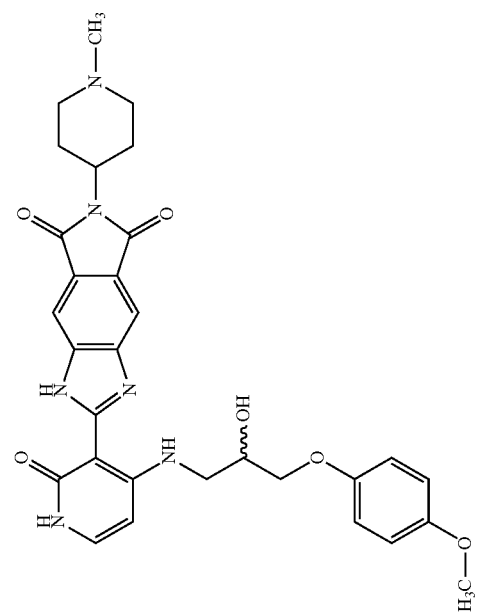 | + | ++ | +++ | + | | − | − | + | | | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 43 | 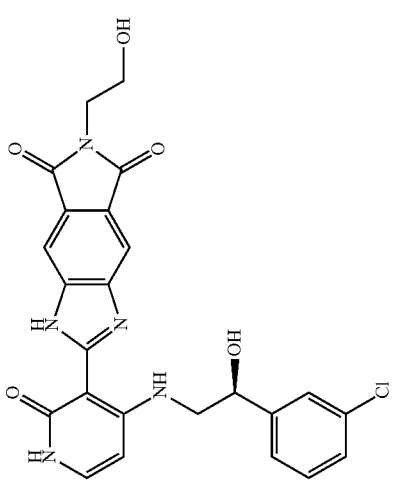 | - | ++ | ++ | ++ | | - | + | + | | | | |
| 44 | 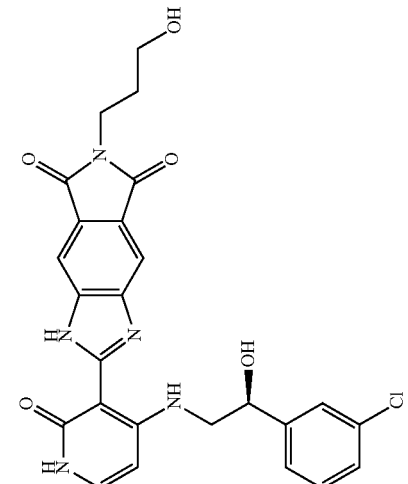 | - | ++ | ++ | ++ | | - | + | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 45 | 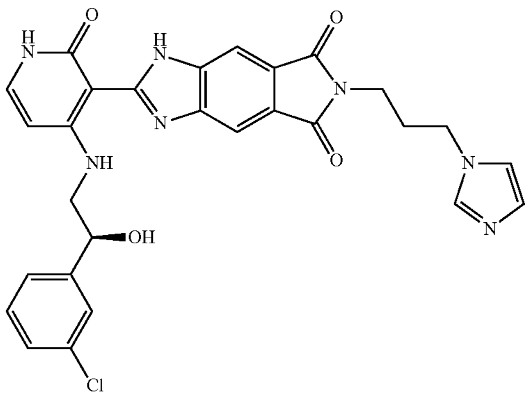 [SMILES: O=C1c2cc3nc(-c4c(NC[C@@H](O)c5cccc(Cl)c5)cc[nH]c4=O)[nH]c3cc2C(=O)N1CCCn1ccnc1] | ++ | ++ | ++ | ++ | | + | + | | | | | |
| 46 | 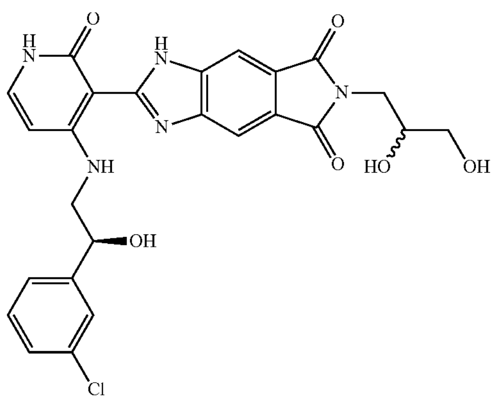 [SMILES: O=C1c2cc3nc(-c4c(NC[C@@H](O)c5cccc(Cl)c5)cc[nH]c4=O)[nH]c3cc2C(=O)N1CC(O)CO] | − | ++ | +++ | − | | + | + | | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 47 | 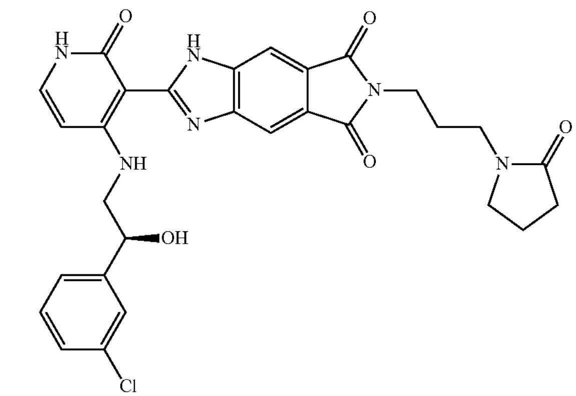 [SMILES: O=C1CCCN1CCCN1C(=O)c2cc3nc(-c4c(NC[C@@H](O)c5cccc(Cl)c5)cc[nH]c4=O)[nH]c3cc2C1=O] | + | ‡ | ‡ | ‡ | | + | + | | | | | |
| 48 | Chiral | + | ‡‡‡ | ‡‡‡ | ‡ | | ‡ | ‡ | | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 49 | 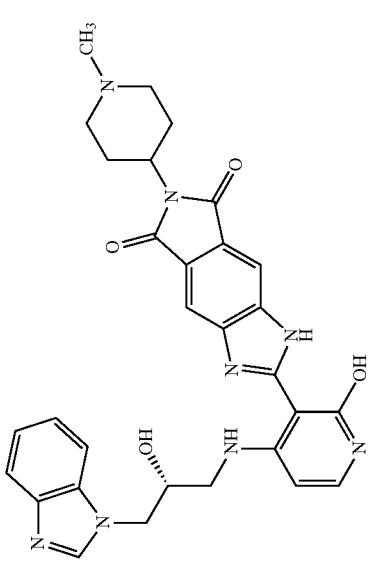 | ++ | ++ | ++ | ++ | | - | - | - | | | | |
| 50 | 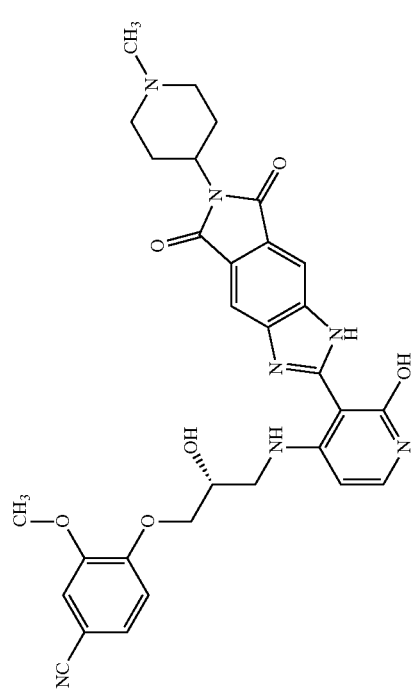 | + | + | ++ | ++ | | - | - | - | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 51 | 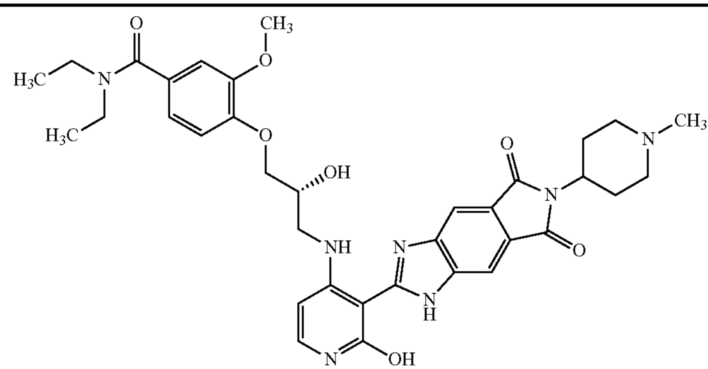 | – | – | – | – | | – | – | – | | | | |
| 52 | 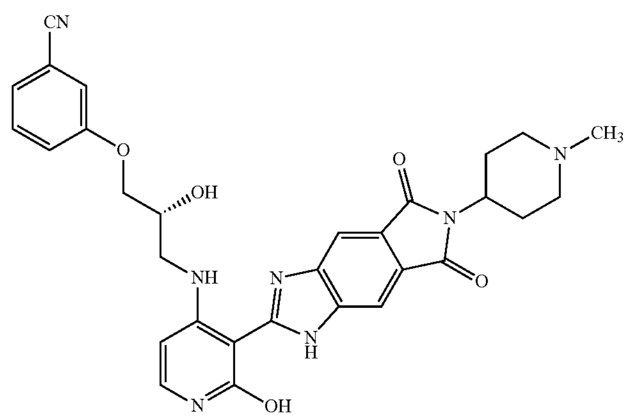 [SMILES: CN1CCC(N2C(=O)c3cc4nc(-c5c(NC[C@@H](O)COc6cccc(C#N)c6)ccnc5O)[nH]c4cc3C2=O)CC1] | ‡‡ | ‡‡ | ‡‡‡ | ‡ | | – | – | – | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 53 | 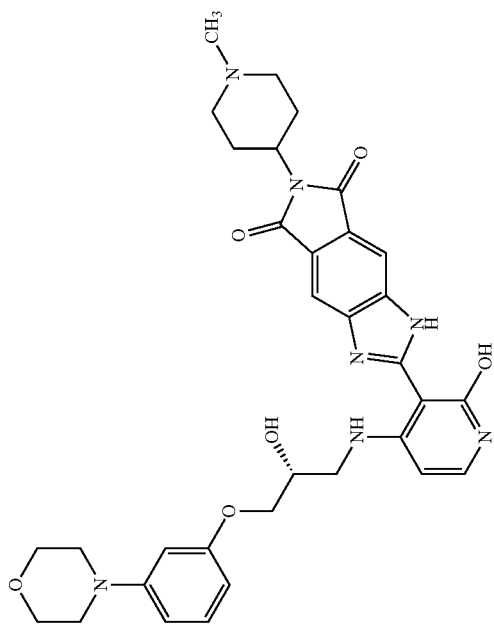 | ++ | + | + | ++ | | | − | − | | | | |
| 54 | 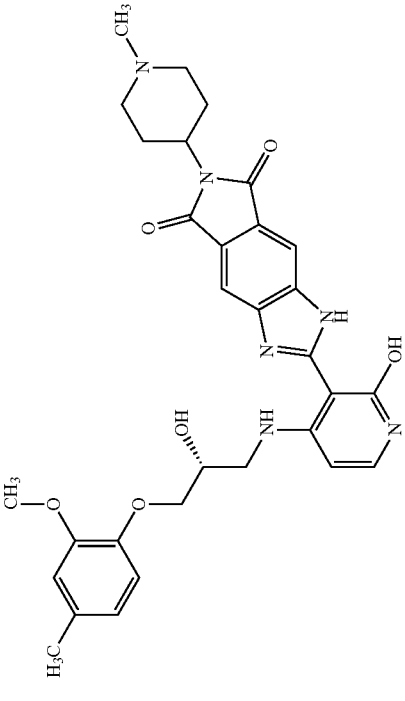 | + | ++ | +++ | − | | + | + | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 55 | (structure) | ++ | ++ | +++ | ++ | | ++ | ++ | ++ | | | | |
| 56 | Chiral (structure) | ++ | ++ | ++ | ++ | | ++ | ++ | ++ | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 57 | (structure) | ++ | ++ | ++ | ++ | | ++ | + | + | | | | |
| 58 | Chiral (structure) | ++ | ++ | ++ | + | | + | + | + | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 59 | 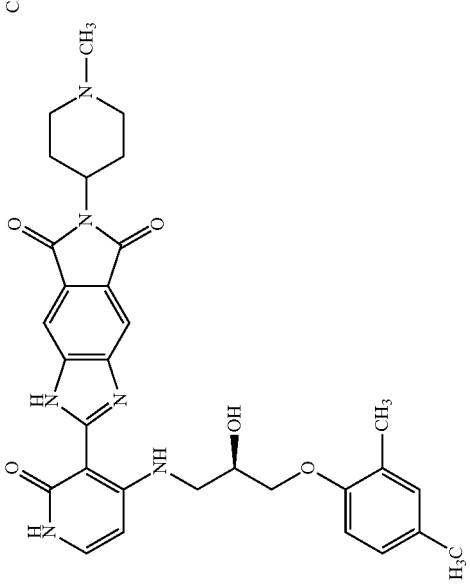 Chiral | ++ | +++ | +++ | ++ | | ++ | ++ | + | + | | ++ | ++ |
| 60 | 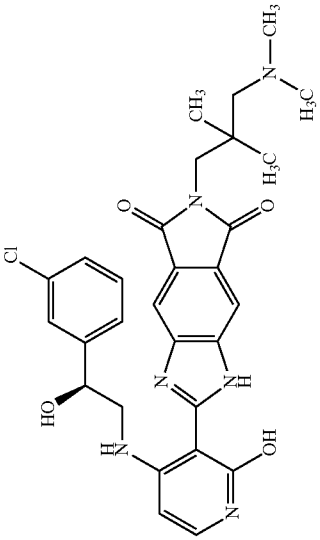 | + | ++ | ++ | ++ | | − | − | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 61 | 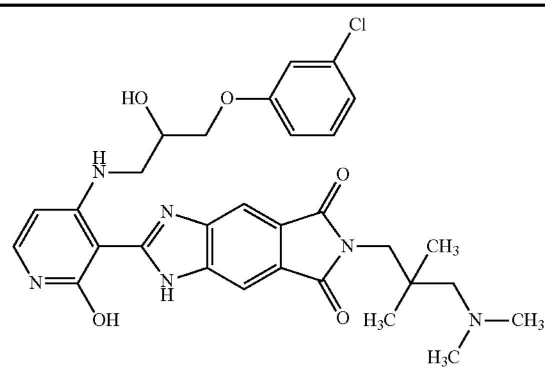 | - | + | ‡ | + | | - | - | - | | | | |
| 62 | 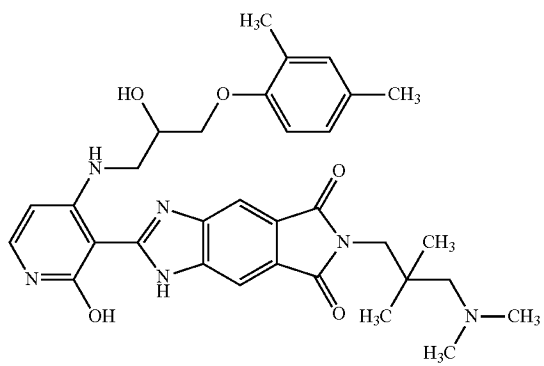 [SMILES: Cc1ccc(OCC(O)CNc2ccnc(O)c2-c2nc3cc4c(cc3[nH]2)C(=O)N(CC(C)(C)CN(C)C)C4=O)c(C)c1] | + | ‡ | ‡‡‡ | + | | + | + | ‡ | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 63 | 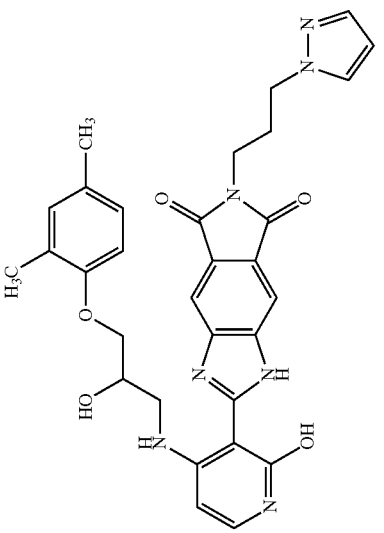 | ++ | - | - | - | | - | - | - | | | | |
| 64 | 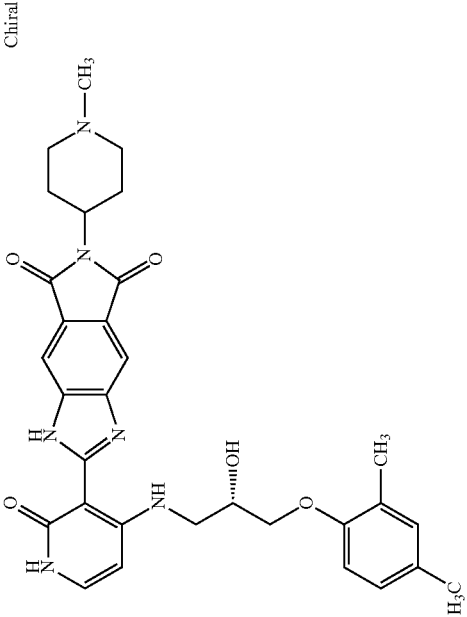 Chiral | + | ++ | +++ | ++ | | + | - | + | | | | - |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 65 | 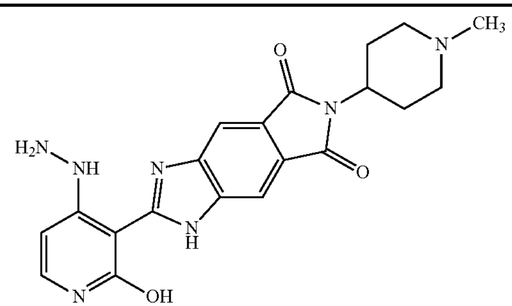 | - | + | + | + | | | | - | | | | |
| 66 | 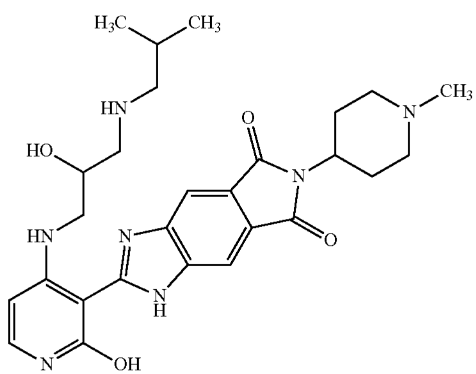 [SMILES: CC(C)CNCC(O)CNc1ccnc(O)c1-c1nc2cc3c(cc2[nH]1)C(=O)N(C1CCN(C)CC1)C3=O] | - | | | | | | | - | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 67 | 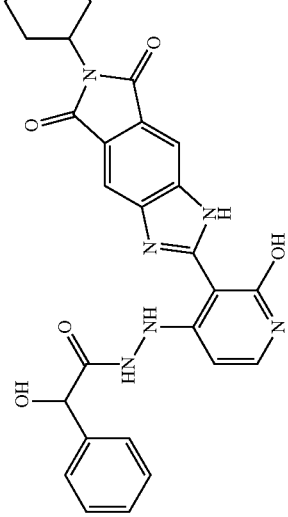 | + | + | − | ++ | | − | − | − | | | | |
| 68 | 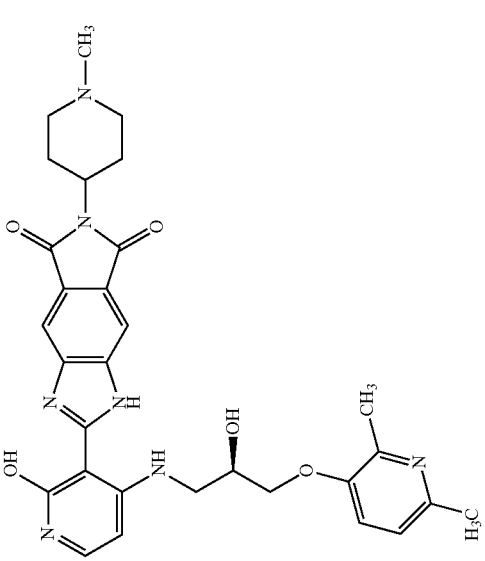 | + | ++ | +++ | ++ | | | − | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 69 | 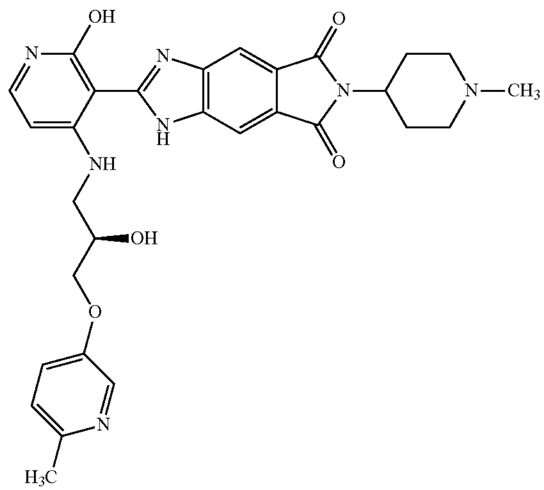 [SMILES: Cc1ccc(OC[C@H](O)CNc2ccnc(O)c2-c2nc3cc4c(cc3[nH]2)C(=O)N(C2CCN(C)CC2)C4=O)cn1] | + | ++ | ++ | ++ | | – | – | – | | | | |
| 70 | 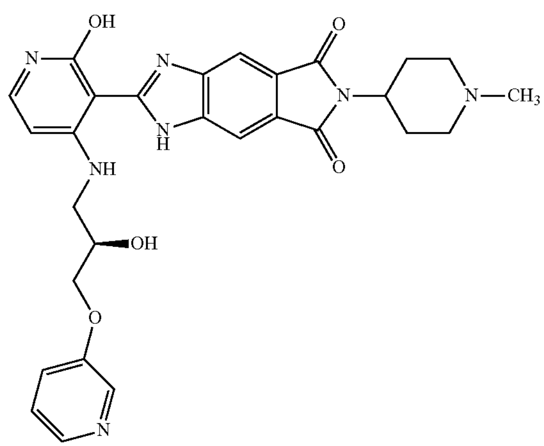 [SMILES: CN1CCC(N2C(=O)c3cc4nc(-c5c(NC[C@@H](O)COc6cccnc6)ccnc5O)[nH]c4cc3C2=O)CC1] | + | + | + | ++ | | – | – | – | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 71 | 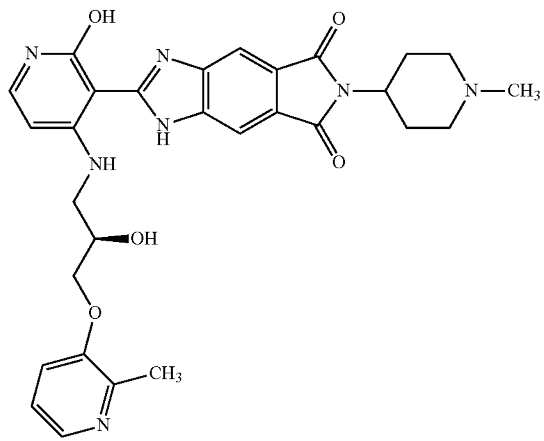 [SMILES: Cc1ncccc1OC[C@H](O)CNc1ccnc(O)c1-c1nc2cc3c(cc2[nH]1)C(=O)N(C1CCN(C)CC1)C3=O] | + | ++ | ++ | + | | - | - | - | | | | |
| 72 | 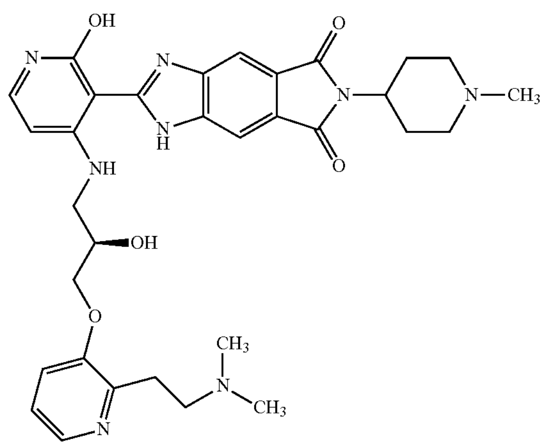 [SMILES: CN(C)CCc1ncccc1OC[C@H](O)CNc1ccnc(O)c1-c1nc2cc3c(cc2[nH]1)C(=O)N(C1CCN(C)CC1)C3=O] | ++ | ++ | ++ | ++ | | - | - | - | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 73 | 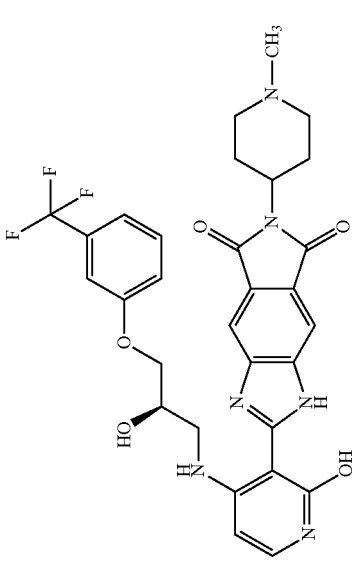 | + | ++ | ++ | ++ | | - | ++ | ++ | | | | |
| 74 | 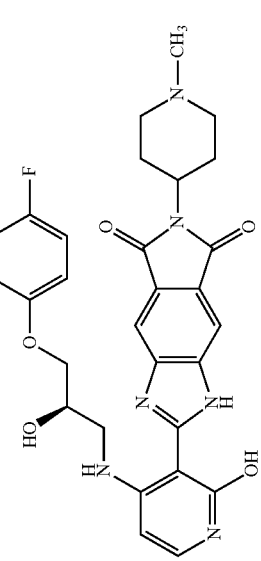 | + | ++ | ++ | ++ | | ++ | ++ | ++ | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 75 | 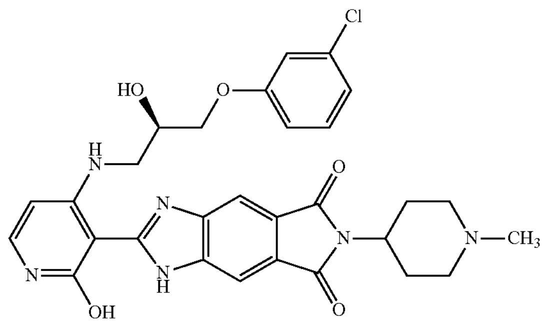 [SMILES: CN1CCC(N2C(=O)c3cc4nc(-c5c(NC[C@@H](O)COc6cccc(Cl)c6)ccnc5O)[nH]c4cc3C2=O)CC1] | ‡ | ‡ | ‡ | ‡ | | ‡ | ‡ | ‡ | | | | |
| 76 | 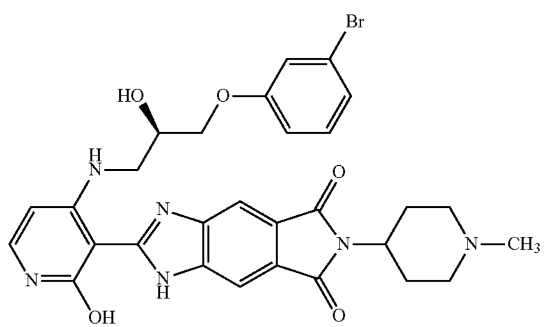 | ‡ | ‡ | ‡ | ‡ | | ‡ | ‡ | ‡ | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 77 | 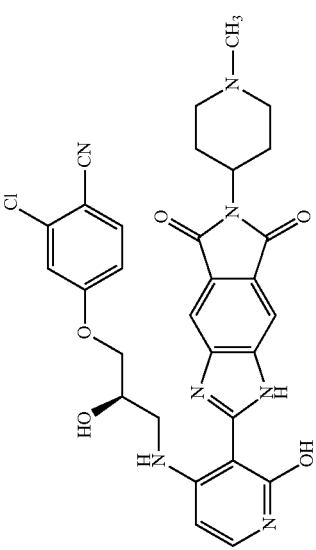 | ++ | + | ++ | ++ | | - | - | - | | | | |
| 78 | 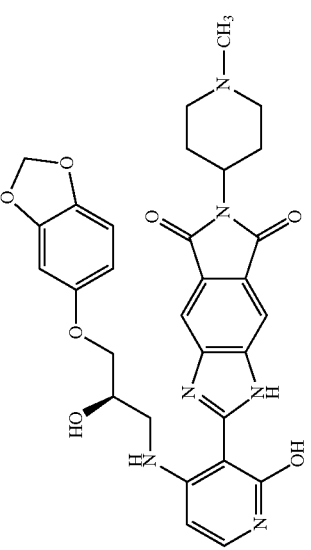 | ++ | ++ | +++ | ++ | | - | + | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 79 | 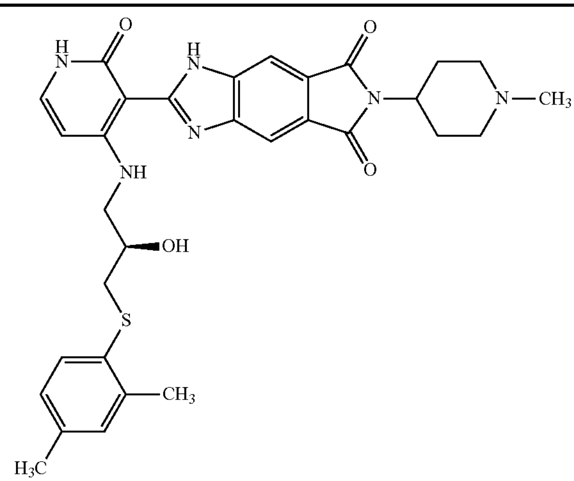 | ++ | ++ | ++ | ++ | | + | + | ++ | | | | |
| 80 | 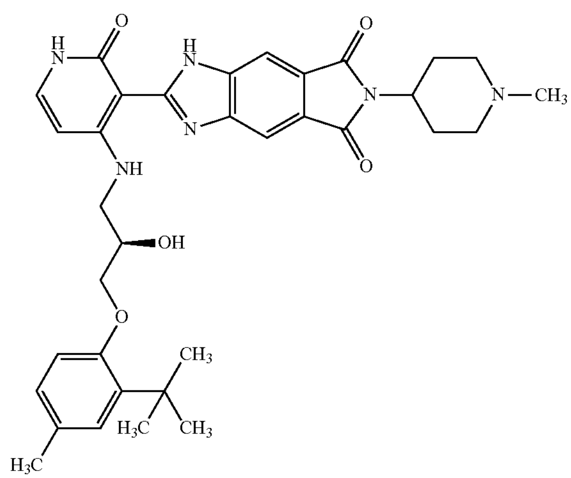 [SMILES: Cc1ccc(OC[C@H](O)CNc2cc[nH]c(=O)c2-c2nc3cc4c(cc3[nH]2)C(=O)N(C2CCN(C)CC2)C4=O)c(C(C)(C)C)c1] | ++ | + | ++ | + | | − | + | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 81 | 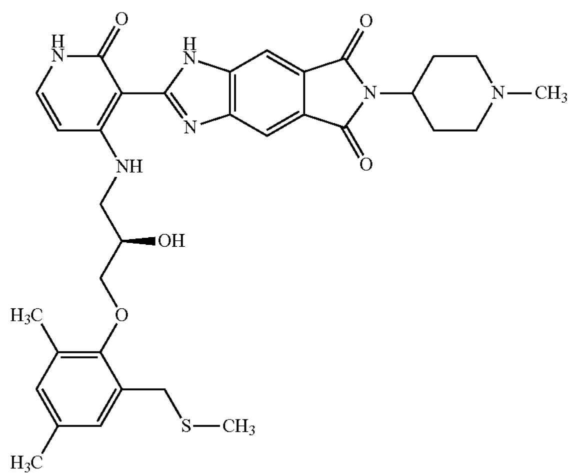 [SMILES: CSCc1cc(C)cc(C)c1OC[C@H](O)CNc1cc[nH]c(=O)c1-c1nc2cc3c(cc2[nH]1)C(=O)N(C1CCN(C)CC1)C3=O] | ++ | + | ++ | + | | + | + | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 82 | (structure) | ++ | ++ | +++ | ++ | | - | - | - | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 83 | 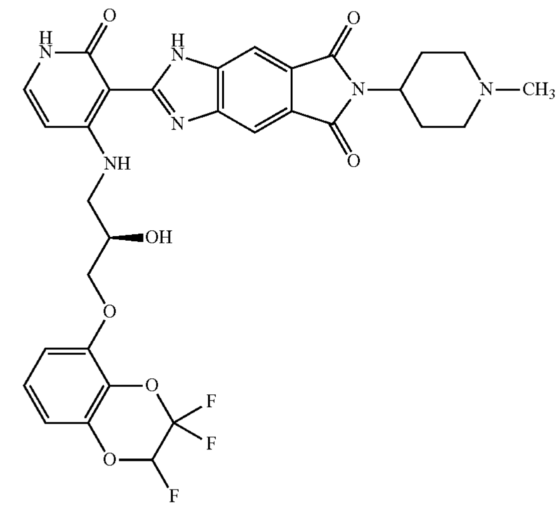 [SMILES: CN1CCC(N2C(=O)c3cc4nc(-c5c(NC[C@@H](O)COc6cccc7c6OC(F)(F)C(F)O7)cc[nH]c5=O)[nH]c4cc3C2=O)CC1] | ‡ | +++ | +++ | ‡ | | - | - | - | | | | |
| 84 | 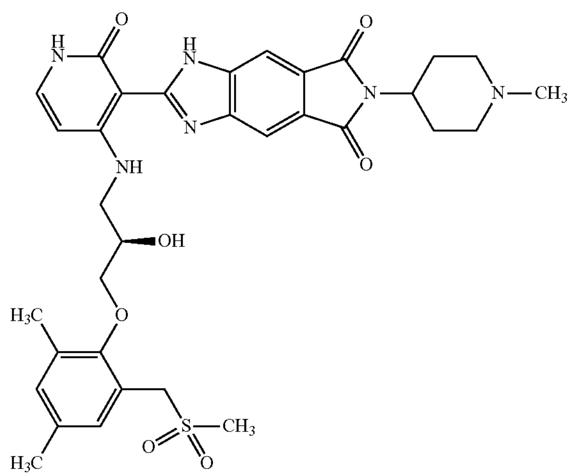 [SMILES: Cc1cc(C)c(OC[C@H](O)CNc2cc[nH]c(=O)c2-c2nc3cc4c(cc3[nH]2)C(=O)N(C2CCN(C)CC2)C4=O)c(CS(C)(=O)=O)c1] | ‡ | ‡ | ‡ | ‡ | | - | - | - | | ‡ | ‡ | ‡ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 85 | 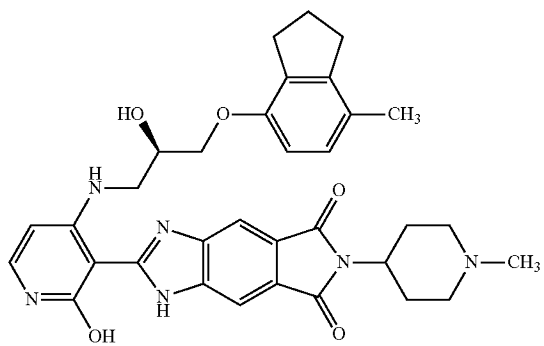 [SMILES: Cc1ccc(OC[C@H](O)CNc2ccnc(O)c2-c2nc3cc4c(cc3[nH]2)C(=O)N(C2CCN(C)CC2)C4=O)c2c1CCC2] | ++ | +++ | +++ | ++ | | ++ | ++ | ++ | | | | |
| 86 | 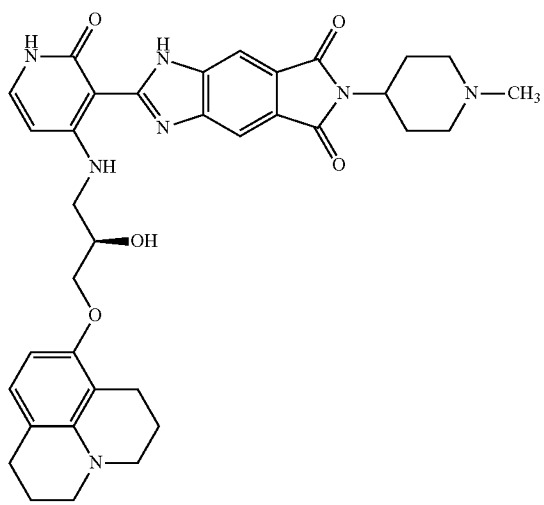 [SMILES: CN1CCC(N2C(=O)c3cc4nc(-c5c(NC[C@@H](O)COc6ccc7c8c6CCCN8CCC7)cc[nH]c5=O)[nH]c4cc3C2=O)CC1] | ++ | + | ++ | ++ | | − | + | + | | | − | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 87 | 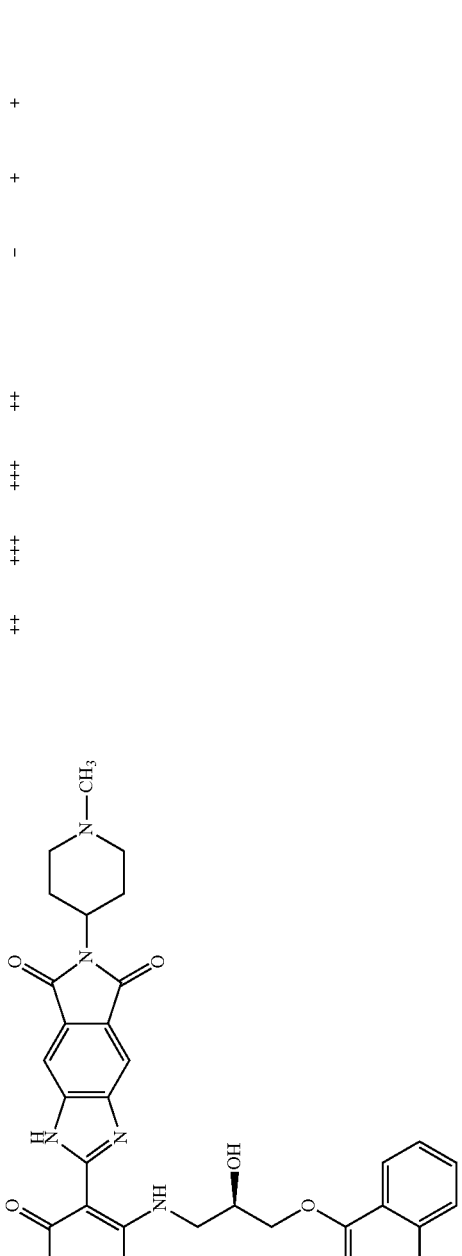 | ++ | +++ | +++ | ++ | | − | + | + | | | + | ++ |
| 88 | 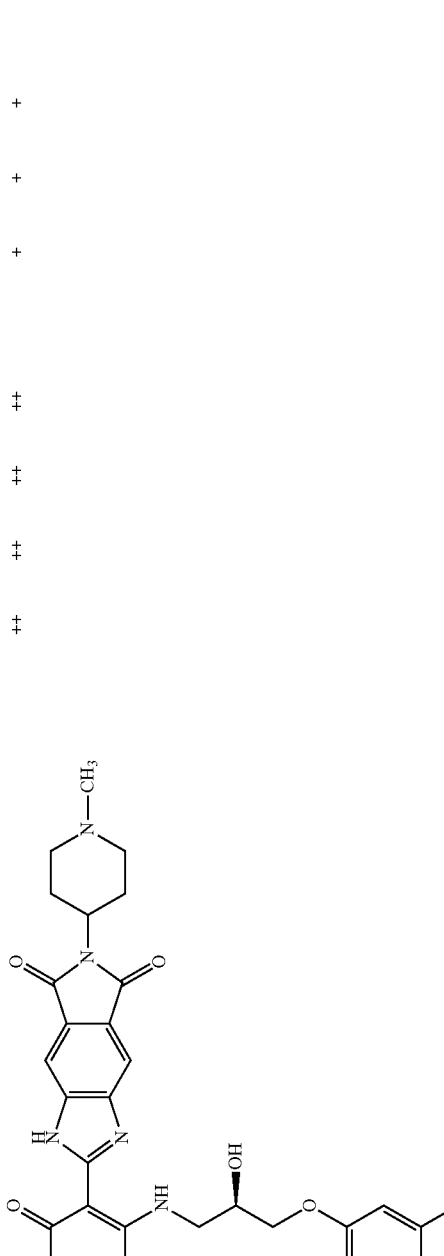 | ++ | ++ | ++ | ++ | | + | + | + | | | + | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 89 | (structure) | ‡ | ‡ | ‡ | ‡ | | + | ‡ | + | | | + | ‡ |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 90 | 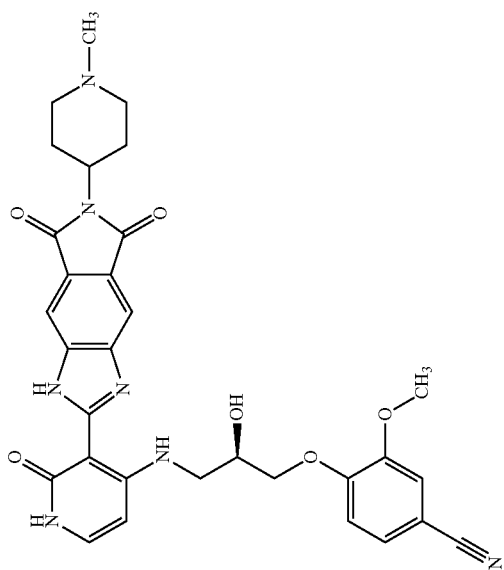 | − | + | + | ++ | | + | ++ | ++ | | | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 91 | 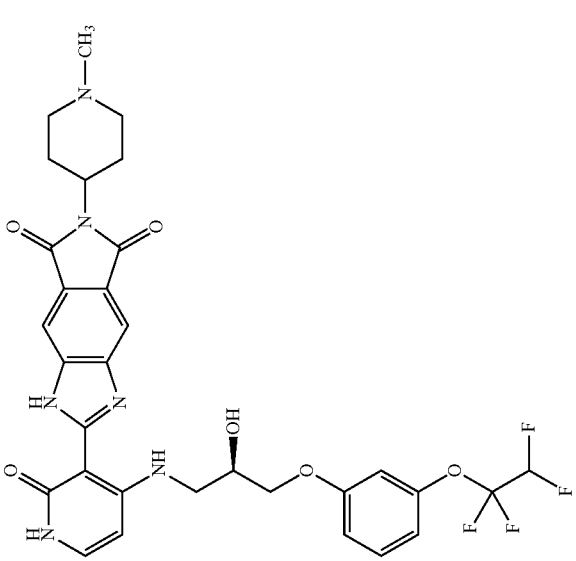 | ++ | ++ | + | ++ | | - | + | - | | | ++ | ++ |
| 92 | 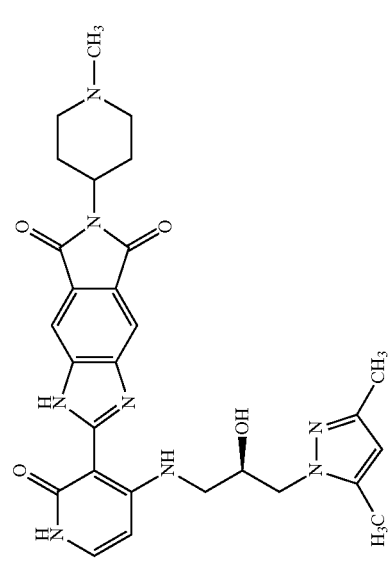 | - | + | + | + | | - | - | - | | | ++ | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 93 | 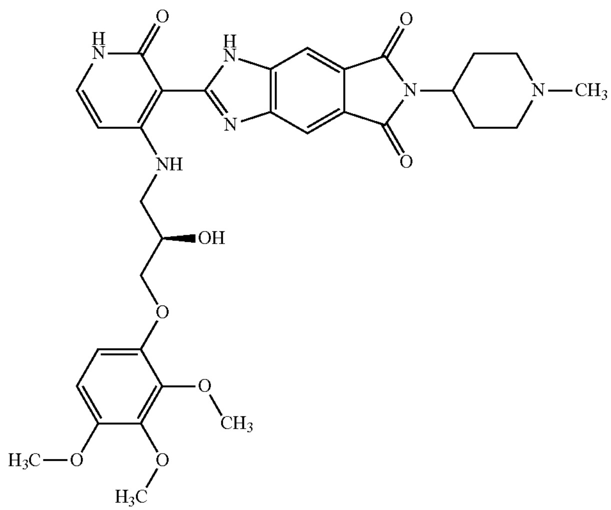 | − | +++ | +++ | − | | − | + | − | + | | ++ | ++ |
| 94 | 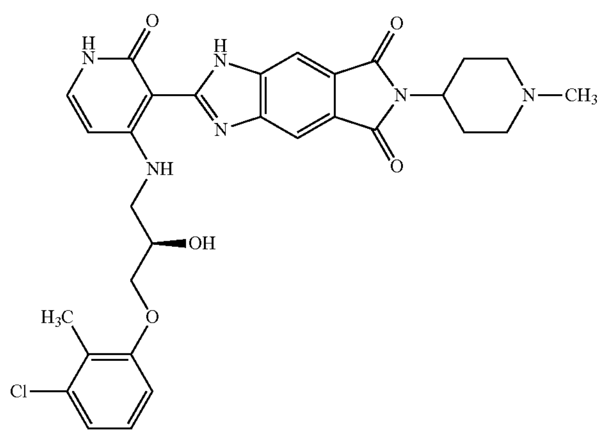 [SMILES: Cc1c(Cl)cccc1OC[C@H](O)CNc1cc[nH]c(=O)c1-c1nc2cc3c(cc2[nH]1)C(=O)N(C1CCN(C)CC1)C3=O] | ++ | +++ | +++ | ++ | | − | − | − | − | | + | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 95 | *(structure: N-methylpiperidine-pyrrolo-benzimidazole-dione linked to pyridinone with NH-CH2-CH(OH)-CH2-O-(2,6-difluoro-3-chlorophenyl))* | ++ | +++ | +++ | ++ | | − | + | + | + | | + | + |
| 96 | *(structure: N-methylpiperidine-pyrrolo-benzimidazole-dione linked to pyridinone with NH-CH2-CH(OH)-CH2-O-(2-fluoro-3-chlorophenyl))* | − | +++ | ++ | + | | − | − | − | + | | + | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 97 | 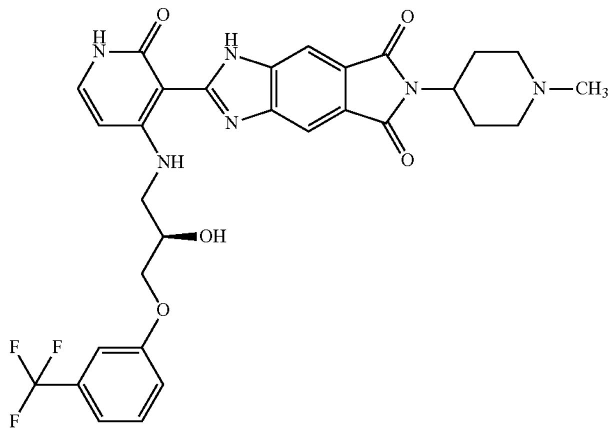 [SMILES: CN1CCC(N2C(=O)c3cc4nc(-c5c(NC[C@@H](O)COc6cccc(C(F)(F)F)c6)cc[nH]c5=O)[nH]c4cc3C2=O)CC1] | + | ++ | ++ | ++ | | - | - | - | - | | + | ++ |
| 98 | 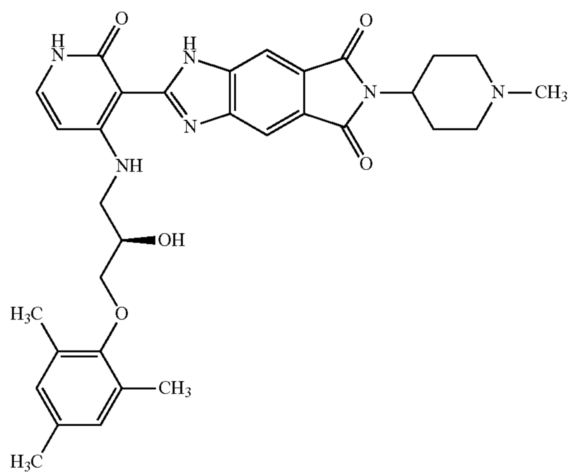 [SMILES: Cc1cc(C)c(OC[C@H](O)CNc2cc[nH]c(=O)c2-c2nc3cc4c(cc3[nH]2)C(=O)N(C2CCN(C)CC2)C4=O)c(C)c1] | ++ | +++ | +++ | + | | - | - | - | | | + | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 99 | 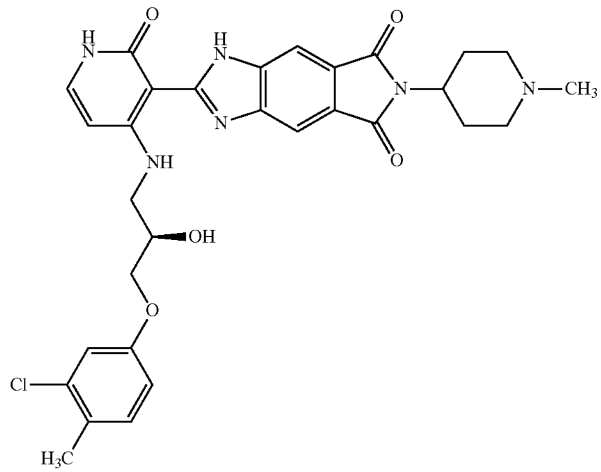 [SMILES: Cc1ccc(OC[C@H](O)CNc2cc[nH]c(=O)c2-c2nc3cc4c(cc3[nH]2)C(=O)N(C2CCN(C)CC2)C4=O)cc1Cl] | + | ++ | +++ | ++ | | - | - | - | | | | - |
| 100 | 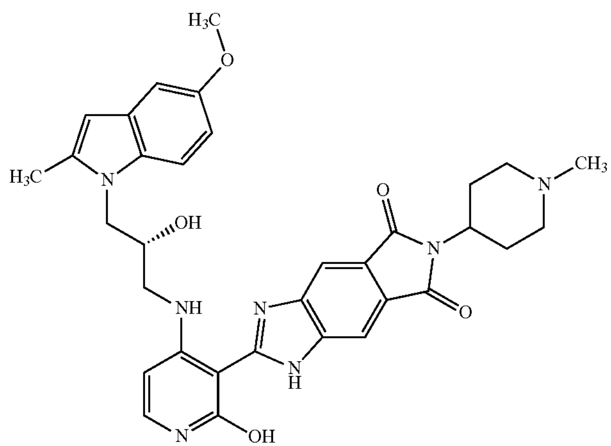 | +++ | ++ | ++ | ++ | | - | + | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 101 | 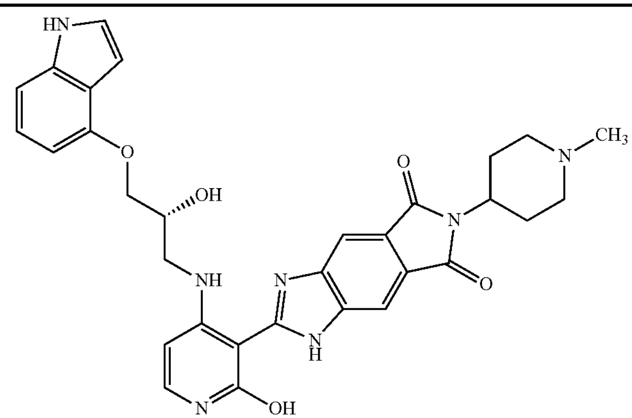 | +++ | +++ | +++ | ++ | | − | − | − | | | | |
| 102 | 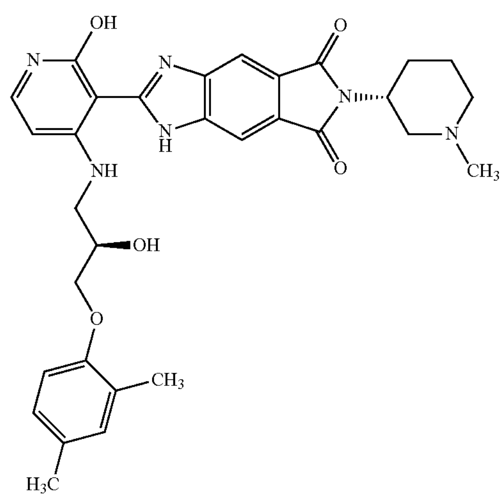 [SMILES: Cc1ccc(OC[C@H](O)CNc2ccnc(O)c2-c2nc3cc4c(cc3[nH]2)C(=O)N([C@@H]2CCCN(C)C2)C4=O)c(C)c1] | − | + | +++ | − | | − | + | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 103 | 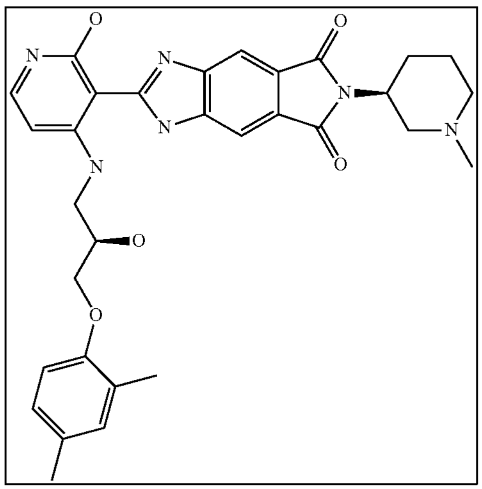 [SMILES: Cc1ccc(OC[C@H](O)CNc2ccnc(O)c2-c2nc3cc4c(cc3[nH]2)C(=O)N([C@H]2CCCN(C)C2)C4=O)c(C)c1] | − | + | +++ | + | | ++ | ++ | ++ | | | | |
| 104 | 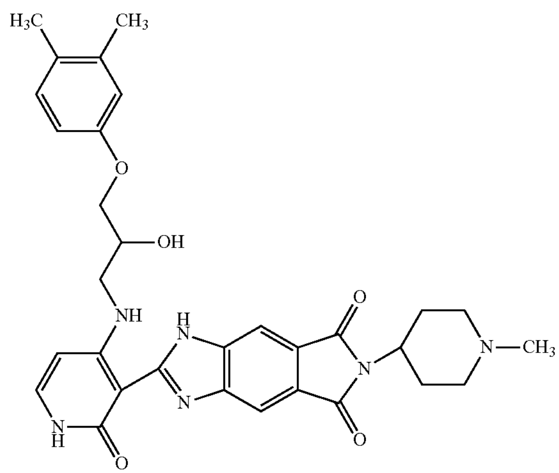 [SMILES: Cc1ccc(OCC(O)CNc2cc[nH]c(=O)c2-c2nc3cc4c(cc3[nH]2)C(=O)N(C2CCN(C)CC2)C4=O)cc1C] | + | +++ | ++ | + | | − | − | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 105 | 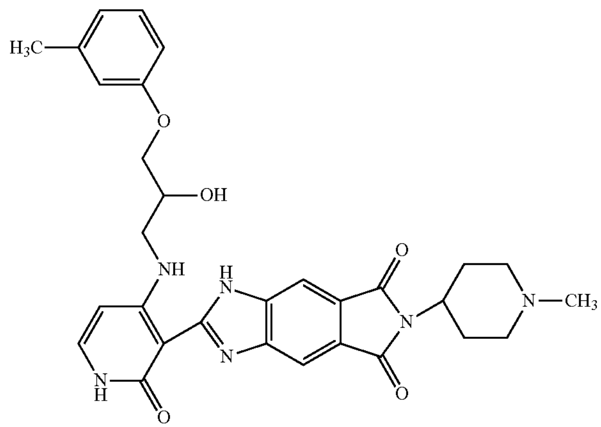 | + | ++ | ++ | ++ | | - | - | + | | | | |
| 106 | 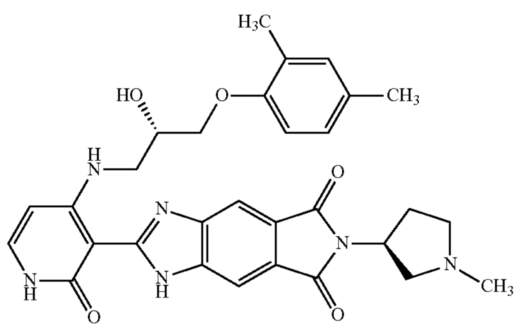 [SMILES: Cc1ccc(OC[C@@H](O)CNc2cc[nH]c(=O)c2-c2nc3cc4c(cc3[nH]2)C(=O)N([C@H]2CCN(C)C2)C4=O)c(C)c1] | ++ | +++ | +++ | ++ | | + | - | + | | | + | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 107 | 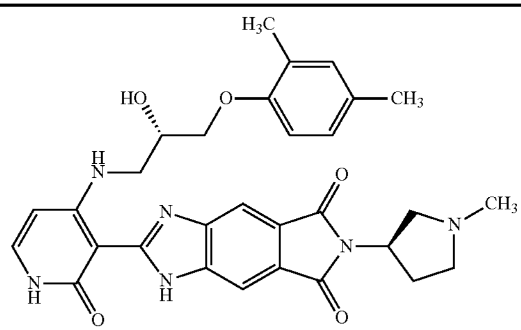 | ++ | +++ | +++ | ++ | | − | − | − | | | + | + |
| 108 | 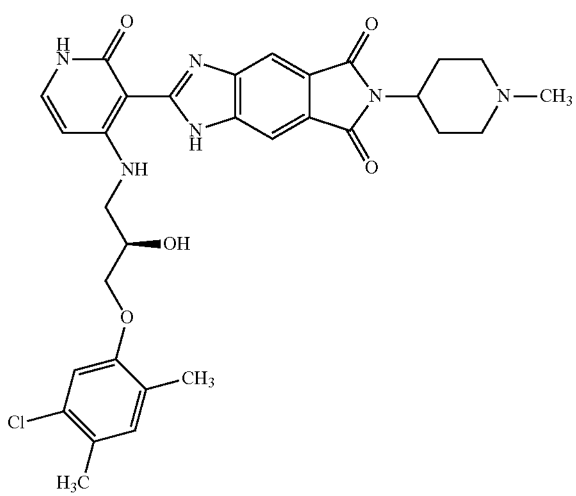 [SMILES: Cc1cc(C)c(OC[C@H](O)CNc2cc[nH]c(=O)c2-c2nc3cc4c(cc3[nH]2)C(=O)N(C2CCN(C)CC2)C4=O)cc1Cl] | ++ | ++ | ++ | ++ | | − | + | | + | | | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 109 | Chiral structure | - | - | - | - | | - | ++ | | | | | |
| 110 | structure | ++ | +++ | +++ | ++ | | + | ++ | + | | | + | + |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 111 | 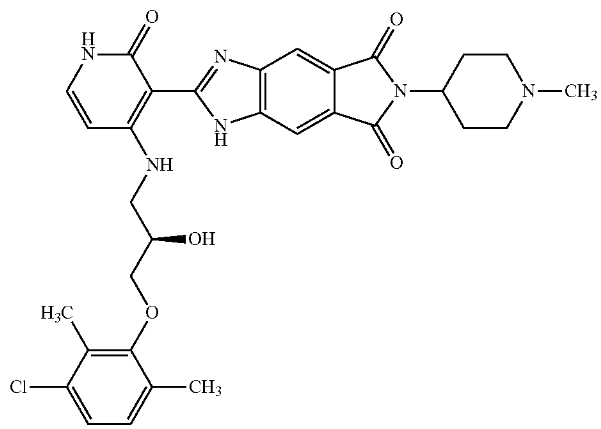 [SMILES: Cc1ccc(Cl)c(C)c1OC[C@H](O)CNc1cc[nH]c(=O)c1-c1nc2cc3c(cc2[nH]1)C(=O)N(C1CCN(C)CC1)C3=O] | ++ | ++ | ++ | ++ | | + | ++ | − | | | | − |
| 112 | 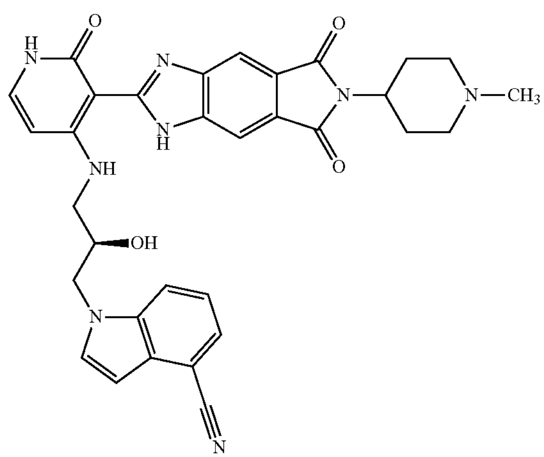 [SMILES: CN1CCC(N2C(=O)c3cc4nc(-c5c(NC[C@@H](O)Cn6ccc7c(C#N)cccc76)cc[nH]c5=O)[nH]c4cc3C2=O)CC1] | ++ | ++ | ++ | ++ | | + | ++ | + | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 113 | 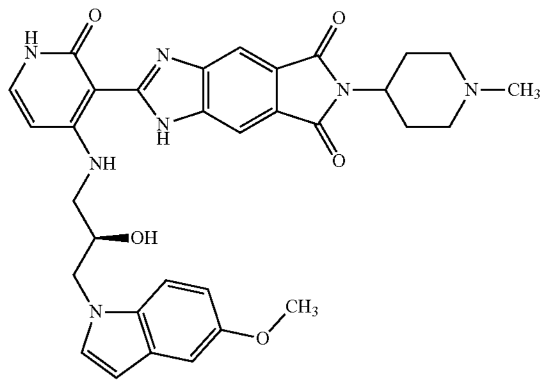 [SMILES: COc1ccc2c(ccn2C[C@H](O)CNc2cc[nH]c(=O)c2-c2nc3cc4c(cc3[nH]2)C(=O)N(C2CCN(C)CC2)C4=O)c1] | +++ | ++ | ++ | ++ | | - | - | - | | | - | |
| 114 | 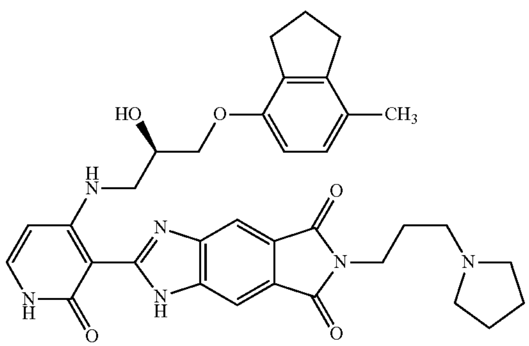 [SMILES: Cc1ccc(OC[C@H](O)CNc2cc[nH]c(=O)c2-c2nc3cc4c(cc3[nH]2)C(=O)N(CCCN2CCCC2)C4=O)c2c1CCC2] | ++ | +++ | +++ | ++ | | - | | - | | | - | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 115 | 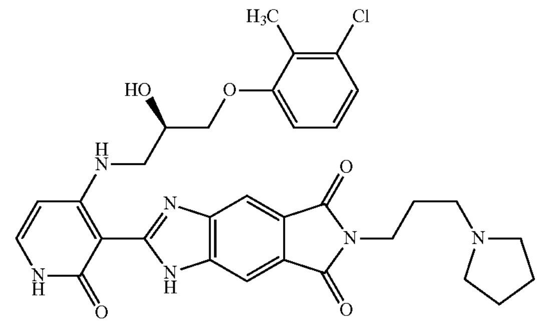 [SMILES: Cc1c(Cl)cccc1OC[C@H](O)CNc1cc[nH]c(=O)c1-c1nc2cc3c(cc2[nH]1)C(=O)N(CCCN1CCCC1)C3=O] | ++ | +++ | +++ | ++ | | − | + | | | | | |
| 116 | 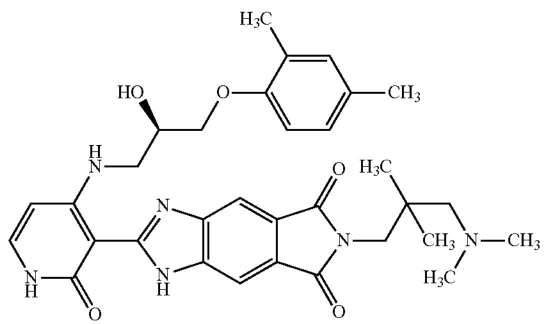 [SMILES: Cc1ccc(OC[C@H](O)CNc2cc[nH]c(=O)c2-c2nc3cc4c(cc3[nH]2)C(=O)N(CC(C)(C)CN(C)C)C4=O)c(C)c1] | + | +++ | +++ | ++ | | − | + | − | | | − | |
| 117 | 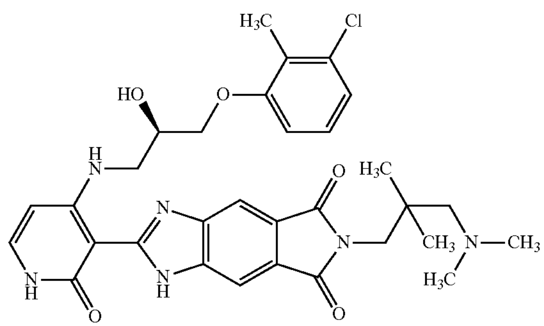 [SMILES: Cc1c(Cl)cccc1OC[C@H](O)CNc1cc[nH]c(=O)c1-c1nc2cc3c(cc2[nH]1)C(=O)N(CC(C)(C)CN(C)C)C3=O] | + | +++ | +++ | ++ | | − | + | | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 118 | 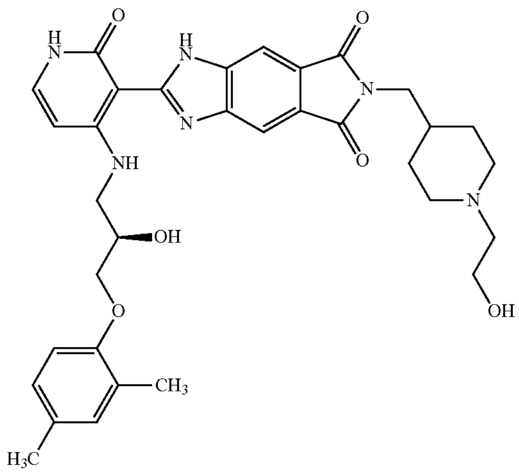 | ++ | +++ | +++ | ++ | | − | + | − | | | − | |
| 119 | 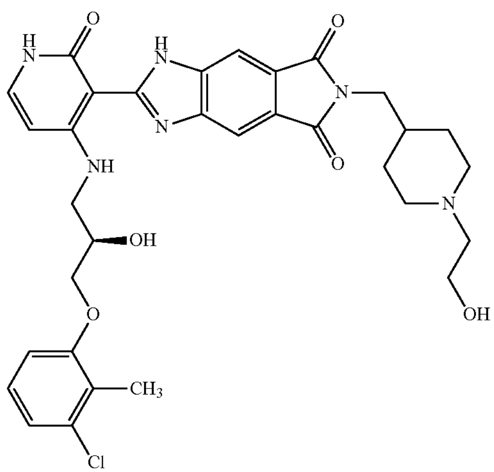 [SMILES: Cc1c(Cl)cccc1OC[C@H](O)CNc1cc[nH]c(=O)c1-c1nc2cc3c(cc2[nH]1)C(=O)N(CC1CCN(CCO)CC1)C3=O] | ++ | +++ | +++ | ++ | | − | − | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 120 | 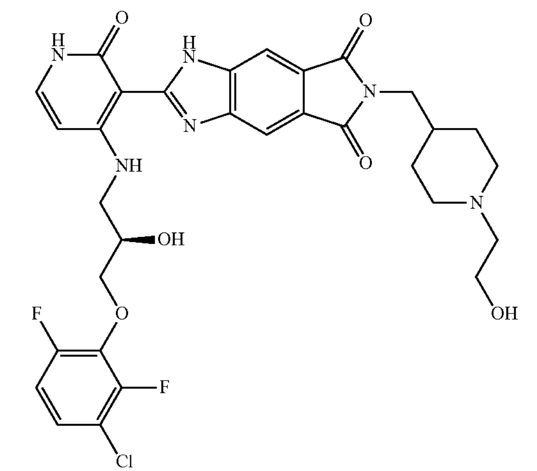 [SMILES: O=C1c2cc3nc(-c4c(NC[C@@H](O)COc5c(F)ccc(Cl)c5F)cc[nH]c4=O)[nH]c3cc2C(=O)N1CC1CCN(CCO)CC1] | ++ | +++ | +++ | ++ | | ++ | ++ | | | | | |
| 121 | 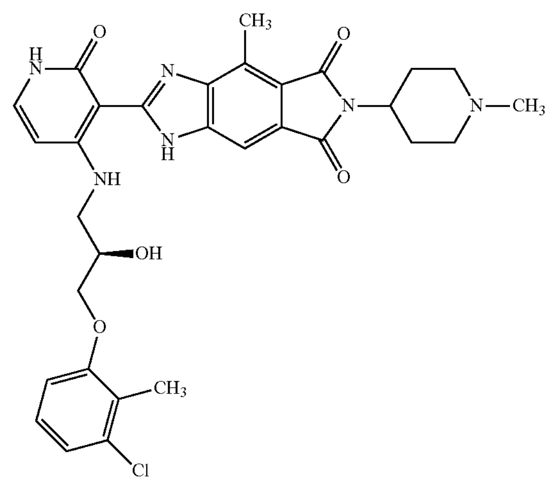 [SMILES: Cc1c(Cl)cccc1OC[C@H](O)CNc1cc[nH]c(=O)c1-c1nc2c(C)c3c(cc2[nH]1)C(=O)N(C1CCN(C)CC1)C3=O] | ++ | ++ | ++ | ++ | | ++ | + | | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 122 | 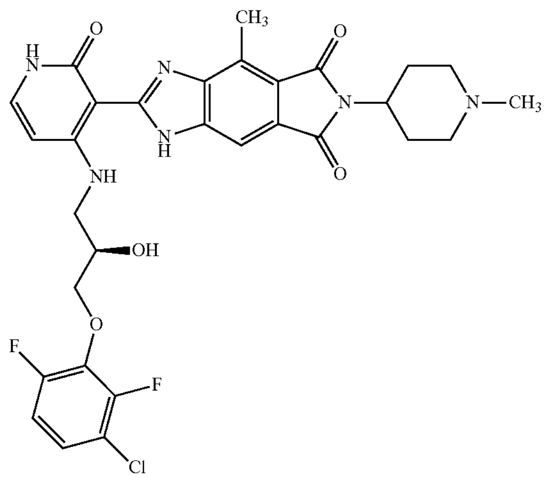 [SMILES: Cc1c2c(cc3[nH]c(-c4c(NC[C@@H](O)COc5c(F)ccc(Cl)c5F)cc[nH]c4=O)nc13)C(=O)N(C1CCN(C)CC1)C2=O] | + | ++ | +++ | ++ | | - | - | | | | | |
| 123 | 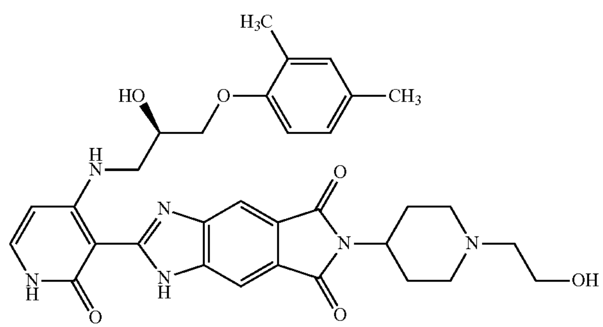 [SMILES: Cc1ccc(OC[C@H](O)CNc2cc[nH]c(=O)c2-c2nc3cc4c(cc3[nH]2)C(=O)N(C2CCN(CCO)CC2)C4=O)c(C)c1] | ++ | ++ | +++ | ++ | | - | - | - | | | - | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 124 | 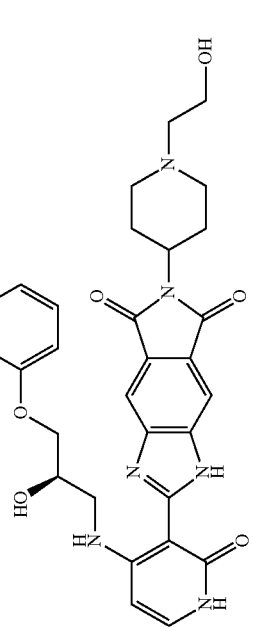 | ‡ | ‡‡ | ‡‡ | ‡‡ | | − | + | − | | | − | |
| 125 | 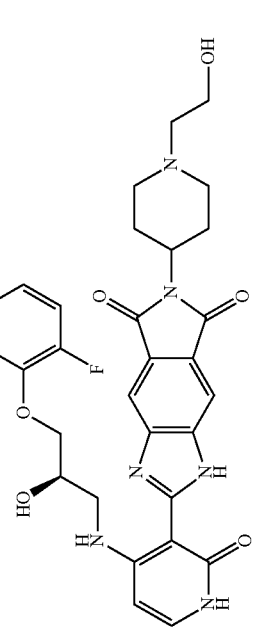 | ‡‡ | ‡‡ | ‡‡‡ | ‡‡ | | − | − | − | | | − | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 126 | 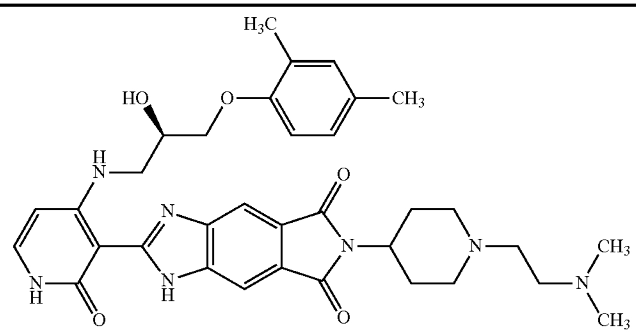 | + | ++ | +++ | ++ | | ++ | ++ | + | | | + | |
| 127 | 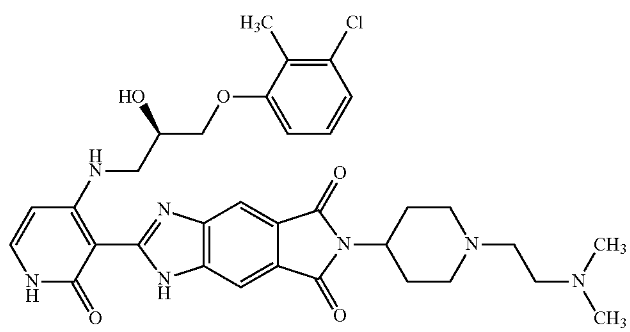 [SMILES: Cc1c(Cl)cccc1OC[C@H](O)CNc1cc[nH]c(=O)c1-c1nc2cc3c(cc2[nH]1)C(=O)N(C1CCN(CCN(C)C)CC1)C3=O] | ++ | ++ | +++ | ++ | | − | − | − | | | − | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 128 | 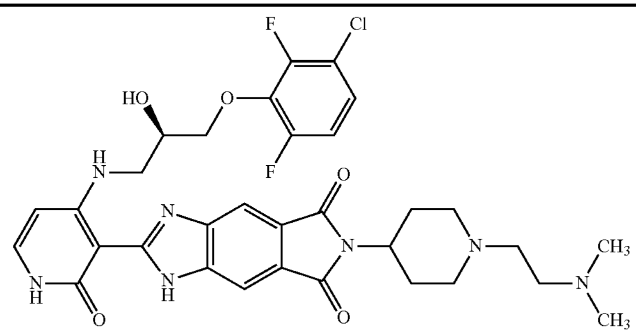 | ++ | ++ | +++ | ++ | | - | - | - | | | | |
| 129 | 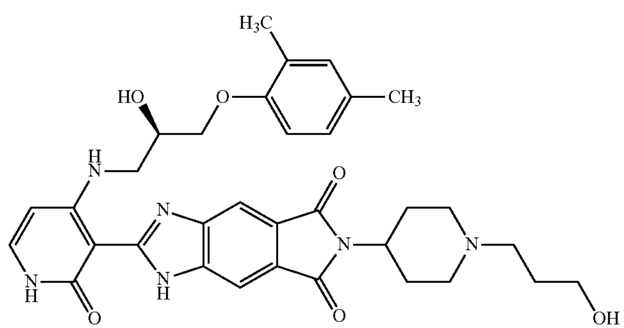 [SMILES: Cc1ccc(OC[C@H](O)CNc2cc[nH]c(=O)c2-c2nc3cc4c(cc3[nH]2)C(=O)N(C2CCN(CCCO)CC2)C4=O)c(C)c1] | ++ | +++ | +++ | ++ | | + | + | + | | | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 130 | 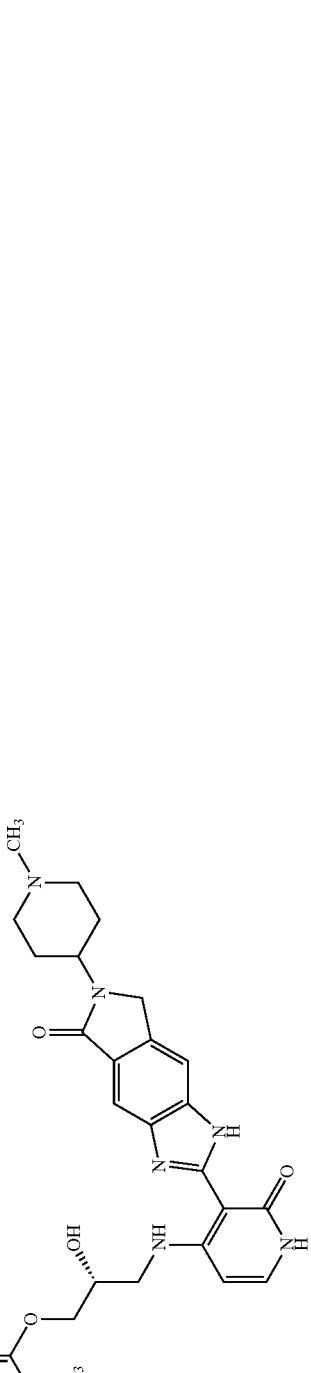 | ++ | +++ | +++ | +++ | | | | - | - | - | ++ | ++ |
| 131 | 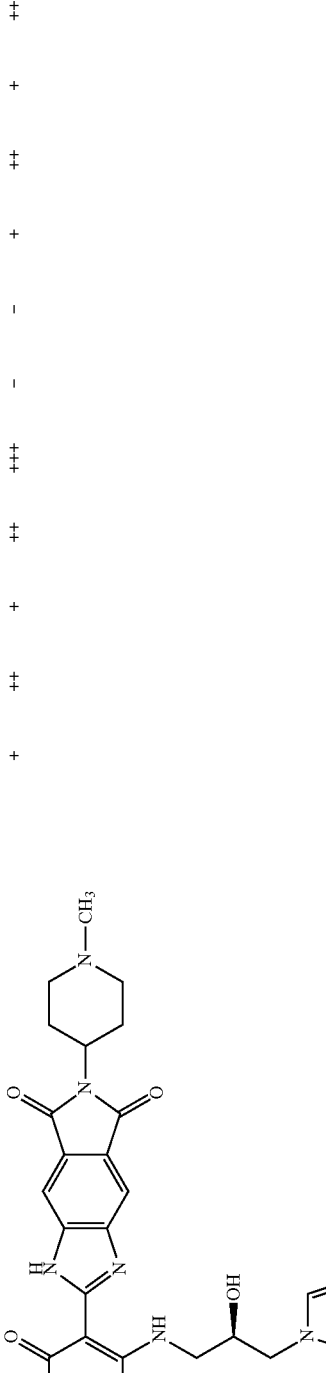 | + | ++ | + | ++ | +++ | - | - | + | ++ | + | ++ | ++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 132 | 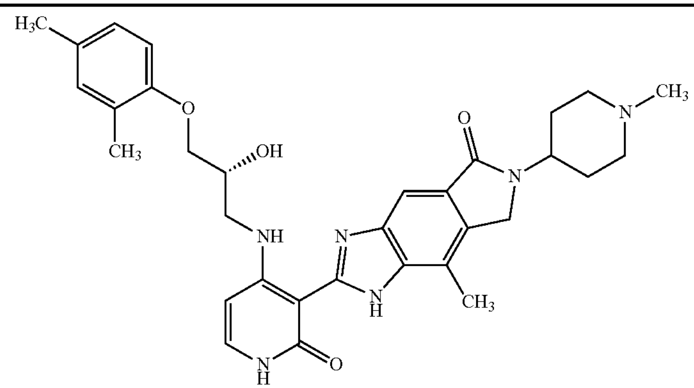 | ++ | +++ | +++ | +++ | | | | - | - | - | +++ | ++ |
| 133 | 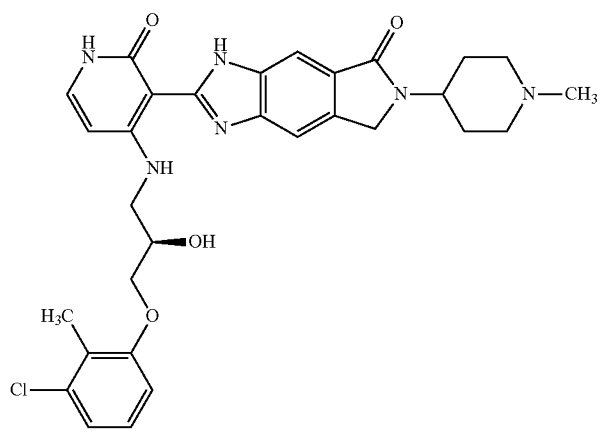 [SMILES: Cc1c(Cl)cccc1OC[C@H](O)CNc1cc[nH]c(=O)c1-c1nc2cc3c(cc2[nH]1)C(=O)N(C1CCN(C)CC1)C3] | ++ | +++ | +++ | +++ | +++ | | | | | | | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 134 | 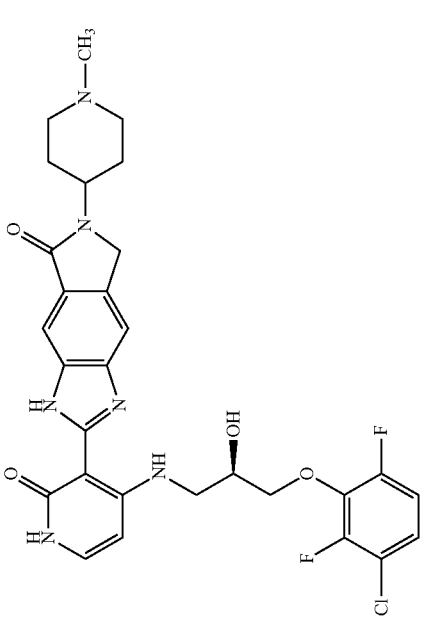 | + | +++ | +++ | +++ | +++ | | | | | | | |
| 135 | 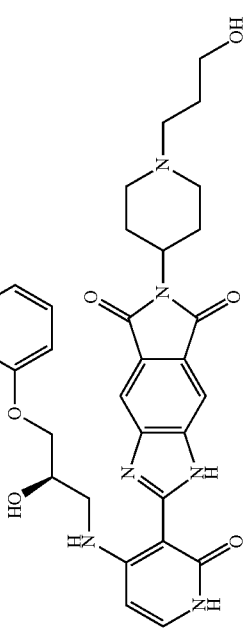 | ++ | ++ | +++ | ++ | +++ | − | | − | | | − | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 136 | 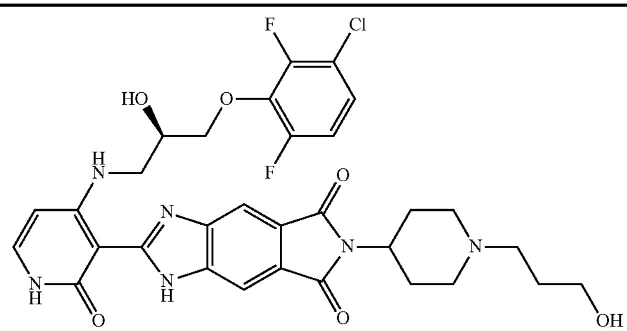 | ++ | ++ | +++ | ++ | | - | - | - | | | - | |
| 137 | 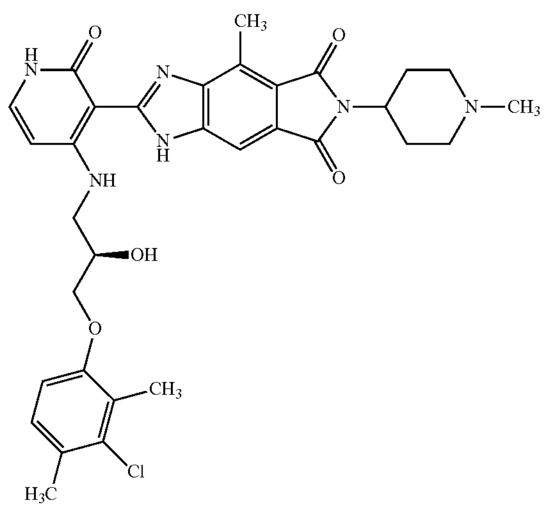 [SMILES: Cc1ccc(OC[C@H](O)CNc2cc[nH]c(=O)c2-c2nc3c(C)c4c(cc3[nH]2)C(=O)N(C2CCN(C)CC2)C4=O)c(C)c1Cl] | + | +++ | ++ | ++ | | | | | | | - | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 138 | 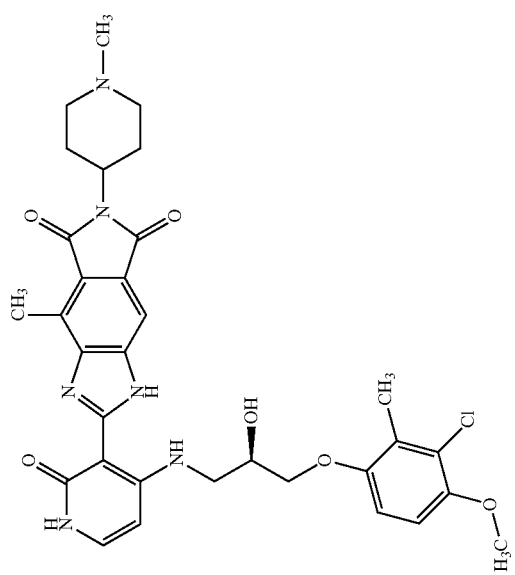 | ++ | +++ | +++ | ++ | | + | ++ | − | | | | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 139 | 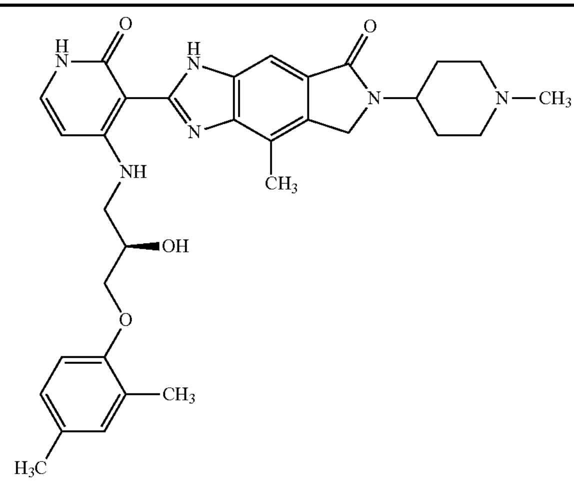 | ++ | +++ | +++ | ++ | | | | − | − | − | ++ | ++ |
| 140 | 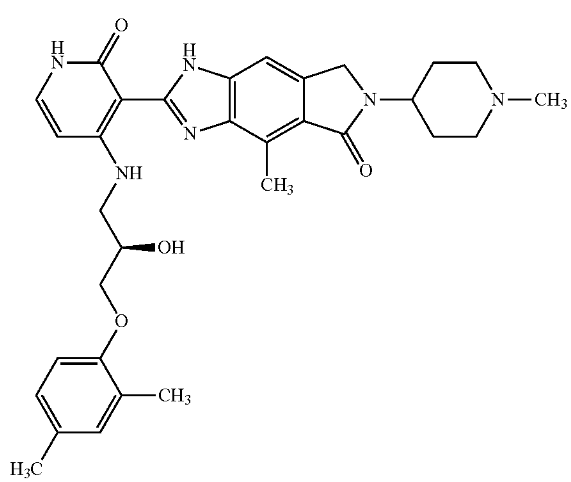 [SMILES: Cc1ccc(OC[C@H](O)CNc2cc[nH]c(=O)c2-c2nc3c(C)c4c(cc3[nH]2)CN(C2CCN(C)CC2)C4=O)c(C)c1] | ++ | +++ | +++ | +++ | | | | + | + | − | +++ | ++ |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 141 | 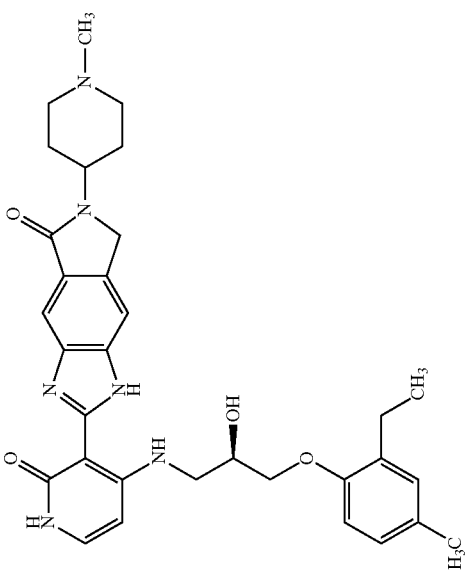 | ++ | +++ | +++ | +++ | | | | - | - | - | +++ | ++ |
| 142 | 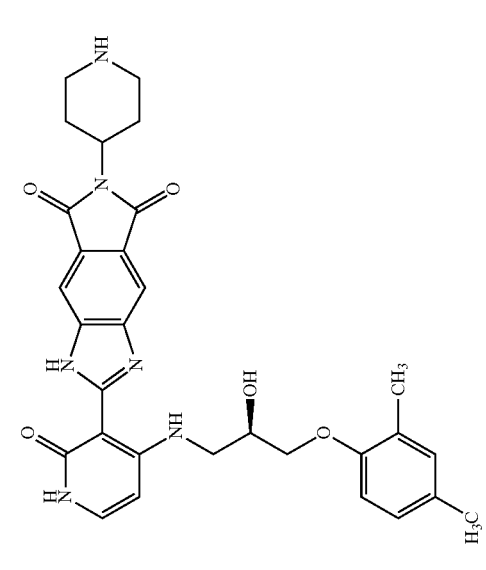 | ++ | +++ | +++ | ++ | | | | + | + | + | +++ | +++ |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 143 | 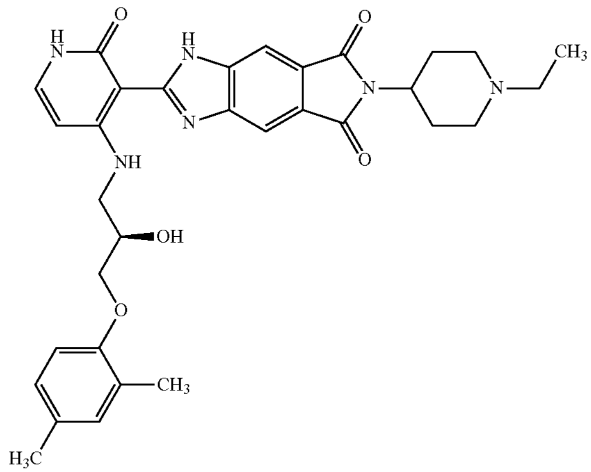 [SMILES: CCN1CCC(N2C(=O)c3cc4nc(-c5c(NC[C@@H](O)COc6ccc(C)cc6C)cc[nH]c5=O)[nH]c4cc3C2=O)CC1] | +++ | ++ | +++ | ++ | | | | | − | − | + | +++ |
| 144 | 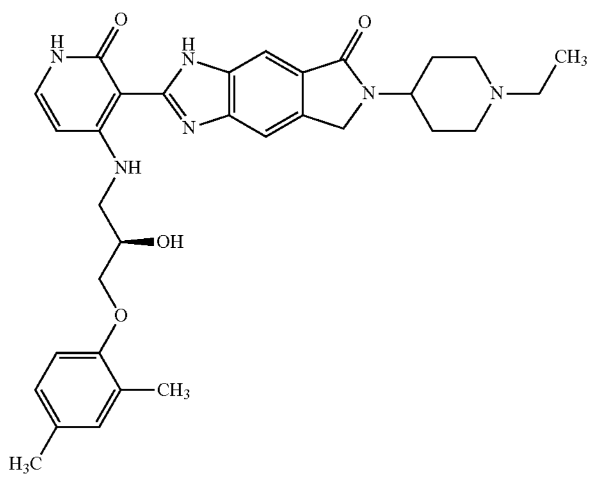 [SMILES: CCN1CCC(N2Cc3cc4nc(-c5c(NC[C@@H](O)COc6ccc(C)cc6C)cc[nH]c5=O)[nH]c4cc3C2=O)CC1] | +++ | ++ | +++ | +++ | | | | − | + | + | ± | ± |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 145 | 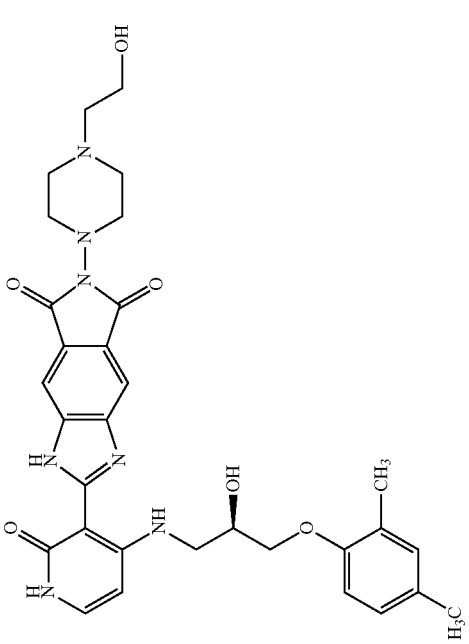 | - | +++ | +++ | + | | - | - | + | + | + | ++ | ++ |
| 146 | 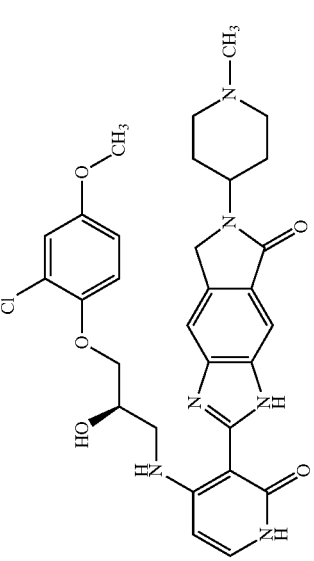 | ++ | +++ | +++ | +++ | | | | | - | - | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 147 | 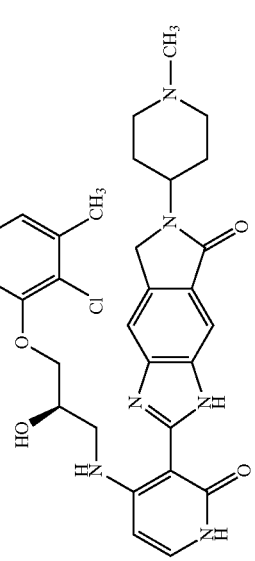 | + | +++ | +++ | +++ | | | | | − | − | ++ | |
| 148 | 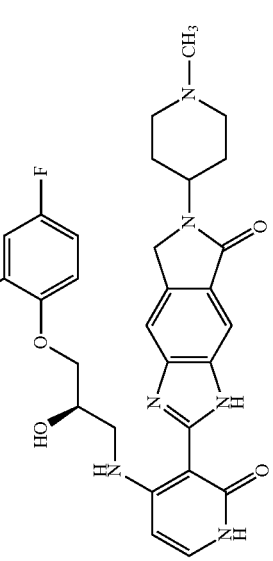 | ++ | +++ | +++ | +++ | | | | | − | + | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 149 | 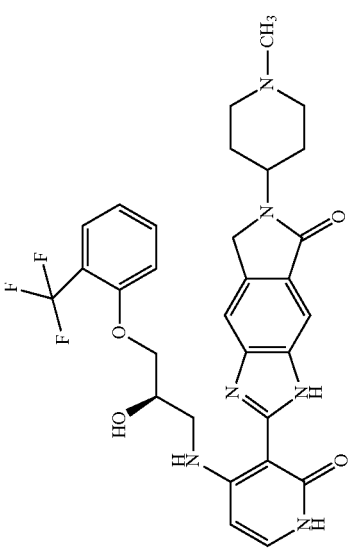 | +++ | +++ | +++ | +++ | | | | | + | − | ++ | |
| 150 | 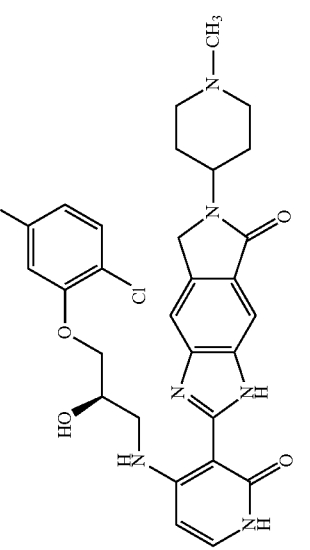 | ++ | +++ | +++ | +++ | | | | | | − | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 151 | 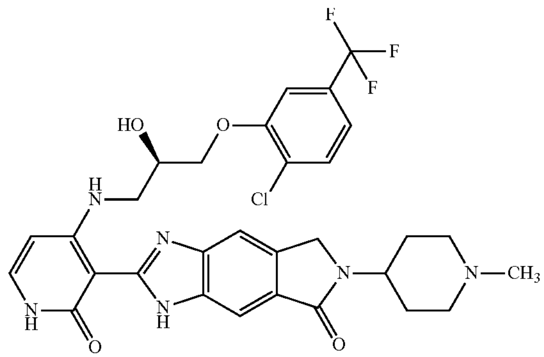 [SMILES: CN1CCC(N2Cc3cc4nc(-c5c(NC[C@@H](O)COc6cc(C(F)(F)F)ccc6Cl)cc[nH]c5=O)[nH]c4cc3C2=O)CC1] | + | +++ | +++ | +++ | | | | | | − | + | |
| 152 | 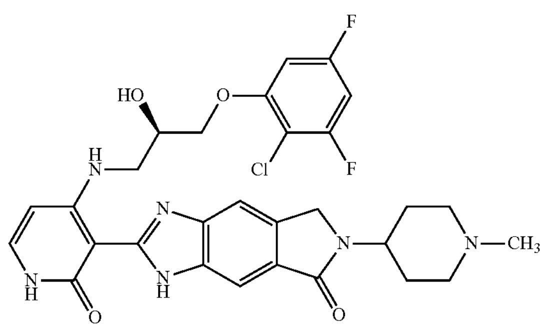 [SMILES: CN1CCC(N2Cc3cc4nc(-c5c(NC[C@@H](O)COc6cc(F)cc(F)c6Cl)cc[nH]c5=O)[nH]c4cc3C2=O)CC1] | ++ | +++ | +++ | +++ | | | | | | − | + | |
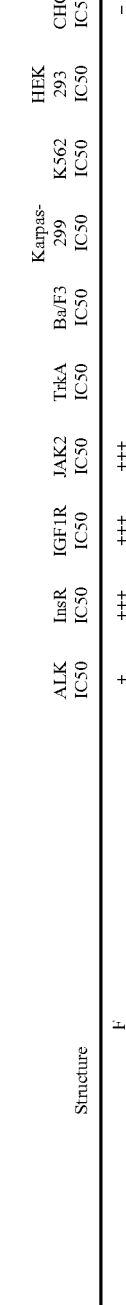

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 153 | 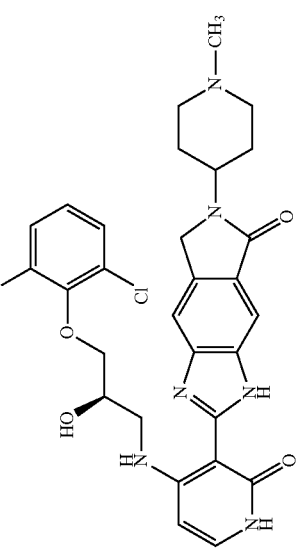 | + | +++ | +++ | +++ | | | | | | − | + | |
| 154 | 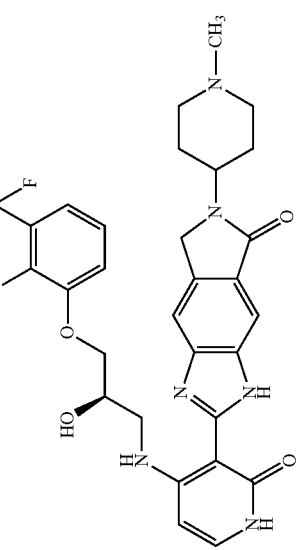 | − | +++ | +++ | +++ | | | | | | − | + | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 155 | 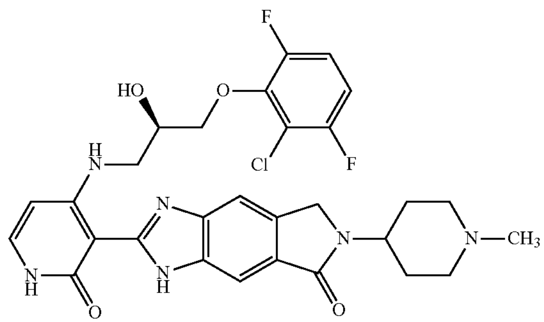 [SMILES: CN1CCC(N2Cc3cc4nc(-c5c(NC[C@@H](O)COc6c(F)ccc(F)c6Cl)cc[nH]c5=O)[nH]c4cc3C2=O)CC1] | + | +++ | +++ | +++ | | | | | | − | + | |
| 156 | 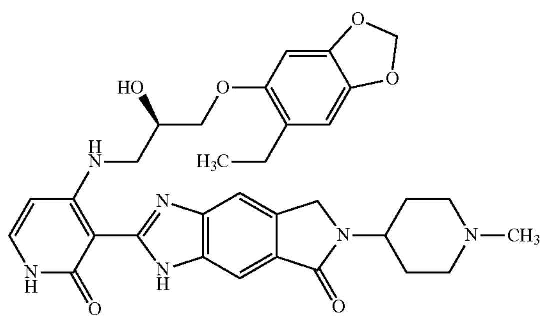 [SMILES: CCc1cc2c(cc1OC[C@H](O)CNc1cc[nH]c(=O)c1-c1nc3cc4c(cc3[nH]1)C(=O)N(C1CCN(C)CC1)C4)OCO2] | ++ | +++ | +++ | +++ | | | | | | − | + | |
| 157 | 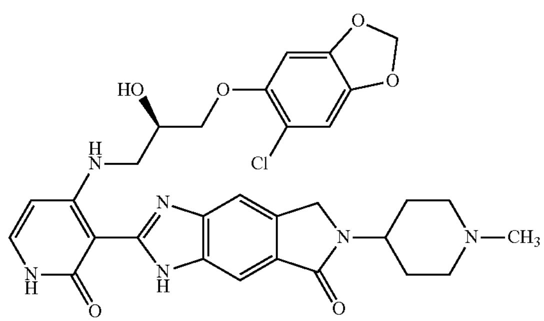 [SMILES: CN1CCC(N2Cc3cc4nc(-c5c(NC[C@@H](O)COc6cc7c(cc6Cl)OCO7)cc[nH]c5=O)[nH]c4cc3C2=O)CC1] | ++ | +++ | +++ | +++ | | | | | | − | − | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 158 | 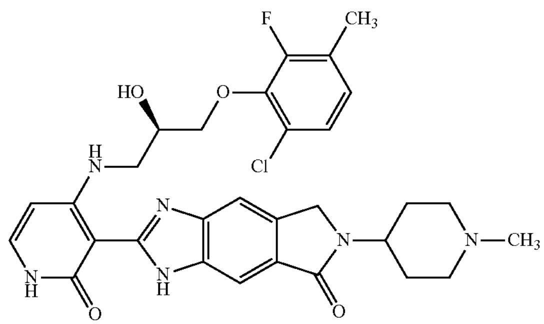 [SMILES: Cc1ccc(Cl)c(OC[C@H](O)CNc2cc[nH]c(=O)c2-c2nc3cc4c(cc3[nH]2)C(=O)N(C2CCN(C)CC2)C4)c1F] | + | +++ | +++ | +++ | | | | | | − | + | |
| 159 | 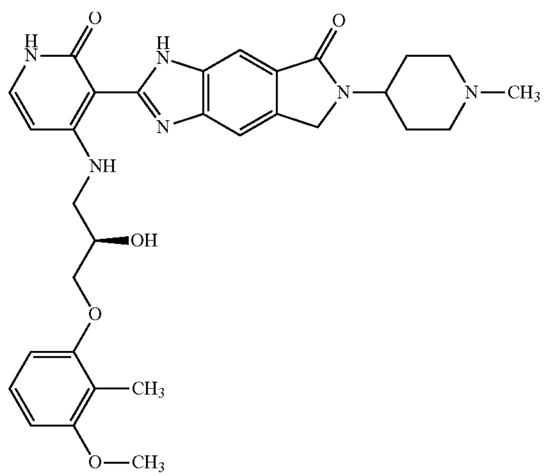 [SMILES: COc1cccc(OC[C@H](O)CNc2cc[nH]c(=O)c2-c2nc3cc4c(cc3[nH]2)C(=O)N(C2CCN(C)CC2)C4)c1C] | + | +++ | +++ | +++ | | | | | | − | + | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 160 | 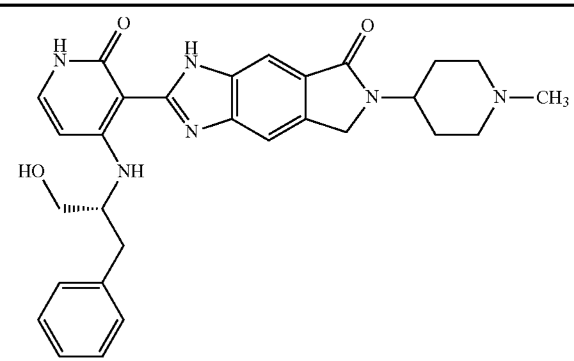 | ++ | +++ | ++ | ++ | | | | | | − | + | |
| 161 | 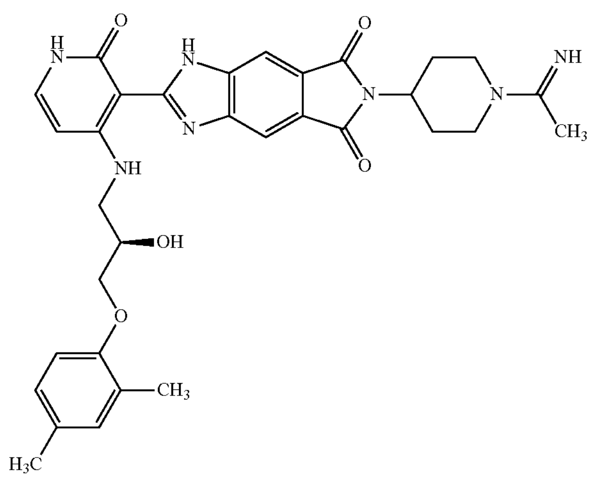 [SMILES: CC(=N)N1CCC(N2C(=O)c3cc4nc(-c5c(NC[C@@H](O)COc6ccc(C)cc6C)cc[nH]c5=O)[nH]c4cc3C2=O)CC1] | ++ | +++ | +++ | ++ | | − | + | − | − | − | + | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 162 | 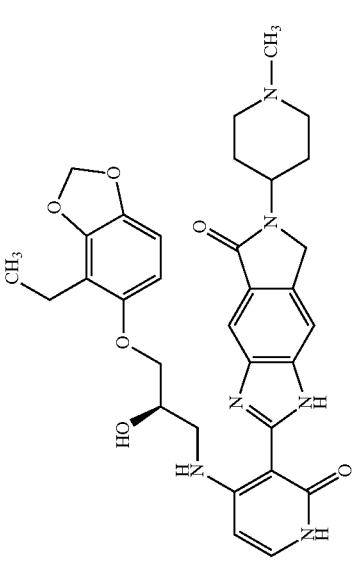 | ++ | +++ | +++ | +++ | | | | | + | + | + | |
| 163 | 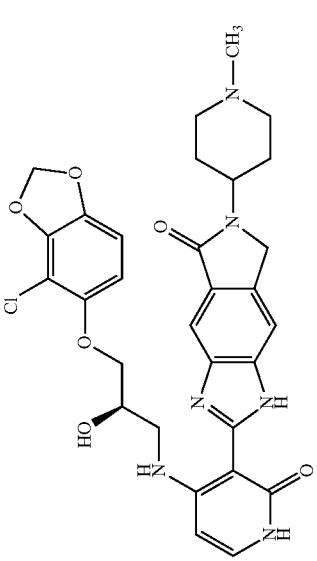 | ++ | +++ | +++ | +++ | | | | | + | − | + | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 164 | 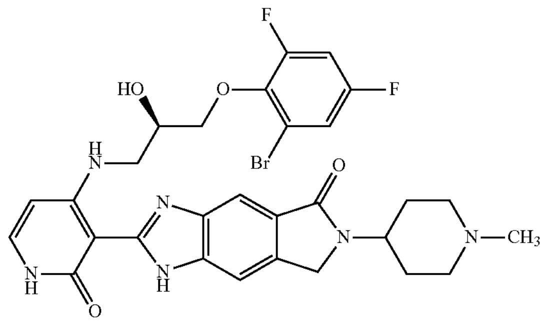 [SMILES: CN1CCC(N2Cc3cc4[nH]c(-c5c(NC[C@@H](O)COc6c(F)cc(F)cc6Br)cc[nH]c5=O)nc4cc3C2=O)CC1] | ‡ | ‡‡‡ | ‡‡‡ | ‡‡‡ | | | | | + | + | + | |
| 165 | 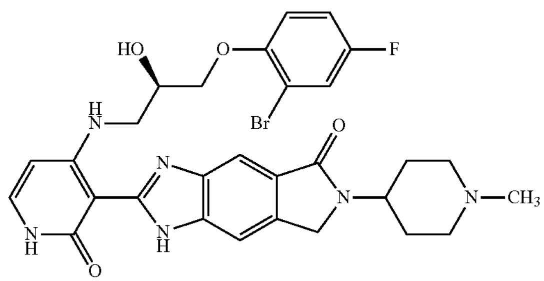 [SMILES: CN1CCC(N2Cc3cc4[nH]c(-c5c(NC[C@@H](O)COc6ccc(F)cc6Br)cc[nH]c5=O)nc4cc3C2=O)CC1] | ‡‡ | ‡‡‡ | ‡‡‡ | ‡‡‡ | | | | | − | + | ‡‡ | |
| 166 | 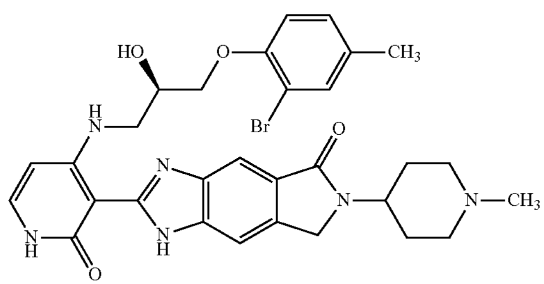 [SMILES: Cc1ccc(OC[C@H](O)CNc2cc[nH]c(=O)c2-c2nc3cc4c(cc3[nH]2)CN(C2CCN(C)CC2)C4=O)c(Br)c1] | ‡‡ | ‡‡‡ | ‡‡‡ | ‡‡‡ | | | | | − | + | ‡‡ | |

TABLE III-continued
| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 167 | 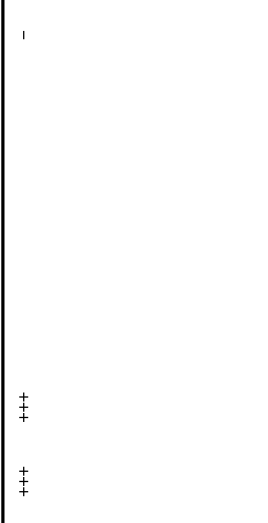 | ++ | +++ | +++ | +++ | | | | | − | − | ++ | |
| 168 | 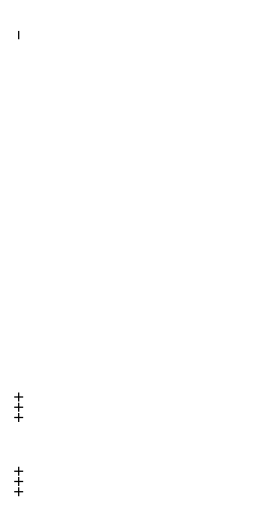 | ++ | +++ | +++ | +++ | | | | | − | − | + | |
| 169 | 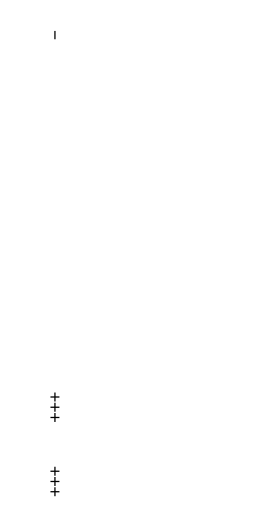 | ++ | +++ | +++ | +++ | | | | | − | − | − | |

TABLE III-continued

| # | Structure | ALK IC50 | InsR IC50 | IGF1R IC50 | JAK2 IC50 | TrkA IC50 | Ba/F3 IC50 | Karpas-299 IC50 | K562 IC50 | HEK 293 IC50 | CHO IC50 | H929 IC50 | MCF7 IGF1R Phosphorylation IC50 |
|---|---|---|---|---|---|---|---|---|---|---|---|---|---|
| 170 | 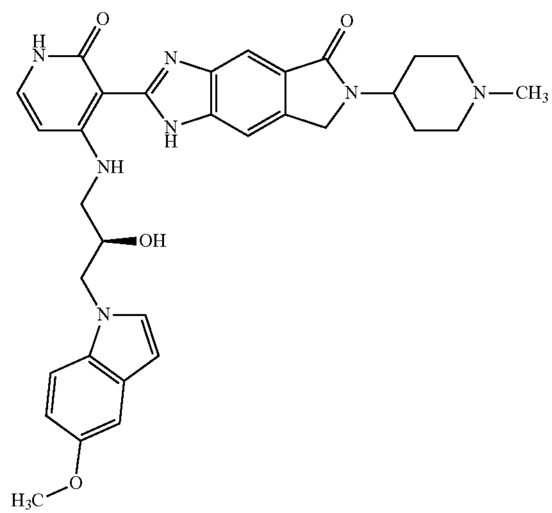 [SMILES: COc1ccc2c(ccn2C[C@H](O)CNc2cc[nH]c(=O)c2-c2nc3cc4c(cc3[nH]2)CN(C2CCN(C)CC2)C4=O)c1] | + | ++ | + | ++ | | | | | | | | |

The IC50 values are represented as ranges where IC50 values in the range below 0.5 μM are indicated by "+++", between 0.5 μM and 5 μM by "++", between 5 μM and 15 μM by "+" and above 15 μM by "−".
Biochemical assays are designated by the name of the tyrosine kinase and the cell proliferation assays by the name of the corresponding cell line; IC50 data for IGF1R phosphorylation inhibition in MCF7 cells as measured by ELISA assay is also included.

TABLE IV

| Structure | HEK IC50 | CHO IC50 | H929 IC50 | MM1S IC50 | MM1R IC50 | UTMC2 IC50 | CPM2 IC50 | KMS11 IC50 | My5 IC50 | KMS12PE IC50 | My7 IC50 | JIN3 IC50 | KMS18 IC50 | U266 IC50 | SKMM2 IC50 | RPMI-8226 IC50 |
|---|---|---|---|---|---|---|---|---|---|---|---|---|---|---|---|---|
| (595) | E | E | A | A | B | B | C | C | C | C | C | C | C | C | D | D |
| (596) | E | E | B | B | C | A | C | C | D | C | C | C | D | C | C | D |

TABLE IV-continued
| Structure | HEK IC50 | CHO IC50 | H929 IC50 | MM1S IC50 | MM1R IC50 | UTMC2 IC50 | CPM2 IC50 | KMS11 IC50 | My5 IC50 | KMS12PE IC50 | My7 IC50 | JJN3 IC50 | KMS18 IC50 | U266 IC50 | SKMM2 IC50 | RPMI-8226 IC50 |
|---|---|---|---|---|---|---|---|---|---|---|---|---|---|---|---|---|
| 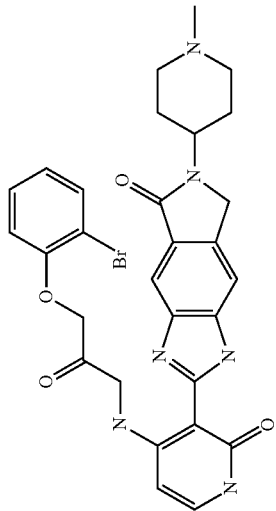 | E | E | B | C | C | B | D | D | D | D | D | D | D | D | D | D |
| 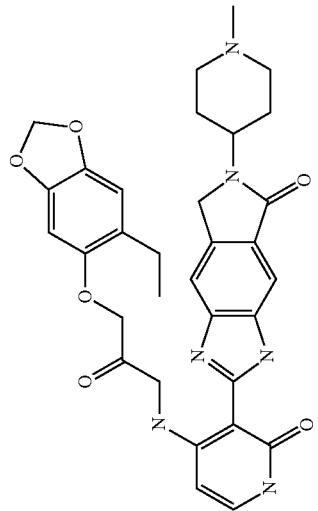 | E | E | A | A | B | A | C | C | C | C | C | C | B | C | C | D |
|  | E | E | B | A | C | A | C | C | D | D | C | C | C | C | D | D |

TABLE IV-continued

| Structure | HEK IC50 | CHO IC50 | H929 IC50 | MM1S IC50 | MM1R IC50 | UTMC2 IC50 | CPM2 IC50 | KMS11 IC50 | My5 IC50 | KMS12PE IC50 | My7 IC50 | JJN3 IC50 | KMS18 IC50 | U266 IC50 | SKMM2 IC50 | RPMI-8226 IC50 |
|---|---|---|---|---|---|---|---|---|---|---|---|---|---|---|---|---|
| | E | E | B | B | C | A | C | C | D | C | D | C | C | C | D | D |
| | E | E | C | C | C | A | C | D | D | D | D | D | D | C | D | D |

The IC50 values of multiple myeloma cell line proliferation inhibition are represented as ranges where IC50 values in the range below 0.5 µM are indicated by "A", between 0.5 µM and 1 µM by "B", between 1 µM and 5 µM by "C", between 5 µM and 20 µM by "D", and at or above 20 µM by "E".

Example 5

Kinase Profiling

Table V shows the results of kinase inhibition profiling of one of the compounds provided herein. The results are reported in terms of degree of inhibition for a particular kinase at fixed concentration of the compound (2 µM) being tested where "−" indicates less than 10% inhibition, "+"—more than 10% but less than 30%, "++"—more than 40% but less than 75% and "+++"—more than 75% inhibition of the target protein kinase compared to the activity of the kinase in a control to which no test compound has been added. Kinase profiling technique which has been used to evaluate compounds is described above and further technical details can be found at Upstate Biotechnologies Web site (http://www.upstatebiotech.com).

TABLE V

| Kinase | Percent Inhibition |
| --- | --- |
| KIT | +++ |
| FGFR1 | +++ |
| FLT1 | +++ |
| IGF1R | +++ |
| IR | +++ |
| MET | − |
| PDGFRb | + |
| TRKA | +++ |
| Abl | ++ |
| Src | +++ |
| ErbB4 | + |
| Flt3 | +++ |
| Flt4 | +++ |
| KDR | ++ |
| PDK1 | − |
| PKBa | − |
| MAPK1 | |
| PKA | − |
| CDK1/Cyclin B | − |
| cRaf | − |

Example 6

Figure 2:
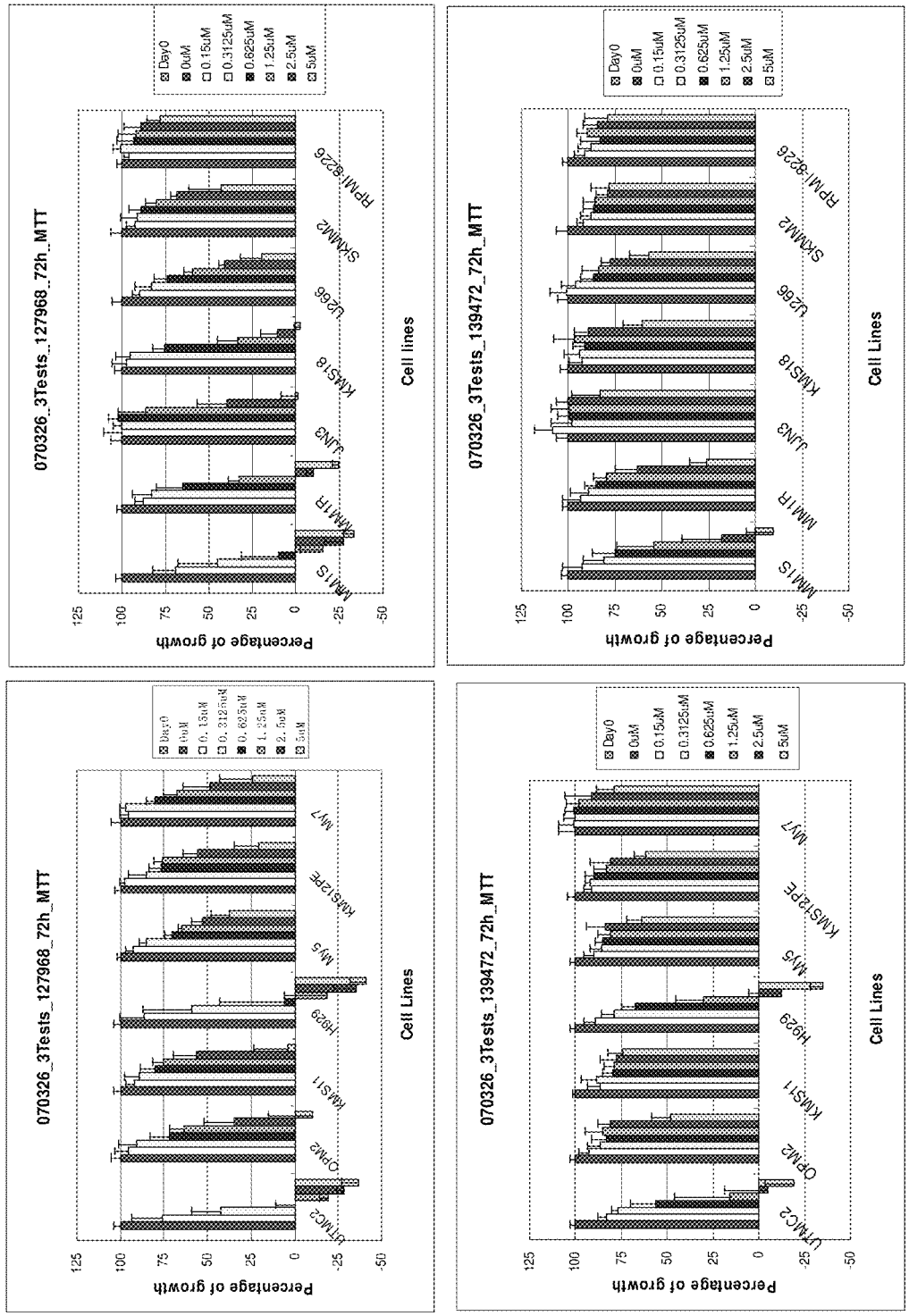
FIG. 2 depicts the effect of compound (2c) (i.e., CRL 139472) on viability of 14 human myeloma cell lines (Columns from left to right refer to a concentration of 0 µM, 0.15 µM, 0.3125 µM, 0.625 µM, 1.25 µM, 2.5 µM, and 5 µM as indicated in FIG. 2).
Figure 3:
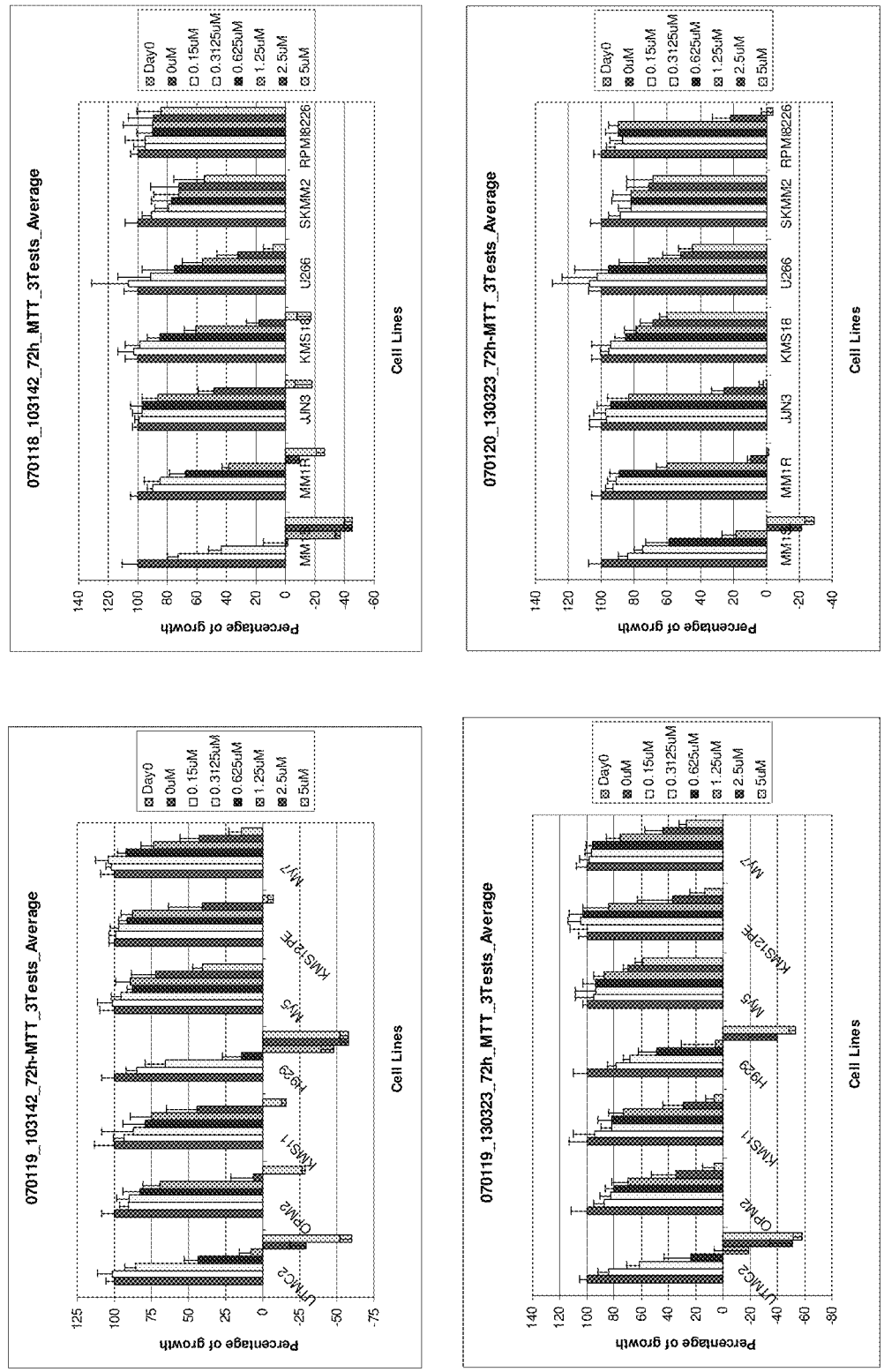
FIG. 3 depicts the effect of compound (2a) (i.e., CRL 103142) and compound (2b) (i.e., CRL 130323) on viability of 14 human myeloma cell lines. 14 human myeloma cell lines were incubated for 72 hrs with indicated concentrations of compound (2a) or compound (2b) and viability was determined by MTT assay. Results are reported as percent of growth (% viability=$(OD_{72h(drug)}-OD_{day0})/(OD_{72(0)}-OD_{day0})$) (Columns from left to right refer to a concentration of 0 µM, 0.15 µM, 0.3125 µM, 0.625 µM, 1.25 µM, 2.5 µM, and 5 µM as indicated in FIG. 3).
Figure 4:
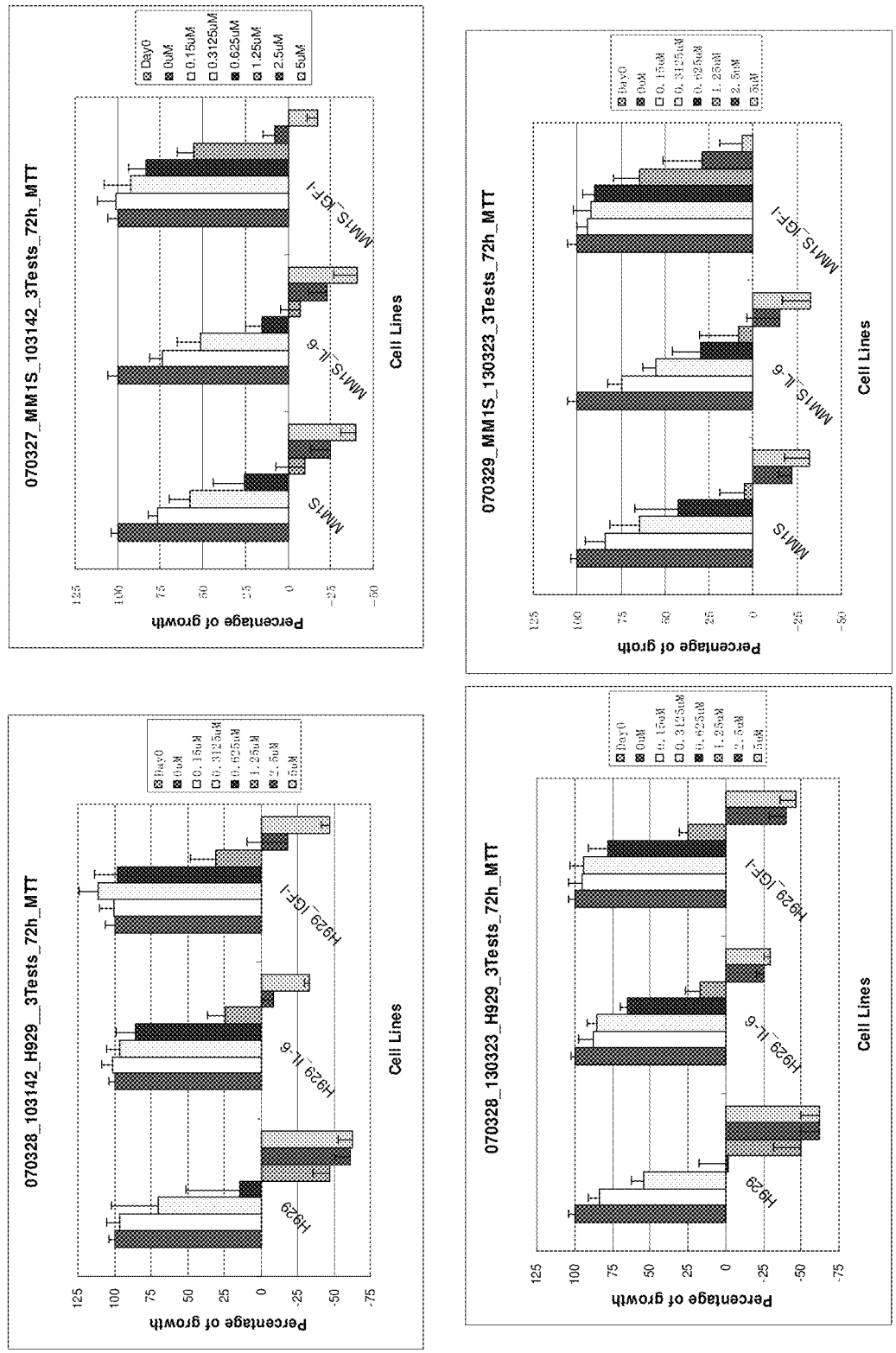
FIGS. 4 and 5 depict the effect of compound (2a) (i.e., CRL 103142) and compound (2b) (i.e., CRL 130323) on viability of H929, MM1S, and Stroma (Columns from left to right refer to a concentration of 0 µM, 0.15 µM, 0.3125 µM, 0.625 µM, 1.25 µM, 2.5 µM, and 5 µM as indicated in FIGS. 4 and 5).
Figure 5:
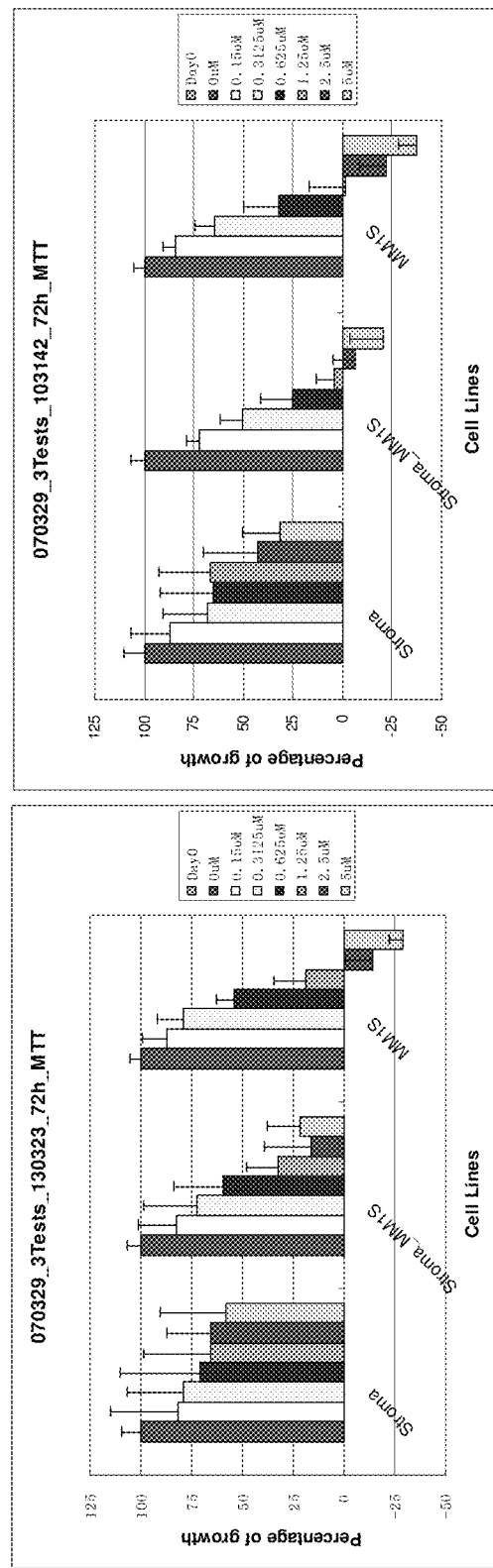

Effect of the Compounds of the Invention on Viability of Human Myeloma Cell Lines 14 human myeloma cell lines were incubated for 72 hours with the compounds of the invention, including compound (2e) (i.e., CRL124901), compound (2c) (i.e., CRL139472), compound (2a) (i.e., CRL103142), compounds (2b) (i.e., CRL130323), compound (21) (i.e., CRL135826), and compound (2h) (i.e., CRL127968) having a concentration of 0 µM, 0.15 µM, 0.3125 µM, 0.625 µM, 1.25 µM, 2.5 µM, and 5 µM. Viability was determined by MTT assay. Results are reported as percent of growth (% viability=(OD$_{72h(drug)}$−OD$_{day0}$)/(OD$_{72(0)}$−OD$_{day0}$) in FIGS. 1-3. FIGS. 4 and 5 showed the results of MTT assay for the compounds of the invention for the following cell lines: H929, H929_IL-6, H929_IGF-1, MM1s, MM1s_IL-6, and MM1s_IGF1.

Example 7

Figure 6:
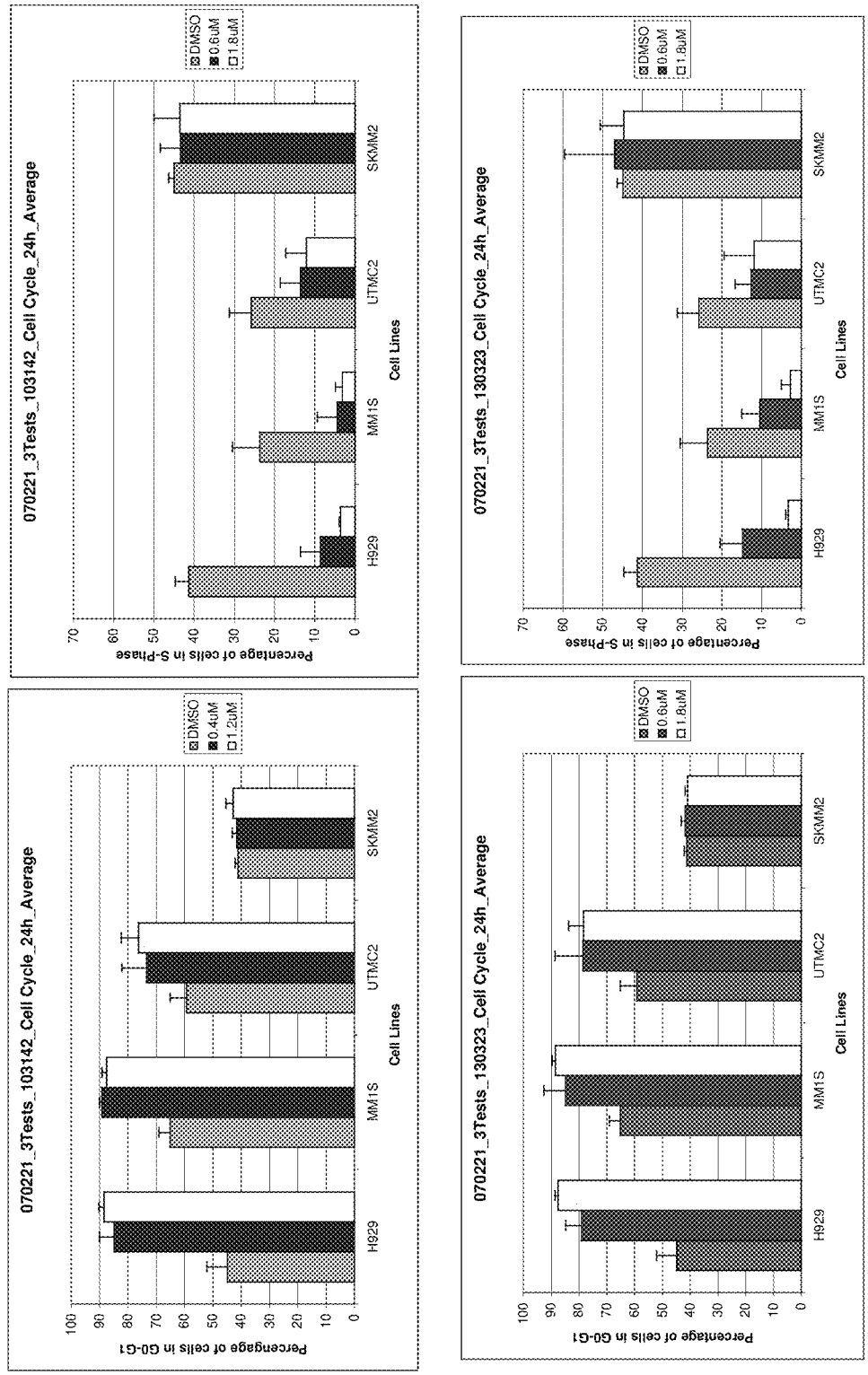
FIG. 6 depicts the effect of compound (2a) (i.e., CRL 103142) and compound (2b) (i.e., CRL 130323) on cell cycle. 4 human myeloma cell lines (3 sensitive and 1 resistant) were incubated for 24 hrs with indicated concentrations of compound (2a) and compound (2b) and effect on cell cycle was assessed by PI staining. Results are reported as percentage of cells in G0-G1 or S phase. Both drugs induced significant G1 growth arrest in sensitive cell lines. Columns from left to right refer to DMSO, 0.4 µM or 0.6 µM, and 1.2 µM as indicated in FIG. 6).

Effect of the Compounds of the Invention on Cell Cycle 4 human myeloma cell lines (3 sensitive and 1 resistant) were incubated for 24 hours with the compounds of the invention, including compounds (2a) and (2b), with a concentration of 0.6 µM and 1.8 µM and effect on cell cycle was assessed by PI staining. Results are reported as percentage of cells in G0-G1 or S phase. Both compounds in FIG. 6 induced significant G1 growth arrest in sensitive cell lines.

Example 8

Figure 7:
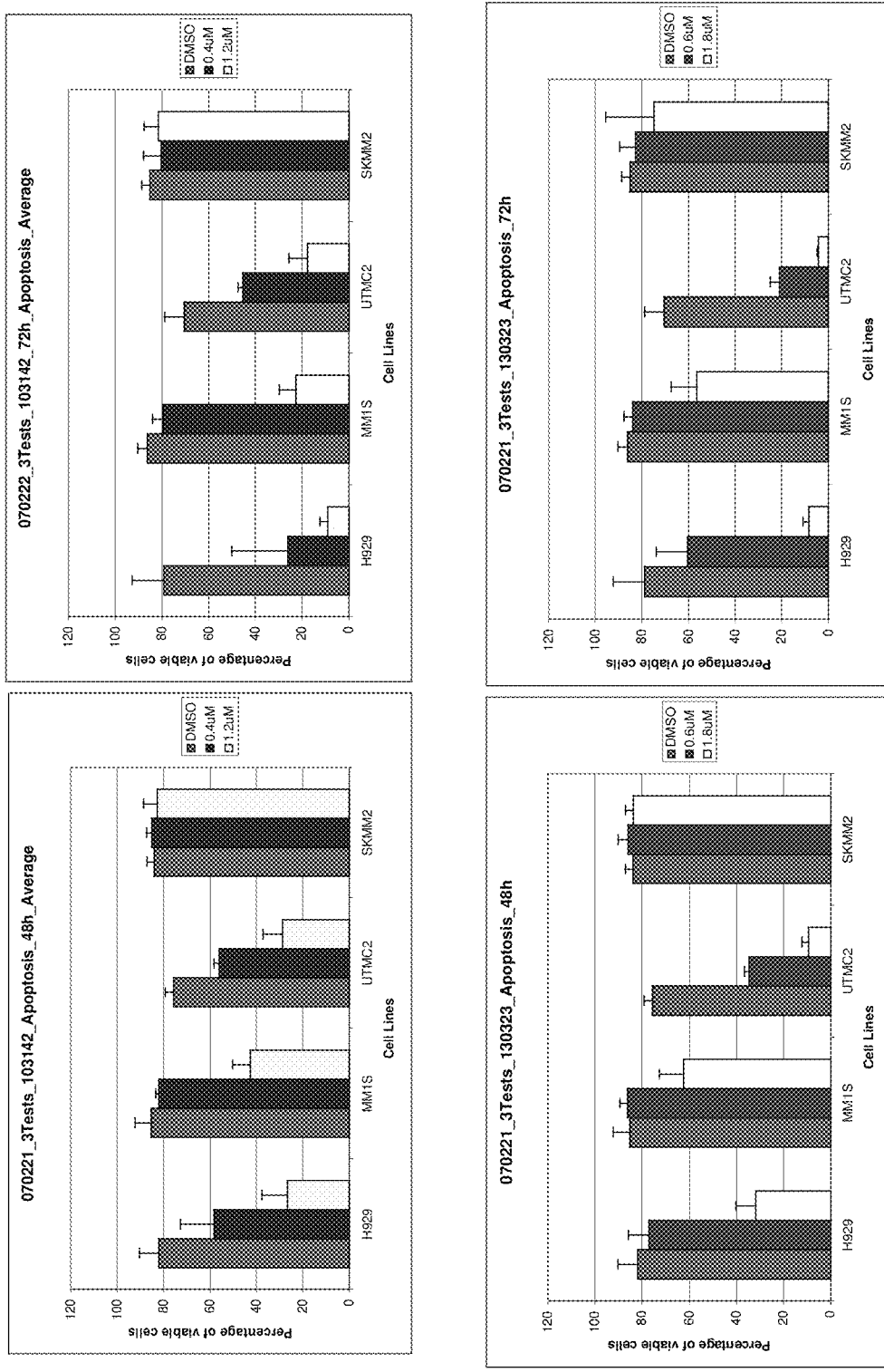
FIG. 7 depicts the effect of compound (2a) (i.e., CRL 103142) and compound (2b) (i.e., CRL 130323) on apoptosis. 4 human myeloma cell lines (3 sensitive and 1 resistant) were incubated for 48 or 72 hrs with indicated concentrations of compound (2a) and compound (2b) and effect on apoptosis was assessed by PI/annexin V staining. Results are reported as percentage of viable (PI–/annexin V–) cells. Both drugs induced significant apoptosis in sensitive cell lines. Columns from left to right refer to DMSO, 0.4 µM or 0.6 µM, and 1.2 µM as indicated in FIG. 7).

Effect of the Compounds of the Invention on Apoptosis 4 human myeloma cell lines (3 sensitive and 1 resistant) were incubated for 48 or 72 hours with the compounds of the invention, including compounds (2a) and (2b), having a concentration of 0.6 µM and 1.8 µM and effect on apoptosis was assessed by PI/annexin V staining. Results are reported as percentage of viable (PI−/annexin V−) cells. As shown in FIG. 7, both tested compounds induced significant apoptosis in sensitive cell lines.

Example 9

Induction of Apoptosis in Myeloma Cells

Figure 8:
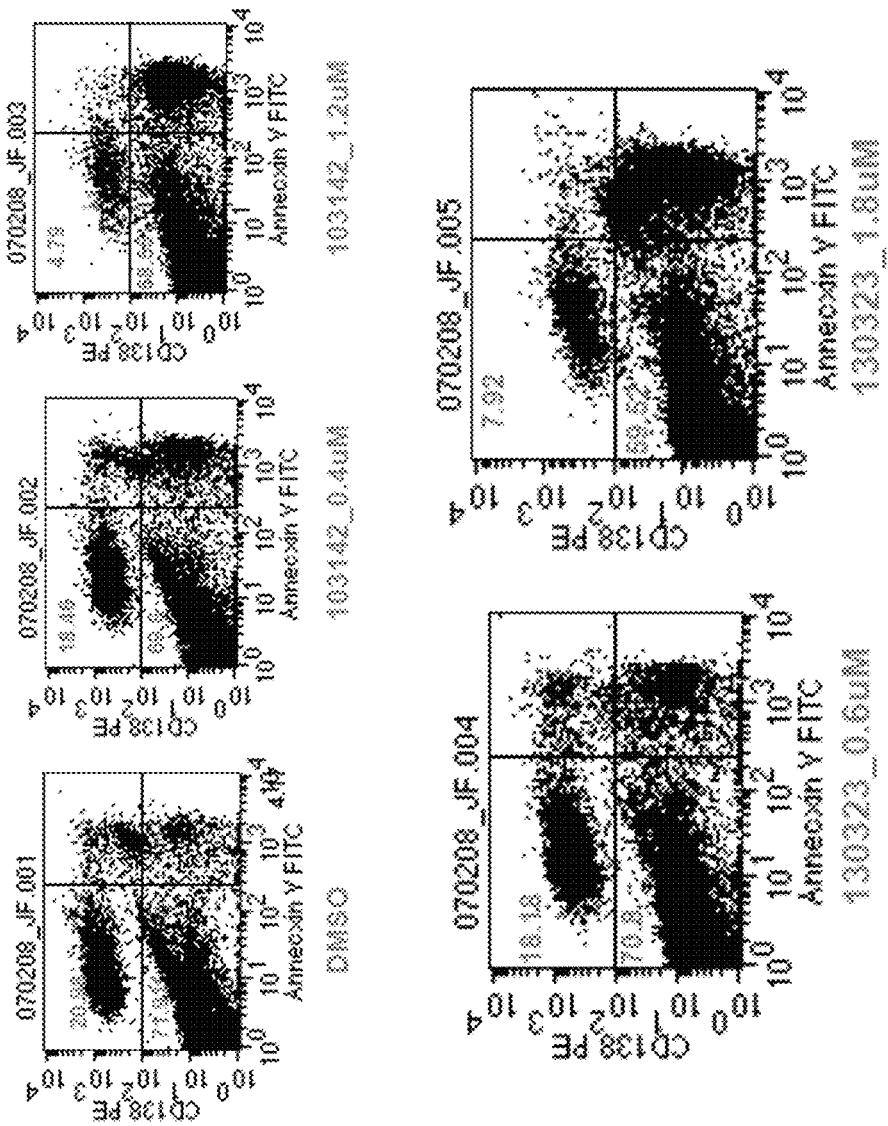
FIG. 8 depicts the apoptosis of myeloma cells induced by the compounds of the invention. Primary patient sample exposed to DMSO or compound (2a) (i.e., CRL 103142) or compound (2b) (i.e., CRL 130323) for 24 hr and indicated concentrations. LUQ-% viable myeloma cells and LLQ-% viable non-myeloma cells. Both drugs induced significant apoptosis of myeloma cells however compound (2b) appears more selective.
Figure 9:
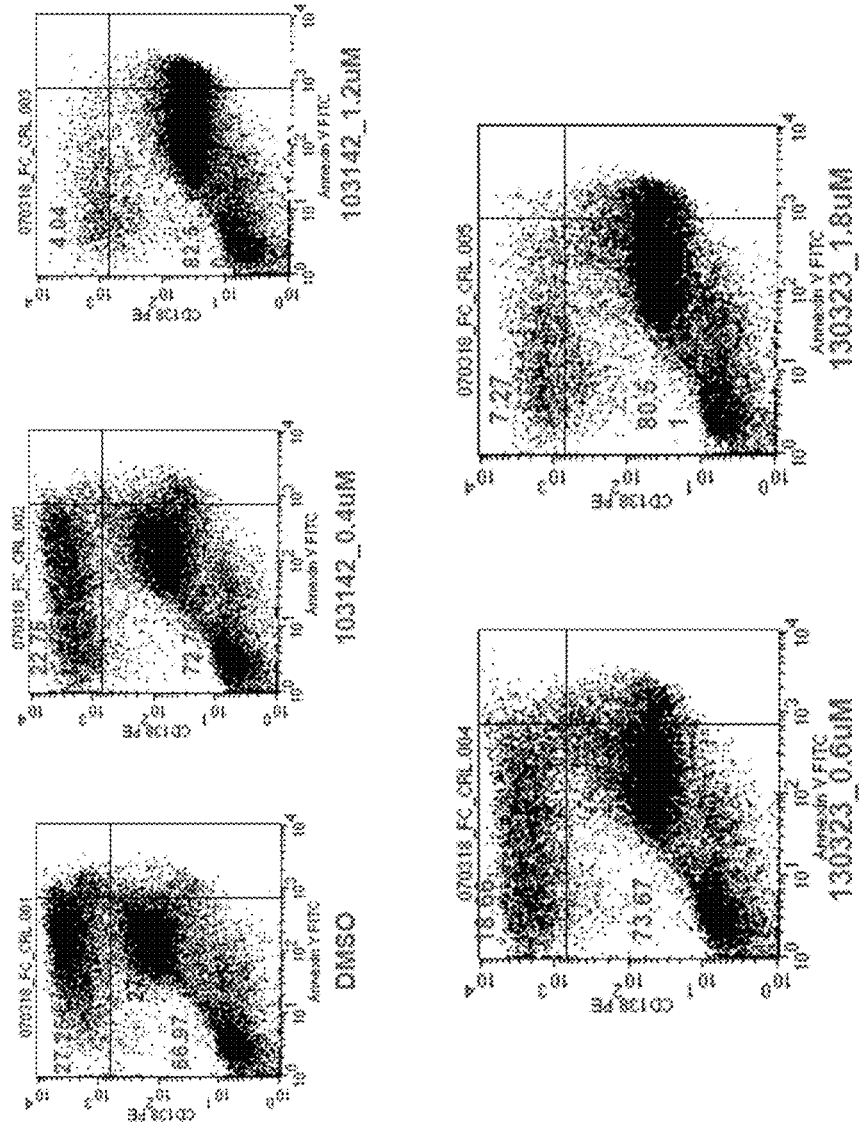
FIG. 9 depicts the apoptosis of myeloma cells induced by the compounds of the invention. Primary patient sample exposed to DMSO or compound (2a) (i.e., CRL 103142) or compound (2b) (i.e., CRL 130323) for 48 hr and indicated concentrations. LUQ-% viable myeloma cells and LLQ-% viable non-myeloma cells. Both drugs induced significant apoptosis of myeloma cells however compound (2b) appears more selective.
Figure 10:
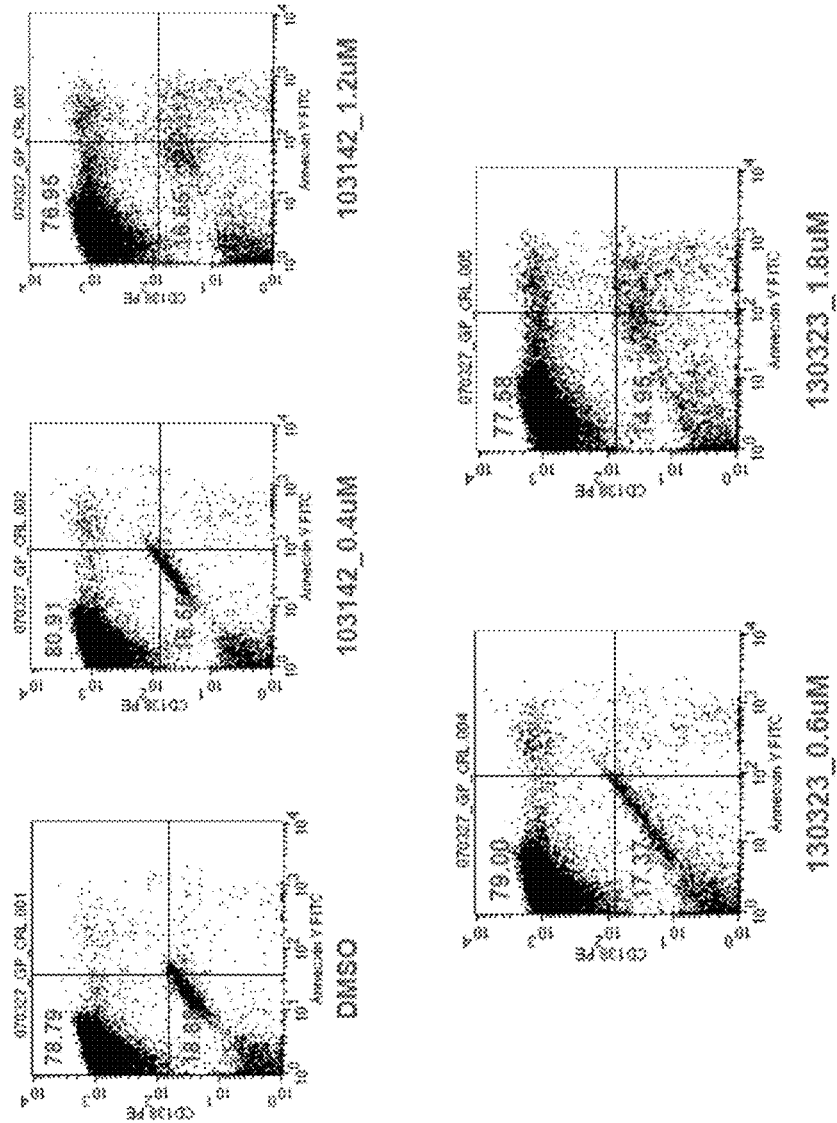
FIG. 10 depicts the apoptosis of myeloma cells induced by the compounds of the invention. Primary patient sample exposed to DMSO or compound (2a) (i.e., CRL 103142) or compound (2b) (i.e., CRL 130323) for 96 hr and indicated concentrations. LUQ-% viable myeloma cells and LLQ-% viable non-myeloma cells. Both drugs induced significant apoptosis of myeloma cells however compound (2b) appears more selective.

Primary patient sample exposed to DMSO or the compounds of the invention for 24 hours, 48 hours, and 96 hours and with a concentration of 0.4 µM, 0.6 µM, 1.2 µM, and 1.8 µM. LUQ-% viable myeloma cells and LLQ-% viable non-myeloma cells. The compounds of the invention included significant apoptosis of myeloma cells (FIGS. 8-10). Compound (2b) (CRL130323) is more selective.

These results show the specificity of the compound of the invention as an IGF-1R inhibitor. The compound of the invention had its greatest potency against IGF-1R, about 3-fold less potency against insulin receptor (IR), ALK, TRKA, and FLT3, but much less potency against all other kinases tested. The selectivity of the compound of the invention for IGF-1R versus IR was 6-10 fold. The compound of the invention is active versus myeloma cell lines but is free of non-specific cytotoxicity as mice dosed with a compound of the invention at very high dose did not show increased weight loss, an indicator that the compound has no serious toxicity.

Example 10

Myeloma-Selective Cytotoxicity of Compound (2b) (i.e., CRL130323)

Figure 11:
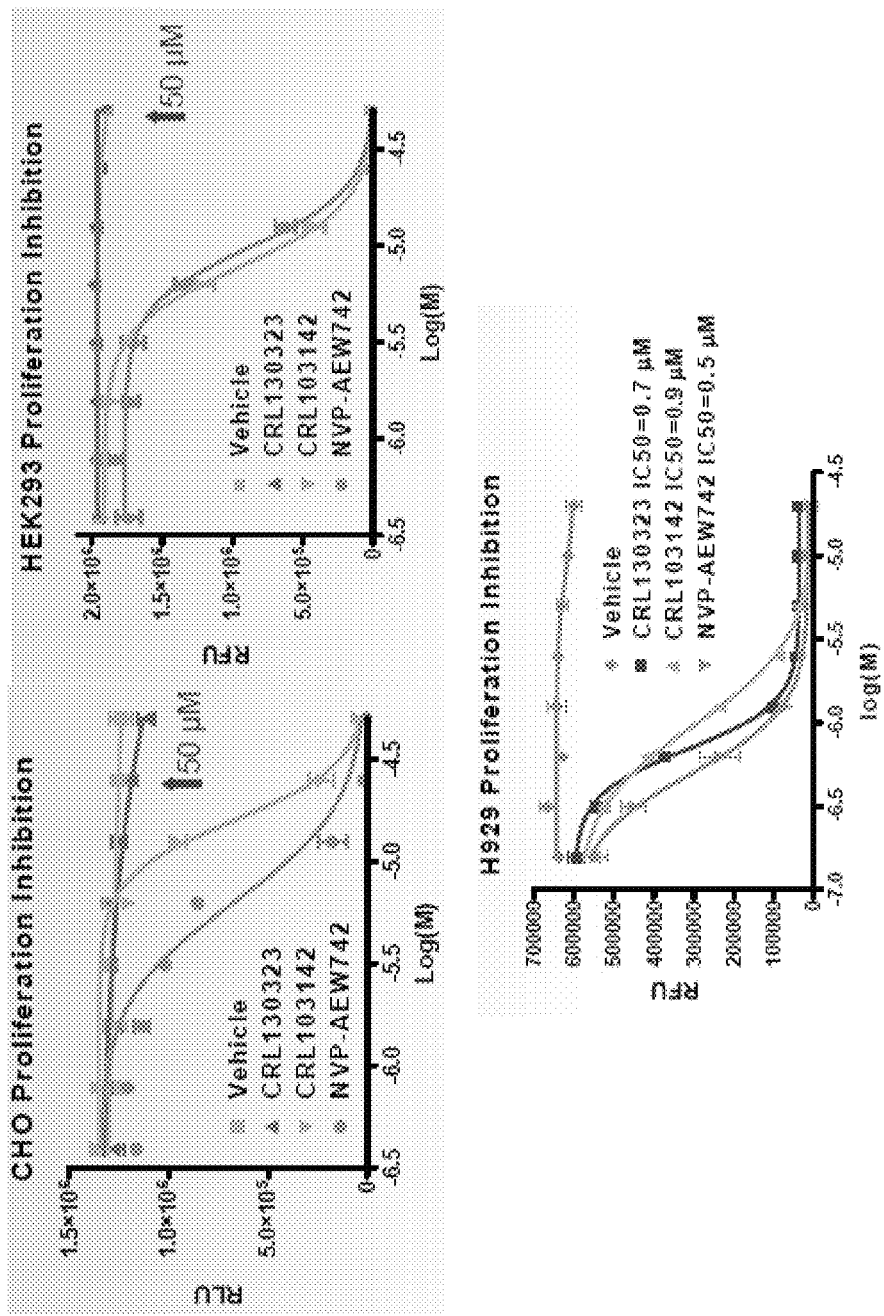
FIG. 11 depicts highly selective compound (2b) (i.e., CRL 130323) towards multiple myeloma lines; compound (2b) has negligible nonspecific cytotoxicity.
Figure 12:
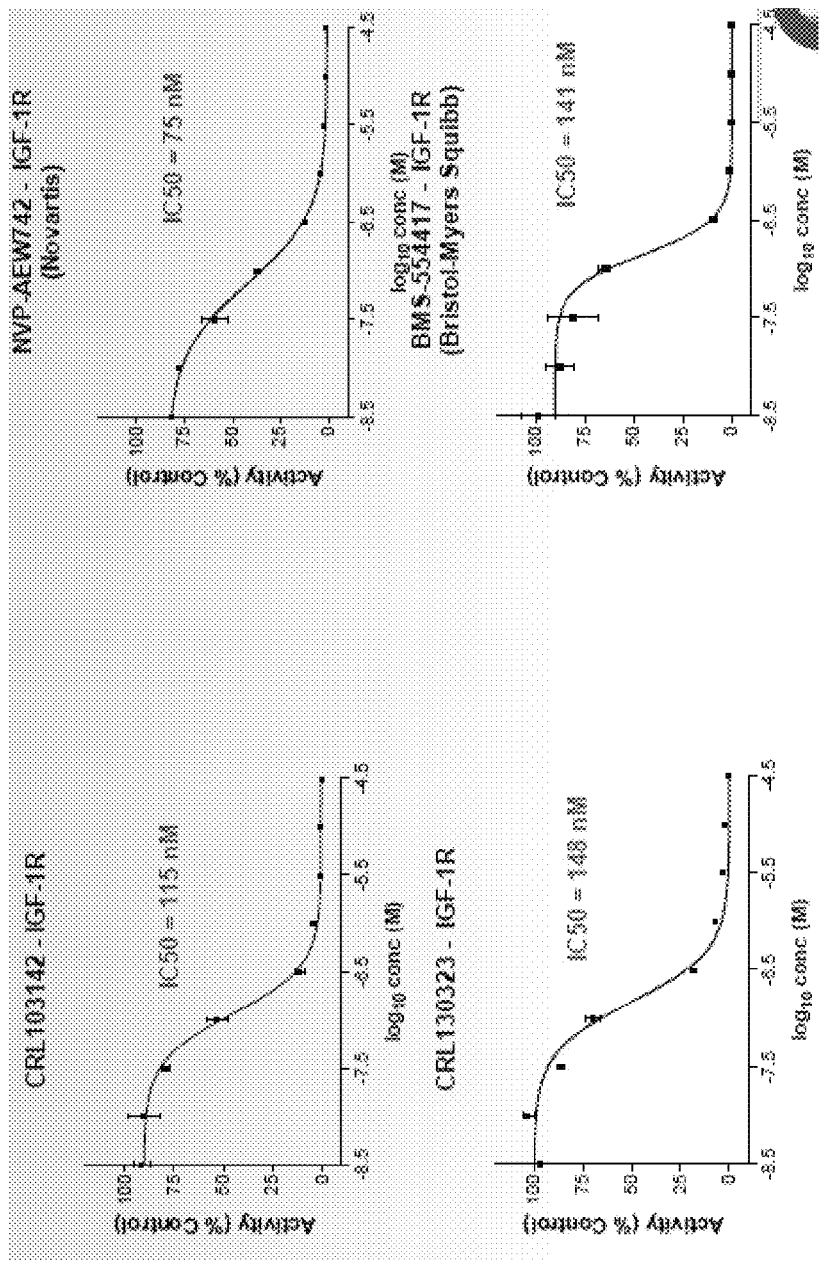
FIG. 12 depicts both compound (2a) (i.e., CRL 103142) and compound (2b) (i.e., CRL 130323) inhibited IGF-1R in vitro in the same potency range as known preclinical compounds.
Figure 13:
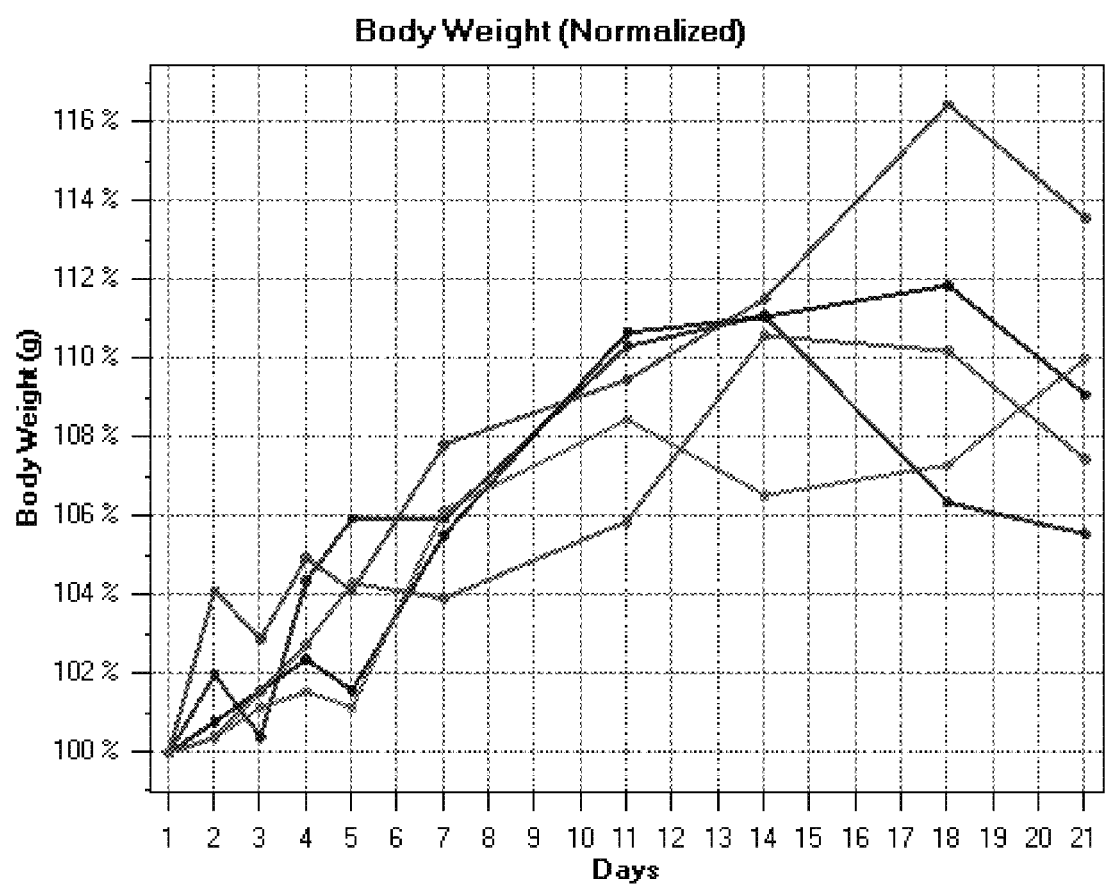
FIG. 13 depicts compound (2b) (i.e., CRL 130323) showed no signs of toxicity in animals at highest doses tested. All the lines showing growth the animals at various doses and without significance between doses collectively demonstrate a lack of toxicity to the animal.

FIG. 11 shows that CRL130323 did not demonstrate toxicity in the normal cell lines CHO and HEK293, whereas other receptor tyrosine kinase inhibitors NVP-AEW742 and CRL103142 demonstrated toxicity in normal cell lines. All the above were active in the multiple myeloma cell line H929. The increased selectivity of CRL130323 was observed despite comparable IGF-1R potency (FIG. 12, left side). In vivo data in FIG. 13 also suggested no observable toxicity for CRL130323 based the absence of an effect of body weight.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method of treating multiple myeloma in a subject in need thereof comprising administering to said subject an insulin-like growth factor receptor-1 (IGF-1R) inhibitor, wherein said IGF-1R inhibitor is a compound of formula I,

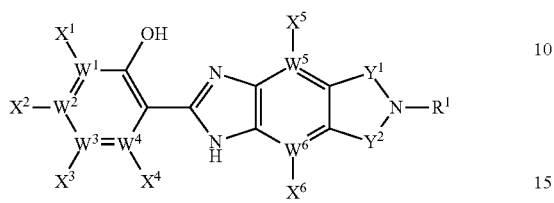

wherein:
each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

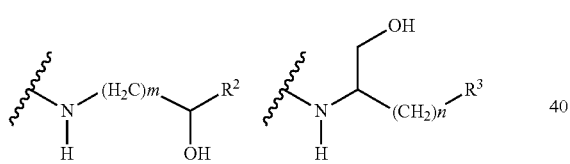

wherein:
m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —(CH$_2$)$_p$-M$^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein M$^1$ is O, S, and p is an integer between 0 and 4;

$R^3$ is selected from optionally substituted aryl, heteroaryl, wherein the heteroaryl is imidazoyl, pyridinyl, benzo-dioxanyl, benzo-imidazolyl or indolyl, —(CH$_2$)$_o$-aryl, or —(CH$_2$)$_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

$Y^1$ is

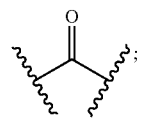 [SMILES: *C(*)=O]

$Y^2$ is

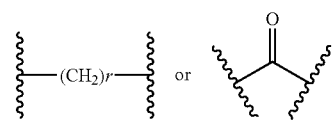

wherein: r is 1; and $R^1$ is independently selected from optionally substituted nitrogen containing heterocyclyl; nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl-carboxamido, sulfonamido, SO$_2$-alkyl, SO-alkyl, CO-alkyl, CO$_2$-alkyl, cyano, cyanoalkyl, ketoalkyl, and methanesulfonylalkyl, or a pharmaceutically acceptable salt thereof.

2. The method of claim 1, wherein said compound is selected from the group consisting of (2a)

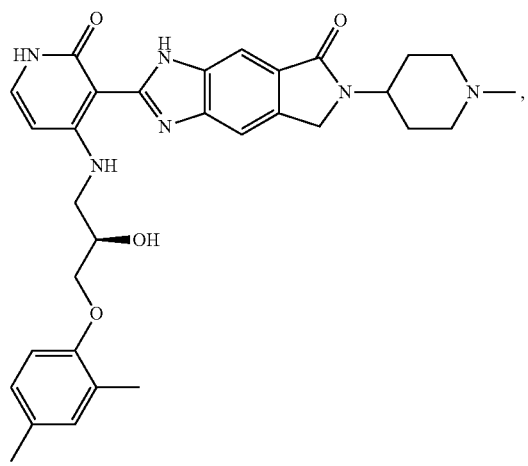

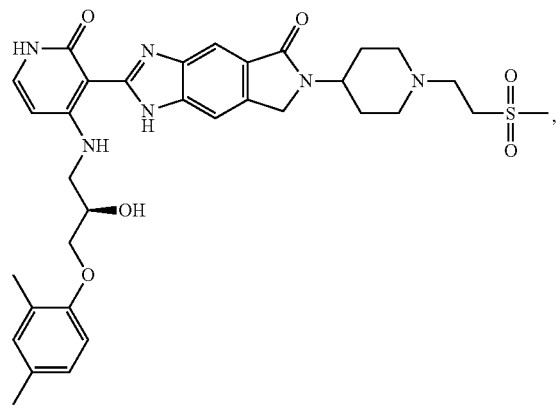
(2b)
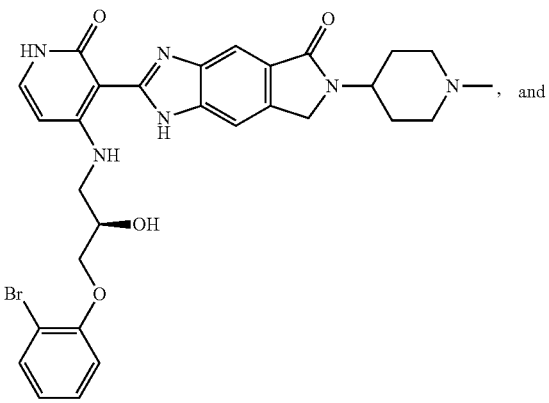
(2h)
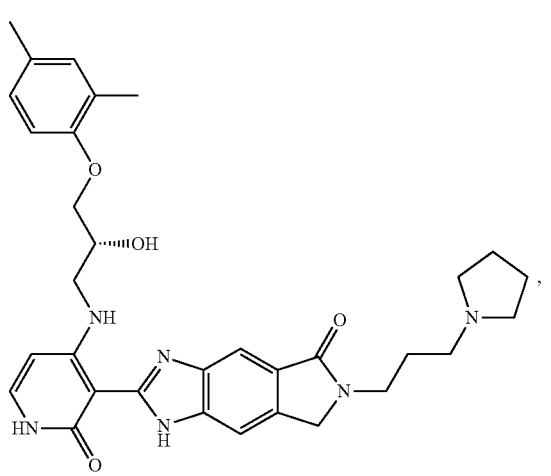
(2c)
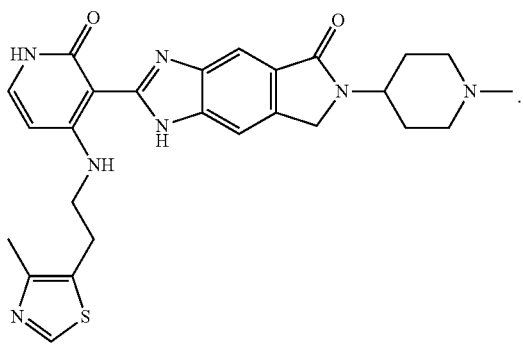
(2i)
3. The method of claim 1, wherein said compound is
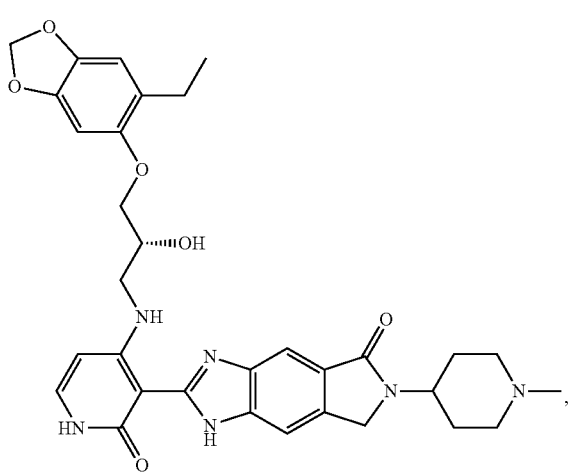
(2e)
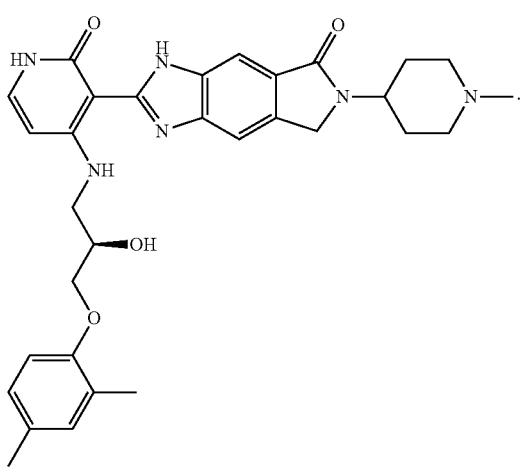
(2a)

4. The method of claim 1, wherein said compound is

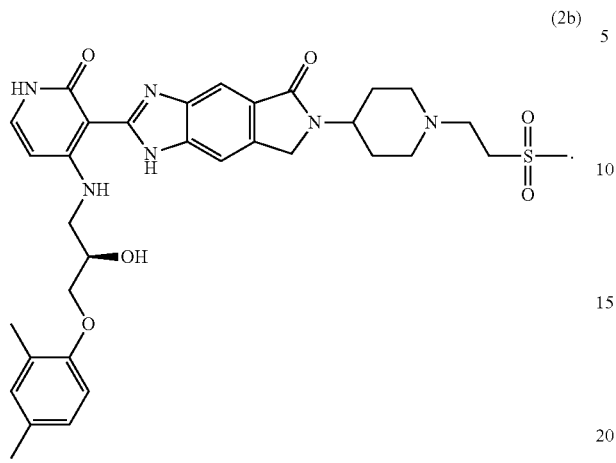

(2b)

5. The method of claim 1, further comprising administering at least one other anti-cancer agent.

6. A method of treating multiple myeloma in a subject comprising administering to said subject a composition comprising an insulin-like growth factor receptor-1 (IGF-1R) inhibitor, wherein said IGF-1R inhibitor is a compound of formula I,

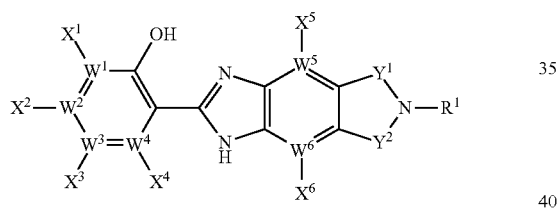

wherein:
each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

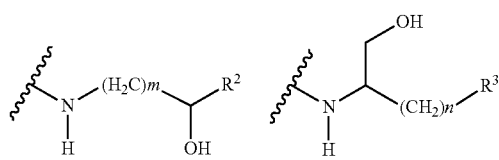

wherein:
m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —$(CH_2)_p$-$M^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein $M^1$ is O, S, and p is an integer between 0 and 4;

$R^3$ is selected from optionally substituted aryl, heteroaryl, wherein the heteroaryl is imidazoyl, pyridinyl, benzo-dioxanyl, benzo-imidazolyl or indolyl, —$(CH_2)_o$-aryl, or —$(CH_2)_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

$Y^1$ is

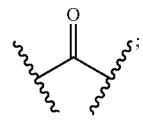 [SMILES: *C(*)=O]

$Y^2$ is

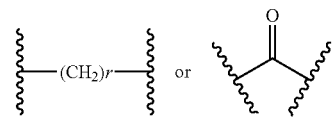

wherein: r is 1; and $R^1$ is independently selected from optionally substituted nitrogen containing heterocyclyl;

nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl-carboxamido, sulfonamido, $SO_2$-alkyl, SO-alkyl, CO-alkyl, $CO_2$-alkyl, cyano, cyanoalkyl, ketoalkyl, and methanesulfonylalkyl, or a pharmaceutically acceptable salt thereof.

7. The method of claim 6, wherein said composition further comprises at least one other anti-cancer agent.

8. The method of claim 6, wherein said compound is selected from the group consisting of
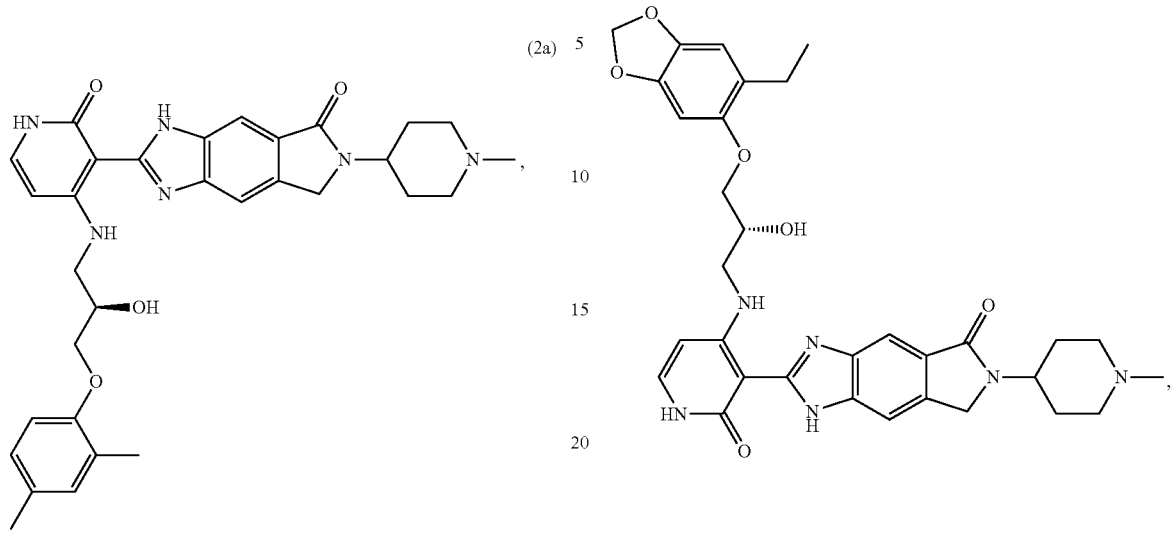
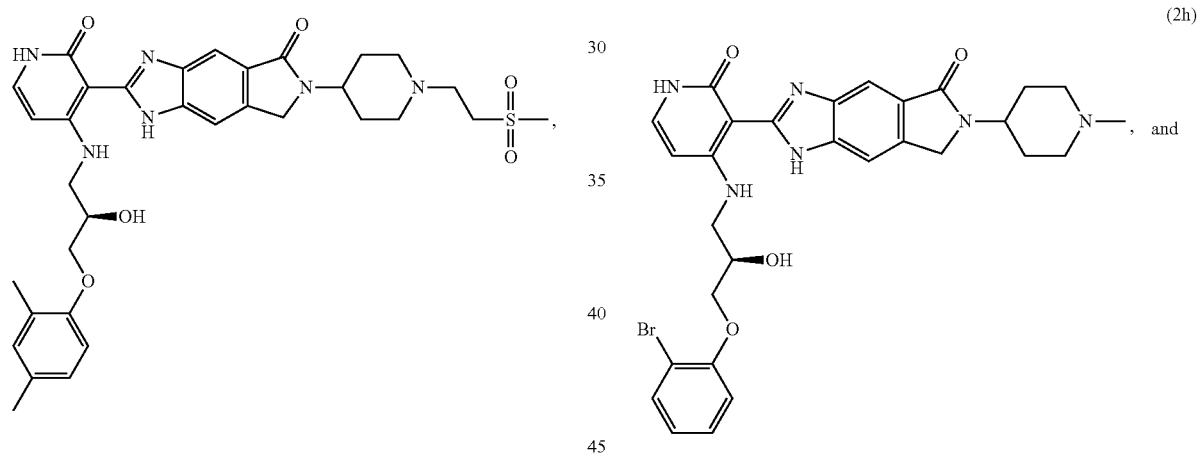
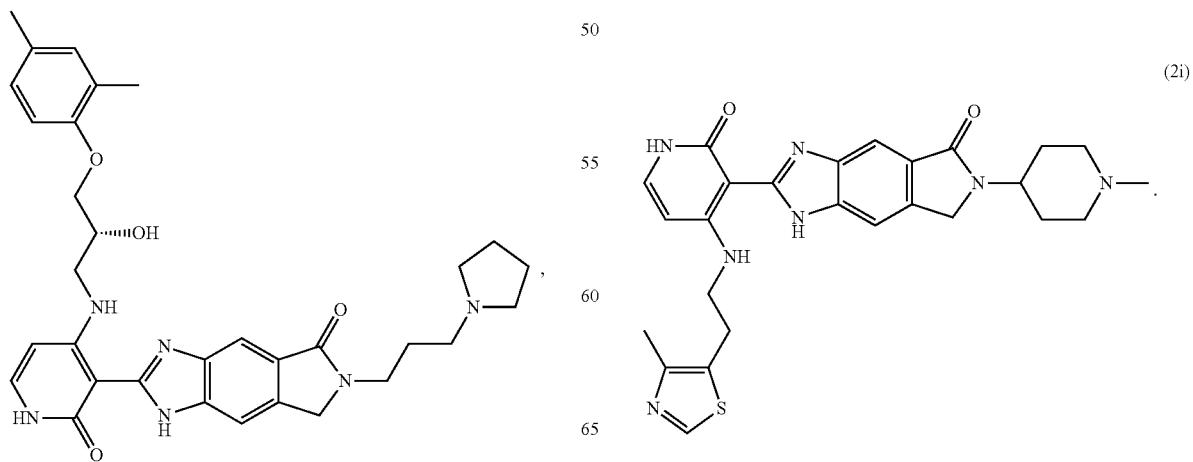

9. The method of claim 6, wherein said compound is

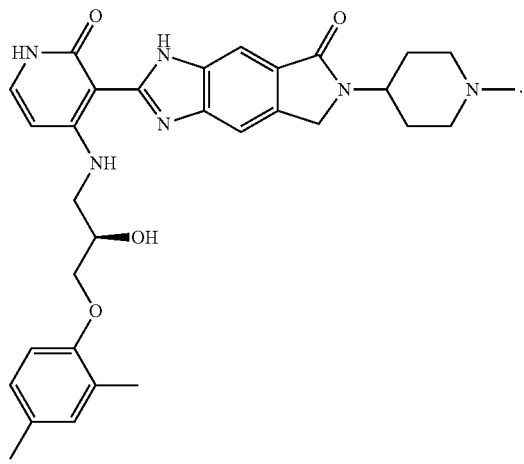
(2a)

10. The method of claim 6, wherein said compound is

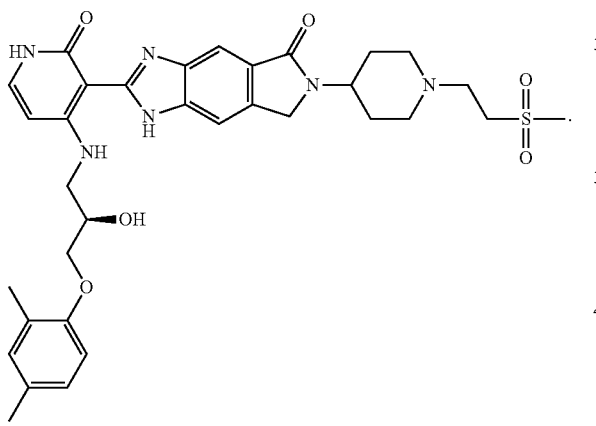
(2b)

11. A method of treating a condition or disorder associated with an insulin-like growth factor receptor-1 (IGF-1R), comprising administering to a subject in need thereof an IGF-1R inhibitor, wherein said IGF-1R inhibitor is a compound of formula I,

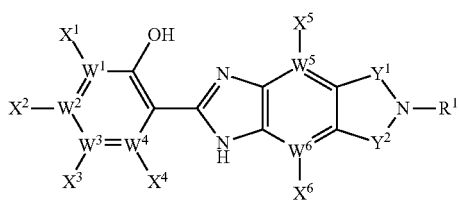

wherein:
each $W^1$ through $W^4$ is independently a carbon atom or a nitrogen atom, wherein one of $W^1$-$W^4$ is nitrogen, and $W^5$ and $W^6$ are carbon, with the proviso that when any $W^1$ through $W^4$ is N, then the corresponding substituent(s) $X^1$ through $X^4$ is (are) absent;

each $X^1$ through $X^3$ is independently selected from hydrogen, hydroxy, halogen, lower alkyl, lower alkoxy, haloalkyl, trifluoromethyl, nitro, cyano, primary, secondary or tertiary amino;

each $X^5$ and $X^6$ is independently selected from hydrogen and lower alkyl;

$X^4$ is selected from hydrogen, halogen, or is selected from the following groups:

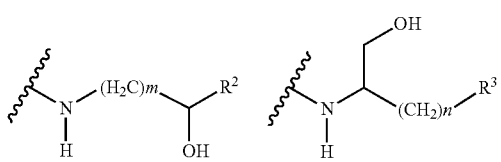

wherein:

m is an integer from 1 to 4, and n is an integer from 0 to 4;

$R^2$ is selected from optionally substituted aryl, heteroaryl wherein said heteroaryl is imidazoyl, pyridinyl, benzo-dioxanyl, benzo-dioxolyl, benzo-imidazolyl or indolyl, or —$(CH_2)_p$-$M^1$-aryl, substituted by substituents independently selected from a group consisting of hydrogen, lower alkoxy, aryloxy, benzyloxy, alkylthio, hydroxy, halogen, trifluoromethyl, trifluoromethoxy, trifluoromethylthio, lower alkyl, lower alkenyl, methylenedioxy, trimethylene, cyano, nitro, tertiary amino, such as dimethylamino, carboxamide, lower alkylsulfonyl, lower alkylthio, optionally substituted aryl or heteroaryl, wherein $M^1$ is O, S, and p is an integer between 0 and 4;

$R^3$ is selected from optionally substituted aryl, heteroaryl, wherein the heteroaryl is imidazoyl, pyridinyl, benzo-dioxanyl, benzo-imidazolyl or indolyl, —$(CH_2)_o$-aryl, or —$(CH_2)_o$-heteroaryl, substituted by a substituent independently selected from a group consisting of hydrogen, lower alkoxy, hydroxy, halogen, trifluoromethyl, trifluoromethoxy, lower alkyl, cyano, nitro, primary, secondary or tertiary amino, carboxamide, optionally substituted aryl or heteroaryl, wherein o is 0 to 5;

$Y^1$ is

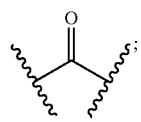 [SMILES: *C(*)=O]

$Y^2$ is

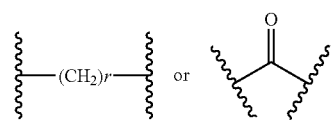

wherein: r is 1; and

R¹ is independently selected from optionally substituted nitrogen containing heterocyclyl;

nitrogen containing heterocyclylalkyl; wherein said heterocyclyl and heterocyclylalkyl are piperidinyl, pyrrolidinyl, piperazinyl, azetidinyl, morpholinyl, or quinucleodinyl; and nitrogen containing heteroarylalkyl, wherein substitutions are selected from: hydrogen, lower alkyl, hydroxy, lower alkoxy, amino, di-(lower alkyl)aminoalkyl-carboxamido, sulfonamido, $SO_2$-alkyl, SO-alkyl, CO-alkyl, $CO_2$-alkyl, cyano, cyanoalkyl, ketoalkyl, and methanesulfonylalkyl, or a pharmaceutically acceptable salt thereof, wherein said condition or disorder is blood cancer.

12. The method of claim 11, wherein said condition or disorder is multiple myeloma.

13. The method of claim 11, further comprising administering at least one other anti-cancer agent.

14. The method of claim 11, wherein said compound is selected from the group consisting of

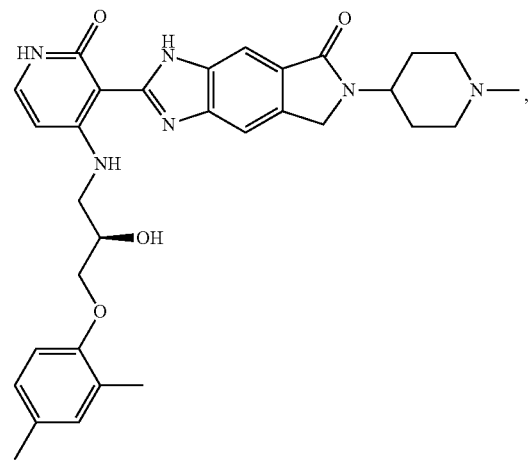
(2a)

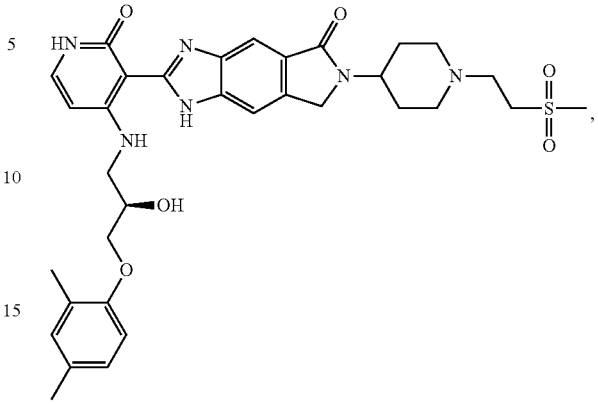
(2b)

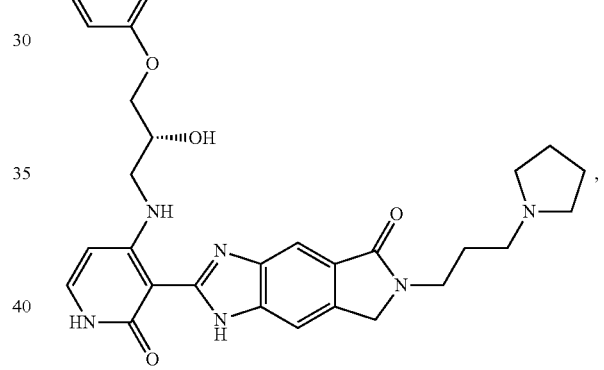
(2c)

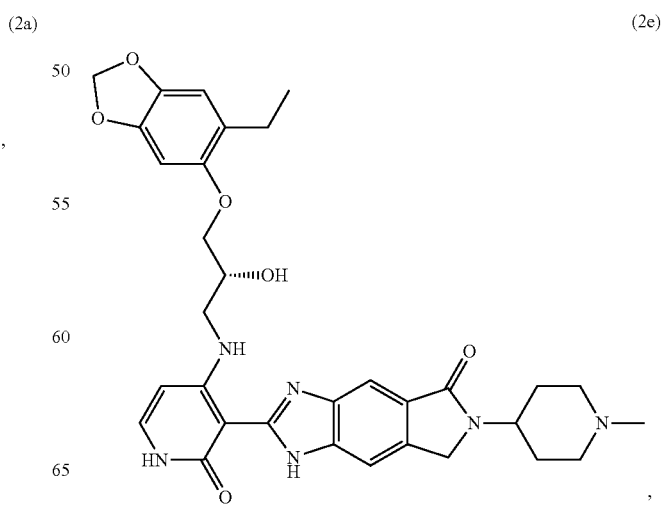
(2e)

-continued
(2h)
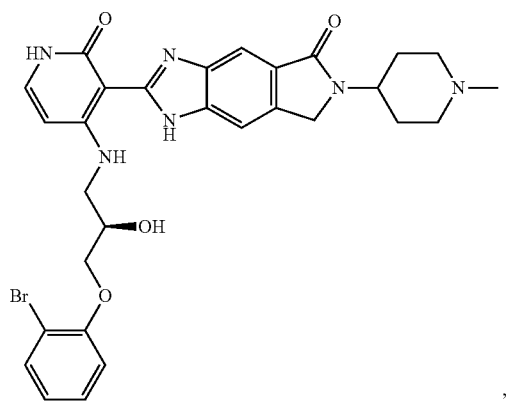
(2i)
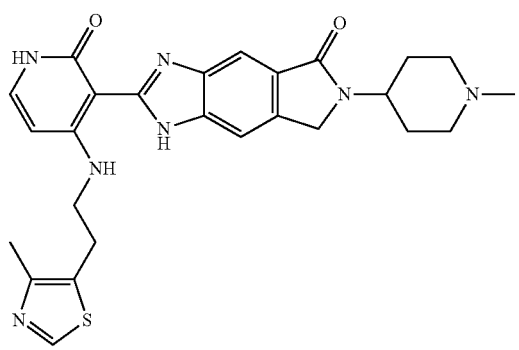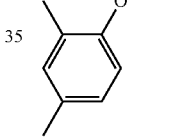
15. The method of claim 11, wherein said compound is
(2a)
16. The method of claim 11, wherein said compound is
(2b)
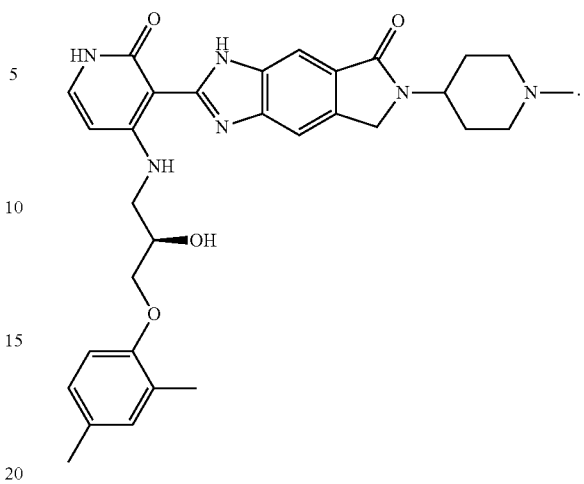
* * * * *